(12) United States Patent
Salituro et al.

(10) Patent No.: US 11,149,054 B2
(45) Date of Patent: Oct. 19, 2021

(54) OXYSTEROLS AND METHODS OF USE THEREOF

(71) Applicant: Sage Therapeutics, Inc., Cambridge, MA (US)

(72) Inventors: Francesco G. Salituro, Marlborough, MA (US); Albert Jean Robichaud, Boston, MA (US); Gabriel Martinez Botella, Wayland, MA (US); Boyd L. Harrison, Princeton Junction, NJ (US); Andrew Griffin, L'Ile Bizard (CA)

(73) Assignee: SAGE THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 16/343,235

(22) PCT Filed: Oct. 18, 2017

(86) PCT No.: PCT/US2017/057277
§ 371 (c)(1),
(2) Date: Apr. 18, 2019

(87) PCT Pub. No.: WO2018/075699
PCT Pub. Date: Apr. 26, 2018

(65) Prior Publication Data
US 2019/0248829 A1    Aug. 15, 2019

Related U.S. Application Data

(60) Provisional application No. 62/409,761, filed on Oct. 18, 2016, provisional application No. 62/409,772, filed on Oct. 18, 2016, provisional application No. 62/409,767, filed on Oct. 18, 2016, provisional application No. 62/409,764, filed on Oct. 18, 2016, provisional application No. 62/409,774, filed on Oct. 18, 2016.

(51) Int. Cl.
| | | |
|---|---|---|
| *C07J 9/00* | (2006.01) | |
| *C07J 17/00* | (2006.01) | |
| *A61P 25/20* | (2006.01) | |
| *A61P 25/28* | (2006.01) | |
| *A61P 25/22* | (2006.01) | |
| *A61P 19/02* | (2006.01) | |
| *A61P 25/18* | (2006.01) | |
| *A61P 1/00* | (2006.01) | |
| *A61P 25/16* | (2006.01) | |
| *A61P 35/00* | (2006.01) | |
| *C07J 43/00* | (2006.01) | |

(52) U.S. Cl.
CPC ..  *C07J 9/00* (2013.01); *A61P 1/00* (2018.01); *A61P 19/02* (2018.01); *A61P 25/16* (2018.01); *A61P 25/18* (2018.01); *A61P 25/20* (2018.01); *A61P 25/22* (2018.01); *A61P 25/28* (2018.01); *A61P 35/00* (2018.01); *C07J 17/00* (2013.01); *C07J 43/003* (2013.01)

(58) Field of Classification Search
CPC ........................................................... C07J 9/00
USPC ......................................................... 549/427
See application file for complete search history.

(56) References Cited

U.S. PATENT DOCUMENTS

| | | |
|---|---|---|
| 2,594,323 A | 4/1952 | Levin et al. |
| 3,079,385 A | 2/1963 | Bertin et al. |
| 3,206,459 A | 9/1965 | Cross |
| 4,071,625 A | 1/1978 | Grunwell et al. |
| 5,232,917 A | 8/1993 | Bolger et al. |
| 5,376,645 A | 12/1994 | Stella et al. |
| 5,595,996 A | 1/1997 | Graham et al. |
| 5,888,996 A | 3/1999 | Farb |
| 5,925,630 A | 7/1999 | Upasani et al. |
| 6,407,086 B2 | 6/2002 | Faarup et al. |
| 6,645,953 B2 | 11/2003 | Gronvald et al. |
| 6,884,796 B2 | 4/2005 | Faarup et al. |
| 8,034,798 B2 | 10/2011 | Baulieu et al. |

(Continued)

FOREIGN PATENT DOCUMENTS

| | | |
|---|---|---|
| CN | 1254716 | 5/2008 |
| FR | 2850023 A1 | 7/2004 |

(Continued)

OTHER PUBLICATIONS

Luu et al., "Oxysterols: Old Tale, New Twists", Annual Reviews. Pharmacol. Toxicol. (2016), vol. 56, pp. 447-467.

(Continued)

*Primary Examiner* — Taofiq A Solola
(74) *Attorney, Agent, or Firm* — Haley Guiliano LLP

(57) ABSTRACT

Compounds are provided according to Formula (I): and pharmaceutically acceptable salts thereof, and pharmaceutical compositions thereof; wherein $R_2$, $R^3$, $R^4$, $R^5$, and and $R^6$ are as defined herein. Compounds of the present invention are contemplated useful for the prevention and treatment of a variety of conditions.

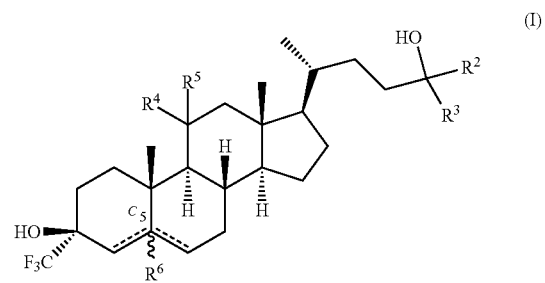

8 Claims, No Drawings

(56) References Cited

U.S. PATENT DOCUMENTS

| | | |
|---|---|---|
| 8,247,436 B2 | 8/2012 | Baettig et al. |
| 8,604,011 B2 | 12/2013 | Mellon |
| 8,673,843 B2 | 3/2014 | Moskal et al. |
| 8,829,213 B2 | 9/2014 | Peng et al. |
| 10,201,550 B2 | 2/2019 | Salituro et al. |
| 10,227,375 B2 | 3/2019 | Martinez Botella et al. |
| 10,259,840 B2 | 4/2019 | Harrison et al. |
| 10,696,712 B2 | 6/2020 | Salituro et al. |
| 10,723,758 B2 | 7/2020 | Harrison et al. |
| 2004/0048838 A1 | 3/2004 | Gronvald et al. |
| 2005/0101573 A1 | 5/2005 | Faarup et al. |
| 2006/0199790 A1 | 9/2006 | Baulieu et al. |
| 2008/0193423 A1 | 8/2008 | Brunton et al. |
| 2008/0269183 A1 | 10/2008 | Mellon et al. |
| 2008/0319026 A1 | 12/2008 | Gant et al. |
| 2010/0034781 A1 | 2/2010 | Parhami et al. |
| 2010/0087411 A1 | 4/2010 | Barraclough et al. |
| 2011/0160223 A1 | 6/2011 | Dingledine et al. |
| 2011/0190249 A1 | 8/2011 | Rees et al. |
| 2012/0035156 A1 | 2/2012 | Alberati et al. |
| 2012/0040916 A1 | 2/2012 | Moon et al. |
| 2012/0041016 A1 | 2/2012 | Frincke |
| 2012/0115169 A1 | 5/2012 | Mullenix et al. |
| 2013/0210792 A1 | 8/2013 | Song et al. |
| 2014/0045943 A1 | 2/2014 | Khan et al. |
| 2014/0148412 A1 | 5/2014 | Hogenkamp |
| 2014/0235600 A1 | 8/2014 | Covey et al. |
| 2014/0335050 A1 | 11/2014 | Haggerty et al. |
| 2015/0158903 A1 | 6/2015 | Upasani et al. |
| 2015/0291654 A1 | 10/2015 | Upasani et al. |
| 2015/0376225 A1 | 12/2015 | Dugar et al. |
| 2016/0022701 A1 | 1/2016 | Reddy et al. |
| 2016/0031930 A1 | 2/2016 | Martinez Botella et al. |
| 2017/0247405 A1 | 8/2017 | Harrison et al. |
| 2017/0304321 A1 | 10/2017 | Quirk et al. |
| 2017/0305960 A1 | 10/2017 | Botella et al. |
| 2018/0194797 A1 | 7/2018 | Salituro et al. |
| 2018/0200267 A1 | 7/2018 | Salituro et al. |
| 2018/0201643 A1 | 7/2018 | Salituro et al. |
| 2018/0237470 A1 | 8/2018 | Botella et al. |
| 2018/0362573 A1 | 12/2018 | Upasani et al. |
| 2018/0371009 A1 | 12/2018 | Pellicciari et al. |
| 2019/0125764 A1 | 5/2019 | Salituro et al. |
| 2019/0127414 A1 | 5/2019 | Botella et al. |
| 2019/0135854 A1 | 5/2019 | Harrison et al. |
| 2019/0160078 A1 | 5/2019 | Masuoka et al. |
| 2019/0330259 A1 | 10/2019 | Robichaud et al. |
| 2019/0359646 A1 | 11/2019 | Botella et al. |
| 2020/0002371 A1 | 1/2020 | Salituro et al. |
| 2020/0024300 A1 | 1/2020 | Salituro et al. |
| 2020/0123195 A1 | 4/2020 | Salituro et al. |
| 2021/0040138 A1 | 2/2021 | Harrison et al. |

FOREIGN PATENT DOCUMENTS

| | | |
|---|---|---|
| JP | 50140435 | 11/1975 |
| JP | 53082766 | 7/1978 |
| JP | 54163565 | 12/1979 |
| JP | 57035597 | 2/1982 |
| JP | 61254599 | 11/1986 |
| JP | 62187485 | 8/1987 |
| JP | 8268917 A | 10/1996 |
| JP | 09328498 | 12/1997 |
| JP | 2005508368 A | 3/2005 |
| RU | 2194712 C2 | 12/2002 |
| WO | 9427608 A1 | 12/1994 |
| WO | 1995002409 A2 | 1/1995 |
| WO | 1995021617 A1 | 8/1995 |
| WO | 9612705 A1 | 5/1996 |
| WO | WO1996012705 | 5/1996 |
| WO | WO1996040043 | 12/1996 |
| WO | 9700884 A1 | 1/1997 |
| WO | 199905849 | 11/1999 |
| WO | 2000068246 A1 | 11/2000 |
| WO | 2001049703 A2 | 7/2001 |
| WO | 0211708 A2 | 2/2002 |
| WO | 02053577 A2 | 7/2002 |
| WO | 2002079221 A2 | 10/2002 |
| WO | 2003039480 A2 | 5/2003 |
| WO | 03049685 A2 | 6/2003 |
| WO | 2003082893 A2 | 10/2003 |
| WO | 2004055201 A2 | 7/2004 |
| WO | 2005079810 A1 | 9/2005 |
| WO | WO2009001097 | 12/2008 |
| WO | 2009059961 A2 | 5/2009 |
| WO | 2009090063 A1 | 7/2009 |
| WO | 2010075282 A1 | 7/2010 |
| WO | 2010088414 A2 | 8/2010 |
| WO | 2011014661 A2 | 2/2011 |
| WO | 2011028794 A2 | 3/2011 |
| WO | 2011067501 A1 | 6/2011 |
| WO | 2012064501 A1 | 5/2012 |
| WO | 2012142039 A1 | 10/2012 |
| WO | 2013019711 A2 | 2/2013 |
| WO | 2013036835 A1 | 3/2013 |
| WO | WO2013036835 | 3/2013 |
| WO | 2013056181 A1 | 4/2013 |
| WO | 2013163455 A2 | 10/2013 |
| WO | 2014028942 A2 | 2/2014 |
| WO | 2014115167 A2 | 7/2014 |
| WO | 2014120786 A1 | 8/2014 |
| WO | 2014160441 A1 | 10/2014 |
| WO | 2014160480 A1 | 10/2014 |
| WO | 2015195967 A1 | 12/2015 |
| WO | 2016007762 A1 | 1/2016 |
| WO | 2016057713 A1 | 4/2016 |
| WO | 2017007832 A1 | 1/2017 |
| WO | 2017007836 A1 | 1/2017 |
| WO | 2017007840 A1 | 1/2017 |
| WO | 2017037465 A1 | 3/2017 |
| WO | 2018170336 A1 | 9/2018 |

OTHER PUBLICATIONS

Mateos et al., "Activity-regulated cytoskeleton-associated protein in rodent brain is down regulated by high fat diet in vivo and by 27-hydroxycholesterol in vitro", Brain Pathology. vol. 19, No. 1, (2009), pp. 69-80.

Mouriño et al., "Studies on vitamin D (calciferol) and its analogs. 15. 24-Nor-1a.,25-dihydroxyvitamin D3 and 24-nor-25-hydroxy-5,6-trans-vitamin D3", J. Med. Chem., (1978), vol. 21, No. 10, pp. 1025-1029.

Nagano et al., "Chemistry and Biochemistry of Chinese Drugs. Part II. Hydroxylated Sterols, Cytotoxic Towards Cancerous Cells: Synthesis and Testing", Journal of Chemical Research, vol. 9, pp. 218 (1977).

Olkkonen et al., "Oxysterols and Their Cellular Effectors", Biomolecules, vol. 2 (2012), pp. 76-103.

Park-Chung et al., "Distinct sites for inverse modulation of N-methyl-D-aspartate receptors by sulfated steroids", Molecular Pharmacology, vol. 52, No. 6, (1997), pp. 1113-1123.

Partial International Search Report and Provisional Opinion for corresponding Internation Application No. PCT/US2017/057277 dated Dec. 20, 2017.

Partial Supplementary European Search Report for European Application No. 14775126.7 dated Sep. 14, 2016.

Paul et al., "The Major Brain Cholesterol Metabolite 24 (S)-Hydroxycholesterol Is a Potent Allosteric Modulator of N-Methyl-D Aspartate Receptors", Journal of Neuroscience, vol. 33, No. 44, pp. 17290-17300, (2013).

Pubchem, 25-Hydroxycholesterol, CID 65094, pp. 1-6.
Pubchem, CID 132021, pp. 1-15.
Pubchem, CID 54083335, pp. 1-3.
Pubchem, CID 54160779, pp. 1-3.
Pubchem, CID 58455549, pp. 1-4.
Pubchem, CID 66966798, pp. 1-3.
Pubchem, CID 70604305, pp. 1-3.
Pubchem, CID 71508953, pp. 1-13.

Reddy, "Pharmacology of endogenous neuroactive steroids, Crit Rev Neurobiol", 2003;15(3-4) pp. 197-234.

(56) References Cited

OTHER PUBLICATIONS

Schmidt et al., "Inhibitory effect of oxygenated cholestan-3b-ol derivatives on the growth of Mycobacterium tuberculosis", Bioorganic & Medicinal Chemistry Letters, vol. 23, No. 22, (2013), pp. 6111-6113.
Sepe et al., "Total Synthesis and Pharmacological Characterization of Solomonsterol A, a Potent Marine Pregnane-X-Receptor Agonist Endowed with Anti-Inflammatory Activity", Journal of Medicinal Chemistry, vol. 54, (2011), pp. 4590-4599.
Stamp et al., "Plasma Levels and Therapeutic Effect of 25-Hydroxycholcalciferol in Epileptic Patients taking Anticonvulsant Drugs", British Medical Journal, vol. 4, 1972, pp. 9-12.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Steinrauf et al., "Synthesis and Evaluation of Sulfur-Containing Steroids Against Methylmercuric Chloride Toxicity", Journal of Pharmaceutical Sciences, vol. 67, No. 12, pp. 1739-1743, (1978).
Svoboda et al. (Am J Med Genet C Semin Med Genet (2012), pp. 285-294) (Year: 2012).
Takano et al., "Simple Synthesis of 3b, 24-Dihydroxychol-5-EN-7-ONE by Oxidative Cleavage of the Side Chain of Cholesterol", Chemistry Letters, vol. 14, No. 8, (1985), pp. 1265-1266.
Tierney et al., "Abnormalities of Cholesterol Metabolism in Autism Spectrum Disorders", Am J Med Genet B Neuropsychiatr Genet. vol. 141B, No. 6, (2006), pp. 666-668.
Tomek et al., "NMDA Receptor Modulators in the Treatment of Drug Addiction", Pharmaceuticals (Basel), 2013, vol. 6, No. 2, pp. 251-258.
Vincent Chen et al., "The chemical biology of clinicall tolerated NMDA receptor antagonists", Journal of Neurochemistry, (2006), pp. 1611-1626.
Wolozin et al., "The Cellular Biochemistry of Cholesterol and Statins: Insights into the Pathophysiology and Therapy of Alzheimer's Disease" vol. 10, No. 2, 2004, pp. 127-146.
Wong et al., An efficient and convenient transformation of a-haloketones to a-hydroxyketones using cesium formate. Journal of Organometallic Chemistry 2006, 694, 3452-3455.
Xilour et al., "Neuroprotective effects of steroid analogues on P19-N neurons", Neurochemistry International, (2007), vol. 50, No. 4, pp. 660-670.
Yan et al., "Characterization of a synthetic steroid 24-keto-cholest-5-en-3b, 19-diol as a neuroprotectant", CNS Neuroscience & Therapeutics, vol. 21, No. 6, (2015), pp. 486-495.
Yang et al., "New cytotoxic oxygenated sterols from marine bryozoan Bugula neritina". Natural Product Research, vol. 25, No. 16, (2011), pp. 1505-1511.
Yoon-Seok et al., "Neuroprotective Effects of Ginsenoside Rg3 against 24-0H-cholesterol-induced Cytotoxicity in Cortical Neurons", Journal of Ginseng Research, vol. 34, No. 3, pp. 246-253, (2010).
Zuliani et al., "Plasma 24S-hydroxycholesterol levels in elderly subjects with late onset Alzheimer's disease or vascular dementia: a case-control study" BMC Neurology, vol. 11, No. 121, pp. 1-8, (2011).
Björkhem et al., "Oxysterols in the circulation of patients with the Smith-Lemli-Opitz syndrome: abnormal levels of 24S- and 27-hydroxycholesterol", Journal of Lipid Research, vol. 42, 2001, pp. 366-371.
Bukelis et al., "Smith-Lemli-Opitz Syndrome and Autism Spectrum Disorder", American Journal of Psychiatry, 2007, vol. 164, pp. 1655-1661.
Cancer [online], [retrieved on Jul. 6, 2007]. Retrieved from the internet, URL http://www.nlm.nih.gov/medlineplus/cancer.html>.
Cecil Textbook of Medicine, 20th edition (1996), vol. 2, pp. 1992-1996.
Cecil Textbook of Medicine, 20th edition (1996), vol. 2, pp. 2050-2057.
Citraro et al., "Effects of some neurosteroids injected into some brain areas of WAG/Rij rats, an animal model of generalized absence epilepsy", Neuropharmacology, (2006), vol. 50, No. 8, pp. 1059-1071.
Collingridge, "The NMDA receptor as a target for cognitive enhancement", Neuropharmacology. (2013), pp. 13-26, abstract.
Connick et al., "Program No. 613 1/B86", 2009 Neuroscience Meeting Planner. Chicago, IL: Society for Neuroscience, (2009).
Cook et al., "24-hydroxycholesterol sulfation by human cytosolic sulfotransferases: Formation of monosulfates and disulfates, molecular modeling, sulfatase sensitivity, and inhibition of liver x receptor activation", Drug Metabolism and Disposition, vol. 37, No. 10, (2009), pp. 2069-2078.
Corman et al., "Structure-Activity Relationships for Side Chain Oxysterol Agonists of the Hedgehog Signaling Pathway", ACS Medicinal Chemistry Letters, Aug. 28, 2012, 3, 828-833.
Dross et al., "Steroids CCLXXIN 1. Biologically-Active Labile Ethers IV2. The Synthesis of 22-Oxa-25-Azacholesterol and Related Compounds", Steroids, Elsevier Science Publishers, vol. 5, No. 5, pp. 585-598, (1965).
Database Chemical Abstracts Service, Xiangdong et al. "Highly stereoselective synthesis of 24R,25- and 24S, 25-dihydroxysteroid". Database acession No. 2001:174431, (2000).
Dayal et al., "Stereospecific synthesis of 3b-hydroxylated bile alcohols", Journal of Lipid Research, vol. 25, No. 6, (1984), pp. 646-650.
Extended European Search Report for Application No. 15809462.3 dated Nov. 29, 2017.
Extended European Search Report for Application No. 16821920.2 dated Jan. 31, 2019.
Extended European Search Report for Application No. 16821924.4 dated Jan. 31, 2019.
Extended European Search Report for Application No. 16821926.9 dated Jan. 31, 2019.
Extended European Search Report for European Application No. 14775126.7.
Extended European Search Report for European Application No. 15849514.3 dated May 23, 2018.
Extended European Search Report for PCTUS2014/026784 dated Aug. 17, 2016.
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.
Festa et al., "Exploitation of Cholane Scaffold for the Discovery of Potent and Selective Farnesoid X Receptor (FXR) and G-Protein Coupled Bile Acid Receptor 1 (GP-BAR1) Ligands", Journal of Medicinal Chemistry, vol. 57, No. 20, (2014), pp. 8477-8495.
Foster et al., "Effect of steroids on 13-adrenoceptor-mediated relaxation of pig bronchus", Br. J. Pharmac. vol. 78, 1983, pp. 441-445.
Golub et al., "Molecular classification of cancer: Class discovery and class prediction by gene expression monitoring", Science (1999), vol. 286, pp. 531-537.
Gunatilaka et al., "Bioactive Ergost-5-ENE-3b, 7a-DIOL Derivatives from Pseudobersama Mossambicensis", Journal of Natural Products, vol. 55, No. 11, (1992), pp. 1648-1654.
Hoffmeister et al., "Zur Chemie des Ecdysons, III: Vergleichende spektrometrische Untersuchungen an a.b-ungesättigten Steroidketonen", Chemische Berichte, (1965), vol. 98, pp. 2361-2375.
Iida et al., "An improved method for the capillary gas chromatographic derivatization of polyhydroxylated steroids having terthydroxyl groups", Analytical Sciences, 2003. vol. 19, pp. 1317-1321.
International Search Report and Written Opinion for corresponding International Application No. PCT/US14/26633 dated Jul. 14, 2014.
International Search Report and Written Opinion for corresponding International Application No. PCT/US15/36510 dated Sep. 15, 2015.
International Search Report and Written Opinion for corresponding International Application No. PCT/US17/25535 dated Jul. 3, 2017.
International Search Report and Written Opinion for corresponding International Application No. PCT/US17/31374 dated Jul. 17, 2017.

(56) References Cited

OTHER PUBLICATIONS

International Search Report and Written Opinion for corresponding International Application No. PCT/US2012/054261 dated Nov. 28, 2012.
International Search Report and Written Opinion for corresponding International Application No. PCT/US2014/026784 dated Jul. 8, 2014.
International Search Report and Written Opinion for corresponding International Application No. PCT/US2015/054551 dated Jan. 8, 2016.
International Search Report and Written Opinion for corresponding International Application No. PCT/US2016/041160 dated Oct. 28, 2016.
International Search Report and Written Opinion for corresponding International Application No. PCT/US2016/041168 dated Sep. 15, 2016.
International Search Report and Written Opinion for corresponding International Application No. PCT/US2016/041175 dated Sep. 16, 2016.
International Search Report and Written Opinion for corresponding International Application No. PCT/US2017/041199 dated Aug. 29, 2017.
International Search Report and Written Opinion for corresponding International Application No. PCT/US2017/054657 dated Nov. 21, 2017.
International Search Report and Written Opinion for corresponding International Application No. PCT/US2017/057276 dated Nov. 12, 2017.
International Search Report and Written Opinion for corresponding International Application No. PCT/US2017/057277 dated Feb. 20, 2018.
Karaki et al., "Structure-activity relationship studies of Niemann-Pick type C1-like 1 (NPC1L1) ligands identified by screening assay monitoring pharmacological chaperone effect", Bioorganic & Medicinal Chemistry, vol. 21, Issue 17, (2013), pp. 5297-5309.
Khripach et al., "Synthesis of (24S)-Hydroxy-and (24S)-24,25-Epoxycholesterol Analogues, Potential Agonists of Nuclear LXR Receptors", Russian Journal of Bioorganic Chemistry, Kluwer Academic Publishers-Plenum Publishers, NE, vol. 32, No. 6, pp. 586-594, (2006).
Knoppert et al., "Position Paper: Paediatric Age Categories to be Used in Differentiating Between Listing on a Model Essential Medicines List for Children", 2007, pp. 1-5.
Kurosawa et al., "Synthesis of 19-Hydroxylated Bile Acids and Identification of 3a,7a,12a,19-Tetrahydroxy-5b-cholan-24oic Acid in Human Neonatal Urine" 1995, Chem. Pharm. Bull, vol. 43, No. 9, pp. 1551-1557.
Lala et al., "Role of nitric oxide in tumor progression: Lessons from experimental tumors", Cancer and Metastasis Reviews, (1998), 17 (1), pp. 91-106.
Leoni et al., "Oxysterols as biomarkers in neurodegenerative diseases", Chemistry and Physics of Lipids, vol. 164 (2011), pp. 515-524.
Lettré, et al., "Mehrwertige Alkohole aus Sterinen und Sterinderivaten, VI Steroide mit Strukturmerkmalen des Ecdysons und der Elatericine", Justus Liebigs Annalen der Chemie, (1972), vol. 758, pp. 89-110. English Abstract.
Li et al., "Synthesis of 7a-hydroxy derivatives of regulatory oxysterols", Steroids, vol. 65, No. 9, (2000), pp. 529-535.
Linsenbardt et al., "Different oxysterols have opposing actionss at N-methyl-d-aspartate receptors", Neuropharmacology., vol. 85 (2014), pp. 232-242.
Deng et al., "Fluoro analogs of bioactive oxy-steroids: Synthesis of an EBI2 agonist with enhanced metabolic stability," Bioorganic and Medicinal Chemistry Letters, 26:4888-4891 (2016).
Roh et al., "Neuroprotective Effects of Ginsenoside Rg3 against 24-OH-cholesterol-induced Cytotoxicity in Cortical Neurons", Journal of Ginseng Research, 34(3):246-253 (2010).
Berge et al., "Pharmaceutical salts," Journal of Pharmaceutical Sciences, 66(1):1-19 (1977).
Cais et al., "Temperature dependence of NR1/NR2B NMDA receptor channels," Neuroscience, 151(2):428-438 (2008).
Costa et al., "A novel family of negative and positive allosteric modulators of NMDA receptors," Journal of Pharmacology and Experimental Therapeutics, 335(3):614-21 (2010).
Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).
Elbarbry et al., "Cyclosporine-induced changes in drug metabolizing enzymes in hyperlipemic rabbit kidneys could explain its toxicity," Xenobiotica, 40(11):772-781 (2010).
Fukuto et al., "Determination of the Mechanism of Demethlenation of (methylenedioxy)phenyl compounds by cytochrome P450 using deuterium isotope effects," Journal of Medicinal Chemistry, 34(9):2871-2876 (1991).
Gee et al., "GABA-dependent modulation of the C1-ionophore by steroids in rat brain," European Journal of Pharmacology, 136(3):419-423 (1987).
Groden et al., "Determination of Fura-2 dissociation constants following adjustment of the apparent Ca-EGTA association constant for temperature and ionic strength," Cell Calcium, 12:(4)279-287 (1991).
Grynkiewicz et at., "A new generation of Ca2+ indicators with greatly improved fluorescence properties," Journal of Biological Chemistry, 260(6):3440-3345 (1985).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistry, 50(23):4508-4514 (1985).
Hogg et al., "An automated system for intracellular and intranuclear injection," Journal of Neuroscience, Methods, 169(1):65-75 (2008).
Hohmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs—from serendipity to rational design," Pharmacological Reviews, 63(3):750-771 (2011).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jurman et al., "Visual identification of individual transfected cells for electrophysiology using antibody-coated beads," Biotechniques, 17(5):876-881 (1994).
Lutjohann et al., "Cholesterol homeostasis in human brain: evidence for an age-dependent flux of 24S-hydroxycholesterol from the brain into the circulation," PNAS, 93(18):9799-804 (1996).
Madau et al, Program No. 613.2/B87. 2009 Neuroscience Meeting Planner. Chicago, IL: Society for Neuroscience (2009) (3 pages).
Monyer et al., "Heteromeric NMDA receptors: molecular and functional distinction of subtypes," Science, 256(5060):1217-1221 (1992).
Nagasaka et al., "Oxysterol changes along with cholesterol and vitamin D changes in adult phenylketonuric patients diagnosed by newborn mass-screening," Clinica Chimica Acta, 416:54-59 (2013).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883):1306-1308 (1988).
Segal, "Pat hippocampal Neurons in Culture: Responses to Electrical and Chemical Stimuli," Journal of Neurophysiology, 50(6):1249-1264 (1983).
Takahashi et al., "Stereochemistry of reduction of the C-24,25 double bond in the conversion of desmosterol into cholesterol," Tetrahedron Letters, 44(2):341-344 (2003).

(56) References Cited

OTHER PUBLICATIONS

Verdoorn et al., "Functional properties of recombinant rat GABAA receptors depend upon subunit composition," Neuron, 4(6):919-928 (1990).
Vyklicky et al., "Calcium-mediated modulation of N-methyl-D-aspartate (NMDA) responses in cultured rat hippocampal neurones," Journal of Physiology, 470:575-600 (1993).
Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).
Wilen et al., "Strategies in Optical Resolutions," Tetrahedron 33:2725-2736 (1977).
Zhou et al., "Properties of HERG channels stably expressed in HEK 293 cells studied at physiological temperature," Biophysical Journal, 74(1):230-241 (1998).

OXYSTEROLS AND METHODS OF USE THEREOF

RELATED APPLICATIONS

The present application is a U.S. National Phase Application under 35 U.S.C. § 371 of International Application PCT/US2017/057277, filed Oct. 18, 2017, which claims priority to and the benefit of U.S. Provisional Application No. 62/409,761 filed Oct. 18, 2016, U.S. Provisional Application No. 62/409,767 filed Oct. 18, 2016, U.S. Provisional Application No. 62/409,772 filed Oct. 18, 2016, U.S. Provisional Application No. 62/409,774 filed Oct. 18, 2016, and U.S. Provisional Application No. 62/409,764 filed Oct. 18, 2016, each of which are incorporated herein by reference in their entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit $Ca^{2+}$ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxysterols are cholesterol analogs that are modulators of NMDA receptor function. There is a need for new oxysterols that modulate the NMDA receptor for the prevention and treatment of conditions associated with NMDA expression and function. Compounds, compositions, and methods described herein are directed toward this end.

SUMMARY OF THE INVENTION

Provided herein are substituted oxysterols useful for preventing and/or treating a broad range of disorders, including, but not limited to, NMDA-mediated disorders. Further provided are pharmaceutical compositions comprising the compounds of the present invention, and methods of their use and treatment.

In one aspect, provided herein are compounds according to Formula (I-59):

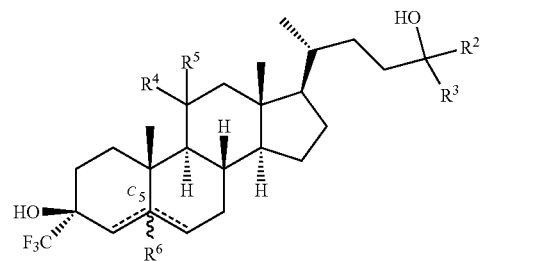

(I-59)

or a pharmaceutically acceptable salt thereof, wherein: each of $R^2$ and $R^3$ is independently hydrogen, alkyl (e.g., $C_1$-$C_6$ alkyl), carbocyclyl, or heterocyclyl, or $R^2$ and $R^3$, together with the carbon atom to which they are attached form a 3-8 membered ring; each of $R^4$ and $R^5$ is independently hydrogen, halo, or —$OR^C$, wherein $R^C$ is hydrogen or alkyl (e.g., $C_1$-$C_6$ alkyl), or $R^4$ and $R^5$, together with the carbon atom to which they are attached form an oxo group; $R^6$ is absent or hydrogen; and ====== represents a single or double bond, wherein when one of ====== is a double bond, the other ====== is a single bond; when both of ====== are single bonds, then $R^6$ is hydrogen; and when one of ====== is a double bond, $R^6$ is absent; provided that the following compounds are excluded:

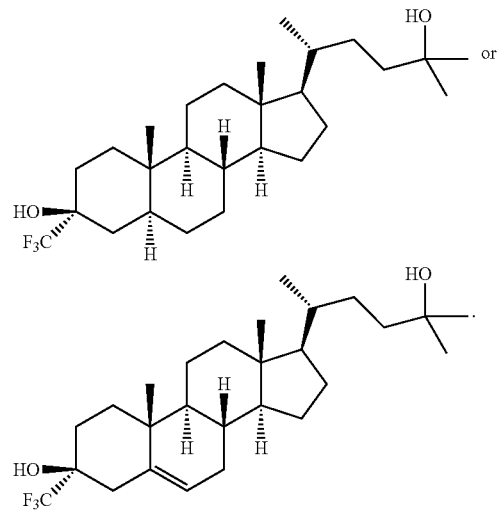

In some embodiments, $R^2$ is hydrogen or alkyl (e.g., $C_1$-$C_6$ alkyl). In some embodiments, $R^2$ is haloalkyl (e.g., $C_1$-$C_6$ haloalkyl).

In some embodiments, each of $R^2$ and $R^3$ is independently alkyl (e.g., substituted $C_1$-$C_6$ alkyl) or hydrogen. In some embodiments, each of $R^2$ and $R^3$ is independently unsubstituted alkyl (e.g., unsubstituted $C_1$-$C_6$ alkyl) or hydrogen. In some embodiments, each of $R^2$ and $R^3$ is independently $C_1$-$C_6$ haloalkyl (e.g., trifluoromethyl) or hydrogen. In some embodiments, each of $R^2$ and $R^3$ is independently hydrogen, carbocyclyl, or heterocyclyl. In some embodiments, each of $R^2$ and $R^3$ is independently $C_2$-$C_6$ alkyl (e.g., isopropyl or tert-butyl) or hydrogen. In some embodiments, each of $R^2$ and $R^3$ is independently hydrogen or $C_3$-$C_6$ alkyl (e.g., isopropyl or tert-butyl).

In some embodiments, at least one of $R^2$ and $R^3$ is $C_3$-$C_6$ alkyl (e.g., isopropyl or tert-butyl), carbocyclyl, or heterocyclyl; or $R^2$ and $R^3$, together with the carbon atom to which they are attached form a 3-8 membered ring. In some embodiments, $R^2$ is isopropyl or tert-butyl and $R^3$ is methyl or hydrogen. In some embodiments, $R^2$ is substituted isopropyl or substituted tert-butyl and $R^3$ is unsubstituted methyl or hydrogen. In some embodiments, $R^2$ is unsubstituted isopropyl or unsubstituted tert-butyl and $R^3$ is unsubstituted methyl or hydrogen. In some embodiments, $R^2$ is tert-butyl and $R^3$ is hydrogen. In some embodiments, $R^2$ is substituted tert-butyl and $R^3$ is hydrogen. In some embodiments, $R^2$ is unsubstituted tert-butyl and $R^3$ is hydrogen. In some embodiments, $R^2$ is trifluoromethyl and $R^3$ is hydrogen. In some embodiments, $R^2$ is trifluoromethyl and $R^3$ is methyl. In some embodiments, $R^2$ is trifluoromethyl and $R^3$ is substituted methyl. In some embodiments, $R^2$ is trifluoromethyl and $R^3$ is unsubstituted methyl. In some embodiments, $R^2$ is methyl and $R^3$ is hydrogen. In some embodiments, $R^2$ is substituted methyl and $R^3$ is hydrogen. In some embodiments, $R^2$ is unsubstituted methyl and $R^3$ is hydrogen.

In some embodiments, the 3-8 membered ring is heterogeneous or homogeneous. In some further embodiments, the heterogeneous or homogeneous 3-8 membered ring is substituted with alkyl, haloalkyl, a 3-6 membered ring, substituted or unsubstituted alkoxy, or OH.

In some embodiments, $R^4$ is —OH or halo (e.g., —F). In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ and $R^3$, together with the carbon atom to which they are attached form a 5-membered ring. In some embodiments, $R^2$ is $C_2$-$C_6$ alkyl (e.g., substituted or unsubstituted isopropyl or substituted or unsubstituted tert-butyl) and $R^3$ is $C_1$-$C_6$ alkyl (e.g., substituted or unsubstituted $C_1$-$C_6$ alkyl). In some embodiments, $R^2$ is unsubstituted $C_2$-$C_6$ alkyl (e.g., unsubstituted isopropyl or unsubstituted tert-butyl) and $R^3$ is unsubstituted $C_1$-$C_6$ alkyl. In some embodiments, $R^2$ and $R^3$, together with the carbon atom to which they are attached form a 6-membered ring.

In some embodiments, $R^2$ is carbocyclyl or heterocyclyl and $R^3$ is hydrogen. In some embodiments, $R^2$ and $R^3$ are hydrogen. In some embodiments, $R^2$ is isopropyl and $R^3$ is hydrogen. In some embodiments, $R^2$ is substituted isopropyl and $R^3$ is hydrogen. In some embodiments, $R^2$ is substituted isopropyl and $R^3$ is hydrogen. In some embodiments, $R^2$ and $R^3$, together with the carbon atom to which they are attached form a 3-8 membered carbocyclic (e.g., cyclohexyl) or heterocyclic (e.g., tetrahydropyranyl or tetrahydropyranyl) ring. In some embodiments, the carbocyclic or heterocyclic ring is substituted (e.g., ring substituted with 1 or 2 halo or alkyl groups). In some embodiments, $R^2$ is cyclobutyl and $R^3$ is hydrogen. In some embodiments, $R^2$ is tetrahydropyranyl and $R^3$ is hydrogen.

In some embodiments, $R^2$ is substituted cyclobutyl and $R^3$ is hydrogen. In some embodiments, $R^2$ is substituted tetrahydropyranyl and $R^3$ is hydrogen. In some embodiments, $R^2$ is unsubstituted cyclobutyl and $R^3$ is hydrogen. In some embodiments, $R^2$ is unsubstituted tetrahydropyranyl and $R^3$ is hydrogen.

In some embodiments, the compound of Formula (I-59) is selected from a compound of Formula (I-A59), (I-B59), or (I-C59):

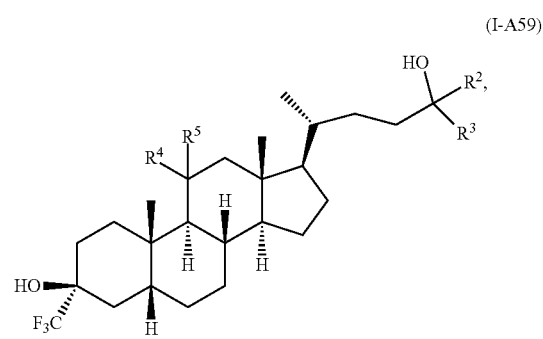

(I-A59)


(I-B59) or

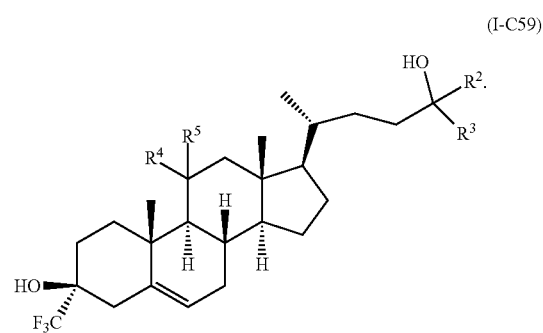

(I-C59)

In some embodiments, the compound of Formula (I-59) is selected from a compound of Formula (I-B59):

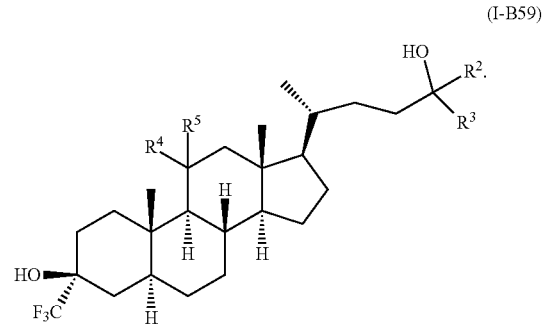

(I-B59)

In some embodiments, the compound of Formula (I-59) is selected from a compound of Formula (I-C59):

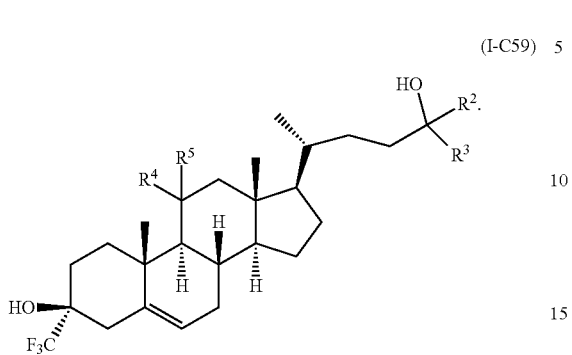
(I-C59)

In some embodiments, at least one of $R^2$ and $R^3$ is hydrogen, $C_1$-$C_6$ alkyl, carbocyclyl, or heterocyclyl; or $R^2$ and $R^3$, together with the carbon atom to which they are attached form a 3-8 membered ring. In some embodiments, the compound of Formula (I-59) is selected from a compound of Formula (I-D59):

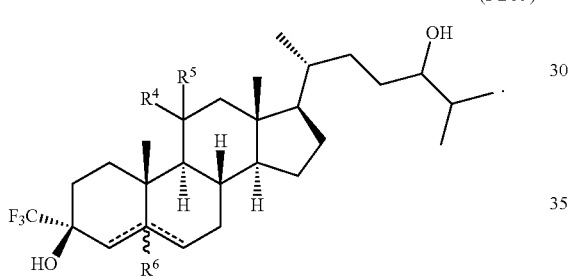
(I-D59)

In some embodiments, the compound of Formula (I-59) is selected from a compound of Formula (I-E59):

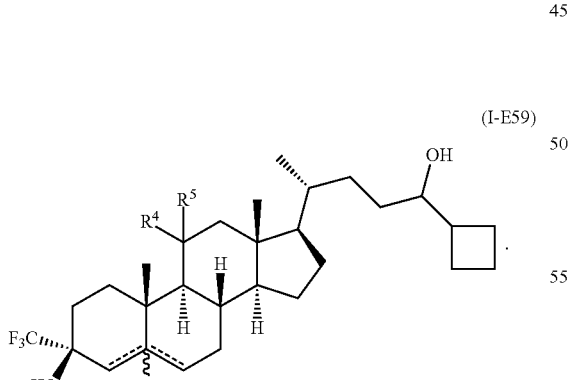
(I-E59)

In some embodiments, the compound of Formula (I-59) is selected from a compound of Formula (I-D-i59) or (I-D-ii59):

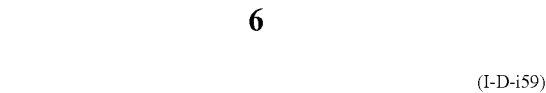

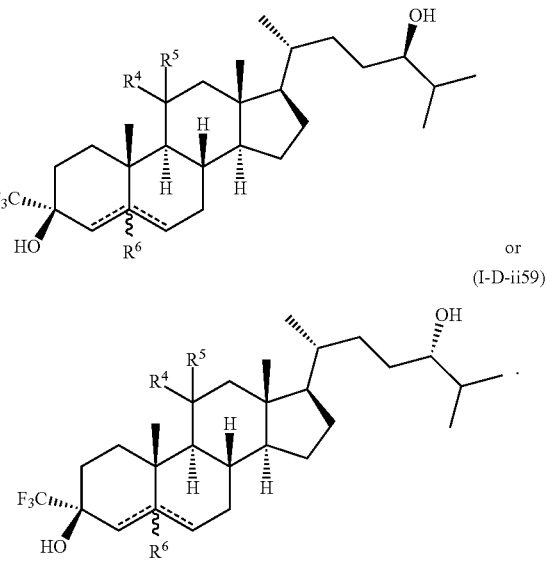

In some embodiments, the compound of Formula (I-59) is selected from a compound of Formula (I-E-i59) or (I-E-ii59):

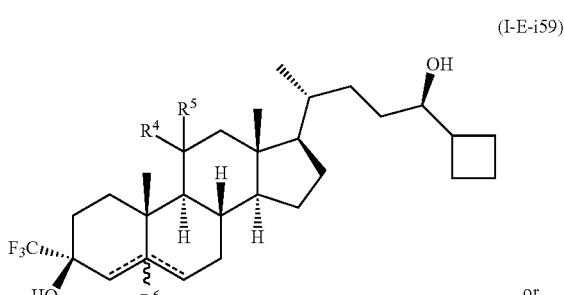

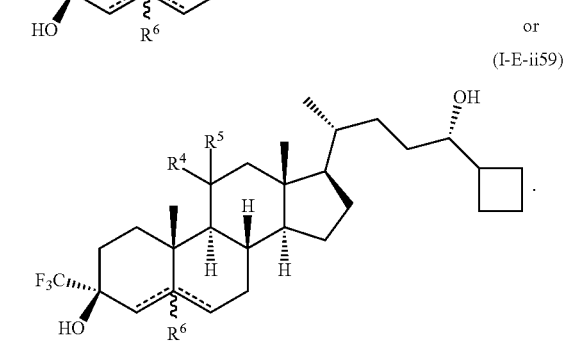

In some embodiments, the compound is:

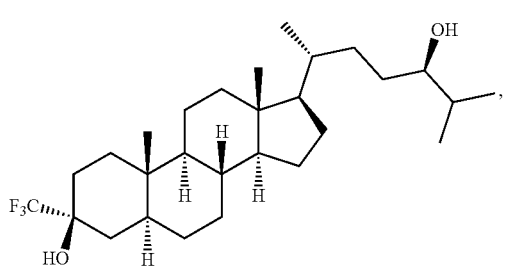

-continued
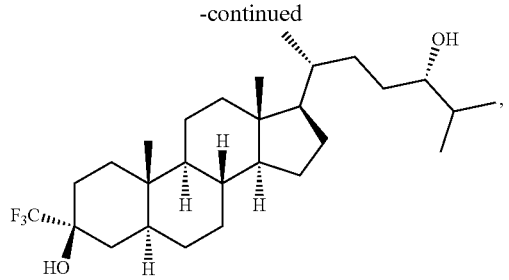
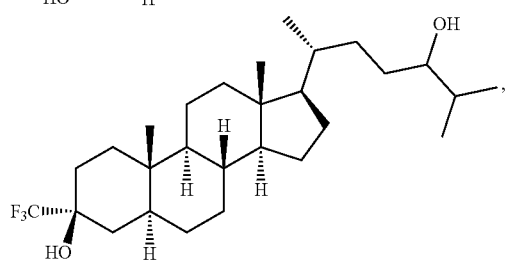
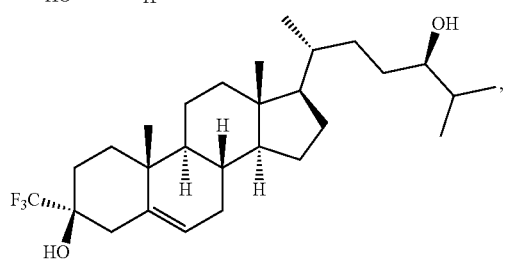
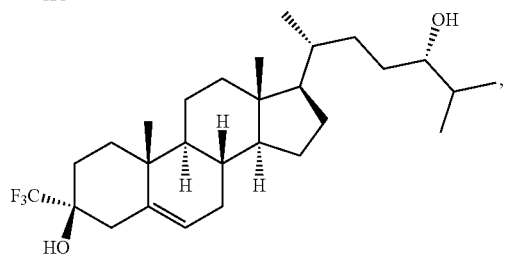
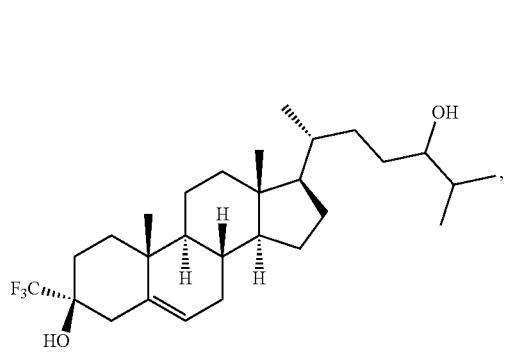
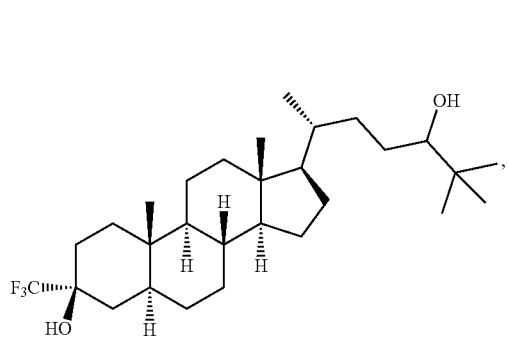
-continued
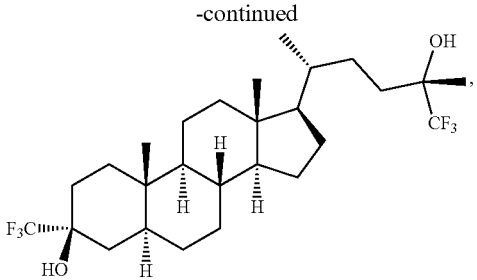
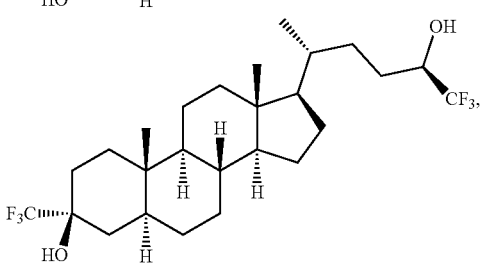
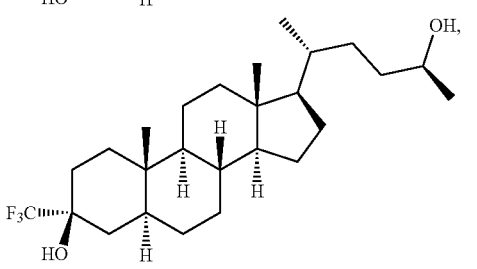
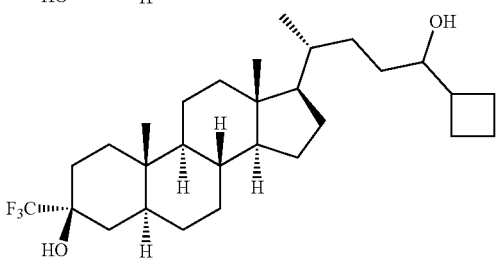
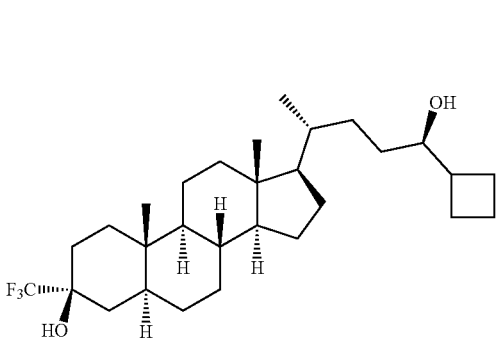

-continued

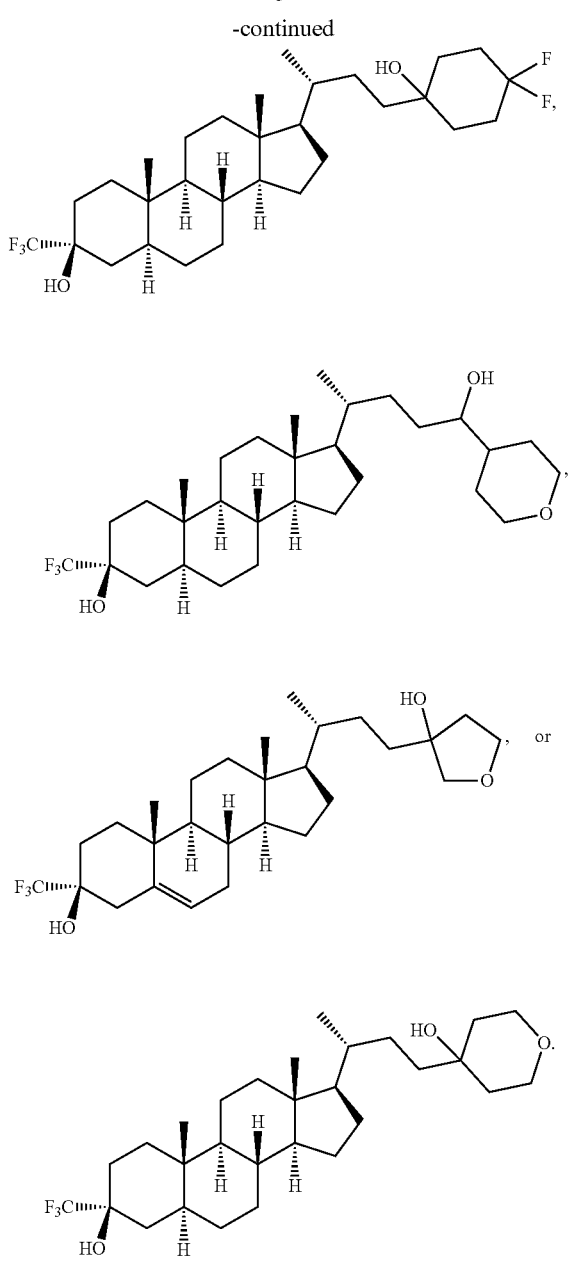

In one aspect, provided herein are compounds according to Formula (I-66):

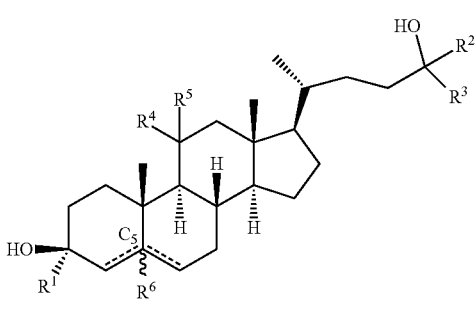

or a pharmaceutically acceptable salt thereof, wherein: $R^1$ is alkyl (e.g., $C_1$-$C_6$ alkyl); $R^2$ is aralkyl, heteroaralkyl, aryl, or heteroaryl; $R^3$ is hydrogen, alkyl (e.g., $C_1$-$C_6$ alkyl), carbocyclyl, heterocyclyl, aryl, or heteroaryl; each of $R^4$ and $R^5$ is independently hydrogen, halo, or —$OR^C$, wherein $R^C$ is hydrogen or $C_1$-$C_3$ alkyl (e.g., unsubstituted or substituted $C_1$-$C_3$ alkyl), or $R^4$ and $R^5$, together with the carbon atom to which they are attached form an oxo group; $R^6$ is absent or hydrogen; and ===== represents a single or double bond, wherein when one of ===== is a double bond, the other ===== is a single bond; when both of ===== are single bonds, then $R^6$ is hydrogen; and when one of ===== is a double bond, $R^6$ is absent.

In some embodiments, $R^1$ is alkyl (e.g., $C_1$-$C_6$ alkyl). In some embodiments, $R^1$ is $C_1$-$C_6$ alkyl (e.g., —$CH_3$, —$CH_2CH_3$, —$CH_2OCH_3$, or —$CF_3$). In some embodiments, $R^1$ is —$CH_3$, —$CF_3$, or —$CH_2CH_3$. In some embodiments, $R^1$ is —$CH_2OR^A$, wherein $R^A$ is $C_1$-$C_6$ alkyl (e.g., $C_1$-$C_3$ alkyl).

It should be appreciated that $C_1$-$C_6$ alkyl, aralkyl, heteroaralkyl, aryl, carbocyclyl, heterocyclyl, aryl, heteroaryl or heteroaryl can be substituted or unsubstituted, for example with cyano, halogen, OH, or alkoxy.

In some embodiments, $R^2$ is aryl (e.g., substituted or unsubstituted aryl, e.g., substituted or unsubstituted phenyl), heteroaryl (e.g., substituted or unsubstituted heteroaryl, e.g., substituted or unsubstituted pyridyl), or aralkyl (e.g., substituted or unsubstituted benzyl). In some embodiments, $R^2$ is phenyl (e.g., substituted or unsubstituted phenyl), pyridyl (e.g., substituted or unsubstituted pyridyl), or benzyl (e.g., substituted or unsubstituted benzyl).

In some embodiments, $R^3$ is hydrogen or alkyl (e.g., $C_1$-$C_6$ alkyl). In some embodiments, $R^3$ is hydrogen, unsubstituted alkyl (e.g., unsubstituted $C_1$-$C_6$ alkyl), or haloalkyl (e.g., —$CF_3$).

In some embodiments, $R^4$ is —OH or halo (e.g., —F).

In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ is aryl (e.g., substituted or unsubstituted aryl, e.g., substituted or unsubstituted phenyl), heteroaryl (e.g., substituted or unsubstituted heteroaryl, e.g., substituted or unsubstituted pyridyl), aralkyl (e.g., substituted or unsubstituted aralkyl, e.g., substituted or unsubstituted benzyl), or heteroaralkyl and $R^3$ is hydrogen or alkyl (e.g., unsubstituted $C_1$-$C_6$ alkyl, e.g., $C_1$-$C_6$ haloalkyl). In some embodiments, $R^2$ is aryl (e.g., substituted or unsubstituted aryl, e.g., substituted or unsubstituted phenyl), heteroaryl(e.g., substituted or unsubstituted heteroaryl, e.g., substituted or unsubstituted pyridyl), aralkyl (e.g., substituted or unsubstituted aralkyl, e.g., substituted or unsubstituted benzyl), or heteroaralkyl and $R^3$ is hydrogen, —$CH_3$, or —$CF_3$.

In some embodiments, $R^1$ is alkyl (e.g., $C_1$-$C_6$ alkyl), $R^2$ is aryl (e.g., substituted or unsubstituted aryl, e.g., substituted or unsubstituted phenyl), heteroaryl (e.g., substituted or unsubstituted heteroaryl, e.g., substituted or unsubstituted pyridyl), aralkyl (e.g., substituted or unsubstituted aralkyl, e.g., substituted or unsubstituted benzyl), or heteroaralkyl, and $R^3$ is hydrogen, —$CH_3$, or —$CF_3$. In some embodiments, $R^1$ is —$CH_3$ or —$CH_2CH_3$, $R^2$ is unsubstituted phenyl, unsubstituted pyridyl, or unsubstituted benzyl, and $R^3$ is hydrogen, —$CH_3$, or —$CF_3$.

In some embodiments, the compound of Formula (I-66) is selected from a compound of Formula (I-A66), (I-B66), or (I-C66):
In some embodiments, the compound is:
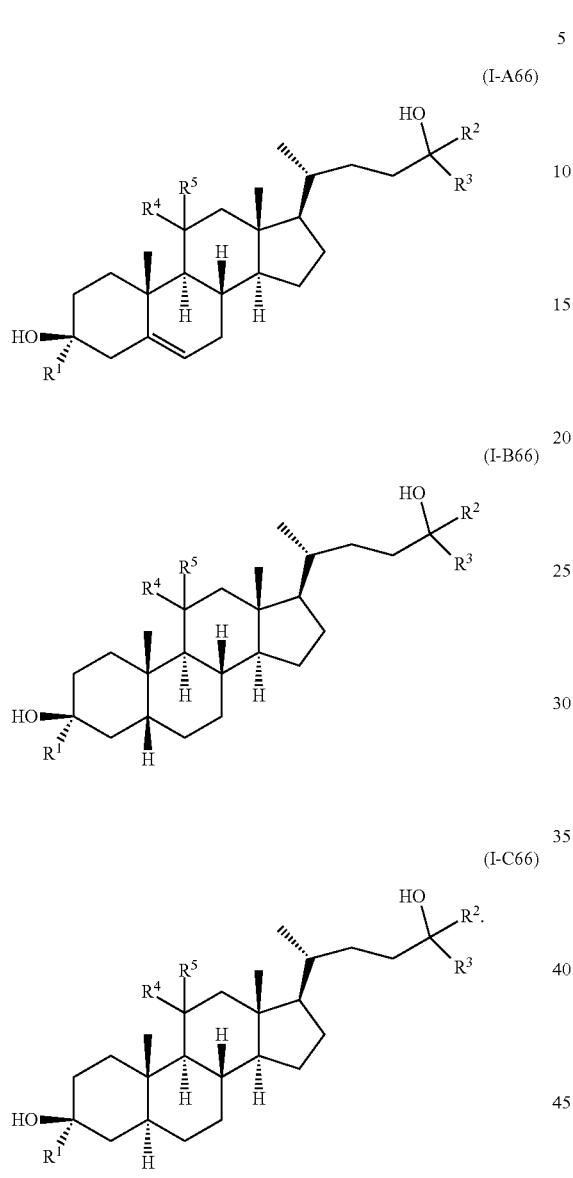
In some embodiments, the compound of Formula (I-66) is selected from a compound of Formula (I-A66):
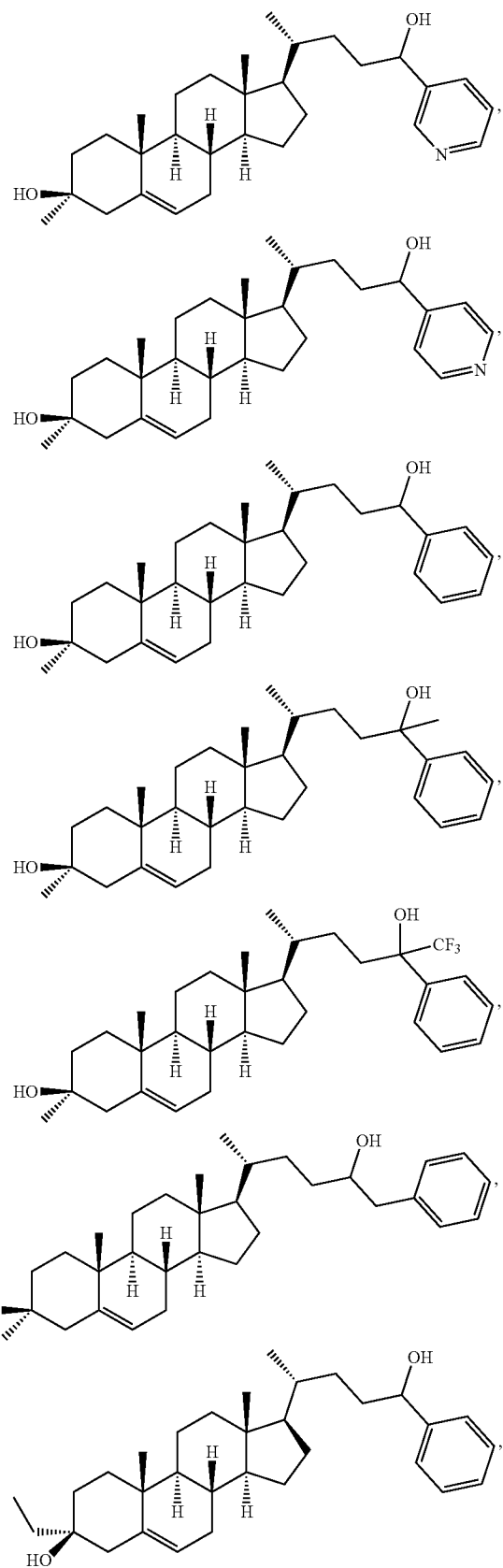

-continued

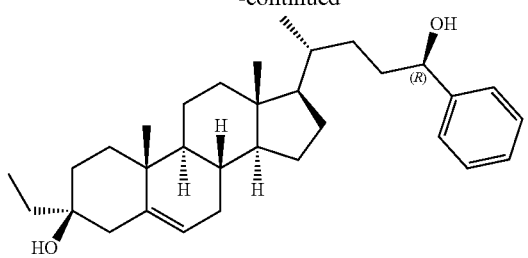, or

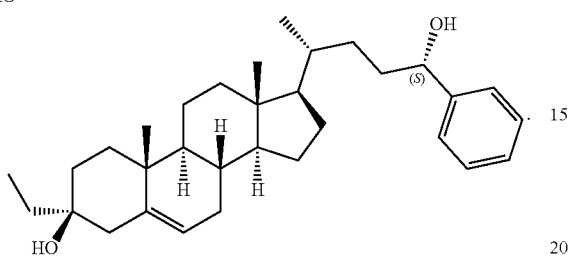.

In one aspect, provided herein are compounds according to Formula (I-61):

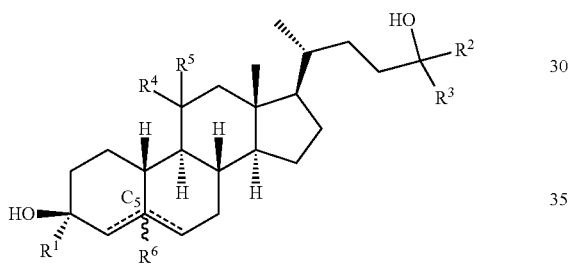

(I-61)

or a pharmaceutically acceptable salt thereof, wherein: $R^1$ is hydrogen or alkyl (e.g., $C_1$-$C_6$ alkyl); each of $R^2$ and $R^3$ is independently hydrogen, alkyl, aryl, heteroaryl, carbocyclyl, or heterocyclyl or $R^2$ and $R^3$, together with the carbon atom to which they are attached for a 3-8 membered ring; each of $R^4$ and $R^5$ is independently hydrogen, halo, or —$OR^C$, wherein $R^C$ is hydrogen or alkyl (e.g., $C_1$-$C_6$ alkyl), or $R^4$ and $R^5$, together with the carbon atom to which they are attached form an oxo group; $R^6$ is absent or hydrogen; and ====== represents a single or double bond, wherein when one of ====== is a double bond, the other ====== is a single bond; when both of ====== are single bonds, then $R^6$ is hydrogen; and when one of ====== is a double bond, $R^6$ is absent; provided that the following compounds are excluded:

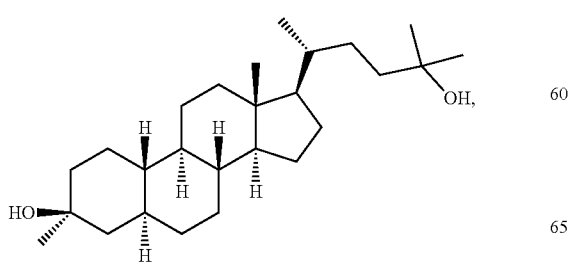,

-continued

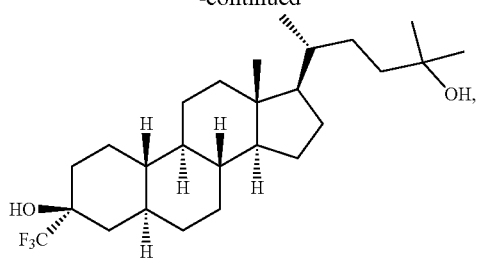,

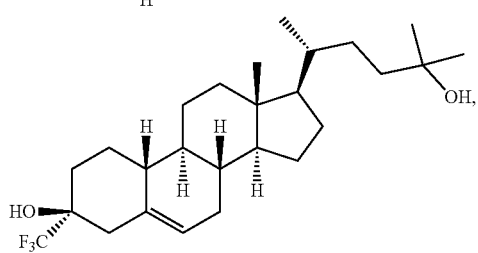,

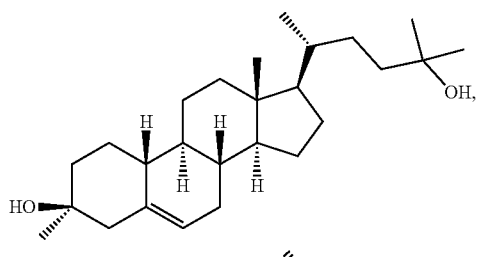,

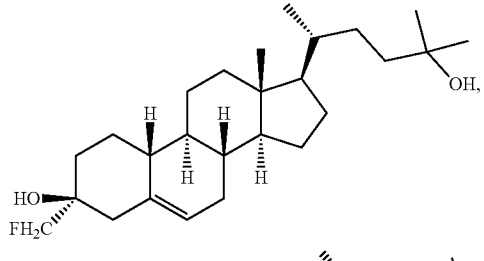,

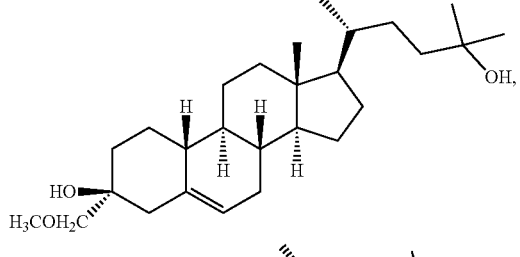,

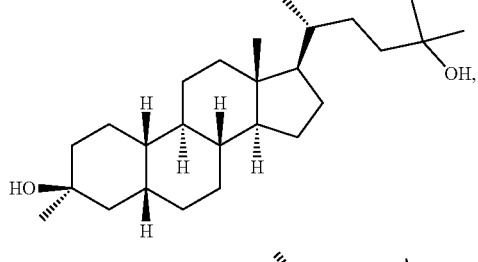,

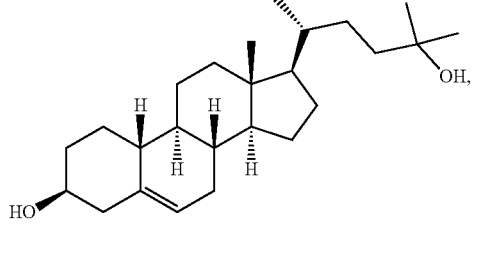,

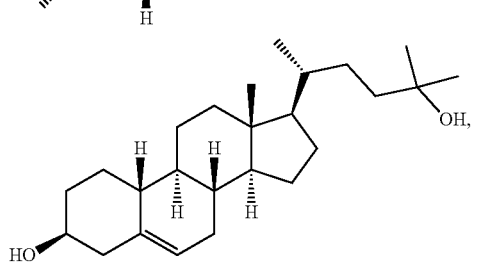,

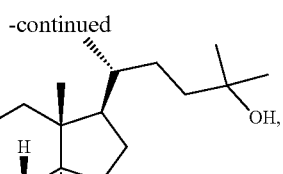
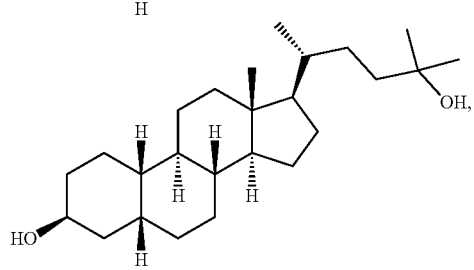
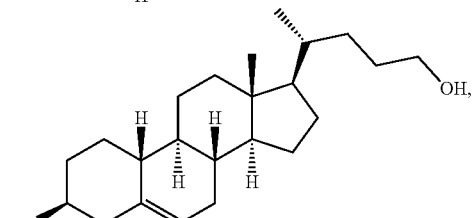
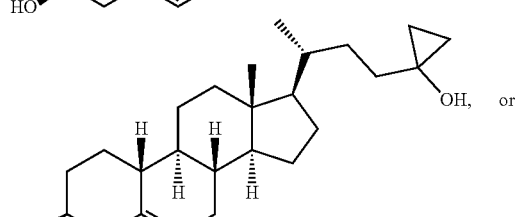

or

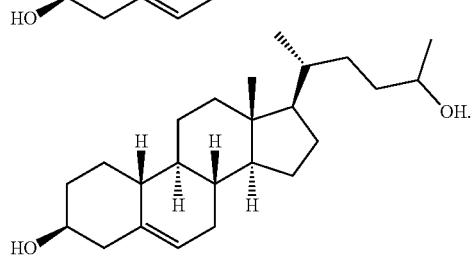

In some embodiments, $R^1$ is alkyl (e.g., $C_1$-$C_6$ alkyl) or hydrogen. In some embodiments, $R^1$ is $C_2$-$C_6$ alkyl (e.g., $C_3$-$C_6$ alkyl) or hydrogen. In some embodiments, $R^1$ is substituted or unsubstituted $C_2$-$C_6$ alkyl (e.g., substituted or unsubstituted $C_3$-$C_6$ alkyl) or hydrogen. In some embodiments, $R^1$ is methyl or ethyl (e.g., substituted or unsubstituted methyl or substituted or unsubstituted ethyl). In some embodiments, $R^1$ is substituted or unsubstituted methyl or substituted or unsubstituted ethyl. In some embodiments, $R^1$ is trifluoromethyl. In some embodiments, $R^1$ is —$CH_2OR^A$, wherein $R^A$ is $C_1$-$C_6$ alkyl (e.g., $C_1$-$C_3$ alkyl).

In some embodiments, $R^2$ is hydrogen or $C_1$-$C_6$ alkyl, (e.g., $C_2$-$C_6$ alkyl). In some embodiments, $R^2$ is hydrogen or substituted or unsubstituted $C_1$-$C_6$ alkyl (e.g., substituted or unsubstituted $C_2$-$C_6$ alkyl). In some embodiments, $R^2$ is hydrogen. In some embodiments, $R^2$ is isopropyl (e.g., substituted or unsubstituted isopropyl). In some embodiments, $R^2$ is substituted or unsubstituted isopropyl. In some embodiments, $R^2$ is haloalkyl (e.g., $C_1$-$C_6$ haloalkyl).

In some embodiments, each of $R^2$ and $R^3$ is independently alkyl (e.g., $C_1$-$C_6$ alkyl) or hydrogen. In some embodiments, each of $R^2$ and $R^3$ is independently substituted or unsubstituted alkyl (e.g., substituted or unsubstituted $C_1$-$C_6$ alkyl) or hydrogen. In some embodiments, $R^2$ and $R^3$, together with the carbon atom to which they are attached for a 3-8 membered ring. In some embodiments, each of $R^2$ and $R^3$ is independently hydrogen or $C_1$-$C_6$ alkyl (e.g. $C_2$-$C_6$ alkyl). In some embodiments, each of $R^2$ and $R^3$ is independently hydrogen or substituted or unsubstituted $C_1$-$C_6$ alkyl, (e.g. substituted or unsubstituted $C_2$-$C_6$ alkyl). In some embodiments, each of $R^2$ and $R^3$ is independently hydrogen or $C_3$-$C_6$ alkyl (e.g., isopropyl). In some embodiments, each of $R^2$ and $R^3$ is independently hydrogen or substituted or unsubstituted $C_3$-$C_6$ alkyl (e.g., substituted or unsubstituted isopropyl).

In some embodiments, $R^4$ is —OH or halo (e.g., —F). In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ and $R^3$ are hydrogen. In some embodiments, $R^2$ is $C_1$-$C_6$ alkyl and $R^3$ is $C_2$-$C_6$ alkyl (e.g., $C_3$-$C_6$ alkyl). In some embodiments, $R^2$ is substituted or unsubstituted $C_1$-$C_6$ alkyl and $R^3$ is substituted or unsubstituted $C_2$-$C_6$ alkyl (e.g., substituted or unsubstituted $C_3$-$C_6$ alkyl). In some embodiments, $R^1$ is ethyl (e.g., substituted or unsubstituted ethyl) and $R^2$ and $R^3$ are methyl (e.g., substituted or unsubstituted methyl). In some embodiments, $R^1$ is substituted or unsubstituted ethyl and $R^2$ and $R^3$ are substituted or unsubstituted methyl. In some embodiments, $R^1$ is ethyl, $R^2$ is isopropyl, and $R^3$ is hydrogen. In some embodiments, $R^1$ is substituted or unsubstituted ethyl, $R^2$ is substituted or unsubstituted isopropyl, and $R^3$ is hydrogen. In some embodiments, $R^1$ is ethyl, $R^2$ is isopropyl, and $R^3$ is methyl. In some embodiments, $R^1$ is substituted or unsubstituted ethyl, $R^2$ is substituted or unsubstituted isopropyl, and $R^3$ is substituted or unsubstituted methyl.

In some embodiments, the compound of Formula (I-61) is a compound of Formula (I-A61), (I-B61), or (I-C61):

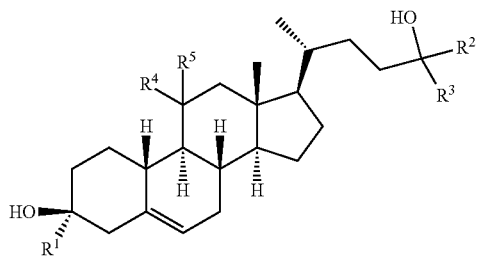

(I-A61)

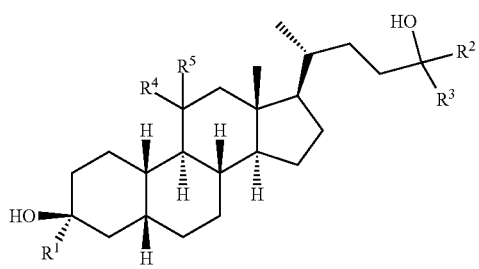

(I-B61)

(I-C61)
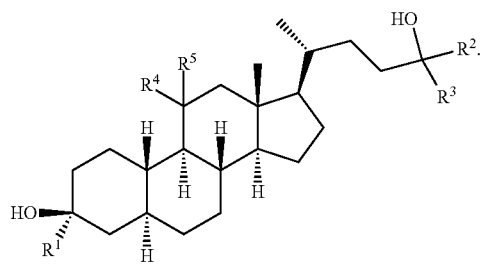
In some embodiments, the compound of Formula (I-61) is selected from a compound of Formula (I-C61):
(I-C61)
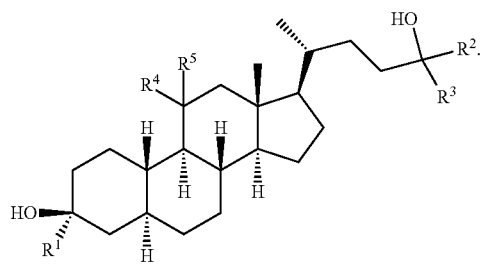
In some embodiments, the compound of Formula (I-61) is selected from a compound of Formula (I-A61):
(I-A61)
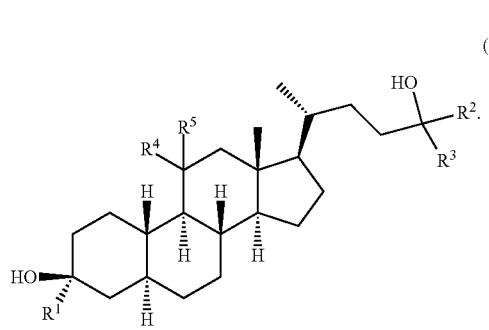
In some embodiments, the compound of Formula (I-61) is selected from a compound of Formula (I-C-i61) or (I-C-ii61):
(I-C-i61)
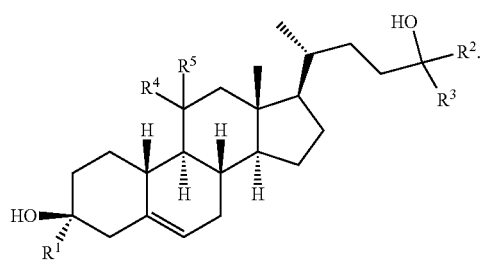
(I-D-ii61)
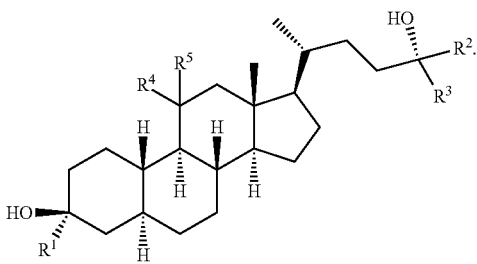
In some embodiments, the compound is:
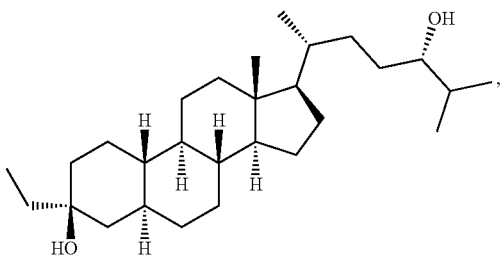
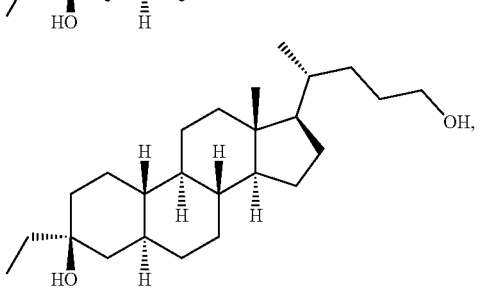

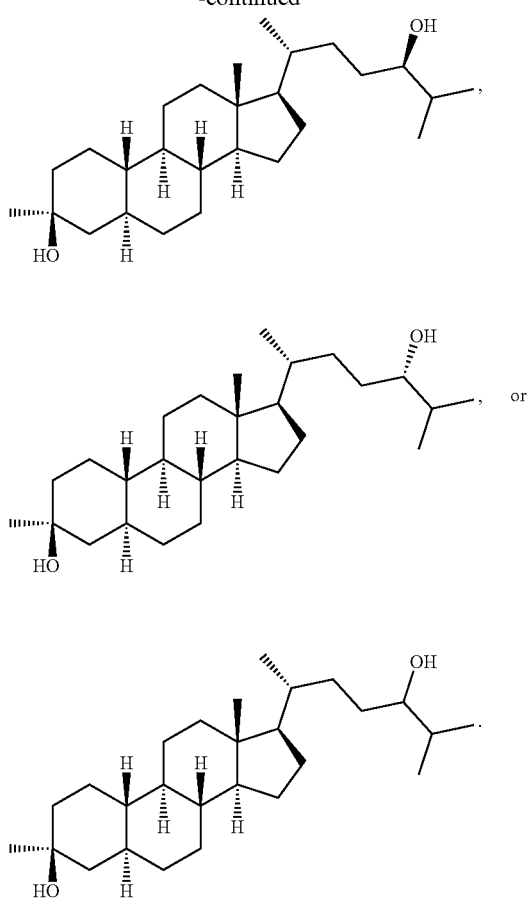

In one aspect, the present invention features a compound of Formula (I-62):

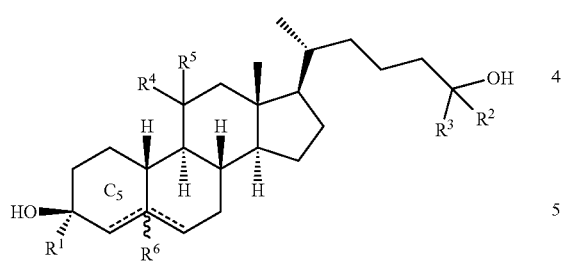

(I-62)

or a pharmaceutically acceptable salt thereof, wherein: $R^1$ is hydrogen or alkyl (e.g., $C_1$-$C_6$ alkyl); each of $R^2$ and $R^3$ is independently hydrogen, alkyl, carbocyclyl, or heterocyclyl or $R^2$ and $R^3$, together with the carbon atom to which they are attached, form a 3-8 membered ring; each of $R^4$ and $R^5$ is independently hydrogen, halo, or —$OR^C$, wherein $R^C$ is hydrogen or alkyl (e.g., $C_1$-$C_6$ alkyl), or $R^4$ and $R^5$, together with the carbon atom to which they are attached form an oxo group; $R^6$ is absent or hydrogen; and ===== represents a single or double bond, wherein when one of ===== is a double bond, the other ===== is a single bond; when both of ===== are single bonds, then $R^6$ is hydrogen; and when one of ===== is a double bond, $R^6$ is absent.

In some embodiments, $R^1$ is alkyl (e.g., $C_1$-$C_6$ alkyl). In some embodiments, $R^1$ is substituted or unsubstituted $C_2$-$C_6$ alkyl (e.g., substituted or unsubstituted $C_3$-$C_6$ alkyl). In some embodiments, $R^1$ is methyl or ethyl (e.g., substituted or unsubstituted methyl or substituted or unsubstituted ethyl). In some embodiments, $R^1$ is substituted or unsubstituted methyl or substituted or unsubstituted ethyl. In some embodiments, $R^1$ is trifluoromethyl. In some embodiments, $R^1$ is —$CH_2OR^A$, wherein RA is $C_1$-$C_6$ alkyl (e.g., $C_1$-$C_3$ alkyl).

In some embodiments, $R^2$ is hydrogen or $C_1$-$C_6$ alkyl, (e.g., $C_2$-$C_6$ alkyl). In some embodiments, $R^2$ is hydrogen or substituted or unsubstituted $C_1$-$C_6$ alkyl (e.g., substituted or unsubstituted $C_2$-$C_6$ alkyl). In some embodiments, $R^2$ is haloalkyl, (e.g., $C_1$-$C_6$ haloalkyl).

In some embodiments, each of $R^2$ and $R^3$ is independently hydrogen or $C_1$-$C_6$ alkyl (e.g. $C_2$-$C_6$ alkyl). In some embodiments, each of $R^2$ and $R^3$ is independently hydrogen or substituted or unsubstituted $C_1$-$C_6$ alkyl (e.g. substituted or unsubstituted $C_2$-$C_6$ alkyl). In some embodiments, each of $R^2$ and $R^3$ is independently alkyl (e.g., $C_1$-$C_6$ alkyl) or hydrogen. In some embodiments, each of $R^2$ and $R^3$ is independently substituted or unsubstituted alkyl (e.g., substituted or unsubstituted $C_1$-$C_6$ alkyl) or hydrogen. In some embodiments, $R^2$ and $R^3$, together with the carbon atom to which they are attached, form a 3-8 membered ring.

In some embodiments, $R^4$ is —OH or halo (e.g., —F). In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^1$ is ethyl (e.g., substituted or unsubstituted ethyl) and $R^2$ and $R^3$ are methyl (e.g., substituted or unsubstituted methyl). In some embodiments, $R^1$ is substituted or unsubstituted ethyl and $R^2$ and $R^3$ are substituted or unsubstituted methyl.

In some embodiments, the compound of Formula (I-62) is a compound of Formula (I-A62), (I-B62), or (I-C62):

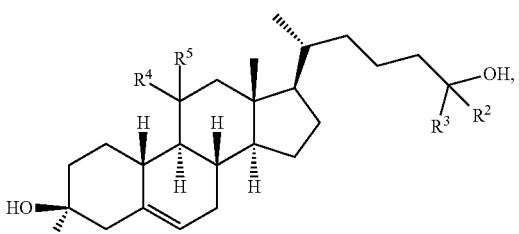

(I-A62)

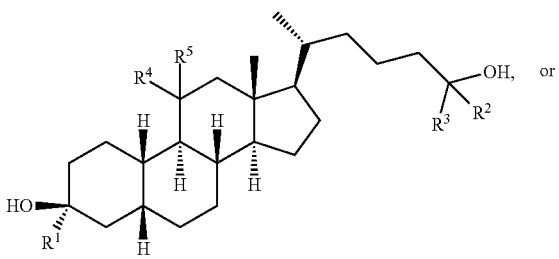

(I-B62) or (I-C62)

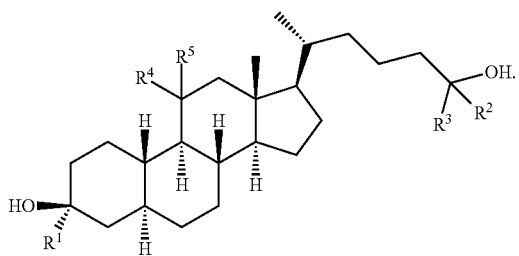

In some embodiments, the compound of Formula (I-62) is selected from a compound of Formula (I-C62):

(I-C62)

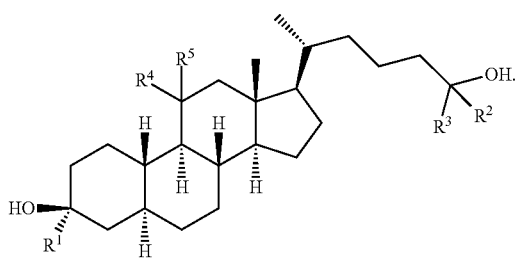

In some embodiments, the compound of Formula (I-62) is selected from a compound of Formula (I-A62):

(I-A62)

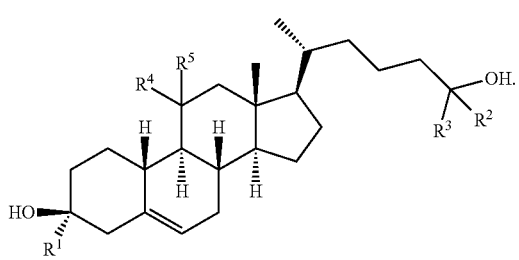

In some embodiments, $R^1$ is ethyl (e.g., substituted or unsubstituted ethyl) and $R^2$ and $R^3$ are methyl (e.g., substituted or unsubstituted methyl). In some embodiments, $R^1$ is substituted or unsubstituted ethyl and $R^2$ and $R^3$ are substituted or unsubstituted methyl.

In some embodiments, the compound of Formula (I-62) is selected from a compound of Formula (I-C-i62) or (I-C-ii62):

(I-C-i62)

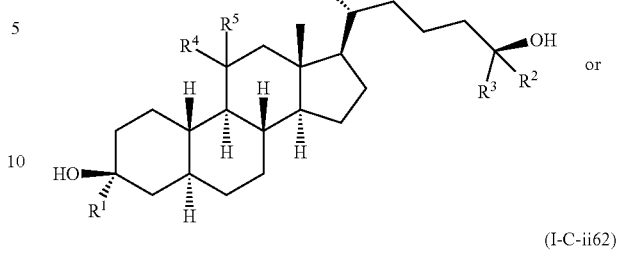

or (I-C-ii62)

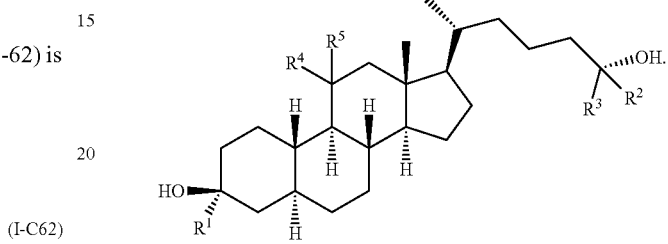

In some embodiments, the compound is

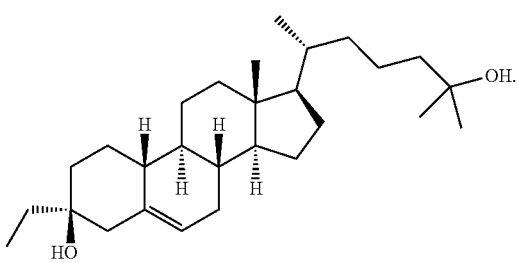

In one aspect, provided herein are compounds according to Formula (I-60):

(I-60)

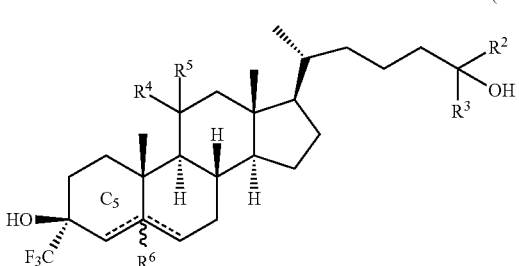

or a pharmaceutically acceptable salt thereof, wherein: each of $R^2$ and $R^3$ is independently hydrogen, alkyl (e.g., $C_1$-$C_6$ alkyl), carbocyclyl, heterocyclyl, aryl, or heteroaryl, or $R^2$ and $R^3$, together with the carbon atom to which they are attached form a 3-8 membered ring; each of $R^4$ and $R^5$ is independently hydrogen, halo, or —$OR^C$, wherein $R^C$ is hydrogen or alkyl (e.g., $C_1$-$C_6$ alkyl), or $R^4$ and $R^5$, together with the carbon atom to which they are attached form an oxo group; $R^6$ is absent or hydrogen; and ====== represents a single or double bond, wherein when one of ====== is a double bond, the other ====== is a single bond; when both of ====== are single bonds, then $R^6$ is hydrogen; and when one of the ====== is a double bond, $R^6$ is absent.

In some embodiments, $R^2$ is alkyl (e.g., $C_1$-$C_6$alkyl) or hydrogen. In some embodiments, $R^2$ is haloalkyl (e.g., $C_1$-$C_6$ haloalkyl). In some embodiments, $R^2$ is substituted or unsubstituted alkyl (e.g., substituted or unsubstituted $C_1$-$C_6$ alkyl) or hydrogen. In some embodiments, $R^2$ is aryl or heteroaryl.

In some embodiments, each of $R^2$ and $R^3$ is independently alkyl (e.g., $C_1$-$C_6$ alkyl) or hydrogen. In some embodiments, each of $R^2$ and $R^3$ is independently substituted or unsubstituted alkyl (e.g., substituted or unsubstituted $C_1$-$C_6$ alkyl) or hydrogen. In some embodiments, each of $R^2$ and $R^3$ is independently unsubstituted alkyl (e.g., unsubstituted $C_1$-$C_6$ alkyl) or hydrogen. In some embodiments, each of $R^2$ and $R^3$ is independently $C_1$-$C_6$ haloalkyl (e.g., trifluoromethyl) or hydrogen. In some embodiments, each of $R^2$ and $R^3$ is independently aryl or heteroaryl. In some embodiments, $R^2$ and $R^3$, together with the carbon atom to which they are attached form a 3-membered ring.

In some embodiments, $R^2$ and $R^3$, together with the carbon atom to which they are attached form a cyclopropane. In some embodiments, $R^2$ and $R^3$, together with the carbon atom to which they are attached form a 3-8 membered carbocyclic or heterocyclic ring.

In some embodiments, $R^2$ is carbocyclyl or heterocyclyl and $R^3$ is hydrogen. In some embodiments, $R^2$ is trifluoromethyl and $R^3$ is hydrogen. In some embodiments, $R^2$ is aryl or heteroaryl and $R^3$ is hydrogen. In some embodiments, $R^2$ and $R^3$ are methyl (e.g., substituted or unsubstituted methyl). In some embodiments, $R^2$ and $R^3$ is substituted methyl. In some embodiments, $R^2$ and $R^3$ is unsubstituted methyl.

In some embodiments, $R^4$ is —OH or halo (e.g., —F). In some embodiments, $R^4$ and $R^5$, together with the carbon atom to which they are attached form an oxo group.

In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, the compound of Formula (I-60) is selected from a compound of Formula (I-A60), (I-B60), or (I-C60):

(I-A60)

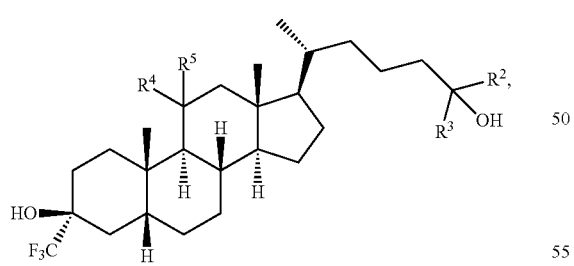

(I-B60)

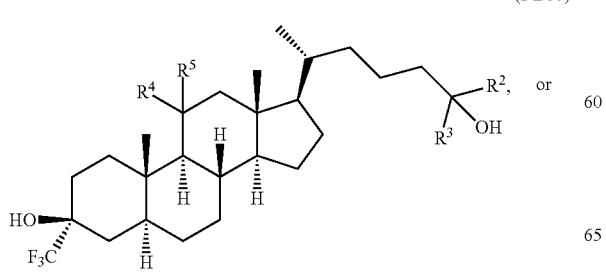

(I-C60)

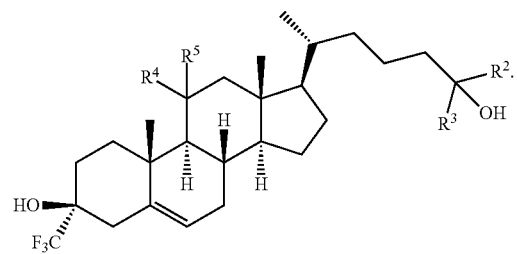

In some embodiments, the compound of Formula (I-60) is selected from a compound of Formula (I-B60):

(I-B60)

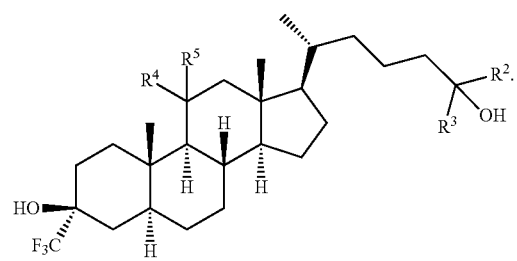

In some embodiments, at least one of $R^2$ and $R^3$ is $C_1$-$C_6$ alkyl, carbocyclyl, heterocyclyl, aryl, or heteroaryl; or $R^2$ and $R^3$, together with the carbon atom to which they are attached, form a 3-8 membered ring.

In some embodiments, $R^2$ is methyl and $R^3$ is hydrogen. In some embodiments, $R^2$ is unsubstituted methyl and $R^3$ is hydrogen. In some embodiments, $R^2$ and $R^3$ are hydrogen.

In some embodiments, the compound is:

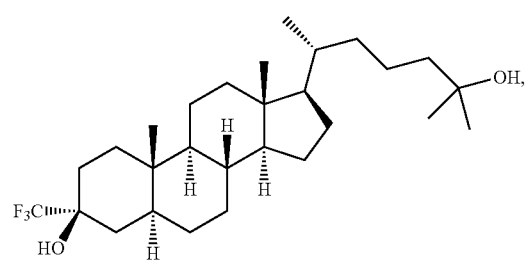

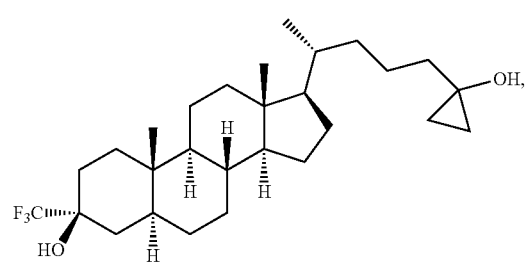

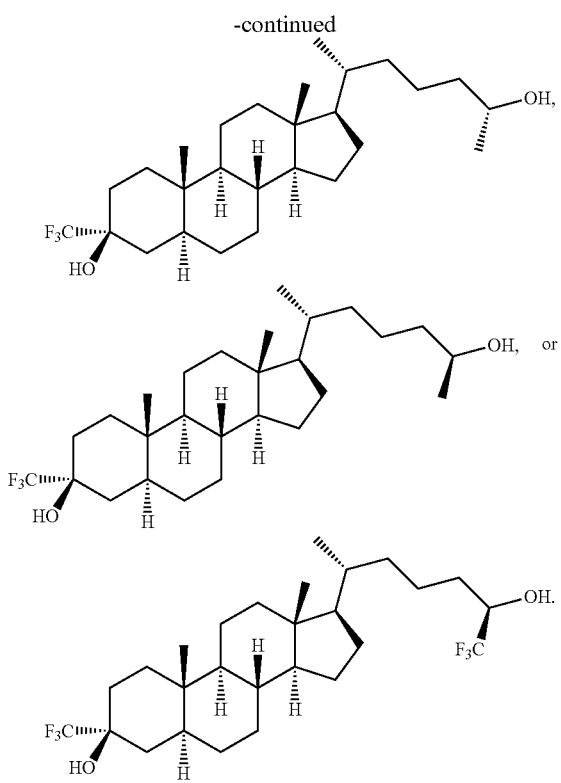

In an aspect, provided herein is a pharmaceutical composition comprising a compound described herein, or pharmaceutically acceptable salt thereof, and a pharmaceutically acceptable carrier.

In an aspect, provided herein is a method of inducing sedation or anesthesia comprising administering to a subject an effective amount of a compound described herein, or pharmaceutically acceptable salt thereof, or pharmaceutical composition thereof.

In an aspect, provided herein is a method for treating or preventing a disorder described herein, comprising administering to a subject in need thereof an effective amount of a compound described herein, or pharmaceutically acceptable salt thereof, or pharmaceutical composition thereof.

In some embodiments, the disorder is a metabolic disorder.

In some embodiments, the disorder is an autoimmune disorder.

In some embodiments, the disorder is rheumatoid arthritis, juvenile idiopathic arthritis, ankylosing spondylitis, psoriatic arthritis, Crohn's disease, ulcerative colitis, and plaque psoriasis.

In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, or colitis.

In some embodiments, the disorder is inflammatory bowel disease.

In some embodiments, the disorder is cancer, diabetes, or a sterol synthesis disorder.

In some embodiments, the disorder is Neuropsychiatric lupus, Depression, OCD, Huntington's disease, ALS, Alzheimer's, Dementia, Parkinson's, MS, Acute liver failure, Glycine encephalopathy, Tinnitus, Neuropathic pain, Migraine, Genetic epilepsy, Seizure, Ataxia, Levodopa-induced dyskinesia, Fragile X, Rett syndrome, Autism Spectrum disorders, Tourette's, Schizophrenia, and Traumatic brain injury.

In an aspect, provided herein is a method for treating or preventing a CNS-related condition comprising administering to a subject in need thereof an effective amount of a compound described herein, or pharmaceutically acceptable salt thereof, or pharmaceutical composition thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia (e.g., frontotemporal dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain; headaches, e.g., migraine headaches), encephalopathy secondary to a medical condition (including hepatic encephalopathy and anti-NMDA receptor encephalitis), seizure disorder (including status epilepticus and monogenic forms of epilepsy such as Dravet's disease), stroke, traumatic brain injury, movement disorder (including Huntington's disease and Parkinson's disease), vision impairment, hearing loss, or tinnitus.

In some embodiments, the disorder is Huntington's disease. In some embodiments, the disorder is Parkinson's disease. In some embodiments, the disorder is an inflammatory disease (e.g., lupus).

In some embodiments, the disorder is a sterol synthesis disorder.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketonuria.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

The "enantiomeric excess" ("e.e.") or "% enantiomeric excess" ("% e.e.") of a composition as used herein refers to an excess of one enantiomer relative to the other enantiomer present in the composition. For example, a composition can contain 90% of one enantiomer, e.g., the S enantiomer, and 10% of the other enantiomer, i.e., the R enantiomer.

$$e.e.=(90-10)/100=80\%.$$

Thus, a composition containing 90% of one enantiomer and 10% of the other enantiomer is said to have an enantiomeric excess of 80%.

The "diastereomeric excess" ("d.e.") or "% diastereomeric excess" ("% d.e.") of a composition as used herein refers to an excess of one diastereomer relative to one or more different diastereomers present in the composition. For example, a composition can contain 90% of one diastereomer, and 10% of one or more different diastereomers.

$$d.e.=(90-10)/100=80\%.$$

Thus, a composition containing 90% of one diastereomers and 10% of one or more different diastereomers is said to have a diastereomeric excess of 80%.

In an alternative embodiment, compounds described herein may also comprise one or more isotopic substitutions. For example, hydrogen may be $^2H$ (D or deuterium) or $^3H$ (T or tritium); carbon may be, for example, 13C or $^{14}C$; oxygen $^4C$; oxygen may be, for example, $^{18}O$; nitrogen may be, for example, $^{15}N$, and the like. In other embodiments, a particular isotope (e.g., $^3H$, $^{13}C$, $^{14}C$, $^{18}O$, or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Aralkyl" is a subset of alkyl and aryl, as defined herein, and refers to an optionally substituted alkyl group substituted by an optionally substituted aryl group.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$)

and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 hetero atoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

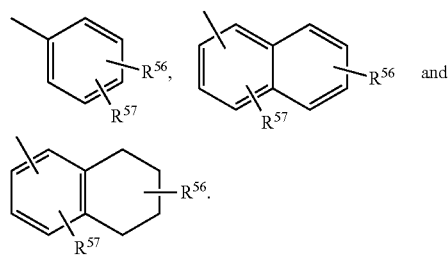

wherein one of $R^{56}$ and $R^{57}$ may be hydrogen and at least one of $R^{56}$ and $R^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$NR$^{59}$, S-alkyl, SOalkyl, SO$_2$alkyl, Saryl, SOaryl, SO$_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, C$_1$-C$_8$ alkyl, C$_1$-C$_4$haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

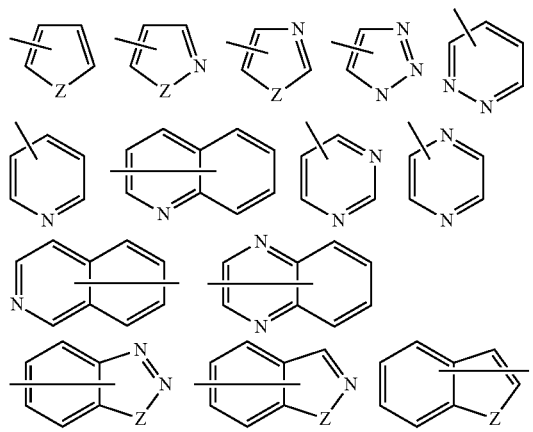

wherein each Z is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_5$), cyclooctenyl ($C_5$), bicyclo[2.2.1]heptanyl ($C_7$), bicyclo[2.2.2]octanyl ($C_5$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or Spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclyl ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10})$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings.

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—$C_1$-$C_8$ alkyl, —C(O)—(CH$_2$)$_t$($C_6$-$C_{10}$ aryl), —C(O)—(CH$_2$)$_t$ (5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —O$R^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$- and aryl-S(O)$_2$—. Exemplary 'substituted alkoxy' groups include, but are not limited to, —O—(CH$_2$)$_t$($C_6$-$C_{10}$ aryl), —O—(CH$_2$)$_t$(5-10 membered heteroaryl), —O—(CH$_2$)$_t$ ($C_3$-$C_{10}$ cycloalkyl), and —O—($CH_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —$OCF_3$, —$OCH_2CF_3$, —$OCH_2Ph$, —$OCH_2$-cyclopropyl, —$OCH_2CH_2OH$, and —$OCH_2CH_2NMe_2$.

"Amino" refers to the radical —$NH_2$.

"Oxo group" refers to —C(=O)—.

"Substituted amino" refers to an amino group of the formula —$N(R^{38})_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —($CH_2$)$_t$($C_6$-$C_{10}$ aryl), —($CH_2$)$_t$(5-10 membered heteroaryl), —($CH_2$)$_t$($C_3$-$C_{10}$ cycloalkyl), or —($CH_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—($CH_2$)$_t$($C_6$-$C_{10}$ aryl), —$NR^{39}$—($CH_2$)$_t$(5-10 membered heteroaryl), —$NR^{39}$—($CH_2$)$_t$($C_3$-$C_{10}$ cycloalkyl), and —$NR^{39}$—($CH_2$)$_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl (—$CF_3$), difluoromethyl (—$CHF_2$), fluoromethyl (—$CH_2F$), chloromethyl (—$CH_2Cl$), dichloromethyl (—$CHCl_2$), tribromomethyl (—$CH_2Br$), and the like.

"Hydroxy" refers to the radical —OH.

"Nitro" refers to the radical —$NO_2$.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2H$, —CHO, —C($OR^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, $NR^{bb}$C(=O)N($R^{bb}$)$_2$, —C(=$NR^{bb}$)$R^{aa}$, —C(=$NR^{bb}$)$OR^{aa}$, —OC(=$NR^{bb}$)$R^{aa}$, —OC(=$NR^{bb}$)$OR^{aa}$, —C(=$NR^{bb}$)N($R^{bb}$)$_2$, —OC(=$NR^{bb}$)N($R^{bb}$)$_2$, $NR^{bb}$C(=$NR^{bb}$)N($R^{bb}$)$_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)$_3$, —OSi($R^{aa}$)$_3$—C(=S)N($R^{bb}$)$_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)$_2R^{aa}$, —OP(=O)$_2R^{aa}$, —P(=O)($R^{aa}$)$_2$, —OP(=O)($R^{aa}$)$_2$, —OP(=O)($OR^{cc}$)$_2$, —P(=O)$_2N(R^{bb})_2$, —OP(=O)$_2N(R^{bb})_2$, —P(=O)(N$R^{bb}$)$_2$, —OP(=O)(N$R^{bb}$)$_2$, —$NR^{bb}P$(=O)($OR^{cc}$)$_2$, —$NR^{bb}P$(=O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B($OR^{cc}$)$_2$, —$BR^{aa}(OR^{cc})$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =NN($R^{bb}$)$_2$, =NN$R^{bb}$C(=O)$R^{aa}$, =NN$R^{bb}$C(=O)$OR^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ haloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, SO$_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides substituted oxysterols useful for preventing and/or treating a broad range of disorders, including, but not limited to, NMDA-mediated disorders.

Compounds

In one aspect, provided herein are compounds according to Formula (I-59):

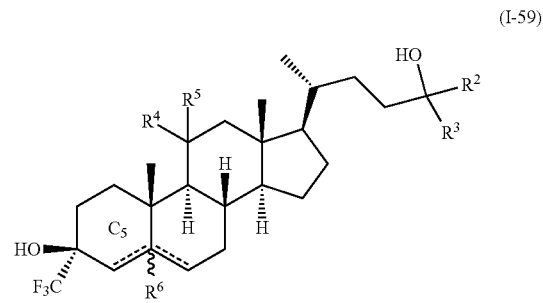

(I-59)

or a pharmaceutically acceptable salt thereof, wherein: each of $R^2$ and $R^3$ is independently hydrogen, alkyl (e.g., $C_1$-$C_6$ alkyl), carbocyclyl, or heterocyclyl, or $R^2$ and $R^3$, together with the carbon atom to which they are attached form a 3-8 membered ring; each of $R^4$ and $R^5$ is independently hydrogen, halo, or —$OR^C$, wherein $R^C$ is hydrogen or alkyl (e.g., $C_1$-$C_6$ alkyl), or $R^4$ and $R^5$, together with the carbon atom to which they are attached form an oxo group; $R^6$ is absent or hydrogen; and ------ represents a single or double bond, wherein when one of ------ is a double bond, the other ------ is a single bond; when both of ------ are single bonds, then $R^6$ is hydrogen; and when one of ------ is a double bond, $R^6$ is absent; provided that the following compounds are excluded:

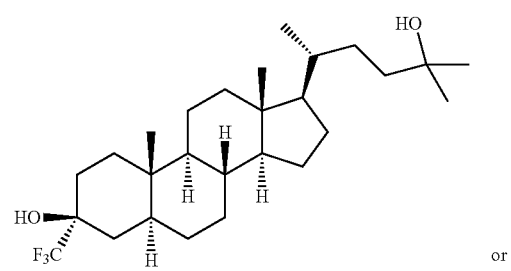

or

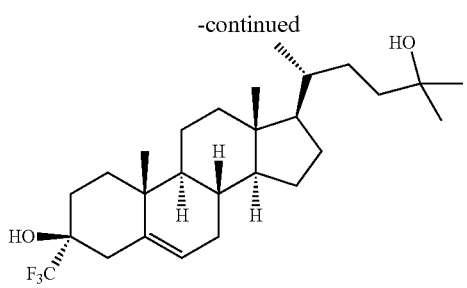

In some embodiments, $R^2$ is hydrogen or alkyl (e.g., $C_1$-$C_6$ alkyl). In some embodiments, $R^2$ is haloalkyl (e.g., $C_1$-$C_6$ haloalkyl).

In some embodiments, each of $R^2$ and $R^3$ is independently alkyl (e.g., substituted $C_1$-$C_6$ alkyl) or hydrogen. In some embodiments, each of $R^2$ and $R^3$ is independently unsubstituted alkyl (e.g., unsubstituted $C_1$-$C_6$ alkyl) or hydrogen. In some embodiments, each of $R^2$ and $R^3$ is independently $C_1$-$C_6$ haloalkyl (e.g., trifluoromethyl) or hydrogen. In some embodiments, each of $R^2$ and $R^3$ is independently hydrogen, carbocyclyl, or heterocyclyl. In some embodiments, each of $R^2$ and $R^3$ is independently $C_2$-$C_6$ alkyl (e.g., isopropyl or tert-butyl) or hydrogen. In some embodiments, each of $R^2$ and $R^3$ is independently hydrogen or $C_3$-$C_6$ alkyl (e.g., isopropyl or tert-butyl).

In some embodiments, at least one of $R^2$ and $R^3$ is $C_3$-$C_6$ alkyl (e.g., isopropyl or tert-butyl), carbocyclyl, or heterocyclyl; or $R^2$ and $R^3$, together with the carbon atom to which they are attached form a 3-8 membered ring. In some embodiments, $R^2$ is isopropyl or tert-butyl and $R^3$ is methyl or hydrogen. In some embodiments, $R^2$ is substituted isopropyl or substituted tert-butyl and $R^3$ is unsubstituted methyl or hydrogen. In some embodiments, $R^2$ is unsubstituted isopropyl or unsubstituted tert-butyl and $R^3$ is unsubstituted methyl or hydrogen. In some embodiments, $R^2$ is tert-butyl and $R^3$ is hydrogen. In some embodiments, $R^2$ is substituted tert-butyl and $R^3$ is hydrogen. In some embodiments, $R^2$ is unsubstituted tert-butyl and $R^3$ is hydrogen. In some embodiments, $R^2$ is trifluoromethyl and $R^3$ is hydrogen. In some embodiments, $R^2$ is trifluoromethyl and $R^3$ is methyl. In some embodiments, $R^2$ is trifluoromethyl and $R^3$ is substituted methyl. In some embodiments, $R^2$ is trifluoromethyl and $R^3$ is unsubstituted methyl. In some embodiments, $R^2$ is methyl and $R^3$ is hydrogen. In some embodiments, $R^2$ is substituted methyl and $R^3$ is hydrogen. In some embodiments, $R^2$ is unsubstituted methyl and $R^3$ is hydrogen.

In some embodiments, $R^4$ is —OH or halo (e.g., —F). In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ and $R^3$, together with the carbon atom to which they are attached form a 5-membered ring. In some embodiments, $R^2$ is $C_2$-$C_6$ alkyl (e.g., substituted or unsubstituted isopropyl or substituted or unsubstituted tert-butyl) and $R^3$ is $C_1$-$C_6$ alkyl (e.g., substituted or unsubstituted $C_1$-$C_6$ alkyl). In some embodiments, $R^2$ is unsubstituted $C_2$-$C_6$ alkyl (e.g., unsubstituted isopropyl or unsubstituted tert-butyl) and $R^3$ is unsubstituted $C_1$-$C_6$ alkyl. In some embodiments, $R^2$ and $R^3$, together with the carbon atom to which they are attached form a 6-membered ring.

In some embodiments, $R^2$ is carbocyclyl or heterocyclyl and $R^3$ is hydrogen. In some embodiments, $R^2$ and $R^3$ are hydrogen. In some embodiments, $R^2$ is isopropyl and $R^3$ is hydrogen. In some embodiments, $R^2$ is substituted isopropyl and $R^3$ is hydrogen. In some embodiments, $R^2$ is substituted isopropyl and $R^3$ is hydrogen. In some embodiments, $R^2$ and $R^3$, together with the carbon atom to which they are attached form a 3-8 membered carbocyclic (e.g., cyclohexyl) or heterocyclic (e.g., tetrahydrofuranyl or tetrahydropyranyl) ring. In some embodiments, the carbocyclic or heterocyclic ring is substituted (e.g., ring substituted with 1 or 2 halo or alkyl groups). In some embodiments, $R^2$ is cyclobutyl and $R^3$ is hydrogen. In some embodiments, $R^2$ is tetrahydropyranyl and $R^3$ is hydrogen.

In some embodiments, $R^2$ is substituted cyclobutyl and $R^3$ is hydrogen. In some embodiments, $R^2$ is substituted tetrahydropyranyl and $R^3$ is hydrogen. In some embodiments, $R^2$ is unsubstituted cyclobutyl and $R^3$ is hydrogen. In some embodiments, $R^2$ is unsubstituted tetrahydropyranyl and $R^3$ is hydrogen.

In some embodiments, the compound of Formula (I-59) is selected from a compound of Formula (I-A59), (I-B59), or (I-C59):

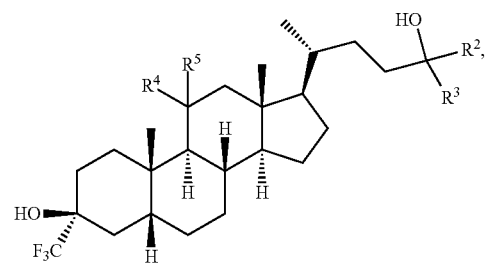

(I-A59)

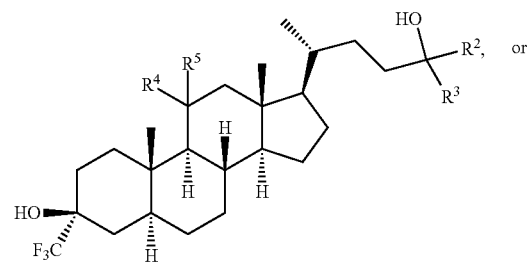

(I-B59) or

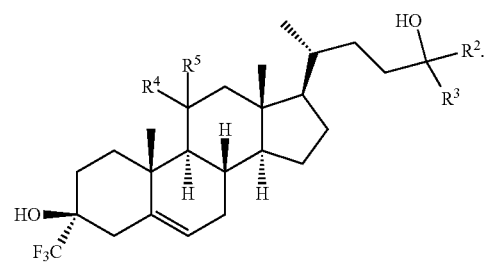

(I-C59)

In some embodiments, the compound of Formula (I-59) is selected from a compound of Formula (I-B59):

(I-B59)

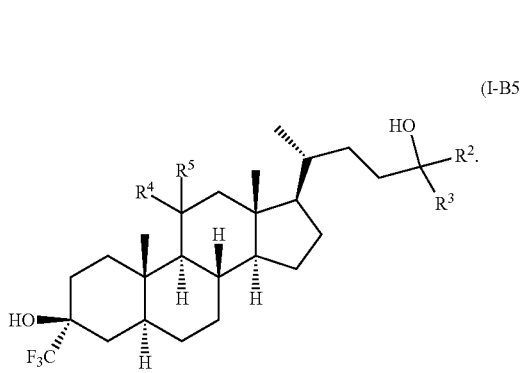

In some embodiments, the compound of Formula (I-59) is selected from a compound of Formula (I-C59):

(I-C59)

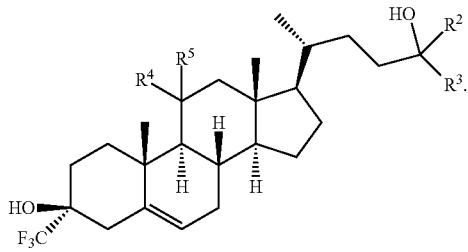

In some embodiments, at least one of $R^2$ and $R^3$ is hydrogen, $C_1$-$C_6$ alkyl, carbocyclyl, or heterocyclyl; or $R^2$ and $R^3$, together with the carbon atom to which they are attached form a 3-8 membered ring. In some embodiments, the compound of Formula (I-59) is selected from a compound of Formula (I-D59):

(I-D59)

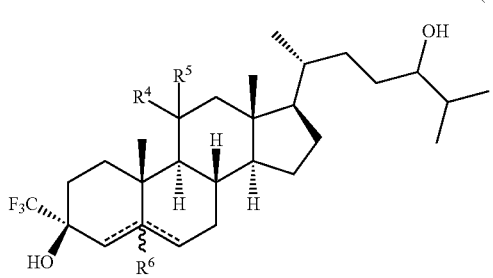

In some embodiments, the compound of Formula (I-59) is selected from a compound of Formula (I-E59):

(I-E59)

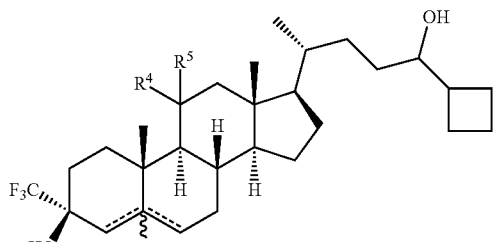

In some embodiments, the compound of Formula (I-59) is selected from a compound of Formula (I-D-i59) or (I-D-ii59):

(I-D-i59)

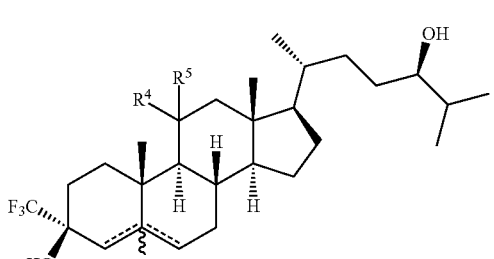

or (I-D-ii59)

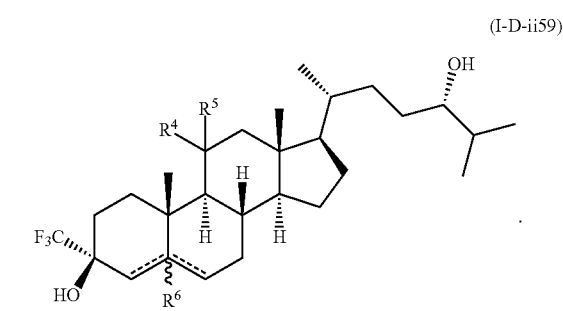

In some embodiments, the compound of Formula (I-59) is selected from a compound of Formula (I-E-i59) or (I-E-ii59):

(I-E-i59)

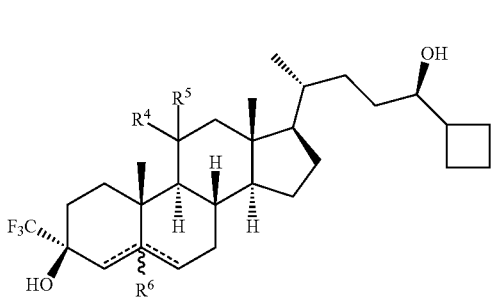

or (I-E-ii59)
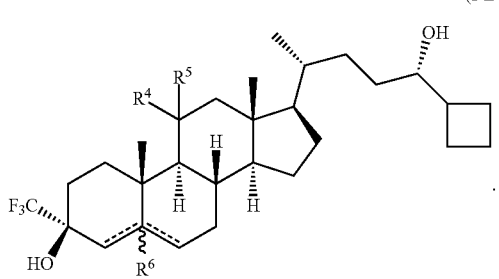
In some embodiments, the compound is:
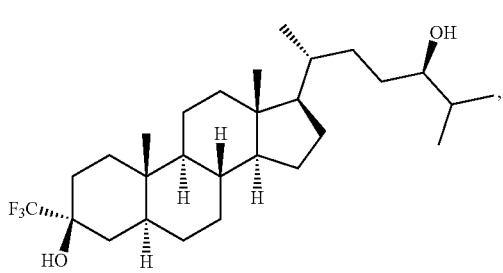
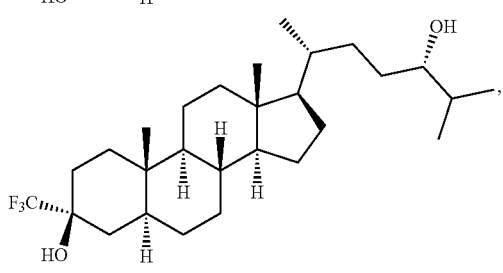
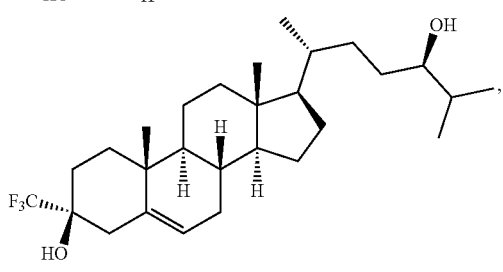
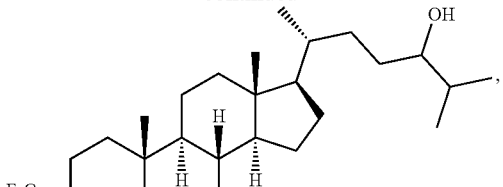
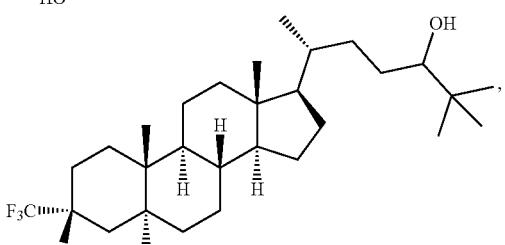
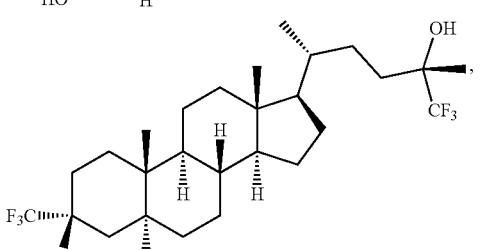
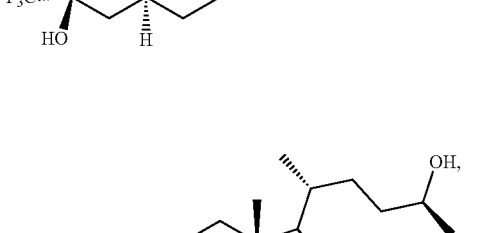
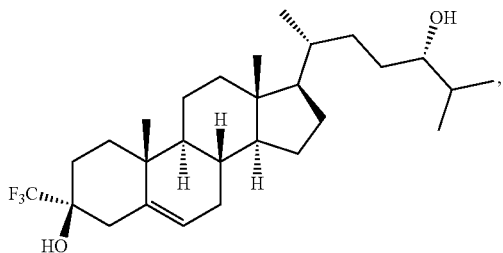
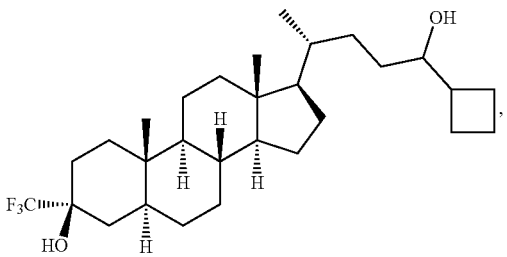

-continued

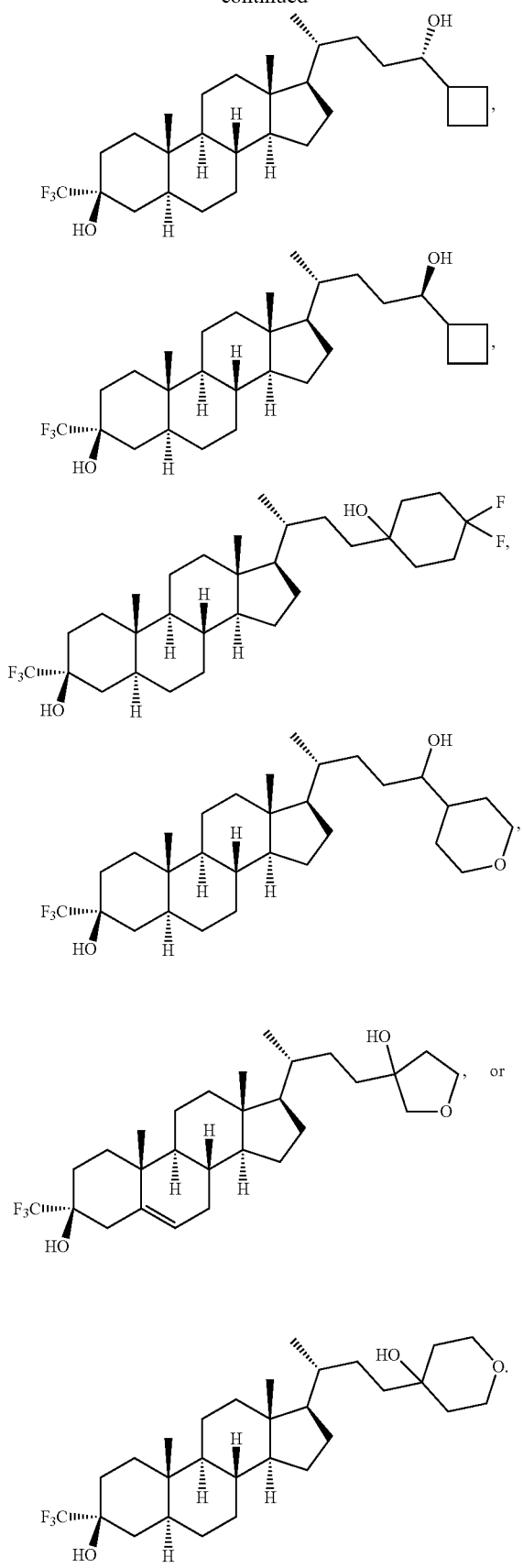

In one aspect, provided herein are compounds according to Formula (I-66):

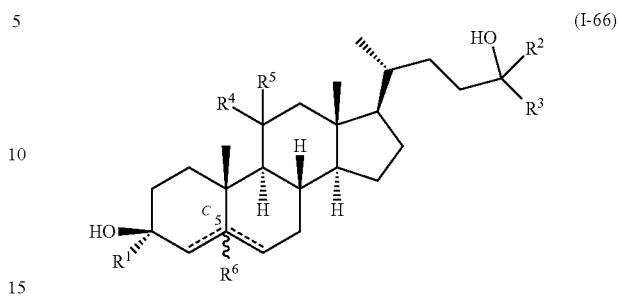

(I-66)

or a pharmaceutically acceptable salt thereof, wherein: $R^1$ is alkyl (e.g., $C_1$-$C_6$ alkyl); $R^2$ is aralkyl, heteroaralkyl, aryl, or heteroaryl; $R^3$ is hydrogen, alkyl (e.g., $C_1$-$C_6$ alkyl), carbocyclyl, heterocyclyl, aryl, or heteroaryl; each of $R^4$ and $R^5$ is independently hydrogen, halo, or —$OR^C$, wherein $R^C$ is hydrogen or $C_1$-$C_3$ alkyl (e.g., unsubstituted or substituted $C_1$-$C_3$ alkyl), or $R^4$ and $R^5$, together with the carbon atom to which they are attached form an oxo group; $R^6$ is absent or hydrogen; and ===== represents a single or double bond, wherein when one of ===== is a double bond, the other ===== is a single bond; when both of ===== are single bonds, then $R^6$ is hydrogen; and when one of ===== is a double bond, $R^6$ is absent.

In some embodiments, $R^1$ is alkyl (e.g., $C_1$-$C_6$ alkyl). In some embodiments, $R^1$ is $C_1$-$C_6$ alkyl (e.g., —$CH_3$, —$CH_2CH_3$, —$CH_2OCH_3$, or —$CF_3$). In some embodiments, $R^1$ is —$CH_3$, —$CF_3$, or —$CH_2CH_3$. In some embodiments, $R^1$ is —$CH_2OR^A$, wherein $R^A$ is $C_1$-$C_6$ alkyl (e.g., $C_1$-$C_3$ alkyl).

In some embodiments, $R^2$ is aryl (e.g., substituted or unsubstituted aryl, e.g., substituted or unsubstituted phenyl), heteroaryl (e.g., substituted or unsubstituted heteroaryl, e.g., substituted or unsubstituted pyridyl), or aralkyl (e.g., substituted or unsubstituted benzyl). In some embodiments, $R^2$ is phenyl (e.g., substituted or unsubstituted phenyl), pyridyl (e.g., substituted or unsubstituted pyridyl), or benzyl (e.g., substituted or unsubstituted benzyl).

In some embodiments, $R^3$ is hydrogen or alkyl (e.g., $C_1$-$C_6$ alkyl). In some embodiments, $R^3$ is hydrogen, unsubstituted alkyl (e.g., unsubstituted $C_1$-$C_6$ alkyl), or haloalkyl (e.g., —$CF_3$).

In some embodiments, $R^4$ is —OH or halo (e.g., —F).

In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ is aryl (e.g., substituted or unsubstituted aryl, e.g., substituted or unsubstituted phenyl), heteroaryl (e.g., substituted or unsubstituted heteroaryl, e.g., substituted or unsubstituted pyridyl), aralkyl (e.g., substituted or unsubstituted aralkyl, e.g., substituted or unsubstituted benzyl), or heteroaralkyl and $R^3$ is hydrogen or alkyl (e.g., unsubstituted $C_1$-$C_6$ alkyl, e.g., $C_1$-$C_6$ haloalkyl). In some embodiments, $R^2$ is aryl (e.g., substituted or unsubstituted aryl, e.g., substituted or unsubstituted phenyl), heteroaryl(e.g., substituted or unsubstituted heteroaryl, e.g., substituted or unsubstituted pyridyl), aralkyl (e.g., substituted or unsubstituted aralkyl, e.g., substituted or unsubstituted benzyl), or heteroaralkyl and $R^3$ is hydrogen, —$CH_3$, or —$CF_3$.

In some embodiments, $R^1$ is alkyl (e.g., $C_1$-$C_6$ alkyl), $R^2$ is aryl (e.g., substituted or unsubstituted aryl, e.g., substituted or unsubstituted phenyl), heteroaryl (e.g., substituted or unsubstituted heteroaryl, e.g., substituted or unsubstituted pyridyl), aralkyl (e.g., substituted or unsubstituted aralkyl, e.g., substituted or unsubstituted benzyl), or heteroaralkyl, and $R^3$ is hydrogen, —$CH_3$, or —$CF_3$. In some embodiments, $R^1$ is —$CH_3$ or —$CH_2CH_3$, $R^2$ is unsubstituted phenyl, unsubstituted pyridyl, or unsubstituted benzyl, and $R^3$ is hydrogen, —$CH_3$, or —$CF_3$.

In some embodiments, the compound of Formula (I-66) is selected from a compound of Formula (I-A66), (I-B66), or (I-C66):

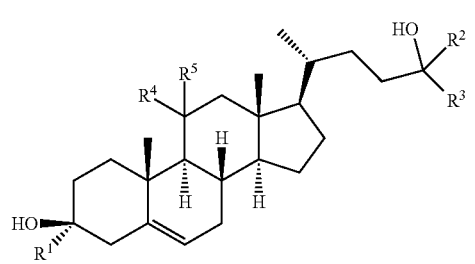
(I-A66)

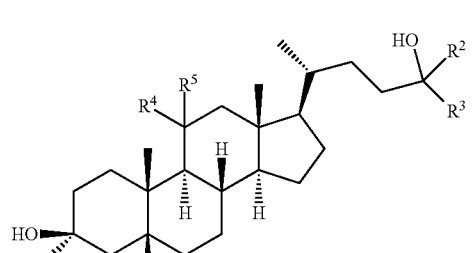
(I-B66)

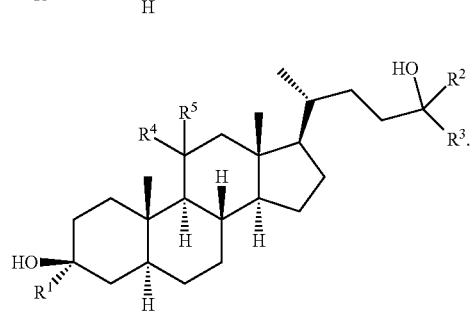
(I-C66)

In some embodiments, the compound of Formula (I-66) is selected from a compound of Formula (I-A66):

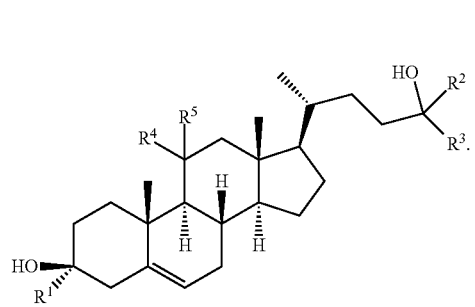
(I-A66)

In some embodiments, the compound is:

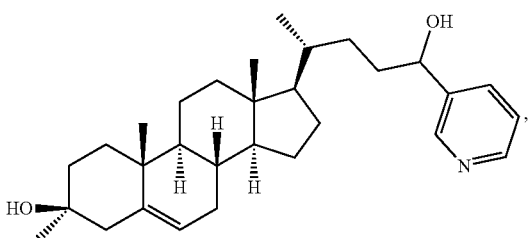

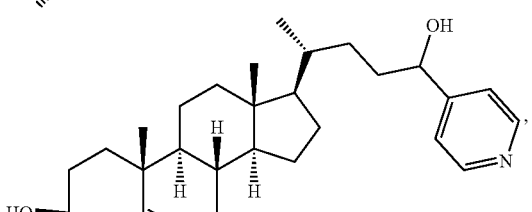

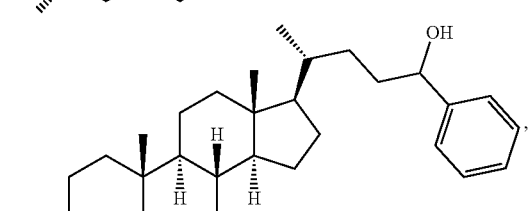

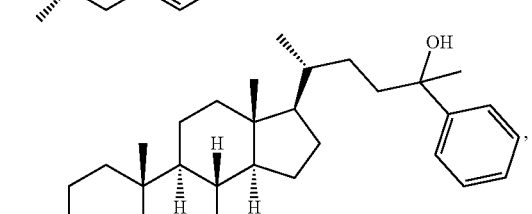

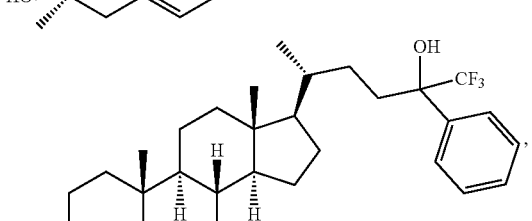

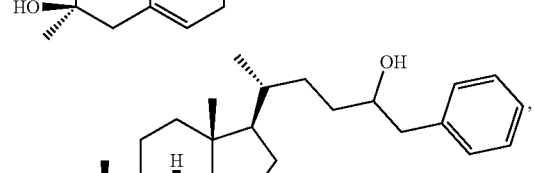

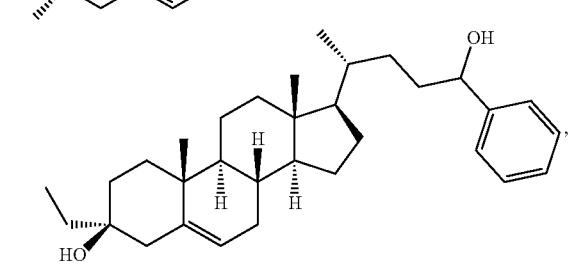

-continued

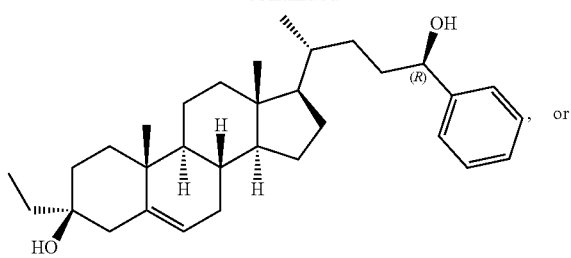, or

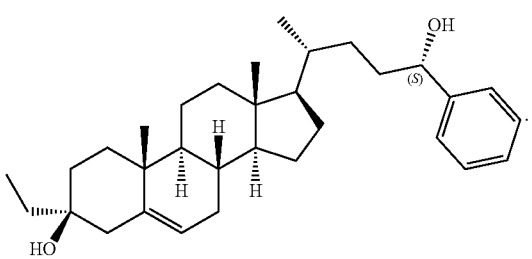.

In one aspect, provided herein are compounds according to Formula (I-61):

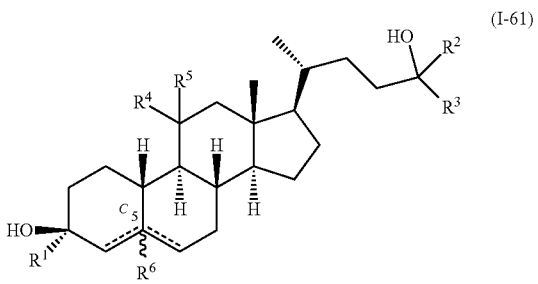
(I-61)

or a pharmaceutically acceptable salt thereof, wherein: $R^1$ is hydrogen or alkyl (e.g., $C_1$-$C_6$ alkyl); each of $R^2$ and $R^3$ is independently hydrogen, alkyl, aryl, heteroaryl, carbocyclyl, or heterocyclyl or $R^2$ and $R^3$, together with the carbon atom to which they are attached for a 3-8 membered ring; each of $R^4$ and $R^5$ is independently hydrogen, halo, or —$OR^C$, wherein $R^C$ is hydrogen or alkyl (e.g., $C_1$-$C_6$ alkyl), or $R^4$ and $R^5$, together with the carbon atom to which they are attached form an oxo group; $R^6$ is absent or hydrogen; and ====== represents a single or double bond, wherein when one of ====== is a double bond, the other ====== is a single bond; when both of ====== are single bonds, then $R^6$ is hydrogen; and when one of ====== is a double bond, $R^6$ is absent; provided that the following compounds are excluded:

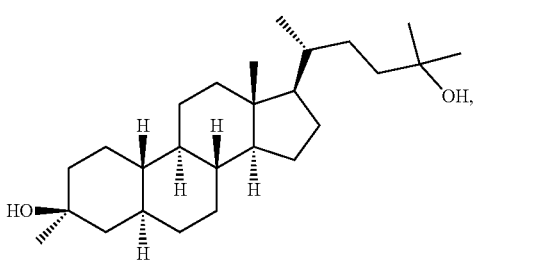

-continued

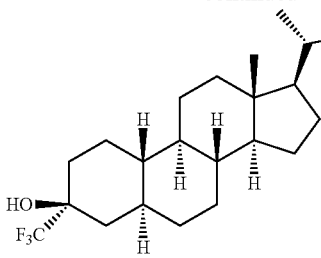,

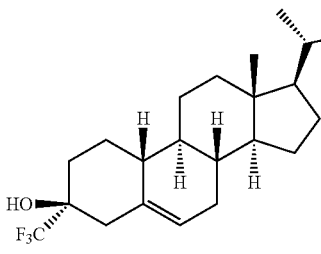,

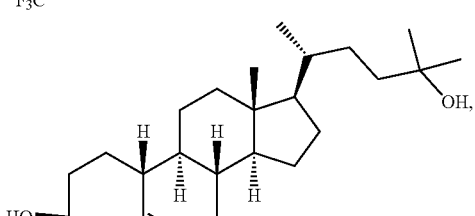,

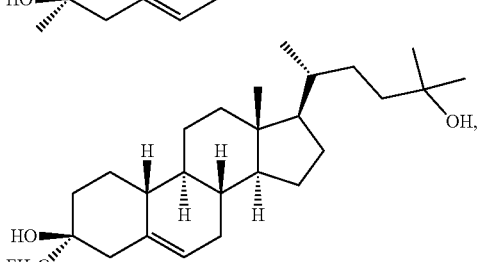,

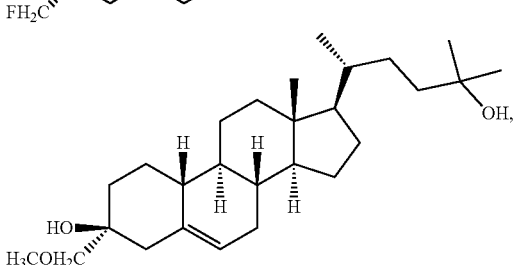,

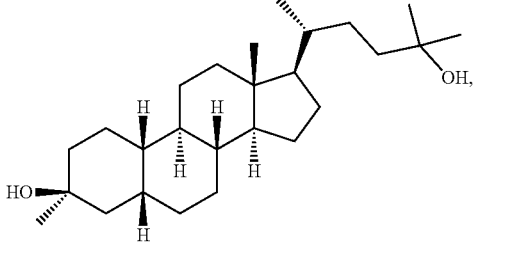,

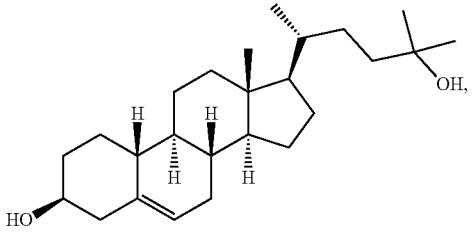

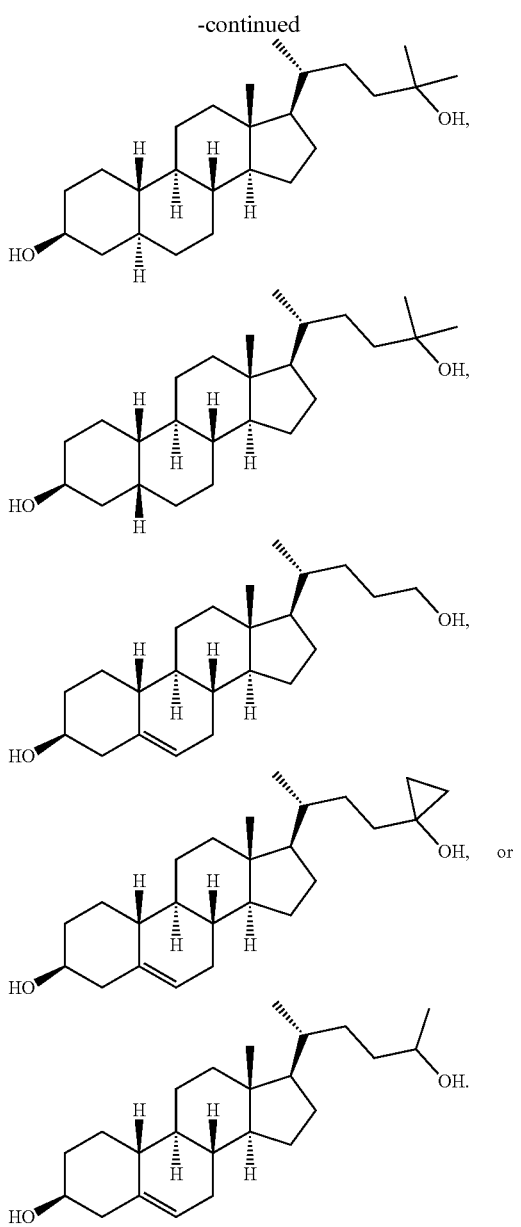

In some embodiments, $R^1$ is alkyl (e.g., $C_1$-$C_6$ alkyl) or hydrogen. In some embodiments, $R^1$ is $C_2$-$C_6$ alkyl (e.g., $C_3$-$C_6$ alkyl) or hydrogen. In some embodiments, $R^1$ is substituted or unsubstituted $C_2$-$C_6$ alkyl (e.g., substituted or unsubstituted $C_3$-$C_6$ alkyl) or hydrogen. In some embodiments, $R^1$ is methyl or ethyl (e.g., substituted or unsubstituted methyl or substituted or unsubstituted ethyl). In some embodiments, $R^1$ is substituted or unsubstituted methyl or substituted or unsubstituted ethyl. In some embodiments, $R^1$ is trifluoromethyl. In some embodiments, $R^1$ is —$CH_2OR^A$, wherein $R^A$ is $C_1$-$C_6$ alkyl (e.g., $C_1$-$C_3$ alkyl).

In some embodiments, $R^2$ is hydrogen or $C_1$-$C_6$ alkyl, (e.g., $C_2$-$C_6$ alkyl). In some embodiments, $R^2$ is hydrogen or substituted or unsubstituted $C_1$-$C_6$ alkyl (e.g., substituted or unsubstituted $C_2$-$C_6$ alkyl). In some embodiments, $R^2$ is hydrogen. In some embodiments, $R^2$ is isopropyl (e.g., substituted or unsubstituted isopropyl). In some embodiments, $R^2$ is substituted or unsubstituted isopropyl. In some embodiments, $R^2$ is haloalkyl (e.g., $C_1$-$C_6$ haloalkyl).

In some embodiments, each of $R^2$ and $R^3$ is independently alkyl (e.g., $C_1$-$C_6$ alkyl) or hydrogen. In some embodiments, each of $R^2$ and $R^3$ is independently substituted or unsubstituted alkyl (e.g., substituted or unsubstituted $C_1$-$C_6$ alkyl) or hydrogen. In some embodiments, $R^2$ and $R^3$, together with the carbon atom to which they are attached for a 3-8 membered ring. In some embodiments, each of $R^2$ and $R^3$ is independently hydrogen or $C_1$-$C_6$ alkyl (e.g. $C_2$-$C_6$ alkyl). In some embodiments, each of $R^2$ and $R^3$ is independently hydrogen or substituted or unsubstituted $C_1$-$C_6$ alkyl, (e.g. substituted or unsubstituted $C_2$-$C_6$ alkyl). In some embodiments, each of $R^2$ and $R^3$ is independently hydrogen or $C_3$-$C_6$ alkyl (e.g., isopropyl). In some embodiments, each of $R^2$ and $R^3$ is independently hydrogen or substituted or unsubstituted $C_3$-$C_6$ alkyl (e.g., substituted or unsubstituted isopropyl).

In some embodiments, $R^4$ is —OH or halo (e.g., —F). In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ and $R^3$ are hydrogen. In some embodiments, $R^2$ is $C_1$-$C_6$ alkyl and $R^3$ is $C_2$-$C_6$ alkyl (e.g., $C_3$-$C_6$ alkyl). In some embodiments, $R^2$ is substituted or unsubstituted $C_1$-$C_6$ alkyl and $R^3$ is substituted or unsubstituted $C_2$-$C_6$ alkyl (e.g., substituted or unsubstituted $C_3$-$C_6$ alkyl). In some embodiments, $R^1$ is ethyl (e.g., substituted or unsubstituted ethyl) and $R^2$ and $R^3$ are methyl (e.g., substituted or unsubstituted methyl). In some embodiments, 10 is substituted or unsubstituted ethyl and $R^2$ and $R^3$ are substituted or unsubstituted methyl. In some embodiments, $R^1$ is ethyl, $R^2$ is isopropyl, and $R^3$ is hydrogen. In some embodiments, $R^1$ is substituted or unsubstituted ethyl, $R^2$ is substituted or unsubstituted isopropyl, and $R^3$ is hydrogen. In some embodiments, $R^1$ is ethyl, $R^2$ is isopropyl, and $R^3$ is methyl. In some embodiments, $R^1$ is substituted or unsubstituted ethyl, $R^2$ is substituted or unsubstituted isopropyl, and $R^3$ is substituted or unsubstituted methyl.

In some embodiments, the compound of Formula (I-61) is a compound of Formula (I-A61), (I-B61), or (I-C61):

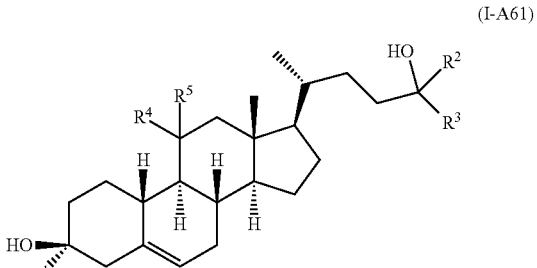

(I-A61)

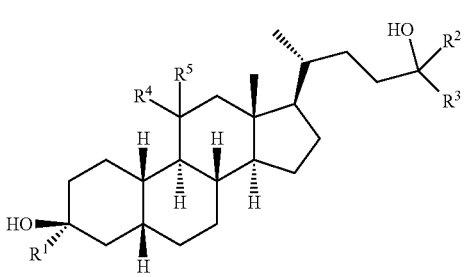

(I-B61)

(I-C61)
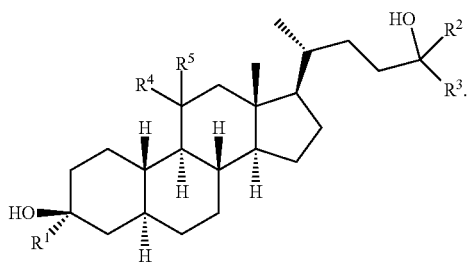
In some embodiments, the compound of Formula (I-61) is selected from a compound of Formula (I-C61):
(I-C61)
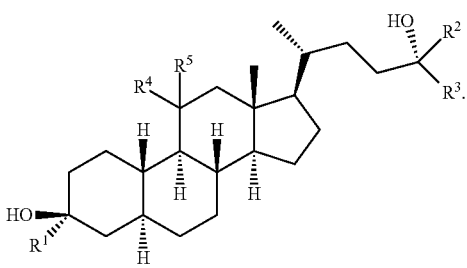
In some embodiments, the compound of Formula (I-61) is selected from a compound of Formula (I-A61):
(I-A61)
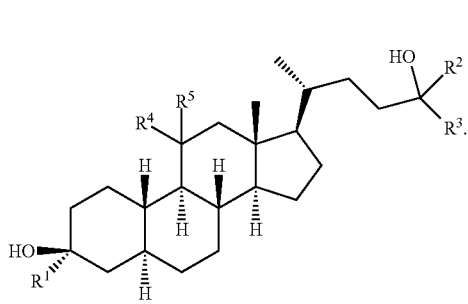
In some embodiments, the compound of Formula (I-61) is selected from a compound of Formula (I-C-i61) or (I-C-ii61):
(I-C-i61)
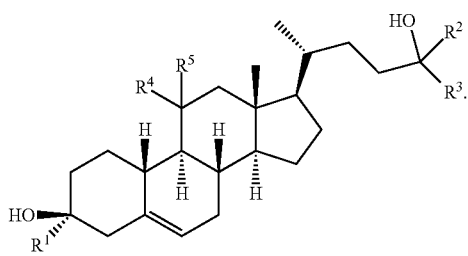
(I-C-ii61)
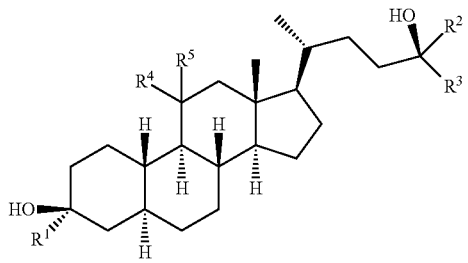
In some embodiments, the compound is:
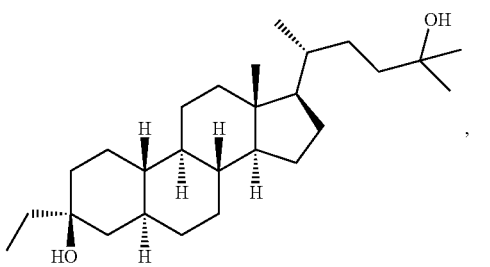
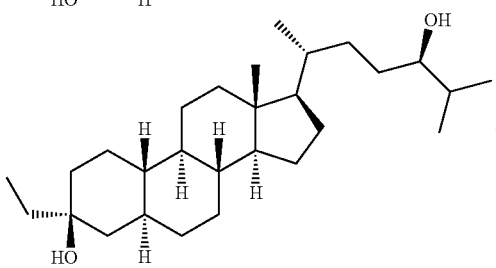
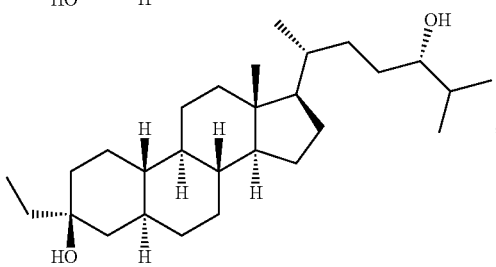
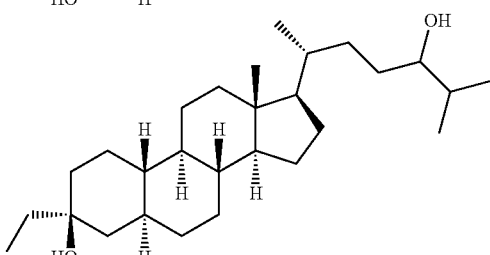
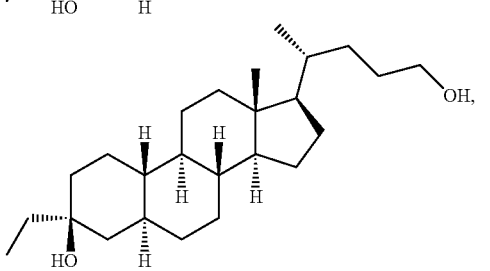

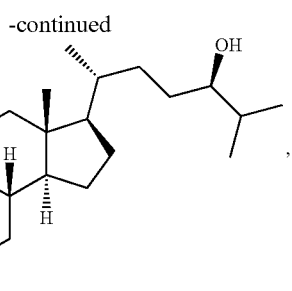

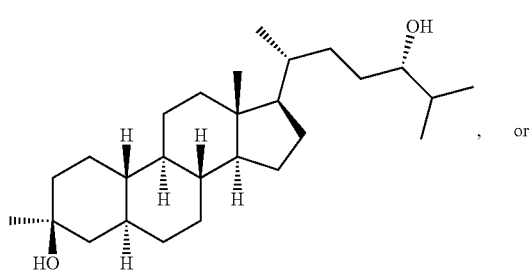

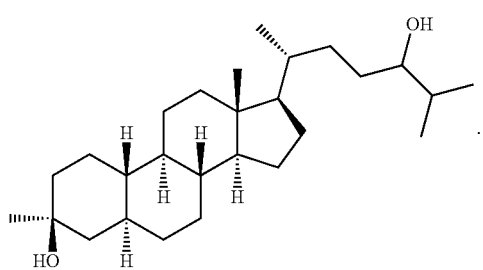

In one aspect, the present invention features a compound of Formula (I-62):

(I-62)

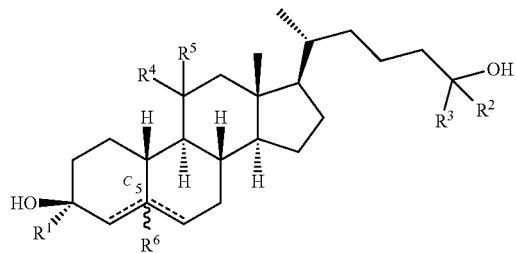

or a pharmaceutically acceptable salt thereof, wherein: $R^1$ is hydrogen or alkyl (e.g., $C_1$-$C_6$ alkyl); each of $R^2$ and $R^3$ is independently hydrogen, alkyl, carbocyclyl, or heterocyclyl or $R^2$ and $R^3$, together with the carbon atom to which they are attached, form a 3-8 membered ring; each of $R^4$ and $R^5$ is independently hydrogen, halo, or —$OR^C$, wherein $R^C$ is hydrogen or alkyl (e.g., $C_1$-$C_6$ alkyl), or $R^4$ and $R^5$, together with the carbon atom to which they are attached form an oxo group; $R^6$ is absent or hydrogen; and ═════ represents a single or double bond, wherein when one of ═════ is a double bond, the other ═════ is a single bond; when both of ═════ are single bonds, then $R^6$ is hydrogen; and when one of ═════ is a double bond, $R^6$ is absent.

In some embodiments, $R^1$ is alkyl (e.g., $C_1$-$C_6$ alkyl). In some embodiments, $R^1$ is substituted or unsubstituted $C_2$-$C_6$ alkyl (e.g., substituted or unsubstituted $C_3$-$C_6$ alkyl). In some embodiments, $R^1$ is methyl or ethyl (e.g., substituted or unsubstituted methyl or substituted or unsubstituted ethyl). In some embodiments, $R^1$ is substituted or unsubstituted methyl or substituted or unsubstituted ethyl. In some embodiments, $R^1$ is trifluoromethyl. In some embodiments, $R^1$ is —$CH_2OR^4$, wherein $R^4$ is $C_1$-$C_6$ alkyl (e.g., $C_1$-$C_3$ alkyl).

In some embodiments, $R^2$ is hydrogen or $C_1$-$C_6$ alkyl, (e.g., $C_2$-$C_6$ alkyl). In some embodiments, $R^2$ is hydrogen or substituted or unsubstituted $C_1$-$C_6$ alkyl (e.g., substituted or unsubstituted $C_2$-$C_6$ alkyl). In some embodiments, $R^2$ is haloalkyl, (e.g., $C_1$-$C_6$ haloalkyl).

In some embodiments, each of $R^2$ and $R^3$ is independently hydrogen or $C_1$-$C_6$ alkyl (e.g. $C_2$-$C_6$ alkyl). In some embodiments, each of $R^2$ and $R^3$ is independently hydrogen or substituted or unsubstituted $C_1$-$C_6$ alkyl (e.g. substituted or unsubstituted $C_2$-$C_6$ alkyl). In some embodiments, each of $R^2$ and $R^3$ is independently alkyl (e.g., $C_1$-$C_6$ alkyl) or hydrogen. In some embodiments, each of $R^2$ and $R^3$ is independently substituted or unsubstituted alkyl (e.g., substituted or unsubstituted $C_1$-$C_6$ alkyl) or hydrogen. In some embodiments, $R^2$ and $R^3$, together with the carbon atom to which they are attached, form a 3-8 membered ring.

In some embodiments, $R^4$ is —OH or halo (e.g., —F). In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^1$ is ethyl (e.g., substituted or unsubstituted ethyl) and $R^2$ and $R^3$ are methyl (e.g., substituted or unsubstituted methyl). In some embodiments, $R^1$ is substituted or unsubstituted ethyl and $R^2$ and $R^3$ are substituted or unsubstituted methyl.

In some embodiments, the compound of Formula (I-62) is a compound of Formula (I-A62), (I-B62), or (I-C62):

(I-A62)

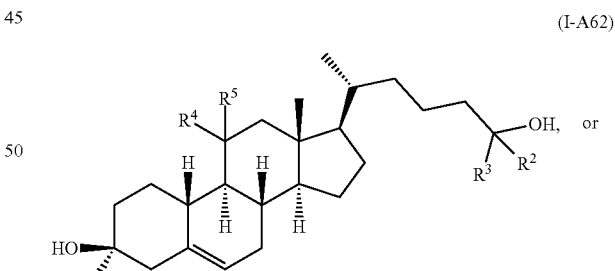

(I-B62)

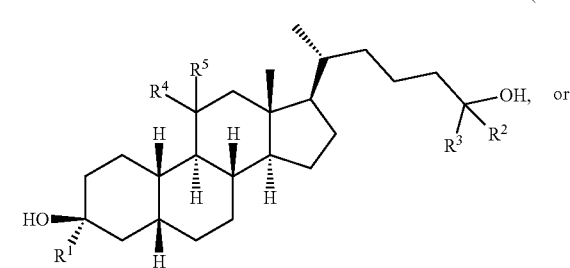

In some embodiments, the compound of Formula (I-62) is selected from a compound of Formula (I-C62):

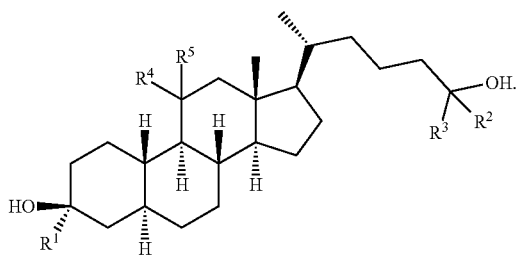
(I-C62)

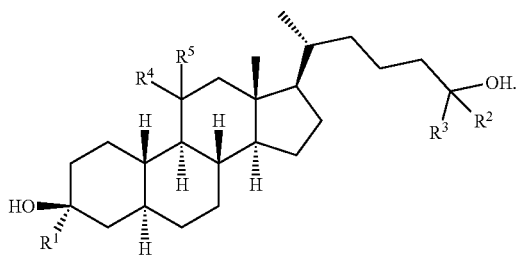
(I-C62)

In some embodiments, the compound of Formula (I-62) is selected from a compound of Formula (I-A62):

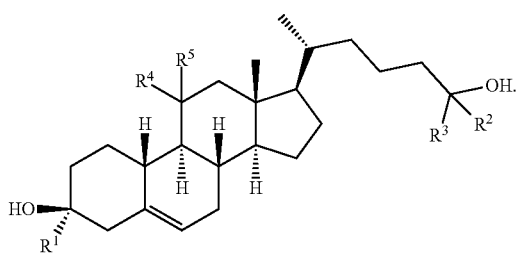
(I-A62)

In some embodiments, $R^1$ is ethyl (e.g., substituted or unsubstituted ethyl) and $R^2$ and $R^3$ are methyl (e.g., substituted or unsubstituted methyl). In some embodiments, $R^1$ is substituted or unsubstituted ethyl and $R^2$ and $R^3$ are substituted or unsubstituted methyl.

In some embodiments, the compound of Formula (I-62) is selected from a compound of Formula (I-C-i62) or (I-C-ii62):

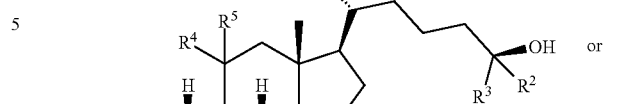
(I-C-i62)

or

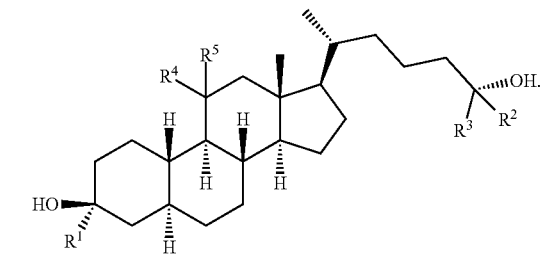
(I-C-ii62)

In some embodiments, the compound is

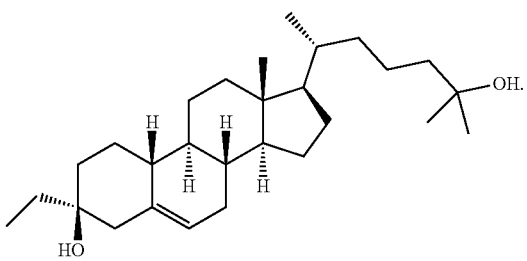

In one aspect, provided herein are compounds according to Formula (I-60):

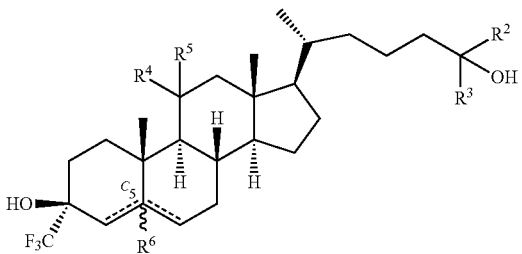
(I-60)

or a pharmaceutically acceptable salt thereof, wherein: each of $R^2$ and $R^3$ is independently hydrogen, alkyl (e.g., $C_1$-$C_6$ alkyl), carbocyclyl, heterocyclyl, aryl, or heteroaryl, or $R^2$ and $R^3$, together with the carbon atom to which they are attached form a 3-8 membered ring; each of $R^4$ and $R^5$ is independently hydrogen, halo, or —$OR^C$, wherein $R^C$ is hydrogen or alkyl (e.g., $C_1$-$C_6$ alkyl), or $R^4$ and $R^5$, together with the carbon atom to which they are attached form an oxo group; $R^6$ is absent or hydrogen; and ===== represents a single or double bond, wherein when one of ===== is a double bond, the other ===== is a single bond; when both of ------ are single bonds, then $R^6$ is hydrogen; and when one of the ------ is a double bond, $R^6$ is absent.

In some embodiments, $R^2$ is alkyl (e.g., $C_1$-$C_6$ alkyl) or hydrogen. In some embodiments, $R^2$ is haloalkyl (e.g., $C_1$-$C_6$ haloalkyl). In some embodiments, $R^2$ is substituted or unsubstituted alkyl (e.g., substituted or unsubstituted $C_1$-$C_6$ alkyl) or hydrogen. In some embodiments, $R^2$ is aryl or heteroaryl.

In some embodiments, each of $R^2$ and $R^3$ is independently alkyl (e.g., $C_1$-$C_6$ alkyl) or hydrogen. In some embodiments, each of $R^2$ and $R^3$ is independently substituted or unsubstituted alkyl (e.g., substituted or unsubstituted $C_1$-$C_6$ alkyl) or hydrogen. In some embodiments, each of $R^2$ and $R^3$ is independently unsubstituted alkyl (e.g., unsubstituted $C_1$-$C_6$ alkyl) or hydrogen. In some embodiments, each of $R^2$ and $R^3$ is independently $C_1$-$C_6$ haloalkyl (e.g., trifluoromethyl) or hydrogen. In some embodiments, each of $R^2$ and $R^3$ is independently aryl or heteroaryl. In some embodiments, $R^2$ and $R^3$, together with the carbon atom to which they are attached form a 3-membered ring.

In some embodiments, $R^2$ and $R^3$, together with the carbon atom to which they are attached form a cyclopropane. In some embodiments, $R^2$ and $R^3$, together with the carbon atom to which they are attached form a 3-8 membered carbocyclic or heterocyclic ring.

In some embodiments, $R^2$ is carbocyclyl or heterocyclyl and $R^3$ is hydrogen. In some embodiments, $R^2$ is trifluoromethyl and $R^3$ is hydrogen. In some embodiments, $R^2$ is aryl or heteroaryl and $R^3$ is hydrogen. In some embodiments, $R^2$ and $R^3$ are methyl (e.g., substituted or unsubstituted methyl). In some embodiments, $R^2$ and $R^3$ is substituted methyl. In some embodiments, $R^2$ and $R^3$ is unsubstituted methyl.

In some embodiments, $R^4$ is —OH or halo (e.g., —F). In some embodiments, $R^4$ and $R^5$, together with the carbon atom to which they are attached form an oxo group.

In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, the compound of Formula (I-60) is selected from a compound of Formula (I-A60), (I-B60), or (I-C60):

(I-A60)

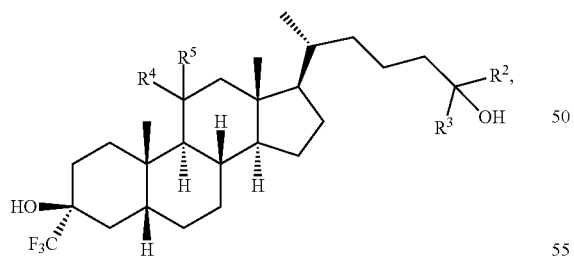

(I-B60)

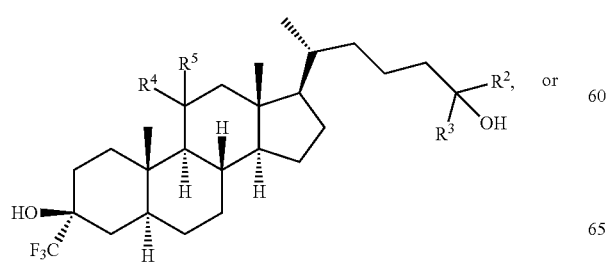

(I-C60)

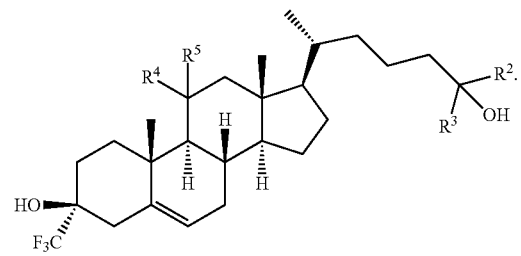

In some embodiments, the compound of Formula (I-60) is selected from a compound of Formula (I-B60):

(I-B60)

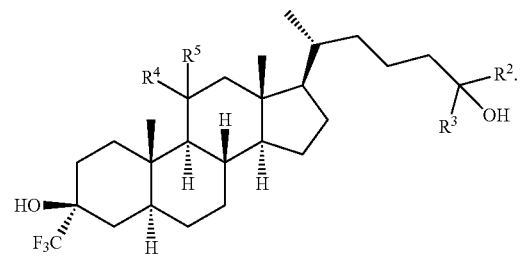

In some embodiments, at least one of $R^2$ and $R^3$ is $C_1$-$C_6$ alkyl, carbocyclyl, heterocyclyl, aryl, or heteroaryl; or $R^2$ and $R^3$, together with the carbon atom to which they are attached, form a 3-8 membered ring.

In some embodiments, $R^2$ is methyl and $R^3$ is hydrogen. In some embodiments, $R^2$ is unsubstituted methyl and $R^3$ is hydrogen. In some embodiments, $R^2$ and $R^3$ are hydrogen.

In some embodiments, the compound is:

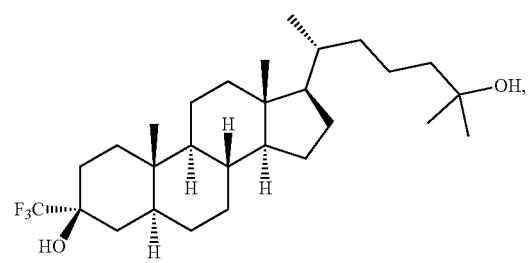

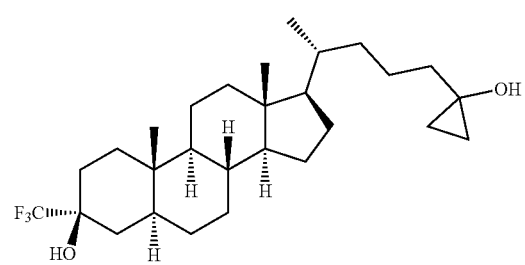

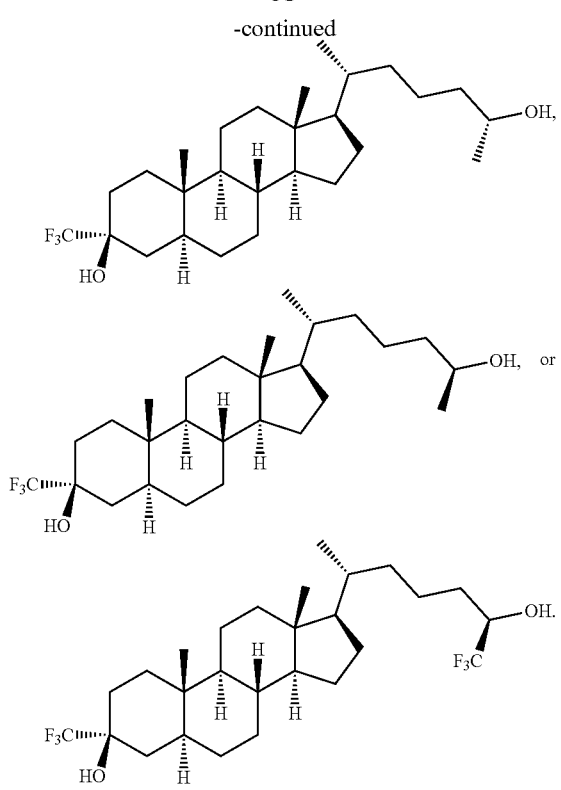

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, $^{18}$O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In another aspect, the invention provides a pharmaceutical composition comprising a pharmaceutically acceptable carrier and an effective amount of a compound of Formula I-59, I-66, I-61, I-62, or I-60.

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of Formula I-59, I-66, I-61, I-62, or I-60 or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound of Formula I-59, I-66, I-61, I-62, or I-60. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of Formula I-59, I-66, I-61, I-62, or I-60. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of Formula I-59, I-66, I-61, I-62, or I-60, or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of Formula I-59, I-66, I-61, I-62, or I-60, or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid: A compound of Formula I-59, I-66, I-61, I-62, or I-60, or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of Formula I-59, I-66, I-61, I-62, or I-60, or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of Formula I-59, I-66, I-61, I-62, or I-60, or pharmaceutically acceptable salt thereof, may be dissolved or suspended in a buffered sterile saline injectable aqueous medium to a concentration of approximately 5 mg/mL.

Exemplary Formulation 6—Tablets: A compound of Formula I-59, I-66, I-61, I-62, or I-60, or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of Formula I-59, I-66, I-61, I-62, or I-60, or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of Formula I-59, I-66, I-61, I-62, or I-60, or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of Formula I-59, I-66, I-61, I-62, or I-60, or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of Formula I-59, I-66, I-61, I-62, or I-60, or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula I-59, I-66, I-61, I-62, or I-60, and pharmaceutically acceptable salts thereof, as described herein, may be used in methods of effecting positive allosteric modulation of an PMDA receptor in a subject in need thereof, comprising administering to the subject a compound of of effecting negative allosteric modulation of an NMDA receptor in a subject in need thereof, comprising administering to the subject a compound of Formula.

Compounds of the present invention, e.g., a compound of Formula I-59, I-66, I-61, I-62, or I-60, and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula I-59, I-66, I-61, I-62, or I-60, and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound of Formula I-59, I-66, I-61, I-62, or I-60, or pharmaceutically acceptable salt thereof, acts as a negative allosteric modulator (NAM) of NMDA, and inhibit NMDA receptor function. In certain embodiments, the present invention, e.g., a compound of Formula I-59, I-66, I-61, I-62, or I-60, or pharmaceutically acceptable salt thereof, acts as a positive allosteric modulator (PAM) of NMDA, and potentiate NMDA receptor function. In certain embodiments, the compound of Formula I-59, I-66, I-61, I-62, or I-60, or pharmaceutically acceptable salt thereof, blocks or reduces the potentiation or inhibition of NMDA receptor function by a naturally-occurring substrate. Such compounds do not act as negative allosteric modulators (NAMs) or positive allosteric modulators (PAMs) of NMDA. In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, or colitis. In some embodiments, the disorder is inflammatory bowel disease.

Exemplary conditions related to NMDA-modulation include, but are not limited to, gastrointestinal (GD disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary conditions (e.g., CNS conditions) related to NMDA-modulation include, but are not limited to, adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, Smith-Lemli-Opitz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In certain embodiments, compounds of the present invention, e.g., a compound of Formula I-59, I-66, I-61, I-62, or I-60, or pharmaceutically acceptable salt thereof, can be used to induce sedation or anesthesia.

In certain embodiments, the compound of Formula I-59, I-66, I-61, I-62, or I-60, or pharmaceutically acceptable salt thereof, is useful in the treatment or prevention of adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, Smith-Lemli-Opitz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In certain embodiments, the compound of Formula I-59, I-66, I-61, I-62, or I-60, or pharmaceutically acceptable salt thereof, is useful in the treatment or prevention of adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), substance abuse-related disorders, dissociative disorders, eating disorders mood disorders (including depression (e.g., postpartum depression), bipolar disorder, dysthymic disorder, suicidality), schizophrenia or other psychotic disorders (including schizoaffective disorder), personality disorders (including obsessive-compulsive personality disorder), autism spectrum disorders (including those involving mutations to the Shank group of proteins (e.g., Shank3)), or post-partum psychosis.

In certain embodiments, the compound of Formula I-59, I-66, I-61, I-62, or I-60, or pharmaceutically acceptable salt thereof, is useful in the treatment or prevention of neurodevelopmental disorders (including Rett syndrome), multiple sclerosis, sterol synthesis disorders, Smith-Lemli-Opitz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), syndromes associated with high titers of anti-NMDA receptor antibodies (including anti-NMDA receptor encephalitis), neurodegenerative disorders, neuroinflammation, neuropsychiatric lupus, Niemann-Pick C disorder, or tinnitus.

In some embodiments, a compound of the invention, e.g., a compound of Formula I-59, I-66, I-61, I-62, or I-60 that acts as a PAM of NMDA receptor function can be useful in the treatment or prevention of conditions (e.g., CNS-related conditions) including schizophrenia or other psychotic disorders (including schizoaffective disorder), sleep disorders (including insomnia), autism spectrum disorders (including those involving mutations to the Shank group of proteins (e.g., Shank3)), multiple sclerosis, movement disorders (including Huntington's disease and Parkinson's disease), attention deficit disorder, attention deficit hyperactivity disorder, metabolic encephalopathies (including phenylketoneuria), post-partum psychosis, and syndromes associated with high titers or anti-NMDA receptor antibodies (including anti-NMDA receptor encephalitis).

In some embodiments, a compound of the invention, e.g., a compound of Formula I-59, I-66, I-61, I-62, or I-60, that acts as a NAM of NMDA receptor function can be useful in the treatment or prevention of conditions (e.g., CNS-related conditions) including anxiety disorders (including obsessive-compulsive disorder, posttraumatic stress disorder, social phobia, generalized anxiety disorder), mood disorders (including depression (e.g., postpartum depression), bipolar disorder, dysthymic disorder, suicidality), personality disorders (including obsessive-compulsive personality disorder), neurodevelopmental disorders (including Rett syndrome), pain (including acute and chronic pain), seizure disorders (including status epilepticus and monogenic forms of epilepsy such as Dravet's disease, and Tuberous Sclerosis Complex (TSC)), stroke, traumatic brain injury, adjustment disorders, neuropsychiatric lupus, and tinnitus.

In some embodiments, a compound of the invention, e.g., a compound of Formula I-59, I-66, I-61, I-62, or I-60, that acts as a PAM or a NAM of NMDA receptor function can be useful in the treatment or prevention of conditions (e.g., CNS-related conditions) including cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), sterol synthesis disorders, and eating disorders.

In another aspect, provided is a method of treating or preventing brain excitability in a subject susceptible to or afflicted with a condition associated with brain excitability, comprising administering to the subject an effective amount of a compound of the present invention, e.g., a compound of Formula I-59, I-66, I-61, I-62, or I-60, or a pharmaceutically acceptable salt thereof.

In yet another aspect, the present invention provides a combination of a compound of the present invention, e.g., a compound of Formula I-59, I-66, I-61, I-62, or I-60, or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and Parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor is an involuntary, at times rhythmic, muscle contraction and relaxation that can involve oscillations or twitching of one or more body parts (e.g., hands, arms, eyes, face, head, vocal folds, trunk, legs). Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor. Other forms of tremor include cerebellar tremor or intention tremor, dystonic tremor, essential tremor, orthostatic tremor, parkinsonian tremor, physiological tremor, psychogenic tremor, or rubral tremor.

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occur in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face.

Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myoclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part.

Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Mood Disorders

Also provided herein are methods for treating a mood disorder, for example clinical depression, postnatal depression or postpartum depression, perinatal depression, atypical depression, melancholic depression, psychotic major depression, cationic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior.

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

Anxiety Disorders

Provided herein are methods for treating anxiety disorders. Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Epilepsy

Epilepsy is a brain disorder characterized by repeated seizures over time. Types of epilepsy can include, but are not limited to generalized epilepsy, e.g., childhood absence epilepsy, juvenile myoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

Abbreviations

PCC: pyridinium chlorochromate; t-BuOK: potassium tert-butoxide; 9-BBN: 9-borabicyclo[3.3.1]nonane; Pd(t-Bu$_3$P)$_2$: bis(tri-tert-butylphosphine)palladium(0); AcCl: acetyl chloride; i-PrMgCl: Isopropylmagnesium chloride; TBSCl: tert-Butyl(chloro)dimethylsilane; (i-PrO)$_4$Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF$_3$: (Trifluoromethyl)trimethylsilane; Ts: p-toluenesulfonyl; Bu: butyl; Ti(OiPr)$_4$: tetraisopropoxytitanium; LAH: Lithium Aluminium Hydride; LDA: lithium diisopropylamide; LiOH.H$_2$O: lithium hydroxide hydrates; MAD: methyl aluminum bis(2,6-di-t-butyl-4-methylphenoxide); MeCN: acetonitrile; NBS: N-bromosuccinimide; Na$_2$SO$_4$: sodium sulfate; Na$_2$S$_2$O$_3$: sodium thiosulfate; PE: petroleum ether; MeCN: acetonitrile; MeOH: methanol; Boc: t-butoxycarbonyl; MTBE: methyl tert-butyl ether; DMSO: dimethylsulfoxide; DMF: N,N-dimethylformamide; 9-BBN: 9-borabicyclo[3.3.1]nonane; MePPh$_3$Br: bromo(methyl)triphenylphosphorane; MeMgBr: Methylmagnesium bromide; MeLi: methyllithium; NaHCO$_3$: sodium bicarbonate.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Unless otherwise indicated, the stereochemistry assigned herein (e.g., the assignment of "R" or "S" to the C24 position of the steroid) may be tentatively (e.g., randomly) assigned. For example, a C24 position may be drawn in the "R" configuration when the absolute configuration is "S." A C24 position may also be drawn in the "S" configuration when the absolute configuration is "R."

The absolute configuration of an asymmetric center can be determined using methods known to one skilled in the art. In some embodiments, the absolute configuration of an asymmetric center in a compound can be elucidated from the X-ray single-crystal structure of the compound. In some embodiments, the absolute configuration of an asymmetric center elucidated by the X-ray crystal structure of a compound can be used to infer the absolute configuration of a corresponding asymmetric center in another compound obtained from the same or similar synthetic methodologies. In some embodiments, the absolute configuration of an asymmetric center elucidated by the X-ray crystal structure of a compound can be used to infer the absolute configuration of a corresponding asymmetric center in another compound coupled with a spectroscopic technique, e.g., NMR spectroscopy, e.g., $^1$H NMR spectroscopy or $^{19}$F NMR spectroscopy.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative oxysterols that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

¹H-NMR reported herein (e.g., for the region between δ (ppm) of about 0.5 to about 4 ppm) will be understood to be an exemplary interpretation of the NMR spectrum (e.g., exemplary peak integratations) of a compound. Exemplary general method for preparative HPLC: Column: Waters RBridge prep 10 μM C18, 19*250 mm. Mobile phase: acetonitrile, water ($NH_4HCO_3$) (30 L water, 24 g $NH_4HCO_3$, 30 mL $NH_3.H_2O$). Flow rate: 25 mL/min.

Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6*50 mm, 3.5 μm at 45 C.

Exemplary general method for SFC: Column: CHIRALPAK® AD CSP (250 mm*30 mm, 10 μm), Gradient: 45% B, A=$NH_3H_2O$, B=MeOH, flow rate: 60 mL/min. For example, AD_3_EtOH_DEA5_40_25ML would indicate: "Column: Chiralpak AD-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp: 35° C.".

Example 1: NMDA Potentiation

NMDA Potentiation
Whole-Cell Patch Clamp of Mammalian Cells (Ionworks Barracuda (IWB))

The whole-cell patch-clamp technique was used to investigate the effects of compounds on GlunN1/GluN2A glutamate receptors expressed in mammalian cells.

HEK293 cells were transformed with adenovirus 5 DNA and transfected with cDNA encoding the human GRIN1/GRIN2A genes. Stable transfectants were selected using G418 and Zeocin-resistance genes incorporated into the expression plasmid and selection pressure maintained with G418 and Zeocin in the medium. Cells were cultured in Dulbecco's Modified Eagle Medium/Nutrient Mixture (D-MEM/F-12) supplemented with 10% fetal bovine serum, 100 μg/ml penicillin G sodium, 100 μg/ml streptomycin sulphate, 100 μg/ml Zeocin, 5 μg/ml blasticidin and 500 μg/ml G418.

Test article effects were evaluated in 8-point concentration-response format (4 replicate wells/concentration). All test and control solutions contained 0.3% DMSO and 0.01% Kolliphor® EL (C5135, Sigma). The test article formulations were loaded in a 384-well compound plate using an automated liquid handling system (SciClone ALH3000, Caliper LifeScienses). The measurements were performed using Ion Works Barracuda platform following this procedure:
Electrophysiological Procedures:
Intracellular solution (mM): 50 mM CsCl, 90 mM CsF, 2 mM $MgCl_2$, 5 mM EGTA, 10 mM HEPES. Adjust to pH 7.2 with CsOH.
Extracellular solution, HB-PS (composition in mM): NaCl, 137; KCl, 1.0; $CaCl_2$, 5; HEPES, 10; Glucose, 10; pH adjusted to 7.4 with NaOH (refrigerated until use).
Holding potential: −70 mV, potential during agonist/PAM application: −40 mV.
Recording Procedure:
Extracellular buffer is loaded into the PPC plate wells (11 μL per well). Cell suspension will be pipetted into the wells (9 μL per well) of the PPC planar electrode.
Whole-cell recording configuration is established via patch perforation with membrane currents recorded by on-board patch clamp amplifiers.
Two recordings (scans) are performed. First, during pre-application of test article alone (duration of pre-application—5 min) and second, during test articles and agonist ($EC_{20}$ L-glutamate and 30 μM glycine) co-application to detect positive modulatory effects of the test article.

Test Article Administration: The first pre-application consists of the addition of 20 μL of 2× concentrated test article solution and, second, of 20 μL of 1× concentrated test article and agonist at 10 μL/s (2 second total application time).

Example 2: NAM and PAM

Whole-Cell Patch Clamp of Mammalian Cells (Ionworks Barracuda (IWB))

The whole-cell patch-clamp technique was used to investigate the effects of positive allosteric modulating activity of test compounds on GlunN1/GluN2A and GluN2B glutamate receptors expressed in mammalian cells.

HEK293 cells were transformed with adenovirus 5 DNA and transfected with cDNA encoding the human GRIN1/GRIN2A genes. Stable transfectants were selected using G418 and Zeocin-resistance genes incorporated into the expression plasmid and selection pressure maintained with G418 and Zeocin in the medium. Cells were cultured in Dulbecco's Modified Eagle Medium/Nutrient Mixture (D-MEM/F-12) supplemented with 10% fetal bovine serum, 100 μg/ml penicillin G sodium, 100 μg/ml streptomycin sulphate, 100 μg/ml Zeocin, 5 μg/ml blasticidin and 500 μg/ml G418.

Test article effects were evaluated in 8-point concentration-response format (4 replicate wells/concentration). All test and control solutions contained 0.3% DMSO and 0.01% Kolliphor® EL (C5135, Sigma). The test article formulations were loaded in a 384-well compound plate using an automated liquid handling system (SciClone ALH3000, Caliper LifeScienses). The measurements were performed using Ion Works Barracuda platform following this procedure:
Electrophysiological Procedures:
  a) Intracellular solution (mM): 50 mM CsCl, 90 mM CsF, 2 mM $MgCl_2$, 5 mM EGTA, 10 mM HEPES. Adjust to pH 7.2 with CsOH.
  b) Extracellular solution, HB-PS (composition in mM): NaCl, 137; KCl, 1.0; $CaCl_2$), 5; HEPES, 10; Glucose, 10; pH adjusted to 7.4 with NaOH (refrigerated until use).
  c) Holding potential: −70 mV, potential during agonist/PAM application: −40 mV.
Recording Procedure:
  a) Extracellular buffer will be loaded into the PPC plate wells (11 μL per well). Cell suspension will be pipetted into the wells (9 μL per well) of the PPC planar electrode.
  b) Whole-cell recording configuration will be established via patch perforation with membrane currents recorded by on-board patch clamp amplifiers.
  c) Two recordings (scans) will be performed. First, during pre-application of test article alone (duration of pre-application—5 mM) and second, during test articles and agonist ($EC_{20}$ L-glutamate and 30 μM glycine) co-application to detect positive modulatory effects of the test article.
Test Article Administration: The first pre-application will consist of the addition of 20 μL of 2× concentrated test article solution and, second, of 20 μL of 1× concentrated test article and agonist at 10 μL/s (2 second total application time).

Potentiating Effect of Positive Allosteric Modulators (PAM) on the Channel

Potentiating effect of positive allosteric modulators (PAM) on the channel will be calclulated as % activation=$(I_{PAM}/I_{EC10\text{-}30})\times 100\% - 100\%$ where $I_{PAM}$ will be the L-glutamate $EC_{10\text{-}30}$-elicited current in presence of various concentrations of test articles and $I_{EC20}$ will be the mean current elicited with L-glutamate $EC_{20}$. PAM concentration-response data will be fitted to an equation of the form:

% Activation=% L-glutamate $EC_{20}$+{(% MAX−% L-glutamate $EC_{20}$)/[1+([Test]/$EC_{50}$)$^N$]}, where [Test] will be the concentration of PAM (test article), $EC_{50}$ will be the concentration of PAM producing half-maximal activation, N will be the Hill coefficient, % L-glutamate $EC_{20}$ will be the percentage of the current Elicited with L-glutamate $EC_{20}$, % MAX is the percentage of the current activated with the highest dose of PAM co-admitted with L-glutamate $EC_{20}$ and % Activation will be the percentage of the current elicited with L-glutamate $EC_{10\text{-}30}$ at each PAM concentration.

The maximal amplitude of the evoked currents are measured and defined as Peak Current Amplitude (PCA).

Automated Patch-Clamp System (QPatch HTX):

In this study, HEK 293 cells stably transfected with glutamate-activated channels of the GRIN1/2A subtype will be used together with submaximal NMDA concentrations (300 μM NMDA, co-application with 8 μM Glycine) to investigate the negative allosteric modulation of the test compounds.

Cell Culture

In general, cells will be passaged at a confluence of about 80% to-90%. For electrophysiological measurements cells will be harvested at a confluence of about 80% to 90% from sterile culture flasks containing culture complete medium. Cells will be transferred as suspension in PBS to the QPatch 16X or QPatch HTX system to the centrifuge/washer directly.

Standard Laboratory Conditions: Cells will be incubated at 37° C. in a humidified atmosphere with 5% $CO_2$ (rel. humidity about 95%).

Culture media: The cells will be continuously maintained in and passaged in sterile culture flasks containing a 1:1 mixture of Dulbecco's modified eagle medium and nutrient mixture F-12 (D-MEM/F-12 1×, liquid, with L-Glutamine) supplemented with 10% fetal bovine serum, 1% Penicillin/Streptomycin solution, and 50 μM AP-5 blocker.

Antibiotics: The complete medium as indicated above is supplemented with 100 μg/mL hygromycin, 15 μg/mL blasticidin and 1 μg/mL puromycin.

Induction of Expression: 2.5 μg/mL tetracycline is added 24 h before start of experiments.

Dose Formulation

Dose levels are in terms of test compounds, as supplied. Vehicle will be added to achieve a stock concentration of 10 mM (storage at −10° C. to −30° C.). A further stock solutions of 1.0 μM will be prepared in DMSO. Details of stock solution usage (thawing, dose formulations) will be documented in the raw data. The time period of stock solution usage will be detailed in the report.

Test Compound Concentrations

Dose levels are in terms of test compounds, as supplied. Vehicle will be added to achieve a stock concentration of 10 mM (storage at −10° C. to −30° C.). A further stock solutions of 1.0 mM will be prepared in DMSO. Details of stock solution usage (thawing, dose formulations) will be documented in the raw data. The time period of stock solution usage will be detailed in the report.

One test concentration of 1.0 μM will be tested.

All test solutions will be prepared by diluting the stock solutions with either Mg-free bath solution only or Mg-free bath solution containing NMDA (300 μM) and glycine (8.0 μM) shortly prior to the electrophysiological experiments and kept at room temperature (19° C. to 30° C.) when in use. 0.1% DMSO will be used as vehicle.

Frequency of preparation: For each test concentration, fresh solutions of test compounds will be prepared every day.

Stability of dose formulation: All preparation times will be documented in the raw data. Any observations regarding instability of test compounds will be mentioned in the raw data.

Storage of dose formulation: On the day of experimentation dose formulations will be maintained at room temperature (19° C. to 30° C.) when in use.

Bath Solutions

For preparing the experiments and for formation of the giga-ohm-seal, the following standard bath solution will be used:

Sodium Chloride: 137 mM; Potassium Chloride: 4 mM; Calcium Chloride: 1.8 mM;

Magnesium Chloride: 1 mM; HEPES: 10 mM; D-Glucose: 10 mM; Cremophor: 0.02%; pH (NaOH): 7.4

The 1× bath solution will be prepared by diluting 10× bath solution without Glucose and 100× Glucose solution with water at least every 7 days. Both stock solutions have been prepared prior to the experimental start of the present study and stored at 1° C. to 9° C. (10× bath solution) or −10° C. to −30° (100× Glucose solution). The batch number(s) of the bath solution(s) used in the experiments will be documented in the raw data. When in use, the 1× bath solution will be kept at room temperature (19° C. to 30° C.). When not in use, the 1× bath solution will be stored at 1° C. to 9° C.

After the giga-seal was formed the following Mg-free bath solution will be used:

Sodium Chloride: 137 mM; Potassium Chloride: 4 mM; Calcium Chloride; 2.8 mM; HEPES: 10 mM; D-Glucose: 10 mM; Cremophor: 0.02%; pH (NaOH): 7.4

This Mg-free bath solution will be prepared as a 1× solution and stored at 1° C. to 9° C. It will be prepared freshly at least every 10 days.

Intracellular Solution

The 1× intracellular solution will be thawed every day out of a frozen 1× intracellular solution, which has been prepared prior to the experimental start of the present study, aliquoted and stored at −10° C. to −30° C. When in use, the 1× intracellular solution will kept at room temperature (19° C. to 30° C.). Remaining 1× intracellular solution will be stored in the fridge (1° C. to 9° C.). The 1× intracellular solution will include the components outlined below:

Potassium Chloride: 130 mM; Magnesium Chloride: 1 mM; Mg-ATP: 5 mM; HEPES: 10 mM; EGTA: 5 mM; pH (KOH): 7.2

Cell Treatment

For this study, cells will continuously be perfused with NMDA/Glycine, Test Compound or Test Compound/NMDA/Glycin.

In every case, at least 30-second prewash steps with a test compound will be performed in between applications. For details see Table A below.

Each experiment type will be analyzed in at least n=3 isolated cells. The NMDA and Glycine stock solutions will be prepared prior to the experimental start of the present study, stored frozen (−10° C. to −30° C.) until the day of experimentation. Shortly prior to the electrophysiological experiments, frozen stock solutions will be thawed and diluted.

Control: The effect of vehicle (0.1% DMSO) and D-(−)-2-Amino-5-phosphonopentanoic acid (AP-5) (100 μM) will be measured at three cells every second week, in order to assure successful expression of NMDA receptors.

The 50 mM stock solution of AP-5 has been prepared prior to the experimental start of the present study, aliquoted and stored frozen (−10° C. to −30° C.) until the day of experimentation. Shortly prior to the electrophysiological experiments the frozen stock solution will be thawed and then diluted in Mg-free bath solution containing NMDA (300 μM) and glycine (8.0 μM), to give a final perfusion concentration of 100 μM.

Experimental Procedure

Cells are transferred as suspension in serum-free medium to the QPatch HTX system and kept in the cell storage tank/stirrer during experiments. All solutions applied to cells including the intracellular solution will be maintained at room temperature (19° C. to 30° C.).

During the sealing process standard bath solution described above will be used. All solutions applied to cells including the pipette solution will be maintained at room temperature (19° C. to 30° C.). After formation of a Gigaohm seal between the patch electrodes and transfected individual HEK293 cells only Mg-free bath solution will be perfused and the cell membrane will be ruptured to assure electrical access to the cell interior (whole-cell patch-configuration). Inward currents will be measured upon application of 300 μM NMDA (and 8.0 μM Glycine) to patch-clamped cells for 5 sec. During the entire experiment the cells will be voltage-clamped at a holding potential of −80 mV.

For the analysis of test compounds, NMDA receptors will be stimulated by 300 μM NMDA and 8.0 μM Glycine and test compound combinations described below. Thirty-second prewash steps with a test compound will be performed in between applications.

TABLE A

Application Protocol; use dependence of test compounds

| Appl. # | Duration (s) | Application |
|---|---|---|
| 1 | 4 | NMDA/Glycine |
| 2 | 30 | Bath |
| 3 | 4 | NMDA/Glycine |
| 2 repetitions | | |
| 4 | 30 | 1 μM Test Compound |
| 5 | 4 | 1 μM Test Compound + NMDA/Glycine |
| 6 repetitions | | |
| 6 | 30 | Bath |
| 7 | 4 | NMDA/Glycine |
| 2 repetitions | | |

TABLE B

Application Protocol; control experiments

| Appl. # | Duration (s) | Application |
|---|---|---|
| 1 | 4 | NMDA/Glycine |
| 2 | 30 | Bath |
| 3 | 4 | NMDA/Glycine |
| 2 repetitions | | |
| 4 | 30 | Bath |
| 5 | 4 | NMDA/Glycine |
| 6 repetitions | | |
| 6 | 30 | Bath |
| 7 | 4 | NMDA/Glycine + 100 μM AP-5 |
| 2 repetitions | | |

Example 3. Synthesis of Compound 1

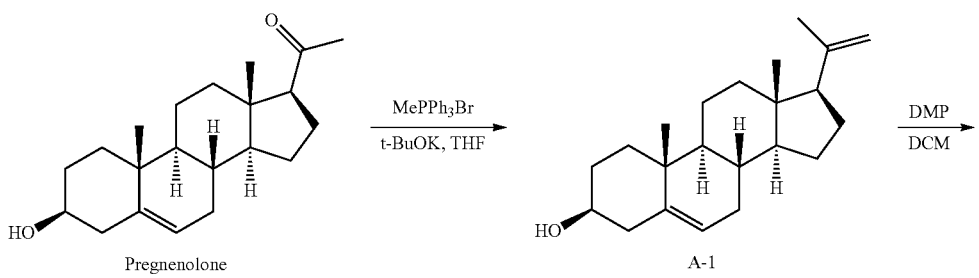

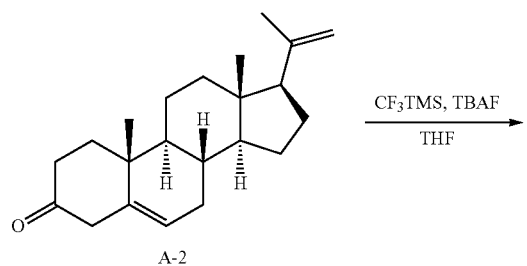

-continued
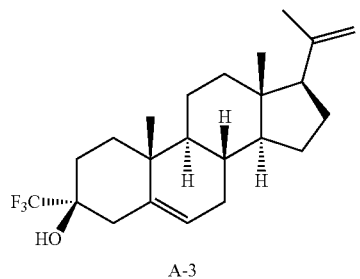
A-3
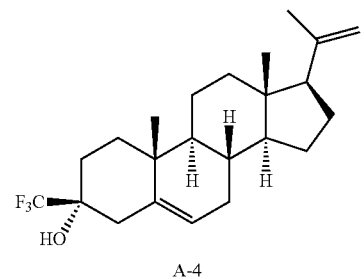
A-4
1) 9-BBN dimer
2) NaOH, H$_2$O$_2$
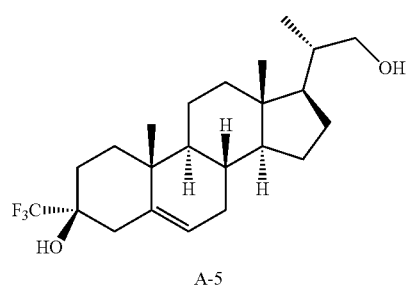
A-5
TsCl
py, DCM
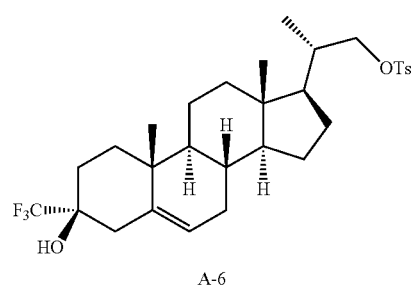
A-6
1) KI
2) PhSO$_2$Na
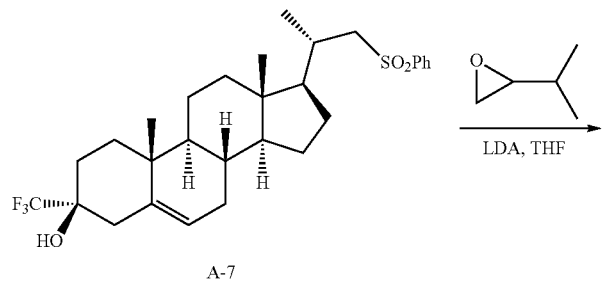
A-7
LDA, THF
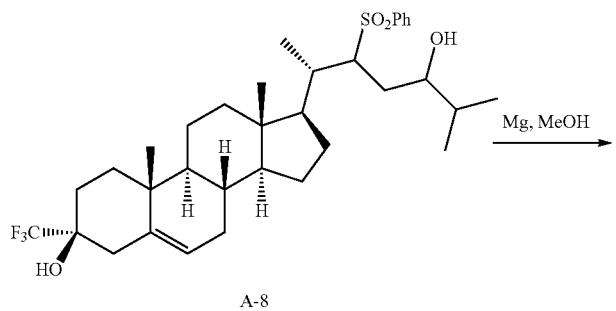
A-8
Mg, MeOH
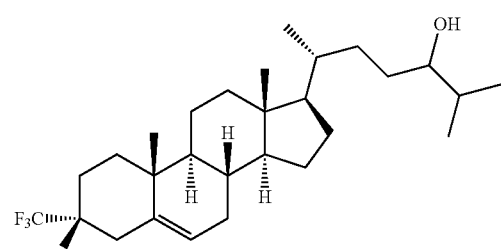
Compound 1

Step 1. To a mixture of MePPh$_3$Br (1.28 kg, 3.6 mol) in THF (4.5 L) was added t-BuOK (404 g, 3.6 mol) at 15° C. under N$_2$. The resulting mixture was stirred at 50° C. for 30 mins. Pregnenolone (950 g, 2.9 mol) was added in portions below 65° C. The reaction mixture was stirred at 50° C. for 1 hour. The combined mixture was quenched with saturated NH$_4$Cl aqueous (1 L) at 15° C. THF layer was separated. The aqueous was extracted with EtOAc (2×2 L). The combined organic phase was concentrated under vacuum to give a solid. The solid was further purified by trituration with MeOH/H$_2$O (1:1, 15 L) at reflux to give A-1 (940 g, 99%) as a solid. $^1$H NMR (400 MHz, CDCl$_3$) δ 5.40-5.32 (m, 1H), 4.85 (s, 1H), 4.71 (s, 1H), 3.58-3.46 (m, 1H), 2.36-2.16 (m, 2H), 2.08-1.94 (m, 2H), 1.92-1.62 (m, 9H), 1.61-1.39 (m, 6H), 1.29-1.03 (m, 4H), 1.01 (s, 3H), 0.99-0.91 (m, 1H), 0.59 (s, 3H).

Step 2. To a solution of A-1 (800 g, 2.54 mol) in DCM (8 L) was added DMP (2.14 kg, 5.08 mol) in portions at 35° C. The reaction mixture was stirred at 35° C. for 20 mins. The reaction mixture was filtered. The filtered cake was washed with DCM (3×1 L). The combined organic phase was washed with saturated Na$_2$S$_2$O$_3$/saturated NaHCO$_3$ aqueous (3:1, 2×1.5 L), brine (1.5 L), dried over Na$_2$SO$_4$, filtered and concentrated under vacuum to give A-2 (794 g, crude) as a solid, which was used for next step directly.

Step 3. To a solution of TBAF (3.04 mL, 1 M in THF, 3.04 mmol, Aldrich) in THF (100 mL) was added TMSCF$_3$ (25.8 g, 182 mmol) followed by a solution of A-2 (19 g, 60.8 mmol) in THF (100 mL) dropwise at 0° C. The mixture was stirred at 0° C. for 30 mins. To the mixture was added TBAF (200 mL, 1 M in THF, 200 mmol) at 0° C. The mixture was stirred at 0° C. for another 30 mins. To the mixture was added saturated aqueous NH$_4$Cl (100 mL) and the mixture was concentrated in vacuum. To the residue was added PE/EtOAc (400 mL, 1:1), the organic layer was separated, which was combined with other two batches (2×10 g of A-2). The combined organic layer was washed with water (300 mL), brine (300 mL), dried over Na$_2$SO$_4$, filtered and concentrated in vacuum to give an oil. The residue was dissolved in DCM (150 mL) and diluted with PE (750 mL). The solution was poured into a silica gel column (500 g, 100-200 mesh) and eluted with PE:DCM:EtOAc=5:1:0.05 to 5:1:0.1 to give A-4 (12 g, 17% yield) as an oil and impure A-3. The impure A-3 was re-crystallized from MeCN (250 mL) to give purified A-3 (6.5 g) as a solid. A-3 recovered from the MeCN filtrate was subjected to silica gel chromatography (PE:DCM:EtOAc=50:1:1 to 20:1:1) to give a crude product which was re-crystallized from MeCN (20 mL) to give purified A-3 (1 g, 16% total yield) as a solid.

Note: A-3 and A-4 were identified from $^3J_{H,CF}$, (FDCS). (*J. Org. Chem.* 2015, 80, 1754.).

A-3: $^1$H NMR (400 MHz, CDCl$_3$) δ 5.43-5.33 (m, 1H), 4.85 (s, 1H), 4.71 (s, 1H); 2.49 (s, 2H); 2.11-1.97 (m, 4H), 1.95-1.32 (m, 14H), 1.30-0.98 (m, 7H), 0.59 (s, 3H).

A-4: $^1$H NMR (400 MHz, CDCl$_3$) δ 5.54-5.41 (m, 1H), 4.86 (s, 1H), 4.72 (s, 1H); 2.78-2.65 (m, 1H); 2.18-1.97 (m, 3H), 1.95-1.35 (m, 16H), 1.32-0.98 (m, 7H), 0.59 (s, 3H).

Step 4. To a solution of A-3 (8 g, 20.9 mmol) in THF (80 mL) was added 9-BBN dimer (5.85 g, 24 mmol). The mixture was stirred at 40° C. for 1 h. The mixture was cooled to 0° C. To the mixture was added EtOH (12 mL), NaOH (41.8 mL, 5 M, aq.) and H$_2$O$_2$ (20.9 mL, 10 M, aq.) dropwise. The mixture was stirred at 50° C. for 1 h and then cooled. To the mixture was added Na$_2$SO$_3$ (100 mL, 25%, aq.). The mixture was extracted with EtOAc (300 mL). The organic layer was separated, purified by silica gel column (PE:EtOAc=10:1 to 5:1) to give A-5 (7.1 g, 85%) as a solid.

$^1$H NMR (400 MHz, CDCl$_3$) δ 5.42-5.32 (m, 1H), 3.64 (dd, J=3.2, 10.4 Hz, 1H), 3.37 (dd, J=6.8, 10.4 Hz, 1H), 2.49 (s, 2H), 2.32-1.92 (m, 4H), 1.92-1.70 (m, 4H), 1.70-1.29 (m, 8H), 1.29-0.91 (m, 11H), 0.71 (s, 3H).

Step 5. To a solution of A-5 (7.1 g, 17.7 mmol) in DCM (30 mL) and pyridine (21 mL) was added TsCl (6.74 g, 35.4 mmol). The mixture was stirred at 15° C. for 2 hrs. To the mixture was added water (5 mL) and the mixture was stirred at 15° C. for 2 hrs. The mixture was concentrated in vacuum. To the residue was added water (100 mL) and EtOAc (200 mL). The organic layer was separated, washed with HCl (100 mL, 0.1 M), water (100 mL) and brine (100 mL). The organic layer was dried over Na$_2$SO$_4$, filtered and concentrated in vacuum to give A-6 (9.8 g, 100%) as a solid.

$^1$H NMR (400 MHz, CDCl$_3$) δ 7.78 (d, J=8.0 Hz, 2H), 7.34 (d, J=8.0 Hz, 2H), 5.48-5.29 (m, 1H), 3.97 (dd, J=2.4, 9.2 Hz, 1H), 3.77 (dd, J=6.4, 9.2 Hz, 1H), 2.48 (s, 2H), 2.45 (s, 3H), 2.10-1.88 (m, 5H), 1.82-1.35 (m, 9H), 1.30-0.82 (m, 12H), 0.64 (s, 3H).

Step 6. To a solution of A-6 (1.05 g, 1.89 mmol) in DMF (5 mL) was added KI (1.25 g, 7.56 mmol). The mixture was stirred at 50° C. for 1 h. To the mixture was added PhSO$_2$Na (0.93 g, 5.67 mmol). The mixture was stirred at 50° C. for 2 hrs. To the mixture was added water (10 mL) and DCM (30 mL). The organic layer was separated, dried over Na$_2$SO$_4$, filtered, concentrated in vacuum and triturated form PE/DCM (10 mL, 5:1) to give A-7 (600 mg, 61%) as a solid.

$^1$H NMR (400 MHz, CDCl$_3$) δ 7.98-7.87 (m, 2H), 7.70-7.52 (m, 3H), 5.39-5.31 (m, 1H), 3.14 (d, J=14.0 Hz, 1H), 2.85 (dd, J=9.6, 14.0 Hz, 1H), 2.48 (s, 2H), 2.20-1.88 (m, 5H), 1.88-1.68 (m, 4H), 1.60-1.33 (m, 5H), 1.30-0.82 (m, 12H), 0.66 (s, 3H).

Step 7. To a solution of i-Pr$_2$NH (576 mg, 5.70 mmol) in THF (10 mL) was added n-BuLi (1.9 mL, 2.5 M in hexane, 4.75 mmol) at −70° C. The mixture was warmed to 0° C. A solution of A-7 (1 g, 1.9 mmol) in THF (8 mL) was added at −70° C. The mixture was stirred at −70° C. for 1 h. To the mixture was added a solution of 2-isopropyloxirane (245 mg, 2.85 mmol) in THF (2 mL) at −70° C. The mixture was stirred at −70° C. for 1 h, warmed to 10° C. and stirred at 10° C. for 16 hrs. To the mixture was added NH$_4$Cl (5 mL, sat. aq.). The mixture was extracted with EtOAc (50 mL). The organic layer was dried over Na$_2$SO$_4$, filtered and concentrated in vacuum to give A-8 (1.2 g crude) as an oil.

Step 8. To a solution of A-8 (1.2 g, 1.96 mmol) in MeOH (60 mL) was added NiBr$_2$ (5 mg, 0.023 mmol) and Mg powder (3.79 g, 156 mmol) was added in portions within 30 mins at 60° C. The mixture was stirred at 60° C. for 10 mins. The mixture was poured into HCl (160 mL, 2 M) and extracted with PE/EtOAc (2×200 mL, 1:1). The combined organic layer was washed with brine (100 mL), dried over Na$_2$SO$_4$, filtered, concentrated in vacuum and purified by silica gel column (100~200 mesh, PE:EtOAc=50:1 to 10:1) twice to give a crude product, which was purified by silica gel column (200~300 mesh, PE:DCM:acetone=1:1:0.01) twice, re-crystallized from MeCN/water (3:1, 5 mL) to give Compound 1 (50 mg, 5%) as a solid.

$^1$H NMR (400 MHz, CDCl$_3$) δ 5.41-5.32 (m, 1H), 3.39-3.28 (m, 1H), 2.49 (s, 2H), 2.10-1.92 (m, 4H), 1.90-1.60 (m, 5H), 1.55-1.33 (m, 8H), 1.31-1.10 (m, 6H), 1.09-0.90 (m, 15H), 0.68 (s, 3H).

LCMS Rt=1.278 min in 2.0 min chromatography, 30-90 AB, MS ESI calcd. for C$_{28}$H$_{44}$F$_3$O [M+H−H$_2$O]$^+$ 453, found 453.

Example 4. Syntheses of Compounds 1-A and 1-B

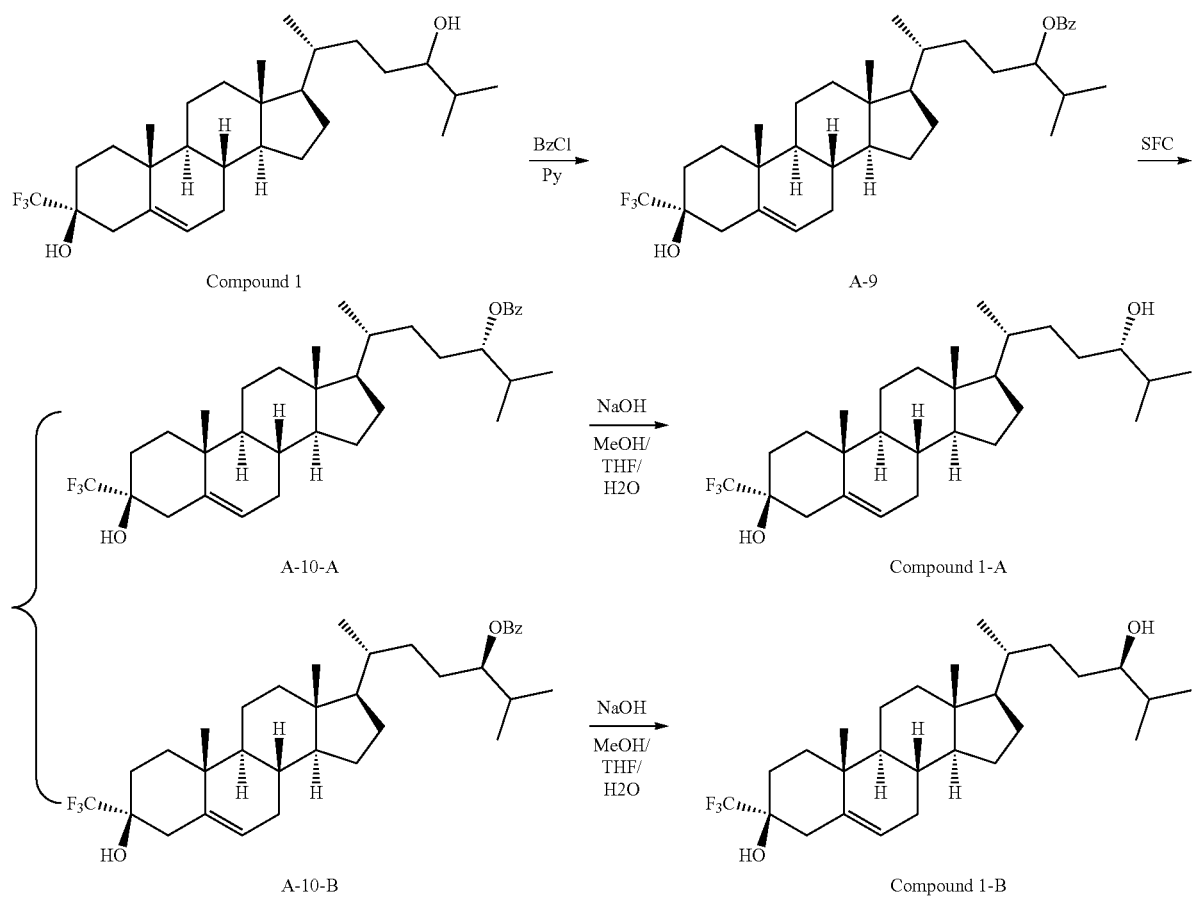

Step 1. To a solution of Compound 1 (100 mg, 0.212 mmol) in pyridine (3 mL) was added benzoyl chloride (59.7 mg, 0.425 mmol) at 25° C. The reaction was stirred at 25° C. for 16 hrs. The reaction was quenched by water (10 mL) and extracted with EtOAc (2×10 mL). The combined organic layers were dried over $Na_2SO_4$, filtered and concentrated in vacuum to give crude product. The crude product was purified by a silica gel column (PE/EtOAc=10/1) to give desired product A-9 (150 mg, crude) as a solid.

LCMS Rt=1.544 min in 2 min chromatography, 30-90 AB, MS ESI calcd. For $C_{35}H_{49}F_3O_3$ [M+Na]+597, found 597.

Step 2. A-9 (580 mg, 1.00 mmol) was purified by SFC separation (column: AD (250 mm*30 mm, 5 um), gradient: 45% B (A=$NH_3H_2O$, B=MeOH), flow rate: 60 mL/min) to give A-10-A (200 mg, 34%, 95.5% d.e. by SFC (Column: Chiralpak AD-3 100×4.6 mm I.D., 3 um, Mobile phase: A: $CO_2$ B: iso-propanol (0.05% DEA).

Gradient: from 5% to 40% of B in 4.5 min and hold 40%, for 2.5 min, then 5% of B for 1 min. Flow rate: 2.8 mL/min Column temperature:40° C.)) as a solid and A-10-B (215 mg, 37%, 99.5% d.e. by SFC (Column: Chiralpak AD-3100×4.6 mm I.D., 3 um, Mobile phase: A: $CO_2$ B: iso-propanol (0.05% DEA).

Gradient: from 5% to 40% of B in 4.5 min and hold 40%, for 2.5 min, then 5% of B for 1 min. Flow rate: 2.8 mL/min Column temperature:40° C.)) as a solid.

A-10-A: $^1$H NMR (400 MHz, $CDCl_3$) δ 8.07-8.02 (m, 2H), 7.58-7.52 (m, 1H), 7.48-7.41 (m, 2H), 5.37-5.35 (m, 1H), 4.99-4.94 (m, 1H), 2.48-2.46 (m, 2H), 2.04-1.89 (m, 4H), 1.82-1.65 (m, 5H), 1.51-1.35 (m, 7H), 1.27-1.08 (m, 4H), 1.05 (s, 4H), 1.02-0.92 (m, 13H), 0.64 (s, 3H).

A-10-B: $^1$H NMR (400 MHz, $CDCl_3$) δ 8.07-8.02 (m, 2H), 7.59-7.52 (m, 1H), 7.49-7.40 (m, 2H), 5.37-5.35 (m, 1H), 5.01-4.92 (m, 1H), 2.48-2.46 (m, 2H), 2.03-1.90 (m, 5H), 1.83-1.66 (m, 3H), 1.83-1.66 (m, 1H), 1.51-1.37 (m, 8H), 1.23-1.11 (m, 3H), 1.05-1.00 (m, 5H), 0.99-0.90 (m, 12H), 0.66 (s, 3H).

Step 2a. To a solution of A-10-A (215 mg, 0.374 mmol) in THF (2 mL) and MeOH (2 mL) was added NaOH (400 mg, 10 mmol) and $H_2O$ (2 mL) at 25° C. The solution was stirred at 50° C. for 48 hrs. The reaction solution was extracted with EtOAc (2×10 mL). The combined organic layers were dried over $Na_2SO_4$, filtered and concentrated in vacuum to give crude product which was triturated with MeCN (2×5 mL) to give desired product Compound 1-A (148 mg, 84%) as a solid.

Compound 1-A: $^1$H NMR (400 MHz, $CDCl_3$) δ 5.38-5.36 (m, 1H), 3.33-3.31 (m, 1H), 2.49-2.48 (m, 2H), 2.08-1.92 (m, 4H), 1.89-1.61 (m, 5H), 1.52-1.37 (m, 5H), 1.32-1.09 (m, 7H), 1.06-0.96 (m, 7H), 0.96-0.87 (m, 10H), 0.68 (s, 3H). LCMS Rt=1.497 min in 2 min chromatography, 30-90 AB, MS ESI calcd. For $C_{28}H_{44}F_3O$ [M+H–$H_2O$]+453, found 453.

Step 2b. To a solution of A-10-B (200 mg, 0.348 mmol) in THF (2 mL) and MeOH (2 mL) was added NaOH (400 mg, 10 mmol) and H$_2$O (2 mL) at 25° C. The solution was stirred at 50° C. for 48 hrs. The reaction solution was extracted with EtOAc (2×10 mL). The combined organic layers were dried over Na$_2$SO$_4$, filtered and concentrated in vacuum to give crude product, which was triturated with MeCN (2×5 mL) to give desired product Compound 1-B (139 mg, 85%) as a solid.

Compound 1-B: $^1$H NMR (400 MHz, CDCl$_3$) δ 5.38-5.36 (m, 1H), 3.33-3.31 (m, 1H), 2.49-2.48 (m, 2H), 2.12-1.92 (m, 5H), 1.89-1.40 (m, 12H), 1.29-1.11 (m, 5H), 1.09-0.98 (m, 6H), 0.95-0.89 (m, 10H), 0.69 (s, 3H)

LCMS Rt=1.500 min in 2 min chromatography, 30-90 AB, MS ESI calcd. For C$_{28}$H$_{44}$F$_3$O [M+H−H$_2$O]$^+$ 453, found 453.

Synthesis of Compound 1-A—Absolute Stereochemistry

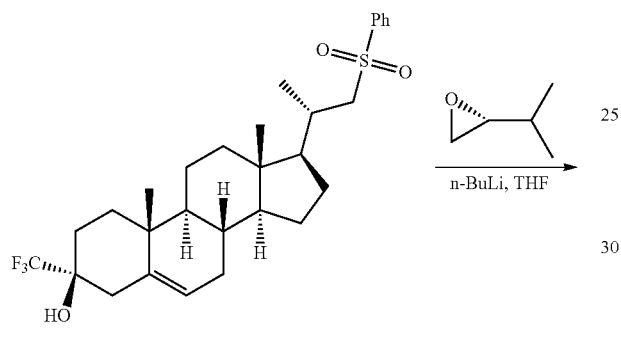

ST-200-CF3_4A

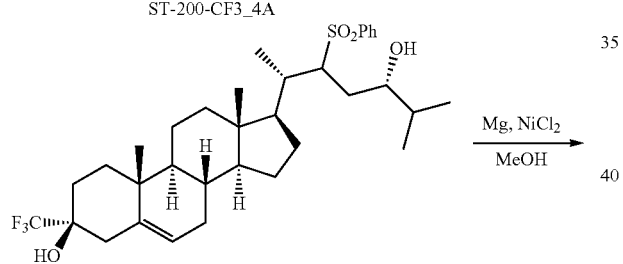

ST-200-096-004_1

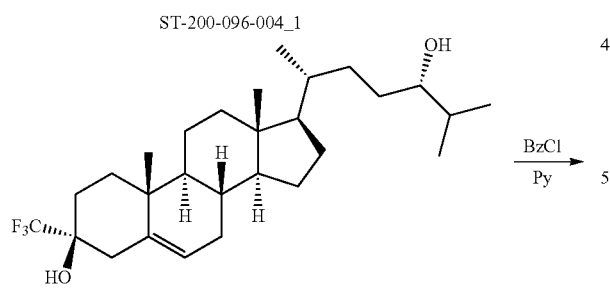

ST-200-096-004_2

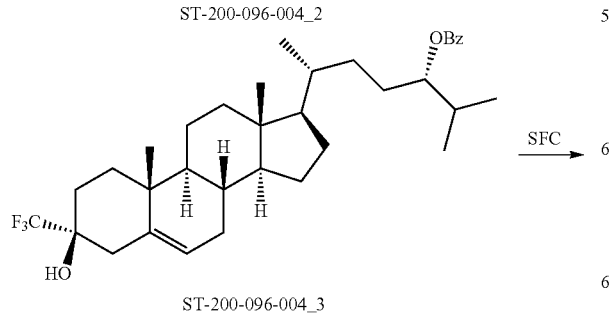

ST-200-096-004_3

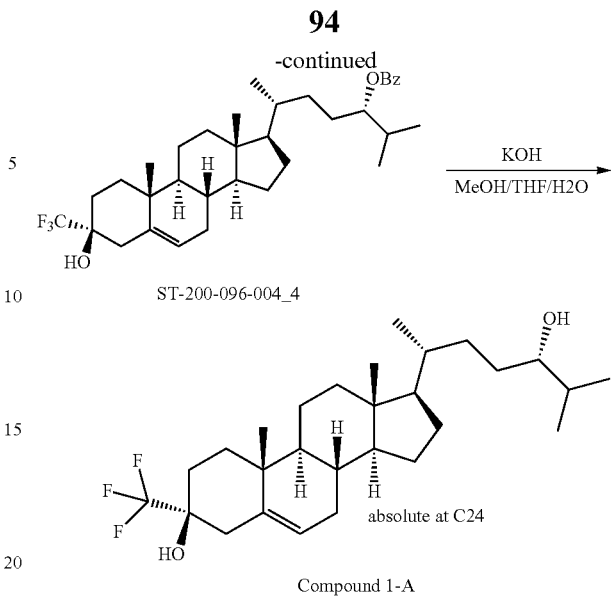

Compound 1-A

The experimental procedures of intermediate ST-200-CF3_4A or A-7 can be found in Example 3.

Synthesis of ST-200-096-004_1

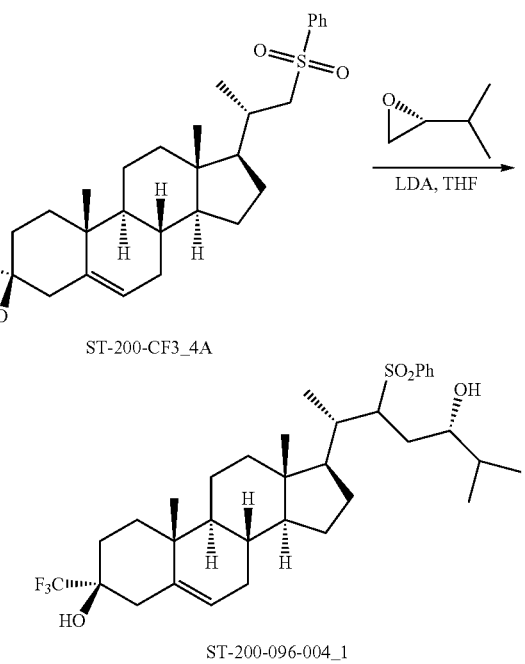

ST-200-096-004_1

To a solution of ST-200-096-004_1 (450 mg, 0.736 mmol) in methanol (30 mL) was added Mg powder (883 mg, 36.8 mmol) under N$_2$ at 65° C. The reaction mixture was quenched with HCl (50 mL) dropwise until the solution became clear. The reaction solution was extracted with EtOAc (3×30 mL). The combined organic layer was washed with sat. NaHCO$_3$ (50 mL), brine (50 mL), dried over Na$_2$SO$_4$, filtered and concentrated. The residue was purified by flash column (0~12% of EtOAc in PE) to give ST-200-096-004_2 (150 mg, 43%) as a solid.

$^1$H NMR (400 MHz, CDCl$_3$) δ 5.40-5.34 (m, 1H), 3.37-3.25 (m, 1H), 2.55-2.40 (m, 2H), 2.09-1.91 (m, 4H), 1.90-

1.70 (m, 3H), 1.69-1.56 (m, 4H), 1.54-1.35 (m, 6H), 1.34-0.97 (m, 12H), 0.96-0.86 (m, 9H), 0.68 (s, 3H).

Synthesis of ST-200-096-004_3

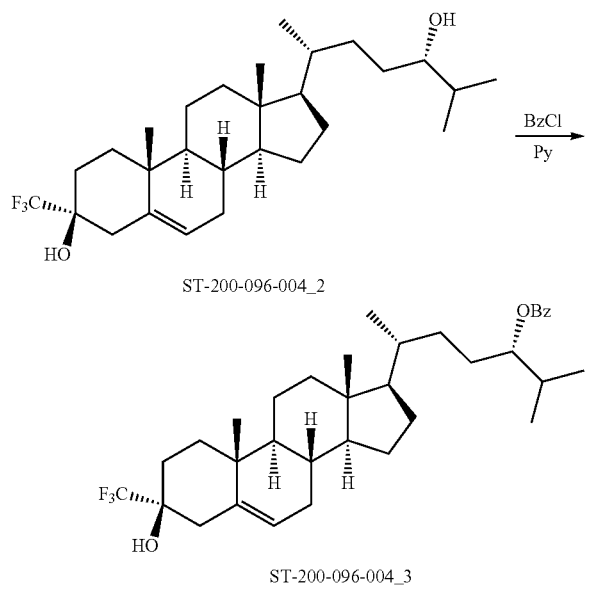

To a solution of ST-200-096-004_2 (150 mg, 0.318 mmol) in pyridine (3 mL) was added BzCl (134 mg, 0.954 mmol) at 0° C. and the reaction was stirred at 25° C. for 2 h. The reaction mixture was diluted with water (50 mL), extracted with EtOAc (2×40 mL). The organic layer was washed with brine (5×50 mL), dried over Na₂SO₄, filtered and concentrated. The crude was purified by silica gel column (PE/EtOAc=10/1 to 4/1) to give ST-200-096-004_3 (120 mg, 66%) as a solid.

The ST-200-096-004_3 (120 mg, 0.208 mmol) was separated by SFC (column: AD (250 mm*30 mm, 5 um)), gradient: 25-25% B (0.1% NH₃H₂O IPA)) to give ST-200-096-004_4 (100 mg, 84%) as a solid.

$^1$HNMR (400 MHz, CDCl₃) δ 8.05 (d, 0.1=8 Hz, 2H), 7.55 (t, J=8 Hz, 1H), 7.44 (t, J=8 Hz, 2H), 5.38-5.34 (m, 1H), 4.98-4.91 (m, 1H), 2.48 (s, 2H), 2.09-1.89 (m, 4H), 1.86-1.67 (m, 4H), 1.53-1.34 (m, 10H), 1.17-1.00 (m, 7H), 0.99-0.91 (m, 12H), 0.64 (s, 3H).

SFC Rt=3.473 min in 10 min chromatography, AD_IPA (DEA)_5_40_2, 8ML_8 MIN, 100% de.

Synthesis of Compound 1-A

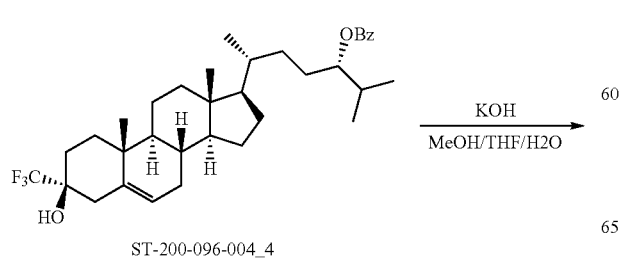

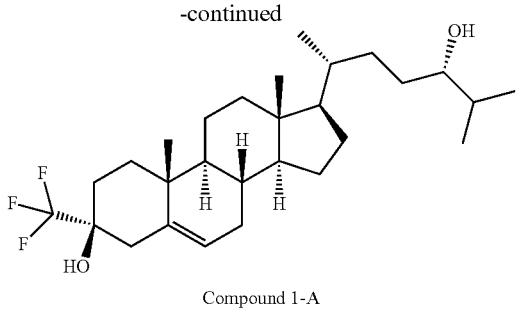

Compound 1-A

To a solution of ST-200-096-004_4 (100 mg, 0.173 mmol) in THF (2 mL) and MeOH (1 mL) and water (1 mL) was added KOH (48.5 mg, 0.865 mmol). The mixture was stirred at 60° C. for 16 hrs. The mixture was poured into water (20 mL) and extracted with EtOAc (2×40 mL). The combined organic layer was washed with brine (30 mL), dried over Na₂SO₄, filtered and concentrated. The residue was purified by flash column (PE/EtOAc=5/1 to 3/1) to give Compound 1-A (48 mg, 59%) as a solid.

$^1$HNMR (400 MHz, CDCl₃) δ 5.40-5.35 (m, 1H), 3.35-3.28 (m, 1H), 2.49 (m, 2H), 2.09-1.93 (m, 4H), 1.89-1.59 (m, 6H), 1.54-1.22 (m, 10H), 1.20-0.97 (m, 9H), 0.95-0.89 (m, 9H), 0.68 (s, 3H).

LCMS Rt=1.265 min in 2.0 min chromatography, 30-90 AB, purity 100%, MS ESI calcd. For $C_{28}H_{44}F_3O$ [M−H₂O+H]=453, found 453.

Example 5. Syntheses of Compounds 2, 2-A, and 2-B

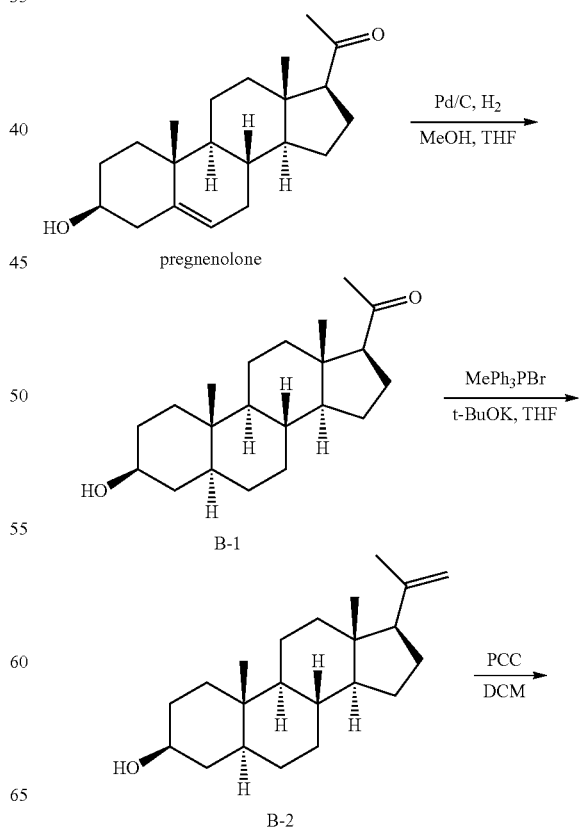

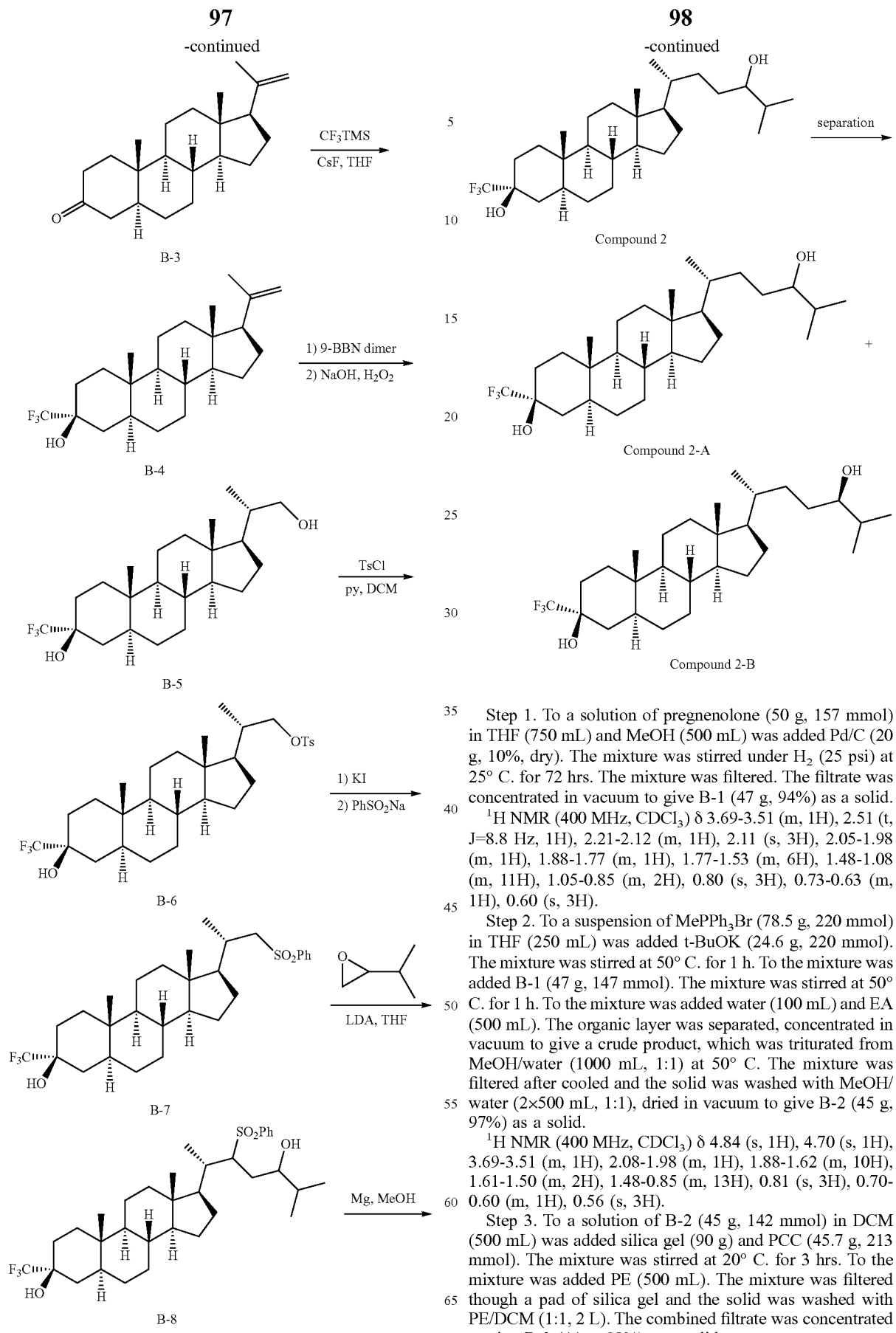

Step 1. To a solution of pregnenolone (50 g, 157 mmol) in THF (750 mL) and MeOH (500 mL) was added Pd/C (20 g, 10%, dry). The mixture was stirred under $H_2$ (25 psi) at 25° C. for 72 hrs. The mixture was filtered. The filtrate was concentrated in vacuum to give B-1 (47 g, 94%) as a solid.

$^1$H NMR (400 MHz, CDCl$_3$) δ 3.69-3.51 (m, 1H), 2.51 (t, J=8.8 Hz, 1H), 2.21-2.12 (m, 1H), 2.11 (s, 3H), 2.05-1.98 (m, 1H), 1.88-1.77 (m, 1H), 1.77-1.53 (m, 6H), 1.48-1.08 (m, 11H), 1.05-0.85 (m, 2H), 0.80 (s, 3H), 0.73-0.63 (m, 1H), 0.60 (s, 3H).

Step 2. To a suspension of MePPh$_3$Br (78.5 g, 220 mmol) in THF (250 mL) was added t-BuOK (24.6 g, 220 mmol). The mixture was stirred at 50° C. for 1 h. To the mixture was added B-1 (47 g, 147 mmol). The mixture was stirred at 50° C. for 1 h. To the mixture was added water (100 mL) and EA (500 mL). The organic layer was separated, concentrated in vacuum to give a crude product, which was triturated from MeOH/water (1000 mL, 1:1) at 50° C. The mixture was filtered after cooled and the solid was washed with MeOH/water (2×500 mL, 1:1), dried in vacuum to give B-2 (45 g, 97%) as a solid.

$^1$H NMR (400 MHz, CDCl$_3$) δ 4.84 (s, 1H), 4.70 (s, 1H), 3.69-3.51 (m, 1H), 2.08-1.98 (m, 1H), 1.88-1.62 (m, 10H), 1.61-1.50 (m, 2H), 1.48-0.85 (m, 13H), 0.81 (s, 3H), 0.70-0.60 (m, 1H), 0.56 (s, 3H).

Step 3. To a solution of B-2 (45 g, 142 mmol) in DCM (500 mL) was added silica gel (90 g) and PCC (45.7 g, 213 mmol). The mixture was stirred at 20° C. for 3 hrs. To the mixture was added PE (500 mL). The mixture was filtered though a pad of silica gel and the solid was washed with PE/DCM (1:1, 2 L). The combined filtrate was concentrated to give B-3 (44 g, 98%) as a solid.

¹H NMR (400 MHz, CDCl₃) δ 4.85 (s, 1H), 4.71 (s, 1H), 2.48-2.20 (m, 3H), 2.12-1.98 (m, 3H), 1.90-1.49 (m, 10H), 1.47-1.08 (m, 8H), 1.01 (s, 3H), 0.99-0.71 (m, 2H), 0.58 (s, 3H).

Step 4. To a solution of B-3 (20 g, 63.5 mmol) in THF (300 mL) was added CsF (19.2 g, 127 mmol). To the mixture was added TMSCF₃ (18.0 g, 127 mmol) dropwise at 10° C. The mixture was stirred at 10° C. for 2 hrs. To the mixture was added TBAF (127 mL, 1 M in THF, 127 mmol) at 10° C. The mixture was stirred at 20° C. for 3 hrs. To the mixture was added water (200 mL). The mixture was concentrated in vacuum to remove THF. To the residue was added EtOAc (300 mL). The organic layer was separated, washed with water (100 mL), brine (100 mL), dried over Na₂SO₄, filtered, concentrated in vacuum, triturated from PE:DCM (500 mL, 20:1), re-crystallized from MeCN (200 mL) to give B-4 (7.1 g) as a solid. The filtrate of trituration and re-crystallization was combined, concentrated in vacuum, purified by silica gel column (PE:EtOAc=30:1 to 10:1) twice to give impure B-4 which was re-crystallized from MeCN (200 mL) to give B-4 (7.6 g, total yield 60%) as a solid.

¹H NMR (400 MHz, CDCl₃) δ 4.84 (s, 1H), 4.70 (s, 1H), 2.11-1.98 (m, 3H), 1.88-1.47 (m, 13H), 1.45-1.05 (m, 9H), 1.00-0.89 (m, 1H), 0.85 (s, 3H), 0.78-0.68 (m, 1H), 0.56 (s, 3H).

Step 5. To s solution of B-4 (14.7 g, 38.2 mmol) in THF (150 mL) was added 9-BBN dimer (10.7 g, 43.9 mmol). The mixture was stirred at 40° C. for 1 h. The mixture was cooled to 0° C. To the mixture was added EtOH (21.8 mL), NaOH (76.3 mL, 5 M, aq.) and H₂O₂ (38.1 mL, 10 M, aq.) dropwise. The mixture was stirred at 50° C. for 1 h. To the mixture was added Na₂SO₃ (200 mL, 25%, aq.) after cooled. The mixture was extracted with EtOAc (500 mL). The organic layer was separated, concentrated in vacuum and triturated form water (400 mL) to give B-5 (15 g, 98%) as a solid.

¹H NMR (400 MHz, CDCl₃) δ 3.68-3.58 (m, 1H), 3.40-3.30 (m, 1H), 2.11-1.91 (m, 2H), 1.89-1.72 (m, 2H), 1.70-1.45 (m, 8H), 1.42-1.06 (m, 11H), 1.03 (d, J=6.4 Hz, 3H), 1.00-0.88 (m, 2H), 0.85 (s, 3H), 0.75-0.68 (m, 1H), 0.67 (s, 3H).

Step 6. To a solution of B-5 (15 g, 17.7 mmol) in DCM (60 mL) and pyridine (42 mL) was added TsCl (14.1 g, 74.4 mmol). The mixture was stirred at 15° C. for 2 hrs. To the mixture was added water (2 mL) and the mixture was stirred at 15° C. for 16 hrs. To the mixture was added water (100 mL). The mixture was extracted with PE/EtOAc (2:1, 300 mL). The organic layer was separated, washed with HCl (200 mL, 1 M), water (100 mL), brine (100 mL), dried over Na₂SO₄, filtered and concentrated in vacuum to give B-6 (23 g, crude) as a solid.

¹H NMR (400 MHz, CDCl₃) δ 7.78 (d, J=8.0 Hz, 2H), 7.34 (d, J=8.0 Hz, 2H), 3.96 (dd, J=3.2, 9.2 Hz, 1H), 3.76 (dd, J=6.8, 9.2 Hz, 1H), 2.45 (s, 3H), 2.10-1.98 (m, 1H), 1.92-1.78 (m, 2H), 1.71-1.30 (m, 11H), 1.30-0.88 (m, 13H), 0.83 (s, 3H), 0.72-0.62 (m, 1H), 0.61 (s, 3H).

Step 7. To a solution of B-6 (23 g, 41.3 mmol) in DMF (100 mL) was added KI (27.3 g, 165 mmol). The mixture was stirred at 50° C. for 1 h. To the mixture was added PhSO₂Na (20.1 g, 123 mmol). The mixture was stirred at 50° C. for 16 hrs. To the mixture was added DCM (200 mL), water (400 mL) and PE (2:1, 400 mL) with stirring. The organic layer was separated, washed with water (100 mL), brine (100 mL), dried over Na₂SO₄, filtered and concentrated to 150 mL in vacuum and a solid was formed. The mixture was filtered, washed with PE (100 mL), dried in vacuum to give B-7 (12 g, 55%) as a solid.

¹H NMR (400 MHz, CDCl₃) δ 7.95-7.88 (m, 2H), 7.70-7.61 (m, 1H), 7.60-7.51 (m, 2H), 3.13 (d, J=13.2 Hz, 1H), 2.84 (dd, J=9.2, 14.0 Hz, 1H), 2.20-1.89 (m, 4H), 1.88-1.44 (m, 8H), 1.43-0.88 (m, 15H), 0.83 (s, 3H), 0.72-0.65 (m, 1H), 0.63 (s, 3H).

Step 8. To a solution of i-Pr₂NH (573 mg, 5.67 mmol) in THF (10 mL) was added BuLi (1.88 mL, 2.5 M in hexane, 4.72 mmol) at −70° C. The mixture was warmed to 0° C. A solution of B-7 (1 g, 1.89 mmol) in THF (8 mL) was added at −70° C. The mixture was stirred at −70° C. for 1 h. To the mixture was added a solution of 2-isopropyloxirane (243 mg, 2.83 mmol) in THF (2 mL) at −70° C. The mixture was stirred at −70° C. for 1 h, 10° C. for 16 hrs and 50° C. for 2 hrs. To the mixture was added NH₄Cl (5 mL, sat. aq.). The mixture was extracted with EtOAc (50 mL). The organic layer was dried over Na₂SO₄, filtered, concentrated in vacuum and purified by silica gel column (PE:EtOAc=12:1 to 8:1) to give B-8 (0.5 g, 43%) as a solid.

¹H NMR (400 MHz, CDCl₃) δ 7.95-7.85 (m, 2H), 7.70-7.52 (m, 3H), 3.63-3.46 (m, 1H), 3.44-3.31 (m, 1H), 2.18-1.61 (m, 8H), 1.55-1.11 (m, 13H), 1.11-0.78 (m, 18H), 0.72-0.60 (m, 2H), 0.50-0.40 (m, 3H).

Step 9. To a solution of B-8 (0.5 g, 0.815 mmol) in MeOH (50 mL) was added NiBr₂ (2 mg, 0.009 mmol). Then magnesium powder (2.22 g, 91.4 mmol) was added in portions within 30 mins at 60° C. The mixture was stirred at 60° C. for 1 h. The mixture was poured into citric acid (200 mL, 10% aq.) and extracted with PE/EtOAc (2×200 mL, 1:1). The combined organic layer was washed with water (100 mL), brine (100 mL), dried over Na₂SO₄, filtered, concentrated in vacuum, purified by silica gel column (PE:EtOAc=20:1 to 10:1) to give Compound 2 (290 mg, 67%) as a solid.

¹H NMR (400 MHz, CDCl₃) δ 3.37-3.28 (m, 1H), 2.12-2.01 (m, 1H), 2.00-1.91 (m, 2H), 1.87-1.77 (m, 2H), 1.71-1.58 (m, 5H), 1.50-1.00 (m, 19H), 0.96-0.88 (m, 10H), 0.85 (s, 3H), 0.72-0.67 (m, 1H), 0.67-0.64 (m, 3H). LCMS Rt=1.340 min in 2.0 min chromatography, 30-90 AB, No MS signal. HRMS ESI calcd. for $C_{28}H_{46}F_3O$ $[M+H-H_2O]^+$ 455.3495, found 455.3489.

Step 10. Compound 2 (264 mg) was separated by silica gel column twice (300~400 mesh, 30*250 mm, PE:EtOAc=30:1 to 15:1) to give Compound 2-A (56 mg, 21%) and Compound 2-B (101 mg, 38%) both as solids.

The diastereomeric ratio of 2-A and 2-B was assessed by conversion of the alcohol to a benzoate ester: To a solution of Compound 2-B (8 mg, 0.017 mmol) in DCM (0.5 mL) was added pyridine (132 mg, 1.68 mmol) and BzCl (23.7 mg, 0.169 mmol). The mixture was stirred at 25° C. for 20 mins. To the mixture was added PE (5 mL). The mixture was washed with NaHCO₃ (2 mL, sat. aq.), HCl (2 mL, 1M, aq.), NaHCO₃ (2 mL, sat. aq.), purified by prep-TLC (PE:DCM=1:1) to give 2-B-Bz for SFC analysis (98.7% de ("Column: Chiralpak AD-3 150×4.6 mm I.D., 3 um Mobile phase: A: CO₂ B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.")).

To a solution of Compound 2-A (3 mg, 0.006 mmol) in DCM (0.5 mL) was added pyridine (50 mg, 0.633 mmol) and BzCl (8.9 mg, 0.063 mmol). The mixture was stirred at 25° C. for 20 mins. To the mixture was added PE (5 mL). The mixture was washed with NaHCO₃ (2 mL, sat. aq.), HCl (2 mL, 1M, aq.), NaHCO₃ (2 mL, sat. aq.), purified by prep-TLC (PE:DCM=1:1) to give 2-A-Bz for SFC analysis (95.0% d.e. (Column: Chiralpak AD-3 150×4.6 mm I.D., 3 um Mobile phase: A: CO₂ B: iso-propanol (0.05% DEA)

Gradient: from 5% to 40% of B in 5 min and hold 40% for 2.5 min, then 5% of B for 2.5 min Flow rate: 2.5 mL/min Column temp.: 35° C.)).

Compound 2-A: $^1$H NMR (400 MHz, CDCl$_3$) δ 3.37-3.28 (m, 1H), 2.12-2.01 (m, 1H), 2.00-1.91 (m, 2H), 1.87-1.77 (m, 2H), 1.71-1.58 (m, 5H), 1.50-1.00 (m, 19H), 0.96-0.88 (m, 10H), 0.85 (s, 3H), 0.72-0.67 (m, 1H), 0.65 (s, 3H). LCMS Rt=1.329 min in 2.0 min chromatography, 30-90 AB, MS ESI calcd. for C$_{28}$H$_{46}$F$_3$O [M+H−H$_2$O]$^+$ 455, found 455.

Compound 2-B: $^1$H NMR (400 MHz, CDCl$_3$) δ 3.37-3.28 (m, 1H), 2.12-2.01 (m, 1H), 2.00-1.91 (m, 2H), 1.87-1.77 (m, 2H), 1.71-1.58 (m, 4H), 1.50-1.30 (m, 10H), 1.30-1.00 (m, 10H), 0.96-0.88 (m, 10H), 0.85 (s, 3H), 0.72-0.67 (m, 1H), 0.66 (s, 3H). LCMS Rt=1.333 min in 2.0 min chromatography, 30-90 AB, MS ESI calcd. for C$_{28}$H$_{46}$F$_3$O [M+H−H$_2$O]$^+$ 455, found 455.

Synthesis of Compound 2-A—Absolute Stereochemistry

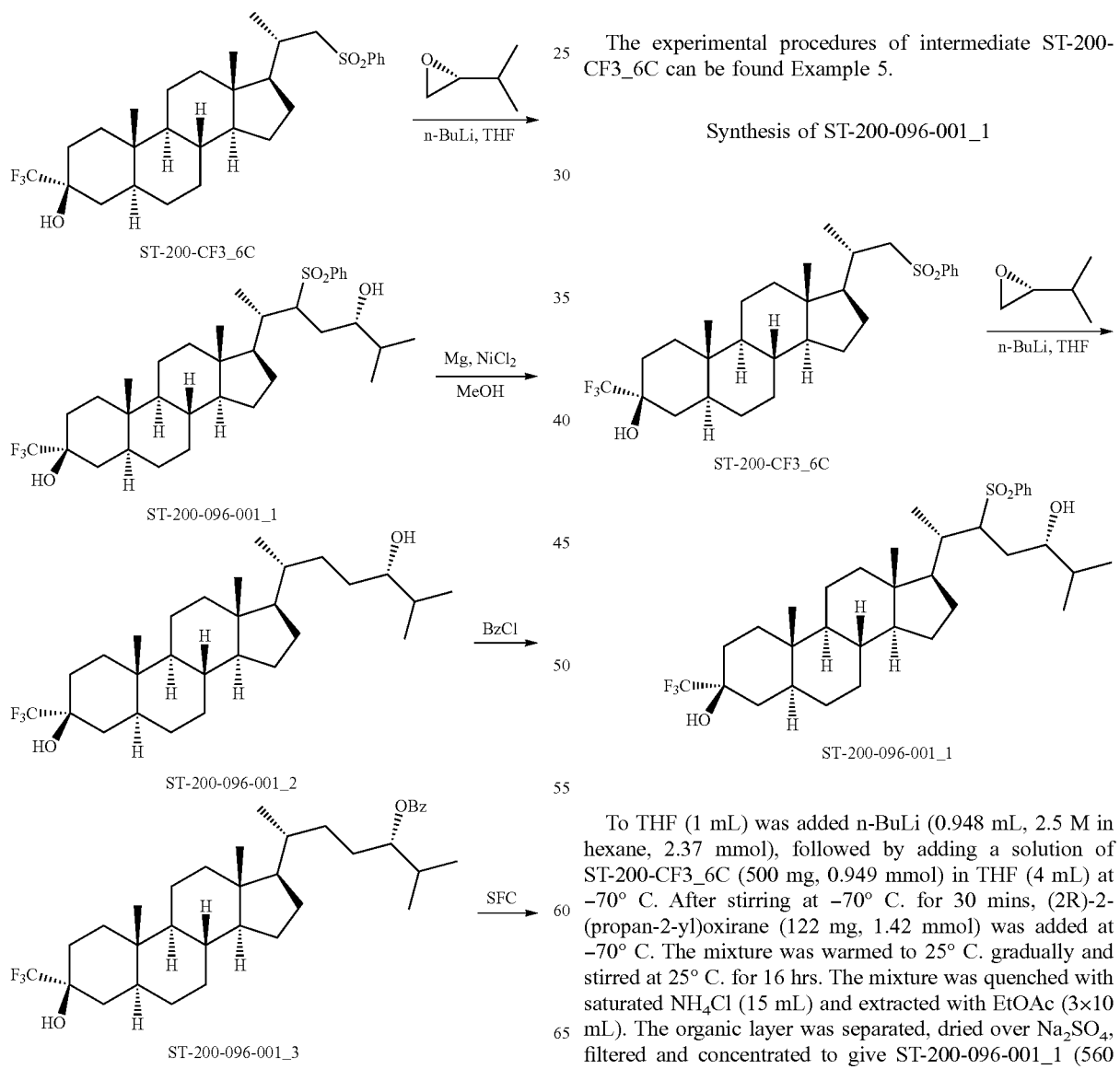

The experimental procedures of intermediate ST-200-CF3_6C can be found Example 5.

Synthesis of ST-200-096-001_1

To THF (1 mL) was added n-BuLi (0.948 mL, 2.5 M in hexane, 2.37 mmol), followed by adding a solution of ST-200-CF3_6C (500 mg, 0.949 mmol) in THF (4 mL) at −70° C. After stirring at −70° C. for 30 mins, (2R)-2-(propan-2-yl)oxirane (122 mg, 1.42 mmol) was added at −70° C. The mixture was warmed to 25° C. gradually and stirred at 25° C. for 16 hrs. The mixture was quenched with saturated NH$_4$Cl (15 mL) and extracted with EtOAc (3×10 mL). The organic layer was separated, dried over Na$_2$SO$_4$, filtered and concentrated to give ST-200-096-001_1 (560 mg, crude) as an oil, which was used directly for next step.

Synthesis of ST-200-096-001_2

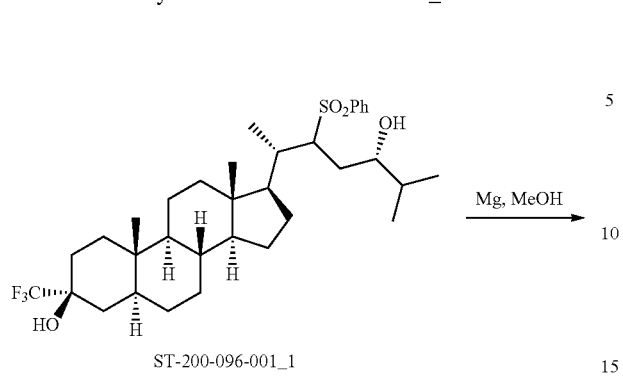

To a solution of ST-200-096-001_1 (560 mg, 0.913 mmol) in methanol (30 mL) was added Mg powder (1.09 g, 45.6 mmol) under $N_2$ at 65° C. The reaction mixture was quenched with HCl (60 mL) dropwise until the solution became clear. The reaction solution was extracted with EtOAc (3×30 mL). The combined organic layer was washed with sat. $NaHCO_3$ (50 mL), brine (50 mL), dried over $Na_2SO_4$, filtered and concentrated. The residue was purified by flash column (0~12% of EtOAc in PE) to give ST-200-096-001_2 (150 mg, 46%) as a solid.

$^1$H NMR (400 MHz, $CDCl_3$) δ 3.35-3.26 (m, 1H), 2.10-1.91 (m, 3H), 1.88-1.76 (m, 2H), 1.71-1.62 (m, 4H), 1.52-1.35 (m, 6H), 1.32-1.20 (m, 7H), 1.17-0.98 (m, 6H), 0.95-0.87 (m, 10H), 0.86-0.80 (m, 4H), 0.72-0.61 (m, 4H).

Synthesis of ST-200-096-001_3

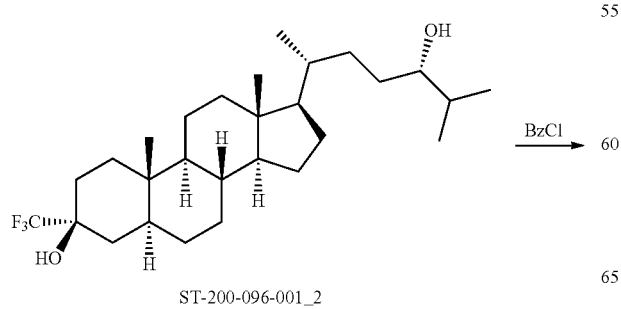

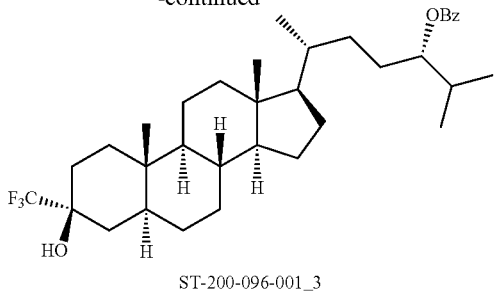

To a solution of ST-200-096-001_2 (200 mg, 0.423 mmol) in pyridine (3 mL) was added BzCl (177 mg, 1.26 mmol) at 0° C. and the reaction was stirred at 25° C. for 2 h. The reaction mixture was diluted with water (50 mL), extracted with EtOAc (2×40 mL). The organic layer was washed with brine (5×50 mL), dried over $Na_2SO_4$, filtered and concentrated. The crude was purified by silica gel column (PE/EtOAc=10/1 to 4/1) to give ST-200-096-001_3 (150 mg, 62%) as an oil.

The ST-200-096-001_3 (150 mg, 0.26 mmol) was separated by SFC (column: AD (250 mm*30 mm, 5 um)), gradient: 30-30% B (A=0.1% $NH_3H_2O$ IPA)) to give ST-200-096-001_3 (120 mg, 81%) as a solid.

$^1$HNMR (400 MHz, $CDCl_3$) δ 8.05 (d, J=8 Hz, 2H), 7.55 (t, J=8 Hz, 1H), 7.44 (t, J=8 Hz, 2H), 4.98-4.91 (m, 1H), 2.09-1.89 (m, 4H), 1.86-1.61 (m, 6H), 1.53-1.34 (m, 8H), 1.27-1.03 (m, 8H), 0.99-0.95 (m, 8H), 0.92-0.83 (m, 7H), 0.71-0.61 (m, 4H).

SFC Rt=4.117 min in 10 min chromatography, AD_3_IPA_EtOH_5_40_25ML, 99% de.

Synthesis of Compound 2-A

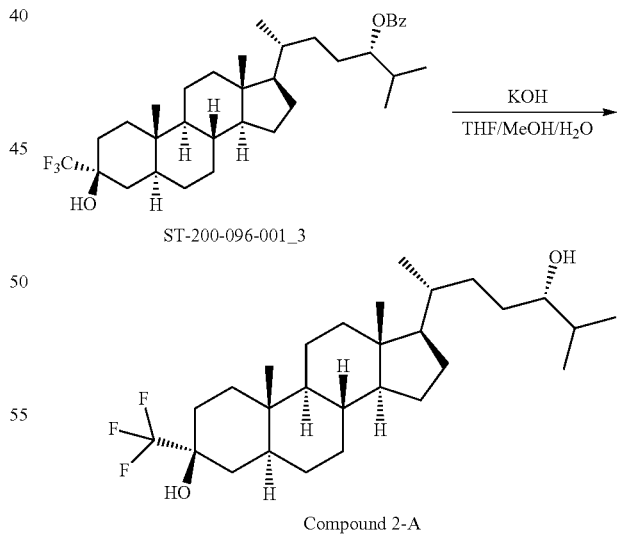

To a solution of ST-200-096-001_3 (120 mg, 0.208 mmol) in THF (2 mL) and MeOH (1 mL) and water (1 mL) was added KOH (57.7 mg, 1.03 mmol). The mixture was stirred at 60° C. for 16 hrs, poured into water (20 mL) and extracted with EtOAc (2×40 mL). The combined organic layer was washed with brine (30 mL), dried over $Na_2SO_4$, filtered and concentrated. The residue was purified by flash column (PE/EtOAc=5/1 to 3/1) to give Compound 2-A (82 mg, 83%) as a solid.

$^1$H NMR (400 MHz, CDCl$_3$) δ 33.34-3.28 (m, 1H), 2.10-1.92 (m, 3H), 1.88-1.75 (m, 2H), 1.71-1.60 (m, 5H), 1.54-1.34 (m, 7H), 1.32-0.98 (m, 12H), 0.93-0.87 (m, 10H), 0.85 (s, 3H), 0.74-0.68 (m, 1H), 0.65 (s, 3H).

MS MS ESI calcd. For C$_{28}$H$_{47}$F$_3$O$_2$Na [M+Na$^+$]=495, found 495.

Example 6. Synthesis of Compound 3

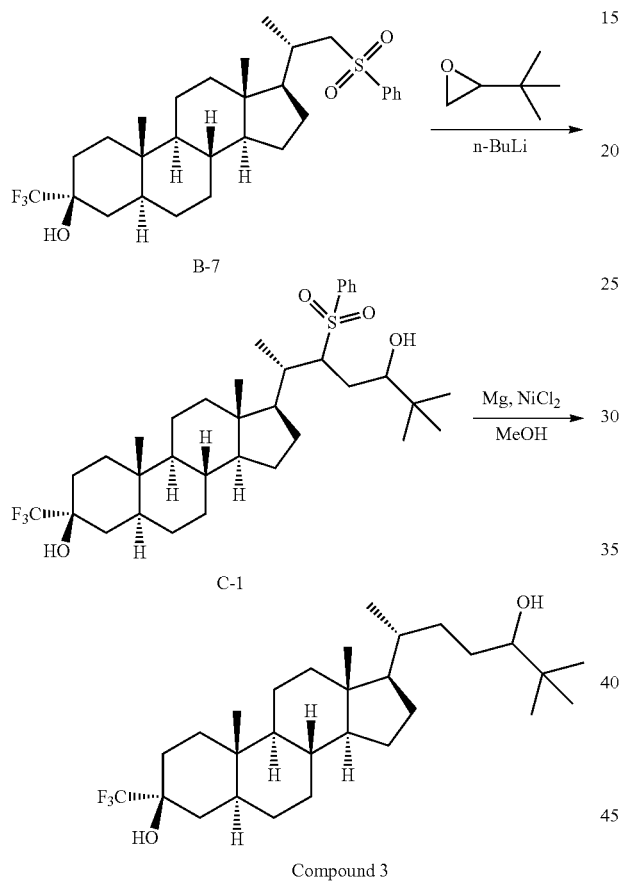

Step 1. To a solution of n-BuLi (568 μL, 2.5 M in hexane, 1.42 mmol) in THF (0.5 mL) at −65° C. under N$_2$ was added a suspension of B-7 (300 mg, 0.5695 mmol) in THF (2.5 mL) drop-wise. The mixture was stirred for 30 minutes at −65° C. 2-(tert-butyl)oxirane (68.4 mg, 0.6834 mmol) was added drop-wise at −65° C. The mixture was stirred for another 30 minutes and then warmed to 25° C. gradually and stirred at 25° C. for 16 hours. The reaction mixture was quenched by saturated NH$_4$Cl aqueous (30 mL), extracted with ethyl acetate (3×20 mL). The combined organic phase was washed with brine (30 mL), dried over Na$_2$SO$_4$, filtered and concentrated under vacuum to give C-1 (380 mg, crude) as a solid, which was used directly for the next step.

Step 2. To a solution of C-1 (380 mg, 0.6062 mmol) and NiCl$_2$ (7.81 mg, 0.06062 mmol) in dry methanol (20 mL) was added Mg powder (580 mg, 24.2 mmol) in 4 portions under N$_2$ with stirring at 50° C. The reaction mixture was stirred at 60° C. for 1 hour. The reaction mixture was cooled and poured into ethyl acetate (150 mL). The mixture was washed with 1 M HCl (3×200 mL), saturated NaHCO$_3$ aqueous (200 mL), brine (200 mL), dried over Na$_2$SO$_4$, filtered and concentrated under vacuum to give a solid, which was purified by silica gel chromatography (PE:EtOAc=8:1) to afford impure Compound 3 (310 mg) as a solid, which was purified by triturating in PE/DCM (15 mL/1 mL) to give Compound 3 (46 mg, 15%) as a solid.

$^1$H NMR (400 MHz, CDCl$_3$) δ 3.16-3.05 (m, 1H), 2.09-2.01 (m, 1H), 2.01-1.92 (m, 2H), 1.89-1.76 (m, 2H), 1.73-1.60 (m, 3H), 1.52-1.33 (m, 8H), 1.32-0.93 (m, 12H), 0.93-0.87 (m, 12H), 0.85 (s, 4H), 0.73-0.61 (m, 4H).

$^{19}$F NMR (400 MHz, CDCl$_3$) δ 78.66.

LCMS Rt=1.354 min in 2 min chromatography, 30-90 AB, MS ESI calcd. for C$_{29}$H$_{48}$F$_3$O [M−H$_2$O+H]$^+$ 469, found 469.

Example 7. Synthesis of Compound 4

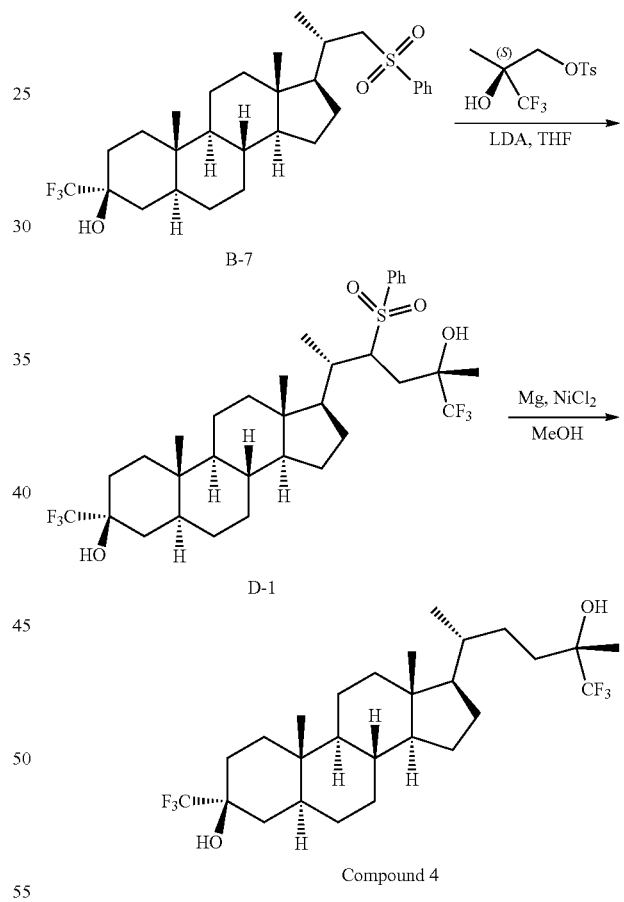

Step 1. To a solution of diisopropylamine (0.2 mL) in THF (0.2 mL) was added butyllithium (0.57 mL, 2.5 M in n-hexane) at −70° C. The mixture was warmed to 25° C. and stirred at 25° C. for 30 minutes. The mixture was cooled to −70° C. and a solution of B-7 (250 mg, 16.5 mmol) in THF (3 mL) was added. After stirring at −70° C. for 1 h, (S)-3,3,3-trifluoro-2-hydroxy-2-methylpropyl 4-methylbenzenesulfonate, see Example 30. (169 mg, 0.57 mmol) was added at −70° C. The mixture was warmed to 25° C. and stirred at this temperature for 16 hours. The mixture was quenched with saturated aqueous NH$_4$Cl (5 mL). The mixture was extracted with EtOAc (2×8 mL), washed with brine (2×20 mL), dried over Na₂SO₄, filtered, concentrated in vacuum to give a crude product D-1 (300 mg, crude) as an oil, which was used in the next step directly.

Step 2. To a solution of D-1 (300 mg, crude) in MeOH (15 mL) was added Mg powder (549 mg, 22.9 mmol) and NiCl₂ (5 mg) at 60° C. The mixture was stirred at 60° C. for 1 h. EtOAc (20 mL) and aq. HCl (30 mL) was added. The mixture was extracted with EtOAc (2×30 mL). The combined organic layers were washed with water (3×50 mL), sat. NaHCO₃ (2×50 mL), brine (2×50 mL) to give a crude product, which was purified by flash column (0-30% of EtOAc in PE) to give Compound 4 (100 mg, impure), which was triturated with CH₃CN (5 mL) at 25° C. to give Compound 4 (50 mg, 50%) as a solid.

$^1$H NMR (400 MHz, CDCl₃) δ 2.10-1.90 (m, 3H), 1.85-1.75 (m, 3H), 1.70-1.60 (m, 5H), 1.50-1.30 (m, 6H), 1.25-1.00 (m, 14H), 0.90-0.80 (m, 7H), 0.70-0.55 (m, 4H).

LCMS Rt=1.264 min in 2 min chromatography, 30-90 AB, MS ESI calcd. For $C_{27}H_{41}F_6O$ [M+H−H₂O]⁺ 495, found 495.

Example 8. Synthesis of Compound E-1

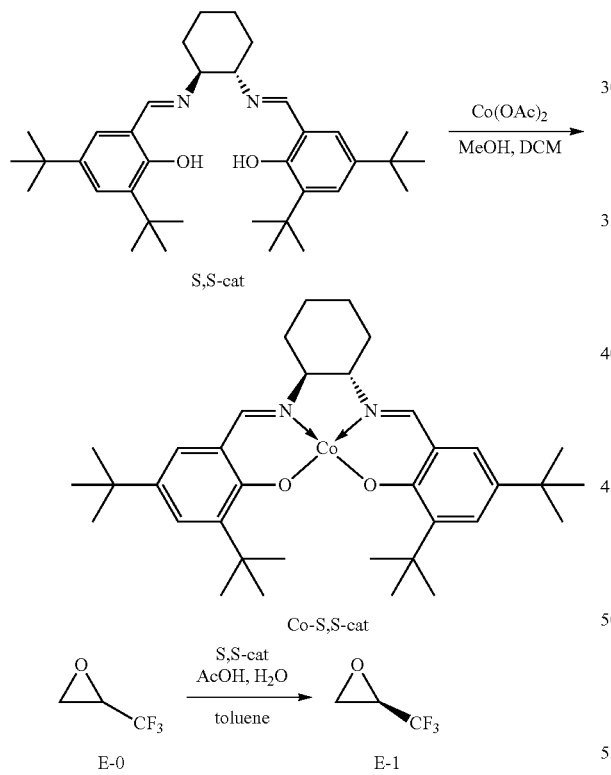

Step 1. To a solution of S,S-cat (2 g, 3.65 mmol) in anhydrous DCM (30 mL) was added a solution of cobalt(II) acetate (775 mg, 4.38 mmol) in MeOH (30 mL) under nitrogen at 20° C. The mixture was stirred for 30 mins at 20° C. and at 0° C. for 1 h. The precipitated solid was filtered, washed with cold MeOH (2×30 mL) and dried in vacuum to give Co—S,S-cat (1.6 g, 73%) as a solid.

Step 2. To a solution of Co—S,S-cat (1.07 g, 1.78 mmol) in toluene (30 mL) was added AcOH (1.12 g, 18.7 mmol). The mixture was stirred at 20° C. for 30 mins. The solution was concentrated in vacuum to give a solid. The resulting catalyst residue was dissolved in neat E-0 (100 g, 892 mmol) at 20° C., the reaction mixture was cooled to 0° C., and water (8.82 g, 490 mmol) was added dropwise. The mixture was warmed to 20° C. and stirred for 48 hrs. E-1 (44 g) was isolated by distillation from the reaction mixture.

$^1$H NMR (400 MHz, DMSO-d6) δ 3.96 (s, 1H), 3.11-2.98 (m, 2H).

The e.e. of E-1 was determined by opening the epoxide with benzylamine. E-1 (200 mg, 1.78 mmol) was added to dry benzylamine (190 mg, 1.78 mmol), and the mixture was stirred at 20° C. for 2 hrs. A solid precipitated, which was triturated from petroleum ether to afford the product (260 mg, 67%) as a solid. The e.e. of this product was determined to be 100% by chiral HPLC (Column: CD-PH 250*4.6 mm I.D., 5 um; Mobile phase: from 10% to 80% of B in A (A:Water with 0.069% TFA B:Acetonitrile); Flow rate: 0.8 mL/min; Column Temperature: 30° C.).

Example 9. Synthesis of Compound 5

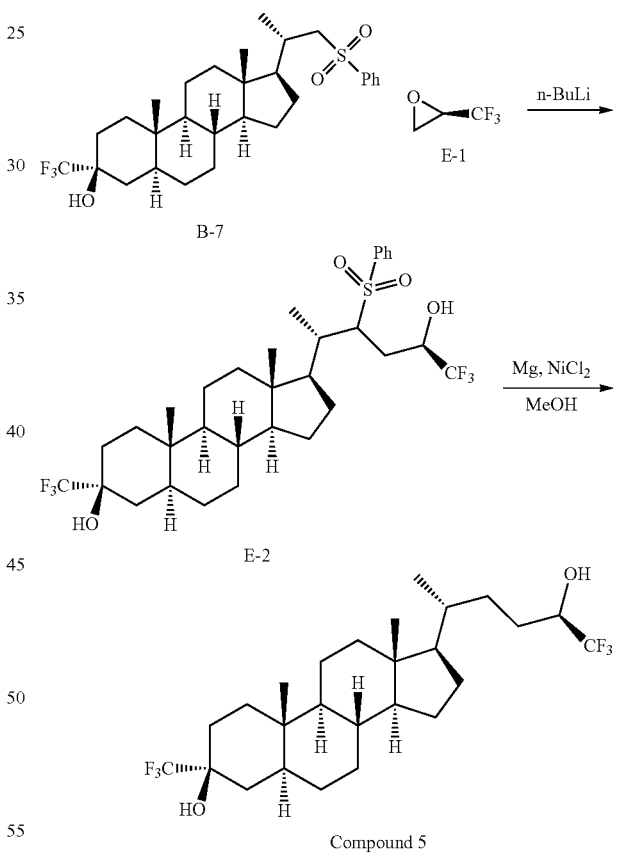

Step 1. To a solution of n-BuLi (0.704 mL, 2.5 M in hexane, 1.76 mmol) in THF (0.5 mL) at −65° C. under N₂ was added a suspension of B-7 (310 mg, 0.588 mmol) in THF (2.5 mL) dropwise and the reaction was stirred for 30 minutes at −65° C. A solution of E-1 (78.9 mg, 0.705 mmol) was added dropwise at −65° C. The mixture was stirred for another 30 minutes and then warmed to 25° C. gradually and stirred at 25° C. for 16 hours. The reaction mixture was quenched by saturated NH₄Cl aqueous (30 mL), extracted with ethyl acetate (3×20 mL). The combined organic phase was washed with brine (30 mL), dried over Na$_2$SO$_4$, filtered and concentrated under vacuum to give E-2 (300 mg, crude) as a solid, which was used directly for the next step.

Step 2. To a solution of E-2 (300 mg, 0.469 mmol) and nickel (II) chloride (15.1 mg, 0.117 mmol) in dry methanol (20 mL) was added magnesium powder (454 mg, 18.7 mmol) under N$_2$ with stirring at 50° C. to initiate continuous hydrogen generation. The reaction mixture was stirred at 60° C. for 1 hour. The reaction mixture was quenched by 2M HCl (100 mL) dropwise at 10° C. until the solid was dissolved. After extracting with EtOAc (2×150 mL), the combined organic layer was washed with sat. NaHCO$_3$ aq. (300 mL), brine (300 mL), dried over Na$_2$SO$_4$, filtered and concentrated under vacuum to give a solid, which was purified by silica gel chromatography (PE:THF=12:1) to give the product. The residue was re-crystallized from MeCN (10 mL) to afford Compound 5 (41 mg, 18%) as a solid.

$^1$H NMR (400 MHz, CDCl$_3$) δ 3.75-3.65 (m, 1H), 2.10-1.95 (m, 3H), 1.90-1.75 (m, 2H), 1.73-1.66 (m, 5H), 1.56-1.30 (m, 14H), 1.29-1.01 (m, 5H), 1.00-0.85 (m, 3H), 0.84 (s, 3H), 0.67-0.60 (m, 4H).

LCMS Rt=1.226 min in 2.0 min chromatography, 30-90 AB.

Example 10. Synthesis of Compound 6

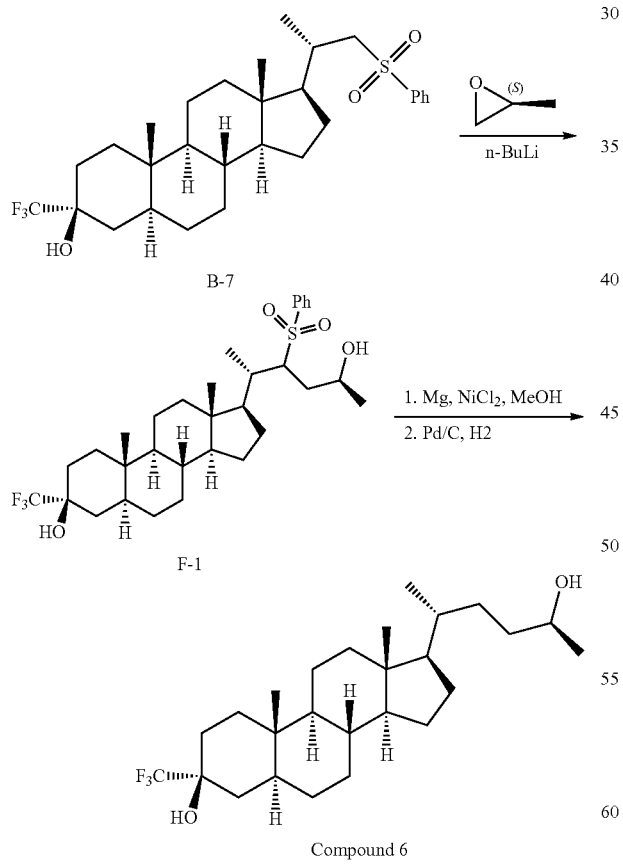

Step 1. To a solution of n-BuLi (0.568 mL, 2.5 M in hexane, 1.42 mmol) in THF (0.5 mL) at −65° C. under N$_2$ was added a suspension of B-7 (250 mg, 0.474 mmol) in THF (2.5 mL) dropwise. After stirring at −65° C. for 30 minutes, a solution of (2S)-2-methyloxirane (32.9 mg, 0.568 mmol) was added dropwise at −65° C. The mixture was stirred for another 30 minutes and then warmed to 25° C. gradually and stirred at 25° C. for 16 hours. The reaction mixture was quenched with saturated NH$_4$Cl aqueous (30 mL), and extracted with ethyl acetate (3×20 mL). The combined organic phase was washed with brine (30 mL), dried over Na$_2$SO$_4$, filtered and concentrated under vacuum to give F-1 (250 mg, crude) as a solid, which was used directly for the next step.

Step 2. To a solution of F-1 (250 mg, 0.427 mmol) and nickel (II) chloride (13.7 mg, 0.106 mmol) in dry methanol (20 mL) was added magnesium powder (413 mg, 17.0 mmol) under N$_2$ with stirring at 50° C. to initiate continuous hydrogen generation. The reaction mixture was stirred at 60° C. for 1 hour. The reaction mixture was quenched by 2M HCl (100 mL) which was added dropwise at 10° C. until the solid was dissolved. After extracting with EtOAc (2×150 mL), the combined organic layer was washed with sat. NaHCO$_3$ aq. (300 mL), brine (300 mL), dried over Na$_2$SO$_4$, filtered and concentrated under vacuum to give a solid, which was purified by silica gel chromatography (PE/THF=12/1) to give impure Compound 6 (100 mg, containing 12% of 22,23-olefin by NMR) as a solid. To a solution of the impure Compound 6 (100 mg, 0.224 mmol) in EtOAc (10 mL) was added Pd/C (26.5 mg, 0.224 mmol) under N$_2$ to remove the undesired olefin. The mixture was degassed under vacuum and purged with H$_2$ several times. The mixture was stirred for 2 hrs at 25° C. under H$_2$. The mixture was filtered and the filtrate was concentrated in vacuum to give residue. The residue was purified by re-crystallization from MeCN (10 mL) to give Compound 6 (35 mg, 19%) as a solid.

$^1$H NMR (400 MHz, CDCl$_3$) δ 3.75-3.65 (m, 1H), 2.10-1.95 (m, 3H), 1.90-1.75 (m, 2H), 1.73-1.66 (m, 4H), 1.56-1.30 (m, 8H), 1.29-1.01 (m, 14H), 1.00-0.85 (m, 4H), 0.84 (s, 3H), 0.67-0.60 (m, 4H).

LCMS Rt=1.222 min in 2.0 min chromatography, 30-90 AB, MS ESI calcd. for C$_{28}$H$_{42}$F$_3$O [M+H−H$_2$O]$^-$ 427, found 427.

Example 11. Syntheses of Compounds 7, 7-A, and 7-B

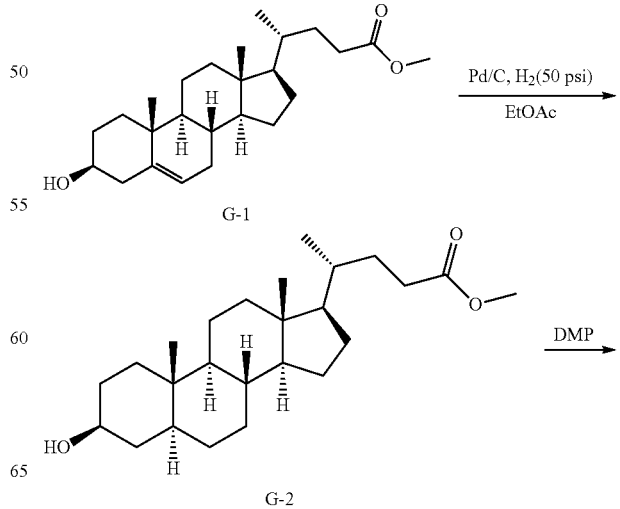

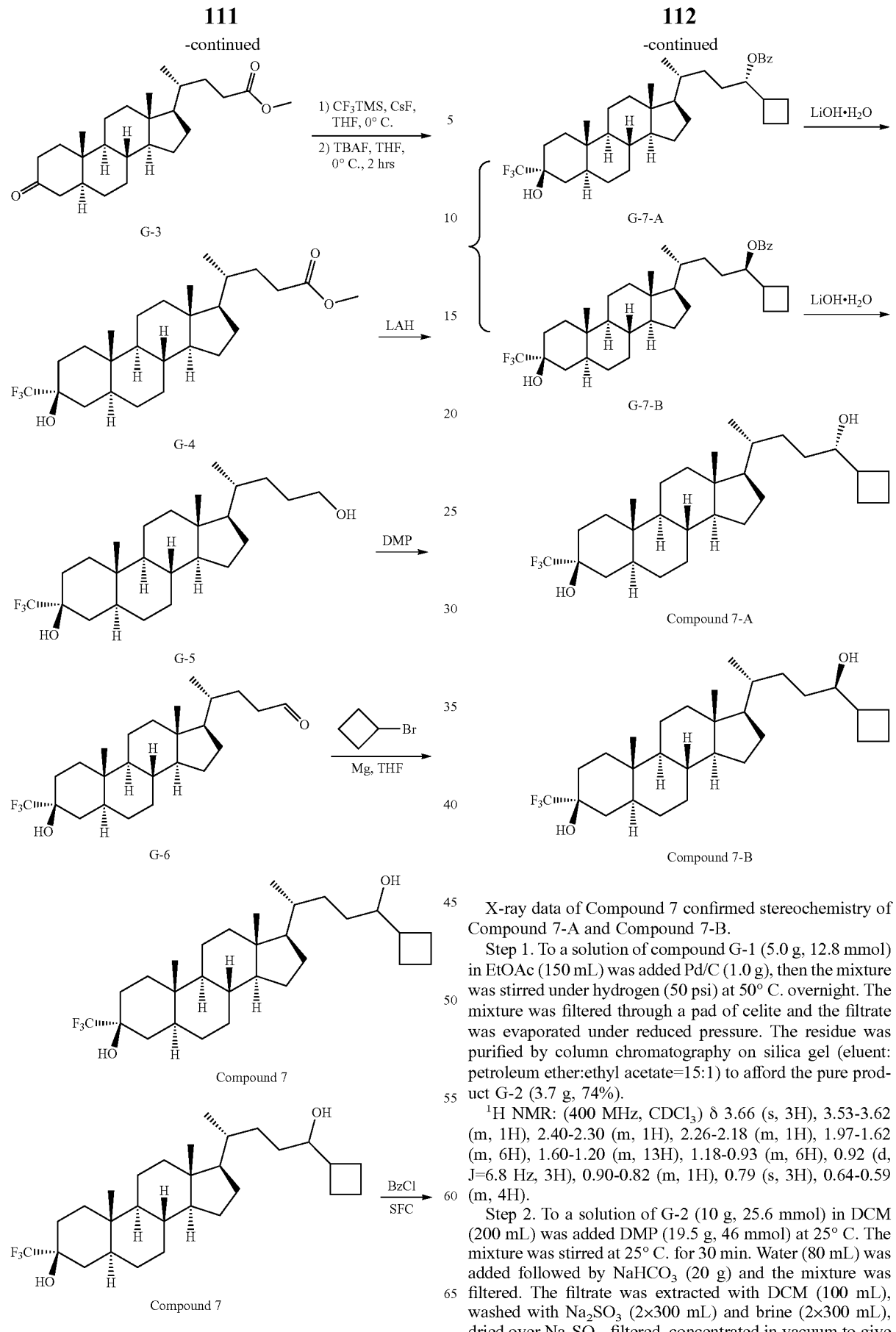

X-ray data of Compound 7 confirmed stereochemistry of Compound 7-A and Compound 7-B.

Step 1. To a solution of compound G-1 (5.0 g, 12.8 mmol) in EtOAc (150 mL) was added Pd/C (1.0 g), then the mixture was stirred under hydrogen (50 psi) at 50° C. overnight. The mixture was filtered through a pad of celite and the filtrate was evaporated under reduced pressure. The residue was purified by column chromatography on silica gel (eluent: petroleum ether:ethyl acetate=15:1) to afford the pure product G-2 (3.7 g, 74%).

$^1$H NMR: (400 MHz, CDCl$_3$) δ 3.66 (s, 3H), 3.53-3.62 (m, 1H), 2.40-2.30 (m, 1H), 2.26-2.18 (m, 1H), 1.97-1.62 (m, 6H), 1.60-1.20 (m, 13H), 1.18-0.93 (m, 6H), 0.92 (d, J=6.8 Hz, 3H), 0.90-0.82 (m, 1H), 0.79 (s, 3H), 0.64-0.59 (m, 4H).

Step 2. To a solution of G-2 (10 g, 25.6 mmol) in DCM (200 mL) was added DMP (19.5 g, 46 mmol) at 25° C. The mixture was stirred at 25° C. for 30 min. Water (80 mL) was added followed by NaHCO$_3$ (20 g) and the mixture was filtered. The filtrate was extracted with DCM (100 mL), washed with Na$_2$SO$_3$ (2×300 mL) and brine (2×300 mL), dried over Na$_2$SO$_4$, filtered, concentrated in vacuum to give a crude product G-3 (9 g) as a solid, which was used in the next step without further purification.

$^1$H NMR (400 MHz, CDCl$_3$) δ 3.66 (s, 3H), 2.41-2.29 (m, 1H), 2.27-2.16 (m, 1H), 2.10-1.91 (m, 3H), 1.88-1.62 (m, 6H), 1.52-0.98 (m, 16H), 0.97-0.87 (m, 4H), 0.84 (s, 3H), 0.73-0.63 (m, 4H).

Step 3. To a mixture of G-3 (7 g, 18.0 mmol) and CsF (5.46 g, 36.0 mmol) in THF (70 mL) was added drop wise TMSCF$_3$ (5.11 g, 36.0 mmol) at 0° C. The mixture was stirred and kept below 10° C. for 10 min. TBAF (45.0 mL, 1 M in THF, 45.0 mmol) was added at 10° C. and the mixture was stirred and kept below 10° C. for 10 min. After that, the mixture was treated with water (200 mL) and extracted with EtOAc (2×200 mL). The combined organic layers was washed with brine (500 mL), dried over Na$_2$SO$_4$, filtered and concentrated in vacuum. The residue was purified by silica gel chromatograph (PE/EtOAc=5/1) to afford G-4 (5.55 g, 67%), 4H), 0.84 (s, 3H), 0.73-0.63 (m, 4H).

Step 4. To a suspension of LiAlH$_4$ (1.03 g, 27.4 mmol) in THF (80 mL) was added a solution of G-4 (6.3 g, 13.7 mmol) in THF (20 mL) under N$_2$ dropwise at 0° C. The reaction was stirred at 25° C. for 2 h. The reaction was quenched with water/THF (1/10, 40 mL) followed by adding 2 M HCl (100 mL) at 0° C. The mixture was extracted with EtOAc (2×100 mL). The combined organic phase was washed with brine (300 mL), dried over Na$_2$SO$_4$, filtered and concentrated to afford G-5 (5 g, crude) as a solid.

$^1$H NMR (400 MHz, CDCl$_3$) δ 3.61 (s, 2H), 2.11-1.92 (m, 4H), 1.90-1.77 (m, 2H), 1.73-1.60 (m, 5H), 1.52-0.98 (m, 17H), 0.96-0.87 (m, 4H), 0.85 (s, 3H), 0.73-0.64 (m, 4H).

Step 5. To a solution of G-5 (3 g, 6.96 mmol) in DCM (30 mL) was added DMP (5.89 g, 13.9 mmol) at 20° C. The reaction mixture was stirred at 20° C. for 20 min and quenched with saturated NaHCO$_3$ aqueous (30 mL) at 20° C. The mixture was filtered. The DCM layer was separated and the aqueous phase was extracted with DCM (30 mL). The combined organic phase was washed with saturated Na$_2$SO$_3$ aqueous (3×50 mL), brine (50 mL), dried over Na$_2$SO$_4$, filtered and concentrated in vacuum, the residue was triturated from CH$_3$CN (5 mL) at 20° C. to give G-6 (1.3 g, 44%) as a solid.

$^1$H NMR (400 MHz, CDCl$_3$) δ 9.78-9.75 (t, J=2.00 Hz, 1H), 2.51-2.20 (m, 2H), 2.11-1.74 (m, 6H), 1.74-0.97 (m, 19H), 0.96-0.87 (m, 4H), 0.85 (s, 3H), 0.73-0.67 (m, 1H), 0.65 (s, 3H).

Step 6. To a suspension of Mg (2 g, 82.2 mmol) and 12 (10 mg) in THF (2 mL) was added a solution of bromocyclobutane (5 g, 37.0 mmol) in THF (8 mL) at 60° C. dropwise. The mixture was stirred at 60° C. for 1 h. The mixture was diluted with THF (10 mL) and used directly. The Grignard reagent was added to a solution of G-6 (0.6 g, 1.40 mmol) in THF (5 mL) at 0° C. The mixture was stirred at 0° C. for 1 h and quenched with NH$_4$Cl (10 mL, sat. aq.). The mixture was extracted with EtOAc (3×20 mL). The organic layer was separated, concentrated in vacuum, purified by silica gel (PE/EtOAc=20/1 to 5/1) to give a crude product, which was re-crystallized from MeCN/H$_2$O (5/2, 15 mL) to give Compound 7 (250 mg, 37%) as a solid.

$^1$H NMR (400 MHz, CDCl$_3$) δ 3.49-3.38 (m, 1H), 2.40-2.25 (m, 1H), 2.10-1.90 (m, 5H), 1.90-1.60 (m, 9H), 1.57-1.18 (m, 14H), 1.17-0.96 (m, 6H), 0.96-0.86 (m, 4H), 0.84 (s, 3H), 0.73-0.62 (m, 4H).

HPLC Rt=6.10 min in 8.0 min chromatography, 50-100 AB.

MS ESI calcd. for C$_{29}$H$_{46}$F$_3$O [M+H−H$_2$O]$^+$ 467, found 467.

Step 7. To a solution of Compound 7 (200 mg, 0.412 mmol) in DCM (5 mL) was added pyridine (650 mg, 8.23 mmol) and BzCl (347 mg, 2.47 mmol). The mixture was stirred at 25° C. for 1 h. The mixture was treated with H$_2$O (5 mL) and washed with HCl (10 mL, 1 M, aq.), NaHCO$_3$ (10 mL, sat. aq.), dried over Na$_2$SO$_4$, filtered, concentrated in vacuum to give a crude product, which was purified by silica gel column (PE/EtOAc=10/1) to give 300 mg of impure product. The impure product was separated by SFC (column: Chiralpak AD-350*4.6 mm I.D., 3 um); Condition: Base-IPA; Gradient: 5-40% B; flow rate: 4 mL/min) to give G-6-A (75 mg, 31%, t$_R$=5.282 min, 100% d.e. ("Column: Chiralpak AD-3 150×4.6 mm I.D., 3 um Mobile phase: A: CO$_2$ B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.")) and G-6-B (88 mg, 36%, t$_R$=4.827 min, 100% d.e. ("Column: Chiralpak AD-3150×4.6 mm I.D., 3 um Mobile phase: A: CO$_2$ B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.")).

Step 8a. To a solution of G-7-A (75 mg, 0.127 mmol) in THF (5 mL) and MeOH (1 mL) was added a suspension of LiOH.H$_2$O (399 mg, 9.52 mmol) in water (1 mL). The mixture was stirred at 60° C. for 24 h. After removing the organic solvent in vacuum, the mixture was treated with H$_2$O (5 mL) and extracted with EtOAc (3×5 mL). The organic layers were washed with brine (2×15 mL), dried over Na$_2$SO$_4$, filtered, concentrated in vacuum. The residue was triturated from CH$_3$CN (2 mL) at 25° C. to give Compound 7-A (43 mg, 70%) as a solid.

$^1$H NMR (400 MHz, CDCl$_3$) δ 3.49-3.41 (m, 1H), 2.37-2.26 (m, 1H), 2.10-1.75 (m, 10H), 1.75-1.60 (m, 4H), 1.52-1.15 (m, 16H), 1.15-0.93 (m, 4H), 0.92-0.82 (m, 7H), 0.73-0.62 (m, 4H).

HPLC Rt=6.78 min in 8.0 min chromatography, 30-90 AB.

MS ESI calcd. for C$_{29}$H$_{46}$F$_3$O [M+H−H$_2$O]$^+$ 467, found 467.

Step 8b. To a solution of G-7-B (88 mg, 0.149 mmol) in THF (5 mL) and MeOH (1 mL) was added a suspension of LiOH.H$_2$O (406 mg, 9.68 mmol) in water (1 mL). The mixture was stirred at 60° C. for 24 h. After removing the organic solvent in vacuum, the mixture was treated with H$_2$O (5 mL) and extracted with EtOAc (3×5 mL). The organic layers were washed with brine (2×15 mL), dried over Na$_2$SO$_4$, filtered, concentrated in vacuum. The residue was triturated from CH$_3$CN (2 mL) at 25° C. to give Compound 7-B (52 mg, 72%) as a solid.

$^1$H NMR (400 MHz, CDCl$_3$) δ 3.48-3.37 (m, 1H), 2.39-2.26 (m, 1H), 2.10-1.74 (m, 10H), 1.72-1.61 (m, 4H), 1.53-1.19 (m, 13H), 1.19-0.94 (m, 7H), 0.94-0.80 (m, 7H), 0.73-0.62 (m, 4H).

HPLC Rt=6.78 min in 8.0 min chromatography, 30-90 AB

MS ESI calcd. for C$_{29}$H$_{46}$F$_3$O [M+H−H$_2$O]$^+$ 467.3495, found 467.3.

Example 12. Synthesis of Compound H-1

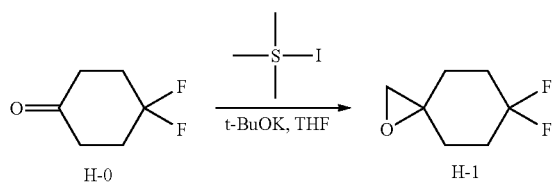

To a suspension of Me₃SI (3.93 g, 19.3 mmol) in THF (20 mL) was added a solution of t-BuOK (3.33 g, 29.8 mmol) in THF (10 mL) under N₂ at 15° C. The suspension was stirred at 15° C. for 30 mins A solution of H-0 (2 g, 14.9 mmol) in THF (5 mL) was added dropwise at 15° C. The mixture was stirred at 15° C. for 16 hrs. The mixture was quenched with Sat.NH₄Cl (50 mL) and extracted with EtOAc (3×20 mL). The combined organic phase was dried over Na₂SO₄, filtered, and concentrated to give H-1 (1.8 g, 82%) as a solid.

$^1$H NMR (400 MHz, CDCl₃) δ 2.72 (s, 2H), 2.20-1.85 (m, 8H).

Example 13. Synthesis of Compound 8

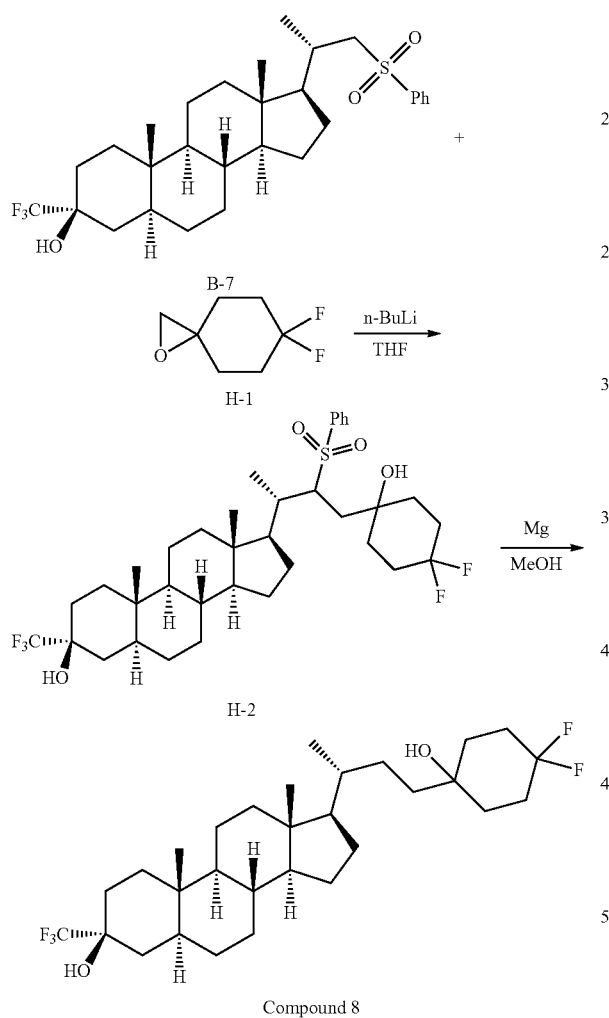

Step 1. To a solution of THF (5 mL) and BuLi (3.78 mL, 2.5 M in hexane, 9.47 mmol) was added a solution of B-7 (2 g, 3.79 mmol) in THF (15 mL) at −70° C. After stirring at −70° C. for 1 h, a solution of H-1 (1.68 g, 5.68 mmol) in THF (5 mL) was added at −70° C. The mixture was stirred at −70° C. for another 1 h. The mixture was warmed to 25° C. and stirred for 16 hrs and quenched by adding NH₄Cl (50 mL, sat. aq.). The mixture was extracted with EtOAc (2×30 mL). The organic layer was separated, dried over Na₂SO₄, filtered, concentrated, and purified by combi-flash (0-10% of EtOAc in PE) to give H-2 (250 mg, 10%) as a solid and 1.8 g of starting material which was recycled.

$^1$H NMR (400 MHz, CDCl₃) δ 8.00-7.92 (m, 2H), 7.73-7.65 (m, 1H), 7.63-7.52 (m, 2H), 3.62-3.55 (m, 1H), 2.37-2.28 (m, 1H), 2.15-1.94 (m, 4H), 1.94-1.85 (m, 6H), 1.85-1.55 (m, 5H), 1.55-1.43 (m, 6H), 1.43-1.10 (m, 10H), 1.10-0.90 (m, 3H), 0.90-0.70 (m, 6H), 0.70-0.57 (m, 1H), 0.55 (s, 3H).

Step 2. To a solution of H-2 (250 mg, 0.37 mmol) in MeOH (15 mL) was added Mg powder (355 mg, 14.8 mmol) at 55° C. The mixture was stirred at 60° C. for 16 hrs. The mixture was quenched with HCl (50 mL, 1N) until the reaction became clear and extracted with DCM (2×30 mL). The combined organic phase was dried over Na₂SO₄, filtered, concentrated and purified by flash column (0-10% of EtOAc in PE) to give Compound 8 (55 mg, 28%) as a solid.

$^1$H NMR (400 MHz, CDCl₃) δ 2.20-1.73 (m, 9H), 1.73-1.58 (m, 7H), 1.58-0.85 (m, 11H), 0.85-1.00 (m, 8H), 1.00-0.86 (m, 5H), 0.85 (s, 3H), 0.72-0.62 (m, 4H).

LCMS Rt=1.286 min in 2 min chromatography, 30-90 AB, MS ESI calcd. for C₃₀H₄₆F₅O [M−H₂O+H]⁺ 517, found 517.

Example 14. Synthesis of Compound 9

To a suspension of Mg (1.37 g, 56.5 mmol) and I₂ (10 mg) in THF (2 mL) was added a solution of 4-chlorotetrahydro-2H-pyran (2.72 g, 22.6 mmol) in THF (8 mL) at 60° C. dropwise. The mixture was stirred at 60° C. for 2 h. The mixture was diluted with THF (10 mL) and used directly. The Grignard reagent was added to a solution of G-6 (0.55 g, 1.28 mmol) in THF (5 mL) at 0° C. The mixture was stirred at 0° C. for 1 h and treated with NH₄Cl (10 mL, sat. aq.). The mixture was extracted with EtOAc (3×20 mL). The organic layer was separated, concentrated in vacuum, purified by silica gel column (PE/EtOAc=20/1 to 5/1) to give a crude product, which was re-crystallized from CH₃CN (10 mL) to give Compound 9 (180 mg, 27%) as a solid.

$^1$H NMR (400 MHz, CDCl₃) δ 4.05-3.97 (m, 2H), 3.41-3.25 (m, 3H), 2.10-1.91 (m, 3H), 1.88-1.57 (m, 7H), 1.55-1.33 (m, 11H), 1.33-0.96 (m, 12H), 0.96-0.86 (m, 4H), 0.85 (s, 3H), 0.72-0.63 (m, 4H).

HPLC Rt=4.73 min in 8.0 min chromatography, 50-100 AB.

MS ESI calcd. for C₃₀H₄₈F₃O₂ [M+H−H₂O]⁺ 497, found 497.

Example 15. Synthesis of Compound J-1

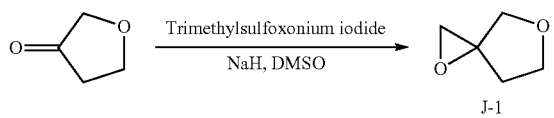

To a mixture of trimethylsulfoxonium iodide (30.6 g, 150 mmol) in THF (100 mL) was added NaH (5.98 g, 60% in mineral oil, 150 mmol) in portions at 0° C. under $N_2$. The mixture was stirred at 0° C. for 30 mins. Dihydrofuran-3 (2H)-one (10 g, 116 mmol) in DMSO (100 mL) was added dropwise at 0° C. The reaction mixture was stirred at 0° C. for 2 hours. The mixture was poured into ice-water (500 mL) in portions, extracted with DCM (2×500 mL). The combined organic phase was washed with brine (500 mL), dried over $Na_2SO_4$, filtered and concentrated at 30° C. The residue was purified by Combi-flash (EtOAc in PE, 0%~40%) to afford J-1 (1.5 g, 13%) as an oil.

$^1$H NMR (400 MHz, CDCl$_3$) δ 4.11-3.90 (m, 3H), 3.66 (d, J=10.0 Hz, 1H), 3.03 (d, J=4.4 Hz, 1H), 2.94 (d, J=4.0 Hz, 1H), 2.34-2.23 (m, 1H), 2.00-1.88 (m, 1H).

Example 16. Synthesis of Compound 10

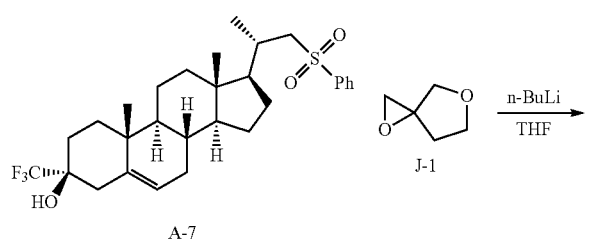

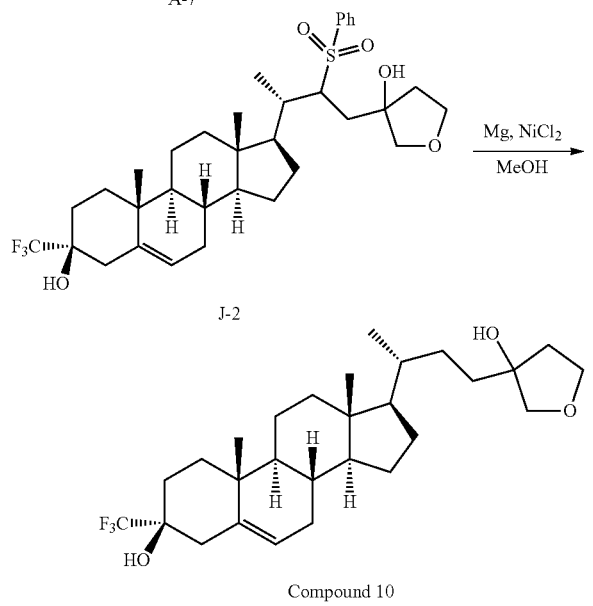

Step 1. To a solution of n-BuLi (0.95 mL, 2.38 mmol, 2.5 M) in THF (2 mL) under $N_2$ at −70° C. was added a suspension of A-7 (see Example 3) (500 mg, 0.95 mmol) in THF (5 mL) drop-wise to give a suspension. After stirring at −70° C. for 30 min, a solution of J-1 (238 mg, 2.38 mmol) in THF (3 mL) was added. Then the reaction was stirred at −70° C. for 10 min and 20° C. for 16 hours. The reaction was quenched with sat.NH$_4$Cl (20 mL), extracted with EtOAc (3×20 mL). The combined organic phase was washed with brine (50 mL), dried over anhydrous sodium sulfate, filtered and concentrated to give the crude product J-2 (500 mg) as a solid, which was used directly in next step.

LCMS Rt=0.925 min in 1.5 min chromatography, 5-95 AB, MS ESI calcd. for $C_{34}H_{47}F_3O_5SNa$ [M+Na]$^+$ 647, found 647.

Step 2. To a solution of J-2 (300 mg, 0.48 mmol) in 20 mL of dry methanol under $N_2$ was added magnesium turnings (466 mg, 19.2 mmol) (activated with 0.5% aqueous HCl, water, dry ethanol, and MTBE) and NiCl$_2$ (12.4 mg, 0.96 mmol) with stirring at 55° C. to initiate continuous hydrogen generation. After the addition of a further two batches of 466 mg of magnesium turnings, most of the starting material was consumed. The reaction mixture was quenched by 2M HCl (100 mL) which was added dropwise at 10° C. until solid was dissolved. After extraction with DCM (3×80 mL), the combined organic phase was washed with brine (100 mL), dried over Na$_2$SO$_4$, filtered and concentrated. The residue was purified by Combi-flash (0%~50% of EtOAc in PE) to afford Compound 10 (46 mg, 20%) as a solid.

$^1$H NMR (400 MHz, CDCl$_3$) δ 5.43-5.32 (m, 1H), 4.08-3.98 (m, 1H), 3.95-3.85 (m, 1H), 3.75-3.66 (m, 1H), 3.59-3.51 (m, 1H), 2.53-2.45 (m, 2H), 2.11-1.87 (m, 6H), 1.82-1.65 (m, 4H), 1.54-1.38 (m, 7H), 1.33-1.12 (m, 6H), 1.08-0.92 (m, 9H), 0.79-0.61 (m, 4H).

LCMS Rt=1.121 min in 2 min chromatography, 30-90 AB, MS ESI calcd. for $C_{30}H_{46}F_3O_3NNa$ [M+MeCN+Na]$^+$ 548, found 548.

Example 17. Synthesis of Compound 11

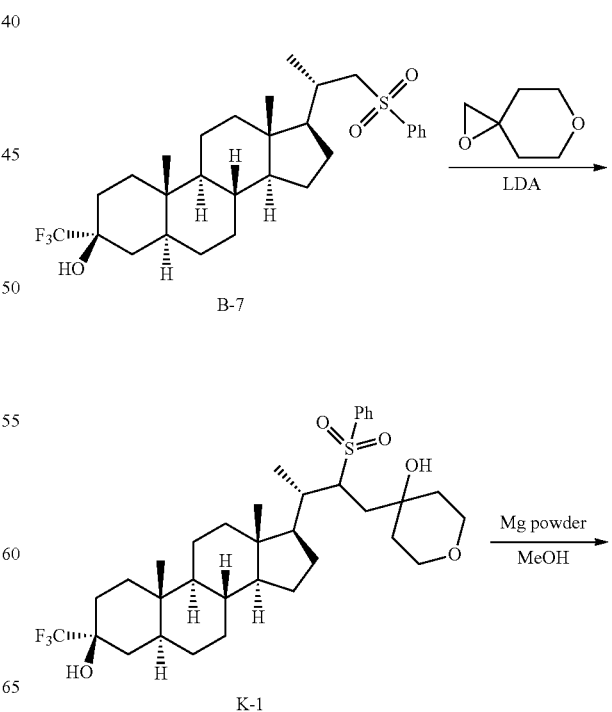

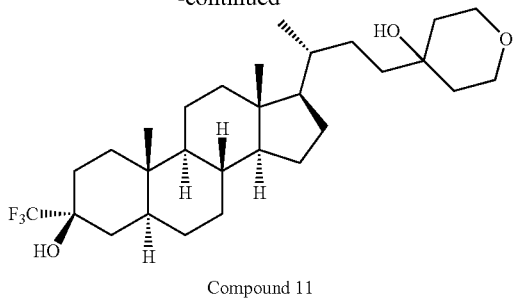

Compound 11

Step 1. To a solution of n-BuLi (452 μL, 2.5 M in hexane, 1.13 mmol) in THF (0.5 mL) at −65° C. under N₂ was added a suspension of B-7 (200 mg, 0.3797 mmol) in THF (2.5 mL) was added drop-wise and stirred for 30 minutes at −65° C. After that, diisopropylamine (114 mg, 1.13 mmol) was added at −65° C., followed by adding 1,6-dioxaspiro[2.5] octane (65.0 mg, 0.5695 mmol) was added drop-wise at −65° C. The mixture was stirred for another 30 minutes and then warmed to 25° C. gradually and stirred at 25° C. for 16 hour. The reaction mixture was quenched by saturated NH₄Cl aqueous (30 mL), extracted with ethyl acetate (3×20 mL). The combined organic phase was washed with brine (30 mL), dried over Na₂SO₄, filtered and concentrated under vacuum to give K-1 (380 mg, crude) as a solid, which was used directly for the next step.

Step 2. To a solution of K-1 (0.348 g, 0.543 mmol) in MeOH (20 mL) was added Mg (0.520 g, 21.7 mmol) and NiCl₂ (3.51 mg, 0.0271 mmol) at 60° C. The mixture was stirred at 60° C. for 1 hour. The reaction mixture was cooled to 25° C. The mixture was added in HCl (20 mL, 1 M in water). The mixture was extracted with EtOAc (2×20 mL), washed with NaHCO₃ (2×40 mL) and brine (2×40 mL), dried over Na₂SO₄, filtered, concentrated in vacuum. The crude residue was purified by silica gel column (PE/EtOAc=10/1 to 2/1) to give 66 mg of impure Compound 11 as a solid, which was triturated from CH₃CN (5 mL) at 25° C. to give Compound 11 (30 mg, 11%) as a solid.

$^1$H NMR (400 MHz, CDCl₃) δ 3.84-3.64 (m, 4H), 2.11-1.90 (m, 3H), 1.87-1.61 (m, 6H), 1.51-1.20 (m, 16H), 1.18-0.96 (m, 7H), 0.94-0.80 (m, 7H), 0.74-0.61 (m, 4H).

LCMS Rt=1.170 min in 2.0 min chromatography, 30-90 AB, MS ESI calcd. for $C_{29}H_{46}F_3O_2$ [M+H−H₂O]⁺ 483, found 483.

Example 18: Synthesis of Compound 1839

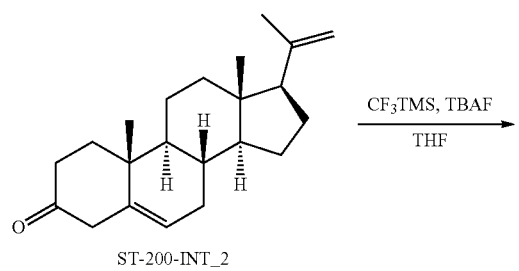

ST-200-INT_2

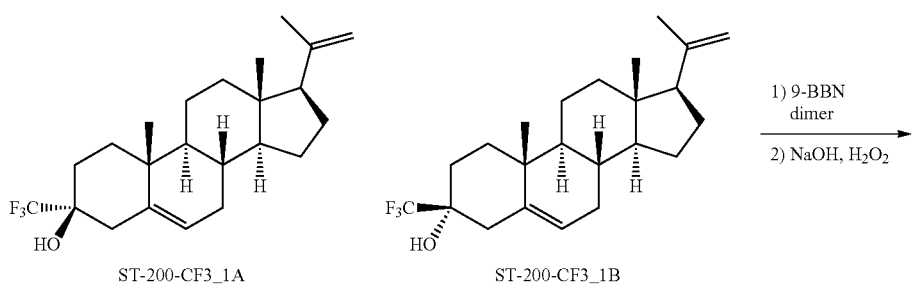

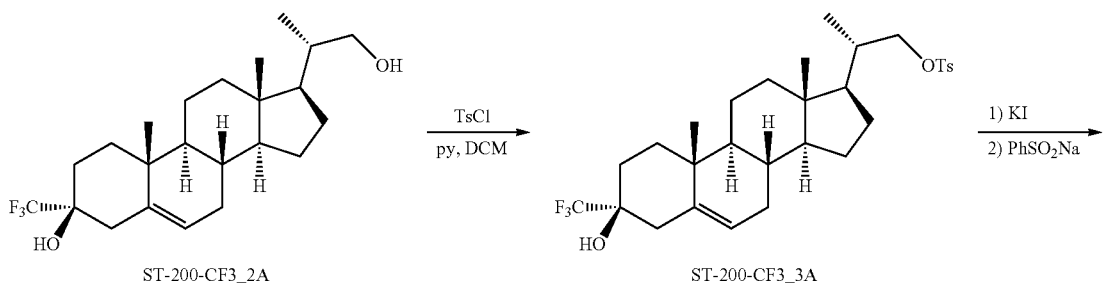

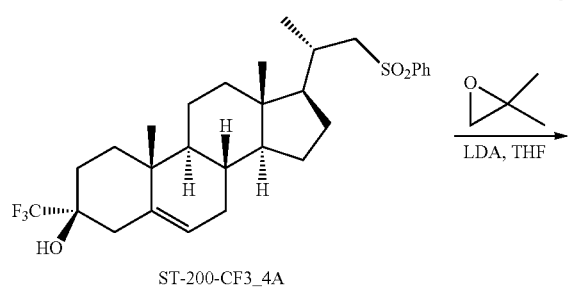

ST-200-CF3_4A

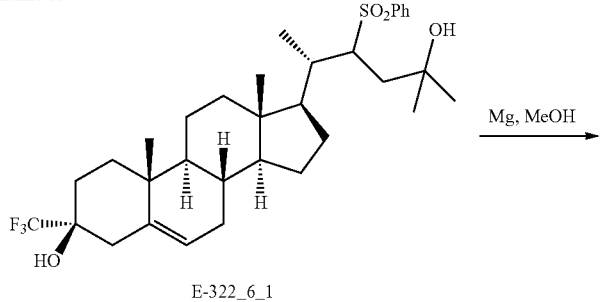

E-322_6_1

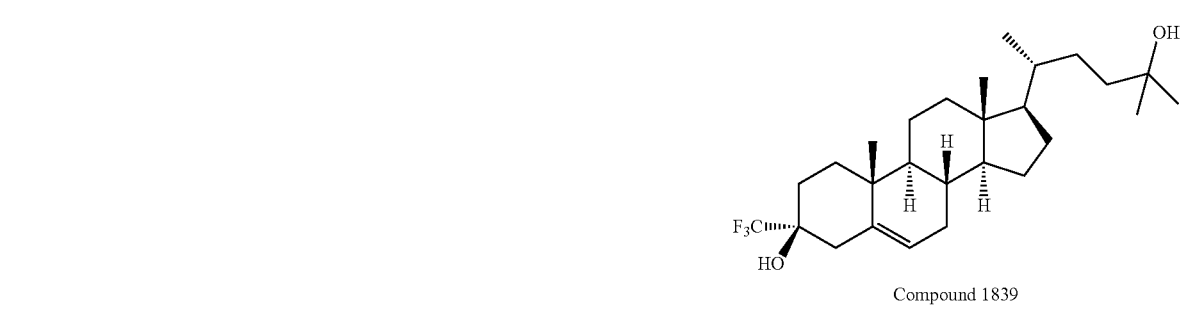

Compound 1839

The experimental of intermediate ST-200-INT_2, or A2, can be found in Example 3.

Synthesis of ST-200-CF3_1A

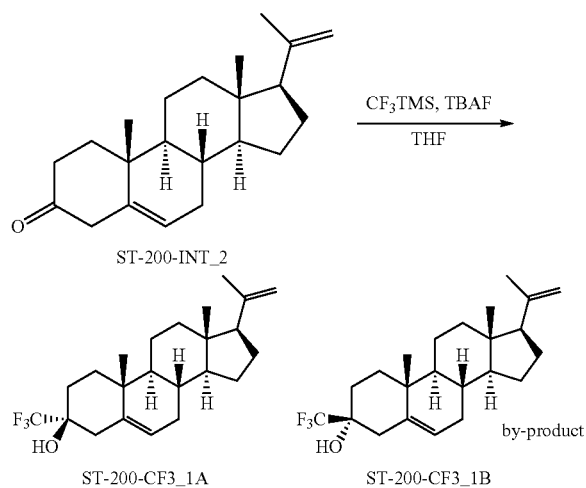

A solution of ST-200-INT_2 (9.5 g, 30.4 mmol) and TMSCF$_3$ (12.9 g, 91.2 mmol) in THF (50 mL) was added dropwise within 30 mins at 0° C. to a suspension of CsF (462 mg, 3.04 mmol) in THF (100 mL). The mixture was stirred at 10° C. for 16 hrs. TLC showed the starting material remained. The mixture was cooled to 0° C. TBAF (3 mL, 1 M in THF, 3 mmol, Aldrich) was added to the mixture at 0° C. The mixture was stirred at 10° C. for 1 h. TBAF (91.2 mL, 1 M in THF, 91.2 mmol) was added to the mixture. The mixture was stirred at 10° C. for another 1 h. The mixture was concentrated in vacuum. The residue was dissolved in EtOAc (100 mL), washed with water (3×100 mL) and concentrated in vacuum to yield a crude product, which was combined with another batch of 9.5 g ST-200-INT_2, purified by silica gel column (PE:EtOAc=30:1 to 20:1) in four parts to give ST-200-CF3_1B (2.3 g, purity 83%, yield 8%) and ST-200-CF3_1A (6.2 g, purity 32%, yield 8%). 3.0 g of impure ST-200-CF3_1A was used in the step directly and another 3.2 g was purified by silica gel column (PE:EtOAc=30:1 to 20:1) and re-crystallized form MeCN (10 mL) to give ST-200-CF3_1A (0.5 g, purity 94%).

Note: ST-200-CF3_1A and ST-200-CF3_1B were identified from $^3J_{H,CF}$, (FDCS). (*J. Org. Chem.* 2015, 80, 1754)

ST-200-CF3_1A:

$^1$H NMR (400 MHz, CDCl$_3$) δ 5.43-5.33 (m, 1H), 4.85 (s, 1H); 4.71 (s, 1H); 2.49 (s, 2H); 2.11-1.97 (m, 4H), 1.95-1.32 (m, 14H), 1.30-0.98 (m, 7H), 0.59 (s, 3H).

ST-200-CF3_1B:

$^1$H NMR (400 MHz, CDCl$_3$) δ 5.54-5.41 (m, 1H), 4.86 (s, 1H); 4.72 (s, 1H); 2.78-2.65 (m, 1H); 2.18-1.97 (m, 3H), 1.95-1.35 (m, 16H), 1.32-0.98 (m, 7H), 0.59 (s, 3H).

Synthesis of ST-200-CF3_2A

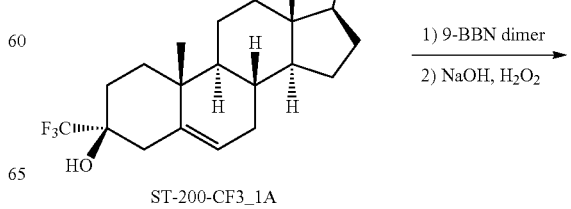

ST-200-CF3_1A

-continued

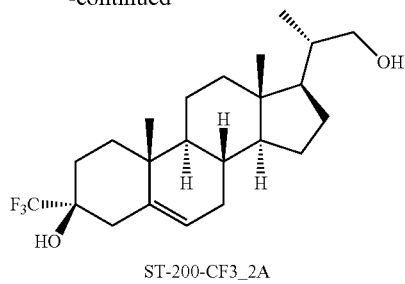
ST-200-CF3_2A

9-BBN dimer (2.19 g, 9.01 mmol) was added to a solution of ST-200-CF3_1A (3 g, impure) in THF (35 mL). The mixture was stirred at 40° C. for 1 h. Next, EtOH (4.5 mL), NaOH (15.6 mL, 5 M, aq.) and $H_2O_2$ (7.83 mL, 10 M, aq.) were added dropwise and the mixture was cooled to 0° C. The mixture was stirred at 50° C. for 1 h. $Na_2SO_3$ (100 mL, 10%, aq.) was added to the mixture after cooling. The mixture was extracted with EtOAc (100 mL). The organic layer was separated, purified by silica gel column (PE:EtOAc=10:1 to 7:1) to give ST-200-CF3_2A (1.2 g, purity 79%, yield 30%) as a solid.

$^1$H NMR (400 MHz, $CDCl_3$) 35.42-5.32 (m, 1H), 3.64 (dd, J=2.8, 10.4 Hz, 1H), 3.36 (dd, J=6.8, 10.4 Hz, 1H), 2.50 (s, 2H), 2.32-1.92 (m, 4H), 1.92-1.70 (m, 4H), 1.70-1.29 (m, 8H), 1.29-0.91 (m, 11H), 0.71 (s, 3H).

Synthesis of ST-200-CF3_3A

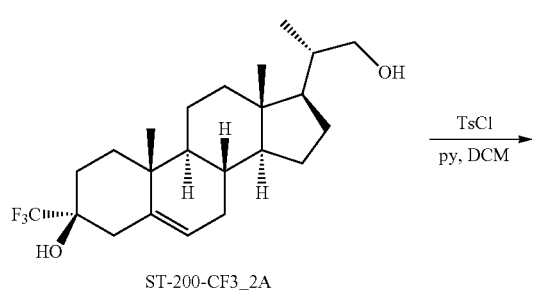

TsCl (1.14 g, 5.98 mmol) was added to a solution of ST-200-CF3_2A (1.2 g, 2.99 mmol) in DCM (5 mL) and py (3.5 mL). The mixture was stirred at 15° C. for 2 hrs. PE (10 mL) was added to the mixture. The mixture was washed with water (10 mL) and brine (10 mL), dried over $Na_2SO_4$, filtered, concentrated in vacuum and purified by silica gel column (PE:DCM:EtOAc=5:1:0.3 to 5:1:0.4) to give ST-200-CF3_3A (1.05 g, 64%) as a solid.

$^1$H NMR (400 MHz, $CDCl_3$) 37.78 (d, J=8.4 Hz, 2H), 7.34 (d, J=8.4 Hz, 2H), 5.40-5.33 (m, 1H), 3.97 (dd, J=2.8, 9.2 Hz, 1H), 3.77 (dd, J=6.4, 9.2 Hz, 1H), 2.48 (s, 2H), 2.45 (s, 3H), 2.10-1.88 (m, 5H), 1.82-1.35 (m, 9H), 1.30-0.82 (m, 12H), 0.64 (s, 3H).

Synthesis of ST-200-CF3_4A

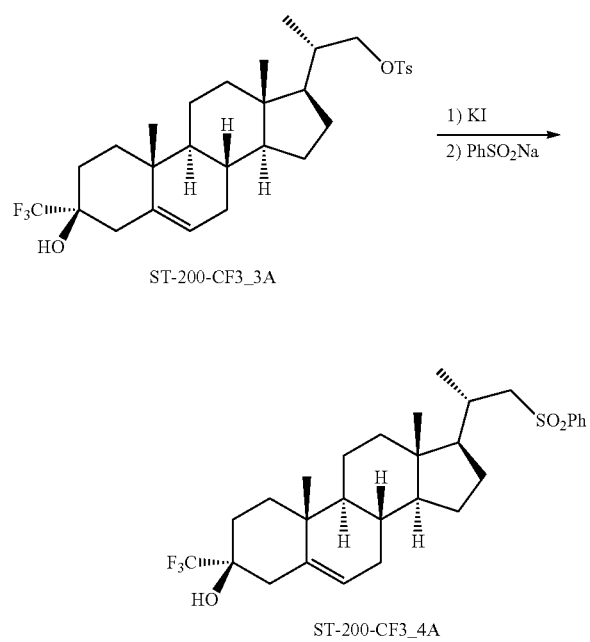

KI (1.25 g, 7.56 mmol) was added to a solution of ST-200-CF3_3A (1.05 g, 1.89 mmol) in DMF (5 mL). The mixture was stirred at 50° C. for 1 h. To the mixture was added $PhSO_2Na$ (0.93 g, 5.67 mmol). The mixture was stirred at 50° C. for 2 hrs. Water (10 mL) and DCM (30 mL) were added to the mixture. The organic layer was separated, dried over $Na_2SO_4$, filtered, concentrated in vacuum and triturated from PE/DCM (10 mL, 5:1) to give ST-200-CF3_4A (600 mg, 61%) as a solid.

$^1$H NMR (400 MHz, $CDCl_3$) δ 7.98-7.87 (m, 2H), 7.70-7.52 (m, 3H), 5.39-5.31 (m, 1H), 3.14 (d, J=14.4 Hz, 1H), 2.85 (dd, J=9.6, 14.0 Hz, 1H), 2.48 (s, 2H), 2.20-1.88 (m, 5H), 1.88-1.68 (m, 4H), 1.60-1.33 (m, 5H), 1.30-0.82 (m, 12H), 0.64 (s, 3H).

Synthesis of E-322_6_1

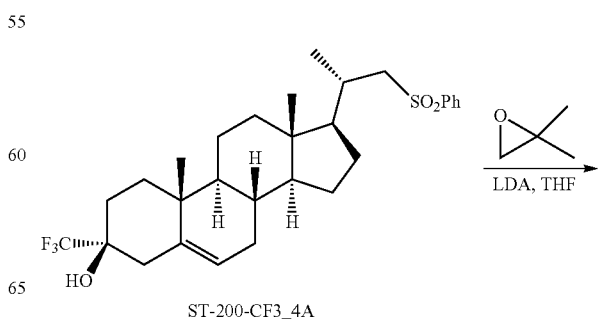
ST-200-CF3_4A

-continued

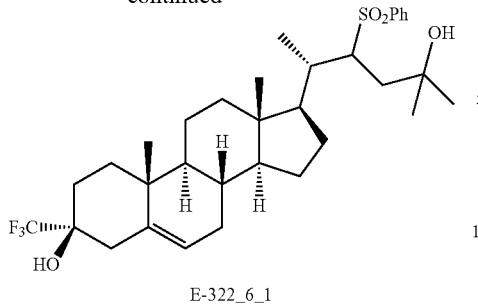

E-322_6_1

Diisopropylamine (3.76 mmol, 380 mg) was added to THF (2 mL) under N$_2$ at −70° C., followed by an addition of n-BuLi (3.42 mmol, 1.36 mL, 2.5M in hexane 3.0 eq). The reaction was allowed to warm to 15° C. and was then re-cooled to −70° C. A suspension of ST-200-CF3_4A (1.14 mmol, 600 mg) in THF (5 mL) was added dropwise to give a suspension. After stirring at −70° C. for 30 min, a solution of 2,2-dimethyloxirane (2.28 mmol, 218 mg, 2.0 eq.) in THF (1 mL) was added over 5 min (slightly exothermic, keeping internal T<−70° C.). Then reaction was stirred at 15° C. for 12 hrs. The reaction was quenched with sat. NH$_4$Cl (30 mL) and extracted with EtOAc (3×10 mL). The combined organic layers were dried over Na$_2$SO$_4$, filtered and concentrated to give ST-200-CF3_5A (600 mg, crude) as a foam.

Synthesis of 1839

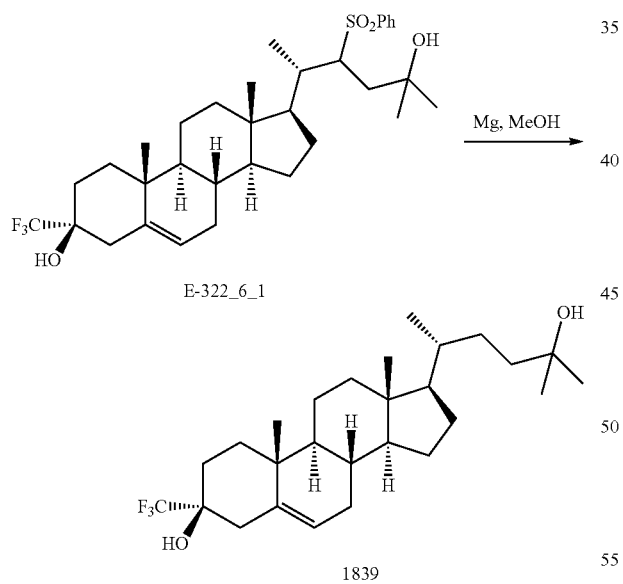

Mg powder (960 mg, 40 mmol) was added to a solution of E-322_6_1 (600 mg, 1 mmol) in MeOH (10 mL) at 55° C. The reaction mixture was stirred at 60° C. under N$_2$ for 2 hrs. The mixture was quenched with HCl (100 mL, 2 M) until the reaction became clear and extracted with DCM (3×20 mL). The combined organic phase was washed with sat. NaHCO$_3$ (50 mL), dried over Na$_2$SO$_4$, filtered, concentrated and purified by combi-flash (0-10% of EtOAc in PE) to give 170 mg impure product, which was purified again by prep-HPLC (column: DuraShell 150*25 mm*5 um), gradient: 75-100% B (A=0.05% HCl/H$_2$O, B=MeCN), flow rate: 30 mL/min) to give 1839 (66 mg, 14%) as a solid.

$^1$H NMR (400 MHz, CDCl$_3$) δ 5.37-5.36 (m, 1H), 2.48 (s, 2H), 2.10-1.92 (m, 4H), 1.90-1.70 (m, 3H), 1.62-1.58 (m, 2H), 1.56-1.35 (m, 7H), 1.34-1.22 (m, 3H), 1.21-1.07 (m, 10H), 1.06 (s, 3H), 1.05-0.98 (m, 2H), 0.93 (d, J=6.8 Hz, 3H), 0.68 (s, 3H).

LCMS Rt=1.277 min in 2.0 min chromatography, 30-90 AB, purity 100%, MS ESI calcd. for C$_{27}$H$_{42}$F$_3$O [M+H−H$_2$O]$^+$ 439, found 439.

Example 19: Synthesis of 1967

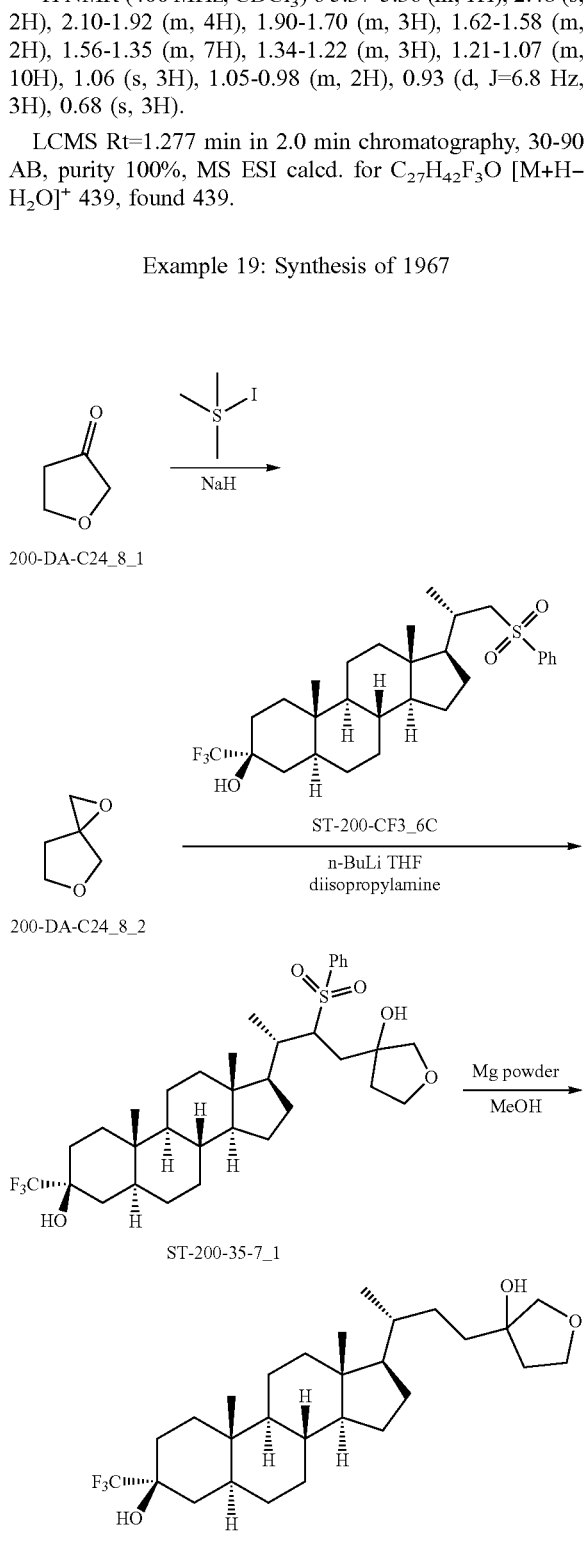

The synthesis of ST-200-CF3_6C or B7 can be found in Example 5.

Synthesis of 200-DA-C24_8_2

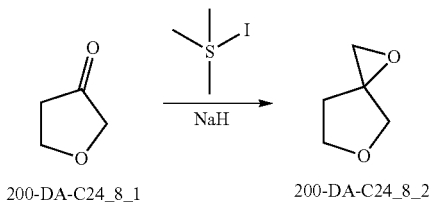

Sodium hydride (18.0 g, 60% in mineral oil, 452 mmol) was added in portions to a mixture of trimethylsulfoxonium iodide (92.2 g, 452 mmol) in THF (300 mL) at 0° C. under $N_2$. The mixture was stirred at 0° C. for 30 min. Dihydrofuran-3(2H)-one (30 g, 348 mmol) in DMSO (300 mL) was added drop-wise at 0° C. The reaction mixture was stirred at 25° C. for 16 hours. The mixture was poured into ice-water (500 mL) in portions, extracted with DCM (2×500 mL). The combined organic phase was washed with brine (500 mL), dried over $Na_2SO_4$, filtered and concentrated at 30° C. to give 200-DA-C24_8_2 (32 g, crude) as an oil. 3 g from the residue was purified by column ($Al_2O_3$, PE) to afford 200-DA-C24_8_2 (0.6 g) as an oil.

$^1$H NMR (400 MHz, $CDCl_3$) δ 4.09-3.90 (m, 4H), 3.03 (d, J=4.4 Hz, 1H), 2.93 (d, J=4.4 Hz, 1H), 2.28 (td, J=8.0, 13.6 Hz, 1H), 1.93 (m, 1H).

Synthesis of ST-200-35-7_1

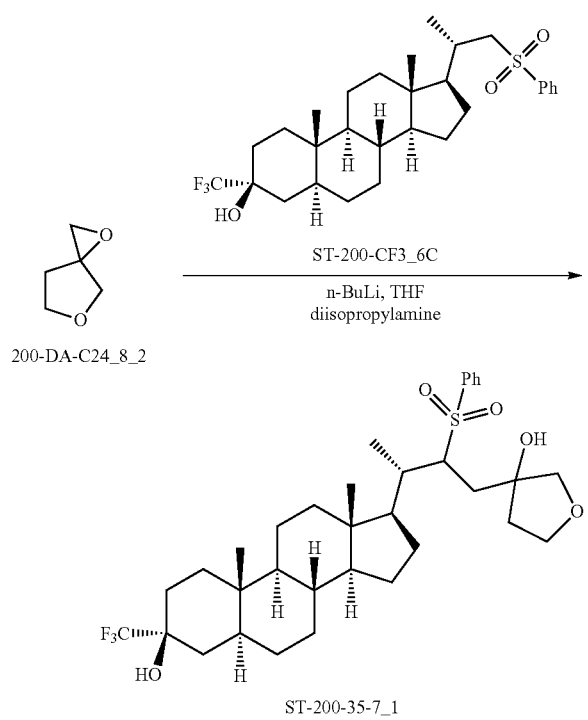

A suspension of ST-200-CF3_6C (500 mg, 0.9493 mmol) in THF (2.5 mL) was added dropwise to a solution of n-BuLi (1.13 mL, 2.5 M in hexane, 2.84 mmol) in THF (0.5 mL) at −65° C. under $N_2$. The mixture was stirred for 30 minutes at −65° C. Diisopropylamine (286 mg, 2.84 mmol) was added at −65° C. Next, 200-DA-C24_8_2 (95.0 mg, 0.9493 mmol) was added drop-wise at −65° C. The mixture was stirred for another 30 minutes and then warmed to 25° C. gradually. The reaction mixture was stirred at 25° C. for 16 hours, quenched by saturated $NH_4Cl$ aqueous (30 mL) and extracted with ethyl acetate (3×20 mL). The combined organic phase was washed with brine (30 mL), dried over $Na_2SO_4$, filtered and concentrated under vacuum to give ST-200-35-7_1 (900 mg, crude) as a solid, which was used directly for the next step.

Synthesis of 1967

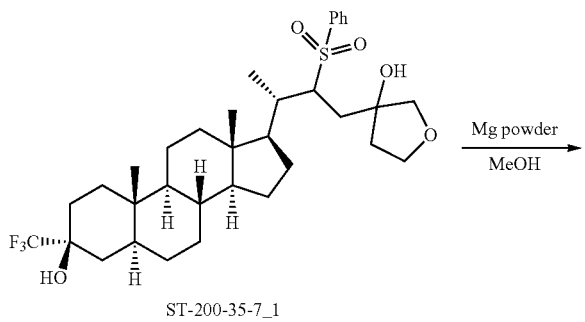

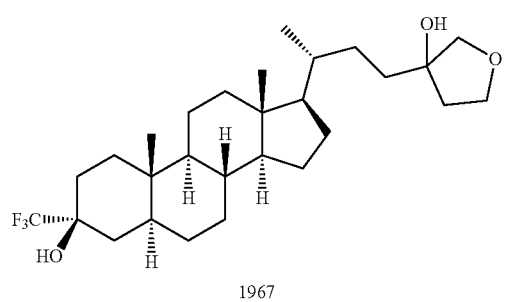

Mg (686 mg, 28.6 mmol) was added to a solution of crude ST-200-35-7_1 (900 mg) in MeOH (10 mL). Next, the reaction mixture was stirred at 60° C. for 2 h under $N_2$. Aqueous HCl (10 mL, 4 M) was added to the reaction mixture, then was extracted with EtOAc (3×10 mL). The combined organic layer was washed with brine (10 mL), dried over $Na_2SO_4$, filtered and concentrated in vacuum to give a crude product. The crude product was purified by silica gel chromatography (PE/EtOAc=30/1 to 10/1) to give impure 1967 (460 mg) as a solid. The impure 1967 (460 mg) was purified by re-crystallization from MeCN (2 mL) to give 1967 (175 mg) as a solid. The mother liquid was concentrated in vacuum to give impure ST-200-35-7 (220 mg) as a solid.

$^1$H NMR (400 MHz, $CDCl_3$) δ 4.10-4.00 (m, 1H), 3.95-3.85 (m, 1H), 3.75-3.65 (m, 1H), 3.55-3.50 (m, 1H), 2.10-2.00 (m, 2H), 2.00-1.85 (m, 3H), 1.85-1.75 (m, 2H), 1.75-1.56 (m, 5H), 1.55-1.40 (m, 6H), 1.40-1.20 (m, 7H), 1.20-1.00 (m, 5H), 1.00-0.88 (m, 4H), 0.85 (s, 3H), 0.75-0.68 (m, 1H), 0.66 (s, 3H).

LCMS Rt=1.148 min in 2.0 min chromatography, 30-90 AB, purity 100%, MS ESI calcd. for $C_{30}H_{48}F_3NO_3Na[M+MeCN+Na]^+$ 550, found 550.

Example 20: Synthesis of 2080 and 2081

Synthesis of DA-35-4_1A & DA-35-4_1B

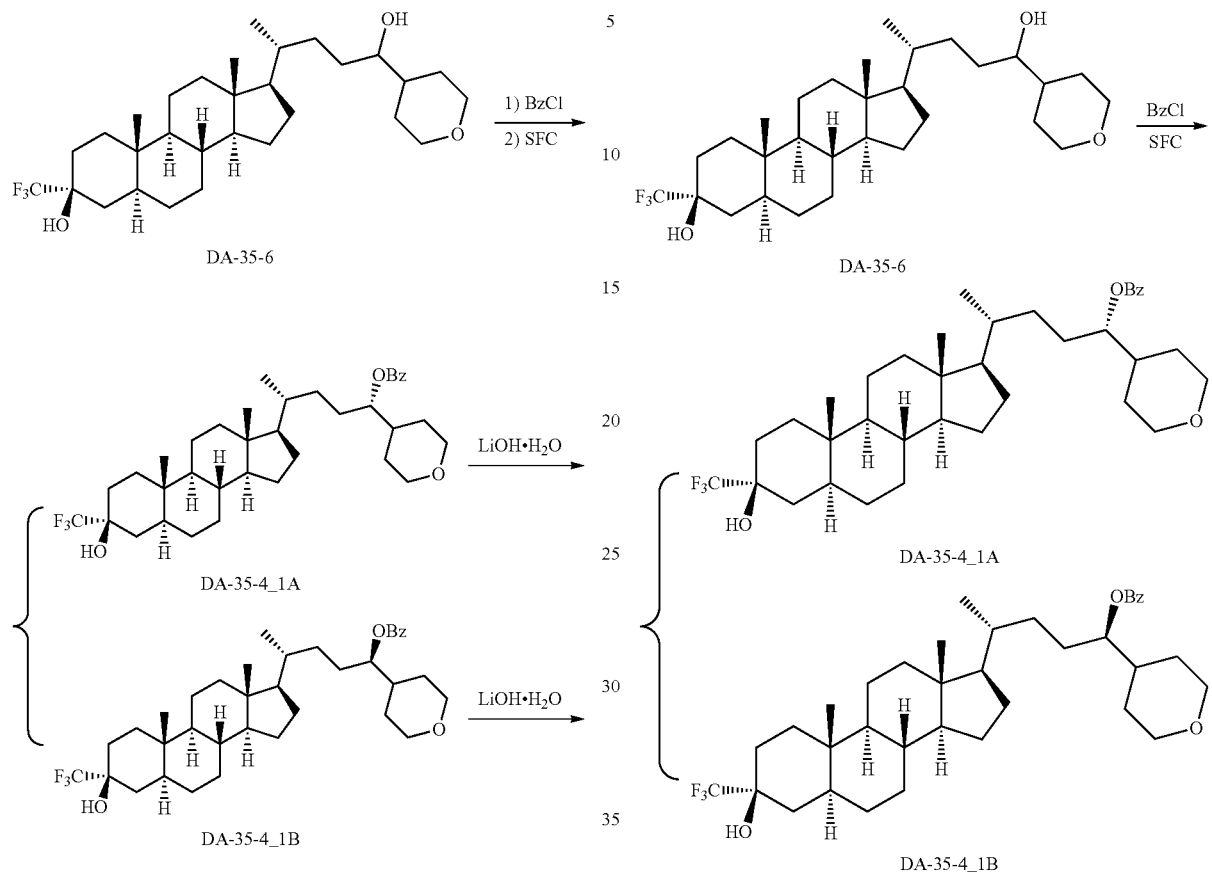

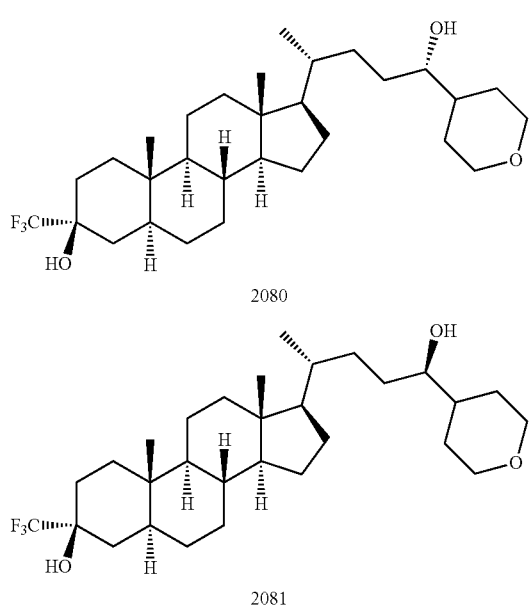

Stereochemistry confirmed by Xray data.

The experimental of Intermediate DA-35-6 can be found in Example 14.

Py (498 mg, 6.30 mmol) and BzCl (531 mg, 3.78 mmol) were added to a solution of DA-35-6 (130 mg, 0.252 mmol) in DCM (5 mL). The mixture was stirred at 25° C. for 6 h and quenched by adding $H_2O$ (5 mL). The mixture was washed with HCl (10 mL, 1 M, aq.), $NaHCO_3$ (10 mL, sat. aq.), dried over $Na_2SO_4$, filtered, and concentrated in vacuum to give a crude product. The crude product was purified by silica gel column (PE:EtOAc=20:1 to 10:1) to give DA-35-4_1 (170 mg, impure). The impure DA-35-4_1 (170 mg) was separated by SFC (column: Chiralpak AD-3 50*4.6 mm I.D., 3 um); Condition: Base-IPA; Gradient: 5-40% B; flow rate: 4 mL/min) to give DA-35-4_1A (56 mg, 36%, Rt=4.889 min, 100% de) and DA-35-4_1B (80 mg, 51%, Rt=5.283 min, 100% de).

DA-35-4_1A:

$^1$H NMR (400 MHz, $CDCl_3$) δ 8.04 (d, J=8.0 Hz, 2H), 7.56 (t, J=8.0 Hz, 1H), 7.45 (t, J=8.0 Hz, 2H), 5.04-4.94 (m, 1H), 4.06-3.94 (m, 2H), 3.44-3.32 (m, 2H), 2.10-1.84 (m, 4H), 1.84-1.58 (m, 8H), 1.53-1.23 (m, 12H), 1.22-0.94 (m, 8H), 0.94-0.80 (m, 7H), 0.72-0.57 (m, 4H).

DA-35-4_1B:

$^1$H NMR (400 MHz, $CDCl_3$) δ 8.04 (d, J=8.0 Hz, 2H), 7.56 (t, J=8.0 Hz, 1H), 7.45 (t, J=8.0 Hz, 2H), 5.05-4.96 (m, 1H), 4.03-3.93 (m, 2H), 3.44-3.30 (m, 2H), 2.10-1.59 (m, 12H), 1.53-1.23 (m, 12H), 1.22-0.94 (m, 8H), 0.93-0.81 (m, 7H), 0.72-0.60 (m, 4H).

Synthesis of 2080

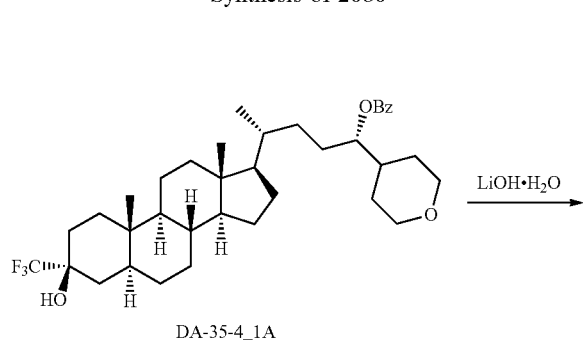

DA-35-4_1A

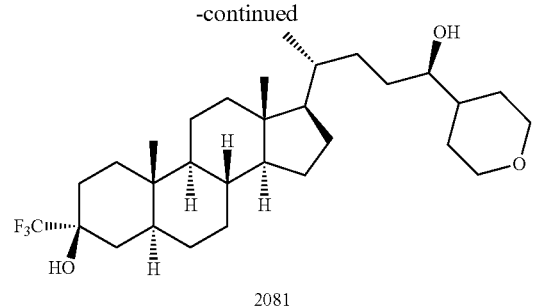

2081

A suspension of LiOH·H$_2$O (405 mg, 9.67 mmol) in water (1 mL) was added to a solution of DA-35-4_1B (80 mg, 0.129 mmol) in THF (5 mL) and MeOH (1 mL). The mixture was stirred at 50° C. for 20 h. The mixture was concentrated in vacuum and treated with H$_2$O (5 mL). The mixture was extracted with EtOAc (3×5 mL). The organic layers were washed with brine (2×15 mL), dried over Na$_2$SO$_4$, filtered, and concentrated in vacuum. The residue was triturated from MeCN (2 mL) at 25° C. to give 2081 (32 mg, 48%) as a solid.

$^1$H NMR (400 MHz, CDCl$_3$) δ 4.05-3.95 (m, 2H), 3.40-3.25 (m, 3H), 2.05-1.90 (m, 4H), 1.89-1.60 (m, 8H), 1.59-1.35 (m, 10H), 1.34-0.95 (m, 11H), 0.94-0.75 (m, 7H), 0.65-0.60 (m, 4H).

LCMS Rt=1.205 min in 2.0 min chromatography, 30-90 AB, purity 100%, MS ESI calcd. for C$_{30}$H$_{48}$F$_3$O$_2$ [M+H−H$_2$O]$^-$ 497, found 497.

2080

A solution of LiOH·H$_2$O (284 mg, 6.78 mmol) in water (1 mL) was added to a solution of DA-35-4_1A (56 mg, 0.090 mmol) in THF (5 mL) and MeOH (1 mL). The mixture was stirred at 50° C. for 20 h. The mixture was concentrated in vacuum and treated with H$_2$O (5 mL). The mixture was extracted with EtOAc (3×5 mL). The organic layers were washed with brine (2×15 mL), dried over Na$_2$SO$_4$, filtered, and concentrated in vacuum. The residue was triturated from MeCN (2 mL) at 25° C. to give 2080 (12 mg, 26%) as a solid.

$^1$H NMR (400 MHz, CDCl$_3$) δ 4.05-3.95 (m, 2H), 3.40-3.25 (m, 3H), 2.05-1.95 (m, 2H), 1.85-1.80 (m, 2H), 1.75-1.25 (m, 17H), 1.24-0.90 (m, 16H), 0.89-0.75 (m, 3H), 0.65-0.60 (m, 4H).

LCMS Rt=1.205 min in 2.0 min chromatography, 30-90 AB, purity 100%, MS ESI calcd. for C$_{30}$H$_{48}$F$_3$O$_2$ [M+H−H$_2$O]$^-$ 497, found 497.

Synthesis of 2081

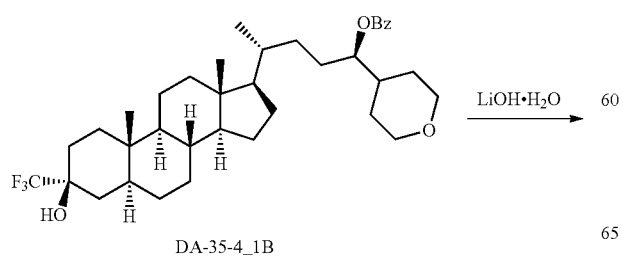

DA-35-4_1B

Example 21: Synthesis of 2184

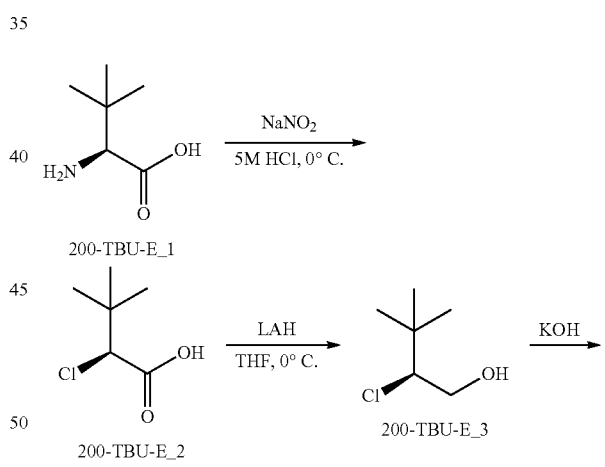

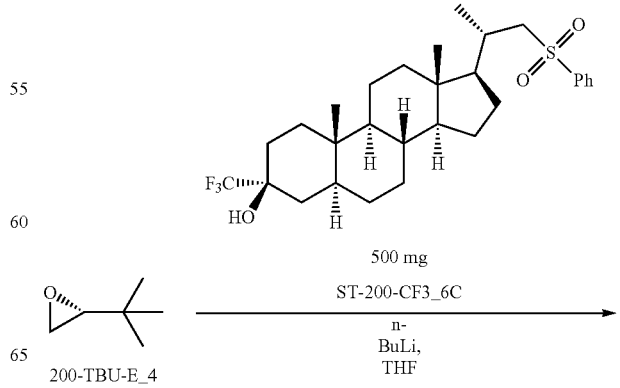

133

-continued

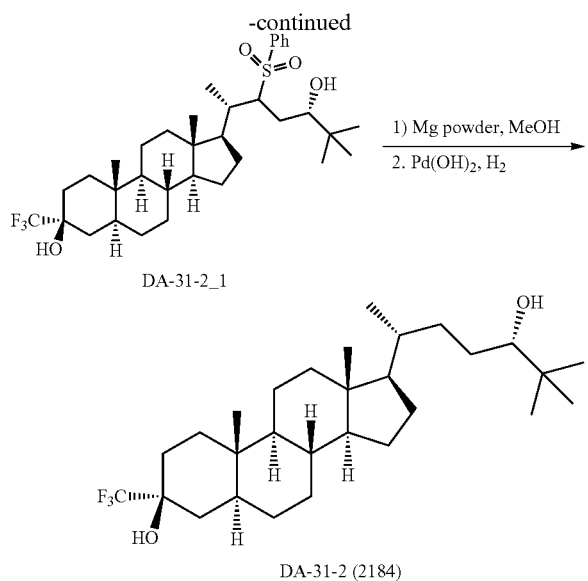

DA-31-2_1

DA-31-2 (2184)

The synthesis of ST-200-CF3_6C or B7 could be found in Example 5.

Synthesis of 200-TBU-E_2

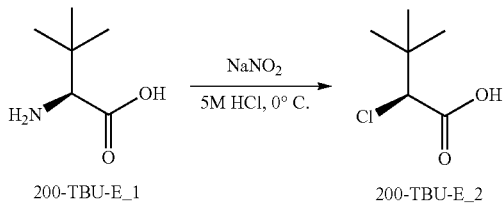

200-TBU-E_1    200-TBU-E_2

200-TBU-E_1 (131 g, 998 mmol) was dissolved in 1690 mL of 5 N hydrochloric acid. The mixture was cooled to 0° C. and a precooled solution of sodium nitrite (109 g, 1.59 mol) in 400 mL of water was added drop-wise, then the reaction mixture was kept below 5° C. After 5 hr, the mixture was stirred at 25° C. for 12 hrs. Solid sodium carbonate (100 g) was added carefully in small portions. The reaction mixture was extracted with isopropyl ether (500 mL*2). The combined organic phases was washed with brine (500 mL), dried over Na$_2$SO$_4$, filtered and concentrated in vacuum. The residue was isolated by distillation to afford 200-TBU-E_2 (48 g, 32%) as a solid.

$^1$H NMR (400 MHz, CDCl$_3$) δ 4.12 (s, 1H), 1.13 (s, 9H).

Synthesis of 200-TBU-E_2

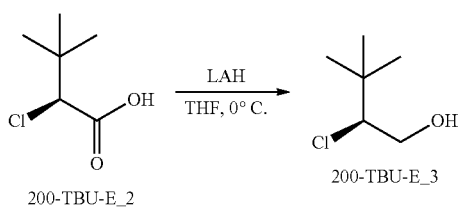

200-TBU-E_2    200-TBU-E_3

134

LiAlH$_4$ (14.4 g, 381 mmol) was added to a solution of 200-TBU-E_2 (48 g, 318 mmol) in THF (500 mL) at 0° C. The mixture was warmed to 25° C. and stirred at 25° C. for 30 mins Water/THF (100 mL, 1/1) was added and the pH was adjusted to 2~3 with HCl (1 mol/L). The mixture was extracted with EA (2×500 mL), washed with brine (2×200 mL), dried over Na$_2$SO$_4$, filtered, and concentrated in vacuum to give 200-TBU-E_3 (36 g, crude) as a solid. This product was used in the next step without further purification.

$^1$H NMR (400 MHz, CDCl$_3$) δ 3.92-3.86 (m, 2H), 3.68-3.63 (m, 1H), 1.04 (s, 9H).

Synthesis of 200-TBU-E_4

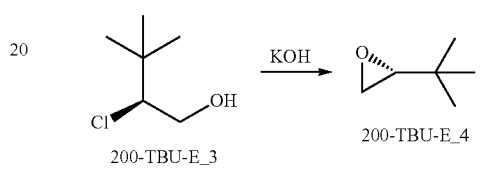

200-TBU-E_3    200-TBU-E_4

200-TBU-E_3 (16 g, 117 mmol) was added to a solution of potassium hydroxide (13.1 g, 234 mmol) in water (13 ml) at 0° C. The ice bath was replaced by a water bath at 20° C. As the cyclization reaction proceeded, a precipitate of potassium chloride formed. After 10 min, the bath temperature was raised slowly to 50° C. The product was isolated by distillation to afford 200-TBU-E_4 (6 g, 51.2%) as an oil. 100% ee after protected with UV group.

$^1$H NMR (400 MHz, CDCl$_3$) δ 2.73-2.71 (m, 1H), 2.64-2.63 (m, 1H), 2.62-2.59 (m, 1H), 0.91 (s, 9H).

Method for ee Checking of Chiral Epoxide

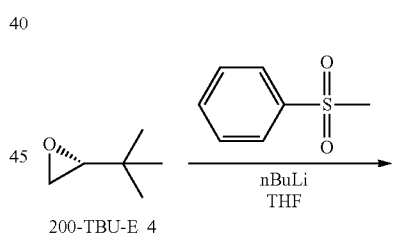

200-TBU-E_4

200-TBU-E_4A n-BuLi (2.5 M, 1.99 mmol, 0.8 mL) was added dropwise to a solution of (methylsulfonyl)benzene (342 mg, 2.19 mmol) in THF (5 mL) was under N$_2$ at −70° C. After stirring at −70° C. for 30 min, a solution of 200-TBU-E_4 (100 mg, 0.998 mmol) was added. Then reaction was stirred at stirred at 25° C. for 12 hours. The mixture was poured into ice-water (100 mL) and extracted with EA (2×50 mL). The combined organic layers were washed with brine (30 mL), dried over Na2SO₄ filtered and concentrated in vacuum. The residue was purified by by silica gel chromatography (PE/EA=5/1) to afford 200-TBU-E_4A (80 mg, 31.3%) as an oil. The ee % of product was determined to be 100% by chiral HPLC.

Synthesis of DA-31-2_1

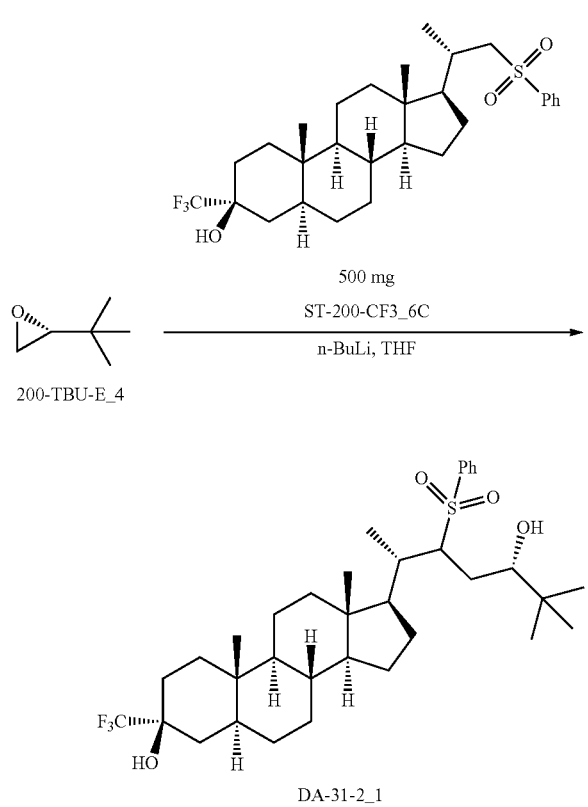

n-BuLi (0.416 mL, 2.5 M, 1.03 mmol) was added to a solution of diisopropylamine (110 mg, 1.09 mmol) in THF (1 mL) under N$_2$ at −70° C. The resulting mixture was stirred at 0° C. for 30 min. The mixture was re-cooled to −70° C. To the mixture was added ST-200-CF3_6C (250 mg, 0.474 mmol) in THF (2 mL) at −70° C. The reaction mixture was stirred at −70° C. for 1 hour. (R)-2-(tert-butyl)oxirane (56.8 mg, 0.568 mmol) in THF (1 mL) was added at −70° C. The reaction mixture was warmed to 15° C. slowly and stirred at 15° C. for 16 h. The reaction mixture was quenched with saturated NH₄Cl aqueous (20 mL) at 0° C. The mixture was extracted with EtOAc (2×20 mL). The combined organic phase was washed with brine (10 mL), dried over Na₂SO₄, filtered and concentrated under vacuum to give crude DA-31-2_1 (300 mg) as a solid.

$^1$H NMR (400 MHz, CDCl$_3$) δ 7.95-7.85 (m, 2H), 7.68-7.63 (m, 1H), 7.60-7.50 (m, 2H), 3.45-3.35 (m, 2H), 3.25-3.15 (m, 1H), 2.60-2.55 (m, 1H), 2.10-1.60 (m, 6H), 1.55-1.20 (m, 11H), 1.20-1.00 (m, 7H), 0.93 (s, 9H), 0.90-0.80 (m, 5H), 0.70-0.50 (m, 3H), 0.45 (s, 3H).

Synthesis of DA-31-2

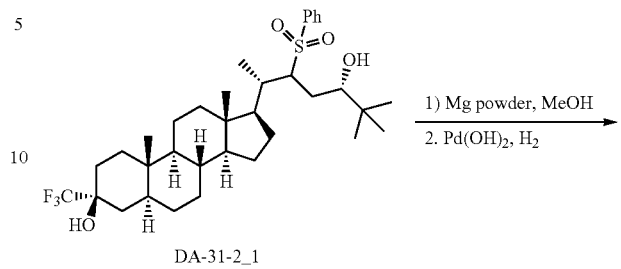

Mg (229 mg, 9.55 mmol) was added to a solution of DA-31-2_1 (300 mg, 0.478 mmol) in MeOH (5 mL). Next, the reaction was stirred at 60° C. for 2 h under N$_2$. Aqueous HCl (10 mL, 4 M) was added to the reaction mixture, then extracted with EtOAc (3×10 mL). The combined organic layer was washed with brine (10 mL), dried over Na$_2$SO$_4$, filtered and concentrated in vacuum to give a crude product. The crude product was purified by silica gel chromatography (PE/EtOAc=30/1 to 10/1) to give impure DA-31-2 (100 mg, impure) as a solid. Dry Pd(OH)$_2$/C (50 mg) was added to a solution of DA-31-2 (100 mg, impure, 0.205 mol) in MeOH/THF=1/1 (4 mL). Next, the reaction mixture was stirred at 50° C. for 16 h under H$_2$ and 50 Psi. The reaction mixture was filtered through a pad of Celite and washed with THF (3×5 mL). The combined organic layer was concentrated in vacuum to give a crude DA-31-2 (85 mg) as a solid, which was purified by re-crystallization from MeCN (2 mL) to give DA-31-2 (60 mg, 71%) as a solid.

$^1$H NMR (400 MHz, CDCl$_3$) δ 3.20-3.05 (m, 1H), 2.10-1.90 (m, 3H), 1.90-1.60 (m, 7H), 1.55-1.40 (m, 5H), 1.40-1.10 (m, 14H), 1.10-1.00 (m, 3H), 0.93 (s, 9H), 0.89 (s, 3H), 0.75-0.66 (m, 1H), 0.65 (s, 3H).

LCMS Rt=1.356 min in 2.0 min chromatography, 30-90 AB, purity 99%, MS ESI calcd. for C$_{29}$H$_{48}$F$_3$O [M−H$_2$O+H]$^+$ 469, found 469.

Example 22: Synthesis of 2285

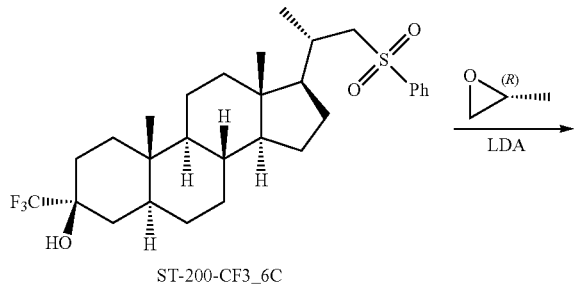

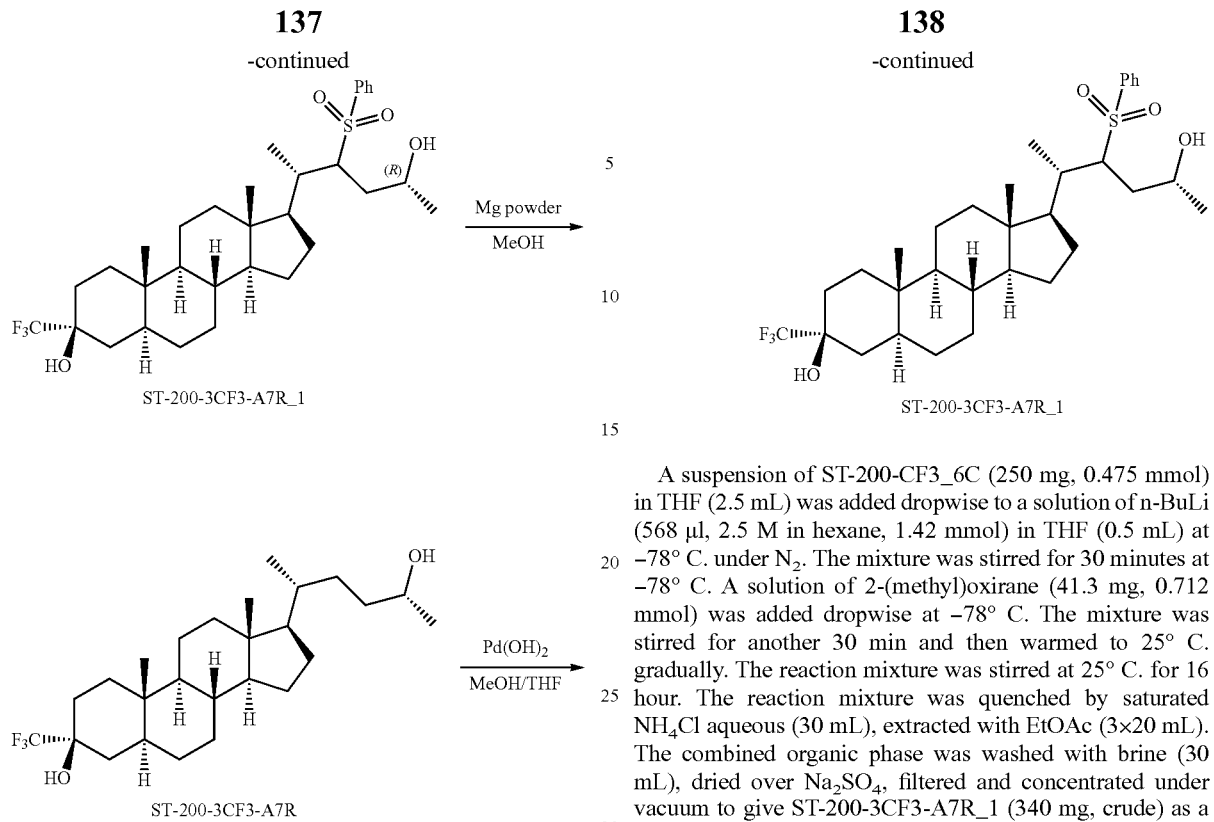

A suspension of ST-200-CF3_6C (250 mg, 0.475 mmol) in THF (2.5 mL) was added dropwise to a solution of n-BuLi (568 μl, 2.5 M in hexane, 1.42 mmol) in THF (0.5 mL) at −78° C. under N₂. The mixture was stirred for 30 minutes at −78° C. A solution of 2-(methyl)oxirane (41.3 mg, 0.712 mmol) was added dropwise at −78° C. The mixture was stirred for another 30 min and then warmed to 25° C. gradually. The reaction mixture was stirred at 25° C. for 16 hour. The reaction mixture was quenched by saturated NH₄Cl aqueous (30 mL), extracted with EtOAc (3×20 mL). The combined organic phase was washed with brine (30 mL), dried over Na₂SO₄, filtered and concentrated under vacuum to give ST-200-3CF3-A7R_1 (340 mg, crude) as a solid, which was used directly for the next step.

Synthesis of 2285

The synthesis of ST-200-CF3_6C or B7 can be found in Example 5.

Synthesis of ST-200-3CF3-A7R_1

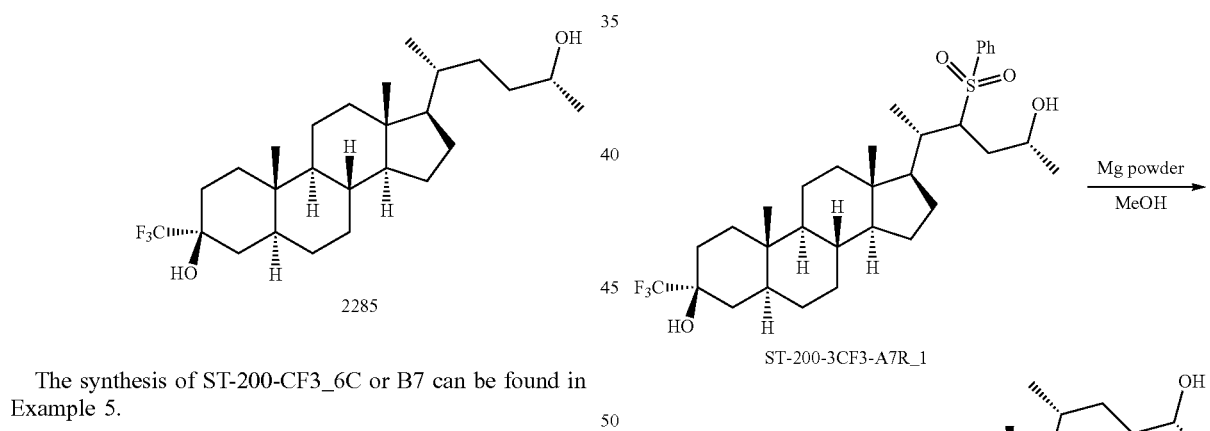

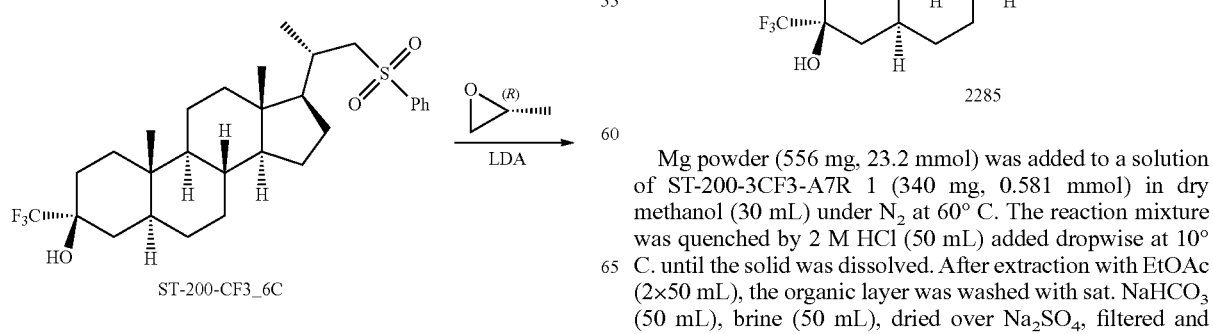

Mg powder (556 mg, 23.2 mmol) was added to a solution of ST-200-3CF3-A7R 1 (340 mg, 0.581 mmol) in dry methanol (30 mL) under N₂ at 60° C. The reaction mixture was quenched by 2 M HCl (50 mL) added dropwise at 10° C. until the solid was dissolved. After extraction with EtOAc (2×50 mL), the organic layer was washed with sat. NaHCO₃ (50 mL), brine (50 mL), dried over Na₂SO₄, filtered and concentrated. The residue was purified by flash column, eluted with PE/EtOAc=20/1 to 5/1, to give 2285 (80 mg, impure containing some 22-23 olefin) as a solid, which was used for next step without further purification.

Synthesis of ST-200-3CF3-A7R

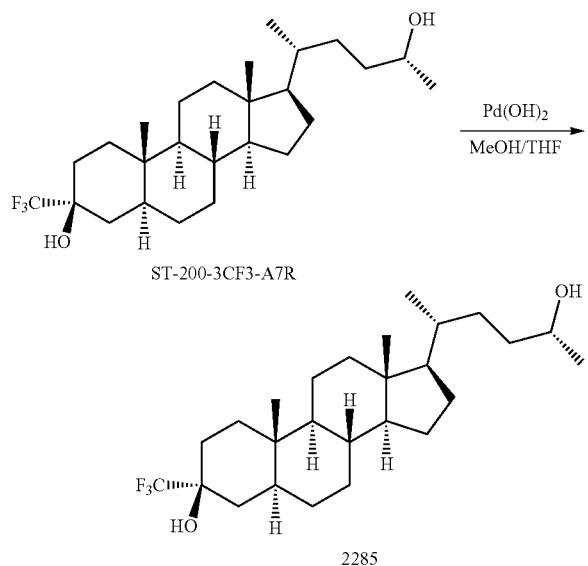

Pd(OH)$_2$ (20%, 126 mg, 0.180 mmol) was added to a solution of 2285 (80 mg, 0.180 mmol) in MeOH/THF (10 mL/10 mL) under Ar. After degassing three times with N$_2$ and H$_2$, the reaction mixture was stirred for 16 h at 50° C. under H$_2$ atmosphere (50 psi). The desired product was produced, the catalyst was removed by suction, and the filtrate was concentrated to give 2285 (50 mg, impure) as a solid, which was triturated with MeCN (3 mL) at 25° C. to give 2285 (36 mg, 45%) as a solid.

2285

$^1$H NMR (400 MHz, CDCl$_3$) δ 3.74-3.72 (m, 1H), 2.08-2.06 (m, 1H), 2.00-1.91 (m, 2H), 1.88-1.75 (m, 2H), 1.74-1.59 (m, 3H), 1.52-1.22 (m, 13H), 1.21-0.96 (m, 10H), 0.95-0.86 (m, 4H), 0.85 (s, 3H), 0.73-0.62 (m, 4H)

LCMS Rt=1.199 min in 2 min chromatography, 30-90 AB, purity 100%, MS ESI calcd. For C$_{26}$H$_{42}$F$_3$O [M+H-H$_2$O]$^+$ 427, found 427.

Example 23: Synthesis of 2392

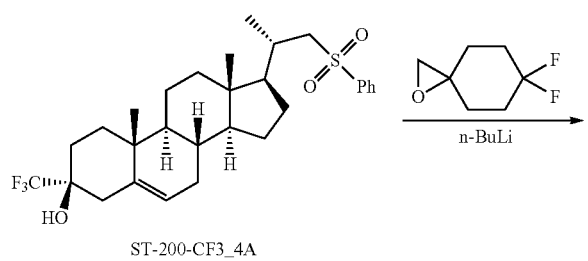

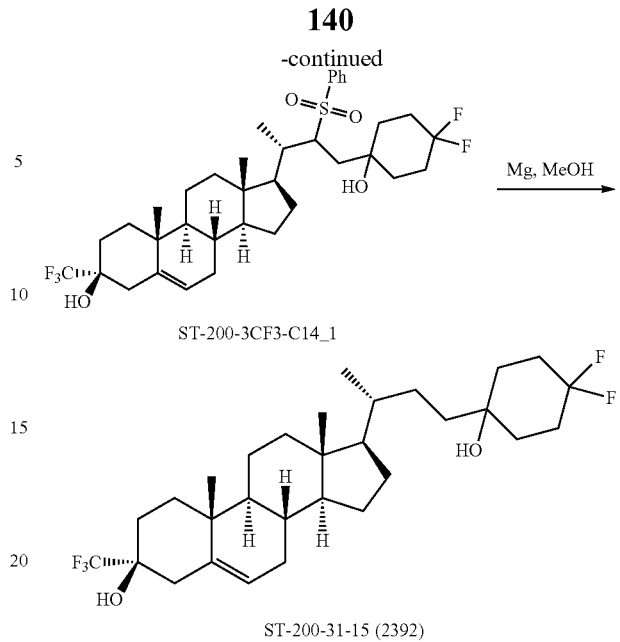

The experimental of intermediate ST-200-CF3_4A or A7 can be found in Example 3.

Synthesis of ST-200-3CF3-C14_1

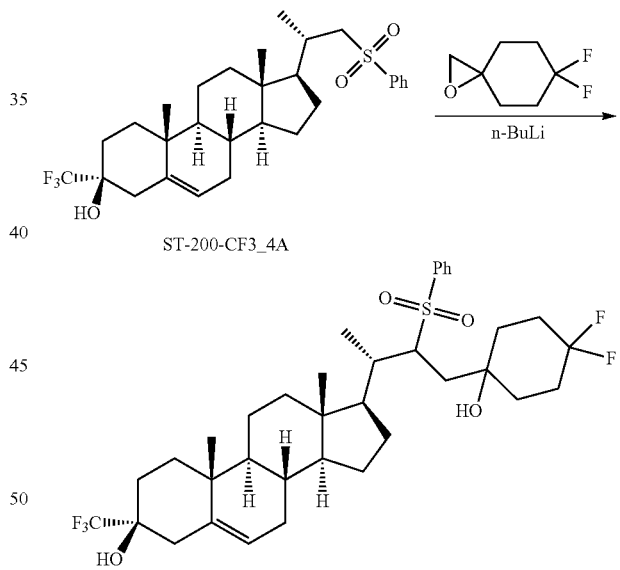

BuLi (0.476 mL, 2.5 M in hexane, 1.19 mmol) was added to THF (0.5 mL). A solution of ST-200-CF3_4A (250 mg, 0.476 mmol) in THF (3 mL) was added at −70° C. The mixture was stirred at −70° C. for 1 h. 6,6-difluoro-1-oxaspiro[2.5]octane (210 mg, 1.42 mmol) was added at −70° C. The mixture was stirred at −70° C. for another 1 h. The mixture was warmed to 25° C. and stirred for 16 hrs. NH$_4$Cl (50 mL, sat. aq.) was added to the mixture, then the mixture was extracted with EtOAc (2×30 mL). The organic layer was separated, dried over Na$_2$SO$_4$, filtered, and concentrated to give ST-200-3CF3-C14_1 (300 mg, crude) as a solid, which was used directly for the next step.

Synthesis of 2392

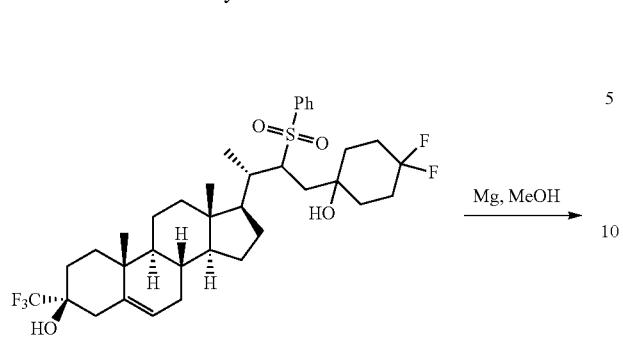

A solution of ST-200-31-15_1 (300 mg, 0.445 mmol) in MeOH (20 mL) was heated at 55° C. Mg powder (427 mg, 17.8 mmol) was added in one portion at 55° C. The mixture was refluxed at 65° C. for 1 h. The mixture was quenched with HCl (50 mL, 1N) until the reaction became clear, then was extracted with DCM (2×30 mL). The combined organic phase was dried over $Na_2SO_4$, filtered, concentrated and purified by flash column (0-10% of EtOAc in PE) to give impure product (110 mg), which was purified again by SFC (column: AD(250 mm*30 mm, 5 um), gradient: 35-35% B (A=0.1% $NH_3$/H2O, B=MeOH), flow rate: 60 mL/min) to give 2392 (72 mg, 30%) as a solid.

$^1$H NMR (400 MHz, $CDCl_3$) δ 5.38-5.35 (m, 1H), 2.49 (s, 2H), 2.20-1.81 (m, 9H), 1.80-1.71 (m, 3H), 1.70-1.58 (m, 5H), 1.56-1.36 (m, 7H), 1.35-1.22 (m, 2H), 1.20-1.08 (m, 4H), 1.06 (s, 3H), 1.04-0.92 (m, 6H), 0.68 (s, 3H).

LCMS Rt=1.248 min in 2.0 min chromatography, 30-90 AB, purity 100%, MS ESI calcd. for $C_{30}H_{44}F_5O$ [M+H-$H_2O$]$^+$ 515, found 515.

Example 24: Synthesis of 2499

The synthesis of DA-31-10_2 can be found in Example 11.

Synthesis of 2499

To a suspension of $LiAlH_4$ (1.03 g, 27.4 mmol) in THF (80 mL) was added a solution of DA-31-10_2 (6.3 g, 13.7 mmol) in THF (20 mL) under $N_2$ dropwise at 0° C. The reaction was stirred at 25° C. for 2 h. The reaction was quenched with water/THF (1/10, 40 mL). To the mixture was added 2 M HCl (100 mL) at 0° C. and extracted with EtOAc (2×100 mL). The combined organic phase was washed with brine (300 mL), dried over $Na_2SO_4$, filtered and concentrated to afford 2499 (5 g, crude) as a solid. 100 mg of the impure DA-31-10_3 was triturated with $CH_3CN$ (5 mL) at 25° C. for 3 hours to give 2499 (52 mg, 52%) as a solid.

$^1$H NMR (400 MHz, $CDCl_3$) δ 3.70-3.50 (m, 2H), 2.10-1.90 (m, 3H), 1.85-1.75 (m, 2H), 1.70-1.60 (m, 4H), 1.50-1.20 (m, 14H), 1.15-0.80 (m, 12H), 0.70-0.60 (m, 4H).

LCMS Rt=1.179 min in 2 min chromatography, 30-90AB_E, purity 100%, MS ESI calcd. For $C_{25}H_{40}F_3O$ [M+H-$H_2O$]+ 413, found 413.

Example 25: Synthesis of 2500

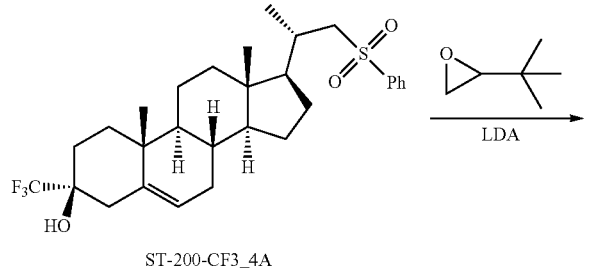

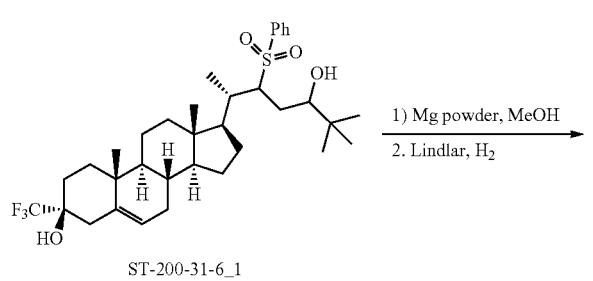

The experimental of intermediate ST-200-CF3_4A can be found in Example 3.

Synthesis of ST-200-31-6_1

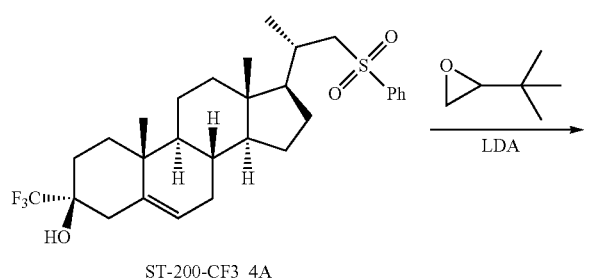

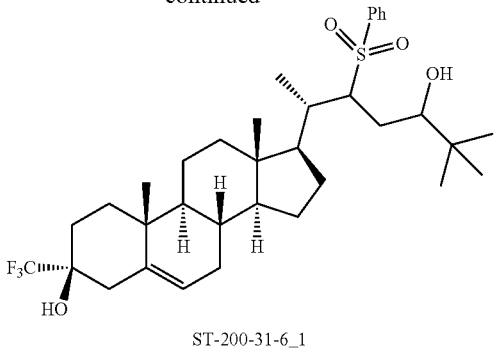

n-BuLi (568 µL, 2.5 M in hexane, 1.42 mmol) was added to a solution of diisopropylamine (143 mg, 1.42 mmol) in THF (0.5 mL) at −78° C. under $N_2$. A suspension of ST-200-CF3_4A (250 mg, 0.476 mmol) in THF (2.5 mL) was added dropwise. The mixture was stirred for 30 minutes at −78° C. A solution of 2-(tert-butyl)oxirane (71.5 mg, 0.715 mmol) was added dropwise at −78° C. The mixture was stirred for another 30 min and then warmed to 25° C. gradually. The reaction mixture was stirred at 25° C. for 16 hour. The reaction mixture was quenched by saturated $NH_4Cl$ aqueous (30 mL), extracted with EtOAc (3×20 mL). The combined organic phase was washed with brine (30 mL), dried over $Na_2SO_4$, filtered and concentrated under vacuum to give ST-200-31-6_1 (350 mg, crude) as a solid, which was used directly for the next step.

Synthesis of 2500

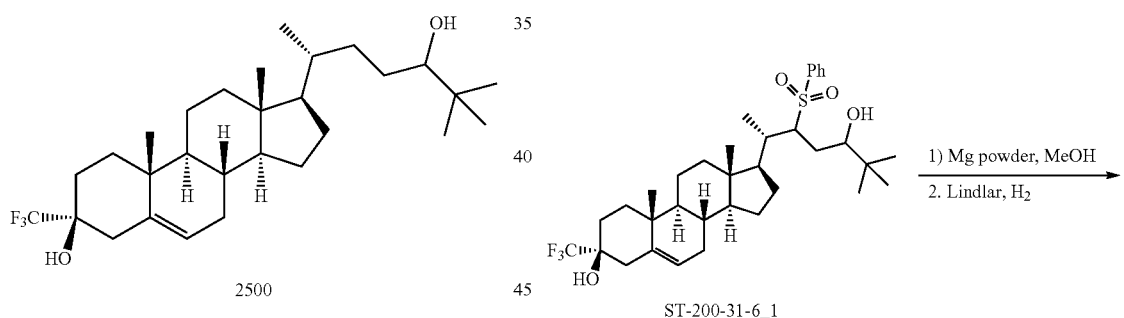

A solution of ST-200-31-6_1 (350 mg, 0.6081 mmol) in MeOH (25 mL) was heated at 60° C. Mg powder (584 mg, 24.3 mmol) was added in four portions at 60° C. The mixture was stirred at 60° C. for 1 h. The mixture was quenched with HCl (50 mL, 2 M) until the reaction became clear and extracted with DCM (2×50 mL). The combined organic phase was dried over $Na_2SO_4$, filtered, concentrated and purified by flash column (0-10% of EtOAc in PE) to give 112 mg of impure product as a solid, which was triturated with MeCN (3 mL) at 25° C. to give 70 mg as a solid. The 70 mg product was dissolved in THF (8 mL) and treated with Lindlar (100 mg) under N₂. The mixture was degassed under vacuum and purged with H₂ (15 psi) several times. The mixture was stirred for 2 hrs at 25° C. under H₂ (15 psi). The mixture was filtered and the filter was concentrated in vacuum. The residue was purified by flash column (0-20% EtOAc in PE) to afford pure 2500 (20 mg) as a solid ¹H NMR (CDCl3,400 MHz) δ 5.40-5.30 (m, 1H), 3.20-3.00 (m, 1H), 2.50-2.45 (s, 2H), 2.05-2.00 (m, 4H), 1.96-1.33 (m, 13H), 1.33-1.20 (m, 7H), 1.20-0.80 (m, 16H), 0.68 (s, 3H).

LCMS Rt=1.404 min in 2 min chromatography, 30-90 AB, purity 100%, MS ESI calcd. For $C_{28}H_{46}F_3O$ [M−H₂O+H]⁺ 467, found 467.

Example 26: Synthesis of 2602

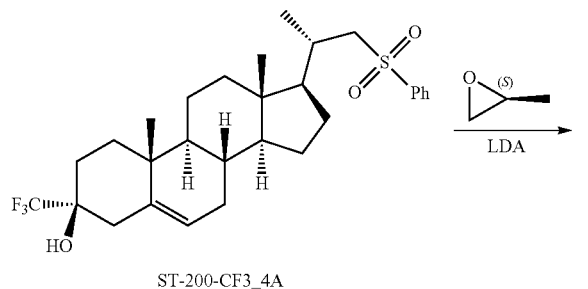

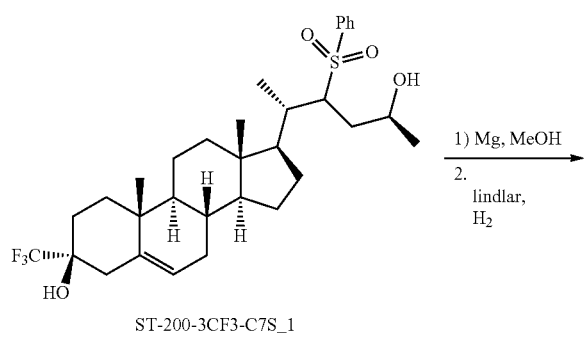

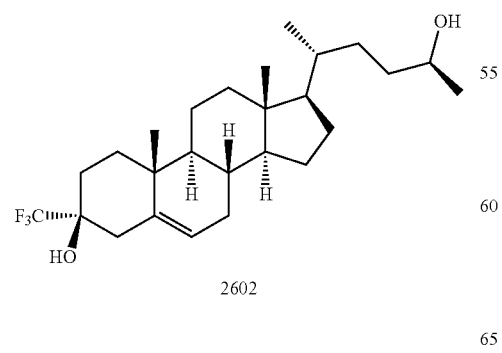

The experimental of intermediate ST-200-CF3_4A or A7 can be found in Example 3.

Synthesis of ST-200-3CF3_C7S_1

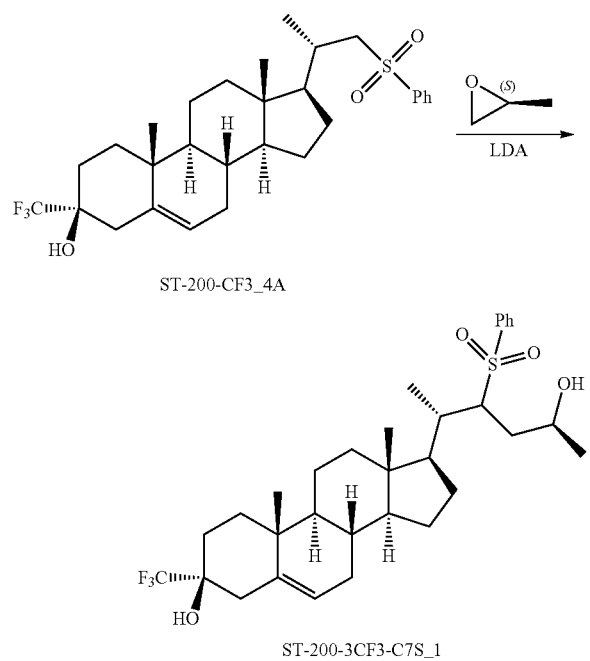

A suspension of ST-200-CF3_4A (250 mg, 0.476 mmol) in THF (2.5 mL) was added dropwise to a solution of n-BuLi (0.568 mL, 2.5 M in hexane, 1.42 mmol) in THF (0.5 mL) at −65° C. under N₂. The mixture was added diisopropylamine (143 mg, 1.42 mmol) and stirred for 30 minutes at −65° C. A solution of (S)-2-methyloxirane (33.1 mg, 0.571 mmol) was added dropwise at −65° C.

The mixture was stirred for another 30 minutes and then warmed to 25° C. gradually. The reaction mixture was stirred at 25° C. for 16 hours. The reaction mixture was quenched by saturated NH₄Cl aqueous (30 mL) and extracted with ethyl acetate (3×20 mL). The combined organic phase was washed with brine (30 mL), dried over Na₂SO₄, filtered and concentrated under vacuum to give ST-200-3CF3-C7S_1 (250 mg, crude) as a solid, which is used directly for the next step.

Synthesis of 2602

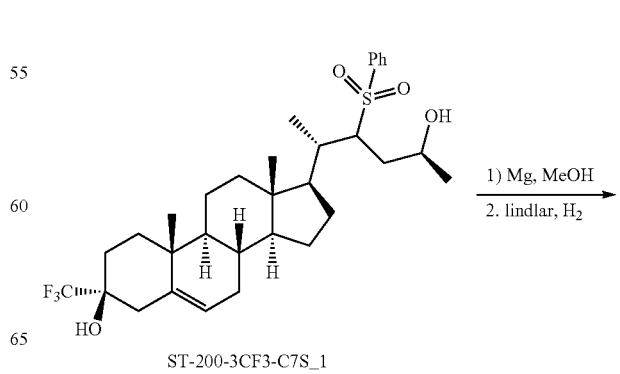

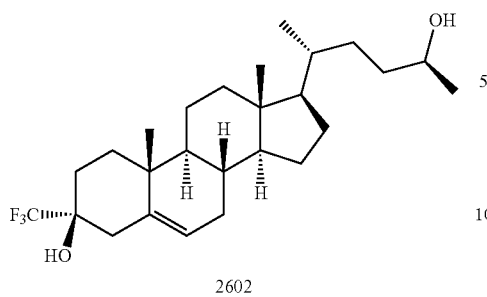

2602

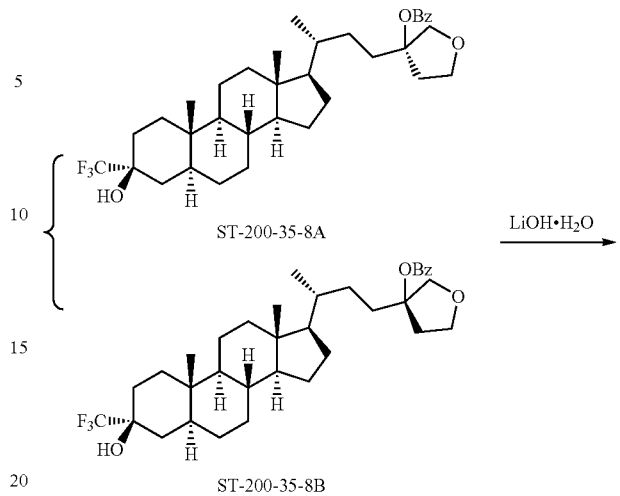

ST-200-35-8A

ST-200-35-8B

LiOH·H$_2$O

Mg powder (415 mg, 17.1 mmol) was added to a solution of ST-200-3CF3-C7S_1 (250 mg, 0.428 mmol) and nickel (II) chloride (13.8 mg, 0.107 mmol) in dry methanol (20 mL) under N$_2$ and the mixture was stirred at 50° C. to initiate continuous hydrogen generation. The reaction mixture was stirred at 60° C. for 1 hour. Next, the reaction mixture was quenched by 2M HCl (100 mL) which was added dropwise at 10° C. until solid was dissolved. After extracting with EtOAc (2×150 mL), the combined organic layer was washed with sat. NaHCO$_3$ aq. (300 mL), brine (300 mL), dried over Na$_2$SO$_4$, filtered and concentrated under vacuum to give a solid, which was purified by silica gel chromatography (PE:EtOAc=4:1) to give 100 mg of solid (the residue was containing 13% 22, 23 alkene). The impure residue was dissolved in THF (20 mL) was added Lindlar (15.9 mg, 0.225 mmol) under N$_2$. The mixture was degassed under vacuum and purged with H$_2$ several times. The mixture was stirred for 2 hrs at 25° C. under H$_2$. The mixture was filtered and the filter was concentrated in vacuum. The residue was purified by SFC (column: C2 250 mm*30 mm, 10 um), gradient: 35-35% B (A=0.1% NH$_3$/H2O, B=EtOH), flow rate: 50 mL/min) to give 2602 (16 mg, 54%) as a solid.

$^1$H NMR (400 MHz, CDCl$_3$) δ 5.40-35 (m, 1H), 3.75-3.65 (m, 1H), 2.50-2.45 (m, 2H), 2.10-1.70 (m, 7H), 1.69-1.50 (m, 6H), 1.49-1.20 (m, 10H), 1.19-0.90 (m, 11H), 0.68 (s, 3H).

LCMS Rt=1.202 min in 2.0 min chromatography, 30-90 AB, purity 100%, MS ESI calcd. for C$_{26}$H$_{40}$F$_3$O [M+H−H$_2$O]$^-$ 425, found 425.

Example 27: Synthesis of 2706 and 2707

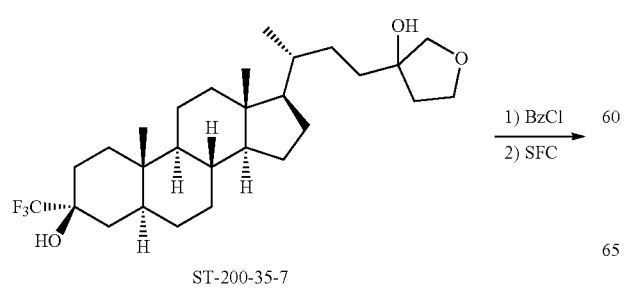

ST-200-35-7

1) BzCl
2) SFC

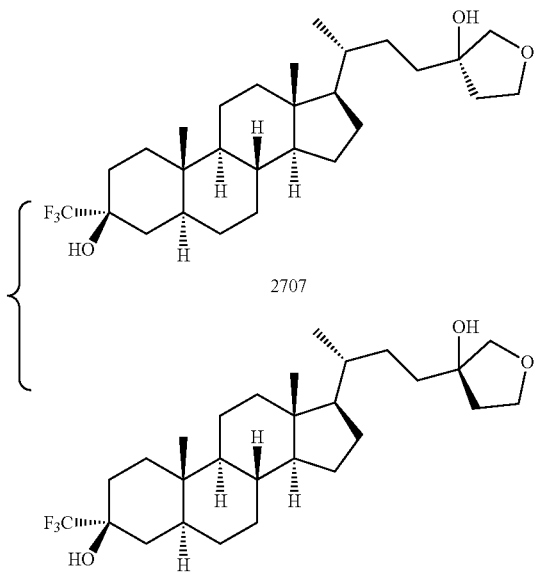

2707

2706

The experimental of intermediate ST-200-CF3_4A can be found in Example 3. ST-200-35-7 can be found in Example 19. The stereochemistry of 2707 was confirmed by X-ray.

Synthesis of ST-200-35-8A/8B

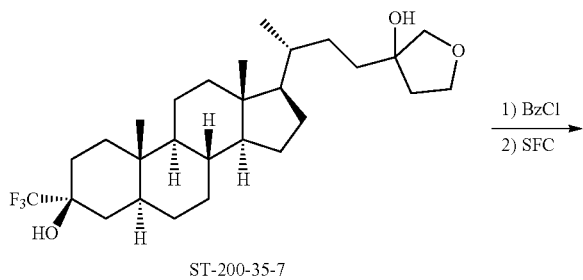

ST-200-35-7

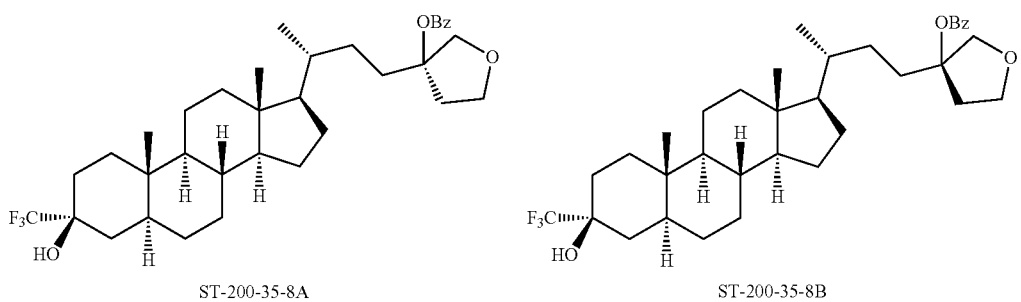

ST-200-35-8A            ST-200-35-8B

BzCl (258 mg, 1.84 mmol) was added to a solution of ST-200-35-7 (300 mg, 0.616 mmol) in pyridine (5 mL) at 0° C. The mixture was stirred for 1 h at 0° C. To the mixture was added water (10 mL) at 0° C. and extracted with DCM (3×10 mL). The organic layer was washed with 1M HCl (10 mL), saturated $Na_2CO_3$ (10 mL) and brine. The mixture was dried over anhydrous $Na_2SO_4$, concentrated in vacuum to give a residue. The residue was purified by prep-TLC (PE/EA=5/1) to give a mixture. The mixture was separated by SFC twice (Instrument: MG-II; Method: Column: AD(250 mm*30 mm, 5 um); Condition: 0.1% $NH_3H2O$ ETOH; Begin B: 40%; End B: 40%; FlowRate(ml/min): 60; Injections: 90) to give peak 1 (Rt=5.134 min) as ST-200-35-8B (44 mg, 12%) and peak 2 (Rt=5.766 min) ST-200-35-8A (38 mg, 10%) both as a solid.

ST-200-35-8B:

SFC Rt=5.134 min in 10.0 min chromatography, AD_3_EtOH_DEA_5_40_25ML, 100% de.

ST-200-35-8A:

Synthesis of 2706

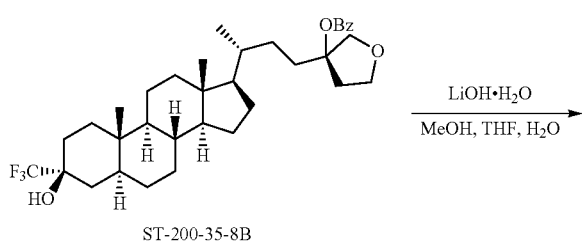

ST-200-35-8B $\xrightarrow{\text{LiOH·H}_2\text{O}}_{\text{MeOH, THF, H}_2\text{O}}$ -continued

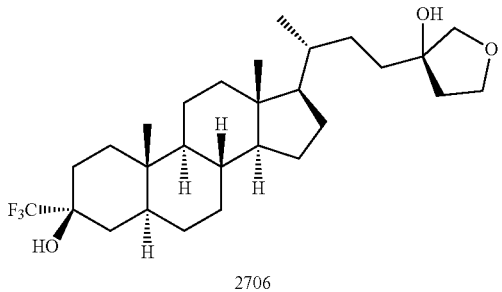

2706

MeOH (0.2 mL), water (0.2 mL) and $LiOH.H_2O$ (31.2 mg, 0.744 mmol) were added to a solution of ST-200-35-8B (44 mg, 0.0744 mmol) in THF (0.4 mL). The mixture was stirred at 50° C. for 16 h. EtOAc (5 mL) and water (2 mL) were added to the mixture. The organic layer was separated, dried over $Na_2SO_4$, filtered, concentrated in vacuum and triturated from MeCN (1 mL) to give 2706 (24 mg, 66%) as a solid.

$^1$H NMR (400 MHz, $CDCl_3$) δ 4.02 (q, J=8.0 Hz, 1H), 3.93-3.83 (m, 1H), 3.69 (d, J=9.2 Hz, 1H), 3.55 (d, J=9.2 Hz, 1H), 2.10-1.79 (m, 7H), 1.75-1.59 (m, 5H), 1.55-0.99 (m, 18H), 0.98-0.88 (m, 4H), 0.85 (s, 3H), 0.75-0.60 (m, 4H).

HPLC Rt=3.97 min in 8.0 min chromatography, 50-100_AB_E, purity 100%.

MS MS ESI calcd. for $C_{28}H_{44}F_3O_2$ $[M+H-H_2O]^+$ 469.3288, found 469.3244.

Synthesis of 2707

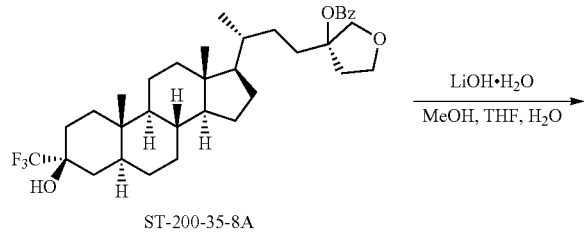

ST-200-35-8A

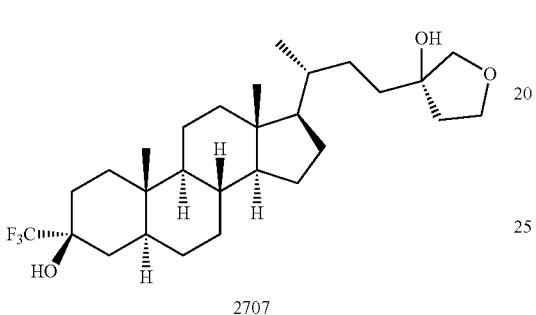

2707

MeOH (0.2 mL), water (0.2 mL) and LiOH.H₂O (26.9 mg, 0.642 mmol) were added to a solution of ST-200-35-8A (38 mg, 0.0643 mmol) in THF (0.4 mL). The mixture was stirred at 50° C. for 16 h. EtOAc (5 mL) and water (2 mL) were added to the mixture. The organic layer was separated, dried over Na₂SO₄, filtered, concentrated in vacuum and triturated from MeCN (1 mL) to give 2707 (21 mg, 67%) as a solid.

$^1$H NMR (400 MHz, CDCl$_3$) δ 4.02 (q, J=8.0 Hz, 1H), 3.94-3.85 (m, 1H), 3.69 (d, J=9.2 Hz, 1H), 3.54 (d, J=9.2 Hz, 1H), 2.10-1.59 (m, 13H), 1.55-0.99 (m, 17H), 0.98-0.88 (m, 4H), 0.85 (s, 3H), 0.75-0.62 (m, 4H).

HPLC Rt=3.93 min in 8.0 min chromatography, 50-100_AB_E, purity 100%.

MS MS ESI calcd. for $C_{28}H_{44}F_3O_2$ [M+H−H₂O]$^+$ 469.3288, found 469.3244.

Example 28: Synthesis of E-2817

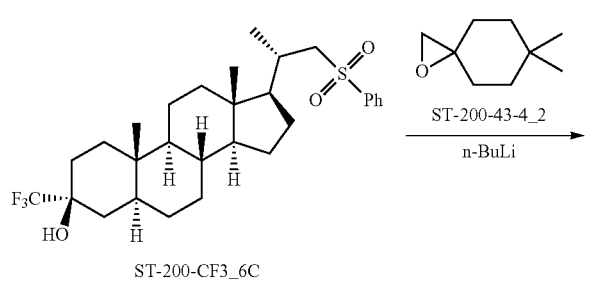

ST-200-CF3_6C

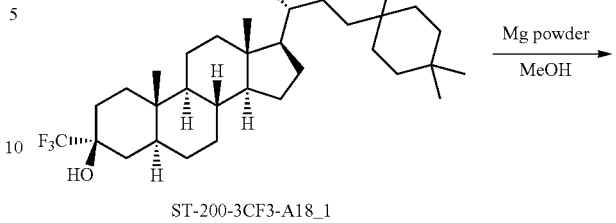

ST-200-3CF3-A18_1

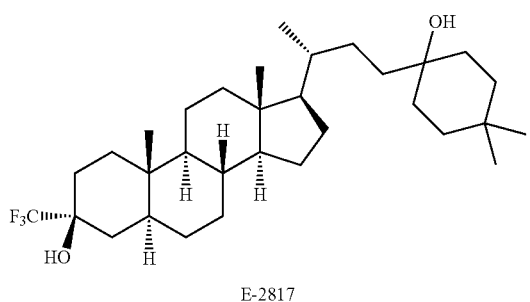

E-2817

The synthesis of ST-200-CF3_6C can be found in Example 5.

The synthesis of ST-200-43-4_2.

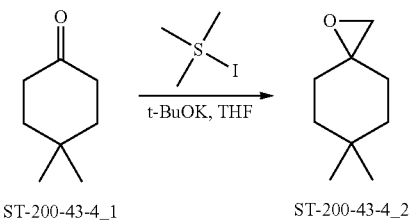

To a suspension of t-BuOK (3.53 g, 31.6 mmol) in THF (30 mL) was added Me₃SI (4.18 g, 20.5 mmol) under N₂ at 15° C. The suspension was stirred at 15° C. for 30 min. To the mixture was added a solution of 200-DA-E31_1A (2 g, 15.8 mmol) in 10 ml of THF dropwise at 15° C. The mixture was stirred at 15° C. for 16 hrs. The mixture was quenched with sat.NH₄Cl (100 mL) and extracted with EtOAc (3×150 mL). The combined organic phase was dried over Na₂SO₄, filtered, and concentrated in vacuum to give 200-DA-E31_1 (1.8 g, 81%) as a liquid.

$^1$H NMR (400 MHz, CDCl$_3$) δ 2.58 (s, 2H), 1.90-1.80 (m, 1H), 1.70-1.55 (m, 2H), 1.54-1.45 (m, 3H), 1.40-1.30 (m, 2H), 1.00-0.90 (m, 6H).

Synthesis of ST-200-3CF3-A18_1

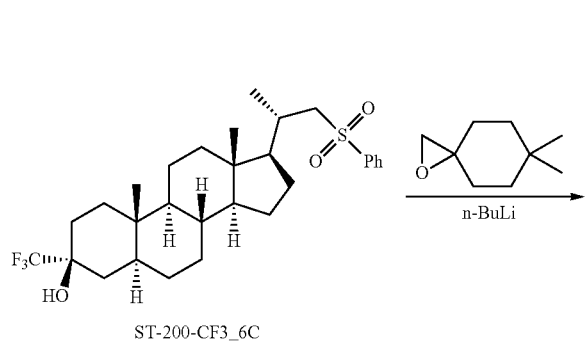

ST-200-CF3_6C

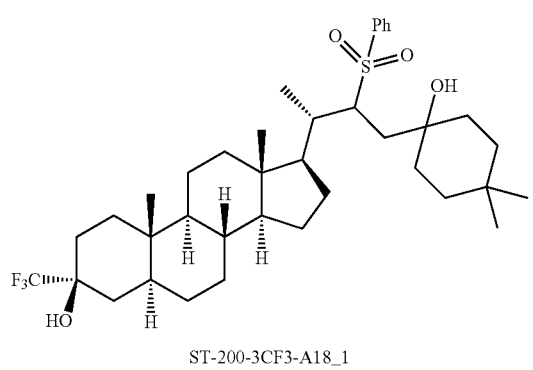

ST-200-3CF3-A18_1

First, n-BuLi (0.5 mL, 2.5 M in hexane, 1.25 mmol) was added To THF (0.5 mL). A solution of ST-200-CF3_6C (250 mg, 0.4746 mmol) in THF (3 mL) was added at −70° C. The mixture was stirred at −70° C. for 1 h. ST-200-43-4_2 (133 mg, 0.9492 mmol) was added at −70° C. The mixture was stirred at −70° C. for another 1 h. The mixture was warmed to 25° C. and stirred for 16 hrs. The reaction mixture was quenched by adding $N_{114}C_1$ (50 mL, sat. aq.) and extracted with EtOAc (2×30 mL). The organic layer was separated, dried over $Na_2SO_4$, filtered, and concentrated to give ST-200-3CF3-A18_1 (390 mg, crude) a solid, which was used directly for the next step.

Synthesis of E-2817

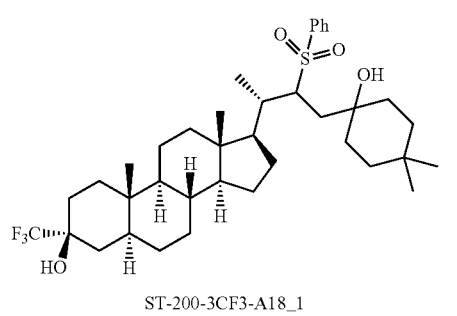

ST-200-3CF3-A18_1

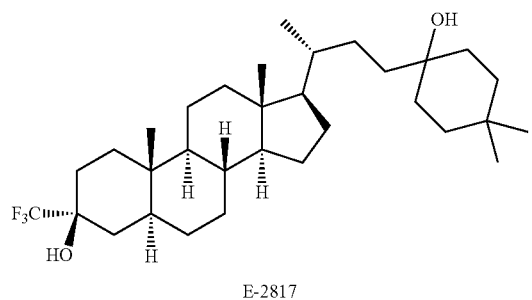

E-2817

A solution of ST-200-3CF3-A18_1 (390 mg, 0.5847 mmol) in MeOH (25 mL) was heated at 60° C. Mg powder (500 mg, 20.8 mmol) was added in four portions at 60° C. The mixture was stirred at 60° C. for 1 h. The mixture was quenched with HCl (50 mL, 2 M) until the reaction became clear and extracted with DCM (2×50 mL). The combined organic phase was dried over $Na_2SO_4$, filtered, concentrated and purified by flash column (0-10% of EtOAc in PE) to give 135 mg of a solid. The impure product was purified by flash column (0-20% of EtOAc in PE) to give E-2817 (101 mg, 75%) as a solid.

$^1$H NMR (CDCl3, 400 MHz) δ 2.08-2.03 (m, 1H), 1.98-1.88 (m, 2H), 1.78-1.73 (m, 2H), 1.73-1.60 (m, 3H), 1.60-1.45 (m, 12H), 1.45-1.27 (m, 7H), 1.27-1.19 (m, 9H), 1.19-1.00 (m, 6H), 0.93-0.84 (m, 9H), 0.75-0.64 (s, 4H).

LCMS Rt=1.463 min in 2 min chromatography, 30-90 AB, purity 100%, MS ESI calcd. For $C_{32}H_{52}F_3O$ [M+H−$H_2O$]$^+$ 509, found 509.

Example 29: Synthesis of 2918

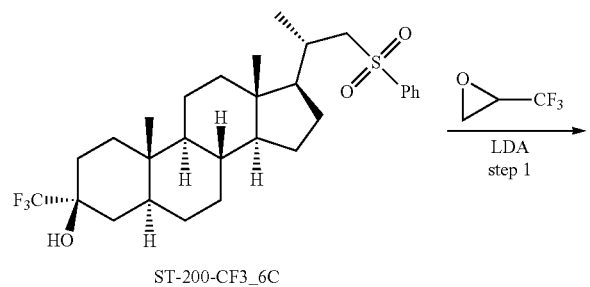

ST-200-CF3_6C

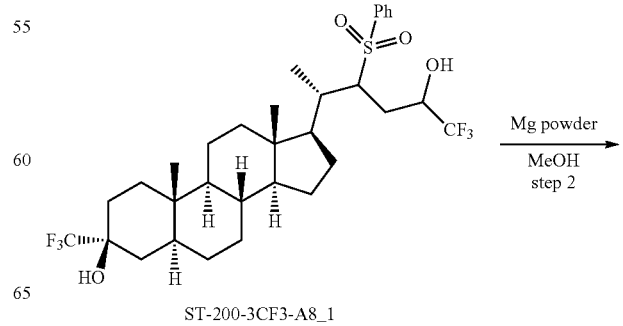

ST-200-3CF3-A8_1

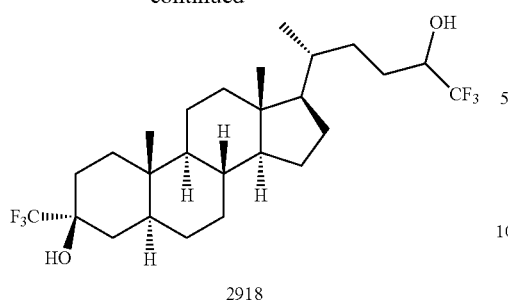

2918

The synthesis of ST-200-CF3_6C can be found in Example 5.

Synthesis of ST-200-3CF3-A8_1

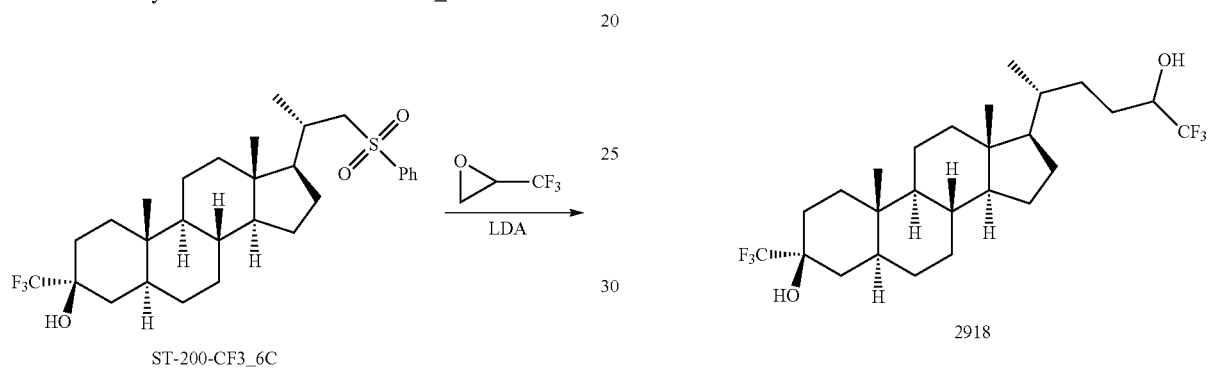

ST-200-CF3_6C

ST-200-3CF3-A8_1

A suspension of ST-200-CF3_6C (250 mg, 0.475 mmol) in THF (2.5 mL) was added dropwise to a solution of n-BuLi (568 µL, 2.5 M in hexane, 1.42 mmol) in THF (0.5 mL) at −78° C. under N$_2$. The mixture was stirred for 30 min at −78° C. A solution of 2-(trifluoromethyl)oxirane (79.7 mg, 0.712 mmol) was added dropwise at −78° C. The mixture was stirred for another 30 min and then warmed to 25° C. gradually. The reaction mixture was stirred at 25° C. for 16 hours. The reaction mixture was quenched by saturated NH$_4$Cl aqueous (30 mL) and extracted with ethyl acetate (3×20 mL). The combined organic phase was washed with brine (30 mL), dried over Na$_2$SO$_4$, filtered and concentrated under vacuum to give ST-200-3CF3-A8_1 (340 mg, crude) as a solid, which was used directly for the next step.

Synthesis of 2918

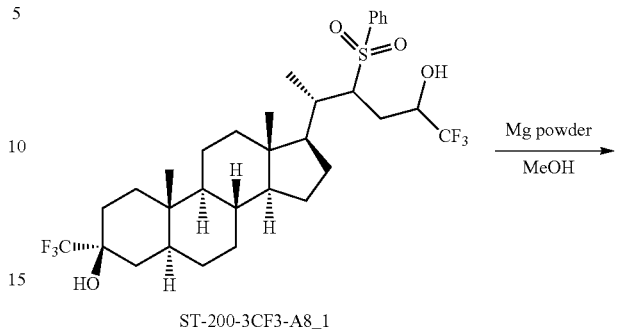

ST-200-3CF3-A8_1

2918

A solution of ST-200-3CF3-A8_1 (340 mg, 0.5322 mmol) in MeOH (25 mL) was heated at 60° C. Mg powder (508 mg, 21.2 mmol) was added in four portions at 60° C. The mixture was stirred at 60° C. for 1 h. The mixture was quenched with HCl (50 mL, 1N) until the reaction became clear and extracted with DCM (2×30 mL). The combined organic phase was dried over Na$_2$SO$_4$, filtered, concentrated and purified by flash column (0-10% of EtOAc in PE) to give 63 mg of a solid, which was triturated from DCM and hexane to give 2918 (5 mg, 2%).

$^1$H NMR (CDCl3, 400 MHz) S 3.90-3.80 (m, 1H), 2.20-1.70 (m, 6H), 1.70-1.50 (m, 7H), 1.50-1.25 (m, 5H), 1.25-1.10 (m, 5H), 1.10-0.80 (m, 12H), 0.70-0.65 (m, 4H).

LCMS Rt=1.219 min in 2 min chromatography, 30-90 AB, purity 100%.

Example 30: Synthesis of 3035

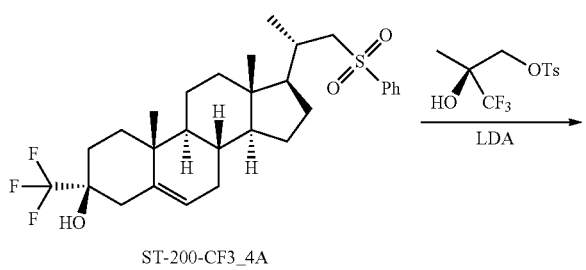

ST-200-CF3_4A

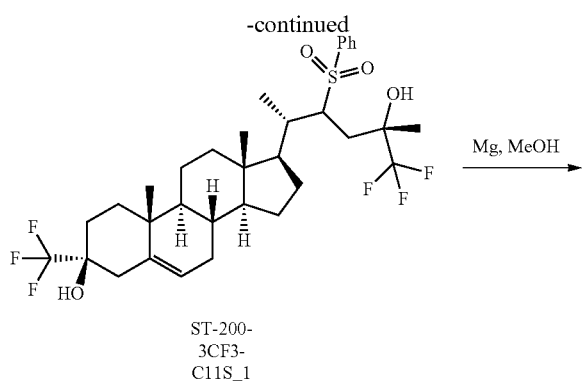

ST-200-3CF3-C11S_1

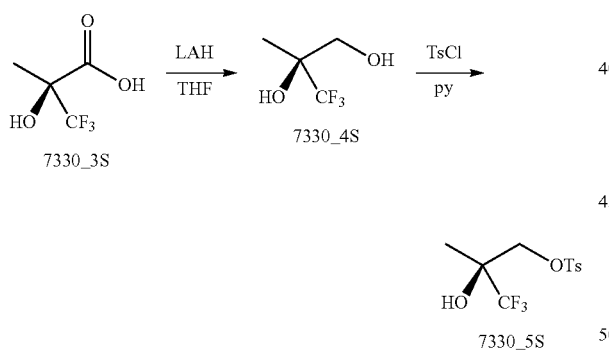

3035

The experimental of intermediate ST-200-CF3_4A can be found in Example 3.

The synthesis of the tosylate:

Synthesis of Tosylate

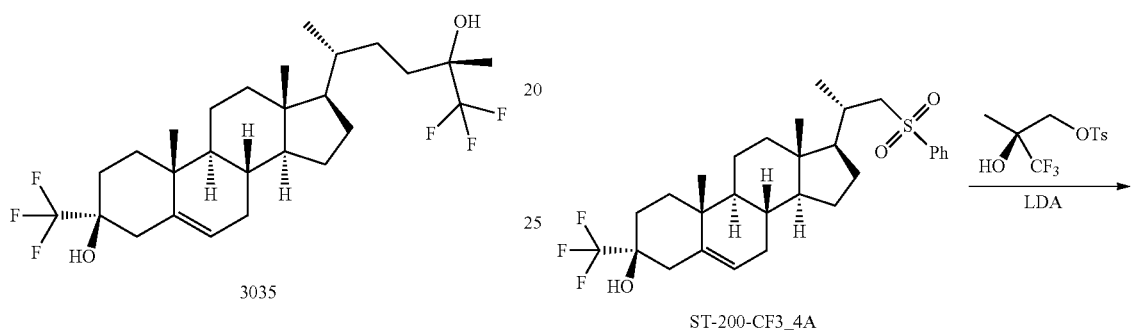

7330_5S

To a suspension of LiAlH$_4$ (45.3 g, 1.26 mol) in THF (1 L) was added dropwise a solution of 7330_3S (100 g, 632 mmol) in THF (500 mL) at 0° C. and the inner temperature raised to about 50° C. After addition, the mixture was stirred at 70° C. for 16 hours. The mixture was quenched with HCl (1 L, 3 M aq.) to pH=2 and extracted with MTBE (3×500 mL). The combined organic phase was dried over Na$_2$SO$_4$, filtered and concentrated under reduced pressure (<40° C.) to give 7330_4S (92 g, crude) as an oil.

$^1$H NMR (400 MHz, CDCl$_3$) δ 3.96-3.92 (m, 1H), 3.58-3.53 (m, 1H), 3.08 (s, 1H), 1.98-1.89 (m, 1H), 1.38 (s, 3H).

To a solution of 7330_4S (50 g, 346 mmol) in pyridine (300 mL) was added 4-methylbenzene-1-sulfonyl chloride (98.9 g, 519 mmol) in portions during 5 minutes at 0° C. The reaction solution was stirred at 20° C. for 16 hrs. The reaction mixture was quenched with 2N HCl (400 mL) to pH=1-2 at 0° C. The inner temperature was maintained below 30° C. and the mixture was extracted with MTBE (3×200 mL). The combined organic layer was dried over Na$_2$SO$_4$, filtered, concentrated and purified by column (0~10% of EtOAc in PE) to give 7330_5S (93 g, 90%, 99.42% ee) as an oil.

$^1$H NMR (400 MHz, CDCl$_3$) δ 7.79 (d, J=7.6 Hz, 2H), 7.37 (d, J=8.0 Hz, 2H), 4.13-4.03 (m, 2H), 2.99 (s, 1H), 2.46 (s, 3H), 1.37 (s, 3H),

LCMS Rt=1.103 min in 2.0 min chromatography, 10-80 AB, purity 100%, no MS detected.

Synthesis of ST-200-3CF3-C11S_1

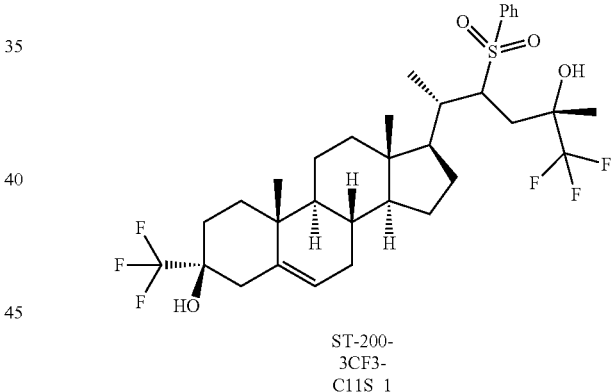

ST-200-CF3_4A

ST-200-3CF3-C11S_1

A suspension of ST-200-CF3_4A (250 mg, 0.48 mmol) in THF (4 mL) was added dropwise to a solution of n-BuLi (0.48 mL, 2.5 M in hexane, 1.19 mmol) in THF (1 mL) at −70° C. under N$_2$. After stirring for 30 minutes at −70° C., diisopropylamine (120 mg, 1.19 mmol) was added dropwise at −70° C., followed by adding (S)-3,3,3-trifluoro-2-hydroxy-2-methylpropyl 4-methylbenzenesulfonate (212 mg, 0.71 mmol) dropwise at −70° C. The mixture was stirred for another 30 min and then warmed to 25° C. gradually. The reaction mixture was stirred at 25° C. for 24 hour. The reaction mixture was quenched by saturated NH$_4$Cl aqueous (5 mL), extracted with EtOAc (3×10 mL). The combined organic phase was washed with brine (30 mL), dried over Na$_2$SO$_4$, filtered and concentrated under vacuum to give ST-200-3CF3-C11S_1 (480 mg, crude), which was used directly.

Synthesis of 3035

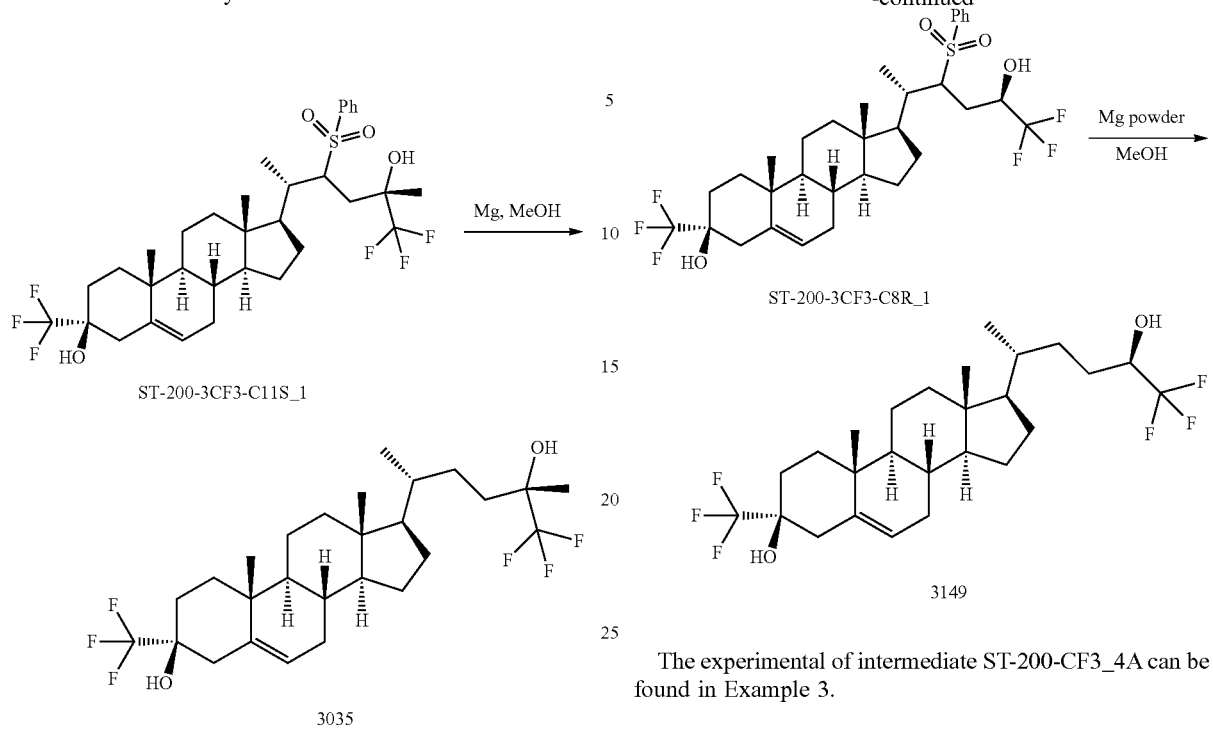

Mg powder (705 mg, 29.4 mmol) and NiCl$_2$ (1 mg, 0.007 mmol) were added with stirring to a solution of ST-200-3CF3-C11S_1 (480 mg, 0.74 mmol) in 50 mL of anhydrous MeOH under N$_2$ at 60° C. The reaction mixture was quenched by 2 M HCl (10 mL) until the solid was dissolved. The mixture was extracted with EtOAc (3×20 mL). The combined organic layer was washed with sat. NaHCO$_3$ (50 mL), brine (50 mL), dried over Na$_2$SO$_4$, filtered and concentrated. The residue was purified by flash column (0~20% of EtOAc in PE) to give a crude product, which was further purified by re-crystallized from MeCN (10 mL) at 85° C. to give 3035 (53 mg, 21%) as a solid.

$^1$H NMR (400 MHz, CDCl$_3$) δ 5.41-5.34 (m, 1H), 2.53-2.46 (s, 2H), 2.08-1.92 (m, 4H), 1.91-1.58 (m, 7H), 1.54-1.35 (m, 7H), 1.33-1.30 (s, 3H), 1.29-1.08 (m, 5H), 1.07-1.05 (s, 3H), 1.05-0.91 (m, 5), 0.73-0.63 (s, 3).

LCMS R$_f$=1.213 min in 2 min chromatography, 30-90AB_2 MIN_E, purity 99%.

Example 31: Synthesis of 3149

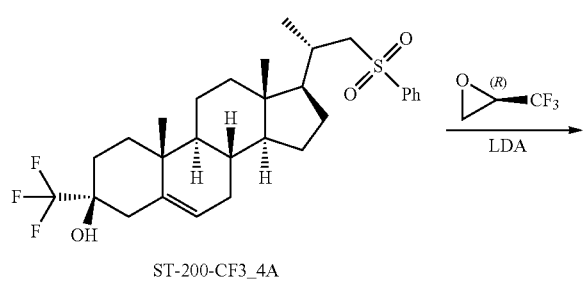

The experimental of intermediate ST-200-CF3_4A can be found in Example 3.

Synthesis of ST-200-3CF3_C8R_1

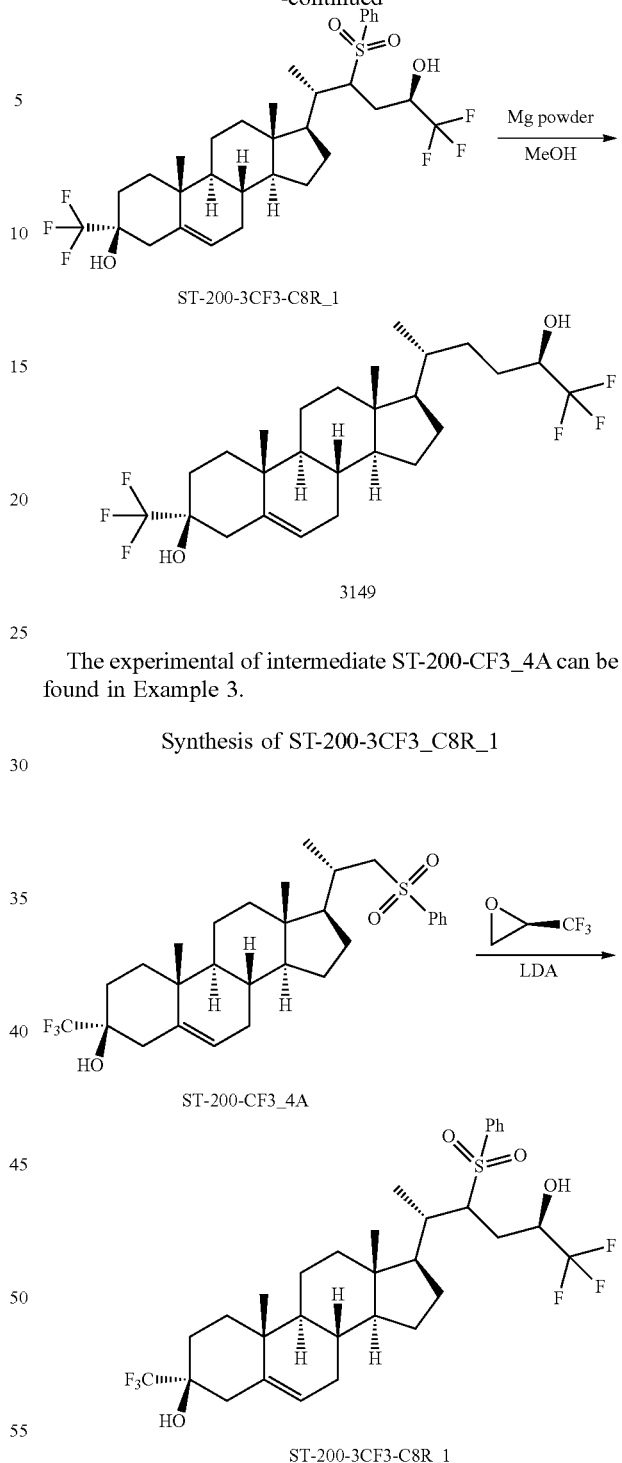

A suspension of ST-200-CF3_4A (250 mg, 0.476 mmol) in THF (2.5 mL) was added dropwise to a solution of n-BuLi (0.568 mL, 2.5 M in hexane, 1.42 mmol) in THF (0.5 mL) at −65° C. under N$_2$. After adding diisopropylamine (143 mg, 1.42 mmol) and stirring for 30 minutes at −65° C., a solution of (R)-2-(trifluoromethyl) oxirane (63.9 mg, 0.571 mmol) was added dropwise at −65° C. The mixture was stirred for another 30 minutes and then warmed to 25° C. gradually. The reaction mixture was stirred at 25° C. for 16 hours. The reaction mixture was quenched by saturated NH₄Cl aqueous (30 mL) and extracted with ethyl acetate (3×20 mL). The combined organic phase was washed with brine (30 mL), dried over Na₂SO₄, filtered and concentrated under vacuum to give ST-200-3CF3-C8R_1 (250 mg, crude) as a solid, which was used directly for the next step.

Synthesis of 3149

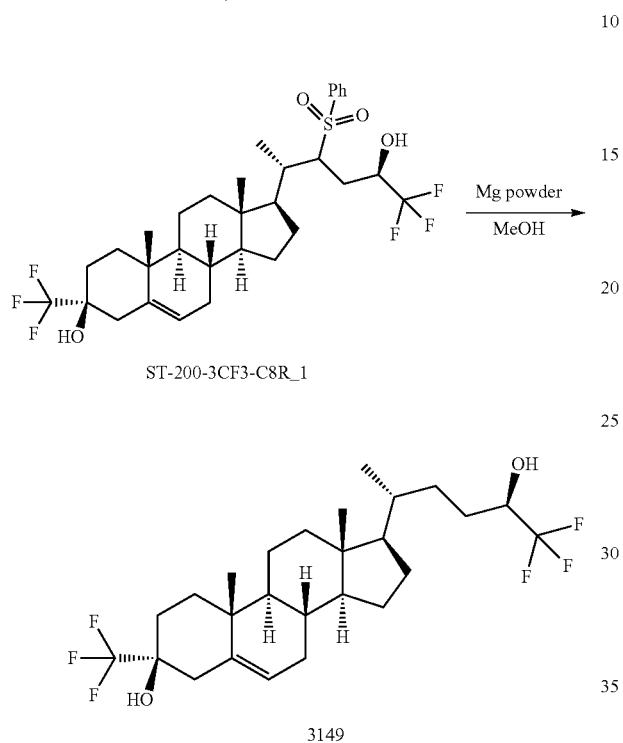

3149

Mg powder (379 mg, 15.6 mmol) was added to a solution of ST-200-3CF3-C8R_1 (250 mg, 0.392 mmol) and nickel (II) chloride (12.7 mg, 0.098 mmol) in dry methanol (50 mL) under N₂ at 50° C. While adding Mg, the mixture was stirred to initiate continuous hydrogen generation. Next, the reaction mixture was stirred at 60° C. for 1 hour. The reaction mixture was quenched by 2M HCl (100 mL) which was added dropwise at 10° C. until solid was dissolved. After extracting with EtOAc (2×150 mL), the combined organic layer was washed with sat. NaHCO₃ aq. (300 mL), brine (300 mL), dried over Na₂SO₄, filtered and concentrated under vacuum to give a solid, which was purified by silica gel chromatography (PE/THF=4/1) to give a crude product, which was re-crystallized from MeCN (10 mL) to give a impure product (30 mg, 15%). The impure product (30 mg, 0.068 mmol) was purified by SFC (column: AD 250 mm*30 mm, 10 um), gradient: 20-20% B (A=0.1% NH₃/H2O, B=EtOH), flow rate: 60 mL/min) to give 3149 (12 mg, 40%) as a solid.

¹H NMR (400 MHz, CDCl₃) δ 5.40-5.35 (m, 1H), 3.75-3.65 (m, 1H), 2.50-2.45 (m, 2H), 2.10-1.70 (m, 11H), 1.69-1.50 (m, 10H), 1.49-0.90 (m, 10H), 0.69 (s, 3H).

HPLC Rt=6.25 min in 1.2 min chromatography, 30-90 AB, purity 98%.

HRMS ESI calcd. for $C_{26}H_{39}F_6O_2$ [M+H]⁻ 497.2849, found 497.2842.

Example 32: Synthesis of 3266

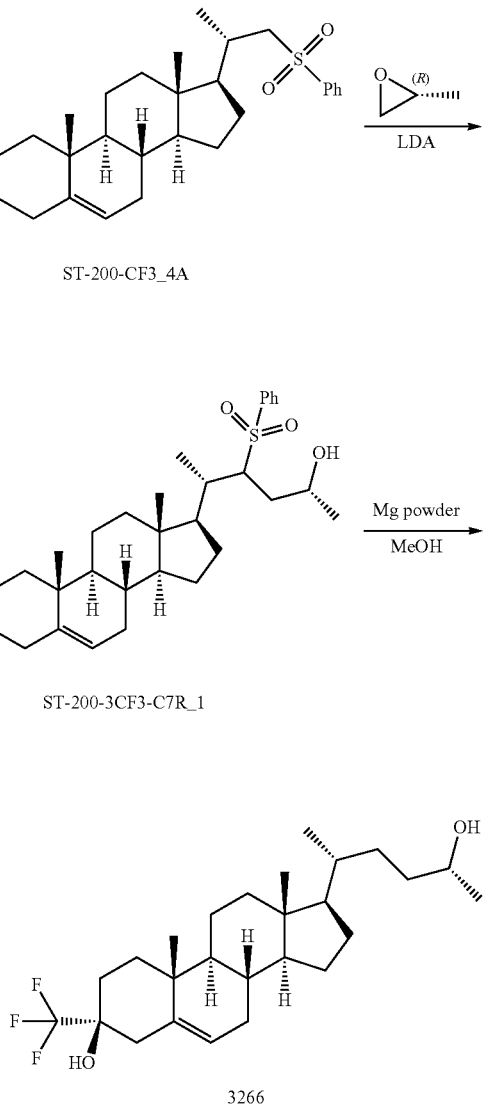

3266

The experimental of intermediate ST-200-CF3_4A can be found in Example 3.

Synthesis of ST-200-3CF3-C7R_1

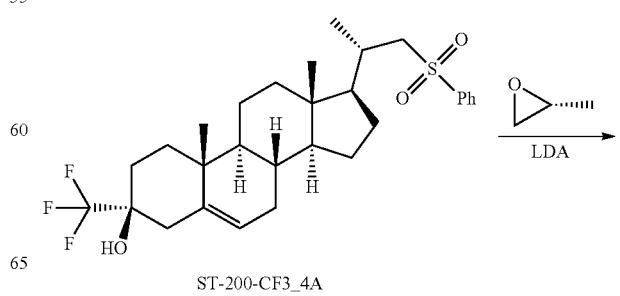

ST-200-CF3_4A

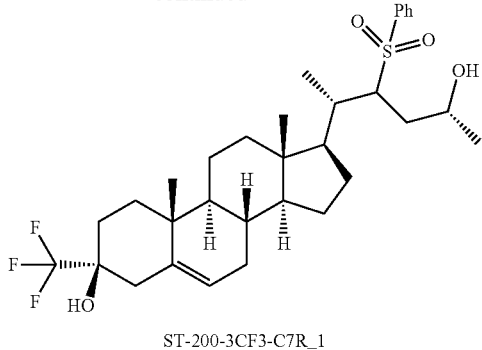

ST-200-3CF3-C7R_1

A suspension of ST-200-CF3_4A (250 mg, 0.476 mmol) in THF (4 mL) was added dropwise to a solution of n-BuLi (568 mL, 2.5 M in hexane, 1.42 mmol) in THF (1 mL) at −65° C. under $N_2$. After stirring at −65° C. 30 minutes, diisopropylamine (143 mg, 1.42 mmol) was added at −65° C. After that, (R)-2-methyloxirane (82.4 mg, 1.42 mmol) was added dropwise at −65° C. The mixture was stirred for another 30 minutes and then warmed to 25° C. gradually. The reaction mixture was stirred at 25° C. for 16 hours. The reaction was quenched with sat. $NH_4Cl$ aq. (50 mL), extracted with EtOAc (3×50 mL). The combined organic layers were dried over $Na_2SO_4$, filtered and concentrated to give a crude product as a solid, which was used directly for the next step.

Synthesis of 3266

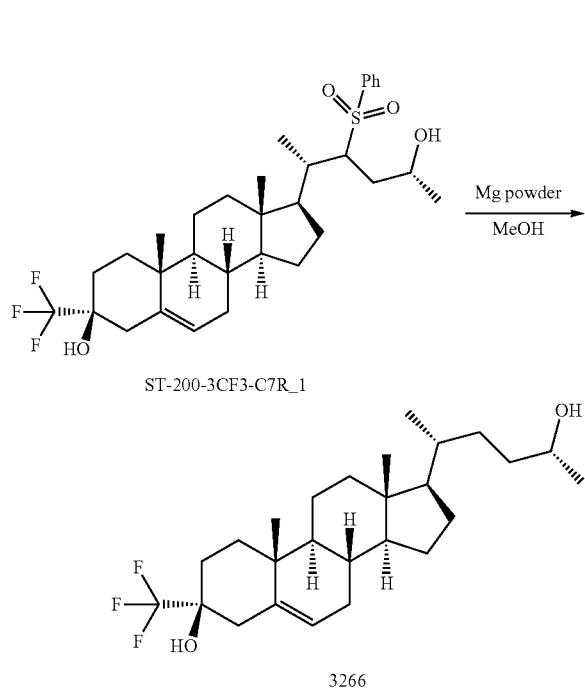

Mg powder (410 mg, 17.1 mmol) was added in four portions by stirring into a solution of ST-200-3CF3_C7R_1 (250 mg, 0.428 mmol) and $NiCl_2$ (5.52 mg, 0.043 mmol) in dry methanol (20 mL) under $N_2$ at 50° C. After stirring at 60° C. for 1 hour, the mixture was quenched with HCl (50 mL, 1N) until the reaction became clear and extracted with EtOAc (3×30 mL). The combined organic phase was dried over $Na_2SO_4$, filtered, concentrated. The residue was purified by flash column (0-15% of EtOAc in PE) to give an impure product (100 mg, 0.225 mmol, impure, containing 13% 22,23 alkene). Lindlar catalyst (200 mg, 0.225 mmol) was added to a solution of impure product in THF (20 mL) under $N_2$. The mixture was degassed under vacuum and purged with Hz several times. The mixture was stirred for 2 hours at 25° C. The reaction mixture was filtered through a pad of Celite and washed with THF (3×10 mL). The filtrate was concentrated to give a impure product, which was triturated from n-hexane (10 mL) at 68° C. for 2 hours to give a impure product as a solid. The impure product was purified by silica gel chromatography (PE/EtOAc=0 to 5/1) to give 3266 (48 mg, impure) as a solid, which was purified by SFC(Column: AD (150×46 mm, 3 um), Gradient: 5%-40% B (A: $CO_2$ B: ethanol) Flow rate: 2.5 mL/min) to afford 3266 (10 mg) as a solid.

$^1$H NMR (400 MHz, $CDCl_3$) δ 5.40-5.33. (m, 1H), 3.78-3.65 (m, 1H), 2.52-2.45 (m, 2H), 2.08-1.65 (m, 7H), 1.58-1.32 (m, 7H), 1.32-1.23 (m, 4H), 1.23-0.75 (m, 16H), 0.68 (s, 3H).

LCMS Rt=1.149 min in 2.0 min chromatography, 30-90 AB, purity 100%, MS ESI calcd. for $C_{26}H_{40}F_3O$ [M+H−$H_2O$]$^+$ 425, found 425.

Example 33: Synthesis of 3382

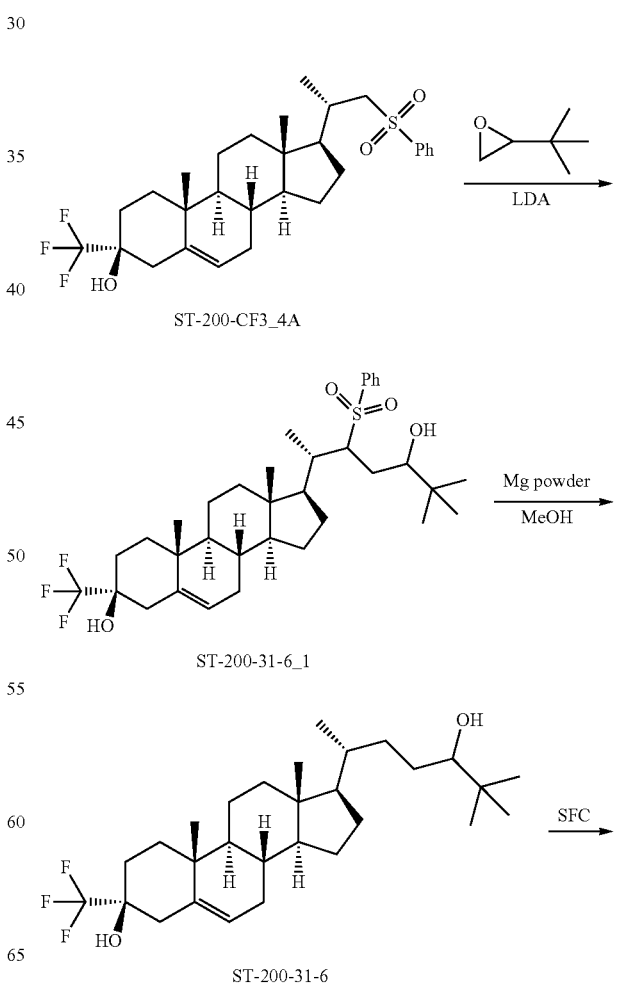

165

-continued

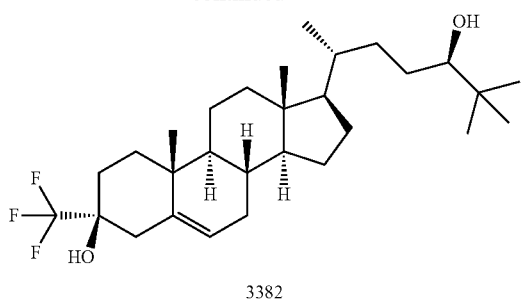

3382

Stereochemistry was assigned based on synthesis with chiral epoxide, see Example 35 for synthesis.

The experimental of intermediate ST-200-CF3_4A can be found in Example 3.

Synthesis of ST-200-31-6_1

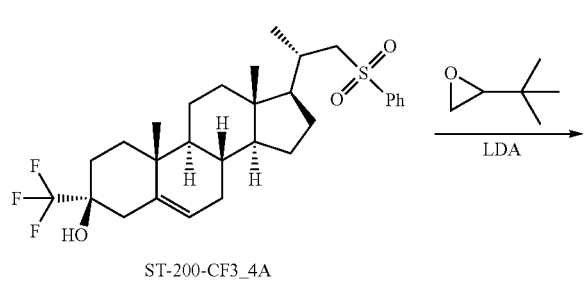

ST-200-CF3_4A

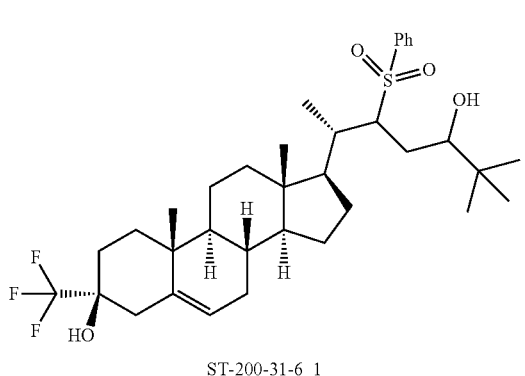

ST-200-31-6_1

A suspension of ST-200-CF3-4A (500 mg, 0.95 mmol) in THF (4 mL) was added dropwise to a solution of n-BuLi (0.95 mL, 2.5 M in hexane, 2.38 mmol) in THF (1 mL) at −70° C. under $N_2$. After stirring for 30 minutes at −70° C., a solution of diisopropylamine (240 mg, 2.38 mmol) was added dropwise at −70° C., followed by adding a solution of 2-(tert-butyl)oxirane (142 mg, 1.42 mmol) dropwise at −70° C. The mixture was stirred at −70° C. for another 30 min and then warmed to 25° C. gradually. After stirring for at 25° C. for 24 hour, the reaction mixture was quenched by saturated $NH_4Cl$ aqueous (5 mL), extracted with EtOAc (3×20 mL). The combined organic phase was washed with brine (40 mL), dried over $Na_2SO_4$, filtered and concentrated under vacuum to give ST-200-31-6_1 (650 mg, crude), which was used directly.

166

Synthesis of ST-200-31-6

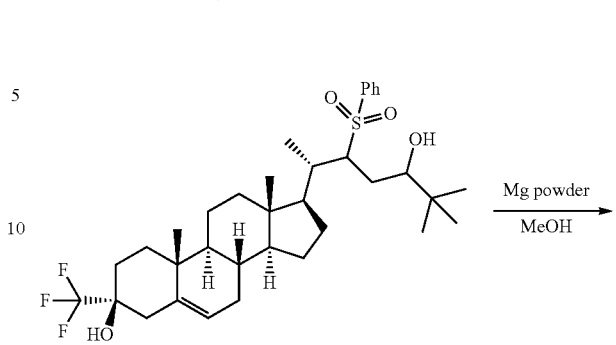

ST-200-31-6_1

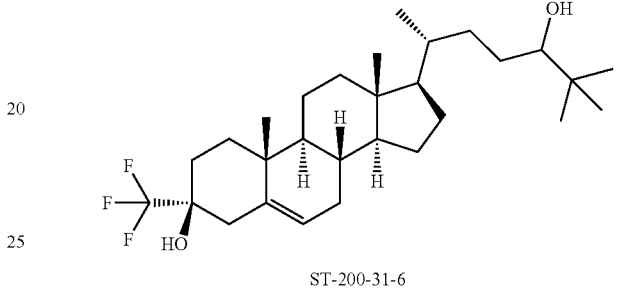

ST-200-31-6

Mg powder (998 mg, 41.6 mmol) and $NiCl_2$ (5 mg, 0.05 mmol) were added with stirring to a solution of ST-200-31-6 (650 mg, 1.04 mmol) in 100 mL of anhydrous MeOH under $N_2$ at 60° C. The reaction mixture was quenched by 2 M HCl (50 mL) until solid was dissolved. The mixture was extracted with EtOAc (3×100 mL). The combined organic layer was washed with sat. $NaHCO_3$ (150 mL), brine (150 mL), dried over $Na_2SO_4$, filtered and concentrated. The residue was purified by flash column (0~15% of EtOAc in PE) to give impure ST-200-31-6 as a solid. Lindlar catalyst (200 mg) was added to a solution of the ST-200-31-6 in EtOAc (10 mL) under $N_2$. The suspension was degassed under vacuum and purged with $H_2$ for three times. Then the solution was hydrogenated under 15 psi of hydrogen at 25° C. for 4 h. The mixture was filtered through a pad of celite and washed with EtOAc (3×10 mL). The filtrate was concentrated and concentrated to give ST-200-31-6 (210 mg, 43%) as a solid.

$^1$H NMR (400 MHz, $CDCl_3$) δ 5.39-5.34 (m, 1H), 3.18-3.06 (m, 1H), 2.49 (s, 2H), 2.17 (s, 1H), 2.02-1.58 (m, 7H), 1.53-1.29 (m, 9H), 1.22-0.97 (m, 10H), 0.95-0.84 (m, 13H), 0.72-0.65 (m, 3H).

Synthesis of 3382

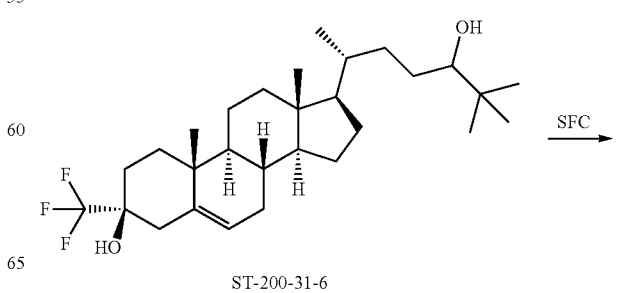

ST-200-31-6

-continued

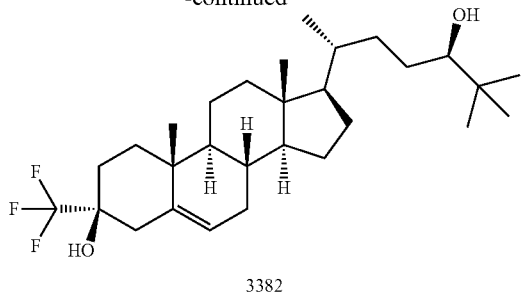

3382

-continued

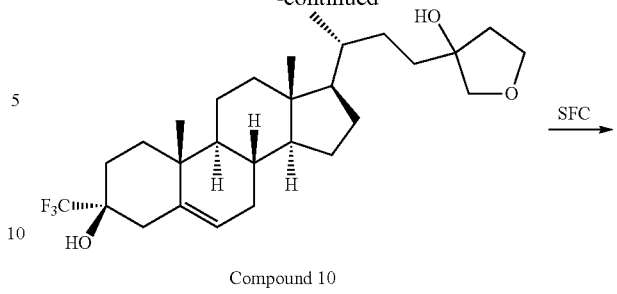

Compound 10

SFC

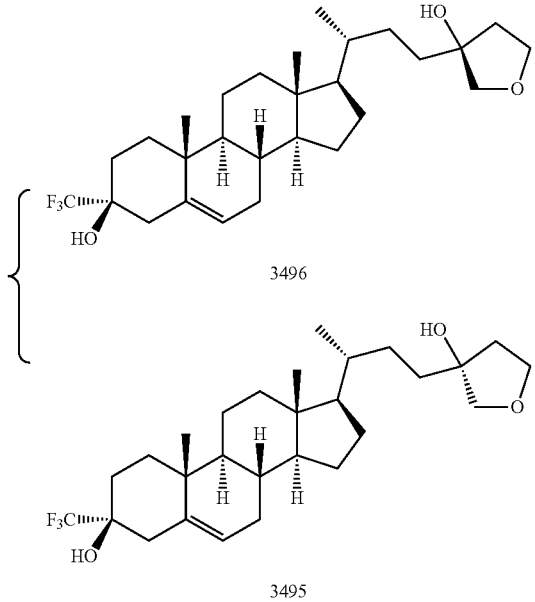

3496

3495

ST-200-31-6 (210 mg, 0.43 mmol) was purified by SFC (column: AD (250 mm*30 mm, 10 um)), gradient: 20-20% B (A=0.1% NH₃/H₂O, B=EtOH), flow rate: 50 mL/min) to give 3382 (90 mg, 43%) as a solid.

$^1$H NMR (400 MHz, CDCl$_3$) δ 5.42-5.34 (m, 1H), 3.19-3.12 (m, 1H), 2.48 (s, 2H), 2.09-1.67 (m, 8H), 1.53-1.23 (m, 12H), 1.22-0.98 (m, 8H), 0.95-0.84 (m, 12H), 0.69 (s, 3H).

LCMS Rt=1.440 min in 2 min chromatography, 30-90AB_2 MIN_E, purity 100%, MS ESI calcd. for $C_{29}H_{46}F_3O$ $[M+H-H_2O]^+$ 467, found 467.

SFC_E1 Rt=4.337 min in 10 min chromatography, AD_3_EtOH_DEA_5_40_25ML, purity: 100%.

Example 34: Synthesis of 3495 and 3496

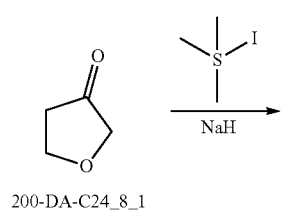

200-DA-C24_8_1

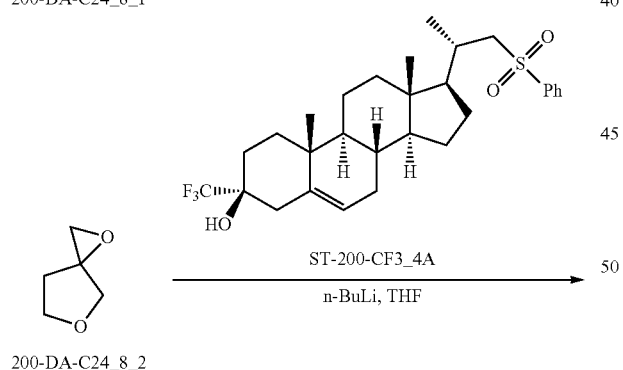

ST-200-CF3_4A n-BuLi, THF

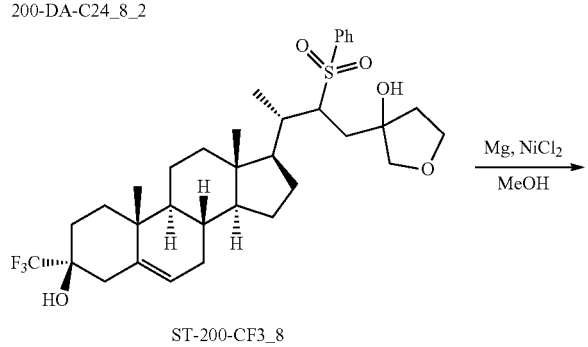

ST-200-CF3_8

Mg, NiCl$_2$

MeOH

The stereochemistry for 3496 was determined by X-ray data. The experimental of intermediate ST-200-CF3_4A can be found in Example 3.

Synthesis of 200-DA-C24_8_2

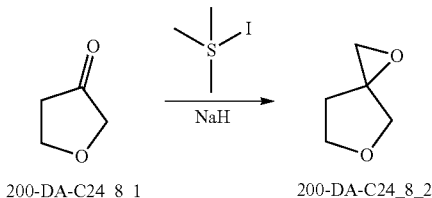

200-DA-C24_8_1          200-DA-C24_8_2

Sodium hydride (5.98 g, 60% in mineral oil, 150 mmol) was added in portions to a mixture of trimethylsulfonium iodide (30.6 g, 150 mmol) in THF (100 mL) at 0° C. under N₂. The mixture was stirred at 0° C. for 30 min. Dihydrofuran-3(2H)-one (10 g, 116 mmol) in DMSO (100 mL) was added dropwise at 0° C. The reaction mixture was stirred at 0° C. for 2 hours. The mixture was poured in portions into ice-water (500 mL) and extracted with DCM (2×500 mL). The combined organic phase was washed with brine (500 mL), dried over Na₂SO₄, filtered and concentrated to afford 200-DA-C24_8_2 (4 g, crude, 34%) as an oil at 18° C., which was used directly for the next step.

Synthesis of ST-200-CF3_8

Synthesis of Compound 10

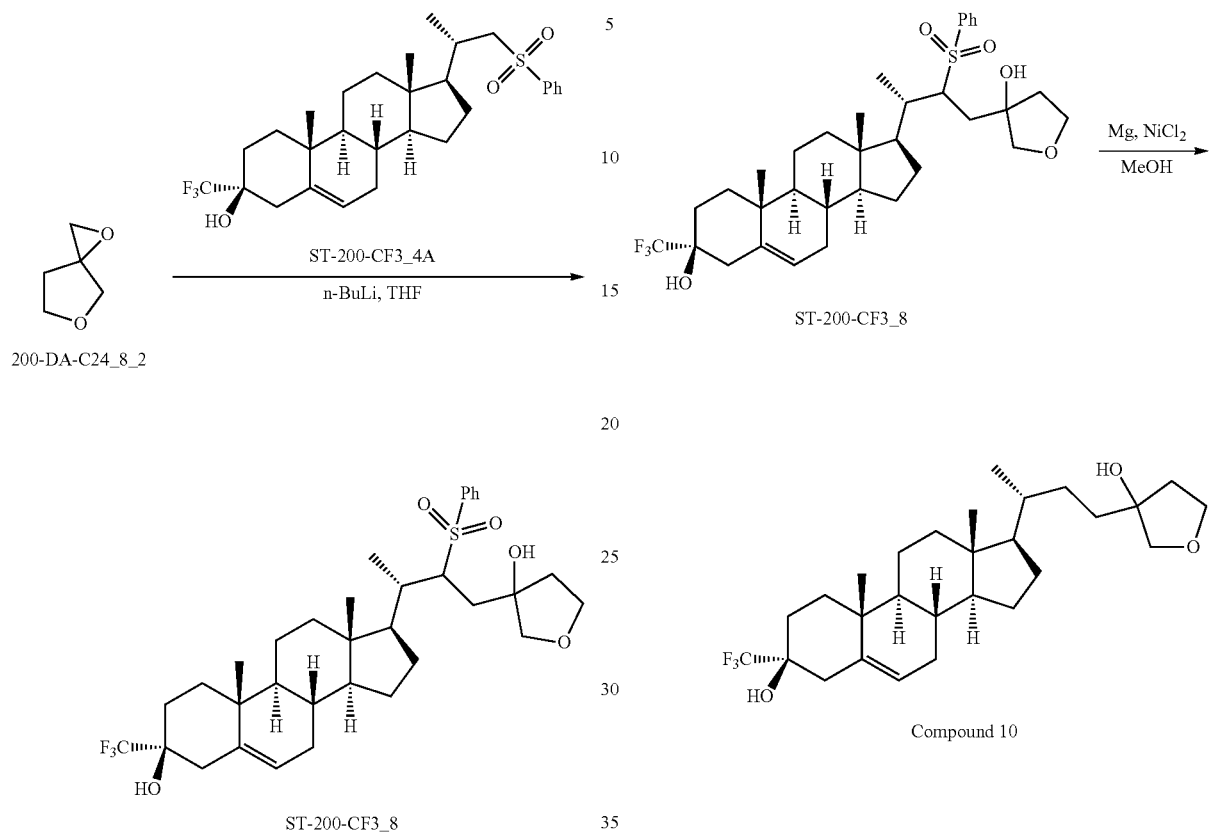

Butyllithium (2.71 mL, 2.5 M in n-hexane, 6.79 mmol) was added to a solution of diisopropylamine (714 mg, 7.33 mmol) in THF (3 mL) at −70° C. The mixture was warmed to 0° C. and stirred at 0° C. for 30 minutes. The mixture was cooled to −70° C. and 200-DA-C24_8_2 (300 mg, 2.99 mmol) in THF (2 mL) was added. The mixture was stirred at −70° C. for 1 h. ST-200-CF3_4A (1.42 g, 2.71 mmol) in THF (2 mL) was added at −70° C. The mixture was warmed to 25° C. and stirred at this temperature for 16 hours. The mixture was quenched with Sat NH$_4$Cl (10 mL). The mixture was extracted with EtOAc (2×10 mL). The organic phase was washed with brine (2×10 mL), dried over Na$_2$SO$_4$, filtered, concentrated in vacuum. The crude product purified by flash column (0~50% of EtOAc in PE) to give ST-200-CF3_8 (280 mg, 17%) as a solid, which was used directly for the next step.

Nickel (II) chloride (580 μg, 4.48 μmol) and Mg powder (435 mg, 17.9 mmol) were added in four portions to a solution of ST-200-CF3_8 (280 mg, 0.448 mmol) in 50 mL of dry methanol under N$_2$ at 60° C. The reaction mixture was quenched by 1M HCl (150 mL) which was added dropwise until solid was dissolved. After extracting with EtOAc (3×50 mL), the organic layer was washed with sat. NaHCO$_3$ (50 mL), brine (50 mL), dried over Na$_2$SO$_4$, filtered and concentrated. The residue was purified by flash column (0~20% of EtOAc in PE) to give Compound 10 (210 mg, 97%) as a solid.

$^1$H NMR CDCl$_3$ 400 MHz δ 5.39-5.35 (m, 1H), 3.93-3.82 (m, 1H), 3.72-3.68 (m, 1H), 3.59-3.51 (m, 1H), 2.49 (s, 2H), 2.10-1.80 (m, 8H), 1.80-1.62 (m, 4H), 1.60-1.39 (m, 7H), 1.39-1.12 (m, 6H), 1.12-0.91 (m, 9H), 0.69 (s, 3H).

Synthesis of 3495 and 3496

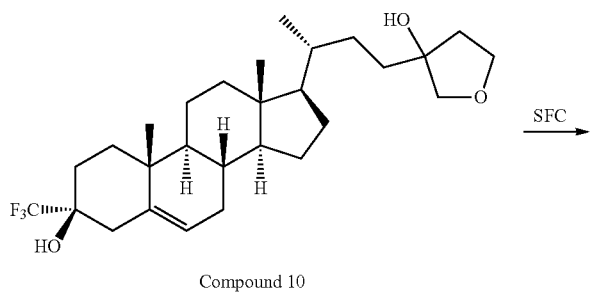

Compound 10 →SFC

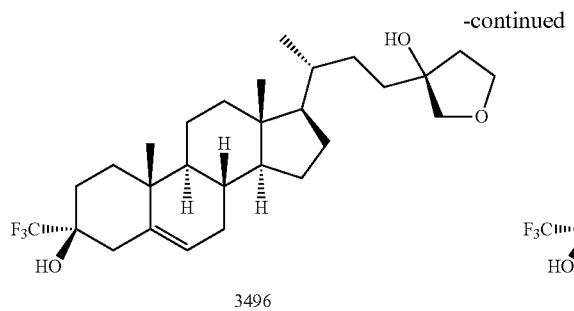

3496

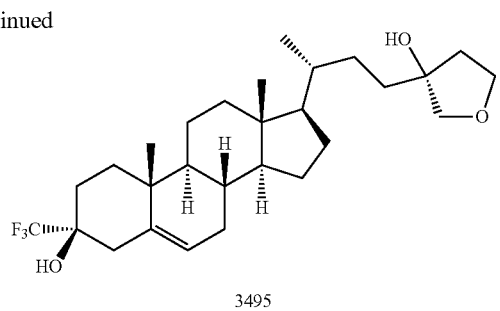

3495

10 (280 mg, 0.577 mmol) was purified by SFC (column: AS (250 mm*30 mm, 5 um), gradient: 20-20% B (A=0.1% NH$_3$/H$_2$O, B=EtOH), flow rate: 60 mL/min) to give 3495 (20 mg, 7%) as a solid and 3496 (32 mg, 11%) as a solid.

3495

$^1$H NMR CDCl$_3$ 400 MHz δ 5.39-5.35 (m, 1H), 4.05-3.98 (m, 1H), 3.93-3.85 (m, 1H), 3.72-3.68 (m, 2H), 3.59-3.51 (m, 1H), 2.49 (s, 2H), 2.05-1.72 (m, 9H), 1.55-1.40 (m, 7H), 1.72-1.40 (m, 7H), 1.40-0.90 (m, 9H), 0.69 (s, 3H).

LCMS Rt=1.081 min in 2.0 min chromatography, 30-90AB_2 MIN_E.M, purity 100%, MS ESI calcd. for C$_{28}$H$_{42}$F$_3$O$_2$ [M+H−H$_2$O]$^+$ 467, found 467.

3496

$^1$H NMR CDCl$_3$ 400 MHz δ 5.39-5.35 (m, 1H), 4.05-3.98 (m, 1H), 3.90-3.85 (m, 1H), 3.72-3.68 (m, 1H), 3.59-3.51 (m, 1H), 2.49 (s, 2H), 2.05-1.72 (m, 10H), 1.68-1.1.60 (m, 2H), 1.52-1.25 (m, 8H), 1.25-0.92 (m, 13H), 0.69 (s, 3H).

LCMS Rt=1.095 min in 2.0 min chromatography, 30-90AB_2 MIN_E.M, purity 100%, MS ESI calcd. for C$_{28}$H$_{42}$F$_3$O$_2$ [M+H−H$_2$O]$^+$ 467, found 467.

Example 35: Synthesis of 3507

Stereochemistry assigned based on synthesis with chiral epoxide.

The experimental of intermediate ST-200-31-6 can be found in Example 33.

Synthesis of ST-200-31-5

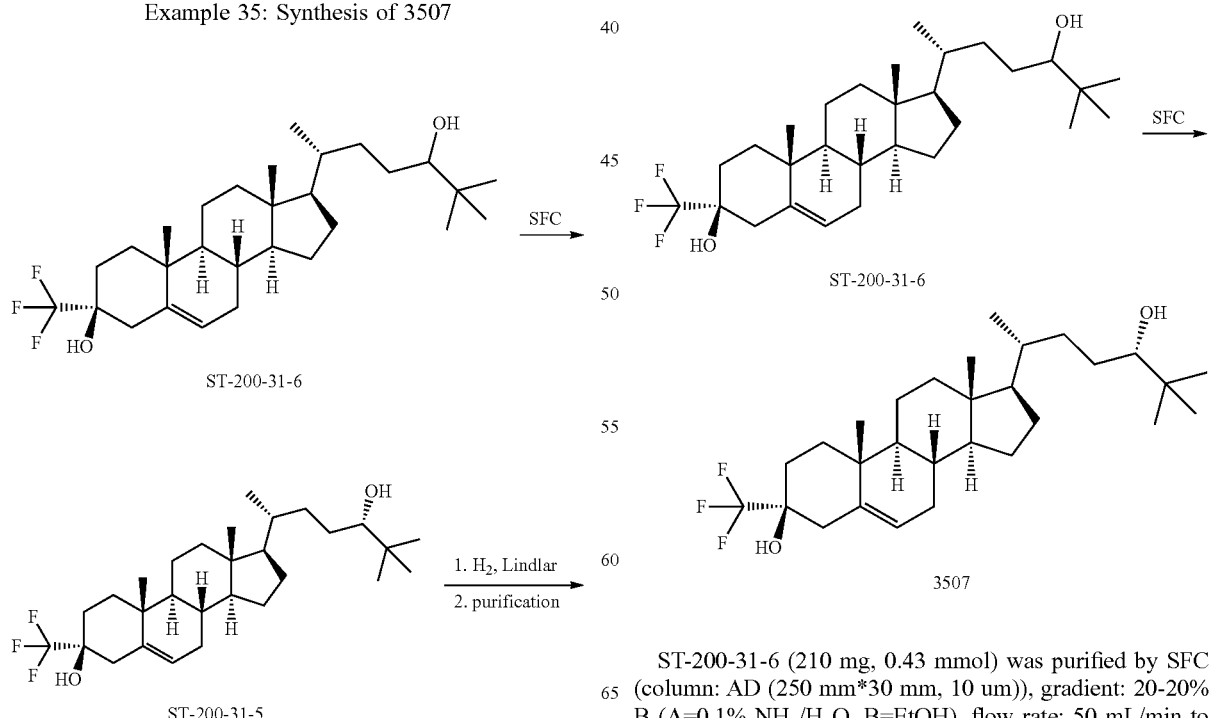

ST-200-31-6 (210 mg, 0.43 mmol) was purified by SFC (column: AD (250 mm*30 mm, 10 um)), gradient: 20-20% B (A=0.1% NH$_3$/H$_2$O, B=EtOH), flow rate: 50 mL/min to give impure 3507 (100 mg, 45%) as a solid.

$^1$H NMR (400 MHz, CDCl$_3$) δ 5.42-5.33 (m, 1H), 3.15-3.06 (m, 1H), 2.48 (s, 2H), 2.08-1.92 (m, 4H), 1.89-1.57 (m, 6H), 1.53-1.23 (m, 8H), 1.21-0.97 (m, 10H), 0.96-0.83 (m, 12H), 0.68 (s, 3H).

Synthesis of 3507

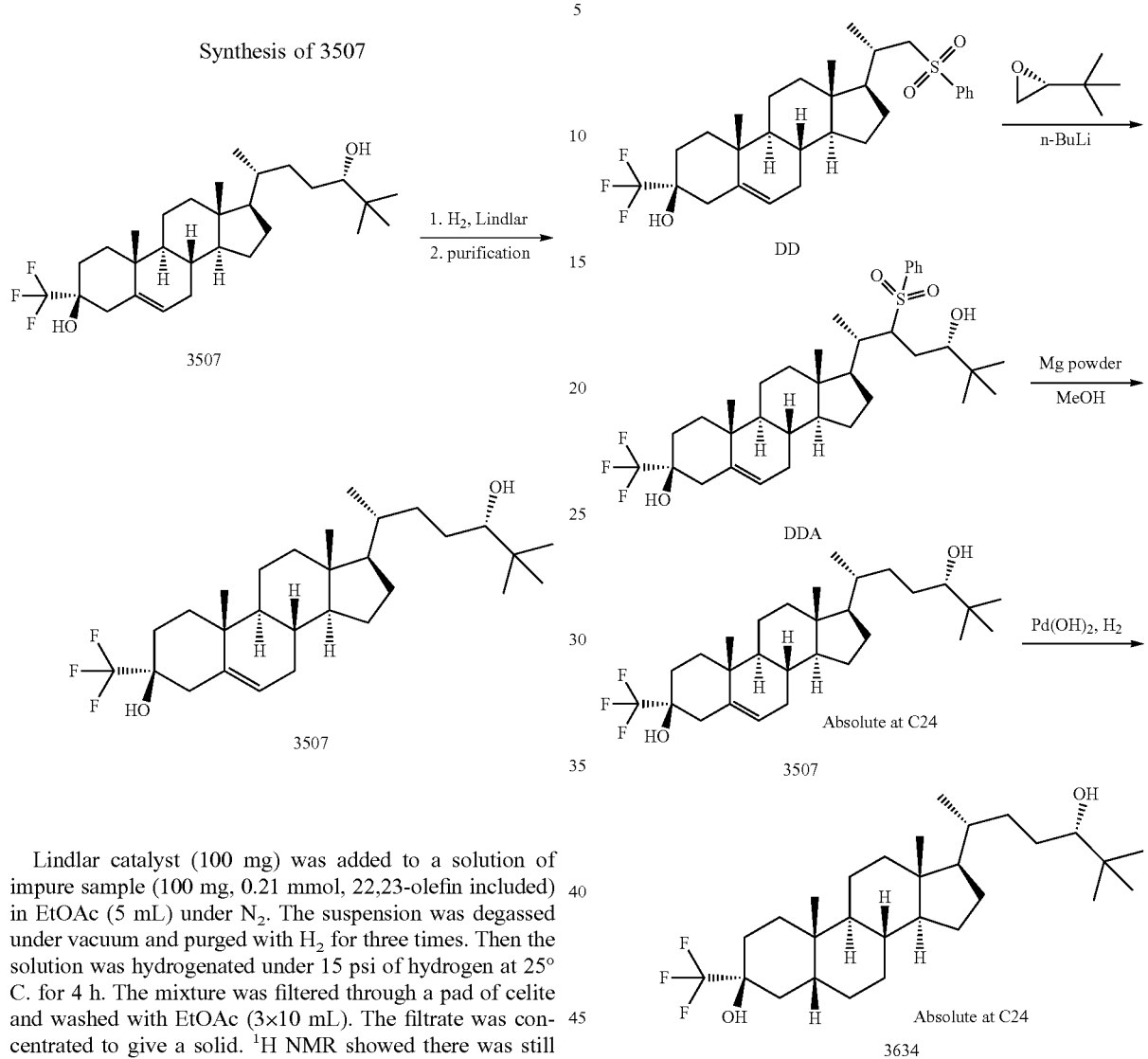

Lindlar catalyst (100 mg) was added to a solution of impure sample (100 mg, 0.21 mmol, 22,23-olefin included) in EtOAc (5 mL) under N$_2$. The suspension was degassed under vacuum and purged with H$_2$ for three times. Then the solution was hydrogenated under 15 psi of hydrogen at 25° C. for 4 h. The mixture was filtered through a pad of celite and washed with EtOAc (3×10 mL). The filtrate was concentrated to give a solid. $^1$H NMR showed there was still contained 12.5% 22,23-olefin. The impure 3507 was dissolved in THF/MeOH (3/3 mL) and treated with Lindlar (100 mg) under N$_2$. The suspension was degassed under vacuum and purged with H$_2$ for three times. Then the solution was hydrogenated under 15 psi of hydrogen at 25° C. for 4 h. The mixture was filtered through a pad of celite and washed with THF (3×10 mL). The filtrate was concentrated and triturated from PE (5 mL) to give 3507 as a solid, which was triturated in n-hexane (5 mL) at 25° C. to give 3507 (40 mg, 40%) as a solid.

$^1$H NMR (400 MHz, CDCl$_3$) δ 5.42-5.34 (m, 1H), 3.13-3.06 (m, 1H), 2.48 (s, 2H), 2.09-1.94 (m, 4H), 1.89-1.57 (m, 6H), 1.54-1.34 (m, 6H), 1.32-1.08 (m, 5H), 1.07-0.97 (m, 7H), 0.94 (d, J=6.4 Hz, 3H), 0.89 (s, 9H), 0.68 (s, 3H).

LCMS Rt=1.298 min in 2 min chromatography, 30-90AB_2 MIN_E, purity 100%, MS ESI calcd. for C$_{29}$H$_{46}$F$_3$O [M+H−H$_2$O]$^+$ 467, found 467.

SFC_E1 Rt=3.887 min in 10 min chromatography, AD_3_EtOH_DEA_5_40_25ML, 100% de.

Synthesis Confirming Stereochemistry for 3507 and 3634

To a solution of THF (0.5 mL) was added n-BuLi (0.8 mL, 2.5 M in hexane, 2 mmol), was added a solution of DD (420 mg, 0.8 mmol) in THF (2 mL) at −70° C. After stirring at −70° C. for 1 h, (R)-2-(tert-butyl)oxirane (120 mg, 1.2 mmol) in THF (0.5 mL) was added at −70° C. The mixture was stirred at −70° C. for another 1 h and warmed to 25° C. and stirred for 16 hours. The reaction mixture was quenched with sat. NH$_4$Cl (10 mL) and extracted with EtOAc (2×5 mL). The organic layer was separated, dried over anhydrous Na$_2$SO$_4$, filtered and concentrated. The residue (400 mg) was used directly for next step.

To a mixture of DDA (400 mg, crude) in MeOH (30 mL) was added NiCl$_2$ (8.29 mg, 0.64 mmol) at 25° C. Then the mixture was warmed to 60° C., Mg powder (671 mg, 25.5 mmol) was added in three bathes. The reaction was quenched with HCl (1M, 10 mL), the mixture was extracted with EtOAc (2×30 mL). The combined organic layer was washed with brine (20 mL), dried over Na$_2$SO$_4$, filtered and concentrated. The residue was purified by flash-combi (0~30% of EtOAc in PE) to give 3507 (110 mg, impure) as a solid, which was further purified by SFC ((column: AD(250 mm*30 mm, 10 um)), gradient: 30-30% B (A=0.1% NH$_3$/H$_2$O IPA, B=EtOH), flow rate: 50 mL/min) to give 3507 (100 mg) as a solid.

$^1$H NMR (400 MHz, CDCl$_3$) δ 5.40-5.34 (m, 1H), 3.14-3.02 (m, 1H), 2.48 (s, 2H), 2.10-1.91 (m, 3H), 1.90-1.69 (m, 4H), 1.69-1.51 (m, 6H), 1.51-1.27 (m, 7H), 1.22-0.98 (m, 8H), 0.98-0.92 (m, 3H), 0.89 (s, 9H), 0.68 (s, 3H).

LCMS Rt=1.322 min in 2 min chromatography, 30-90AB_2 MIN_E, purity 100%, MS ESI calcd. for C$_{29}$H$_{46}$F$_3$O [M+H−H$_2$O]$^+$ 467, found 467.

SFC Rt=3.804 min in 10 min chromatography, AD_3_EtOH_DEA_5_40_25ML, 100% de.

To a solution of 3507 (70 mg) in THF (10 mL) was added Pd(OH)$_2$/C (20%, dry, 100 mg). The mixture was stirred under H$_2$ (50 psi) at 50° C. for 18 h. The mixture was filtered and concentrated in vacuum. The residue was purified by flash-combi (0~15% of EtOAc in PE) to give 3634 (13 mg, 19%) as a solid.

$^1$H NMR (400 MHz, CDCl$_3$) δ 3.17-2.98 (m, 1H), 2.14-1.78 (m, 4H), 1.78-1.60 (m, 6H), 1.57-1.34 (m, 7H), 1.34-1.00 (m, 13H), 0.98 (s, 3H), 0.92 (m, 3H), 0.89 (s, 9H), 0.65 (s, 3H).

LCMS Rt=1.349 min in 2.0 min chromatography, 30-90_AB_E, purity 100%, no MS signal.

MS MS ESI calcd. for C$_{29}$H$_{48}$F$_3$O [M+H−H$_2$O]$^+$ 469, found 469.

Example 36: Synthesis of 3634

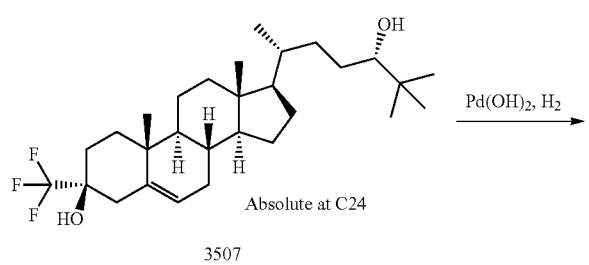

3507  Absolute at C24

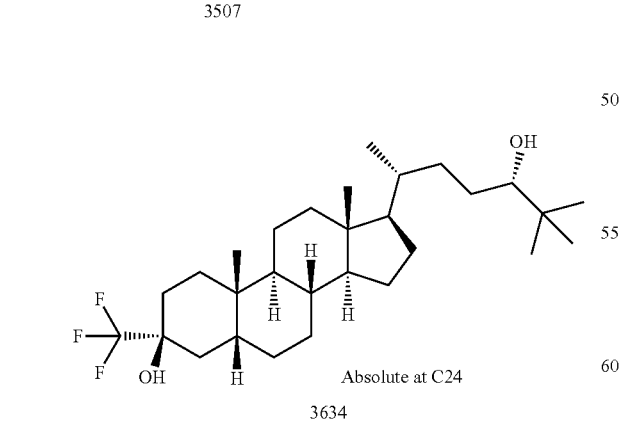

3634  Absolute at C24

The experimental procedures of intermediate 3507 can be found in Example 3.

Synthesis 3634

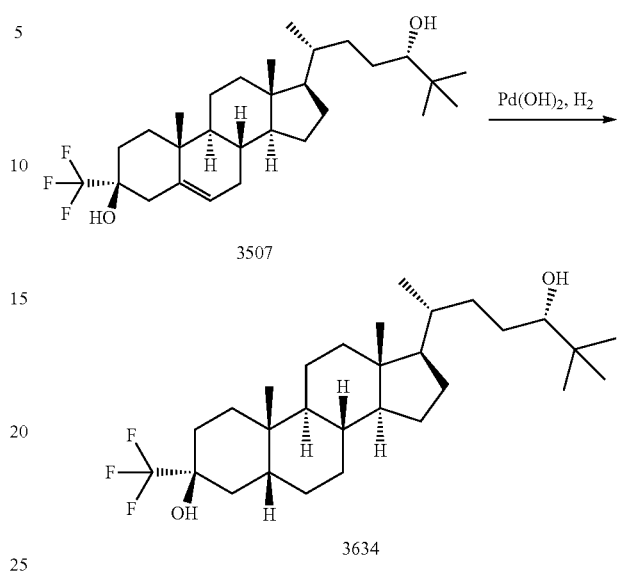

3507

3634

To a solution of 3507 (70 mg) in THF (10 mL) was added Pd(OH)$_2$/C (20%, dry, 100 mg). The mixture was stirred under H$_2$ (50 psi) at 50° C. for 18 h. The mixture was filtered and concentrated in vacuum. The residue was purified by flash-combi (0~15% of EtOAc in PE) to give 3634 (13 mg, 19%) as a solid.

$^1$H NMR (400 MHz, CDCl$_3$) δ 3.17-2.98 (m, 1H), 2.14-1.78 (m, 4H), 1.78-1.60 (m, 6H), 1.57-1.34 (m, 7H), 1.34-1.00 (m, 13H), 0.98 (s, 3H), 0.92 (m, 3H), 0.89 (s, 9H), 0.65 (s, 3H).

LCMS Rt=1.349 min in 2.0 min chromatography, 30-90_AB_E, purity 100%, no MS signal.

MS MS ESI calcd. for C$_{29}$H$_{48}$F$_3$O [M+H−H$_2$O]$^+$ 469, found 469.

Example 37: Synthesis of 3788

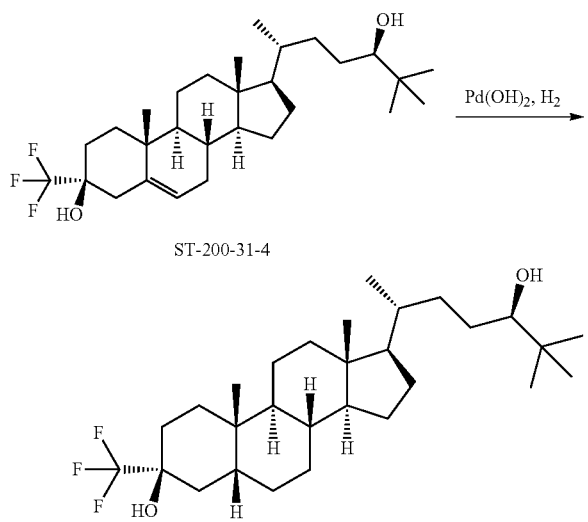

ST-200-31-4

3788

The experimental of intermediate ST-200-31-4 can be found in Example 33.

Synthesis of 3788

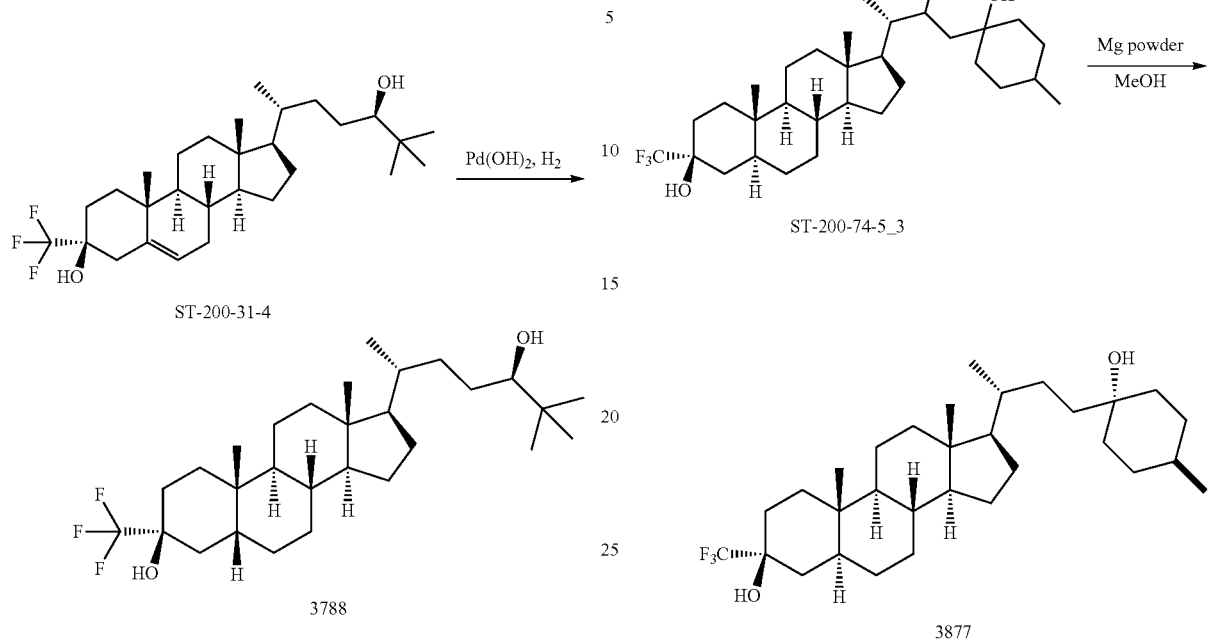

Pd(OH)₂/C (100 mg) was added to a solution of ST-200-31-4 (60 mg, 0.12 mmol) in THF/MeOH (5 mL/5 mL) and the mixture was degassed and back-filled with H₂ three times. Next, the reaction was stirred at 50° C. under 50 psi of H₂ for 16 h. The reaction mixture was filtered through a pad of celite washed with EtOAc (100 mL). The filtrate was concentrated to give impure ST-200-31-3B as a solid. To a solution of the impure ST-200-31-4 in THF/MeOH (3 mL/3 mL) was added Pd(OH)₂/C (50 mg) and the mixture was degassed and back-filled with H₂ for 3 times. After that, the reaction was stirred at 50° C. under 50 psi of H₂ for 72 h. The reaction mixture was filtered through a pad of celite washed with EtOAc (100 mL). The filtrate was concentrated to give 40 mg of crude product, which was triturated in n-hexane (2×3 mL) to give 3788 (7 mg, 17%) as a solid.

$^1$H NMR (400 MHz, CDCl₃) δ 3.19-3.08 (m, 1H), 2.13-1.81 (m, 4H), 1.77-1.58 (m, 4H), 1.54-1.35 (m, 9H), 1.34-1.01 (m, 13H), 1.01-0.96 (m, 3H), 0.94-0.86 (m, 12H), 0.66 (s, 3H).

LCMS Rt=1.313 min in 2.0 min chromatography, 30-90AB_2 MIN_E, purity 98%, MS ESI calcd. for C₂₉H₄₈F₃O [M+H−H₂O]⁺ 469, found 469.

Example 38: Synthesis of 3877 and 3886

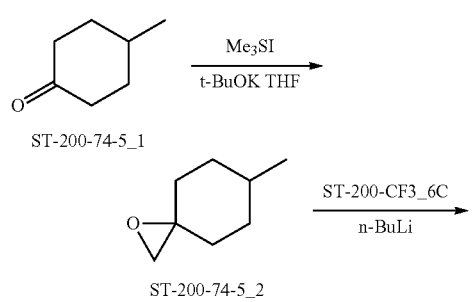

Stereochemistry for 3877 is shown below; assigned by NMR.

Synthesis of ST-200-74-5_1

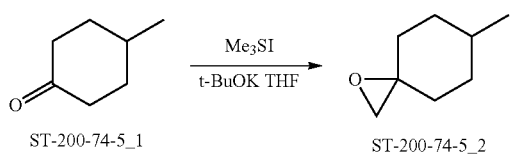

Me₃SI (4.71 g, 23.1 mmol) was added to a suspension of t-BuOK (3.98 g, 35.6 mmol) in THF (40 mL) under N₂ at 35° C. After stirring at 35° C. for 30 mins, a solution of ST-200-74-5_1 (2 g, 17.8 mmol) was added dropwise at 35° C. The mixture was stirred at 35° C. for 16 hrs, quenched with sat.NH₄Cl (50 mL) and extracted with EtOAc (3×50 mL). The combined organic phase was dried over Na₂SO₄, filtered and concentrated in vacuum to give ST-200-74-5_2 (1.8 g, crude) as liquid which was used directly for next step.

Synthesis of ST-200-74-5_3

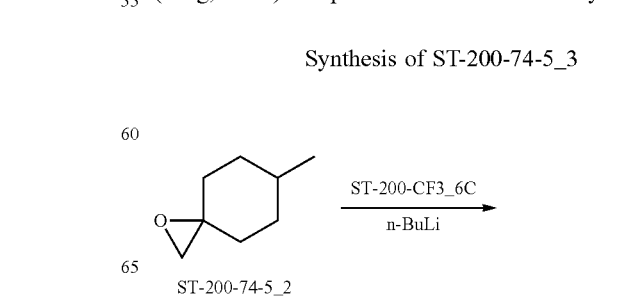

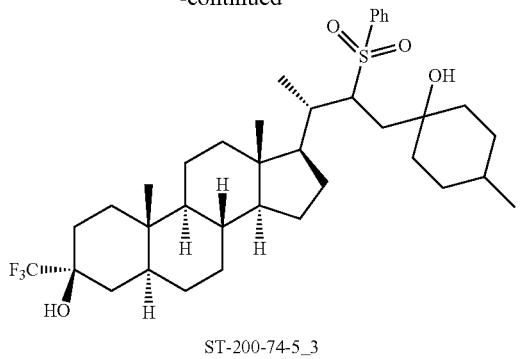

ST-200-74-5_3 n-BuLi (0.948 mL, 2.5 M in hexane, 2.37 mmol) was added to THF (5 mL). A solution of ST-200-CF3_6C (500 mg, 0.949 mmol) in THF (15 mL) was added at −70° C. After stirring at −70° C. for 1 h, 6-methyl-1-oxaspiro[2.5]octane (358 mg, 2.84 mmol) was added at −70° C. The mixture was stirred at −70° C. for another 1 hour, then warmed to 15° C. and stirred for 16 hrs. After quenching with NH$_4$Cl (50 mL), the mixture was extracted with EtOAc (2×30 mL). The organic layer was separated, dried over Na$_2$SO$_4$, filtered, concentrated, and purified by combi-flash (0-20% of EtOAc in PE) to give ST-200-74-5_3 (350 mg, crude) as a solid, which was used directly for the next step.

Synthesis of 3877

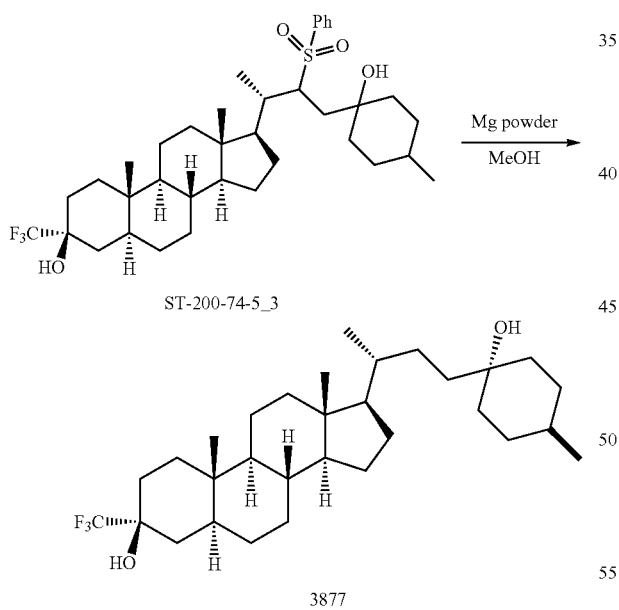

A solution of ST-200-74-5_3 (350 mg, 0.536 mmol) in MeOH (30 mL) was heated at 65° C. Mg powder (513 mg, 21.4 mmol) was added in one portion at 65° C. The mixture was refluxed at 65° C. for 1 h. The mixture was quenched with HCl (40 mL, 2N) until the reaction became clear and extracted with DCM (2×30 mL). The combined organic layer was dried over Na$_2$SO$_4$, filtered, concentrated and purified by silica gel chromatography (0-12% of EtOAc in PE) to give 3877 (12 mg, 4%) as a solid.

3877:

$^1$H NMR (400 MHz, CDCl$_3$) δ 2.11-1.90 (m, 3H), 1.89-1.74 (m, 2H), 1.73-1.58 (m, 5H), 1.53-1.43 (m, 6H), 1.42-1.19 (m, 14H), 1.18-0.96 (m, 7H), 0.96-0.80 (m, 10H), 0.74-0.60 (m, 4H).

LCMS Rt=1.728 min in 2 min chromatography, 30-90AB_2 MIN_E, purity 100%.

MS ESI Scan (2.939-3.092 min, 10 scans) Frag=50.0 V, 80-100_1_4 min·m, MS ESI calcd. For C$_3$H$_{51}$F3O$_2$Na [M+Na]$^+$ 535, found 535.

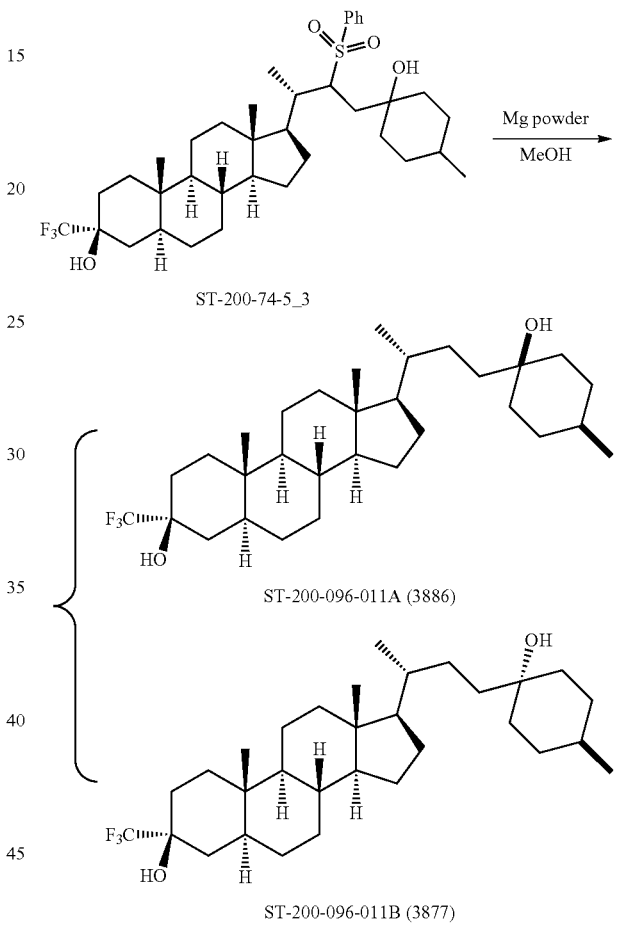

Synthesis of ST-200-096-011A/B

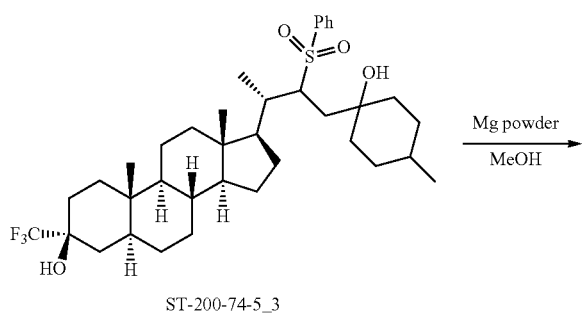

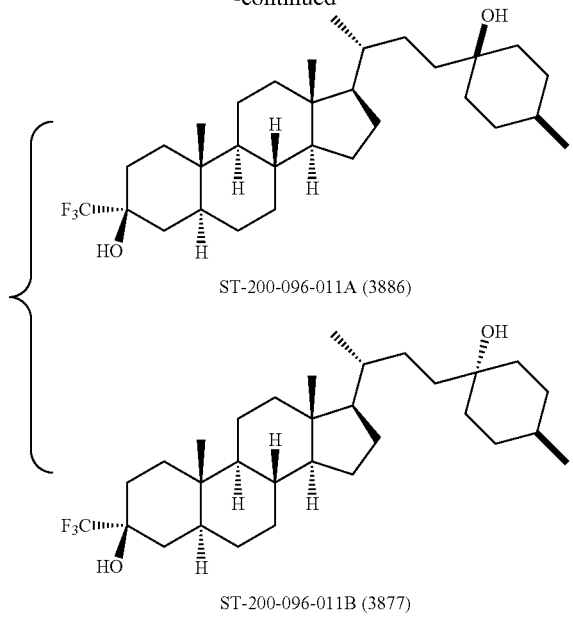

ST-200-096-011A (3886)

ST-200-096-011B (3877)

To a solution of ST-200-74-5_3 (700 mg, 1.07 mmol) in MeOH (40 mL) was added NiCl$_2$ (27.6 mg, 0.214 mmol) and Mg powder (1.02 g, 41.8 mmol) at 65° C. in one portion. The mixture was stirred at 65° C. for 10 minutes. Another Mg powder (513 mg, 22.3 mmol) was added in one portion. After stirring at 65° C. for 10 minutes, the mixture was quenched with HCl (200 mL, 1N) and extracted with EtOAc (3×50 mL). The combined organic phase was dried over Na$_2$SO$_4$, filtered, concentrated and purified by combi-flash (0-15% of EtOAc in PE) to give ST-200-096-011A (63 mg, 11%, Peak 1) and ST-200-096-011B (114 mg, 20%, Peak 2) as a solid.

3877
$^1$H NMR (400 MHz, CDCl$_3$) δ 2.09-1.93 (m, 3H), 1.90-1.76 (m, 2H), 1.73-1.57 (m, 8H), 1.51-1.34 (m, 8H), 1.33-1.18 (m, 6H), 1.17-0.98 (m, 8H), 0.97-0.87 (m, 7H), 0.84 (s, 3H), 0.73-0.63 (m, 4H).

LCMS Rt=1.391 min in 2 min chromatography, 30-90AB_2 MIN_E, purity 100%.

MS ESI Scan (1.955-2.16 min, 8 scans) Frag=50.0 V, 80-100_1_4 min·m, MS ESI calcd. For C$_{31}$H$_{51}$F3O$_2$Na [M+Na]$^+$ 535, found 535.

$^1$H NMR (400 MHz, CDCl$_3$) δ 2.09-2.00 (m, 2H), 1.99-1.89 (m, 1H), 1.87-1.76 (m, 2H), 1.71-1.61 (m, 3H), 1.55-0.42 (m, 10H), 1.41-1.19 (m, 13H), 1.14-0.96 (m, 6H), 0.95-0.86 (m, 7H), 0.84 (s, 3H), 0.72-0.62 (m, 4H).

LCMS Rt=1.450 min in 2 min chromatography, 30-90AB_2 MIN_E, purity 100%.

MS ESI Scan (1.938-2.617 min, 9 scans) Frag=50.0 V, 80-100_1_4 min·m, MS ESI calcd. For C$_{31}$H$_{51}$F3O$_2$Na [M+Na]$^+$ 535, found 535.

Example 39: Synthesis of 3983

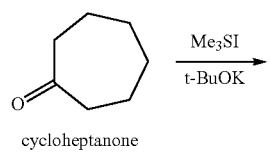

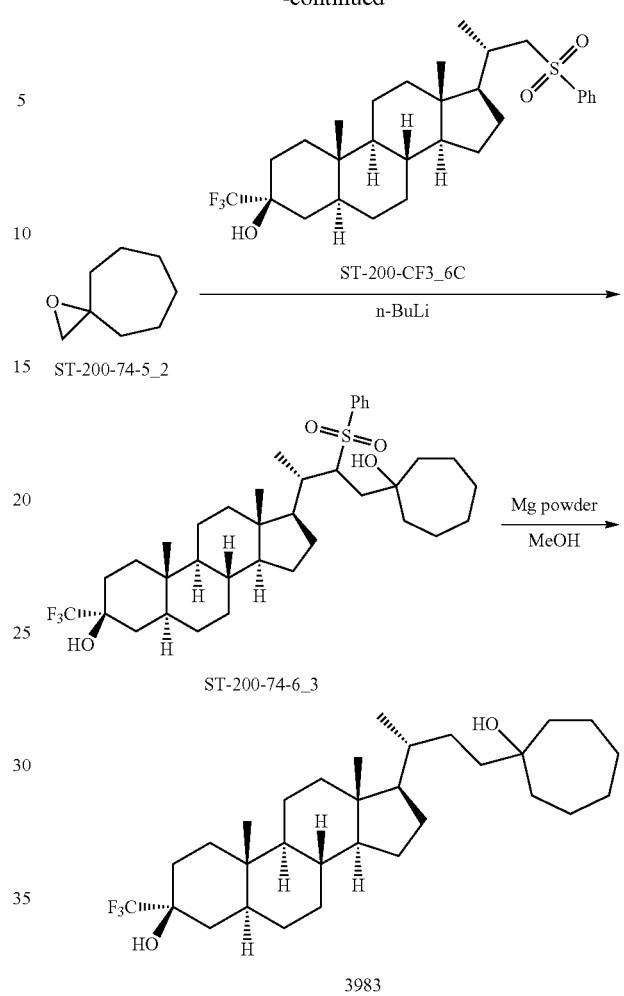

ST-200-74-6_3

3983

See Example 5 for synthesis of ST-200-CF3_6C.

Synthesis of ST-310-15-22

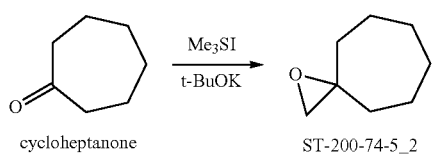

cycloheptanone              ST-200-74-5_2

A solution of Me$_3$SI (13.6 g, 66.7 mmol) and t-BuOK (17.8 mL, 5M in THF, 89.0 mmol) in DMSO (100 mL) was stirred and heated at 25° C. for 30 min under N$_2$. Cycloheptanone (5 g, 44.5 mmol) was added to the reaction mixture and stirred at 25° C. for 3 hrs. The reaction was treated with water (300 mL), extracted with EtOAc (2×100 mL). The combined organic phase was washed with water (2×300 mL), brine (2×300 mL), dried over anhydrous Na$_2$SO$_4$, filtered and concentrated in vacuum to afford ST-200-74-5_2 (4 g, 71%) as a liquid.

$^1$H NMR (400 MHz, CDCl$_3$) δ 2.59 (s, 2H), 1.72-1.50 (m, 12H).

Synthesis of ST-310-15-2_3

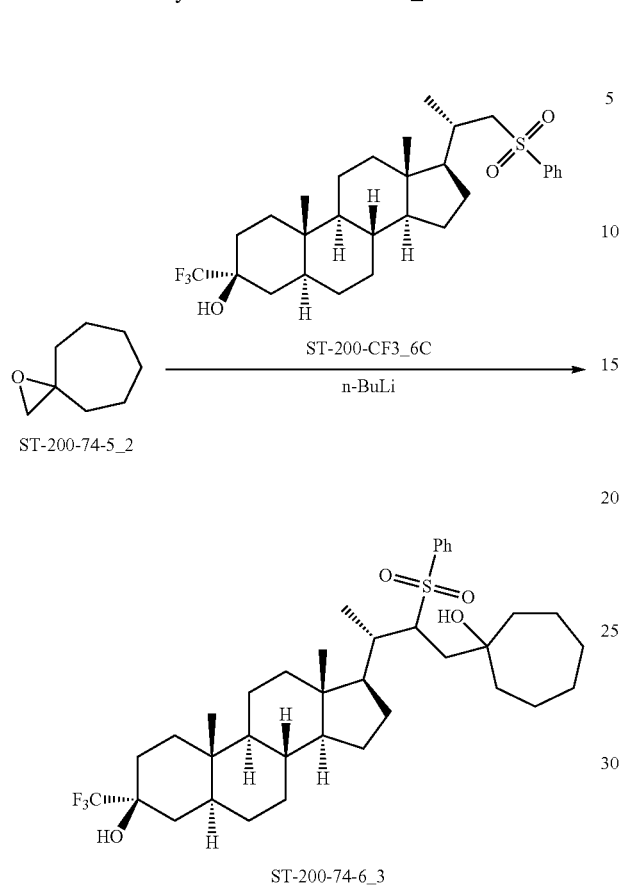

Added n-BuLi (0.568 mL, 1.42 mmol, 2.5 M in hexane) was added to a solution of ST-200-CF3_6C (300 mg, 0.569 mmol) in THF (3 mL) at −70° C. under N$_2$. After cooling to −70° C., 1-oxaspiro [2.6] nonane (107 mg, 0.853 mmol) was added. The reaction was allowed to warm to 25° C. and was stirred for 12 hours at 25° C. The reaction was quenched with NH$_4$Cl (10 mL, sat. aq.), water (50 mL) and extracted with EtOAc (3×10 mL). The combined organic phase was concentrated to give a residue, which was purified by silica gel chromatography (PE/EtOAc=10/1~5/1) to give compound ST-200-74-6_3 (200 mg, impure) as an oil. The crude mixture was used directly for the next step.

Synthesis of 3983

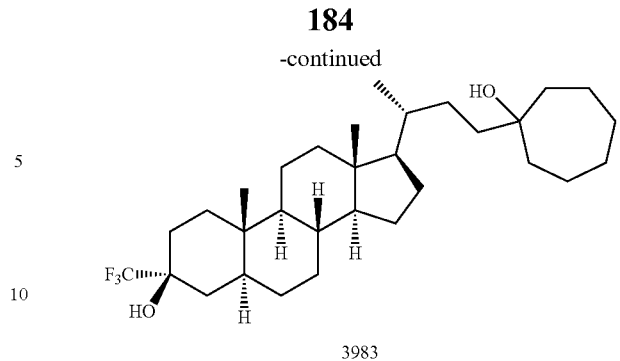

A solution of ST-200-74-6_3 (200 mg, 306 umol) in MeOH (50 mL) was heated to 60° C. Mg powder (371 mg, 15.3 mmol) was added in four portions at 60° C. After stirring at 60° C. for 1 h, the mixture was quenched with HCl (50 mL, 2 M) until the reaction became clear and extracted with EtOAc (2×50 mL). The combined organic phase was dried over Na$_2$SO$_4$, filtered and concentrated and purified by flash column (0-40% of EtOAc in PE) to give 3983 (15 mg, 12%) as a solid.

$^1$H NMR (400 MHz, CDCl$_3$) δ 2.12-2.00 (s, 1H), 1.99-1.92 (m, 2H), 1.89-1.77 (m, 2H), 1.74-1.57 (m, 10H), 1.57-1.52 (m, 6H), 1.41-1.17 (m, 13H), 1.16-0.95 (m, 7H), 0.94-0.82 (m, 6H), 0.72-0.63 (m, 4H).

LCMS Rt=0.690 min in 2 min chromatography, 30-90 AB, purity 100%.

HRMS MS ESI calcd. for C$_{31}$H$_{50}$F$_3$O [M+H−H$_2$O]$^+$ 495, found 495.

Example 40: Synthesis of 4023

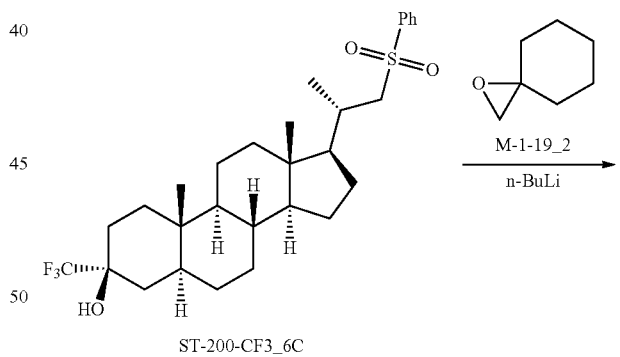

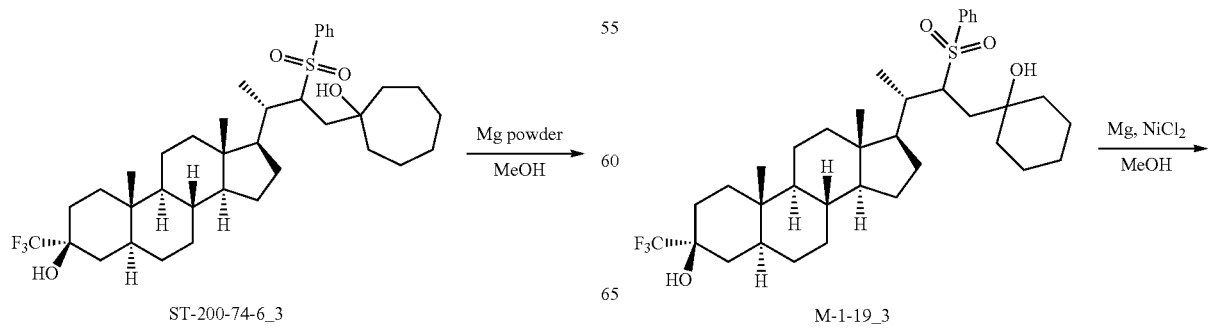

185
-continued

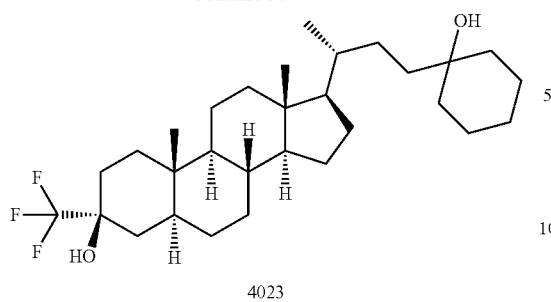

4023

The synthesis of ST-200-CF3_6C can be found in Example 5.

Synthesis of M-1-19_3

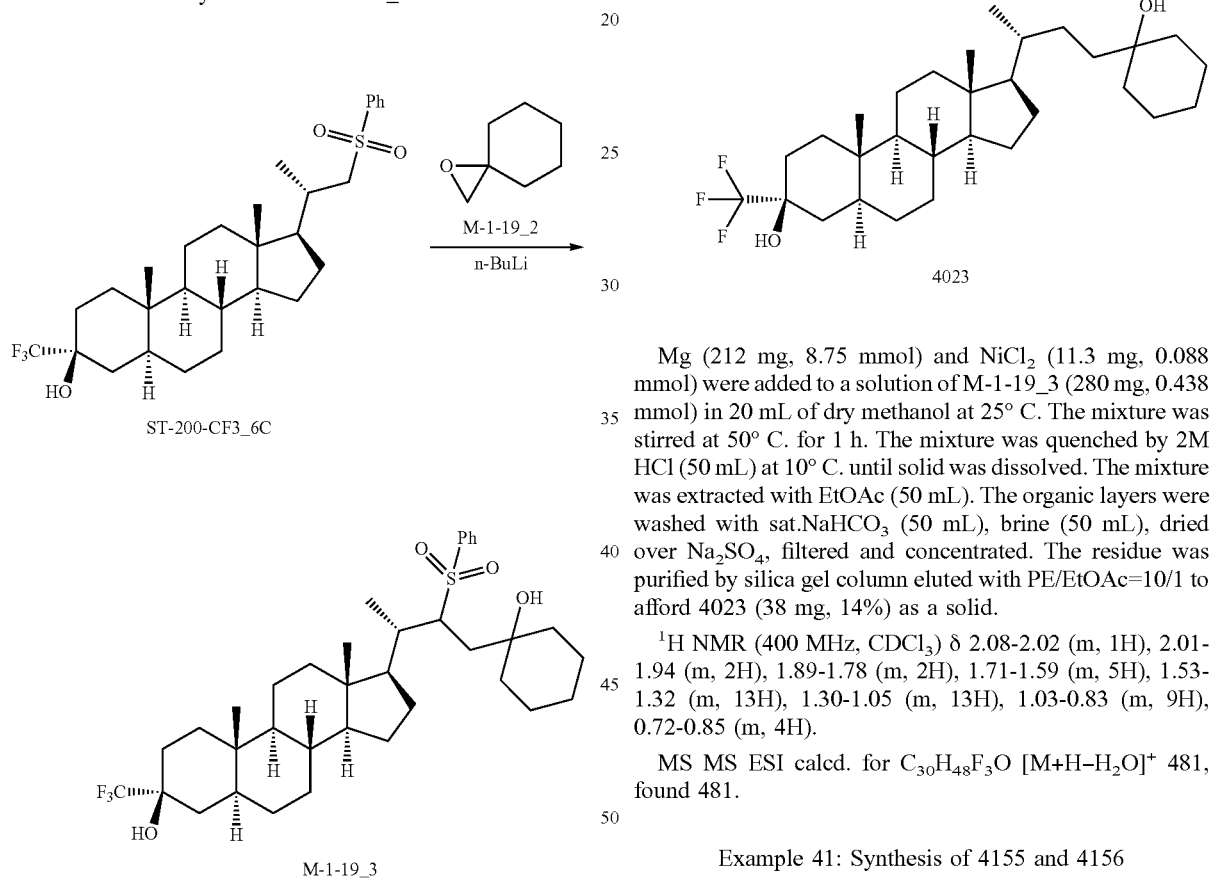

n-BuLi (2.5 M, 1.42 mmol, 0.568 mL) was added to THF (2 mL) under N₂ at −70° C. Next, a suspension of ST-200-CF3_6C (300 mg, 0.569 mmol) in THF (2 mL) was added drop-wise to give a suspension. After stirring at −70° C. for 30 min, a solution of 1-oxaspiro[2.5]octane (126 mg, 1.13 mmol) was added. The reaction was stirred at stirred at 25° C. for 16 hours. The mixture was poured into ice-water (20 mL) and extracted with EtOAc (2×30 mL). The combined organic layers were washed with brine (30 mL), dried over Na₂SO₄, filtered and concentrated in vacuum to afford M-1-19_3 (280 mg, crude) as a solid, which was used directly for the next step.

186
Synthesis of 4023

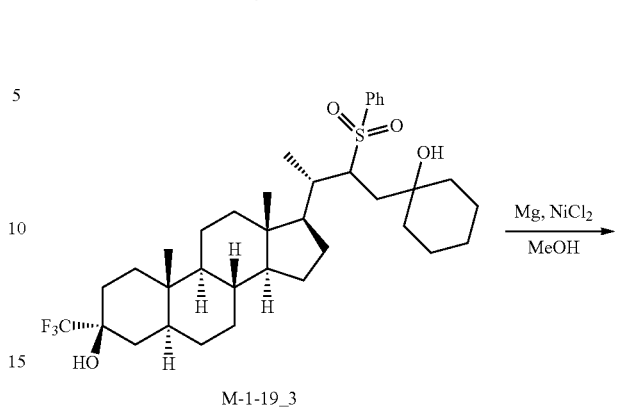

Mg (212 mg, 8.75 mmol) and NiCl₂ (11.3 mg, 0.088 mmol) were added to a solution of M-1-19_3 (280 mg, 0.438 mmol) in 20 mL of dry methanol at 25° C. The mixture was stirred at 50° C. for 1 h. The mixture was quenched by 2M HCl (50 mL) at 10° C. until solid was dissolved. The mixture was extracted with EtOAc (50 mL). The organic layers were washed with sat.NaHCO₃ (50 mL), brine (50 mL), dried over Na₂SO₄, filtered and concentrated. The residue was purified by silica gel column eluted with PE/EtOAc=10/1 to afford 4023 (38 mg, 14%) as a solid.

$^1$H NMR (400 MHz, CDCl$_3$) δ 2.08-2.02 (m, 1H), 2.01-1.94 (m, 2H), 1.89-1.78 (m, 2H), 1.71-1.59 (m, 5H), 1.53-1.32 (m, 13H), 1.30-1.05 (m, 13H), 1.03-0.83 (m, 9H), 0.72-0.85 (m, 4H).

MS MS ESI calcd. for $C_{30}H_{48}F_3O$ [M+H−H$_2$O]$^+$ 481, found 481.

Example 41: Synthesis of 4155 and 4156

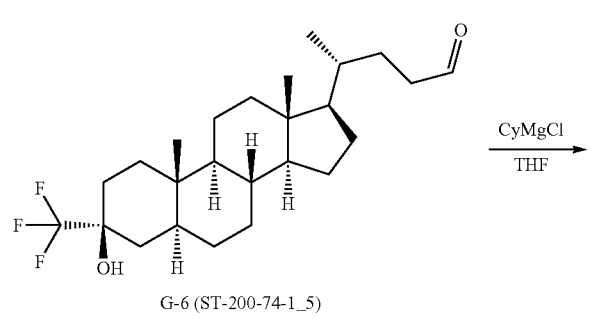

G-6 (ST-200-74-1_5)

187

-continued

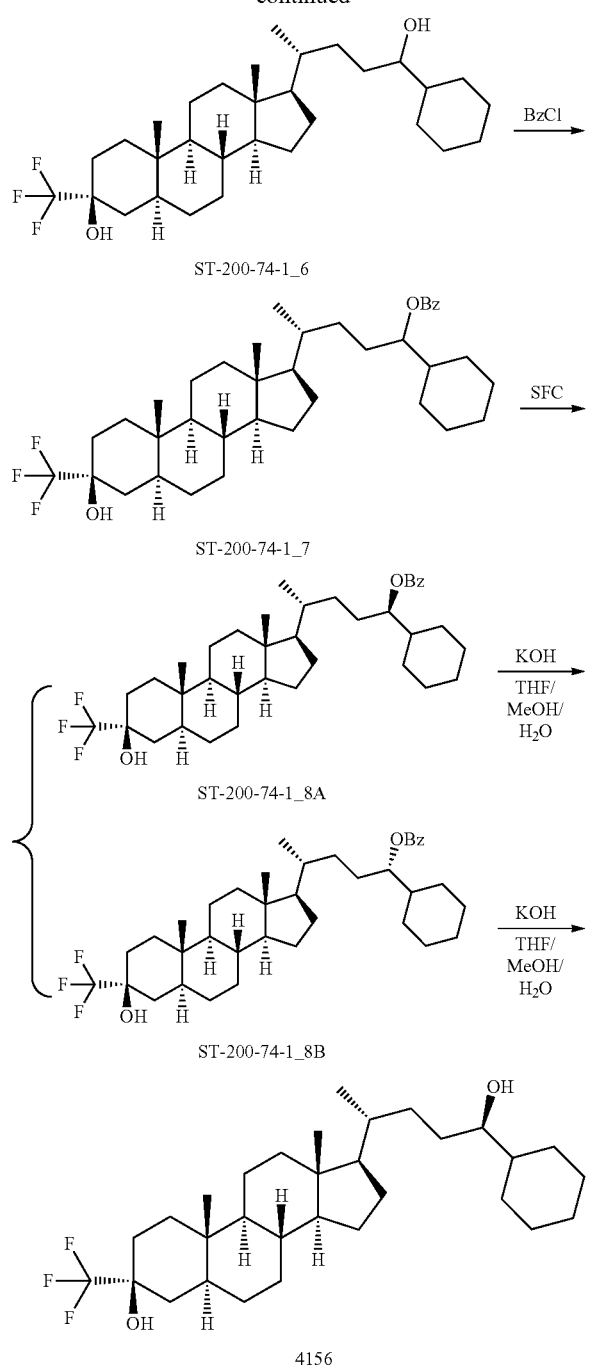

See Example 11 for synthesis of ST-200-74-1_5.

188

Synthesis of ST-200-74-1_6

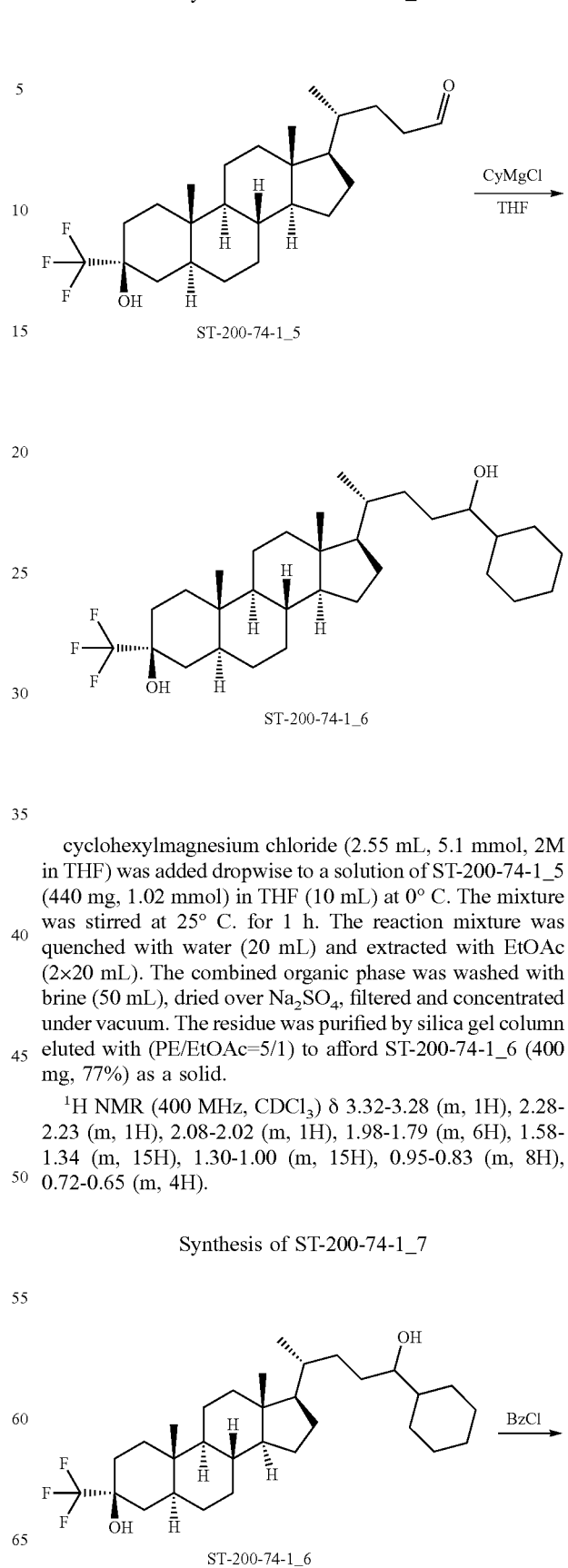

cyclohexylmagnesium chloride (2.55 mL, 5.1 mmol, 2M in THF) was added dropwise to a solution of ST-200-74-1_5 (440 mg, 1.02 mmol) in THF (10 mL) at 0° C. The mixture was stirred at 25° C. for 1 h. The reaction mixture was quenched with water (20 mL) and extracted with EtOAc (2×20 mL). The combined organic phase was washed with brine (50 mL), dried over $Na_2SO_4$, filtered and concentrated under vacuum. The residue was purified by silica gel column eluted with (PE/EtOAc=5/1) to afford ST-200-74-1_6 (400 mg, 77%) as a solid.

$^1$H NMR (400 MHz, $CDCl_3$) δ 3.32-3.28 (m, 1H), 2.28-2.23 (m, 1H), 2.08-2.02 (m, 1H), 1.98-1.79 (m, 6H), 1.58-1.34 (m, 15H), 1.30-1.00 (m, 15H), 0.95-0.83 (m, 8H), 0.72-0.65 (m, 4H).

Synthesis of ST-200-74-1_7

-continued

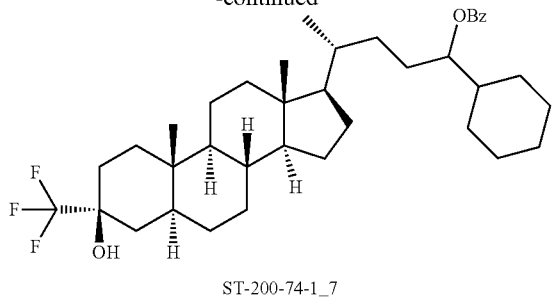

ST-200-74-1_7

Benzoyl chloride (164 mg, 1.17 mmol) was added to a solution of ST-200-74-1_6 (400 mg, 0.78 mmol) in Pyridine (4 mL) at 25° C. The mixture was stirred at 25° C. for 12 hrs. The mixture was poured into water (50 mL) and extracted with ethyl acetate (2×50 mL). The combined organic layers was washed with brine (20 mL), dried over $Na_2SO_4$, filtered and concentrated in vacuum. The residue was purified by silica gel column eluted with (PE/EtOAc=10/1) to afford ST-200-74-1_7 (315 mg, 65%) as an oil.

$^1$H NMR (400 MHz, CDCl3) δ 8.06-8.04 (m, 2H), 7.62-7.50 (m, 1H), 7.46-7.43 (m, 2H), 4.98-4.90 (m, 1H), 2.07-2.04 (m, 1H), 1.95-1.92 (m, 1H), 1.82-1.55 (m, 10H), 1.54-1.30 (m, 10H), 1.28-1.05 (m, 13H), 0.99-0.93 (m, 10H), 0.67-0.61 (m, 4H).

Synthesis of ST-200-74-1_8A, 8B

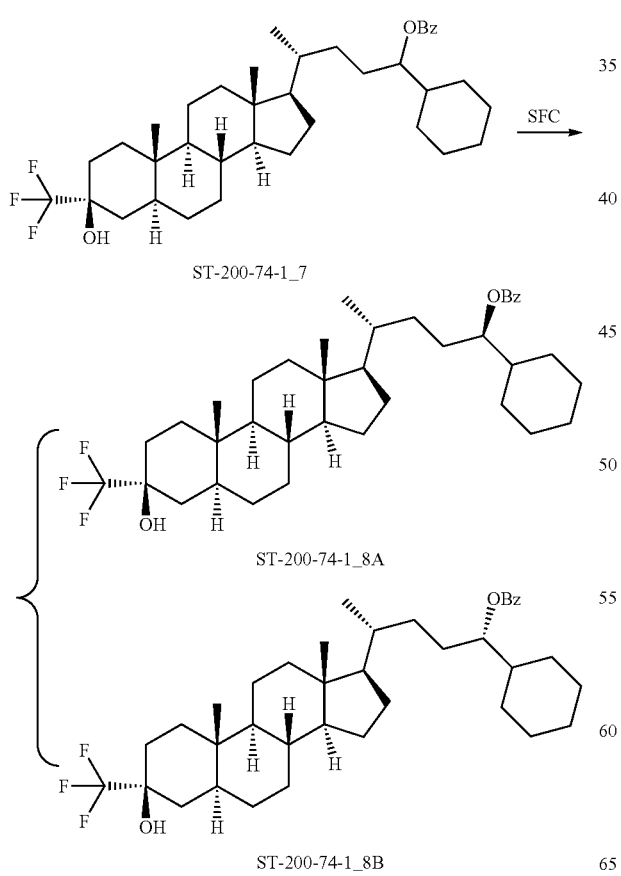

ST-200-74-1_7

SFC →

ST-200-74-1_8A

ST-200-74-1_8B

ST-200-74-1_7 (315 mg) was purified by SFC (Column: AD (250 mm*30 mm, 5 um), Condition: 0.1% $NH_3.H_2O$, IPA, Gradient: from 40% to 40%, FlowRate (ml/min): 60 mL/min, 25° C.) to afford ST-200-74-1_8A (115 mg, 37%) and ST-200-74-1_8B (108 mg, 35%) as a solid.

ST-200-74-1_8A $^1$H NMR (400 MHz, CDCl$_3$) δ 8.06-8.03 (m, 2H), 7.58-7.53 (m, 1H), 7.46-7.43 (m, 2H), 4.98-4.90 (m, 1H), 2.07-2.02 (m, 1H), 1.96-1.91 (m, 2H), 1.84-1.62 (m, 12H), 1.53-1.24 (m, 11H), 1.22-0.96 (m, 12H), 0.94-0.83 (m, 7H), 0.70-0.64 (m, 1H), 0.61 (s, 3H).

ST-200-74-1_8B $^1$H NMR (400 MHz, CDCl$_3$) δ 8.06-8.03 (m, 2H), 7.58-7.53 (m, 1H), 7.46-7.43 (m, 2H), 4.98-4.90 (m, 1H), 2.07-1.91 (m, 3H), 1.84-1.69 (m, 7H), 1.67-1.48 (m, 9H), 1.43-1.32 (m, 4H), 1.30-1.02 (m, 13H), 1.01-0.84 (m, 9H), 0.7-0.62 (m, 4H).

Synthesis of 4156

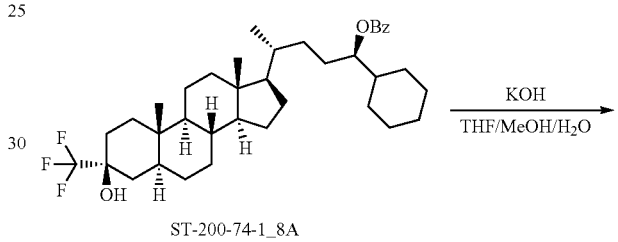

ST-200-74-1_8A $\xrightarrow{\text{KOH}}{\text{THF/MeOH/H}_2\text{O}}$

4156

KOH (52.1 mg, 0.93 mmol) was added to a solution of ST-200-74-1_8A (115 mg, 0.186 mmol) in THF (2 mL), MeOH (1 mL) and water (1 mL). The mixture was stirred at 60° C. for 16 hrs. The mixture was poured into water (20 mL) and extracted with EtOAc (2×40 mL). The combined organic layer was washed with brine (30 mL), dried over $Na_2SO_4$, filtered and concentrated. The residue was purified by flash column (PE/EtOAc=5/1 to 3/1) to give 4156 (56 mg, 59%) as a solid.

$^1$H NMR (400 MHz, CDCl$_3$) δ 3.31-3.27 (m, 1H), 2.08-2.02 (m, 1H), 1.98-1.93 (m, 2H), 1.84-1.72 (m, 5H), 1.70-1.60 (m, 7H), 1.51-1.46 (m, 2H), 1.42-1.36 (m, 3H), 1.34-1.11 (m, 13H), 1.06-0.85 (m, 13H), 0.72-0.65 (m, 4H).

MSMS ESI calcd. for $C_{31}H_{50}F_3O$ [M+H–H$_2$O]$^+$ 495, found 495.

Synthesis of 4155

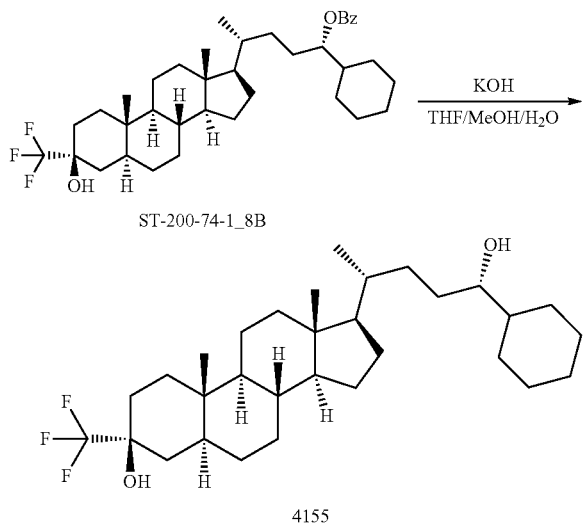

ST-200-74-1_8B

4155

KOH (49 mg, 0.875 mmol) was added to a solution of ST-200-74-1_8B (108 mg, 0.175 mmol) in THF (2 mL), MeOH (1 mL) and water (1 mL). The mixture was stirred at 60° C. for 16 hrs. The mixture was poured into water (20 mL) and extracted with EtOAc (2×40 mL). The combined organic layer was washed with brine (30 mL), dried over $Na_2SO_4$, filtered and concentrated. The residue was purified by flash column (PE/EtOAc=5/1 to 3/1) to give 4155 (56 mg, 62%) as a solid.

$^1$H NMR (400 MHz, $CDCl_3$) δ 3.31-3.27 (m, 1H), 2.08-2.02 (m, 1H), 1.98-1.93 (m, 2H), 1.84-1.72 (m, 5H), 1.70-1.60 (m, 6H), 1.51-1.34 (m, 9H), 1.31-0.97 (m, 17H), 0.95-0.85 (m, 6H), 0.72-0.65 (m, 4H).

MS MS ESI calcd. for $C_{31}H_{51}F_3O_2Na$ [M+Na]$^+$ 535, found 535.

Synthesis Confirming Stereochemistry of 4155

$^1$H NMR (400 MHz, $CDCl_3$) δ 2.75-2.65 (m, 2H), 2.55-2.50 (m, 1H), 1.90-1.80 (m, 1H), 1.78-1.58 (m, 4H), 1.30-1.00 (m, 6H)

To a suspension of $C_3H_9IS$ (117 g, 578 mmol) in THF (300 mL) was added a solution of t-BuOK (99.6 g, 890 mmol) in THF (400 mL) slowly under $N_2$ at 30° C. The suspension was stirred at 30° C. for 30 min. Then ST-200-096-008_1 (50 g, 445 mmol) in 100 ml of THF was added dropwise to the mixture at 0° C. After stirring at 30° C. for 16 hrs, the mixture was poured into sat.$NH_4Cl$ (600 mL) and extracted with EtOAc (2×200 mL). The combined organic phase was washed with brine (400 mL), dried over $Na_2SO_4$, filtered, and concentrated at 40° C. under reduced pressure to give ST-200-096-008_2 (55 g, crude) as a liquid.

$^1$H NMR (400 MHz, $CDCl_3$) δ 2.75-2.65 (m, 2H), 2.55-2.50 (m, 1H), 1.90-1.80 (m, 1H), 1.78-1.58 (m, 4H), 1.30-1.00 (m, 6H)

To a solution of R,R-cat (190 mg, 0.316 mmol) in toluene (3 mL) was added AcOH (189 mg, 3.16 mmol). The mixture was stirred at 25° C. under air for 30 min and concentrated in vacuum to leave a crude brown solid. The resulting catalyst residue was dissolved in 2-cyclohexyloxirane (10 g, 79.2 mmol) at 25° C. The reaction flask was cooled to 0° C., and $H_2O$ (783 g, 43.5 mmol) was added dropwise over 5 min. After stirring at 25° C. for 24 hrs, ((2R)-2-cyclohexyloxirane (2 g, 15.8 mmol, 20.0%) was isolated by distillation from the reaction mixture. To a solution of ST-200-096-008_3 (50 mg, 0.396 mmol) and TEA (39.9 mg, 0.396 mmol) in MeOH (3 mL) was added naphthalene-2-thiol (63.4 mg, 0.396 mmol) at 25° C. After stirring at 25° C. for 2 hrs, the ee % of (2R)-2-cyclohexyloxirane was determined to be 82.7% by chiral HPLC.

SFC Peak 1: Rt=2.033 min in 10 min chromatography, Chiralpak AD-3100×4.6 mm I.D., 3 μm, 82.7% ee.

To THF (1 mL) was added BuLi (1.12 mL, 2.5 M in hexane, 2.82 mmol). A solution of ST-200-CF3_6C (600 mg, 1.13 mmol) in THF (6 mL) was added at −70° C. The mixture was stirred at −70° C. for 1 h. (2R)-2-cyclohexyloxirane (213 mg, 1.69 mmol) was added at −70° C. After stirring at 30° C. and stirred for 16 hrs, the reaction mixture was quenched with sat.$NH_4Cl$ (50 mL) and extracted with EtOAc (2×30 mL). The combined organic layer were washed with $NH_4Cl$ (50 mL), dried over $Na_2SO_4$, filtered, concentrated to give crude product (700 mg) as a foam solid, which was used for next step directly.

To a solution of ST-200-096-008_4 (700 mg, 1.07 mmol) in MeOH (60 mL) was added $NiCl_2$ (27.6 mg, 0.214 mmol) and Mg powder (1.02 g, 42.8 mmol) at 65° C. in one portion. The mixture was stirred at 65° C. for 10 minutes. Another Mg powder (513 g, 21.4 mmol) was added in one portion. After stirring at 65° C. for 10 minutes, the mixture was quenched with HCl (120 mL, 1N) and extracted with EtOAc (3×50 mL). The combined organic phase was dried over $Na_2SO_4$, filtered, concentrated and purified by combi-flash (0-15% of EtOAc in PE) to give ST-200-096-008 (300 mg, 55%) as a solid.

$^1$H NMR (400 MHz, $CDCl_3$) δ 3.35-3.25 (m, 1H), 2.10-2.01 (m, 1H), 2.00-1.91 (m, 1H), 1.78-1.72 (m, 5H), 1.71-1.58 (m, 9H), 1.56-1.10 (m, 19H), 1.09-0.98 (m, 4H), 0.97-0.86 (m, 4H), 0.84 (s, 3H), 0.72-0.60 (m, 4H)

To a solution of ST-200-096-008 (300 mg, 0.585 mmol) in pyridine (5 mL) was added benzoyl chloride (164 mg, 1.17 mmol) at 25° C. After stirring at 25° C. for 12 hours, the mixture was poured into water (50 mL) and extracted with ethyl acetate (2×30 mL). The combined organic layers was washed with brine (50 mL), dried over $Na_2SO_4$, filtered and concentrated in vacuum. The residue was purified by silica gel column eluted with (PE/EtOAc=10/1) to afford ST-200-096-008_5 (300 mg) as a solid, which was separated by SFC (column: AD(250 mm*30 mm, 5 um), gradient: 35-35% B (A=0.05% $NH_3/H_2O$, B=MeOH), flow rate: n/a mL/min) to give 100% de product (190 mg, 52% yield for 2 steps) as a solid.

$^1$H NMR (400 MHz, $CDCl_3$) δ 8.08-8.01 (m, 2H), 7.58-7.52 (m, 1H), 7.58-7.40 (m, 2H), 4.98-4.90 (m, 1H), 2.19-2.10 (m, 2H), 1.97-1.89 (m, 1H), 1.83-1.58 (m, 12H), 1.56-1.35 (m, 8H), 1.34-0.95 (m, 15H), 0.94-0.89 (m, 3H), 0.88-0.79 (m, 4H), 0.70-0.59 (m, 4H).

SFC Peak 1: Rt=5.105 min and Peak 2 Rt=5.644 min in 10 min chromatography, AD_3_EtOH_DEA_5_40_25ML ("Column: Chiralpak AD-3150×4.6 mm I.D., 3 um Mobile phase: A: CO2 B: iso-propanol (0.05% DEA) Gradient: from 5% to 40% of B in 5 min and hold 40% for 2.5 min, then 5% of B for 2.5 min Flow rate: 2.5 mL/min Column temp.: 35° C.").

SFC Peak 1: Rt=5.313 min in 10 min chromatography, AD_3_EtOH_DEA_5_40_25ML, 100.0% de.

To a solution of ST-200-096-008_5 (190 mg, 0.308 mmol) in THF (2 mL) and MeOH (4 mL) and water (1 mL) was added NaOH (246 mg, 6.16 mmol). After stirring at 50° C. for 16 hrs, the mixture was poured into water (20 mL) and extracted with EtOAc (2×20 mL). The combined organic layer was washed with brine (30 mL), dried over Na$_2$SO$_4$, filtered and concentrated. The residue was purified by flash column (PE/EtOAc=5/1 to 3/1) to give ST-200-096-008 (126 mg, 80%) as a solid.

$^1$H NMR (400 MHz, CDCl$_3$) δ 3.35-3.25 (m, 1H), 2.10-2.01 (m, 2H), 2.00-1.91 (m, 1H), 1.78-1.72 (m, 5H), 1.71-1.58 (m, 5H), 1.56-1.50 (m, 5H), 1.49-1.18 (m, 13H), 1.17-0.95 (m, 8H), 0.94-0.86 (m, 4H), 0.84 (s, 3H), 0.70-0.61 (m, 4H).

LCMS Rt=1.389 min in 2 min chromatography, 30-90AB_2 MIN_E, purity 100%.

MS ESI Scan (1.981-2.144 min, 11 scans) Frag=50.0 V, 80-100_1_4 min·m, MS ESI calcd. For C$_{31}$H$_{51}$F$_3$O$_2$Na [M+Na]$^+$ 535, found 535.

Example 42: Synthesis of 4258 and 4259

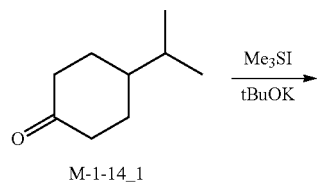

M-1-14_1

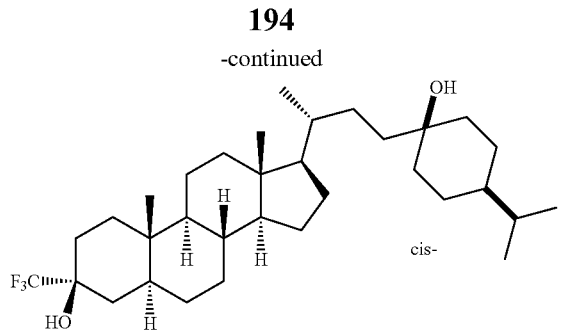

4259

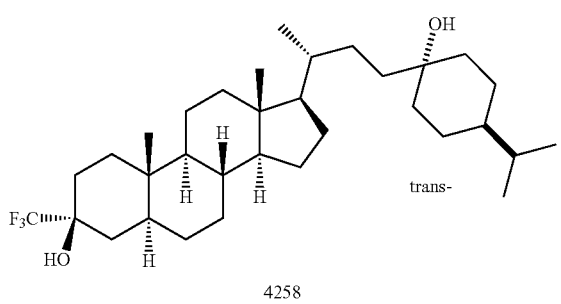

4258

The stereochemistry for 4259 was confirmed by Xray data. The synthesis of ST-200-CF3_6C can be found in Example 5.

Synthesis of M-1-14_2

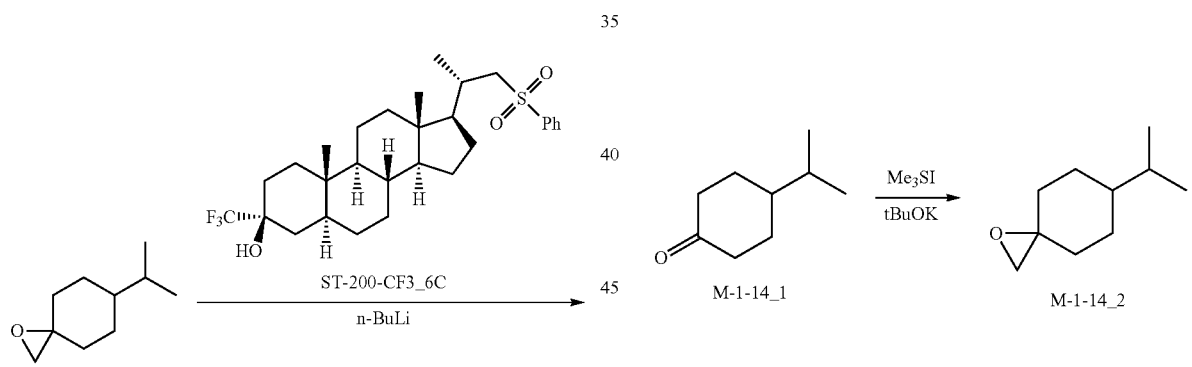

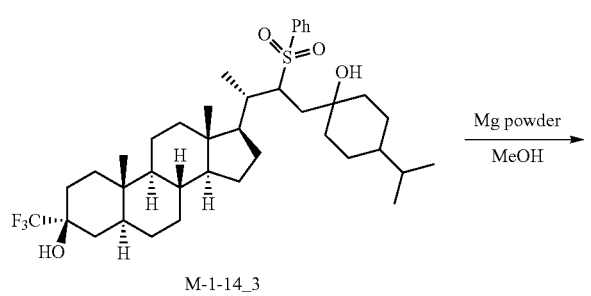

M-1-14_3

To a suspension of Me3SI (1.88 g, 9.26 mmol) in THF (10 mL) was slowly added a solution of t-BuOK (1.59 g, 14.2 mmol) in THF (5 mL) under N$_2$ at 15° C. The suspension was stirred at 15° C. for 30 min. Then a solution of M-1-14_1 (1 g, 7.13 mmol) in 5 ml of THF was added dropwise to the mixture at 0° C. After addition, the mixture was stirred at 15° C. for 16 hrs. The reaction was quenched with sat.NH$_4$Cl (60 mL) and extracted with MTBE (3×30 mL). The combined organic phase was washed with brine (100 mL), dried over Na$_2$SO$_4$, filtered, and concentrated at 40° C. under reduced pressure to give M-1-14_2 (1 g, crude) as a liquid.

$^1$H NMR (400 MHz, CDCl$_3$) δ 2.65-2.55 (m, 2H), 1.90-1.80 (m, 3H), 1.74-1.66 (m, 1H), 1.60-1.46 (m, 1H), 1.42-1.22 (m, 2H), 1.21-1.10 (m, 3H), 0.92-0.80 (m, 6H).

Synthesis of M-1-14_3

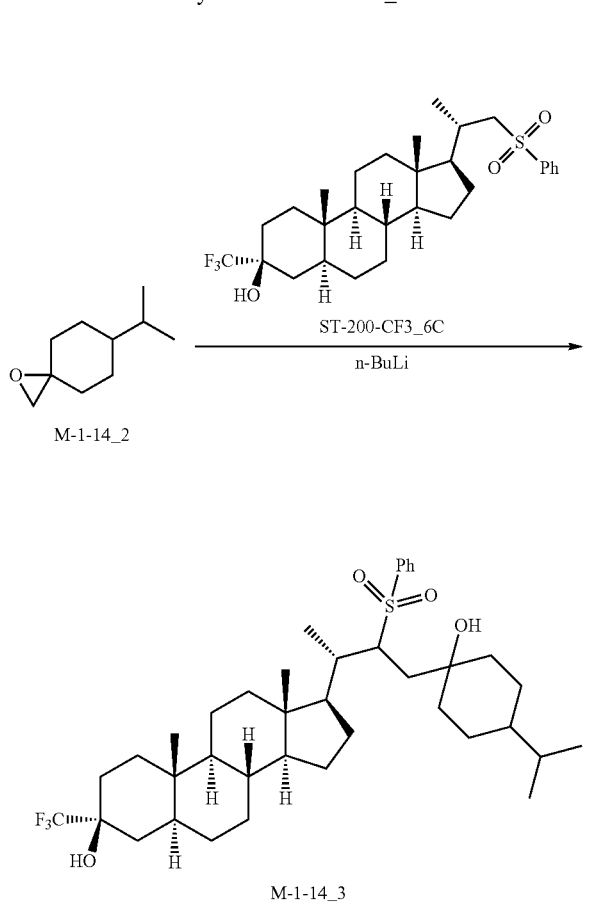

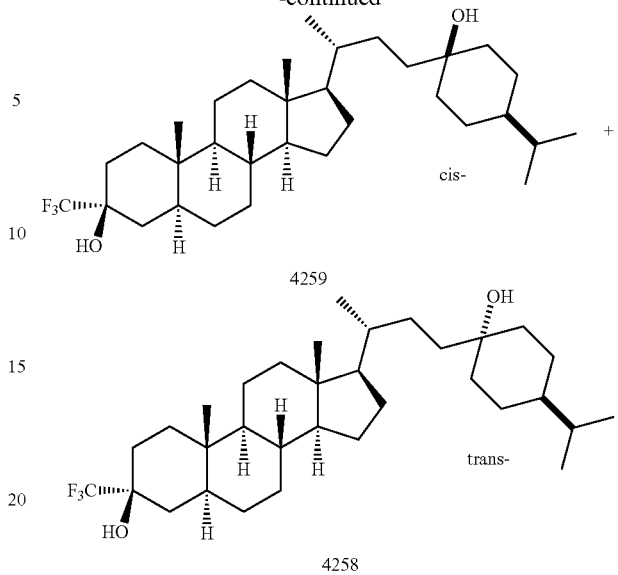

To THF (0.5 mL) was added n-BuLi (0.568 mL, 2.5 M in hexane, 1.42 mmol) at −70° C. A solution of ST-200-CF3_6C (300 mg, 0.569 mmol) in THF (2.5 mL) was added dropwise at −70° C. After stirring at −70° C. for 1 h, 6-isopropyl-1-oxaspiro[2.5]octane (131 mg, 0.853 mmol) was added. The mixture was stirred at −70° C. for another 1 h. Then the reaction mixture was warmed to 15° C. and stirred for 16 hrs. The mixture was quenched with NH$_4$Cl (50 mL, sat. aq.) and extracted with EtOAc (2×30 mL). The combined organic phase was dried over Na$_2$SO$_4$, filtered, and concentrated to give M-1-14_3 (350 mg, crude) as a solid, which was used for next step directly.

Synthesis of 4259 and 4258

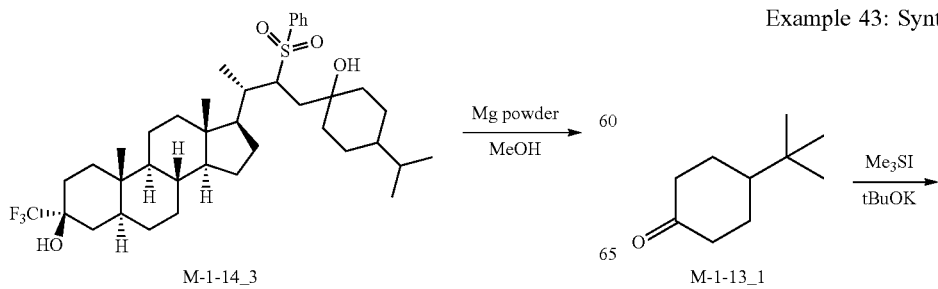

To a solution of M-1-14_3 (350 mg, 0.513 mmol) in MeOH (30 mL) was added NiCl$_2$ (13.2 mg, 0.102 mmol) and Mg powder (492 mg, 20.5 mmol) at 65° C. in one portion. After stirring at 65° C. for 10 minutes, another Mg powder (244 mg, 10.2 mmol) was added in one portion. The mixture was stirred at 65° C. for another 10 minutes. The mixture was quenched with HCl (50 mL, 2N) until the reaction became clear and extracted with EtOAc (3×20 mL). The combined organic layer was washed with sat. NH$_4$Cl (50 mL), dried over Na$_2$SO$_4$, filtered, concentrated and purified by silica gel chromatography (0-15% of EtOAc in PE) to give 4258 (24 mg, 8.6%, 4258) and 4259 (50 mg, 18%, 4259) as a solid.

4258

$^1$H NMR (400 MHz, CDCl$_3$) δ 2.10-2.01 (m, 1H), 2.00-1.92 (m, 2H), 1.89-1.56 (m, 12H), 1.51-1.33 (m, 8H), 1.32-1.18 (m, 6H), 1.17-0.98 (m, 9H), 0.98-0.89 (m, 4H), 0.88-0.83 (m, 9H), 0.74-0.63 (m, 4H).

HPLC Rt=7.214 min in 10.0 min chromatography, 50-100AB_E, purity 98.8%.

MS 80-100_1_4 min·m, MS ESI calcd. for C$_{33}$H$_{54}$F$_3$O [M+H−H$_2$O]$^+$ 523, found 523.

4259

$^1$H NMR (400 MHz, CDCl$_3$) δ 2.10-2.01 (m, 1H), 1.98-1.91 (m, 2H), 1.89-1.75 (m, 2H), 1.73-1.569 (m, 6H), 1.55-1.33 (m, 11H), 1.32-1.14 (m, 10H), 1.13-0.92 (m, 7H), 0.91-0.83 (m, 12H), 0.73-0.62 (m, 4H).

LCMS Rt=1.816 min in 2.0 min chromatography, 30-90AB_E, purity 100%.

MS 80-100DB_1_4 min·m, MS ESI calcd. for C33H54F3O [M+H−H2O]$^+$ 523, found 523.

Example 43: Synthesis of 4360

Synthesis of M-1-14_3

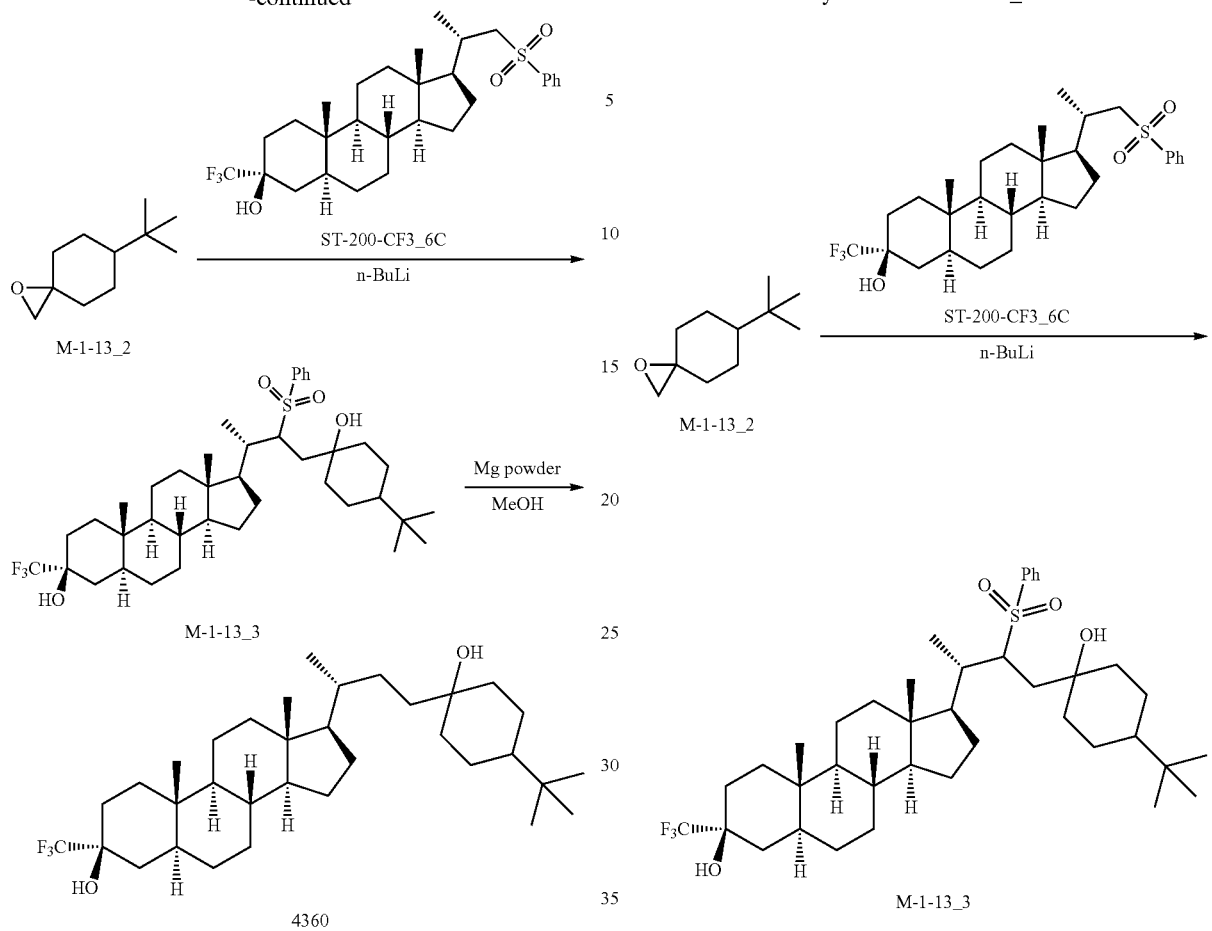

Synthesis of M-1-13_2

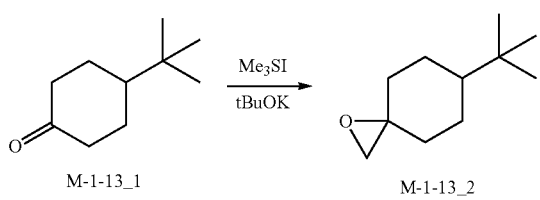

To a suspension of C₃H₉IS (17.1 g, 84.2 mmol) in THF (100 mL) was added a solution of t-BuOK (14.4 g, 129 mmol) in THF (50 mL) slowly under $N_2$ at 15° C. The suspension was stirred at 15° C. for 30 min. Then M-1-13_1 (10 g, 64.8 mmol) in 50 ml of THF was added dropwise to the mixture at 0° C. After addition, the mixture was stirred at 15° C. for 16 hrs. The mixture was poured into sat.NH₄Cl (300 mL) and extracted with EtOAc (3×100 mL). The combined organic phase was washed with brine (300 mL), dried over Na₂SO₄, filtered, and concentrated at 40° C. under reduced pressure to give M-1-13_2 (9 g, crude) as a liquid.

¹H NMR (400 MHz, CDCl₃) δ 2.65-2.55 (m, 2H), 1.92-1.72 (m, 4H), 1.42-1.22 (m, 3H), 1.21-1.01 (m, 2H), 0.88 (s, 9H).

To THF (0.5 mL) was added n-BuLi (0.568 mL, 2.5 M in hexane, 1.42 mmol). A solution of ST-200-CF3_6C (300 mg, 0.569 mmol) in THF (2.5 mL) was added at −70° C. After stirring at −70° C. for 1 h, 6-(tert-butyl)-1-oxaspiro[2.5]octane (143 mg, 0.853 mmol) was added at −70° C. The mixture was stirred at −70° C. for another 1 h, then warmed to 15° C. and stirred for 16 hrs. The reaction was quenched with sat.NH₄Cl (50 mL) and extracted with EtOAc (2×30 mL). The organic layer was separated, dried over Na₂SO₄, filtered, and concentrated to give M-1-13_3 (350 mg, crude) as a solid, which was used for next step directly.

Synthesis of 4360

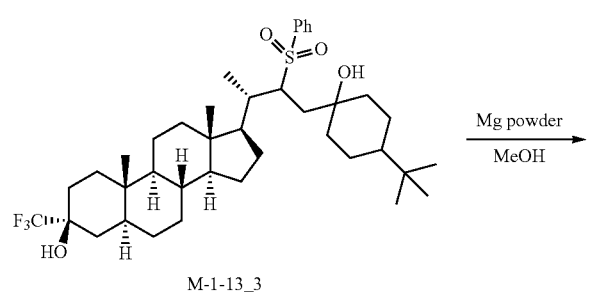

-continued

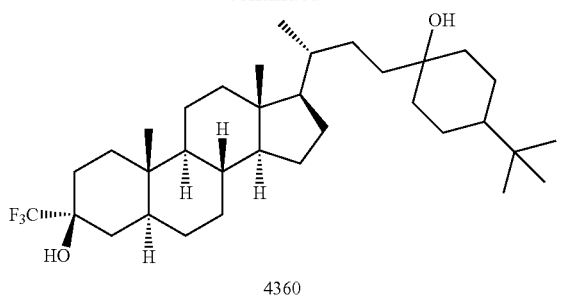

4360

To a solution of M-1-133 (350 mg, 0.503 mmol) in MeOH (30 mL) was added NiCl$_2$ (12.8 mg, 0.100 mmol) and Mg powder (482 mg, 20.1 mmol) at 65° C. in one portion. The mixture was stirred at 65° C. for 10 minutes. Then another batch of Mg powder (240 mg, 10.0 mmol) was added at 65° C. in one portion. The mixture was stirred at 65° C. for another 10 minutes. The reaction was quenched with HCl (50 mL, 2N) until the reaction became clear and extracted with EtOAc (3×20 mL). The combined organic layer was washed with sat. NH$_4$Cl (50 mL), dried over Na$_2$SO$_4$, filtered, concentrated and purified by silica gel chromatography (0-15% of EtOAc in PE) to give 4360 (30 mg, 11%) as a solid.

$^1$H NMR (400 MHz, CDCl$_3$) δ 2.10-2.02 (m, 1H), 1.99-1.91 (m, 2H), 1.87-1.77 (m, 2H), 1.72-1.56 (m, 7H), 1.53-1.43 (m, 4H), 1.42-1.19 (m, 13H), 1.19-0.97 (m, 7H), 0.96-0.88 (m, 5H), 0.88-0.82 (m, 12H), 0.72-0.64 (m, 4H).

HPLC Rt=7.685 min in 10.0 min chromatography, 50-100AB_E, purity 98.3%.

MS 80-100_1_4 min·m, MS ESI calcd. for C$_{34}$H$_{56}$F$_3$O [M+H−H$_2$O]$^+$ 537, found 537.

Example 44: Synthesis of 4475 and 4476

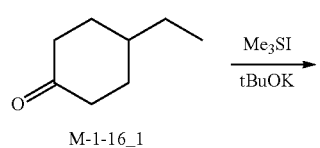

M-1-16_1

-continued

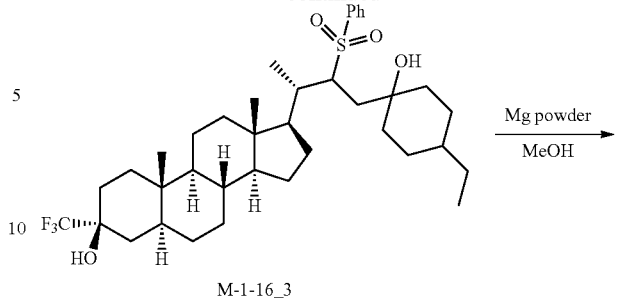

M-1-16_3

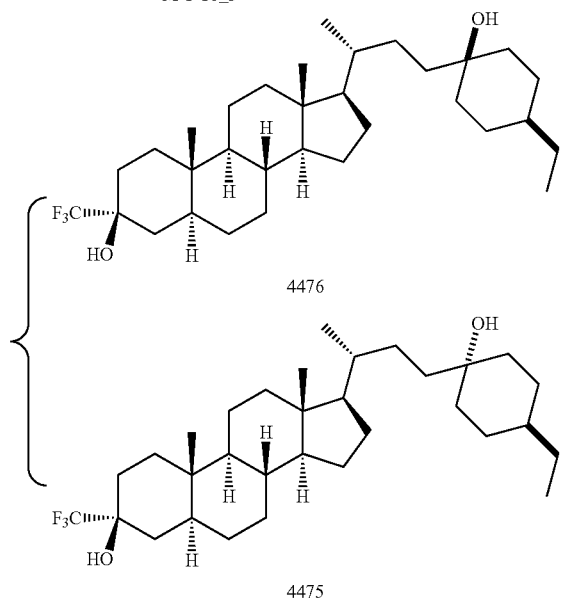

4476

4475

The stereochemistry for 4476 was confirmed by X-ray data.

The synthesis of ST-200-CF3_6C can be found in Example 5.

Synthesis of M-1-16_2

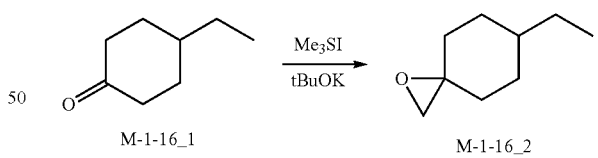

To a suspension of Me$_3$SI (2.08 g, 10.2 mmol) in THF (10 mL) was added a solution of t-BuOK (1.76 g, 15.8 mmol) in THF (5 mL) slowly under N$_2$ at 15° C. The suspension was stirred at 15° C. for 30 mins. Then M-1-16_1 (1 g, 7.13 mmol) in THF (5 ml) was added dropwise to the mixture at 0° C. After the addition, the mixture was stirred at 15° C. for 16 hrs. The mixture was poured into sat.NH$_4$Cl (60 mL), extracted with EtOAc (3×30 mL). The combined organic phase was washed with brine (100 mL), dried over Na$_2$SO$_4$, filtered and concentrated at 40° C. under reduced pressure to give M-1-16_2 (800 mg, crude) as a liquid.

$^1$H NMR (400 MHz, CDCl$_3$) δ 2.67-2.53 (m, 2H), 1.94-1.70 (m, 4H), 1.64-1.00 (m, 8H), 0.97-0.83 (m, 3H).

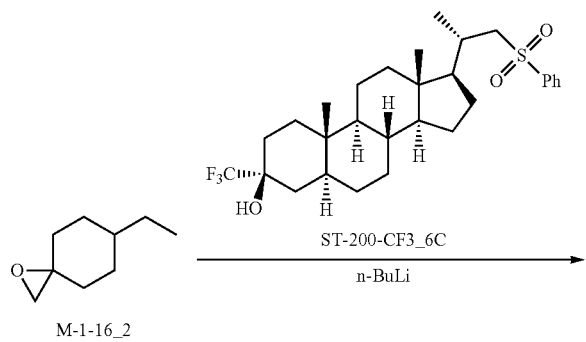

ST-200-CF3_6C

M-1-16_2

Synthesis of M-1-16_3

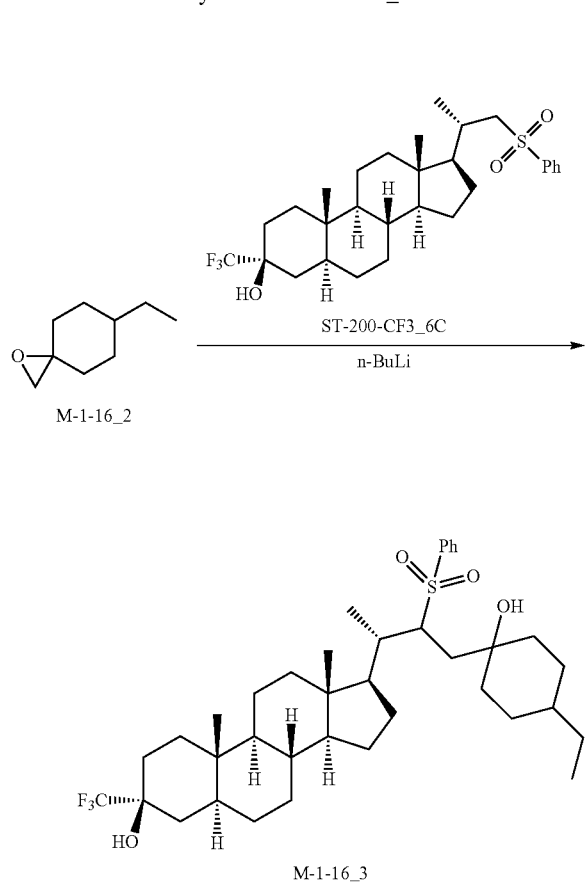

n-BuLi (0.756 mL, 2.5 M in hexane, 1.89 mmol) was diluted with THF (0.5 mL). A solution of ST-200-CF3_6C (400 mg, 0.759 mmol) in THF (2.5 mL) was added dropwise at −70° C. The mixture was stirred at −70° C. for 1 h. 6-methoxy-1-oxaspiro[2.5]octane (158 mg, 1.13 mmol) was added at −70° C. The mixture was stirred at −70° C. for another 1 h. The mixture was warmed to 15° C. and stirred for 16 hrs. To the mixture was added NH$_4$Cl (15 mL.). The mixture was extracted with EtOAc (3×15 mL). The combined organic layer was dried over Na$_2$SO$_4$, filtered and concentrated to give M-1-12_3 (350 mg, crude) as an oil, which was used for the next step directly.

Synthesis of 4476 and 4475

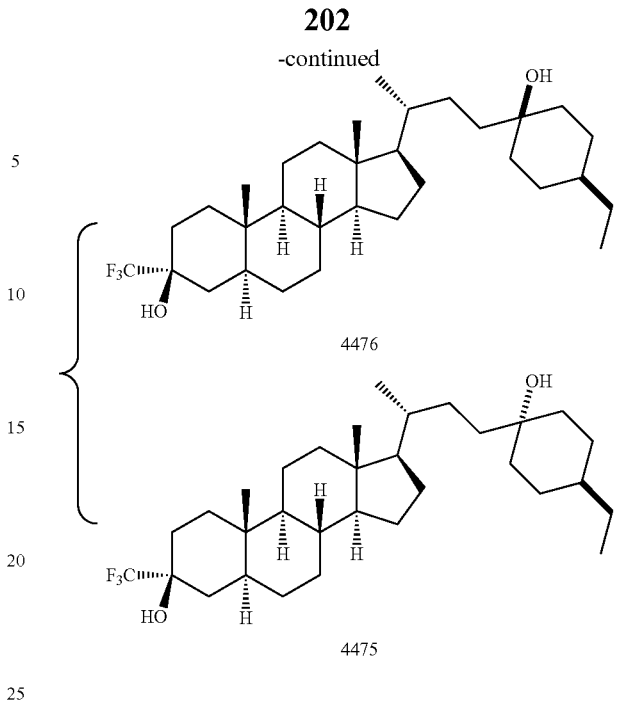

To a solution of M-1-16_3 (350 mg, 0.524 mmol) in MeOH (30 mL) was added NiCl$_2$ (20 mg, 0.157 mmol) and Mg powder (626 mg, 26.1 mmol) at 65° C. in one portion. The mixture was stirred at 65° C. for 1 hr. The mixture was quenched with HCl (30 mL, 2N) until the reaction became clear and extracted with EtOAc (3×20 mL). The combined organic layer was washed with sat. NH$_4$Cl (50 mL), dried over Na$_2$SO$_4$, filtered, concentrated and purified by silica gel chromatography (0-15% of EtOAc in PE) to give 34 mg, 12.3%, 4476 as a solid and 57 mg, 21%, 4475 as a solid.

4476

$^1$H NMR (400 MHz, CDCl$_3$) δ 2.11-2.02 (m, 1H), 2.01-1.92 (m, 2H), 1.90-1.76 (m, 3H), 1.75-1.60 (m, 7H), 1.59-1.55 (m, 2H), 1.52-1.43 (m, 3H), 1.42-1.19 (m, 13H), 1.17-0.96 (m, 9H), 0.94-0.90 (m, 3H), 0.89-0.83 (m, 6H), 0.74-0.62 (m, 4H).

LCMS Rt=1.591 min in 2 min chromatography, 30-90 AB, purity 100%, no MS signal.

MS: MS ESI calcd. For C$_{32}$H$_{52}$F$_3$O [M+H−H$_2$O]$^+$ 509, found 509.

4475

$^1$H NMR (400 MHz, CDCl$_3$) δ 2.11-2.02 (m, 1H), 2.00-1.91 (m, 2H), 1.89-1.75 (m, 2H), 1.73-1.52 (m, 10H), 1.51-1.33 (m, 7H), 1.32-1.18 (m, 10H), 1.17-0.96 (m, 7H), 0.95-0.81 (m, 10H), 0.73-0.62 (m, 4H).

LCMS Rt=1.679 min in 2 min chromatography, 30-90 AB, purity 100%, no MS signal.

MS: MS ESI calcd. For C$_{32}$H$_{52}$F$_3$O [M+H−H$_2$O]$^+$ 509, found 509.

Example 45: Synthesis of 4555 and 4585

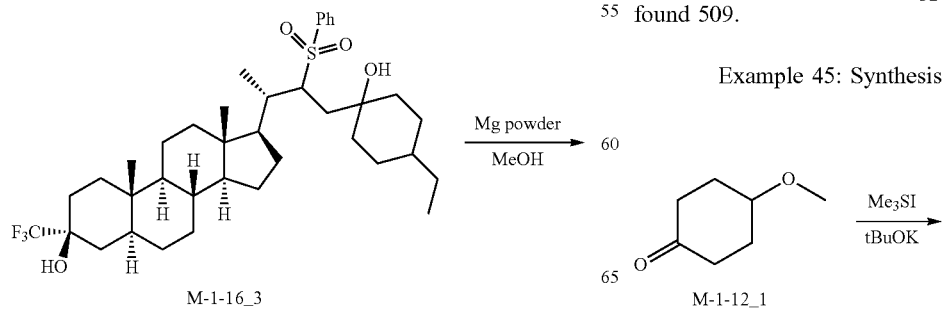

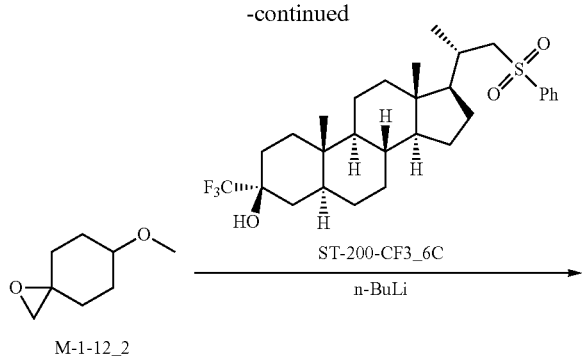

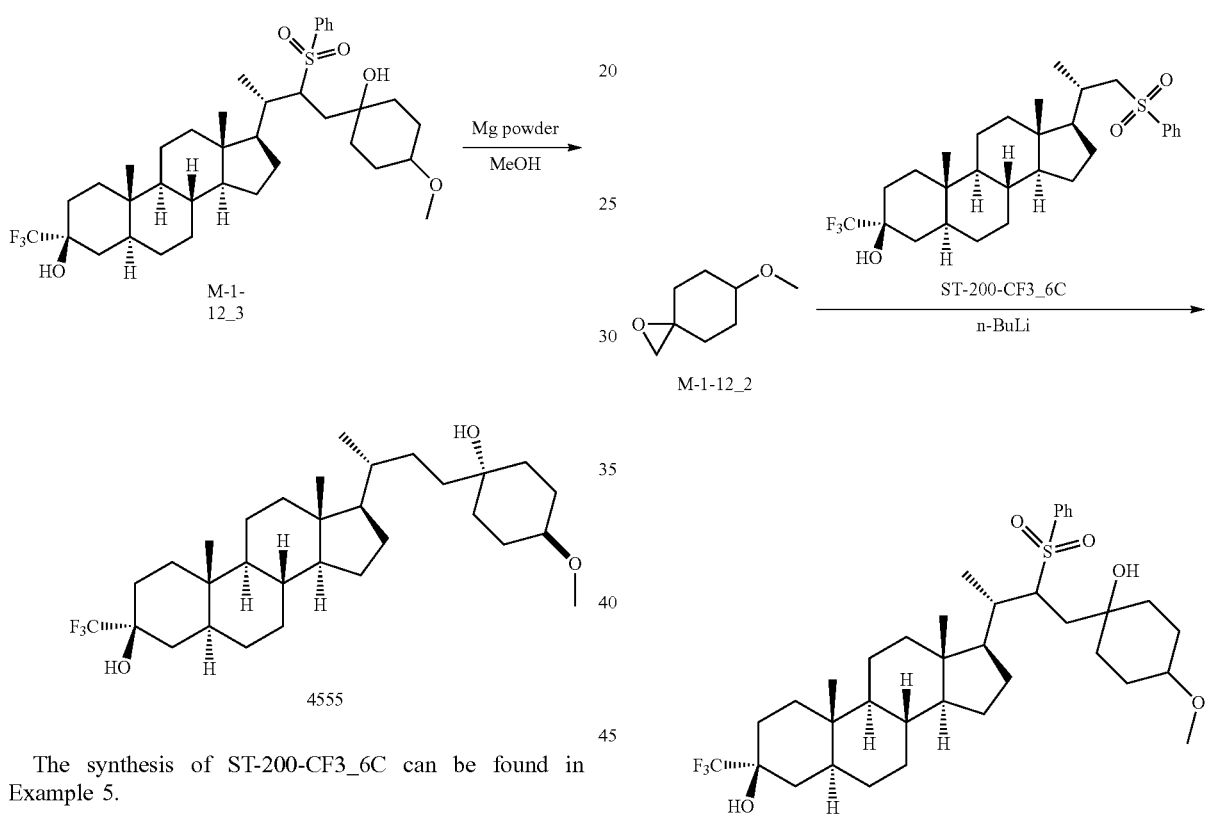

The synthesis of ST-200-CF3_6C can be found in Example 5.

Synthesis of M-1-12_2

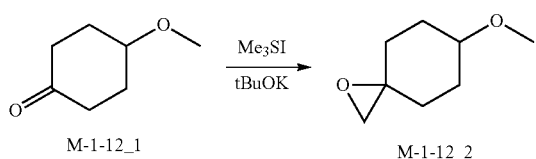

A solution of t-BuOK (1.74 g, 15.6 mmol) in THF (5 mL) was slowly added to a suspension of $C_3H_9IS$ (2.06 g, 10.1 mmol) in THF (10 mL) under $N_2$ at 15° C. The suspension was stirred at 15° C. for 30 min. Then M-1-12_1 (1 g, 7.80 mmol) in 5 ml of THF was added dropwise to the mixture at 0° C. After stirring at 15° C. for 16 hours, the mixture was poured into sat. $NH_4Cl$ (60 mL) and extracted with EtOAc (3×30 mL). The combined organic phase was washed with brine (100 mL), dried over $Na_2SO_4$, filtered, and concentrated at 40° C. under reduced pressure to give M-1-12_2 (1 g, crude) as liquid.

$^1$H NMR (400 MHz, $CDCl_3$) δ 3.48-3.25 (m, 4H), 2.68-2.26 (m, 2H), 1.98-1.85 (m, 2H), 1.84-1.66 (m, 3H), 1.65-1.55 (m, 2H), 1.48-1.41 (m, 1H).

Synthesis of A-1-12_3 n-BuLi (0.568 mL, 2.5 M in hexane, 1.42 mmol) was added to THF (0.5 mL). A solution of ST-200-CF3_6C (300 mg, 0.569 mmol) in THF (2.5 mL) was added at −70° C. After stirring at −70° C. for 1 h, 6-methoxy-1-oxaspiro[2.5] octane (121 mg, 0.853 mmol) was added at −70° C. The mixture was stirred at −70° C. for another 1 h. The mixture was warmed to 15° C. and stirred for 16 hrs. The reaction mixture was quenched with $NH_4Cl$ (50 mL, sat. aq.) and extracted with EtOAc (2×30 mL). The organic layer was separated, dried over $Na_2SO_4$, filtered, and concentrated to give M-1-12_3 (350 mg, crude) as a solid, which was used for next step directly.

Synthesis of 4555

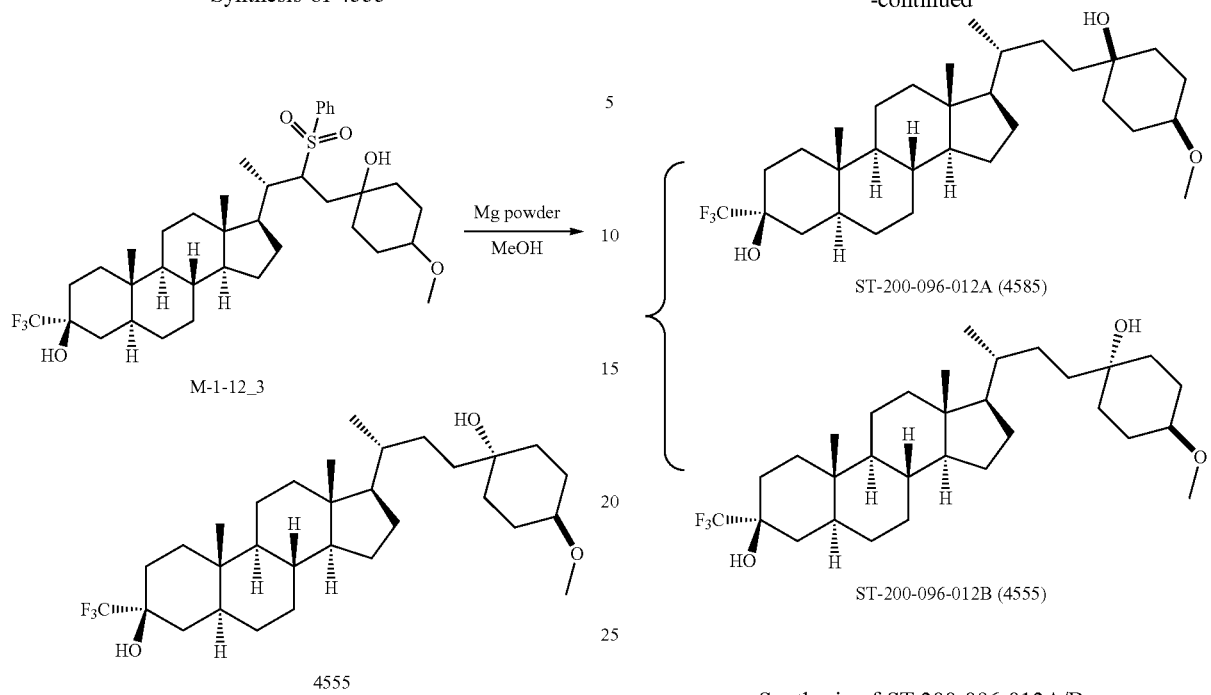

NiCl$_2$ (13.4 mg, 0.104 mmol) and Mg powder (501 mg, 20.9 mmol) were added in one portion to a solution of M-1-12_3 (350 mg, 0.523 mmol) in MeOH (40 mL) at 65° C. The mixture was stirred at 65° C. for 10 minutes. Another portion of Mg powder (250 mg, 10.4 mmol) was added. After stirring at 65° C. for 10 minutes, the mixture was quenched with HCl (60 mL, 1N) and extracted with EtOAc (3×20 mL). The combined organic phase was dried over Na$_2$SO$_4$, filtered, concentrated and purified by combi-flash (0-15% of EtOAc in impure M-12 (100 mg) as a solid, which was hydrogenated (dry Pd(OH)$_2$ (40 mg), MeOH (10 mL), 50° C., 50 si for 48 hrs). The suspension was filtered and the filtrate was concentrated and purified by combi-flash (0-30% of EtOAc in PE) to give pure 4555 (6 mg, 15%, 4555) as a solid.

$^1$H NMR (400 MHz, CDCl$_3$) δ 3.34 (s, 3H), 3.17-3.07 (m, 1H), 2.10-2.01 (m, 1H), 2.00-1.91 (m, 2H), 1.88-1.75 (m, 4H), 1.71-1.57 (m, 6H), 1.52-1.43 (m, 4H), 1.42-1.32 (m, 5H), 1.31-1.18 (m, 7H), 1.17-1.06 (m, 5H), 1.05-0.96 (m, 2H), 0.95-0.87 (m, 4H), 0.84 (s, 3H), 0.73-0.63 (m, 4H).

LCMS Rt=1.321 min in 2.0 min chromatography, 30-90AB_E, purity 100%.

MS 50-100_1_4 min·m, MS ESI calcd. for C$_{31}$H$_{51}$F$_3$O$_3$Na [M+Na]$^+$ 551, found 551.

Synthesis of ST-200-096-012A/B

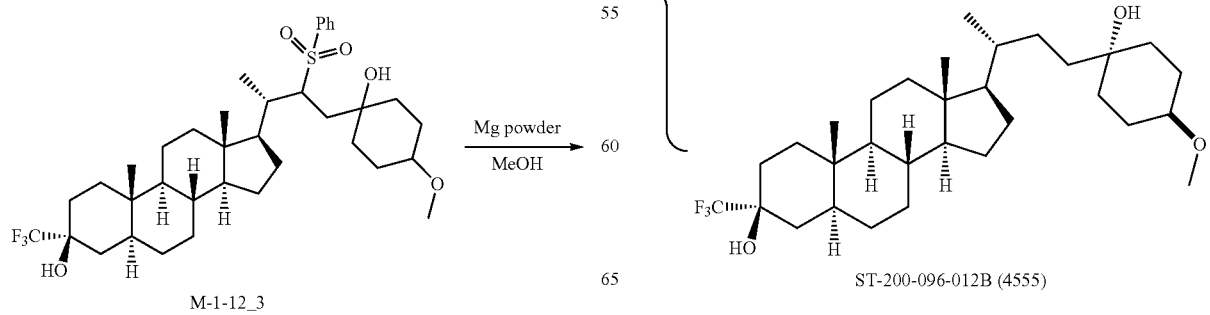

To a solution of M-1-12_3 (500 mg, 0.747 mmol) in MeOH (40 mL) was added NiCl$_2$ (19.2 mg, 0.149 mmol) and Mg powder (715 mg, 29.8 mmol) at 65° C. in one portion. The mixture was stirred at 65° C. for 10 minutes. Another Mg powder (355 mg, 14.9 mmol) was added in one portion. The mixture was stirred at 65° C. for 10 minutes again, quenched with HCl (200 mL, 1N) and extracted with EtOAc (3×50 mL). The combined organic phase was dried over Na$_2$SO$_4$, filtered, concentrated and purified by combi-flash (0-15% of EtOAc in PE) to give ST-200-096-012A (57 mg, 14%, Peak 1) and ST-200-096-012B (26 mg, 6.6%, Peak 2) as a solid.

4555

$^1$H NMR (400 MHz, CDCl$_3$) δ 3.34 (s, 3H), 3.17-3.07 (m, 1H), 2.09-1.91 (m, 3H), 1.88-1.76 (m, 4H), 1.70-1.61 (m, 5H), 1.56-1.44 (m, 6H), 1.43-1.19 (m, 11H), 1.17-0.95 (m, 7H), 0.95-0.85 (m, 4H), 0.84 (s, 3H), 0.72-0.61 (m, 4H).

LCMS Rt=1.269 min in 2.0 min chromatography, 30-90AB_E, purity 100%.

MS 50-100_1_4 min·m, MS ESI calcd. for C$_{31}$H$_{51}$F$_3$O$_3$Na [M+Na]$^+$ 551, found 551.

4585

$^1$H NMR (400 MHz, CDCl$_3$) δ 3.39-3.34 (m, 1H), 3.31 (s, 3H), 2.11-2.02 (m, 2H), 1.98-1.91 (m, 1H), 1.87-1.75 (m, 4H), 1.73-1.60 (m, 6H), 1.56-1.33 (m, 10H), 1.32-1.05 (m, 10H), 1.04-0.93 (m, 3H), 0.93-0.86 (m, 4H), 0.84 (s, 3H), 0.72-0.63 (m, 4H).

LCMS Rt=1.257 min in 2.0 min chromatography, 30-90AB_E, purity 100%.

MS 50-100_1_4 min·m, MS ESI calcd. for C$_{31}$H$_{51}$F$_3$O$_3$Na [M+Na]$^+$ 551, found 551.

Example 46: Synthesis of 4656 and 4657

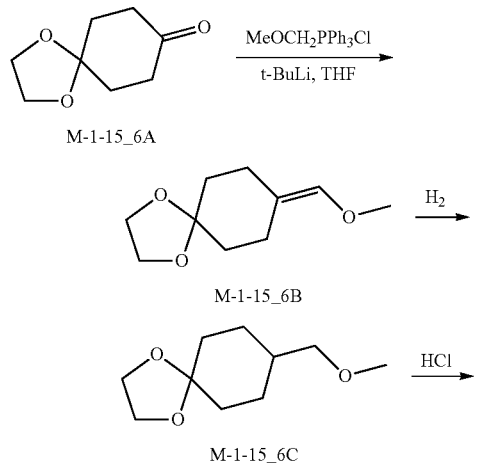

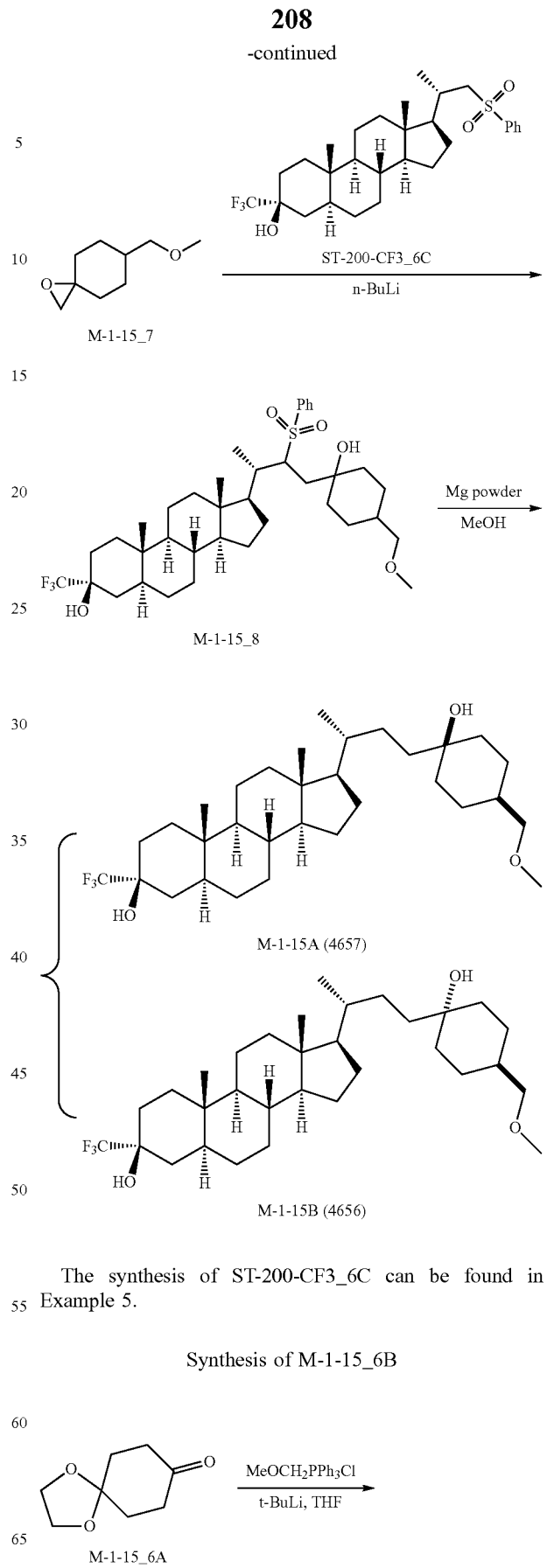

The synthesis of ST-200-CF3_6C can be found in Example 5.

Synthesis of M-1-15_6B

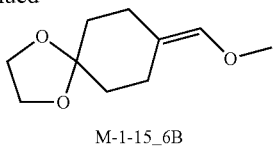

M-1-15_6B

Tert-butyllithium (44.3 mL, 12.9 mmol, 1.3 M in n-hexane) was added to a solution of chloro(methoxymethyl)triphenylphosphorane (21.9 g, 64 mmol) in THF (100 mL) at 0° C. After stirring for 1 hour at 0° C., M-1-15_6A (5 g, 32.0 mmol) in THF (30 mL) was added at 0° C. and the reaction mixture was stirred at 15° C. for 12 hours. The reaction mixture was quenched with water (60 mL) and extracted with EtOAc (3×150 mL). The combined organic layers were dried over anhydrous Na$_2$SO$_4$, filtered and concentrated to give the crude. The crude was purified by column chromatography with PE/EA=20/1-3/1 to give M-1-15_6B (5.55 g, 94%) as an oil.

$^1$HNMR (400 MHz, CDCl$_3$) δ 5.78 (s, 1H), 3.97-3.91 (m, 4H), 3.53 (s, 3H), 2.31 (t, J=6.4 Hz, 2H), 2.1-2.06 (m, 2H), 1.68-1.59 (m, 4H).

Synthesis of M-1-15_6C

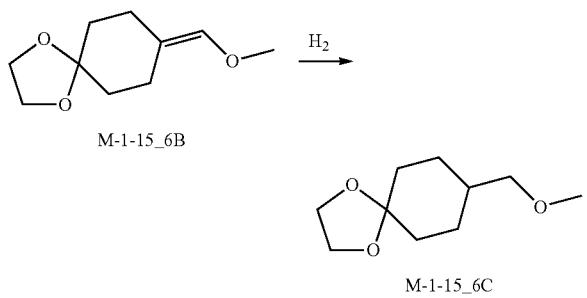

Pd/C (1 g) under N$_2$ at 10° C. was added to solution of M-1-15_6B (5.55 g, 30.1 mmol) in methanol (60 mL). The suspension was degassed under vacuum and purged with H$_2$ three times. The mixture was stirred under H$_2$ (50 psi) at 25° C. for 16 hours to give a suspension. The reaction mixture was filtered through a pad of Celite (2 cm) and the filter cake was washed with methanol (3×20 mL). The filtrate was concentrated to give M-1-15_6C (4.95 g, 88%) as an oil.

$^1$HNMR (400 MHz, CDCl$_3$) δ=3.97-3.88 (m, 4H), 3.32 (s, 3H), 3.20 (d, J=6.5 Hz, 2H), 1.75 (br d, J=9.3 Hz, 4H), 1.68-1.47 (m, 3H), 1.31-1.17 (m, 2H).

Synthesis of M-1-15_6

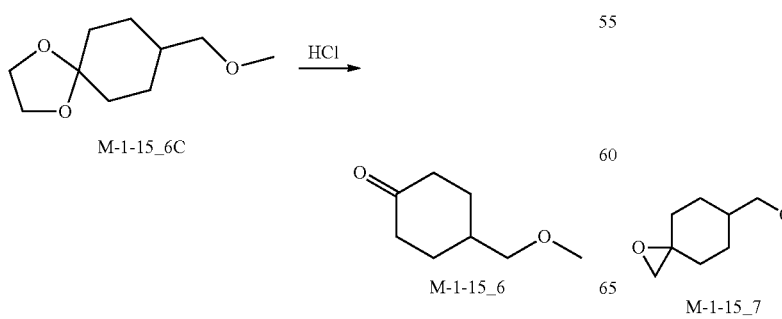

HCl (13.0 mL, 5 M) was added to a solution of M-1-15_6C (2 g, 10.7 mmol) in THF (20 mL). The reaction mixture was stirred at 10° C. for 48 hours, then 25° C. for 2 hours. The reaction mixture was concentrated to give a residue, which was basified to pH~10 with NaOH (2 M) and extracted with EtOAc (2×20 mL). The combined organic layers were washed with brine (20 mL), dried over anhydrous Na$_2$SO$_4$, filtered and concentrated to give M-1-15_6 (1.25 g, 82%) as a liquid.

$^1$HNMR (400 MHz, CDCl$_3$) δ 3.35 (s, 3H), 3.30-3.25 (m, 2H), 2.44-2.28 (m, 4H), 2.15-2.06 (m, 2H), 2.05-1.95 (m, 1H), 1.50-1.37 (m, 2H).

Synthesis of M-1-15_7

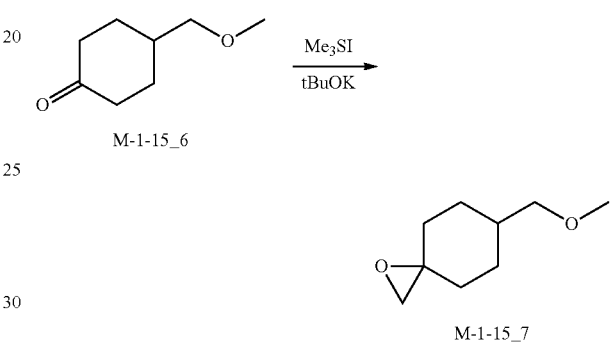

A solution of t-BuOK (787 mg, 7.02 mmol) in THF (2.5 mL) was slowly added to a suspension of Me$_3$IS (930 mg, 4.56 mmol) in THF (5 mL) was added under N2 at 15° C. After stirring at 15° C. for 30 min, then M-1-15_6 (0.5 g, 3.51 mmol) in 2.5 ml of THF was added drop wise to the mixture at 0° C. After the addition, the mixture was stirred at 15° C. for 16 hours, quenched with sat. NH$_4$Cl (10 mL) and extracted with EtOAc (3×20 mL). The combined organic layers were washed with brine (20 mL), dried over anhydrous Na$_2$SO$_4$, filtered and concentrated to give M-1-15_7 (410 mg, crude) as a liquid.

$^1$HNMR (400 MHz, CDCl$_3$) δ 3.34 (s, 3H), 3.30-3.25 (m, 2H), 2.65-2.55 (m, 2H), 1.95-1.80 (m, 4H), 1.75-1.60 (m, 1H), 1.40-1.15 (m, 4H).

Synthesis of M-1-15_8

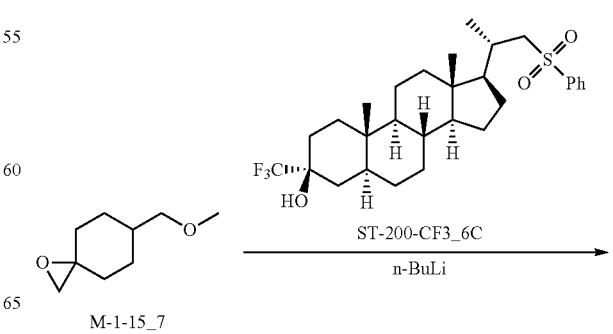

-continued

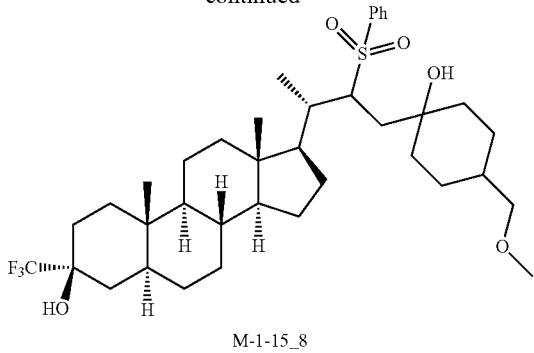

M-1-15_8

A solution of n-BuLi (0.472 mL, 2.5 M in hexane, 1.18 mmol) was added to THF (0.5 mL). A solution of ST-200-CF3_6C (250 mg, 0.474 mmol) in THF (2.5 mL) was added to the mixture at −70° C. The mixture was stirred at −70° C. for 1 hour. M-1-15_7 (111 mg, 0.711 mmol) was added at −70° C. After stirring at −70° C. for another 1 hour, the mixture was warmed to 15° C. and stirred for 16 hrs. The reaction mixture was quenched with NH₄Cl (50 mL, sat. aq) and extracted with EtOAc (2×30 mL). The organic layer was separated, dried over Na₂SO₄, filtered, and concentrated to give M-1-15_8 (250 mg, crude) as a solid, which was used for next step directly.

Synthesis of M-1-15A & M-1-15B

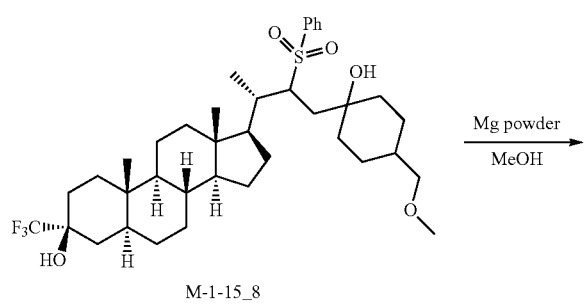

NiCl₂ (9.48 mg, 0.0732 mmol) and Mg powder (350 mg, 14.6 mmol) were added in one portion to a solution of M-1-15_8 (350 mg, 0.513 mmol) in MeOH (30 mL) at 65° C. The mixture was stirred at 65° C. for 10 minutes. Then another portion of Mg powder (175 mg, 7.32 mmol) was added at 65° C. After stirring at 65° C. for another 10 minutes, the mixture was quenched with HCl (50 mL, 2N) until the reaction became clear and extracted with EtOAc (3×20 mL). The combined organic layer was washed with sat. NH₄Cl (50 mL), dried over Na₂SO₄, filtered, concentrated and purified by silica gel chromatography (0-15% of EtOAc in PE) to give M-1-15A (22 mg, 11%, 4656,) and M-1-15B (54 mg, 27%, 4657) as a solid.

NMA-1-15A (4656)

$^1$H NMR (400 MHz, CDCl$_3$) δ 3.27 (s, 3H), 3.24-3.19 (m, 2H), 2.10-2.02 (m, 1H), 1.99-1.92 (m, 2H), 1.88-1.77 (m, 2H), 1.76-1.55 (m, 10H), 1.52-1.34 (m, 8H), 1.32-1.21 (m, 5H), 1.19-0.98 (m, 9H), 0.96-0.87 (m, 4H), 0.84 (s, 3H), 0.72-0.62 (m, 4H).

LCMS Rt=1.327 min in 2.0 min chromatography, 30-90AB_E, purity 100%.

MS 50-100_1_4 min·m, MS ESI calcd. for C$_{32}$H$_{52}$F$_3$O$_2$ [M+H−H$_2$O]$^+$ 525, found 525.

NMA-1-15B (4657)

$^1$H NMR (400 MHz, CDCl$_3$) δ 3.33 (s, 3H), 3.23-3.19 (m, 2H), 2.10-2.01 (m, 1H), 1.99-1.92 (m, 2H), 1.88-1.77 (m, 2H), 1.73-1.55 (m, 8H), 1.53-1.43 (m, 5H), 1.41-1.20 (m, 12H), 1.19-1.07 (m, 4H), 1.06-0.96 (m, 3H), 0.96-0.86 (m, 4H), 0.84 (s, 3H), 0.72-0.62 (m, 4H).

LCMS Rt=1.377 min in 2.0 min chromatography, 30-90AB_E, purity 100%.

MS 50-100_1_4 min·m, MS ESI calcd. for C$_{32}$H$_{52}$F$_3$O$_2$ [M+H−H2O]$^+$ 525, found 525.

Example 47: Synthesis of 4799

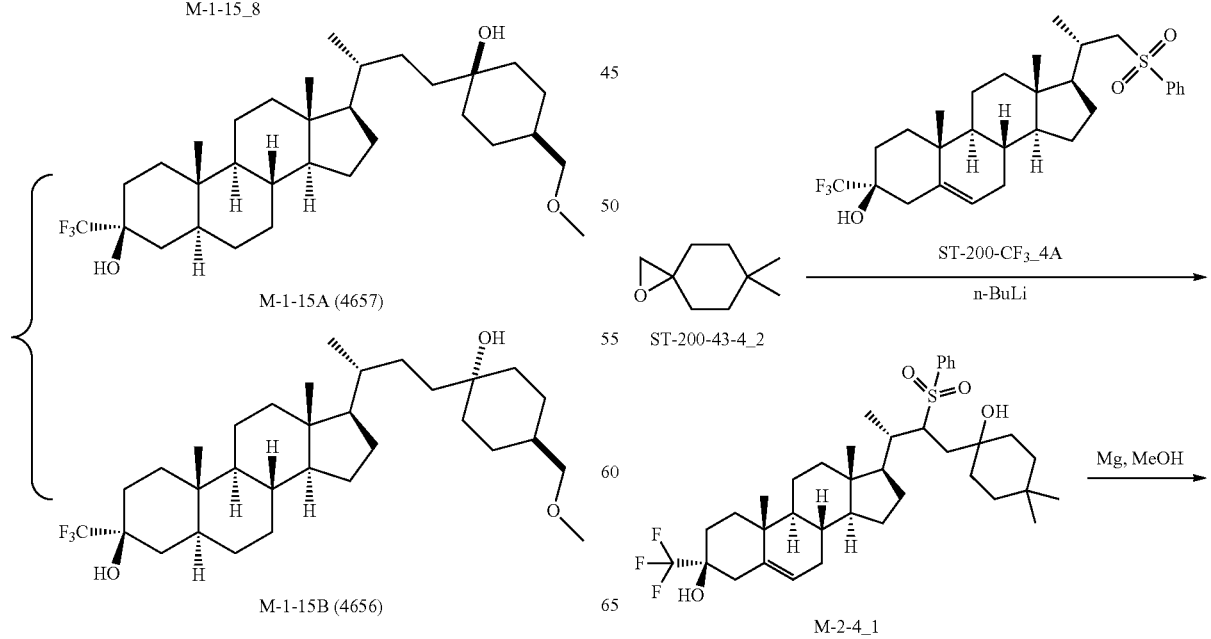

Synthesis of 4799

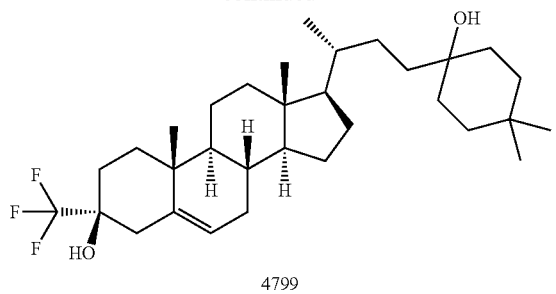

4799

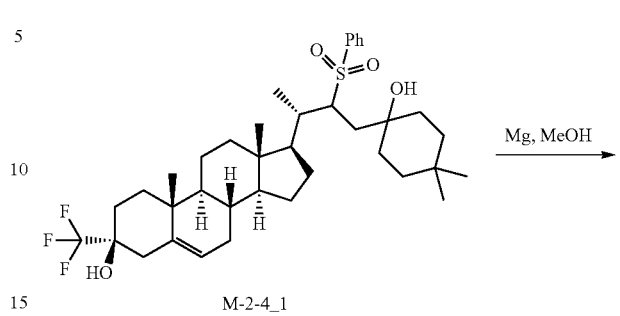

M-2-4_1

Synthesis of M-2-4_1

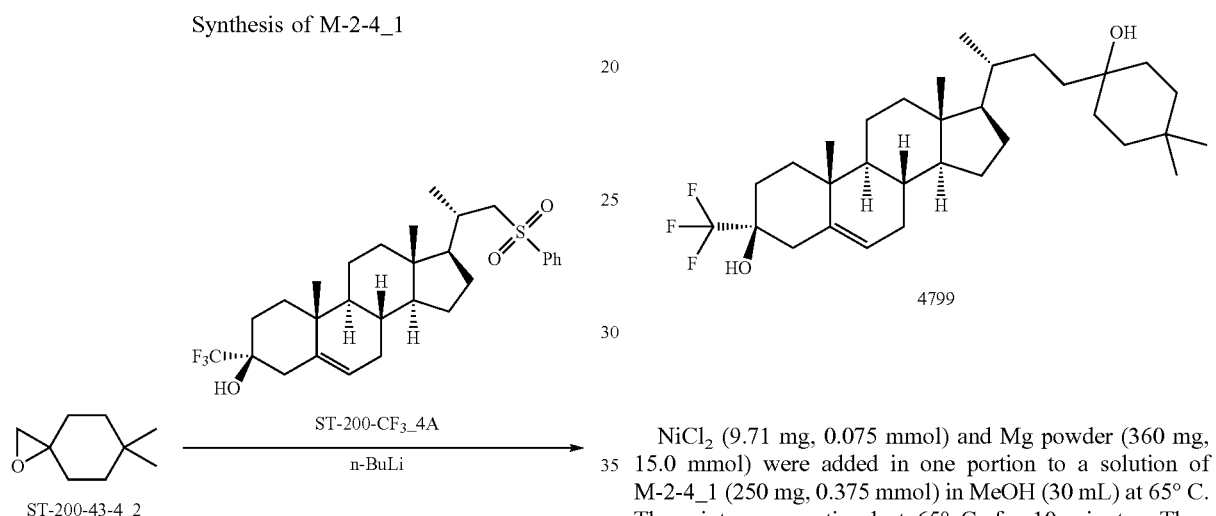

NiCl$_2$ (9.71 mg, 0.075 mmol) and Mg powder (360 mg, 15.0 mmol) were added in one portion to a solution of M-2-4_1 (250 mg, 0.375 mmol) in MeOH (30 mL) at 65° C. The mixture was stirred at 65° C. for 10 minutes. Then another portion of Mg powder (180 mg, 7.5 mmol) was added at 65° C. After stirring at 65° C. for another 10 minutes, the mixture was quenched with HCl (50 mL, 2N) until the reaction became clear and extracted with EtOAc (3×20 mL). The combined organic layer was washed with sat. NH$_4$Cl (50 mL), dried over Na$_2$SO$_4$, filtered, concentrated and purified by silica gel chromatography (0-15% of EtOAc in PE) to give 4799 (56 mg, 28%) as a solid.

$^1$HNMR (400 MHz, CDCl$_3$) δ 5.40-5.33 (m, 1H), 2.48 (s, 2H), 2.08-1.92 (m, 4H), 1.91-1.69 (m, 3H), 1.62-1.56 (m, 2H), 1.53-1.45 (m, 9H), 1.44-1.35 (m, 4H), 1.34-1.23 (m, 2H), 1.22-1.04 (m, 10H), 1.04-0.97 (m, 2H), 0.96-0.90 (m, 6H), 0.87 (s, 3H), 0.68 (s, 3H).

LCMS Rt=1.439 min in 2.0 min chromatography, 30-90AB_E, purity 100%, MS ESI calcd. for C$_{32}$H$_{50}$F$_3$O [M+H-H$_2$O]$^+$ 507, found 507.

A solution of n-BuLi (0.476 mL, 2.5 M in hexane, 1.19 mmol) was added to THF (0.5 mL). A solution of ST-200-CF$_3$_4A (250 mg, 0.476 mmol) in THF (2.5 mL) was added at −70° C. After stirring at −70° C. for 1 hour, ST-200-43-4_2 (100 mg, 0.714 mmol) was added to the mixture at −70° C. The mixture was stirred at −70° C. for another 1 hour. The mixture was warmed to 15° C., stirred for 16 hrs, quenched with NH$_4$Cl (50 mL, sat. aq) and extracted with EtOAc (2×30 mL). The organic layer was separated, dried over Na$_2$SO$_4$, filtered, and concentrated to give M-2-4_1 (250 mg, crude) as a solid, which was used for next step directly.

Example 48: Synthesis of 4805

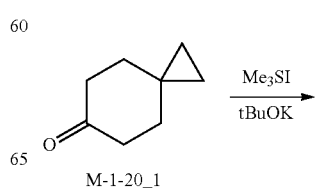

M-1-20_1

215

-continued

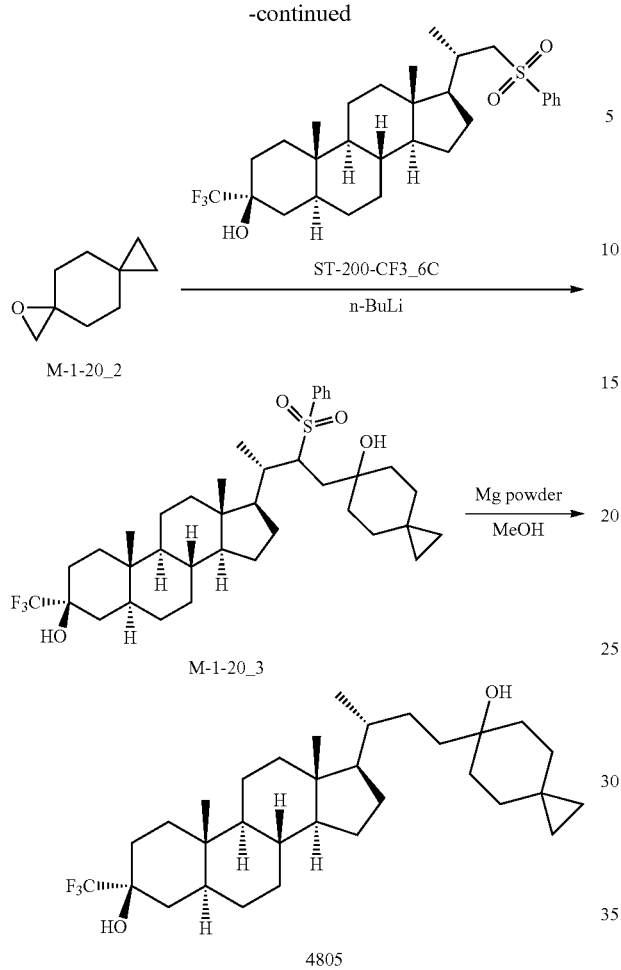

The synthesis of ST-200-CF3_6C can be found in Example 5.

Synthesis of M-1-20_2

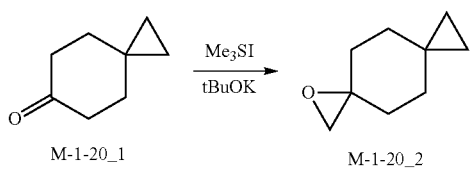

A solution of t-BuOK (902 mg, 8.04 mmol) in THF (4 mL) was slowly added to a suspension of C₃H₉IS (1.06 g, 5.22 mmol) in THF (5 mL) under N₂ at 15° C. After stirring at 20° C. for 30 min, M-1-20_1 (500 mg, 4.02 mmol) in 1 ml of THF was added dropwise to the mixture at 0° C. After addition, the mixture was stirred at 20° C. for 16 hours, quenched with sat. NH₄Cl (40 mL) and extracted with MTBE (3×20 mL). The combined organic phase was washed with brine (2×60 mL), dried over Na₂SO₄, filtered and concentrated at 40° C. under reduced pressure to give M-1-20_2 (390 mg, crude) as a liquid.

$^1$H NMR (400 MHz, CDCl₃) δ 2.63 (s, 2H), 1.74-1.53 (m, 6H), 1.41-1.27 (m, 2H), 0.37-0.26 (m, 4H).

216

Synthesis of M-1-20_3

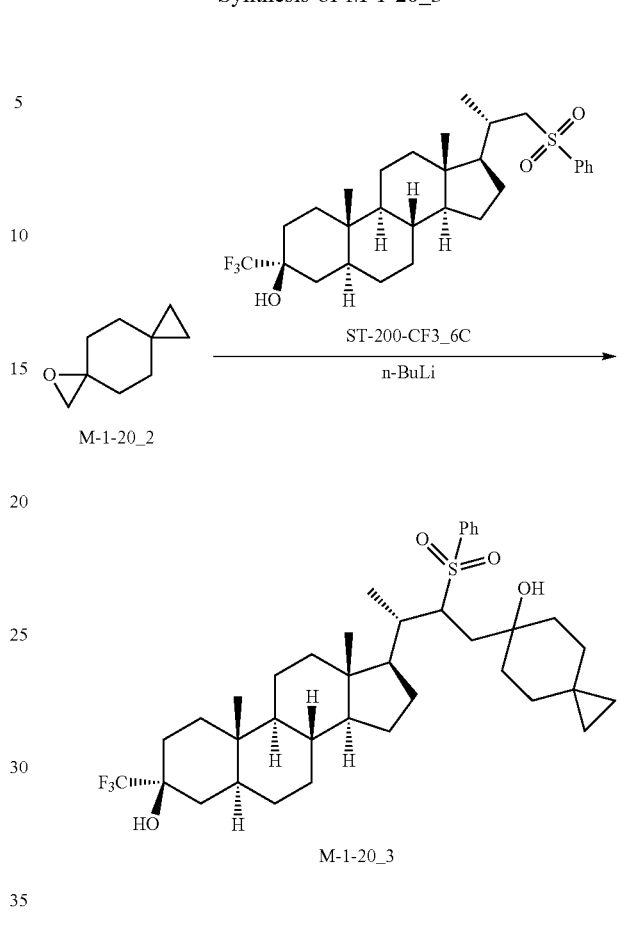

A solution of n-BuLi (0.472 mL, 2.5 M in hexane, 1.18 mmol) was added to THF (0.5 mL). A solution of ST-200-CF3_6C (250 mg, 0.474 mmol) in THF (2.5 mL) was added at −70° C. After stirring at −70° C. for 1 h, M-1-20_2 (98.2 mg, 0.711 mmol) was added at −70° C. The mixture was stirred at −70° C. for another 1 h, warmed to 15° C. for 16 hours, quenched with NH₄Cl (50 mL, sat. aq) and extracted with EtOAc (2×30 mL). The combined organic phase was dried over Na₂SO₄, filtered, and concentrated to give M-1-20_3 (250 mg, crude) as a solid, which was used for next step directly.

Synthesis of 4805

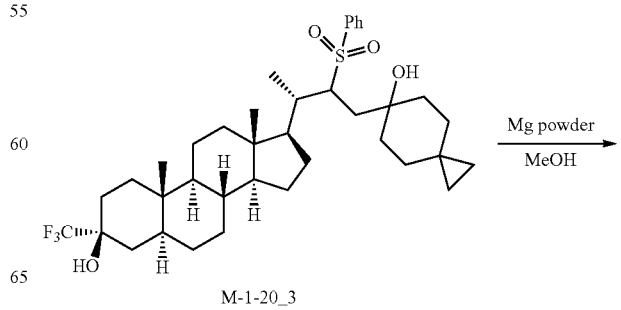

-continued

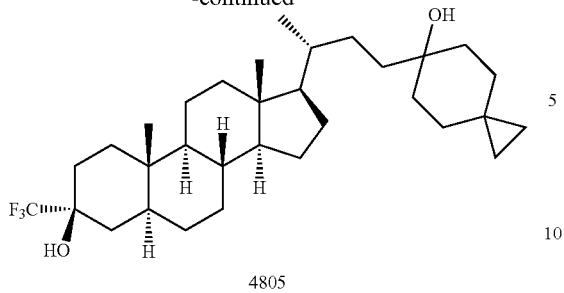

4805

NiCl₂ (9.71 mg, 0.075 mmol) and Mg powder (360 mg, 15.0 mmol) were added in one portion to a solution of M-1-20_3 (250 mg, 0.375 mmol) in MeOH (30 mL) at 65° C. The mixture was stirred at 65° C. for 10 minutes. Then another portion of Mg powder (180 mg, 7.5 mmol) was added at 65° C. After stirring at 65° C. for another 10 minutes, the mixture was quenched with HCl (50 mL, 2N) until the reaction became clear and extracted with EtOAc (3×20 mL). The combined organic layer was washed with sat. NH₄Cl (50 mL), dried over Na₂SO₄, filtered, concentrated and purified by silica gel chromatography (0-15% of EtOAc in PE) to give 4805 (150 mg, 76%) as a solid.

¹H NMR (400 MHz, CDCl₃) δ 2.11-1.94 (m, 3H), 1.89-1.60 (m, 9H), 1.54-1.35 (m, 9H), 1.34-1.19 (m, 6H), 1.18-1.06 (m, 5H), 1.05-0.88 (m, 8H), 0.85 (s, 3H), 0.74-0.62 (m, 4H), 0.33-0.15 (m, 4H).

LCMS Rt=1.414 min in 2.0 min chromatography, 30-90AB_E, purity 100%.

MS 80-100_1_4 min·m, MS ESI calcd. for C₃₂H₅₁F₃O₂Na [M+Na]⁺ 547, found 547.

Example 49: Synthesis of 4906

-continued

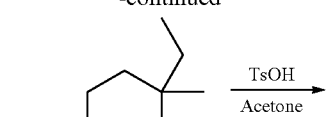

M-1-17_4

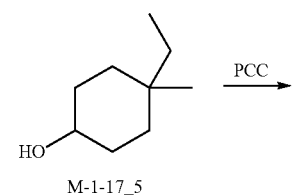

M-1-17_5

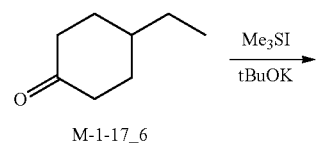

M-1-17_6

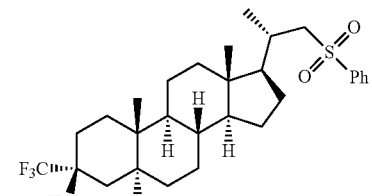

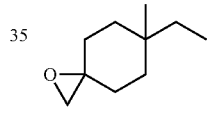

M-1-17_7

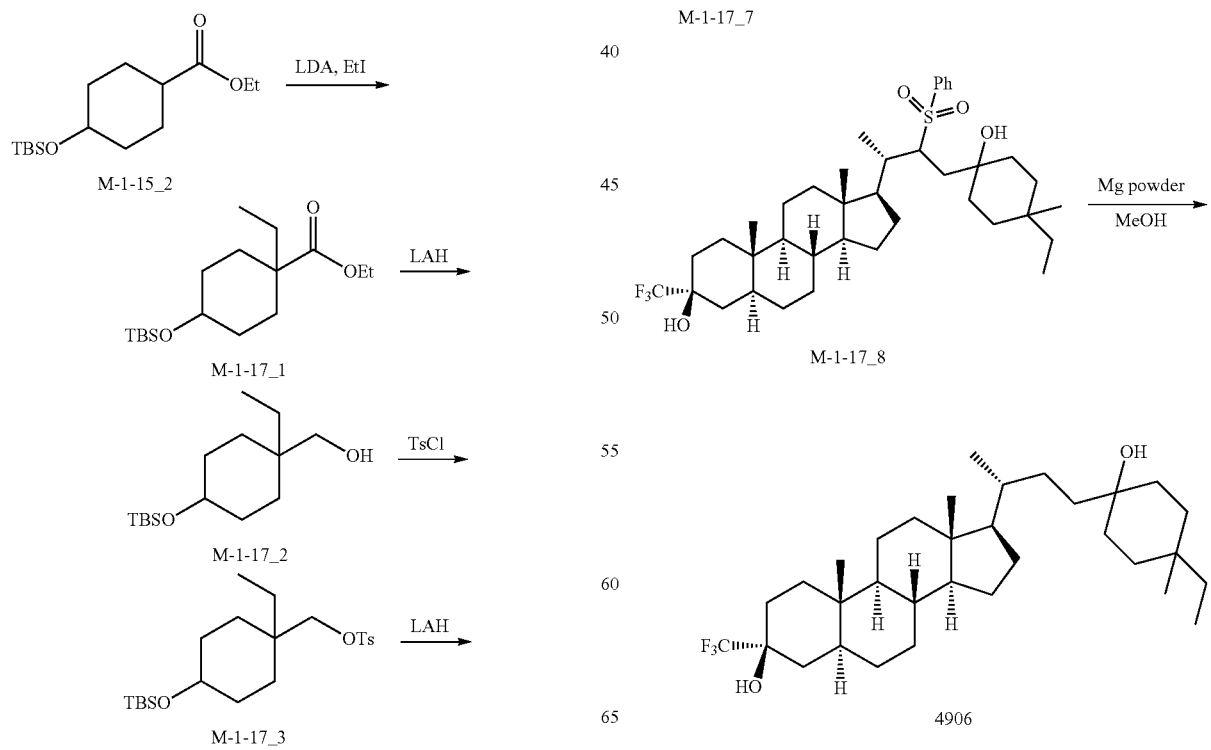

Synthesis of M-1-17_1

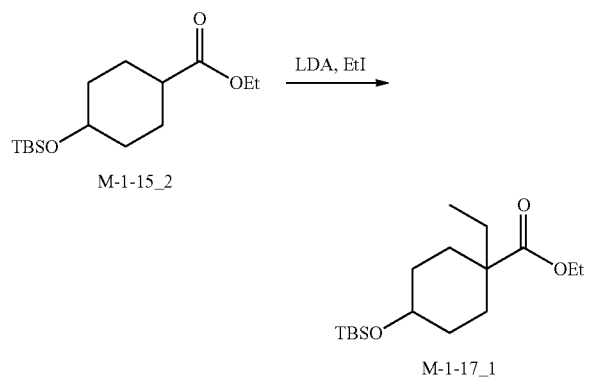

A solution of n-butyllithium (64 mL, 160 mmol, 2.5 M in hexane) was added to a solution of diisopropylamine (17.6 g, 174 mmol) in THF (30 mL) at −70° C. The mixture was warmed to 0° C. and stirred at 0° C. for 30 minutes. The mixture was cooled to −70° C. and M-1-15_2 (20 g, 69.8 mmol) in THF (20 mL) was added. The mixture was stirred at −70° C. for 1 h. Ethyl iodide (43.5 g, 279 mmol) was added. The mixture was warmed to 15° C. and stirred at 15° C. for 5 hours. The mixture was quenched with Sat $NH_4Cl$ (30 mL). The mixture was extracted with EtOAc (2×30 mL). The combined organic phase was washed with brine (2×20 mL), dried over $Na_2SO_4$, filtered and concentrated in vacuum to give a crude M-1-17_1 (21, crude) as an oil.

Synthesis of M-1-17_2

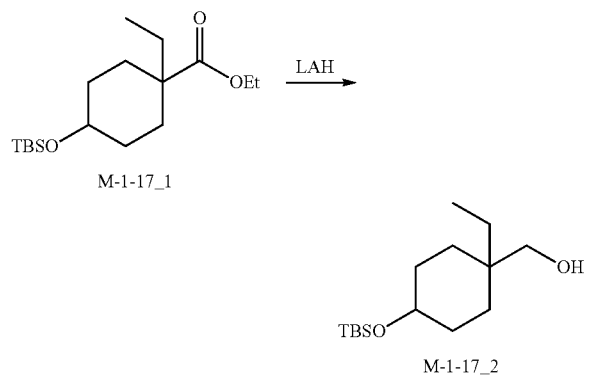

$LiAlH_4$ (5.05 g, 133 mmol) was added in five portions to a solution of M-1-17_1 (21 g, 66.7 mmol) in THF (100 mL) at 0° C. under $N_2$. The mixture was stirred at 20° C. for 4 hours. To the mixture water (20 mL) was added at 0° C. HCl (100 mL, 1 mol/L) was added. The aqueous phase was extracted with EtOAc (50 mL×2). The combined organic phase was washed with saturated brine (2×30 mL), dried over anhydrous $Na_2SO_4$, filtered and concentrated. The residue was purified by flash column (0~20% of EtOAc in PE) to give M-1-17_2 (16.5 g, 91%) as an oil.

$^1$H NMR (400 MHz, $CDCl_3$) δ 3.70-3.55 (m, 1H), 3.55-3.45 (m, 2H), 1.70-1.55 (m, 5H), 1.55-1.10 (m, 9H), 0.95-0.88 (m, 9H), 0.041 (s, 6H).

Synthesis of M-1-17_3

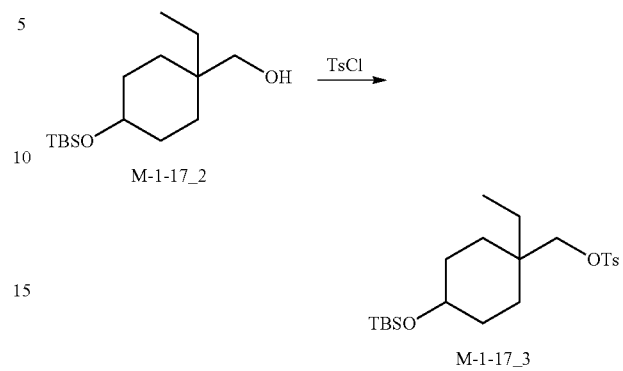

1-methyl-1H-imidazole (7.44 g, 90.7 mmol) and TEA (12.2 g, 121 mmol) were added to a solution of M-1-17_2 (16.5 g, 60.5 mmol) in DCM (100 mL) at 15° C. TsCl (23.0 g, 121 mmol) was added to the solution. The reaction mixture was stirred at 15° C. for 2 hours. The mixture was washed with water (2×100 mL), brine (150 mL), dried over $Na_2SO_4$, filtered and concentrated under vacuum to give M-1-17_3 (24 g, crude) as an oil.

Synthesis of M-1-17_4

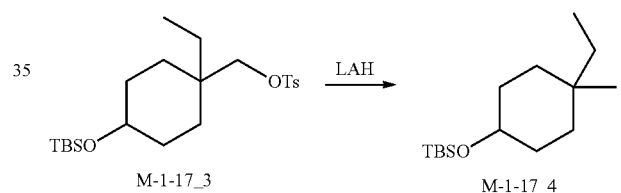

$LiAlH_4$ (5.32 g, 140 mmol) was added in five portions to a solution of M-1-17_3 (24 g, 56.2 mmol) in THF (100 mL) at 0° C. under $N_2$. The mixture was stirred at 20° C. for 4 hours. Water (20 mL) was added to the mixture at 0° C. HCl (100 mL, 1 mol/L) was added. The aqueous phase was extracted with EtOAc (2×50 mL). The combined organic phase was washed with saturated brine (2×30 mL), dried over anhydrous $Na_2SO_4$, filtered and concentrated to give M-1-17_4 (13 g, crude) as an oil.

$^1$H NMR (400 MHz, $CDCl_3$) δ 3.60-3.50 (m, 1H), 1.95-1.70 (m, 3H), 1.70-1.01 (m, 12H), 1.01-0.68 (m, 10H), 0.043 (s, 6H).

Synthesis of M-1-17_5

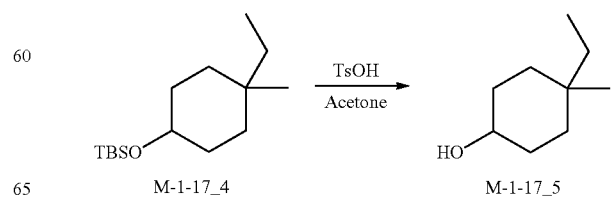

p-TsOH (7.23 g, 38.9 mmol) was added to a solution M-1-17_4 (10 g, 38.9 mmol) in acetone (50 mL). The reaction mixture was stirred at 15° C. for 2 h. Water was added and was extracted with EtOAc (2×30 mL). The combined organics were washed with NaHCO₃ (20 mL, 10%) and brine (30 mL) and dried over Na₂SO₄. The solvent was removed under reduced pressure. The residue was purified by flash column (0~20% of EtOAc in PE) to give M-1-17_5 (6 g, crude) as a an oil.

¹H NMR (400 MHz, CDCl₃) δ 3.70-3.50 (m, 1H), 1.80-1.60 (m, 4H), 1.60-1.40 (m, 5H), 1.40-1.01 (m, 4H), 0.91-0.75 (m, 4H).

Synthesis of M-1-17_6

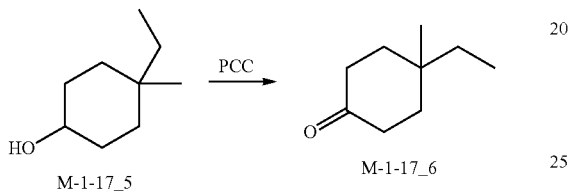

DMP (17.8 g, 42 mmol) was added to a solution of M-1-17_5 (3 g, 21 mmol) in DCM (20 mL). Next, H₂O (7.55 mg, 0.42 mmol) was added to the solution. The reaction was stirred at 15° C. for 30 min. Aqueous saturated NaHCO₃ (10 mL) solution, aqueous saturated Na₂S₂O₃ (10 mL) solution were added to the reaction mixture. The mixture was extracted with DCM (2×20 mL). The combined organic layer was washed with aqueous saturated NaHCO₃ (2×20 mL) solution and brine (20 mL), dried over Na₂SO₄, filtered, concentrated in vacuum and purified by flash column (0~10% of EtOAc in PE) to give M-1-17_6 (2.5 g, 85%) as an oil.

¹H NMR (400 MHz, CDCl₃) δ 2.40-2.28 (m, 4H), 1.72-1.60 (m, 4H), 1.49-1.40 (m, 2H), 1.02 (s, 3H), 0.92-0.85 (m, 3H).

Synthesis of M-1-17_7

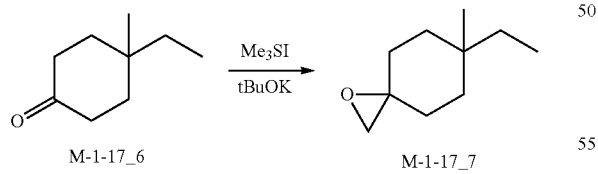

M-1-17_6 (1 g, 7.13 mmol) was added to a stirred solution of trimethylsulfoxonium iodide (3.12 g, 14.2 mmol) and t-BuOK (1.75 g, 15.6 mmol) in THF (10 mL) at 0° C. The reaction mixture was stirred at 10° C. for 16 hours. The reaction mixture was poured into saturated aqueous NH₄Cl (15 mL). The resulting mixture was extracted with EtOAc (3×20 mL). The combined organic layers were washed with brine (20 mL), dried over anhydrous Na₂SO₄, filtered and concentrated to give M-1-17_7 (360 mg, crude) as an oil.

Synthesis of M-1-17_8

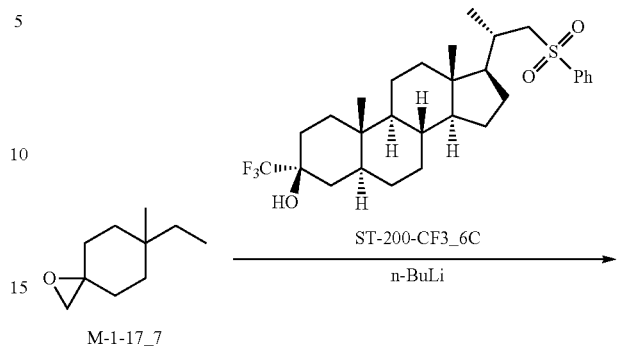

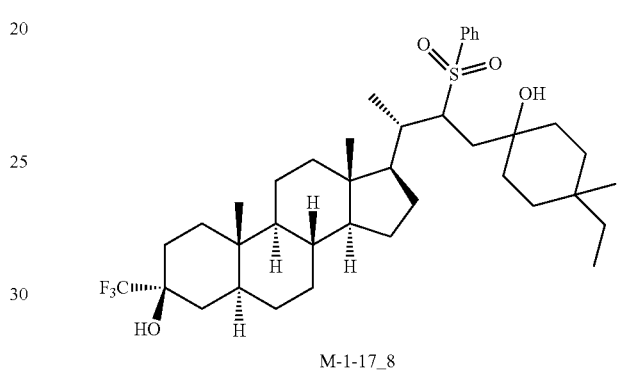

A solution of n-BuLi (0.568 mL, 2.5 M in hexane, 1.42 mmol) was added to THF (0.5 mL). A solution of ST-200-CF3_6C (300 mg, 0.474 mmol) in THF (2.5 mL) was added at −70° C. After stirring at −70° C. for 1 h, M-1-17_7 (131 mg, 0.853 mmol) was added at −70° C. The mixture was stirred at −70° C. for another 1 h, warmed to 15° C. and stirred for 16 hours. The reaction mixture was quenched with NH₄Cl (10 mL, sat. aq) and extracted with EtOAc (2×20 mL). The organic layer was separated, dried over anhydrous Na₂SO₄, filtered and concentrated to give M-1-15_8 (387 mg, crude) as an oil, which was used for the next step directly.

Synthesis of 4906

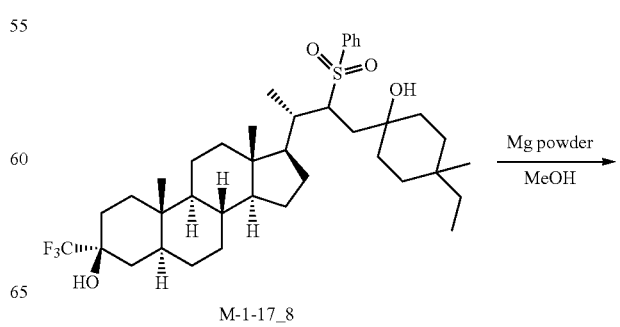

-continued

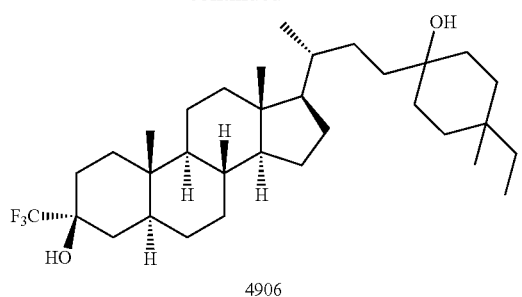

4906

NiCl$_2$ (14.6 mg, 0.113 momⅼ) and Mg powder (550 mg, 22.9 mmol) were added in one portion to a solution of M-1-17_8 (387 mg, 568 μmol) in MeOH (40 mL) at 65° C. After stirring at 65° C. for

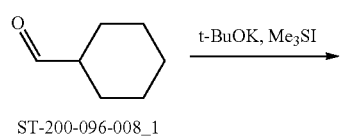

ST-200-096-008_1

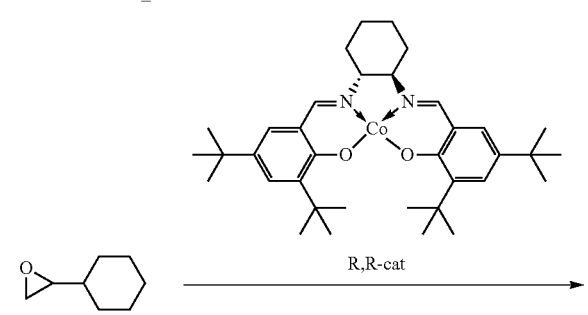

ST-200-096-008_2

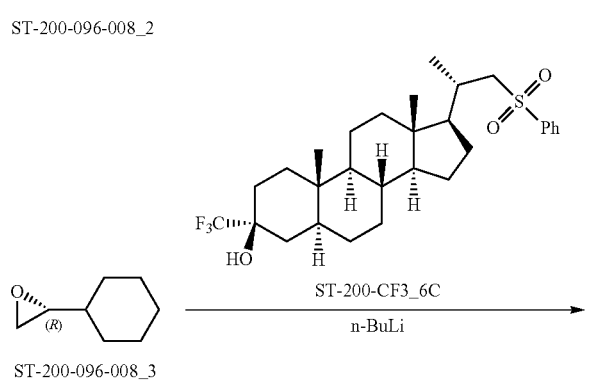

ST-200-096-008_3

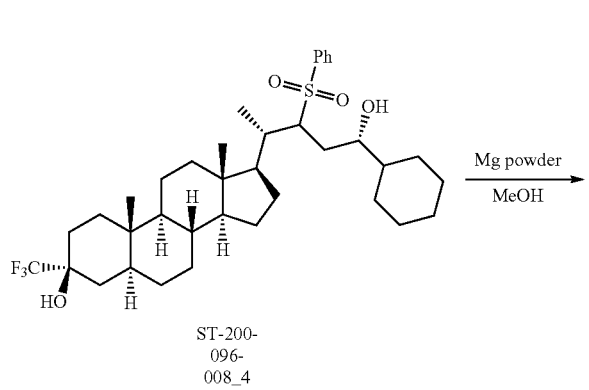

ST-200-096-008_4

-continued

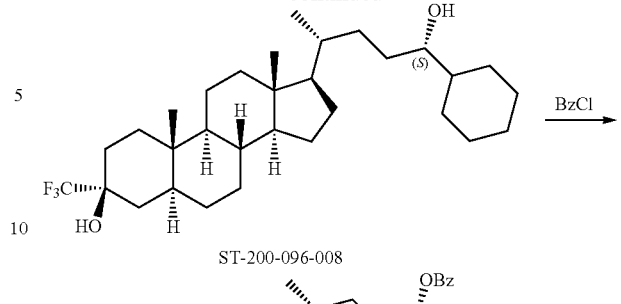

ST-200-096-008

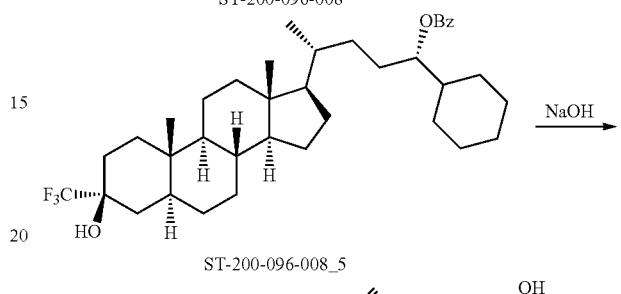

ST-200-096-008_5

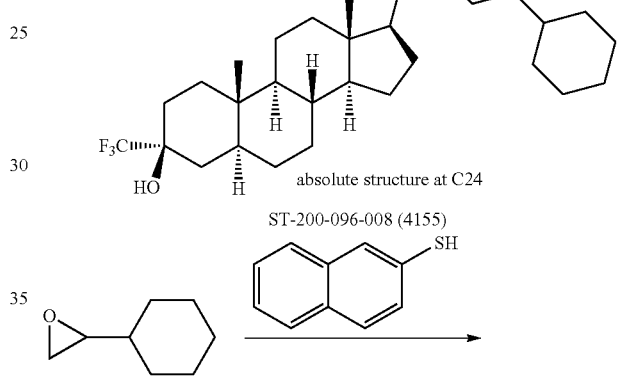

ST-200-096-008 (4155)
absolute structure at C24

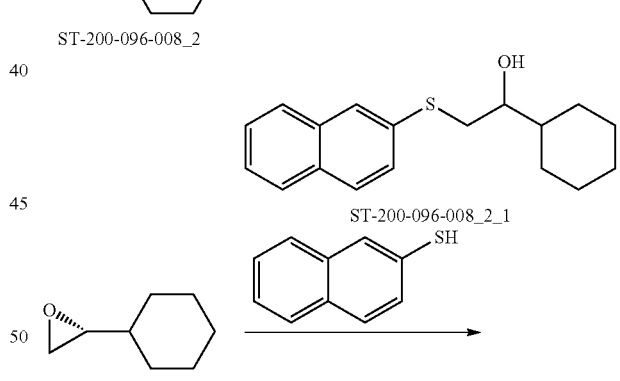

ST-200-096-008_2

ST-200-096-008_2_1

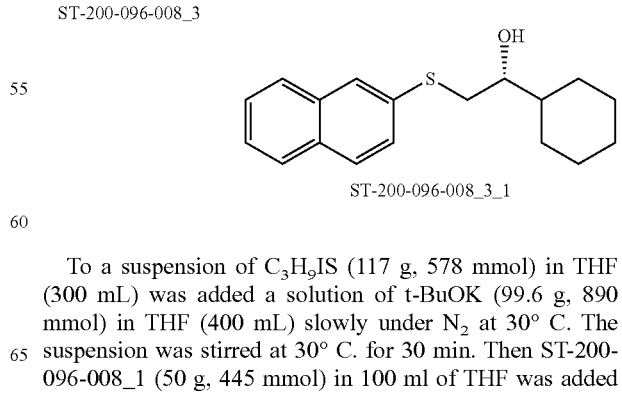

ST-200-096-008_3

ST-200-096-008_3_1

To a suspension of C$_3$H$_9$IS (117 g, 578 mmol) in THF (300 mL) was added a solution of t-BuOK (99.6 g, 890 mmol) in THF (400 mL) slowly under N$_2$ at 30° C. The suspension was stirred at 30° C. for 30 min. Then ST-200-096-008_1 (50 g, 445 mmol) in 100 ml of THF was added dropwise to the mixture at 0° C. After stirring at 30° C. for 16 hrs, the mixture was poured into sat.NH$_4$Cl (600 mL) and extracted with EtOAc (2×200 mL). The combined organic phase was washed with brine (400 mL), dried over Na$_2$SO$_4$, filtered, and concentrated at 40° C. under reduced pressure to give ST-200-096-008_2 (55 g, crude) as a liquid.

10 minutes, another batch of Mg powder (266 mg, 11.1 mmol) was added in one portion at 65° C. The mixture was stirred at 65° C. for another 10 minutes. The reaction mixture was cooled to 20° C. and quenched by HCl (30 mL, 2 M). The resulting mixture was extracted with EtOAc (3×70 mL). The combined organic layers were washed with saturated aqueous NH$_4$Cl (70 mL), brine (70 mL), dried over anhydrous Na$_2$SO$_4$, filtered and concentrated to give the crude. The crude was purified by column chromatography with PE/EtOAc=0/1-5/1. The solvent was removed to give 4906 (56 mg, 18%) as a solid.

$^1$H NMR (400 MHz, CDCl$_3$) δ 2.12-2.00 (m, 1H), 2.00-1.93 (m, 1H), 1.90-1.80 (m, 1H), 1.78-1.60 (m, 2H), 1.59-1.50 (m, 7H), 1.49-1.33 (m, 12H), 1.32-1.15 (m, 9H), 1.14-1.0 (m, 7H), 0.99-0.90 (m, 3H), 0.89-0.80 (m, 8H), 0.75-0.70 (m, 1H), 0.70-0.60 (s, 3H).

LCMS Rt=1.550 min in 2.0 min chromatography, 30-90AB_E, purity 100%; special MS ESI calcd. for C$_{33}$H$_{56}$F$_3$O$_2$ [M+H]$^+$ 541, found 541.

Example 50: Synthesis of 5009

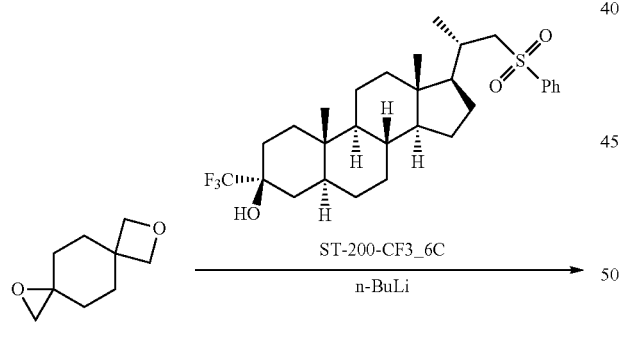

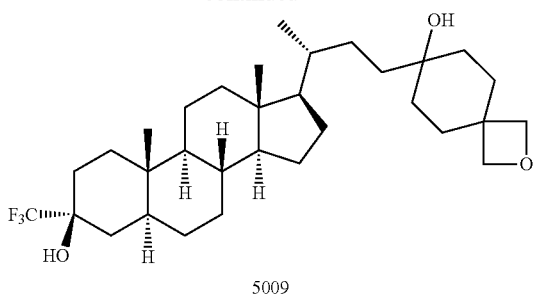

The synthesis of ST-200-CF3_6C can be found in Example 5.

Synthesis of M-1-21_2

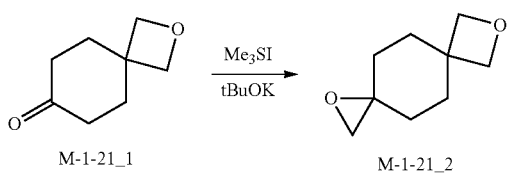

A solution of t-BuOK (797 mg, 7.12 mmol) in THF (3 mL) was added slowly by stirring into a suspension of C$_3$H$_9$IS (942 mg, 4.62 mmol) in THF (5 mL) under N$_2$ at 15° C. After stirring at 20° C. for 30 min, M-1-21_1 (500 mg, 3.56 mmol) in 2 ml of THF was added dropwise to the mixture at 0° C. After addition, the mixture was stirred at 20° C. for 16 hrs, quenched with sat. NH$_4$Cl (40 mL) without monitor and extracted with MTBE (3×20 mL). The combined organic phase was washed with brine (2×60 mL), dried over Na$_2$SO$_4$, filtered, and concentrated at 40° C. under reduced pressure to give M-1-21_2 (360 mg, crude) as a liquid.

$^1$H NMR (400 MHz, CDCl$_3$) δ 4.47-4.42 (m, 4H), 2.61 (s, 2H), 2.06-1.90 (m, 4H), 1.68-1.58 (m, 2H), 1.51-1.41 (m, 2H).

Synthesis of M-1-21_3

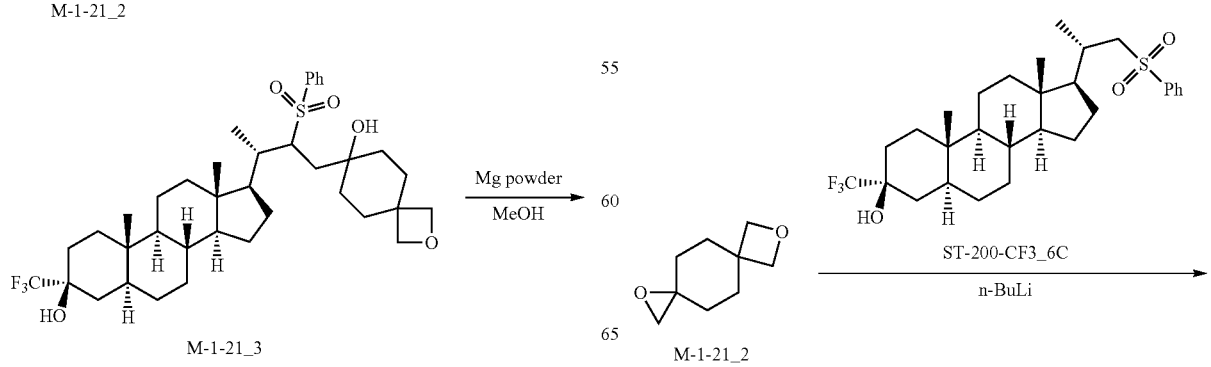

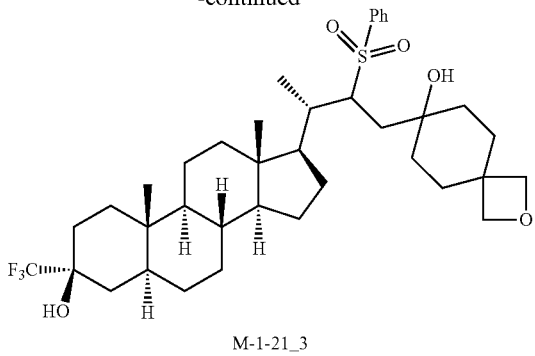

M-1-21_3

A solution of n-BuLi (0.472 mL, 2.5 M in hexane, 1.18 mmol) was added to THF (0.5 mL). A solution of ST-200-CF3_6C (250 mg, 0.474 mmol) in THF (2.5 mL) was added at −70° C. After stirring at −70° C. for 1 h, M-1-21_2 (109 mg, 0.711 mmol) was added at −70° C. The mixture was stirred at −70° C. for another 1 h and then warmed to 15° C. for 16 hrs. The reaction mixture was quenched with NH₄Cl (50 mL, sat. aq) and extracted with EtOAc (2×30 mL). The organic layer was separated, dried over Na₂SO₄, filtered, and concentrated to give M-1-21_3 (250 mg, crude) as a solid, which was used for next step directly.

Synthesis of 5009

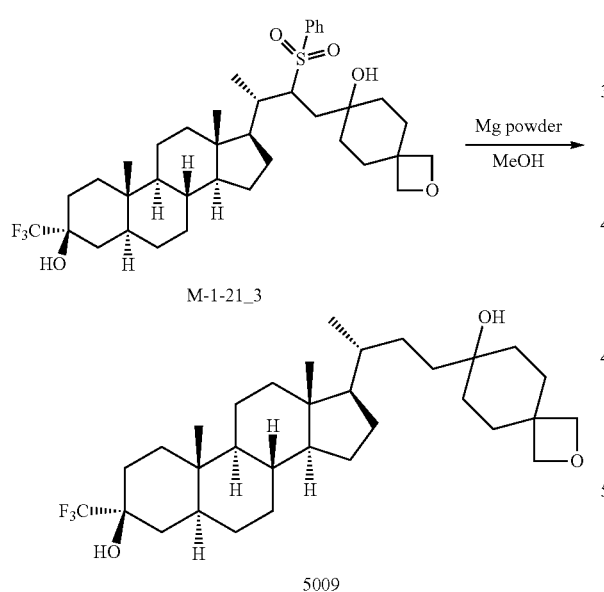

NiCl₂ (9.49 mg, 0.0733 mmol) and Mg powder (350 mg, 14.6 mmol) were added in one portion to a solution of M-1-21_3 (250 mg, 0.367 mmol) in MeOH (30 mL) at 65° C. The mixture was stirred at 65° C. for 10 minutes. Then another Mg powder (178 mg, 7.34 mmol) was added at 65° C. in one portion. After stirring at 65° C. for another 10 minutes, the mixture was quenched with HCl (50 mL, 2N) until the reaction became clear and extracted with EtOAc (3×20 mL). The combined organic layer was washed with sat. NH₄Cl (50 mL), NaHCO₃ (50 mL), dried over Na₂SO₄, filtered, concentrated and purified by silica gel chromatography (0-15% of EtOAc in PE) to give impure 5009 (200 mg,), which was further purified by combi-flash (0-10% of Acetone in DCM) then recrystallized to give 120 mg still impure product. DMAP (13.4 mg, 0.11 mmol) and BzCl (77.3 mg, 0.550 mmol) were added to a solution of impure 5009 (60 mg, 0.110 mmol) in Py (5 mL). The reaction mixture was stirred at 20° C. for 2 hrs. The reaction was quenched with sat. NH₄Cl (30 mL) and extracted with MTBE (2×15 mL). The combined organic phase was washed with brine (40 mL), dried over Na₂SO₄, filtered, concentrated, and purified by prep-TLC (PE:EtOAc=5:1) to give desired product (40 mg, 56%) as a solid. To a solution of above (40 mg, 0.062 mmol) in MeOH (3 mL), THF (1 mL) and H₂O (1 mL) was added NaOH (49.5 mg, 1.24 mmol). After stirring at 50° C. for 1 h, the reaction mixture was quenched with water (5 mL) and extracted with EtOAc (2×3 mL). The combined organic phase was dried over Na₂SO₄, filtered, concentrated and purified by combi-flash (0-30% of EtOAc in PE) to give 5009 (17 mg, 50%) as a solid.

¹H NMR (400 MHz, CDCl₃) δ 3.73 (s, 2H), 3.31 (s, 2H), 2.10-1.90 (m, 3H), 1.88-1.72 (m, 4H), 1.71-1.58 (m, 5H), 1.56-1.41 (m, 7H), 1.40-1.31 (m, 5H), 1.30-1.15 (m, 7H), 1.14-0.93 (m, 5H), 0.92-0.86 (m, 4H), 0.85 (s, 3H), 0.70-0.60 (m, 4H).

LCMS Rt=1.282 min in 2.0 min chromatography, 30-90AB_E, purity 100%.

MS 50-100_1_4 min·m, MS ESI calcd. for C₃₂H₅₀F₃O₂ [M+H−H₂O]⁺ 523, found 523.

Example 51: Synthesis of 5131

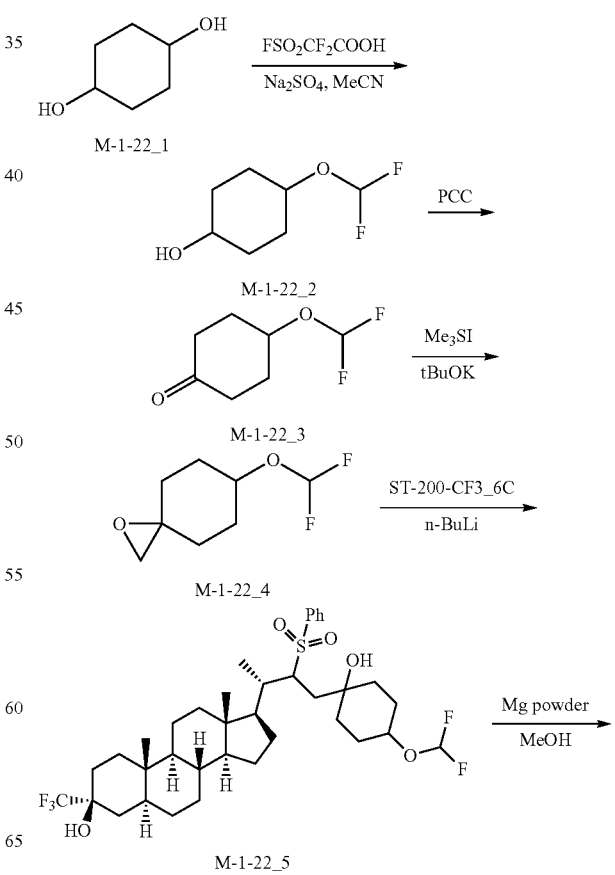

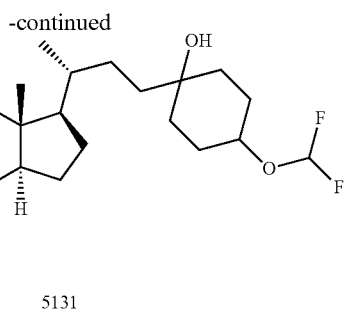

5131

The synthesis of ST-200-CF3_6C can be found in Example 5.

Synthesis of M-1-22_2

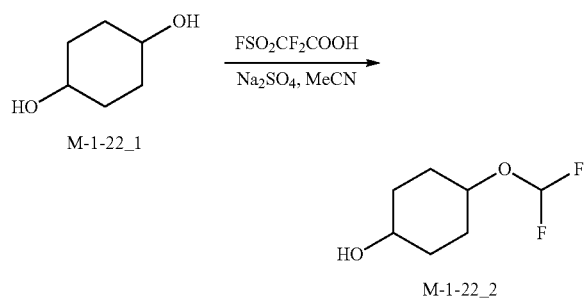

A solution of FSO₂CF₂COOH (18.3 g, 103 mmol) in CH₃CN (30 mL) was added dropwise over a period of 1 hour to a mixture of M-1-22_1 (10 g, 86 mmol) and Na₂SO₄ (6.1 g, 43 mmol) in CH₃CN (120 mL) at 40 to 45° C. After addition, the solution was poured into water (200 mL). The aqueous phase was extracted with DCM (3×100 mL). The combined organic phase was washed with saturated brine (2×200 mL), dried over anhydrous Na₂SO₄, filtered, concentrated and purified by flash column (0~100% of EtOAc in PE) to give M-1-22_2 (6 g, crude) as an oil.

¹H NMR (400 MHz, CDCl₃) δ 6.42-6.02 (m, 1H), 4.30-4.10 (m, 1H), 3.80-3.60 (m, 1H), 2.20-1.30 (m, 8H).

Synthesis of M-1-22_3

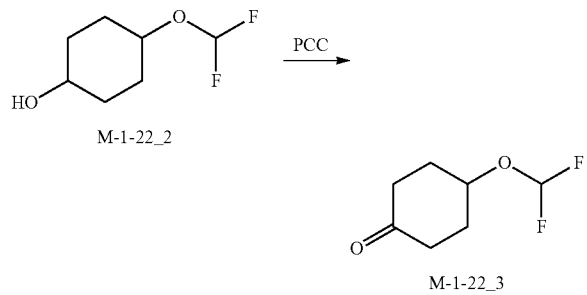

Silica gel (5 g) and PCC (15.5 g, 72.2 mmol) were added to a suspension of M-1-22_2 (6 g, 36.1 mmol) in DCM (100 mL) at 20° C. After stirring at 20° C. for 2 hours, the mixture was filtered and the filter cake was washed with DCM (100 mL). The combined filtrate was concentrated in vacuum and purified by flash column (0100% of EtOAc in PE) to give crude product M-1-22_3 (3.5 g, 59%) as a oil.

¹H NMR (400 MHz, CDCl₃) δ 6.52-6.10 (m, 1H), 4.65-4.55 (m, 1H), 2.70-2.55 (m, 2H), 2.40-2.25 (m, 2H), 2.23-2.11 (m, 2H), 2.10-1.98 (m, 2H).

Synthesis of M-1-22_4

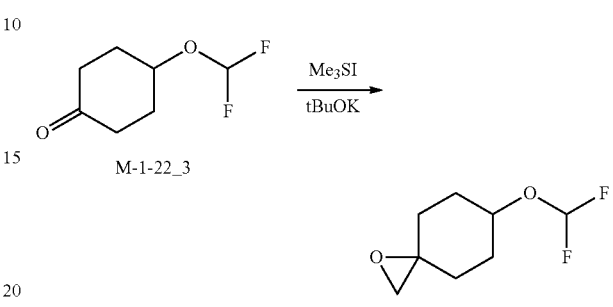

M-1-22_3 (3.1 g, 18.8 mmol) was added to a stirred solution of trimethylsulfoxonium iodide (4.97 g, 24.4 mmol) and t-BuOK (4.21 g, 37.6 mmol) in THF (60 mL) at 0° C. After stirring at 20° C. for 16 hours, the reaction mixture was poured into saturated aqueous NH₄Cl (90 mL) and extracted with EtOAc (3×120 mL). The combined organic layers were washed with brine (120 mL), dried over anhydrous Na₂SO₄, filtered and concentrated to give M-1-22_4 (1.9 g, crude) as an oil, which was purified by combi-flash (0-10% of EtOAc in PE) to give pure M-1-22_4 (300 mg, 23%) as an oil.

¹H NMR (400 MHz, CDCl₃) δ 6.50-6.02 (m, 1H), 4.46-4.35 (m, 0.6H), 4.33-4.23 (m, 0.4H), 2.65 (s, 2H), 2.07-1.86 (m, 5H), 1.74-1.58 (m, 2H), 1.47-1.36 (m, 1H).

Synthesis of M-1-22_5

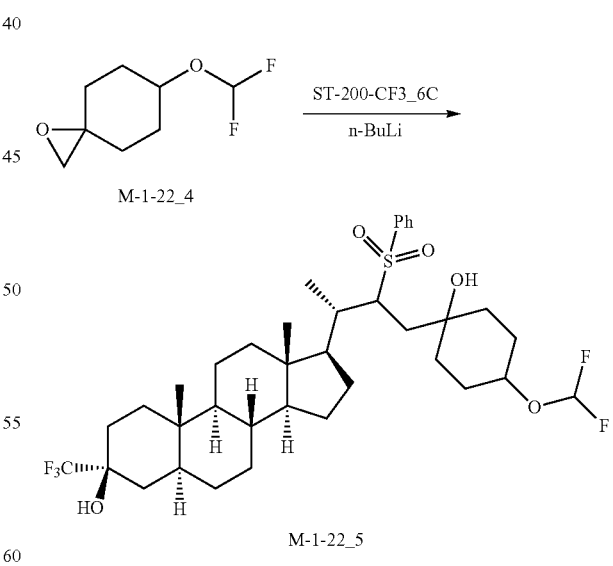

A solution of n-BuLi (378 µL, 2.5 M in hexane, 0.947 mmol) was added to THF (0.5 mL). A solution of ST-200-CF3_6C (200 mg, 0.379 mmol) in THF (2 mL) was added at −70° C. The mixture was stirred at −70° C. for 1 h. M-1-22_4 (101 mg, 0.568 µmol) was added. After stirring at −70° C. for 1 h and 15° C. for 16 hours, the reaction mixture was quenched with sat.NH$_4$Cl (10 mL) and extracted with EtOAc (2×5 mL). The organic layer was separated, dried over anhydrous Na$_2$SO$_4$, filtered and concentrated to give M-1-22_5 (200 mg, crude) as a solid, which was used for the next step directly.

Synthesis of 5131

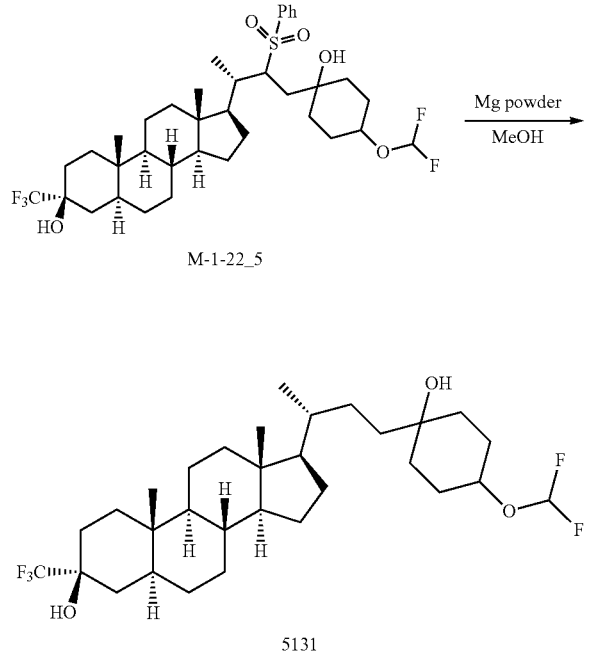

NiCl$_2$ (7.13 mg, 0.0566 mmol) and Mg powder (270 mg, 11.3 mmol) were added in one portion to a solution of M-1-22_5 (200 mg, 0.283 mmol) in MeOH (30 mL) at 65° C. After stirring at 65° C. for 10 minutes, another batch of Mg powder (135 mg, 5.66 mmol) was added at 65° C. in one portion. The mixture was stirred at 65° C. for another 10 minutes, cooled to 20° C., quenched by HCl (20 mL, 2 M) and extracted with EtOAc (3×15 mL). The combined organic layers were washed with saturated aqueous NH$_4$Cl (50 mL), brine (50 mL), dried over anhydrous Na$_2$SO$_4$, filtered and concentrated to give a crude, which was purified by combi-flash (0-15% of EtOAc in PE) to give 5131 (2 mg, 1.25%, 5131) as a solid.

$^1$H NMR (400 MHz, CDCl$_3$) δ 6.45-6.02 (m, 1H), 4.12-4.00 (m, 1H), 2.11-2.02 (m, 1H), 1.97-1.92 (m, 2H), 1.85-1.77 (m, 6H), 1.71-1.62 (m, 5H), 1.51-1.43 (m, 4H), 1.41-1.34 (m, 5H), 1.33-1.25 (m, 4H), 1.24-1.19 (m, 2H), 1.16-0.99 (m, 7H), 0.93-0.87 (m, 4H), 0.84 (s, 3H), 0.68-0.63 (m, 4H).

LCMS Rt=5.826 min in 10.0 min chromatography, 50-100AB_E, purity 96.3%.

MS 50-100_1_4 min·m, MS ESI calcd. for C$_{31}$H$_{48}$F$_5$O$_2$ [M+H−H$_2$O]$^+$ 547, found 547.

Example 52: Synthesis of 5294

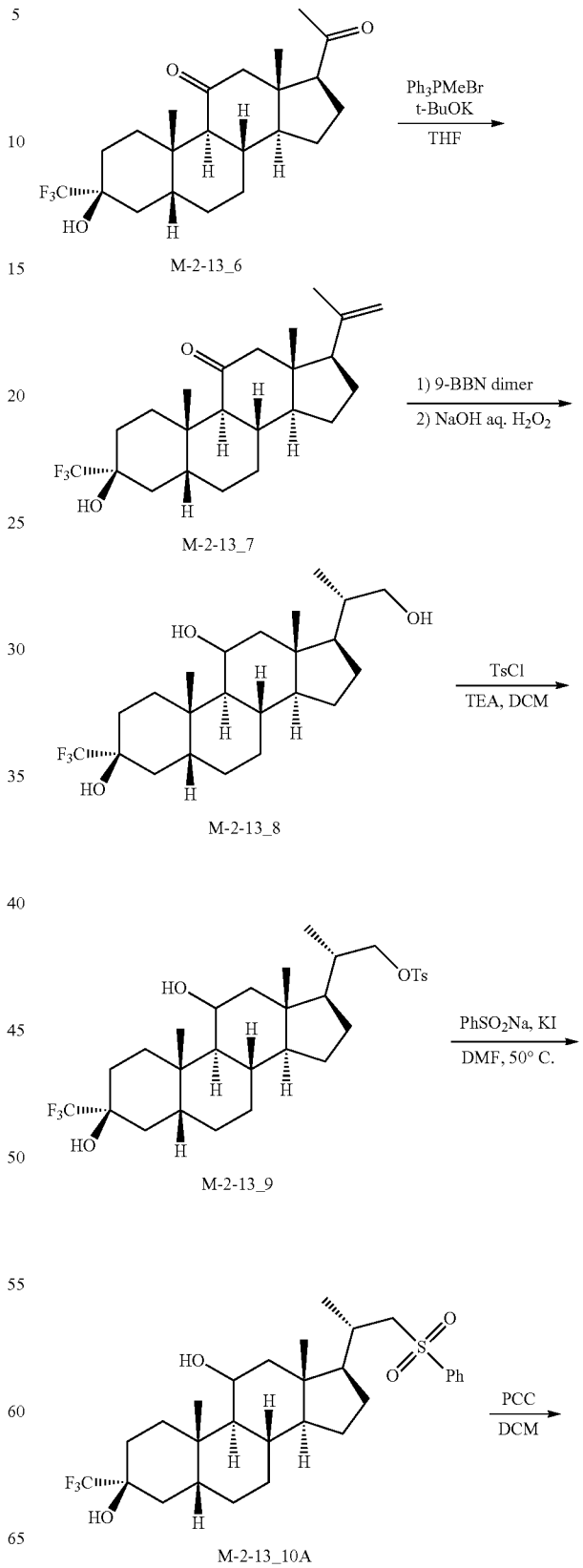

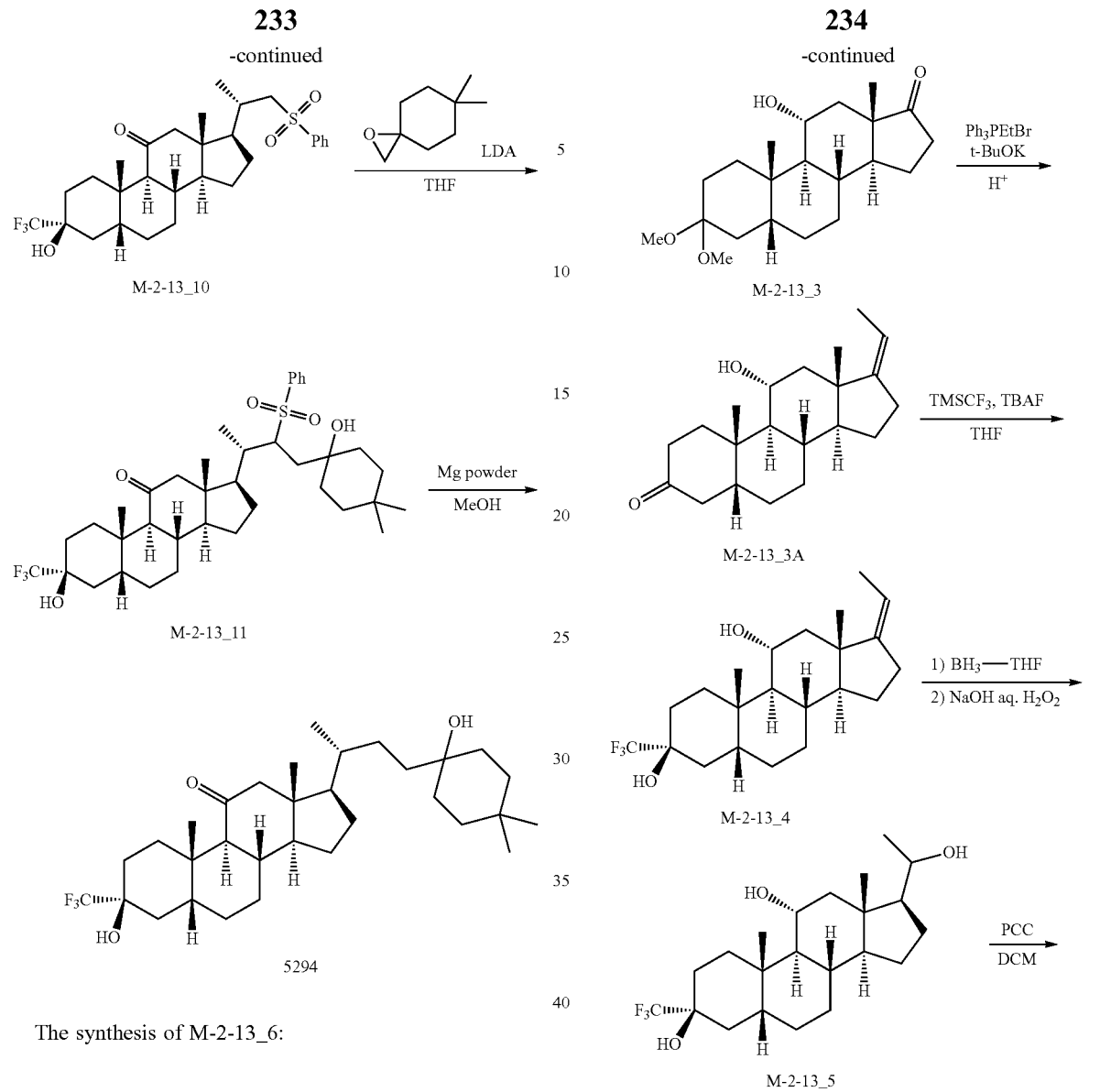

The synthesis of M-2-13_6:

To a solution of M-2-13_1 (50 g, 165 mmol) in THF (500 mL) was added Pd/C (5 g, 10%) and pyridine (2.5 mL). Then the solution was hydrogenated under H₂ balloon at 25° C. for 16 hrs. The mixture was filtered through a pad of celite and the filtrate was concentrated. The residue was dissolved in CH₂Cl₂ (500 mL), washed with aq HCl (100 mL, 1M), brine (300 mL), dried over anhydrous Na₂SO₄, filtered and concentrated in vacuum to afford M-2-13_2 (63 g, crude) as an oil.

¹H NMR (400 MHz, CDCl₃) δ 4.08-3.95 (m, 1H), 2.82-2.72 (m, 1H), 2.71-2.58 (m, 2H), 2.52-2.31 (m, 1H), 2.31-

2.21 (m, 1H), 2.21-2.03 (m, 4H), 2.02-1.87 (m, 2H), 1.70-1.60 (m, 3H), 1.58-1.45 (m, 3H), 1.43-1.22 (m, 4H), 1.14 (s, 3H), 0.88 (s, 3H).

To a suspension of M-2-13_2 (43 g, 141 mmol) in MeOH (200 mL) was added 4-methylbenzenesulfonic acid (2.42 g, 14.1 mmol) at 25° C. under $N_2$. The mixture was stirred at 60° C. for 16 hrs. The reaction mixture was quenched with TEA (2 mL) and concentrated in vacuum to give M-2-13_3 (50 g, crude) as an oil, which was used directly for next step without further purification.

To a suspension of EtPPh$_3$Br (158 g, 426 mmol) in THF (300 mL) was added t-BuOK (47.8 g, 426 mmol) at 25° C. under $N_2$. The mixture was stirred at 60° C. for 30 mins. To the mixture was added M-2-13_3 (50 g, 142 mmol) in THF (300 mL) at 60° C. The mixture was stirred at 60° C. for 16 hrs. The mixture was added sat.NH$_4$Cl solution (200 mL) and extracted with EtOAc (2×200 mL). The combined organic layer was dried over Na$_2$SO$_4$, filtered and concentrated in vacuum to give crude product (200 g), which was used directly in next step without further purification. To a solution of the 200 g crude product in THF (500 mL) was added HCl (137.0 mL, 2 M in THF) at 25° C. The reaction was stirred at 25° C. for 1 h. The reaction was quenched with sat.NaHCO$_3$ solution (200 mL) and extracted with EtOAc (2×200 mL). The combined organic layer was dried over Na$_2$SO$_4$, filtered and concentrated in vacuum to give crude product (220 g). The crude product was purified by a silica gel column (PE/EtOAc=10/1-6/1) to give M-2-13_3A (43 g, impure), which was triturated with (PE/EtOAc=1/1) to give M-2-13_3A (18 g, pure, 42%) as a solid.

$^1$H NMR (400 MHz, CDCl$_3$) δ 5.19-5.08 (m, 1H), 4.06-3.96 (m, 1H), 2.80-2.57 (m, 4H), 2.44-2.33 (m, 1H), 2.28-2.14 (m, 2H), 2.03-1.96 (m, 1H), 1.94-1.76 (m, 3H), 1.68-1.64 (m, 4H), 1.61-1.50 (m, 3H), 1.44-1.19 (m, 5H), 1.14 (s, 3H), 1.03-1.00 (m, 1H), 0.90 (s, 3H). To a solution of M-2-13_3A (8.7 g, 27.4 mmol) in THF (100 mL) was added TBAF (2.05 mL, 2.05 mmol, 1M in THF) and TMSCF$_3$ (7.79 g, 54.8 mmol) under $N_2$ at 10° C. The mixture was stirred at 10° C. for 1 h. To the mixture was added TBAF solution (82.1 mL, 82.1 mmol, 1M in THF). The mixture was stirred at 25° C. for another 1 h. The mixture was concentrated in vacuum. The residue was dissolved in EtOAc (100 mL), washed with water (2×100 mL), dried over Na$_2$SO$_4$, filtered, concentrated in vacuum to afford crude product, which was combined with the batch of 6.9 g of crude product (prepared from 5.8 g of M-2-13_3A) and purified by a silica gel column (PE/EtOAc=8/1-3/1) to give M-2-13_4 (1.1 g, 6%) as colorless oil and M-2-13_4A (9.3 g, 53%) as a solid

M-2-13_4:

$^1$H NMR (400 MHz, CDCl$_3$) δ 5.17-5.08 (m, 1H), 4.01-3.89 (m, 1H), 2.62-2.56 (m, 1H), 2.44-2.32 (m, 2H), 2.28-2.15 (m, 1H), 2.00-1.88 (m, 3H), 1.87-1.73 (m, 3H), 1.69-1.59 (m, 6H), 1.55-1.25 (m, 6H), 1.23-1.13 (m, 2H), 1.09 (s, 3H), 0.95-0.89 (m, 1H), 0.87 (s, 3H).

M-2-13_4A:

1H NMR (400 MHz, CDCl$_3$) δ 5.18-5.07 (m, 1H), 4.02-3.88 (m, 1H), 2.59 (dd, J=11.8 Hz, J=5.0 Hz, 1H), 2.46-2.30 (m, 2H), 2.29-2.13 (m, 1H), 2.02 (s, 1H), 1.99-1.73 (m, 5H), 1.70-1.61 (m, 4H), 1.55-1.26 (m, 8H), 1.23-1.13 (m, 2H), 1.09 (s, 3H), 0.94 (d, J=6.4 Hz, 1H), 0.87 (s, 3H).

To a solution of M-2-13_4 (1.1 g, 2.84 mmol) in THF (30 mL) was added Borane-tetrahydrofuran complex (11.3 mL, 11.3 mmol, 1 M in THF) at 25° C. under $N_2$. The solution was stirred at 25° C. for 1 h. After cooling to 0° C., a solution of EtOH (30 mL) and NaOH (5.67 mL, 5M in H$_2$O, 28.4 mmol) was added very slowly. After addition, H$_2$O$_2$ (2.84 mL, 28.4 mmol, 30% in water) was added slowly and the inner temperature was maintained below 10° C. The mixture was stirred at 25° C. under $N_2$ for 1 h. Water (100 mL) was added to the solution and extracted with EtOAc (2×50 mL). The combined organic layer was washed sat. Na$_2$S$_2$O$_3$ solution (50 mL), dried over Na$_2$SO$_4$, filtered and concentrated in vacuum to give M-2-13_5 (1 g, crude) as colorless oil, which was directly used for next step.

$^1$H NMR (400 MHz, CDCl$_3$) δ 3.95-3.78 (m, 1H), 3.72-3.65 (m, 1H), 2.71-2.62 (m, 1H), 2.47-2.40 (m, 1H), 2.19-2.11 (m, 1H), 2.10-2.05 (m, 1H), 2.04-2.01 (m, 1H), 2.00-1.84 (m, 3H), 1.77-1.62 (m, 5H), 1.50-1.27 (m, 10H), 1.21-1.14 (m, 3H), 1.11 (s, 3H), 0.98-0.93 (m, 1H), 0.67 (s, 3H).

To a solution of M-2-13_5 (1 g, 2.47 mmol) in DCM (30 mL) was added silica gel (3 g) and PCC (2.65 g, 12.3 mmol) at 25° C. The reaction was stirred at 25° C. for 16 hrs. The reaction mixture was filtered and the filtrate was concentrated in vacuum to give crude product which was purified by a silica gel column (PE/EtOAc=5/1) to give M-2-13_6 (720 mg, 73%) as a solid. The solid was triturated with MeCN (10 mL) to afford M-2-13_6 (12 mg) as a solid and organic layer was concentrated in vacuum to afford M-2-13_6 (700 mg, 99%) as a solid which was used directly for next step.

$^1$H NMR (400 MHz, CDCl$_3$) δ 2.75 (t, J=9.0 Hz, 1H), 2.63-2.43 (m, 3H), 2.33-2.17 (m, 2H), 2.10 (s, 3H), 2.02-1.75 (m, 6H), 1.74-1.70 (m, 1H), 1.68 (s, 1H), 1.66-1.58 (m, 1H), 1.53-1.22 (m, 7H), 1.21 (s, 3H), 0.58 (s, 3H).

LCMS Rt=0.911 min in 2 min chromatography, 30-90 AB, purity 100%, MS ESI calcd. For $C_{22}H_{32}F_3O_3[M+H]^+$ 401, found 401.

Synthesis of M-2-13_7

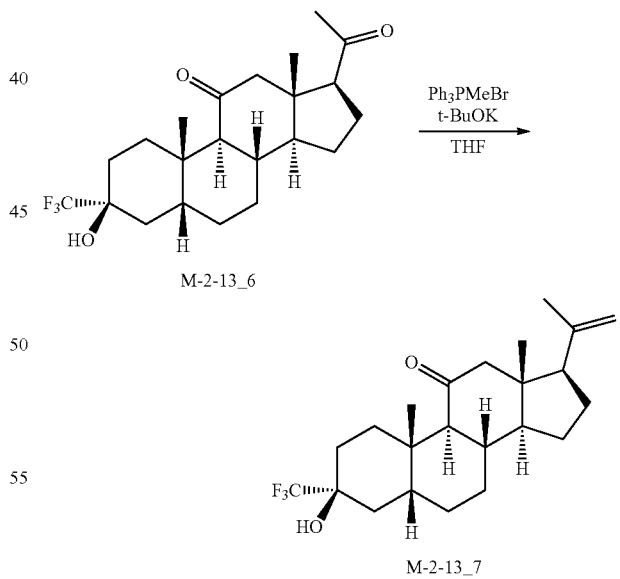

t-BuOK (835 mg, 7.45 mmol) was added to a suspension of MePPh$_3$Br (2.66 g, 7.45 mmol) in THF (30 mL) at 25° C. under $N_2$. After stirring at 50° C. for 30 mins, the mixture was added to a solution of M-2-13_6 (600 mg, 1.49 mmol) in THF (30 mL) at 25° C. The mixture was stirred at 25° C. for 16 hrs. The mixture was quenched with sat.NH$_4$Cl solution (100 mL) and extracted with EtOAc (2×100 mL).

The combined organic layer was dried over Na$_2$SO$_4$, filtered and concentrated in vacuum to afford M-2-13_7 (4 g, crude) as an oil, which was purified by combi-flash (EtOAc in PE, 10%) to afford M-2-13_7 (540 mg, 12%) as a solid.

$^1$H NMR (400 MHz, CDCl$_3$) δ 4.89 (s, 1H), 4.71 (s, 1H), 2.53-2.20 (m, 6H), 2.02-1.73 (m, 7H), 1.72-1.60 (m, 5H), 1.56-1.23 (m, 7H), 1.21 (s, 3H), 0.53 (s, 3H).

Synthesis of M-2-13_8

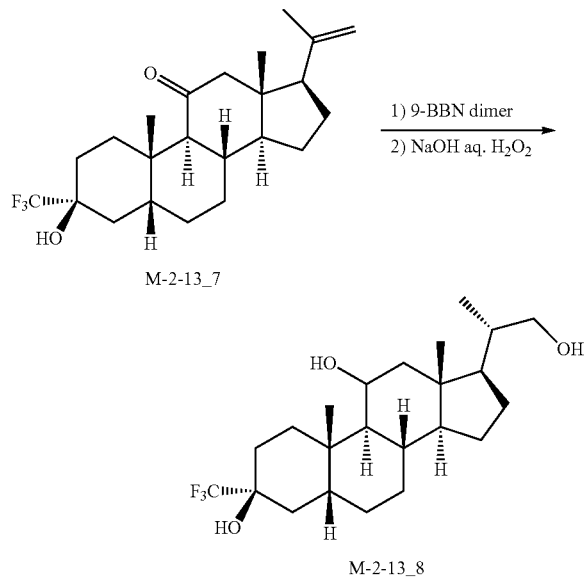

M-2-13_7

M-2-13_8

9-BBN dimer (988 mg, 4.05 mmol) was added to a solution of M-2-13_7 (540 mg, 1.35 mmol) in THF (20 mL) at 0° C. under N$_2$. The solution was stirred at 25° C. for 16 hrs. After cooling to 0° C., a solution of EtOH (10 mL) and NaOH (2.70 mL, 5M in H$_2$O, 13.5 mmol) were added very slowly. After addition, H$_2$O$_2$ (1.35 mL, 13.5 mmol, 30% in water) was added slowly and the inner temperature was maintained below 10° C. The mixture was stirred at 50° C. under N$_2$ for 1 h. The mixture was cooled to 30° C., diluted with water (30 mL) and extracted with EtOAc (2×50 mL). The combined organic layer was washed with sat. Na$_2$S$_2$O$_3$ (50 mL), dried over Na$_2$SO$_4$, filtered and concentrated in vacuum to give M-2-13_8 (2 g, crude) as an oil, which was directly used in next step without further purification.

Synthesis of M-2-13_9

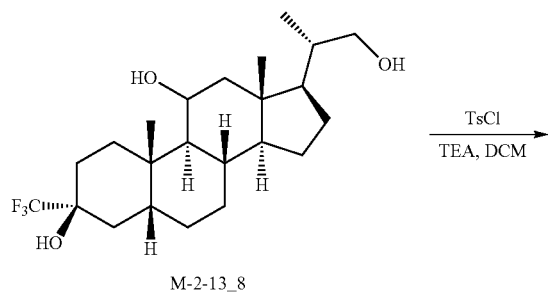

M-2-13_8

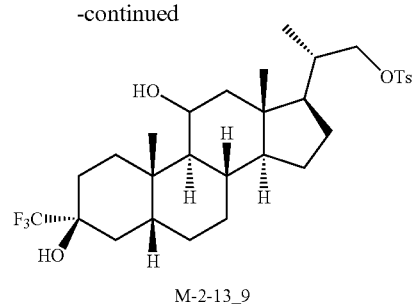

M-2-13_9

TsCl (4.55 g, 23.9 mmol) was added to a solution of M-2-13_8 (2 g, crude) in DCM/TEA (16 mL/2.3 mL) at 25° C. The mixture was stirred at 40° C. for 2 hrs. The reaction was quenched with water (20 mL) and extracted with DCM (2×30 mL). The combined organic layer was washed with brine (2×50 mL), dried over Na$_2$SO$_4$, filtered and concentrated to afford crude product, which was purified by combi-flash column (EtOAc in PE, 12%~15%) to afford M-2-13_9 (580 mg, 21%) as an oil.

$^1$H NMR (400 MHz, CDCl$_3$) δ 7.78 (d, J=8.4 Hz, 2H), 7.34 (d, J=8.0 Hz, 2H), 4.15-4.13 (m, 1H), 3.98-3.94 (m, 1H), 3.81-3.76 (m, 1H), 2.45 (s, 3H), 2.12-2.06 (m, 1H), 2.02-1.89 (m, 3H), 1.85-1.63 (m, 8H), 1.53-1.29 (m, 6H), 1.22 (s, 3H), 1.19-1.02 (m, 6H), 0.99 (d, J=6.8 Hz, 3H), 0.85 (s, 3H).

Synthesis of M-2-13_10A

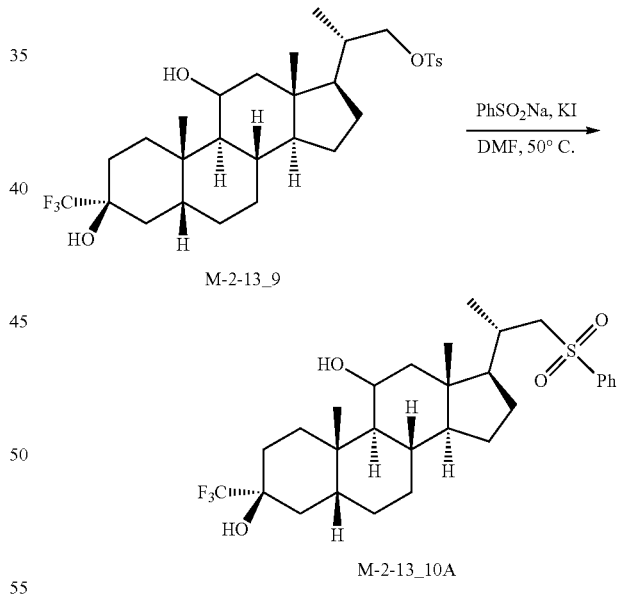

M-2-13_9

M-2-13_10A

KI (838 mg, 5.05 mmol) was added to a solution of M-2-13_9 (580 mg, 1.01 mmol) in DMF (6 mL) at 25° C. under N$_2$. After stirring at 50° C. for 2 hours under N$_2$, the reaction mixture was treated with PhSO$_2$Na (820 mg, 5.00 mmol) and stirred at 50° C. for 16 hrs. The reaction mixture was cooled to 25° C. and treated with water (50 mL). The aqueous phase was extracted with EtOAc (2×50 mL). The combined organic phase was washed with saturated brine (2×100 mL), dried over anhydrous Na$_2$SO$_4$, filtered, concentrated and purified by a silica gel column (PE/EtOAc=8/1~5/1) to afford M-2-13_10A (460 mg, 85%) as a solid.

¹H NMR (400 MHz, CDCl₃) δ 7.93-7.88 (m, 2H), 7.68-7.62 (m, 1H), 7.60-7.53 (m, 2H), 4.15-4.12 (m, 1H), 3.15-3.09 (m, 1H), 2.87-2.80 (m, 1H), 2.13-2.07 (m, 2H), 2.03-1.89 (m, 3H), 1.83-1.64 (m, 6H), 1.47-1.27 (m, 5H), 1.23-1.18 (m, 7H), 1.18-0.95 (m, 7H), 0.87 (s, 3H).

Synthesis of M-2-13_10

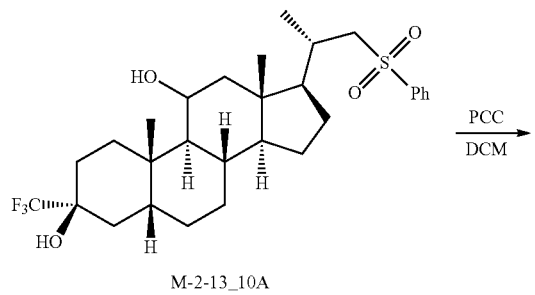

M-2-13_10A

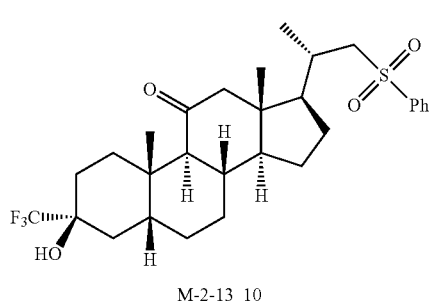

M-2-13_10

Silica gel (600 mg) and PCC (571 mg, 2.65 mmol) were added to a solution of M-2-13_10A (480 mg, 0.884 mmol) in DCM (15 mL) at 25° C. After stirring at 25° C. for 16 hrs, the reaction mixture was filtered and the filtrate was concentrated in vacuum to afford crude product, which was purified by combi-flash column (EtOAc in PE, 15%) to afford M-2-13_10 (280 mg, 59%) as a solid.

¹H NMR (400 MHz, CDCl₃) δ 7.93-7.88 (m, 2H), 7.69-7.62 (m, 1H), 7.60-7.54 (m, 2H), 3.13-3.08 (m, 1H), 2.92-2.82 (m, 1H), 2.61-2.54 (m, 1H), 2.32-2.28 (m, 1H), 2.23-2.16 (m, 1H), 2.14-2.01 (m, 1H), 1.98-1.84 (m, 4H), 1.78-1.65 (m, 5H), 1.53-1.32 (m, 6H), 1.27-1.24 (m, 4H), 1.19 (s, 3H), 1.14 (d, J=6.4 Hz, 3H), 0.62 (s, 3H).

Synthesis of M-2-13_11

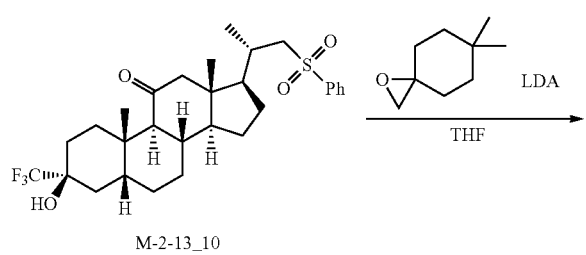

M-2-13_10

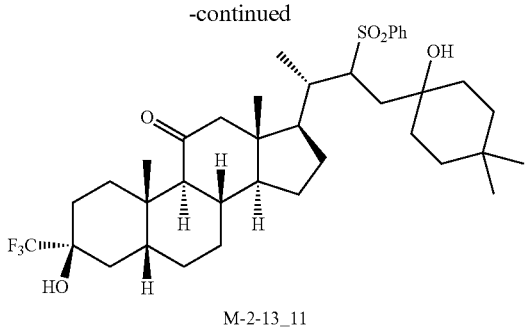

M-2-13_11

DIPA (233 mg, 2.31 mmol) and n-BuLi (0.852 mL, 2.5 M in hexane, 2.13 mmol) were added to THF (0.5 mL) at −78° C. under N₂. The mixture was warmed to 0° C. After re-cooling to −78° C., a solution of M-2-13_10 (330 mg, 0.610 mmol) in THF (2.5 mL) was added. The mixture was stirred at −78° C. for 1 h and treated with 6,6-dimethyl-1-oxaspiro[2.5]octane (128 mg, 0.915 mmol). The mixture was stirred at −78° C. for another 1 h, warmed to 25° C. and stirred at 25° C. for 16 hrs. The reaction mixture was quenched with NH₄Cl (50 mL, sat. aq) and extracted with EtOAc (2×30 mL). The organic layer was separated, dried over Na₂SO₄, filtered, and concentrated to give crude product (380 mg) as an oil, which was used directly for next step without further purification.

Synthesis of 5294

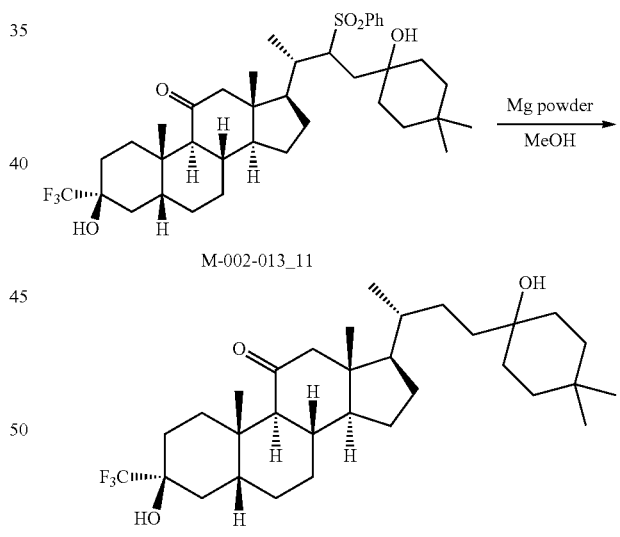

Mg powder (1.07 g, 44.6 mmol) was added to a solution of M-002-013_11 (380 mg, 0.558 mmol) in 40 mL of dry methanol under N₂ at 60° C. The reaction mixture was quenched with HCl (50 mL, 1 M in H₂O) dropwise at 10° C. until solid was dissolved. After extracting with DCM (2×100 mL), the organic layer was washed with sat. NaHCO₃ (50 mL), brine (50 mL), dried over Na₂SO₄, filtered and concentrated. The residue was purified by flash column eluted with PE/EtOAc=10/1-8/1 to give 5294 (35 mg, impure) as an oil. 5294 (35 mg, impure) was purified by a silica gel column (PE/EtOAc=10/1-8/1) to give 5294 (20 mg, impure) as an oil. 5294 (20 mg, 0.037 mmol) was purified by a silica gel column (DCM/acetone=40/1) for the third time to give 5294 (18 mg, impure) as an oil. The impure 5294 (18 mg, impure) was purified by prep. HPLC (column: Xtimate C18 150*25 mm*5 um, gradient: 90-100% B (A=0.1% TFA-ACN, B=acetonitrile), flow rate: 30 mL/min) to give 5294 (1.9 mg, 11%) as a solid.

1H NMR (400 MHz, CDCl$_3$) δ 2.59-2.43 (m, 2H), 2.37-2.16 (m, 2H), 2.05-1.84 (m, 3H), 1.76-1.65 (m, 3H), 1.51-1.38 (m, 14H), 1.26-1.20 (m, 14H), 0.93 (s, 3H), 0.91-0.86 (m, 7H), 0.63 (s, 3H).

LCMS Rt=1.284 min in 2 min chromatography, 30-90 AB, purity 100%, MS ESI calcd. For C$_{32}$H$_{50}$F$_3$O$_2$ [M+H–H$_2$O]$^+$ 523, found 523.

Example 53. Biological Data

Experiments were conducted as described in Example 2. The results are shown in Table 2-59.

TABLE 2-59

| Compound | Avg EC50 2A (nM) | Avg Emax 2A (%) | Avg EC50 2B (nM) | Avg Emax 2B (%) |
|---|---|---|---|---|
| 1839 | 295.4 | 493.3 | 148.2 | 568.5 |
| 1 | 144.9 | 887.0 | 70.9 | 441.9 |
| 2 | 162.7 | 708.9 | 147.1 | 605.2 |
| 2A | 157.9 | 652.6 | 339.1 | 1239.9 |
| 2B | 130.7 | 624.6 | 142.8 | 965.3 |

TABLE 2-59-continued
| Compound | Avg EC50 2A (nM) | Avg Emax 2A (%) | Avg EC50 2B (nM) | Avg Emax 2B (%) |
|---|---|---|---|---|
| 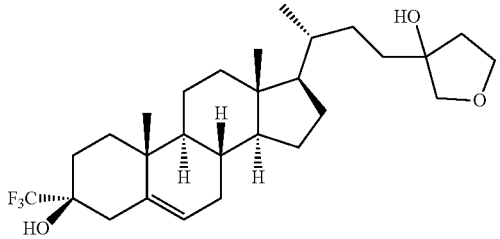 10 | 125.4 | 631.7 | 101.6 | 362.3 |
| 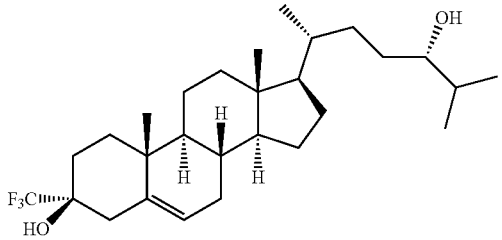 1-A | 109.4 | 274.6 | 81.2 | 250.1 |
| 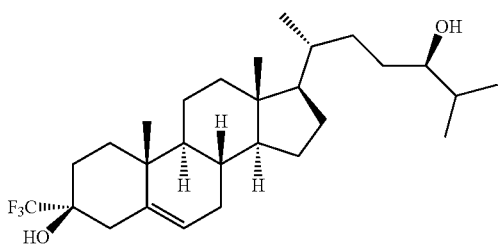 1-B | 31.6 | 262.5 | 33.6 | 284.6 |
| 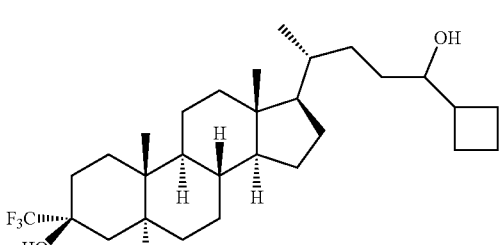 7 | 299.5 | 516.3 | 286.9 | 483.6 |
| 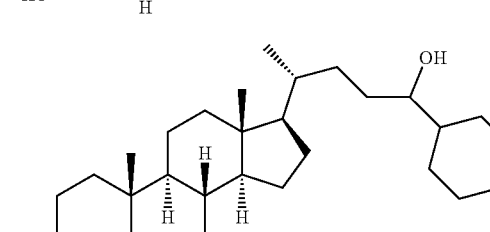 9 | 316.6 | 180.6 | 234.0 | 271.4 |
| 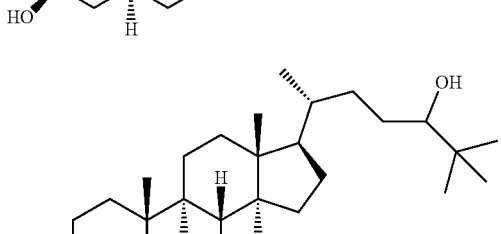 3 | 185.2 | 555.6 | 338.0 | 531.8 |

TABLE 2-59-continued

| Compound | Avg EC50 2A (nM) | Avg Emax 2A (%) | Avg EC50 2B (nM) | Avg Emax 2B (%) |
|---|---|---|---|---|
| 1967 | 170.8 | 347.4 | 113.3 | 373.9 |
| 7-B | 346.8 | 355.7 | 305.8 | 352.1 |
| 7-A | 247.5 | 544.2 | 187.3 | 431.0 |
| 8 | 446.1 | 401.7 | 372.4 | 321.7 |
| 4 | 201.2 | 663.0 | 212.5 | 462.9 |
| 5 | 181.8 | 619.0 | 260.4 | 454.8 |

TABLE 2-59-continued

| Compound | Avg EC50 2A (nM) | Avg Emax 2A (%) | Avg EC50 2B (nM) | Avg Emax 2B (%) |
|---|---|---|---|---|
| 6 | 247.7 | 136.6 | 733.2 | 162.7 |
| 11 | 116.9 | 151.2 | 104.3 | 157.4 |
| 2080 | 165.1 | 77.2 | 186.9 | 146.9 |
| 2081 | 128.8 | 125.8 | 174.7 | 214.9 |
| 2184 | 65.8 | 233.7 | 80.0 | 257.5 |
| 2285 | 763.6 | 204.7 | 494.3 | 219.6 |

TABLE 2-59-continued

| Compound | Avg EC50 2A (nM) | Avg Emax 2A (%) | Avg EC50 2B (nM) | Avg Emax 2B (%) |
|---|---|---|---|---|
| 2392 | 104.4 | 230.1 | 47.5 | 166.2 |
| 2499 | 768.1 | 179.8 | 750.7 | 237.6 |
| 2500 | 63.3 | 302.6 | 91.1 | 300.1 |
| 2602 | 288.6 | 162.6 | 279.0 | 366.6 |
| 2706 | >10000 | 96.8 | 124.0 | 139.3 |

TABLE 2-59-continued

| Compound | Avg EC50 2A (nM) | Avg Emax 2A (%) | Avg EC50 2B (nM) | Avg Emax 2B (%) |
|---|---|---|---|---|
| 2707 | 119.0 | 112.8 | 102.7 | 259.0 |
| E-2817 | 5065.7 | 29.9 | 5373.5 | 20.4 |
| 2918 | 298.0 | 532.0 | 338.9 | 506.1 |
| 3035 | 61.0 | 323.4 | 75.7 | 611.3 |
| 3149 | 69.7 | 292.1 | 60.7 | 471.7 |
| 3266 | 147.5 | 82.6 | 377.4 | 134.7 |

TABLE 2-59-continued

| Compound | Avg EC50 2A (nM) | Avg Emax 2A (%) | Avg EC50 2B (nM) | Avg Emax 2B (%) |
|---|---|---|---|---|
| 3382 | 67.6 | 309.2 | 125.8 | 460.6 |
| 3495 | 96.7 | 107.2 | 168.4 | 145.9 |
| 3496 | 35.11 | 319.0 | 47.6 | 369.3 |
| 3507 | 165.0 | 165.5 | 190.7 | 241.1 |
| 3634 | 422.6 | 220.6 | 404.5 | 378.7 |
| 3788 | 1317.9 | 229.4 | 1121.4 | 410.2 |

TABLE 2-59-continued

| Compound | Avg EC50 2A (nM) | Avg Emax 2A (%) | Avg EC50 2B (nM) | Avg Emax 2B (%) |
|---|---|---|---|---|
| 3877 | >10000 | 42.4 | 512.1 | 71.1 |
| 3983 | 88.1 | 175.9 | 248.0 | 300.4 |
| 4023 | 515.9 | 322.1 | 405.7 | 418.3 |
| 4155 | 441.7 | 163.5 | 611.9 | 198.1 |
| 4156 | >10000 | 10.6 | >10000 | 20.1 |
| 4258 | 1025.3 | 183.9 | 640.5 | 241.7 |

TABLE 2-59-continued

| Compound | Avg EC50 2A (nM) | Avg Emax 2A (%) | Avg EC50 2B (nM) | Avg Emax 2B (%) |
|---|---|---|---|---|
| 4259 | >10000 | −13.3 | >10000 | 24.3 |
| 4360 | >10000 | 38.1 | >10000 | 14.6 |
| 4475 | 461.3 | 363.5 | 265.7 | 354.6 |
| 4476 | >10000 | −3.3 | >10000 | 10.4 |
| 4555 | >10000 | 22.8 | >10000 | 31.9 |
| 4656 | 1601.0 | 134.4 | 2164.5 | 122.0 |

TABLE 2-59-continued

| Compound | Avg EC50 2A (nM) | Avg Emax 2A (%) | Avg EC50 2B (nM) | Avg Emax 2B (%) |
|---|---|---|---|---|
| 4657 | 422.2 | 74.0 | 129.5 | 62.9 |
| 4799 | >10000 | 36.1 | 760.2 | 32.8 |
| 4805 | 356.1 | 175.3 | 362.3 | 129.4 |
| 4906 | >10000 | 8.8 | >10000 | 14.8 |
| 5009 | >10000 | 27.5 | >10000 | 14.5 |
| 5131 | 33.6 | 52.9 | >10000 | 39.0 |

TABLE 2-59-continued
| Compound | Avg EC50 2A (nM) | Avg Emax 2A (%) | Avg EC50 2B (nM) | Avg Emax 2B (%) |
|---|---|---|---|---|
| 5294 | >10000 | 32.4 | >10000 | 13.9 |
| 4585 | 214.6 | 72.2 | 166.3 | 123.0 |
| 3886 | 53.4 | 106.0 | 50.1 | 164.1 |
Example 54: Synthesis of Compound 154
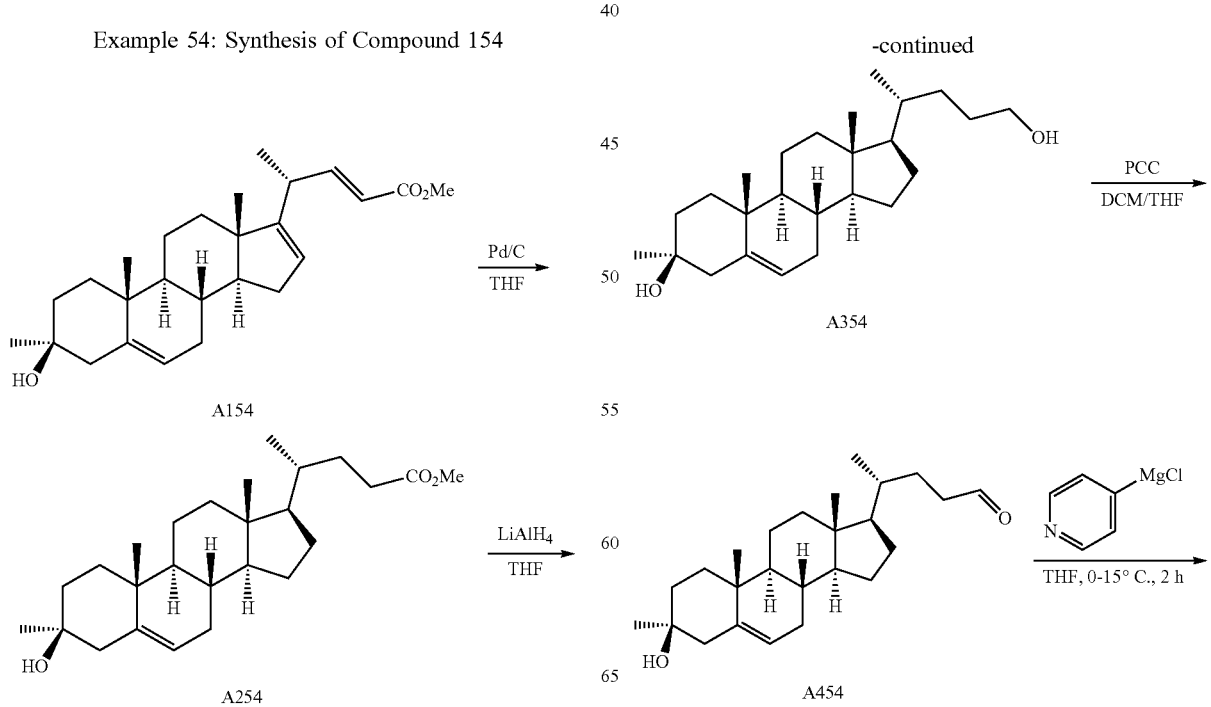

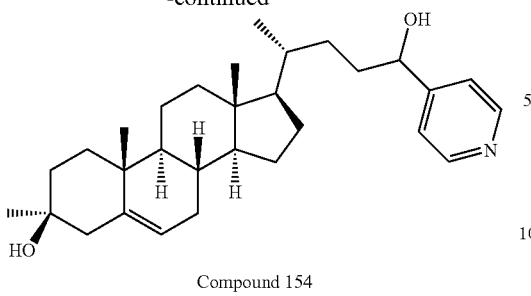

Compound 154

Step 1: To a solution of A154 (2 g, 5.01 mmol) (see WO2014/160480 for synthesis) and Pd/C (200 mg, 10%) in THF (30 mL) was hydrogenated under 15 psi of hydrogen at 25° C. for 3 h. The mixture was filtered through a pad of celite and the filtrate was concentrated in vacuum to afford crude A254 (1.8 g) as a solid.

Step 2: To a solution of A254 (1.8 g, 4.47 mmol) in THF (25 mL) was added a solution LiAlH$_4$ (339 mg, 8.94 mmol) in THF (5 mL) drop wise below 15° C. The solution was stirred at 15° C. for 2 h. The reaction was quenched by the addition of saturated aqueous NH$_4$Cl (20 mL) at 0° C. The resulting mixture was extracted with EtOAc (2×50 mL). The combined organic layer was washed with brine (2×30 mL) and concentrated in vacuum to afford crude A354 (1.6 g) as a solid.

Step 3: A mixture of A354 (1.6 g, 4.27 mmol) in DCM (10 mL) and THF (10 mL) was added PCC (2.27 g, 10.6 mmol) at 25° C. The reaction was stirred at 25° C. for 3 hrs. The solution was filtered and the filter cake was washed with DCM (25 mL). The combined filtrate was concentrated in vacuum. The residue was purified by silica gel column, eluting with PE/EtOAc=8/1 to give A454 (0.9 g, 54%) as a solid.

Step 4

Step 4a: Generation of 4-pyridylmagnesium Chloride Solution

To a suspension of 4-bromopyridine hydrochloride (1 g, 5.14 mmol) in THF (4 mL) was added isopropylmagnesium chloride (5.1 mL, 2 M in THF, 10.2 mmol) at 0° C. The mixture was stirred at 15° C. for 1 h. The 4-pyridylmagnesium chloride solution (ca. 0.5 M in THF) was used directly.

Step 4b: To a solution of A454 (100 mg, 0.268 mmol) in THF (1 mL) was added freshly prepared 4-pyridylmagnesium chloride (5.36 mL, ca. 0.5 M in THF, 2.68 mmol) at 0° C. The mixture was stirred at 15° C. for 1 h. To the mixture was added NH$_4$Cl (2 mL, 10% aq.). The mixture was extracted with EtOAc (10 mL). The organic layer was separated, purified by prep-TLC (DCM:MeOH=15:1), re-crystallized from MeCN (2 mL) and dried in vacuum to give Compound 154 (31 mg, 26%) as a solid.

$^1$H NMR (400 MHz, CDCl$_3$) δ 8.57 (d, J=4.4 Hz, 2H), 7.28-7.26 (m, 2H), 5.34-5.26 (m, 1H), 4.71-4.58 (m, 1H), 2.47-2.37 (m, 1H), 2.03-1.90 (m, 4H), 1.85-1.61 (m, 5H), 1.56-1.46 (m, 8H), 1.39-1.04 (m, 9H), 1.04-0.85 (m, 9H), 0.70-0.62 (m, 3H).

LCMS Rt=0.806 min in 2.0 min chromatography, 30-90AB, MS ESI calcd. for C$_{30}$H$_{46}$NO$_2$ [M+H]$^+$ 452, found 452.

Example 55. Synthesis of Compound 255

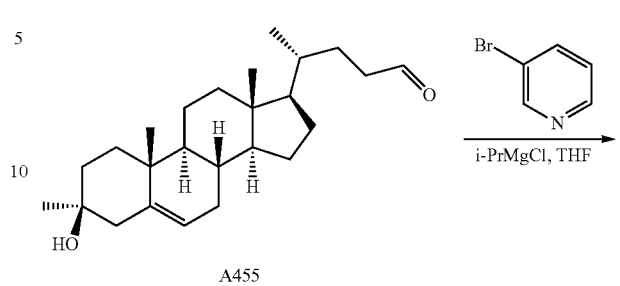

A455

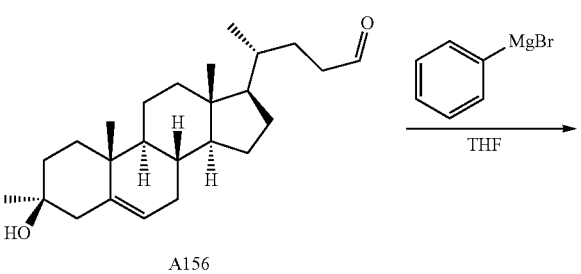

Compound 255

To a solution of 3-bromopyridine (423 mg, 2.68 mmol) in THF (10 mL) under N$_2$ was added i-PrMgCl (1.34 mL, 2.68 mmol, 2M) dropwise at 15° C. The reaction was stirred at 15° C. for 30 min. A solution of A455 (100 mg, 0.268 mmol) was added. The reaction was stirred at 15° C. for 2 h. The reaction was quenched with saturated NH$_4$Cl (20 mL), extracted with EtOAc (3×20 mL). The combined organic phase was washed with brine (50 mL), dried over Na$_2$SO$_4$, filtered and concentrated. The residue was purified by column chromatography (MeOH in DCM gradient, 0%-10%) to afford crude product (50 mg), which was then recrystallized from MeCN (15 mL) to afford Compound 255 (8 mg, 7% yield) as a solid.

$^1$H NMR (400 MHz, CDCl$_3$) δ 8.60-8.55 (m, 1H), 8.55-8.51 (m, 1H), 7.73-7.68 (m, 1H), 7.32-7.28 (m, 1H), 5.32-5.27 (m, 1H), 4.73-4.63 (m, 1H), 2.45-2.37 (m, 1H), 2.01-1.65 (m, 9H), 1.56-1.33 (m, 9H), 1.28-1.04 (m, 8H), 1.03-0.86 (m, 9H), 0.66 (s, 3H).

Example 56. Syntheses of Compounds 356 and 456

A156

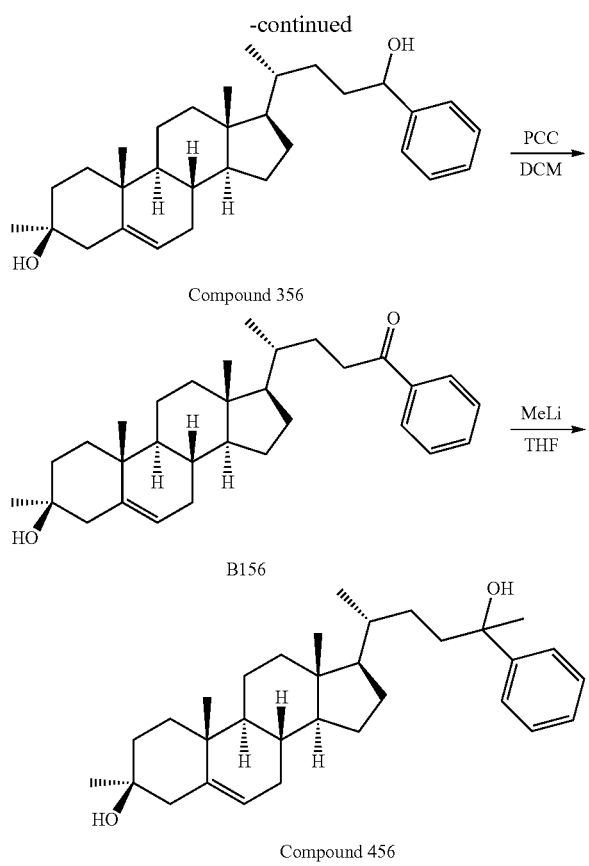

Compound 356

B156

Compound 456

Step 1: To a solution of A456 (300 mg, 0.8 mmol) in THF (5 mL) was added phenylmagnesium bromide (2.01 mL, 1 M in ether, 2.01 mmol) dropwise at −60° C. The mixture was stirred at 25° C. for 1 h. The mixture was poured into water (50 mL) and extracted with EtOAc (2×50 mL). The combined organic layer was washed with brine (100 mL), dried over Na$_2$SO$_4$, filtered and concentrated to afford Compound 356 (315 mg, crude) as a solid. 115 mg of Compound 356 was purified by prep-HPLC separation (column: Phenomenex Synergi C18 150*30 mm*4 um, gradient: 95% B (water (0.05% HCl)-ACN), flow rate: 25 mL/min) to give Compound 356 (31 mg) as a solid.

$^1$H NMR (400 MHz, CD$_3$OD) δ 7.34-7.28 (m, 4H), 7.27-7.24 (m, 1H), 5.31-5.30 (m, 1H), 4.57-4.51 (m, 1H), 2.45-2.42 (m, 1H), 2.02-1.96 (m, 3H), 1.95-1.78 (m, 5H), 1.60-1.52 (m, 9H), 1.20-0.72 (m, 18H), 0.72-0.71 (m, 3H).

LCMS Rt=1.248 min in 2.0 min chromatography, 30-90 AB, MS ESI calcd. for C$_{31}$H$_{43}$ [M+H−2H$_2$O]$^+$ 415, found 415.

Step 2: A mixture of Compound 356 (200 mg, 0.44 mmol) in DCM (3 mL) was added PCC (190 mg, 0.89 mmol) at 25° C. for 1 h. The solution was filtered and the filtered cake was washed with DCM (2×10 mL). The combined filtrate was concentrated in vacuum. The residue was purified by silica gel column eluted with (PE/EtOAc=10/1) to give B156 (150 mg, 72%) as a solid.

$^1$H NMR (400 MHz, CDCl$_3$) δ 8.01-7.95 (m, 2H), 7.58-7.54 (m, 1H), 7.50-7.45 (m, 2H), 5.32-5.30 (m, 1H), 3.03-2.90 (m, 2H), 2.41-2.40 (m, 1H), 2.05-1.96 (m, 7H), 1.52-1.48 (m, 9H), 1.17-0.94 (m, 16H), 0.70 (s, 3H).

Step 3: To a solution of B156 (80 mg, 0.18 mmol) in THF (5 mL) was added dropwise MeLi (0.28 mL, 1.6 M in ether, 0.4 mmol) at −60° C. The mixture was stirred at 25° C. for 1 h. The mixture was poured into water (50 mL) and extracted with EtOAc (2×50 mL). The combined organic layer was washed with brine (100 mL), dried over Na$_2$SO$_4$, filtered and concentrated. The residue was purified by prep-HPLC separation (column: Phenomenex Synergi C18 150*30 mm*4 um, gradient: 65-95% B (water (0.05% HCl)-ACN), flow rate: 25 mL/min) to give Compound 456 (24 mg, 29%) as a solid.

$^1$H NMR (400 MHz, CD$_3$OD) δ 7.42-7.40 (m, 2H), 7.32-7.28 (m, 2H), 7.20-7.17 (m, 1H), 5.29-5.28 (m, 1H), 2.43-2.40 (m, 1H), 1.98-1.93 (m, 4H), 1.75-1.50 (m, 16H), 1.48-0.88 (m, 18H), 0.67-0.65 (m, 3H).

LCMS Rt=1.289 min in 2.0 min chromatography, 30-90 AB, MS ESI calcd. for C$_{32}$H$_{45}$ [M+H−2H$_2$O]$^+$ 429, found 429.

Example 57. Synthesis of Compound C0

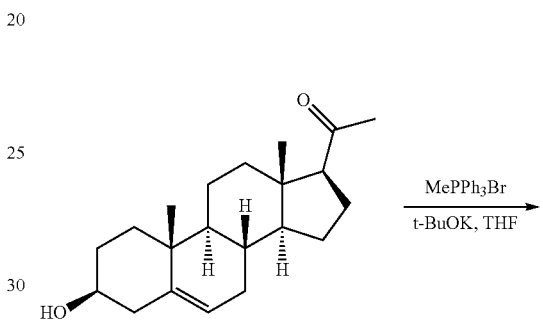

Pregnenolone

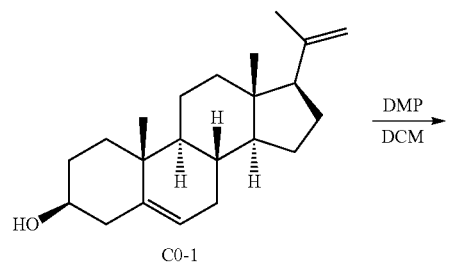

C0-1

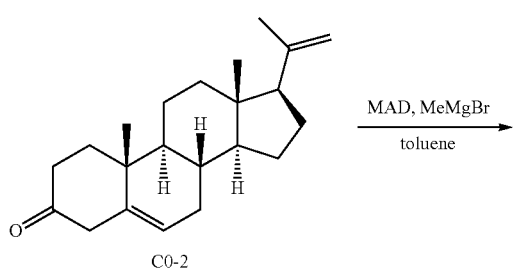

C0-2

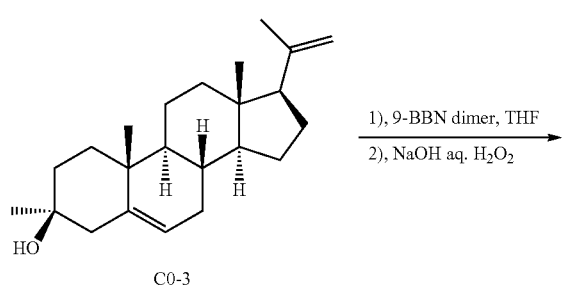

C0-3

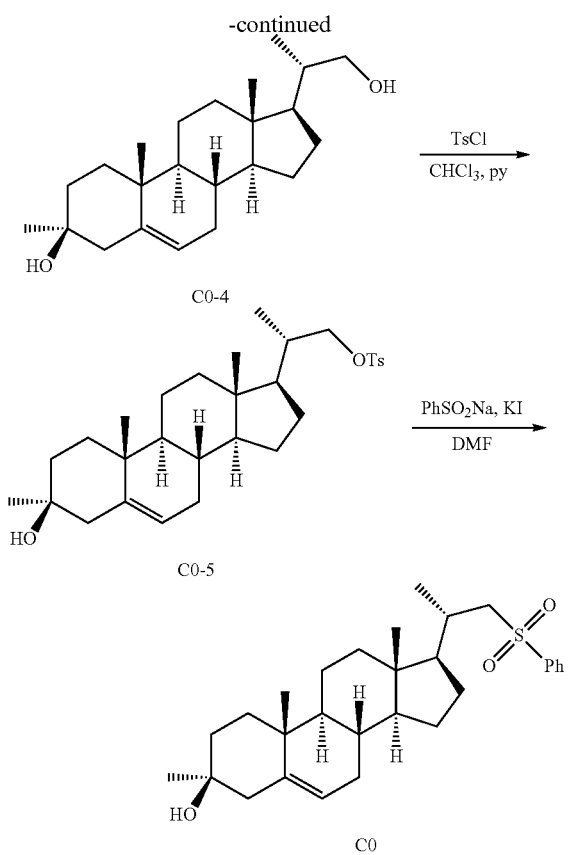

Step 1: To a mixture of MePPh₃Br (1.28 kg, 3.6 mol) in THF (4.5 L) was added t-BuOK (404 g, 3.6 mol) at 15° C. under N₂. The resulting mixture was stirred at 50° C. for 30 min. Pregnenolone (950 g, 2.9 mol) was added in portions below 65° C. The reaction mixture was stirred at 50° C. for 1 hour. The combined mixture was quenched with saturated NH₄Cl aqueous (1 L) at 15° C. and the THF layer was separated. The aqueous layer was extracted with EtOAc (2×2 L). The combined organic phase was concentrated under vacuum to give a solid. The solid was further purified by trituration with MeOH/H₂O (1:1, 15 L) at reflux to give C0-1 (940 g, 99%) as a solid.

¹H NMR (400 MHz, CDCl₃) δ 5.40-5.32 (m, 1H), 4.85 (s, 1H), 4.71 (s, 1H), 3.58-3.46 (m, 1H), 2.36-2.16 (m, 2H), 2.08-1.94 (m, 2H), 1.92-1.62 (m, 9H), 1.61-1.39 (m, 6H), 1.29-1.03 (m, 4H), 1.01 (s, 3H), 0.99-0.91 (m, 1H), 0.59 (s, 3H).

Step 2: To a solution of C0-1 (800 g, 2.54 mol) in DCM (8 L) was added DMP (2.14 kg, 5.08 mol) in portions at 35° C. The reaction mixture was stirred at 35° C. for 20 mins. The reaction mixture was filtered. The filtered cake was washed with DCM (3×1 L). The combined organic phase was washed with saturated Na₂S₂O₃/saturated NaHCO₃ aqueous (3:1, 2×1.5 L), brine (1.5 L), dried over Na₂SO₄, filtered and concentrated under vacuum to give C0-2 (794 g, crude) as a solid, which was used for next step directly.

Step 3: To a solution of BHT (1.97 kg, 8.94 mol) in toluene (1 L) was added AlMe₃ (2.14 L, 2.0 M in toluene, 4.28 mol) drop-wise below 25° C. under N₂ atmosphere. The resulting mixture was stirred at 25° C. for 1 hour. C0-2 (794 g, 2.16 mol) in DCM (3 L) was added at -70° C. The mixture was stirred at -70° C. for 1 hour. MeMgBr (862 mL, 3.0 M in diethyl ether, 2.59 mol) was added at -70° C. The reaction mixture was stirred at -70° C. for 10 min. The mixture was quenched by saturated critic acid (3 L), extracted with EtOAc (2×2 L). The combined organic phase was washed with brine (2 L), dried over Na₂SO₄, filtered and concentrated under vacuum to give a residue, which was triturated from MeCN (3 L) at 25° C. to give C0-3 (340 g, 43%) as a solid.

¹H NMR (400 MHz, CDCl₃) δ 5.34-5.26 (m, 1H), 4.85 (s, 1H), 4.71 (s, 1H), 2.50-2.35 (m, 1H), 2.07-1.94 (m, 3H), 1.91-1.84 (m, 1H), 1.83-1.63 (m, 8H), 1.58-1.33 (m, 6H), 1.27-1.13 (m, 3H), 1.12 (s, 3H), 1.10-1.05 (m, 1H), 1.02 (s, 3H), 1.00-0.92 (m, 1H), 0.58 (s, 3H).

Step 4: To a mixture of C0-3 (149 g, 453 mmol) and 9-BBN dimer (127 g, 520 mmol) was added THF (1 L) at 15° C. under N₂. The reaction mixture was stirred at 60° C. for 1 hour. The mixture was cooled to 15° C. EtOH (208 g, 4.53 mol) was added at 15° C. NaOH aqueous (906 mL, 5 M, 4.53 mol) was added drop-wise at 15° C. H₂O₂ (514 g, 30%, 4.53 mol) was added dropwise at 15° C. The obtained mixture was stirred at 60° C. for 1 hour. A solid was produced. The solid was washed with ethanol (200 mL) to give a solid, which was triturated with EtOH (2.3 L) at reflux and water (2.5 L) at 80° C. successively to give C0-4 (131 g, 84%) as a solid.

¹H NMR (400 MHz, CDCl₃) δ 5.35-5.24 (m, 1H), 3.67-3.61 (m, 1H), 3.42-3.33 (m, 1H), 2.50-2.35 (m, 1H), 2.07-1.92 (m, 3H), 1.88-1.65 (m, 3H), 1.60-1.38 (m, 9H), 1.37-1.26 (m, 3H), 1.26-1.12 (m, 4H), 1.11 (s, 3H), 1.08 (s, 1H), 1.05 (d, J=6.8 Hz, 3H), 1.01 (s, 3H), 1.00-0.91 (m, 1H), 0.70 (s, 3H).

Step 5: To a solution of C0-4 (131 g, 378 mmol) in CHCl₃ (600 mL) and pyridine (420 mL) was added TsCl (187 g, 982 mmol) at 15° C. The mixture was stirred at 15° C. for 2 hrs. The reaction mixture was concentrated under vacuum to remove most of CHCl₃. Water (3 L) was added. A solid was produced and filtered. The solid was washed with water (6×4 L) and dissolved in DCM (3.5 L), dried over Na₂SO₄, filtered and concentrated under vacuum to give C0-5 (177 g, 94%) as a solid.

¹H NMR (400 MHz, CDCl₃) δ 7.78 (d, J=8.4 Hz, 2H), 7.34 (d, J=8.0 Hz, 2H), 5.34-5.25 (m, 1H), 3.96 (dd, J=3.2, 9.6 Hz, 1H), 3.79 (dd, J=6.4, 9.2 Hz, 1H), 2.45 (s, 3H), 2.50-2.35 (m, 1H), 2.02-1.88 (m, 3H), 1.81-1.61 (m, 4H), 1.58-1.33 (m, 8H), 1.24-1.12 (m, 4H), 1.11 (s, 3H), 1.09-1.01 (m, 2H), 1.00 (s, 3H), 0.98-0.86 (m, 3H), 0.64 (s, 3H).

Step 6: To a solution of C0-5 (177 g, 353 mmol) in DMF (1.8 L) was added KI (281 g, 1694 mmol) at 15° C. The mixture was stirred at 60° C. for 1 h. To the DMF mixture was added PhSO₂Na (211 g, 1.06 mol). The mixture was stirred at 60° C. for 2 hrs. The reaction mixture was cooled to 25° C. The mixture was poured into water (20 L) and some solid was produced. The mixture was filtered. The filtered cake was washed with water (3×2 L) and dissolved in DCM (5 L). The solution was washed with water (2×1 L), brine (2×1 L), dried over Na₂SO₄, filtered, concentrated in vacuum to give a crude product as a solid, which was re-crystallized from toluene (2.5 L) to give C0 (121 g, 73%) as a solid. The re-crystallization filtrate was concentrated under vacuum to give a crude C0 (20 g) as a solid.

¹H NMR (400 MHz, CDCl₃) δ 7.91 (d, J=7.5 Hz, 2H), 7.69-7.61 (m, 1H), 7.61-7.53 (m, 2H), 5.31-5.24 (m, 1H), 3.14 (d, J=14.0 Hz, 1H), 2.85 (dd, J=9.2, 14.0 Hz, 1H), 2.50-2.35 (m, 1H), 2.16-2.03 (m, 1H), 2.01-1.88 (m, 3H), 1.80-1.64 (m, 3H), 1.56-1.34 (m, 7H), 1.20 (d, J=6.8 Hz,

3H), 1.17-1.11 (m, 3H), 1.10 (s, 3H), 1.08-1.01 (m, 2H), 1.00 (s, 3H), 0.98-0.87 (m, 2H), 0.65 (s, 3H).

Example 58. Syntheses of Compound C3-1 and C3-2

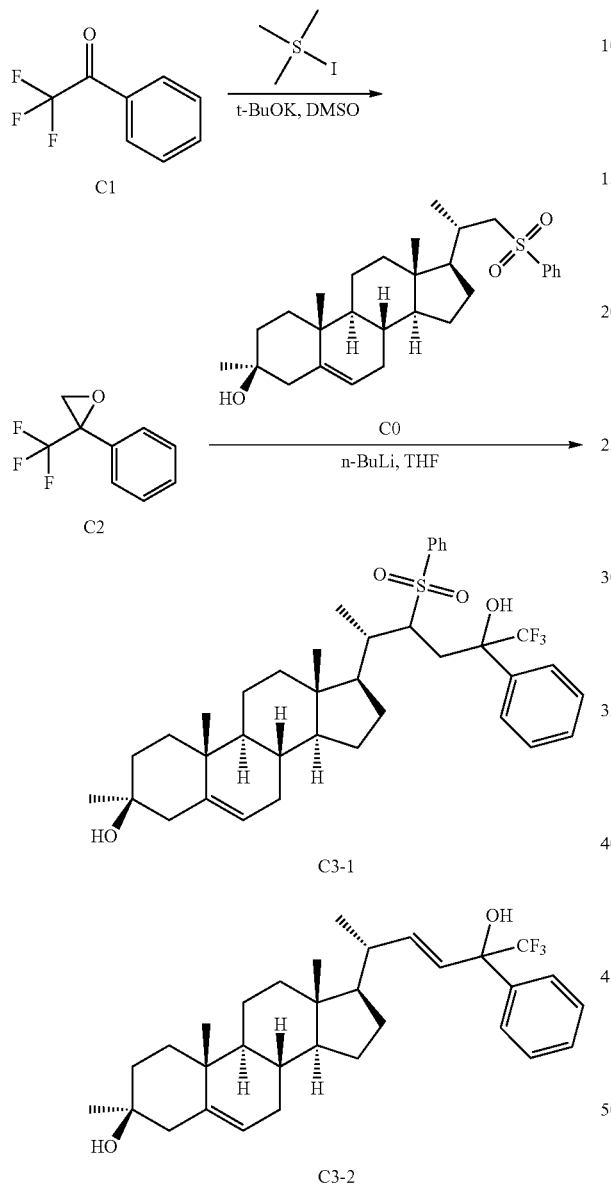

Step 1: To a solution of t-BuOK (3.22 g, 28.7 mmol) in DMSO (30 mL) was added trimethylsulfonium iodide (6.42 g, 31.5 mmol) at 20° C. and stirred for 30 min under $N_2$. A solution of C1 (5 g, 28.7 mmol) in DMSO (8 mL) was added and stirred for 16 h at 20° C. The reaction mixture was diluted with EtOAc (50 mL) and water (50 mL). The aqueous layer was back-extracted with EtOAc (50 mL). The combined organic layers were dried over $Na_2SO_4$, filtered and concentrated in vacuum to give crude product which was purified by a silica gel column (PE/EtOAc=3/1) to give C2 (1.9 g, 35%) as an oil.

$^1$H NMR (400 MHz, CDCl$_3$) δ 7.55-7.52 (m, 2H), 7.43-7.35 (m, 3H), 3.43-3.40 (m, 1H), 2.95-2.92 (m, 1H).

Step 2: To THF (2 mL) under $N_2$ at −70° C. was added n-BuLi (1.7 mL, 4.24 mmol). After that, a suspension of C0 (500 mg, 1.06 mmol) in THF (5 mL) was added drop-wise to give a suspension. After stirring at −70° C. for 30 min, a solution of C2 (398 mg, 2.12 mmol) in THF (2 mL) was added. Then reaction was stirred at −70° C. for 10 min and then stirred at 20° C. for 16 hours. The reaction mixture was quenched with water (10 mL). The mixture was extracted with EtOAc (3×50 mL). The combined organic phases were washed with brine (100 mL), dried over $Na_2SO_4$, filtered and concentrated under vacuum to give crude product which was purified by a silica gel column (PE/EtOAc=10/1) to give C3-1 (320 mg, 46%) as a solid and C3-2 (50 mg, impure). C3-1 was used directly for the next step. C3-2 was purified by HPLC separation (column: Phenomenex Synergi C18 150*30 mm*4 um, gradient: 82-95% B (A=0.05% HCl-ACN, B=acetonitrile), flow rate: 25 mL/min) to give Compound C3-1 (25 mg, 5%) as a solid.

Example 59. Synthesis of Compound 559

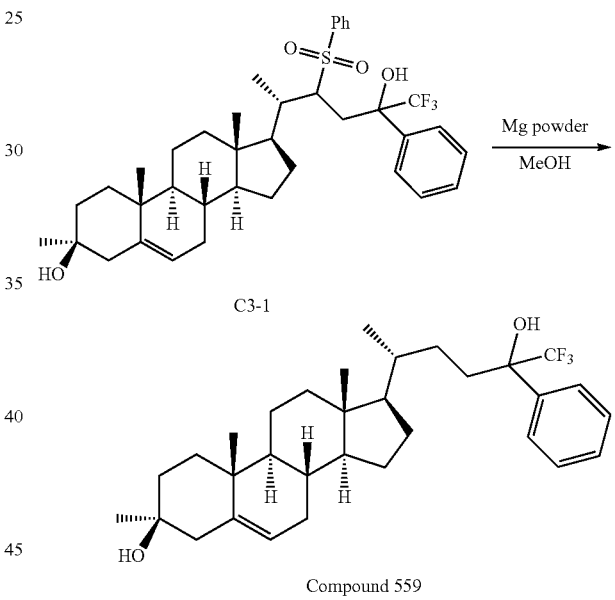

Compound 559

To a solution of C3-1 (320 mg, 0.486 mmol) in MeOH (10 mL) was added Mg powder (349 mg, 14.5 mmol) was added at 60° C. The mixture was stirred at 60° C. for 2 h. Then another portion of Mg powder (349 mg, 14.5 mmol) was added. The final reaction was stirred at 60° C. for 16 hours. The mixture was quenched with HCl (100 mL, 1 M) until the reaction became clear and extracted with DCM (2×30 mL). The combined organic phase was dried over $Na_2SO_4$, filtered, concentrated and purified by a silica gel column (PE/EtOAc=10/1 to 8/1) to give Compound 559 (20 mg, 6%) as a solid.

$^1$H NMR (400 MHz, CDCl$_3$) δ 7.52-7.50 (m, 2H), 7.43-7.31 (m, 3H), 5.29-5.28 (m, 1H), 2.43-2.40 (m, 1H), 2.29-2.28 (m, 1H), 2.10-1.60 (m, 7H), 1.52-1.21 (m, 8H), 1.19-0.94 (m, 14H), 0.93-0.91 (m, 5H), 0.63 (d, J=10.8 Hz, 3H).

LCMS Rt=1.465 min in 2 min chromatography, 10-80 AB, MS ESI calcd. for $C_{32}H_{44}F_3O$ [M−H$_2$O+H]$^+$ 501, found 501.

Example 60. Synthesis of Compound 660, 6051, and 6052

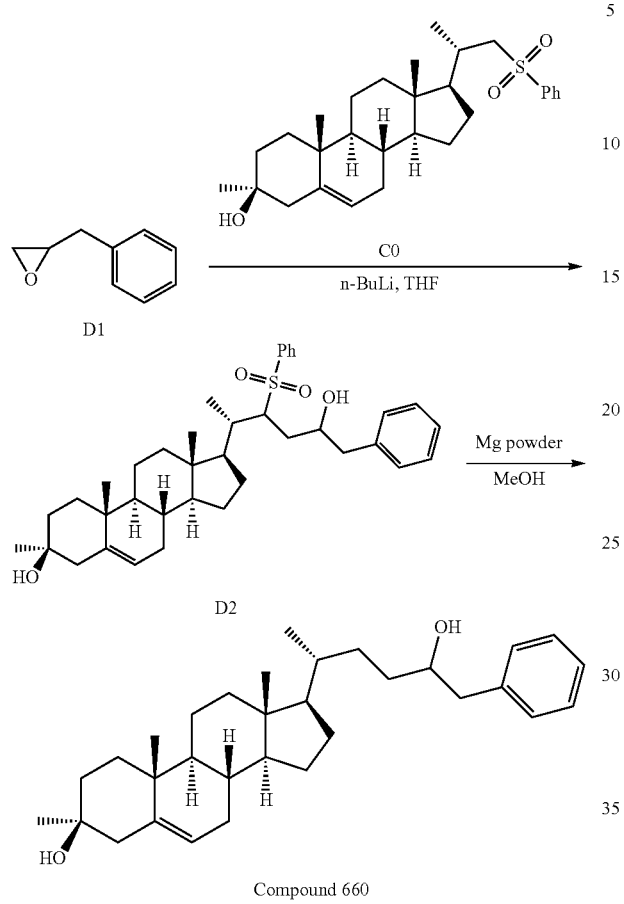

Step 1: To THF (2 mL) under N₂ at −70° C. was added n-BuLi (1.7 mL, 4.24 mmol). After that, a suspension of C0 (500 mg, 1.06 mmol) in THF (5 mL) was added drop-wise to give a suspension. After stirring at −70° C. for 30 min, a solution of D1 (284 mg, 2.12 mmol) in THF (2 mL) was added. Then reaction was stirred at −70° C. for 10 min and then stirred at 20° C. for 16 hours. The reaction mixture was quenched with water (10 mL). The mixture was extracted with EtOAc (3×50 mL). The combined organic phases were washed with brine (100 mL), dried over Na₂SO₄, filtered and concentrated under vacuum to give crude product which was purified by a silica gel column (PE/EtOAc=10/1) to give D2 (60 mg, 9%) as a solid.

¹H NMR (400 MHz, CDCl₃) δ 7.91-7.81 (m, 2H), 7.69-7.49 (m, 3H), 7.33-7.31 (m, 2H), 7.24-7.20 (m, 2H), 7.12-6.98 (m, 1H), 5.32-5.28 (m, 1H), 3.26-3.23 (m, 1H), 2.88-2.65 (m, 2H), 2.57-2.47 (m, 1H), 2.42-2.38 (m, 1H), 2.27-2.07 (m, 1H), 2.04-1.61 (m, 9H), 1.53-1.30 (m, 9H), 1.19-0.93 (m, 11H), 0.93-0.60 (m, 4H), 0.43 (s, 2H).

Step 2: To a solution of D2 (118 mg, 0.195 mmol) in MeOH (3 mL) was added Mg powder (280 mg, 11.7 mmol) at 60° C. The final reaction was stirred at 60° C. for 16 hours. The mixture was quenched with HCl (100 mL, 1M) until the reaction became clear and extracted with DCM (2×30 mL). The combined organic phase was dried over Na₂SO₄, filtered, concentrated and purified by a silica gel column (PE/EtOAc=10/1 to 8/1) to give Compound 660 (32 mg, 35%) as a solid.

¹H NMR (400 MHz, CDCl₃) δ 7.32-7.30 (m, 2H), 7.25-7.21 (m, 3H), 5.31-5.29 (m, 1H), 3.77-3.75 (m, 1H), 2.89-2.81 (m, 1H), 2.63-2.57 (m, 1H), 2.44-2.40 (m, 1H), 2.06-1.92 (m, 3H), 1.91-1.60 (m, 5H), 1.58-1.21 (m, 12H), 1.20-0.88 (m, 15H), 0.68 (s, 3H).

LCMS Rt=1.466 min in 2 min chromatography, 10-80 AB, MS ESI calcd. for $C_{32}H_{47}O$ $[M-H_2O+H]^+$ 447, found 447.

Synthesis of 6010, 6051, and 6052

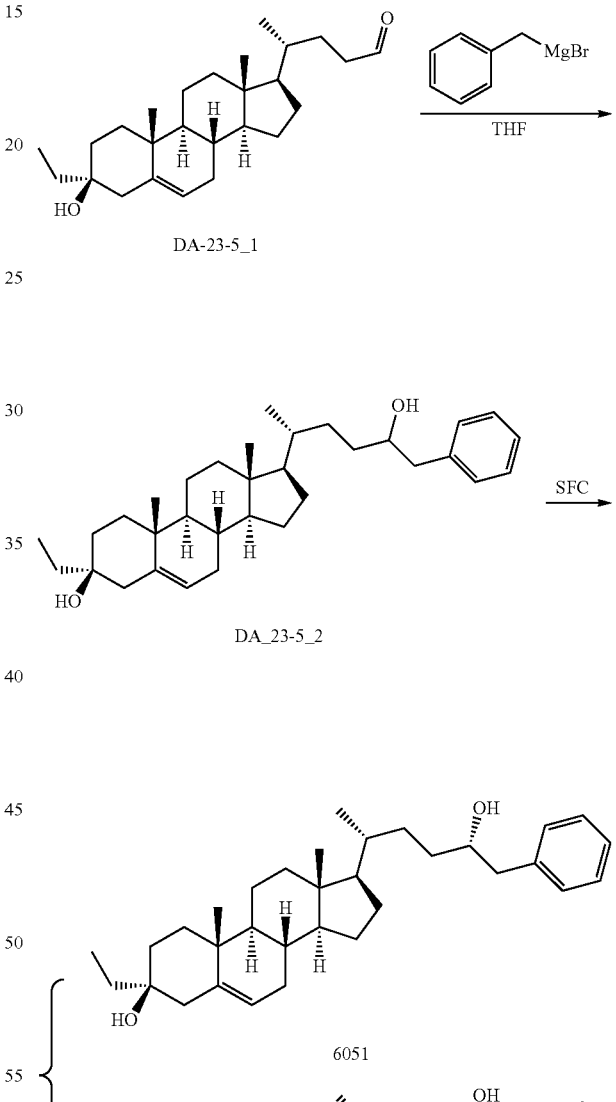

Synthesis of 6010

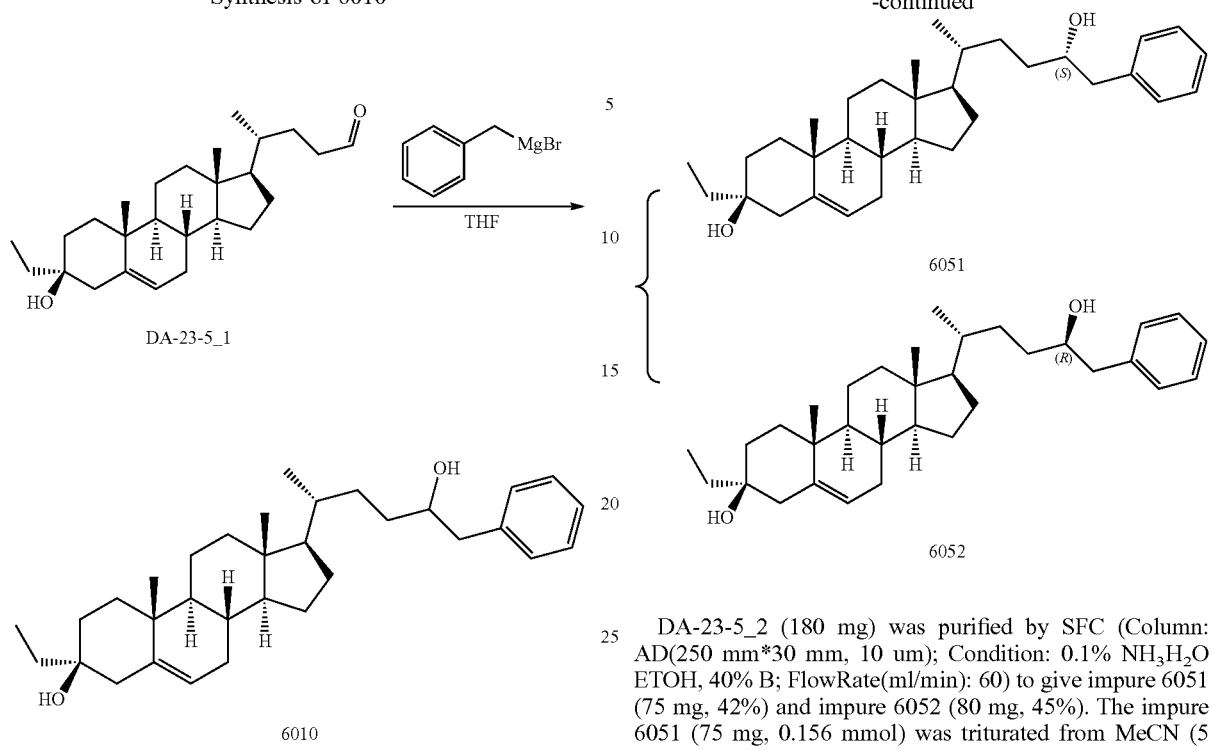

To a solution of DA-23-5_1 (400 mg, 1.03 mmol) in THF (6 mL) was added benzylmagnesium bromide (10.3 mL, 10.3 mmol, 1M in THF) at −70° C. under $N_2$. Then the mixture was stirred at 25° C. for 1 h. The reaction was treated with Sat. $NH_4Cl$ (10 mL), EtOAc (10 mL) and $H_2O$ (5 mL). The mixture was extracted with EtOAc (3×10 mL). The combined organic layers were washed with brine (3×30 mL), dried over $Na_2SO_4$, filtered, concentrated. The residue was purified by flash column (PE/EA=100/1 to 12/1) to give DA-23-5_2 (6010) (222 mg, 45%) as a solid.

$^1$H NMR (400 MHz, $CDCl_3$) δ 7.40-7.28 (m, 2H), 7.25-7.15 (m, 3H), 5.30-5.20 (m, 1H), 3.80-3.70 (m, 1H), 2.90-2.30 (m, 3H), 2.05-1.60 (m, 9H), 1.50-1.30 (m, 9H), 1.30-0.90 (m, 16H), 0.90-0.80 (m, 3H), 0.68 (s, 3H).

LCMS Rt=1.356 min in 2 min chromatography, 30-90AB_E, purity 100%, MS ESI calcd. For $C_{33}H_{49}O$ [M+H−$H_2O$]$^+$ 461, found 461.

Synthesis of 6051 and 6052

DA-23-5_2 (180 mg) was purified by SFC (Column: AD(250 mm*30 mm, 10 um); Condition: 0.1% $NH_3H_2O$ ETOH, 40% B; FlowRate(ml/min): 60) to give impure 6051 (75 mg, 42%) and impure 6052 (80 mg, 45%). The impure 6051 (75 mg, 0.156 mmol) was triturated from MeCN (5 mL) at 25° C. to give 6051 (40 mg, 54%) as a solid. The impure 6052 (80 mg) was triturated from MeCN (5 mL) at 25° C. to give 6052 (48 mg, 60%) as a solid.

6051

$^1$H NMR (400 MHz, $CDCl_3$) δ 7.40-7.28 (m, 2H), 7.25-7.15 (m, 3H), 5.30-5.20 (m, 1H), 3.80-3.70 (m, 1H), 2.90-2.30 (m, 3H), 2.05-1.60 (m, 9H), 1.50-1.30 (m, 9H), 1.30-0.90 (m, 16H), 0.90-0.80 (m, 3H), 0.68 (s, 3H).

LCMS Rt=1.444 min in 2 min chromatography, 30-90AB_E, purity 100%, MS ESI calcd. For $C_{33}H_{49}O$ [M+H−$H_2O$]$^+$ 461, found 461.

6052

$^1$H NMR (400 MHz, $CDCl_3$) δ 7.40-7.28 (m, 2H), 7.25-7.15 (m, 3H), 5.30-5.20 (m, 1H), 3.80-3.70 (m, 1H), 2.90-2.30 (m, 3H), 2.05-1.60 (m, 9H), 1.50-1.30 (m, 9H), 1.30-0.90 (m, 16H), 0.90-0.80 (m, 3H), 0.68 (s, 3H).

LCMS Rt=1.446 min in 2 min chromatography, 30-90AB_E, purity 100%, MS ESI calcd. For $C_{33}H_{49}O$ [M+H−$H_2O$]$^+$ 461, found 461.

Example 61. Syntheses of Compounds 761, 861, and 961

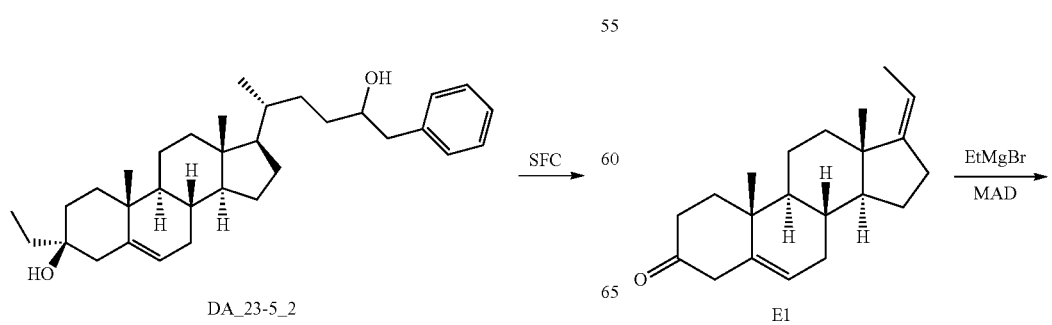

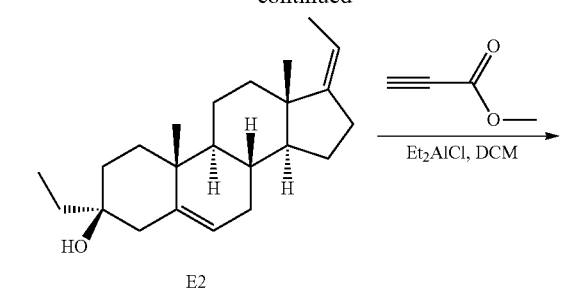

E2

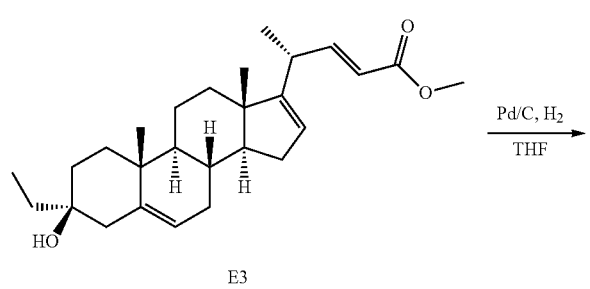

E3

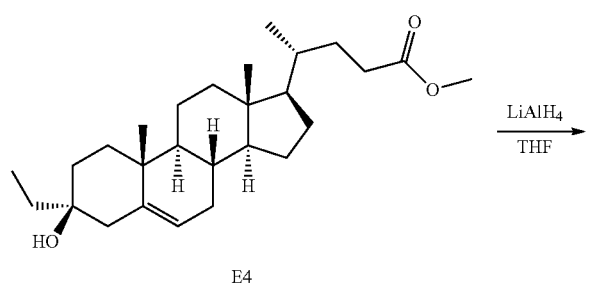

E4

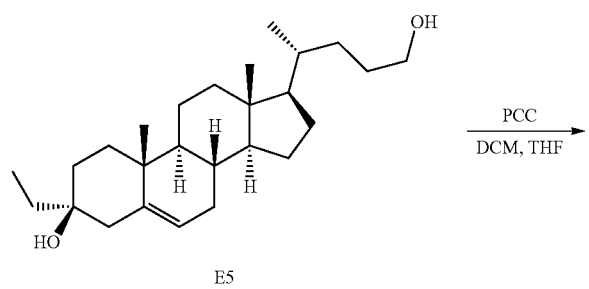

E5

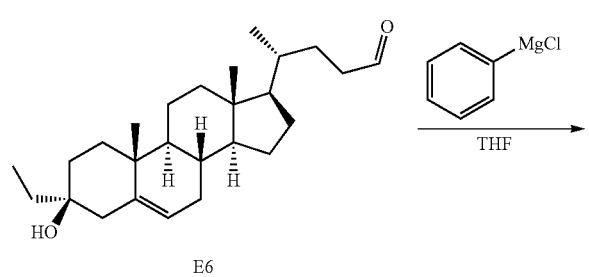

E6

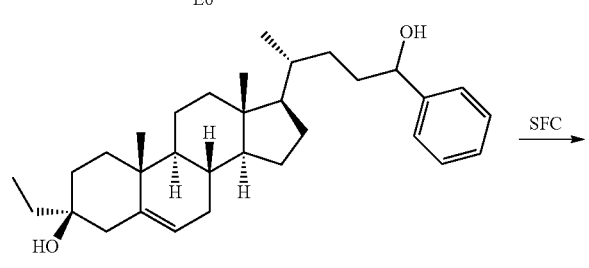

Compound 761

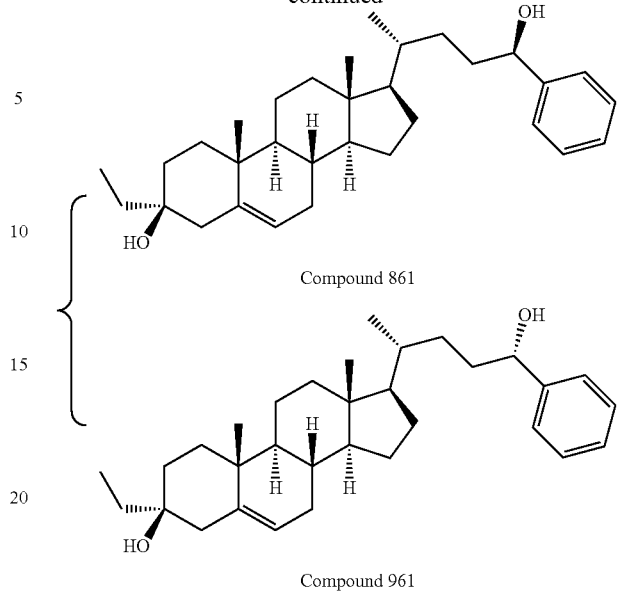

Compound 861

Compound 961

Step 1: To a solution of 2,6-di-tert-butyl-4-methylphenol (220 g, 1.0 mol) in toluene (250 mL) was added AlMe$_3$ (250 mL, 501 mmol, 2 M in toluene) dropwise below 25° C. The solution was stirred at 25° C. for 1 h. Then a solution of E1, synthesis can be found in WO2017007840 (50 g, 167 mmol) in DCM (400 mL) was added dropwise at −78° C. After stirring at −78° C. for 1 h, EtMgBr (167 mL, 501 mmol, 3M in ethyl ether) was added dropwise at −78° C. The resulting solution was stirred at −78° C. to −50° C. for 3 h. The reaction was quenched with saturated citric acid (100 mL) at −78° C. After stirring at 25° C. for 30 min, the resulting mixture was filtered and the filtrate was extracted with DCM (3×100 mL). The combined organic layer was dried over Na$_2$SO$_4$, filtered and concentrated in vacuo. The crude product was combined and purified by a silica gel column (PE/EtOAc=5/1) to give 38 g of the crude product as a solid, which was recrystallized from PE to give E2 as a solid (13.5 g, 13%).

$^1$H NMR (CDCl$_3$) 400 MHz δ 5.33-5.26 (m, 1H), 5.23-5.10 (m, 1H), 2.45-1.90 (m, 6H), 1.78-0.70 (m, 28H).

Step 2: To a solution of E2 (13 g, 39.5 mmol) and methyl propiolate (8.29 g, 98.7 mmol) in anhydrous DCM (100 mL) under N$_2$ at 0° C. was added diethylaluminum chloride (1 M in hexane, 158 mL, 158 mmol) dropwise. The mixture was stirred at 20° C. for 16 hours. The reaction mixture was poured into ice-water, extracted with DCM (3×300 mL). The extracts were dried over anhydrous sodium sulfate, filtered and concentrated. The residue was purified by column chromatography on silica gel (PE/EtOAc=5/1) to give E3 (14 g, 86%) as a solid.

$^1$H NMR (CDCl$_3$) 400 MHz δ 6.93 (dd, J=15.6 Hz, 8.0 Hz, 1H), 5.81 (d, J=8.0 Hz, 1H), 5.42-5.38 (m, 1H), 5.33-5.24 (m, 1H), 3.73 (s, 3H), 3.05-2.95 (m, 1H), 2.40-2.30 (m, 1H), 2.10-1.95 (m, 3H), 1.90-1.65 (m, 4H), 1.60-1.25 (m, 9H), 1.88 (d, J=7.2 Hz, 3H), 1.15-0.95 (m, 6H), 0.84 (t, J=7.6 Hz, 3H), 0.78 (s, 3H).

Step 3: To a solution of E3 (9 g, 21.8 mmol) in THF (100 mL) was added Pd/C (2 g, wet 10%) at 15° C. After degassing and back-fill with H$_2$ for three times, the reaction mixture was stirred for 16 h at 15° C. with H$_2$ balloon. The mixture was filtered through a pad of celite. The filtrate was concentrated in vacuo to give crude E4 (8.7 g, crude) as a solid.

<sup>1</sup>H NMR (CDCl<sub>3</sub>) 400 MHz δ 5.35-5.25 (m, 1H), 3.69 (s, 3H), 2.40-2.15 (m, 4H), 2.10-1.40 (m, 17H), 2.15-0.80 (m, 16H), 0.70 (s, 3H).

Step 4: To a solution of E4 (5 g, 12.0 mmol) in THF (100 mL) was added lithium aluminium hydride (1.13 g, 30.0 mmol) at 0° C. Then the reaction was stirred at 25° C. for 5 min. Then the reaction was quenched by aqueous NH<sub>4</sub>Cl solution (50 mL) and aqueous citric acid (30 mL) to pH=4-5. Then the reaction solution was extracted with EtOAc (3×100 mL). The combined organic layers were dried over Na<sub>2</sub>SO<sub>4</sub>, filtered and concentrated in vacuo to give crude product E5 (4 g, 80%) as a solid.

<sup>1</sup>H NMR (CDCl<sub>3</sub>) 400 MHz δ 5.35-5.25 (m, 1H), 3.18-3.05 (m, 2H), 2.40-2.32 (m, 1H), 2.08-1.80 (m, 18H), 1.80-0.80 (m, 19H), 0.68 (s, 3H).

Step 5: To a solution of E5 (1 g, 2.57 mmol) in DCM (15 mL) and THF (15 mL) was added PCC (1.10 g, 5.14 mmol). The resulting reaction mixture was stirred at 25° C. for 2 hours. The combined organic phase was dried, concentrated and purified by flash chromatography (0-15% of EtOAc in PE) to give E6 (700 mg, 70%) as a solid.

<sup>1</sup>H NMR (CDCl<sub>3</sub>) 400 MHz δ 9.77 (s, 1H), 5.30-5.26 (m, 1H), 2.46-2.35 (m, 2H), 2.04-1.57 (m, 12H), 1.50-0.83 (m, 23H), 0.68 (m, 3H).

Step 6: To a solution of E6 (400 mg, 1.03 mmol) in THF (10 mL) was added phenylmagnesium chloride (3.5 mL, 1.5 mmol, 3M in ether) at −70° C. under N<sub>2</sub>. Then the mixture was stirred at 20° C. for 20 min. The reaction was treated with saturated NH<sub>4</sub>Cl (4 mL), EtOAc (5 mL), and H<sub>2</sub>O (3 mL). The mixture was extracted with EtOAc (3×6 mL). The combined organic layers were washed with brine (2×15 mL), dried over Na<sub>2</sub>SO4, filtered, concentrated in vacuum, purified by column chromatography on silica gel (PE/EA=30/1 to 10/1) to give Compound 761 (300 mg, 62%) as a solid.

<sup>1</sup>H NMR (400 MHz, CDCl<sub>3</sub>) δ 7.40-7.30 (m, 4H), 7.30-7.20 (m, 1H), 5.32-5.26 (m, 1H), 4.64-4.52 (m, 1H), 2.38-2.34 (m, 1H), 2.06-1.88 (m, 3H), 1.86-1.15 (m, 24H), 1.12-1.00 (m, 3H), 1.00-0.78 (m, 7H), 0.66 (s, 3H).

LCMS Rt=1.303 min in 2 min chromatography, 30-90 AB, MS ESI calcd. For C<sub>32</sub>H<sub>45</sub> [M+H−2H<sub>2</sub>O]<sup>+</sup> 429, found 429.

Step 7: Compound 761 (300 mg) was purified by SFC (Column: OD (250 mm*30 mm, 10 um); Condition: 0.1% NH<sub>3</sub>—H<sub>2</sub>O ETOH, 40% B; Flow Rate (ml/min): 60) to give Compound 861 (40 mg, 22%) as a solid and Compound 10 (59 mg, 33%) as a solid.

Compound 861: <sup>1</sup>H NMR (400 MHz, CDCl<sub>3</sub>) δ 7.39-7.30 (m, 4H), 7.30-7.20 (m, 1H), 5.32-5.26 (m, 1H), 4.64-4.52 (m, 1H), 2.39-2.34 (m, 1H), 2.06-1.90 (m, 3H), 1.86-1.15 (m, 24H), 1.12-1.00 (m, 3H), 1.00-0.80 (m, 7H), 0.66 (s, 3H).

LCMS Rt=1.413 min in 2 min chromatography, 30-90AB_2 MIN_E, MS ESI calcd. For C<sub>32</sub>H<sub>45</sub> [M+H−2H<sub>2</sub>O]<sup>+</sup> 429, found 429.

Compound 961: <sup>1</sup>H NMR (400 MHz, CDCl<sub>3</sub>) δ 7.39-7.30 (m, 4H), 7.30-7.20 (m, 1H), 5.31-5.26 (m, 1H), 4.64-4.52 (m, 1H), 2.39-2.34 (m, 1H), 2.06-1.90 (m, 3H), 1.86-1.35 (m, 17H), 1.28-1.20 (m, 2H), 1.20-0.80 (m, 13H), 0.66 (s, 3H).

LCMS Rt=1.425 min in 2 min chromatography, 30-90AB, MS ESI calcd. For C<sub>32</sub>H<sub>45</sub> [M+H−2H<sub>2</sub>O]<sup>+</sup> 429, found 429.

Synthesis of 861 to Determine Stereochemistry

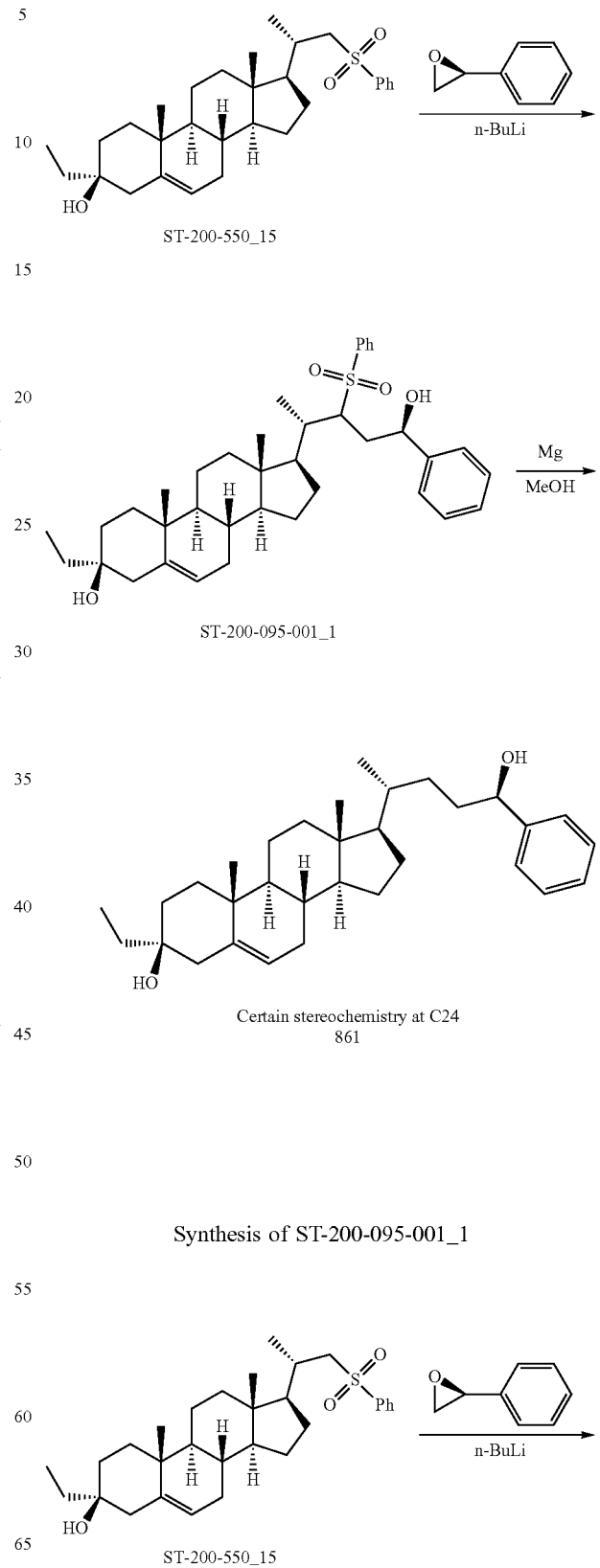

Synthesis of ST-200-095-001_1

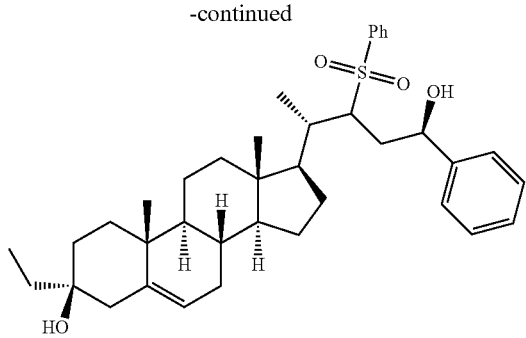

ST-200-095-001_1

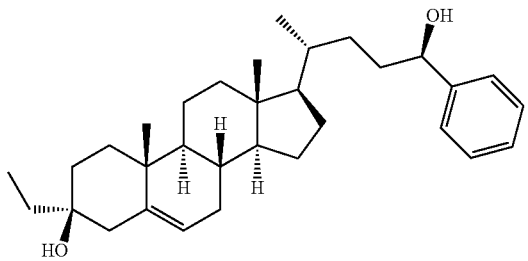

ST-200-095-001

To a freshly distilled anhydrous THF (1 mL) was added n-BuLi (2.47 mL 6.18 mmol, 2.5 M in n-hexane) drop-wise at −70° C. Then a solution of ST-200-550_15 (1 g, 2.06 mmol) in anhydrous THF (10 mL) was drop-wise. After stirring at −70° C. for 1 h, (2S)-2-phenyloxirane (371 mg, 3.09 mmol) was added at −70° C. and the reaction was stirred for another 1 h. The reaction mixture was stirred at 25° C. (room temperature) for 12 h. The reaction was quenched by saturated NH₄Cl.aq (100 mL). The aqueous phase was extracted with EtOAc (3×50 mL). The combine organic phase was washed with saturated brine (2×50 mL), drive over anhydrous Na₂SO₄, filtered and concentrated in vacuum to give ST-200-095-001_1 (1.1 g, crude) as an oil, which was used directly for the next step.

Synthesis of ST-200-095-001

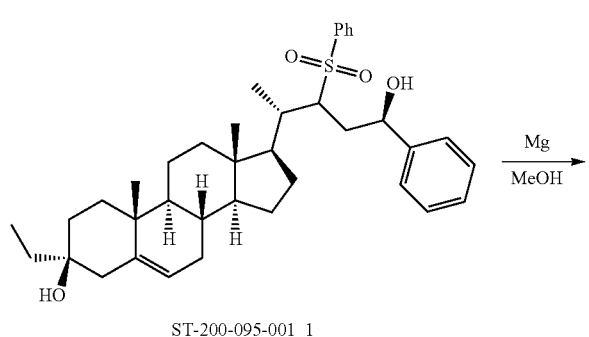

ST-200-095-001_1

To a solution of ST-200-095-001_1 (1.1 g, crude) in MeOH (100 mL) was added Mg powder (2.17 g, 90.5 mmol) and NiCl₂ (40 mg) at 25° C. under N₂. After stirring at 60° C. for 1 h under N₂, the reaction mixture was quenched with HCl (300 mL, 1 M) until the reaction became clear. The aqueous phase was extracted with EtOAc (3×100 mL). The combined organic phase was washed with saturated brine (2×100 mL), dried over anhydrous Na₂SO₄, filtered and concentrated. The residue was purified by silica gel chromatography (PE/EtOAc=8/1 to 5/1) to afford ST-200-095-001 (0.65 g, 77%, impure) as a solid.

The ST-200-095-001 (650 mg, 1.39 mmol) was re-crystallized from MeCN (40 mL) to give ST-200-095-001 (580 mg, 69%, impure) as a solid.

The ST-200-095-001 (300 mg, 0.6455 mmol) was purified by SFC (Instrument: SFC-16, Column:OD(250 mm*30 mm, 5 um), Condition:0.1% NH₃H₂O ETOH, Begin B:45%, End B:45%, FlowRate(ml/min):60, Injections:70) to give ST-200-095-001 (256 mg, 59%) as a solid.

$^1$H NMR (400 MHz, CDCl₃) δ 7.88-7.81 (m, 4H), 7.80-7.23 (m, 3H), 5.32-5.25 (m, 1H), 4.65-4.61 (m, 1H), 2.40-2.30 (m, 1H), 2.06-1.90 (m, 3H), 1.88-1.64 (m, 5H), 1.51-1.05 (m, 15H), 1.04-0.79 (m, 12H), 0.66 (s, 3H).

LCMS Rt=1.287 min in 2 min chromatography, 30-90AB_2 MIN_E, purity 100%, MS ESI calcd. for $C_{32}H_{45}$ [M+H−2H₂O]⁺ 429, found 429.

Example 63: Synthesis of 6347 and 6348

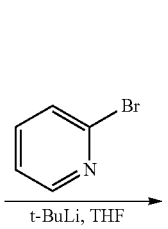

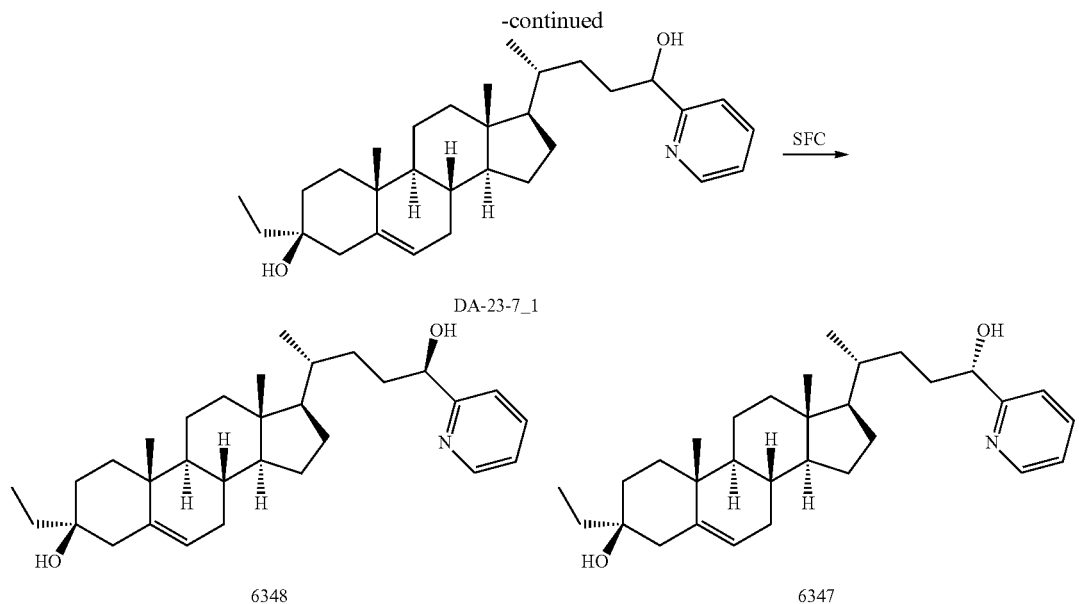

Synthesis of DA-23-3_1 (aka DA-28-1)

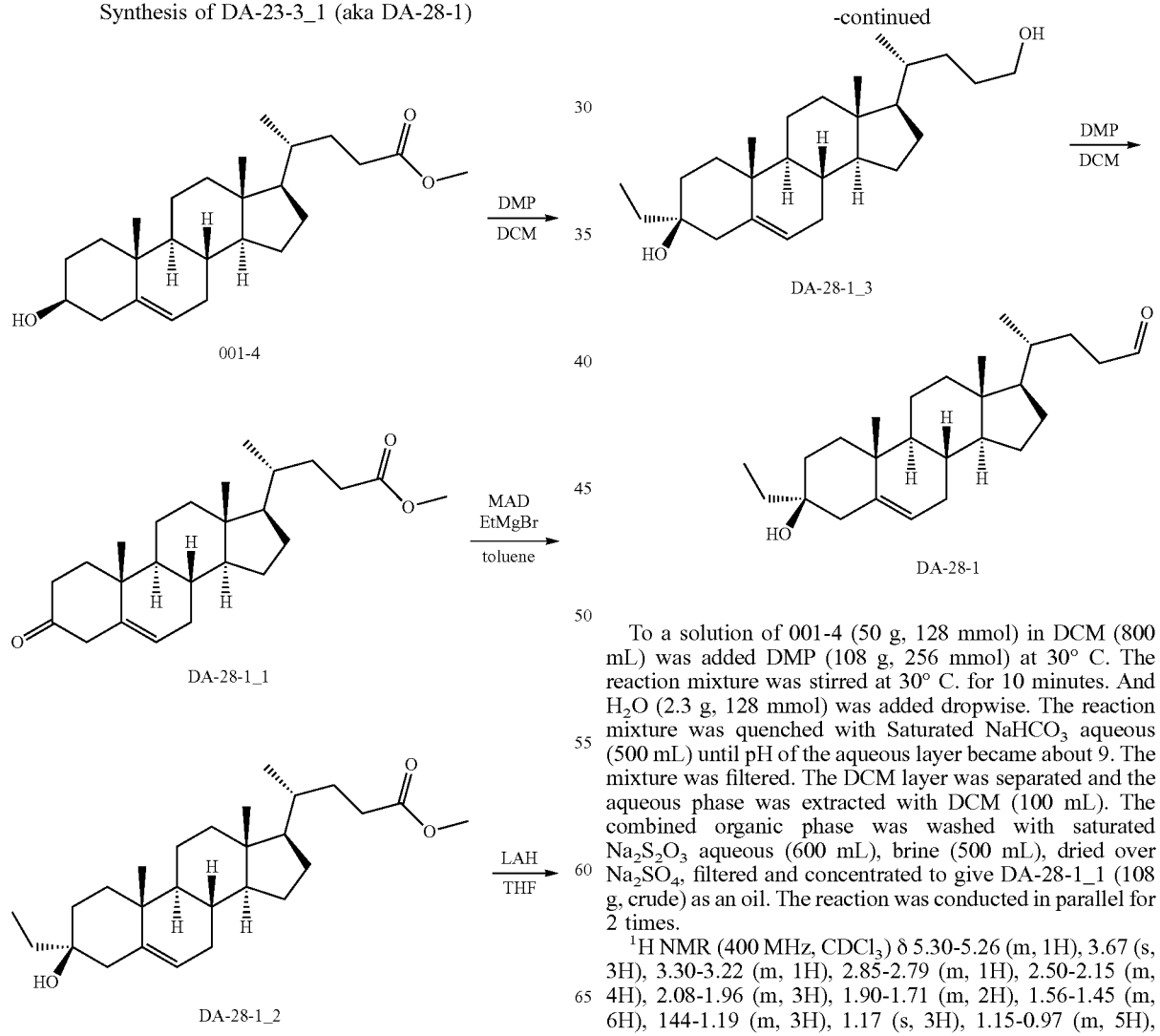

To a solution of 001-4 (50 g, 128 mmol) in DCM (800 mL) was added DMP (108 g, 256 mmol) at 30° C. The reaction mixture was stirred at 30° C. for 10 minutes. And H$_2$O (2.3 g, 128 mmol) was added dropwise. The reaction mixture was quenched with Saturated NaHCO$_3$ aqueous (500 mL) until pH of the aqueous layer became about 9. The mixture was filtered. The DCM layer was separated and the aqueous phase was extracted with DCM (100 mL). The combined organic phase was washed with saturated Na$_2$S$_2$O$_3$ aqueous (600 mL), brine (500 mL), dried over Na$_2$SO$_4$, filtered and concentrated to give DA-28-1_1 (108 g, crude) as an oil. The reaction was conducted in parallel for 2 times.

$^1$H NMR (400 MHz, CDCl$_3$) δ 5.30-5.26 (m, 1H), 3.67 (s, 3H), 3.30-3.22 (m, 1H), 2.85-2.79 (m, 1H), 2.50-2.15 (m, 4H), 2.08-1.96 (m, 3H), 1.90-1.71 (m, 2H), 1.56-1.45 (m, 6H), 144-1.19 (m, 3H), 1.17 (s, 3H), 1.15-0.97 (m, 5H), 0.96-0.88 (m, 3H), 0.70 (s, 3H).

To a solution of BHT (367 g, 1.67 mmol) in toluene (1000 mL) under nitrogen at 0° C. was added trimethylaluminum (2 M in toluene, 418 mL, 837 mmol) dropwise. The mixture was stirred at 0° C. for 30 min and used directly as a solution of MAD (0.59 M in toluene) without further purification. To the solution of MAD (0.59 M in toluene, 1410 mL, 837 mmol) under nitrogen at −78° C. was added a solution of DA-28-1_1 (108 g, 279 mmol) in toluene (500 mL) dropwise. The mixture was stirred at −78° C. for 30 min. EtMgBr (3 M in diethyl ether, 278 mL, 837 mmol, 3M in ether) was added dropwise. The resulting mixture was stirred at −78° C. for 1 hr. The reaction mixture was poured to ice-cooled aqueous citric acid (1000 mL), extracted with EtOAc (2×500 mL). The combined organic layer was washed with brine (500 mL), dried over anhydrous sodium sulfate, filtered and concentrated. The residue was purified by column chromatography on silica gel (0-20% of EtOAc in PE) to give DA-28-1_2 (95 g, impure) as an oil. The reaction was conducted in parallel for 2 times.

$^1$H NMR (400 MHz, CDCl$_3$) δ 5.30-5.26 (m, 1H), 3.65 (s, 3H), 2.48-2.18 (m, 4H), 2.08-1.91 (m, 2H), 1.90-1.76 (m, 4H), 1.75-1.61 (m, 4H), 1.60-1.48 (m, 5H), 1.47-1.22 (m, 5H), 1.17 (s, 1H), 1.16-1.02 (m, 3H), 1.01-0.96 (m, 2H), 0.95-0.90 (m, 1H), 0.89-0.82 (m, 4H), 0.81-0.76 (m, 2H), 0.67 (s, 3H).

To a solution of DA-28-1_2 (60 g, 144 mmol) in THF (1200 mL) under N$_2$ at 0° C. was added LiAlH$_4$ (8.19 g, 216 mmol) in portions. The reaction was stirred at 20° C. for 30 min. The reaction was quenched with 2 M HCl (600 mL) at 0° C. till pH of the aqueous phase was about 2. The mixture was filtered. The solid was collected and the aqueous layer was extracted with EtOAc (2×400 mL). The combined organic phase was washed with sat.NaHCO$_3$ (600 mL), dried over Na$_2$SO$_4$, filtered and concentrated to give crude product, which was purified with the solid by trituration with MeCN (800 mL) to give DA-28-1_3 (45 g, 81%) as a solid.

$^1$H NMR (400 MHz, CDCl$_3$) δ 5.30-5.26 (m, 1H), 3.65-3.56 (m, 2H), 2.40-2.32 (m, 1H), 2.10-2.00 (m, 1H), 1.99-1.90 (m, 2H), 1.89-1.58 (m, 5H), 1.56-1.31 (m, 10H), 1.30-1.19 (m, 3H), 1.18-1.03 (m, 8H), 1.02-0.88 (m, 5H), 0.87-0.78 (m, 3H), 0.68 (s, 3H).

To a solution of DA-28-1_3 (45 g, 115 mmol) in DCM (800 mL) was added DMP (97.5 g, 230 mmol) at 20° C. The reaction mixture was stirred at 20° C. for 10 min. The reaction mixture was quenched with Saturated NaHCO$_3$ aqueous (500 mL) at 20° C. The mixture was filtered. The DCM layer was separated and the aqueous phase was extracted with DCM (200 mL). The combined organic phase was washed with saturated Na$_2$S$_2$O$_3$ aqueous (3×500 mL), sat.NaHCO$_3$ (500 mL), water (500 mL), dried over Na$_2$SO$_4$, filtered, concentrated. Combined with another batch from 25 g of DA-28-1_3, the crude product was triturated with MeCN (500 mL) to give DA-028-1 (48 g) as a solid. 500 mg of impure DA-28-1 was purified by flash column (0-15% of EtOAc in PE) to give DA-28-1 (194 mg, 39%) as a solid.

$^1$H NMR (400 MHz, CDCl$_3$) δ 9.77 (s, 1H), 5.30-5.27 (m, 1H), 2.50-2.32 (m, 3H), 2.05-1.94 (m, 3H), 1.93-1.67 (m, 3H), 1.66-1.58 (m, 3H), 1.56-1.22 (m, 10H), 1.20-1.04 (m, 4H), 1.02 (s, 3H), 1.00-0.90 (m, 5H), 0.89-0.80 (m, 3H), 0.68 (s, 3H).

LCMS Rt=1.229 min in 2.0 min chromatography, 30-90 AB, purity 100%, MS ESI calcd. for C$_{26}$H$_{41}$O [M+H−H$_2$O]$^+$ 369, found 369.

Synthesis of DA-23-7_1

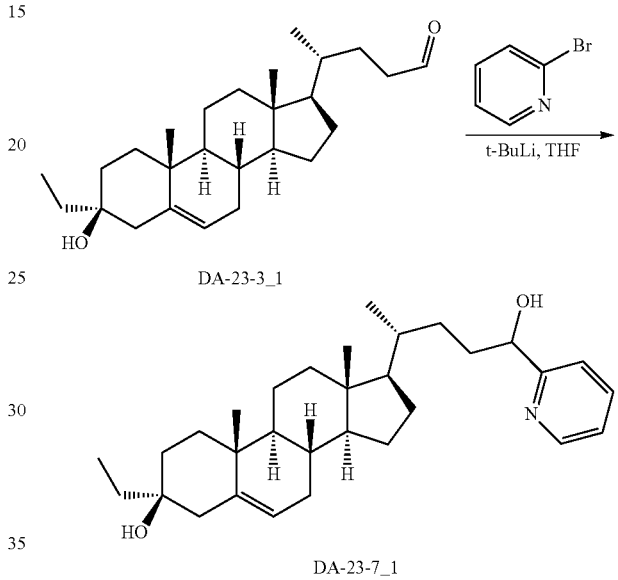

Pyridin-2-yllithium (437 mg, 5.15 mmol) was added to a solution of DA-23-3_1 (400 mg, 1.03 mmol) in THF (3 mL) at −70° C. The mixture was stirred at 25° C. for 1 hr. The mixture was quenched with Sat. NH$_4$Cl (20 mL), extracted with EtOAc (3×15 mL). The combined organic layers were washed with brine (30 mL×3), dried over Na$_2$SO$_4$, filtered, concentrated in vacuum to give a crude product, which was purified by silica gel chromatography (PE/EtOAc=30/1 to 6/1) to afford DA-23-7_1 (200 mg, 42%) as a solid.

$^1$H NMR CDCl$_3$ Bruker_P_400 MHz δ 8.59-8.55 (m, 1H), 7.72-7.64 (m, 1H), 7.25-7.16 (m, 2H), 5.32-5.24 (m, 1H), 4.75-4.62 (m, 1H), 4.10-4.00 (m, 1H), 2.40-2.30 (m, 1H), 2.07-1.30 (m, 16H), 1.30-0.80 (m, 20H), 0.65 (s, 3H).

Synthesis of 6347 and 6348

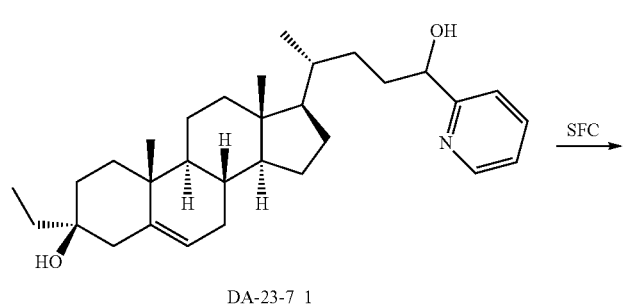

DA-23-7_1

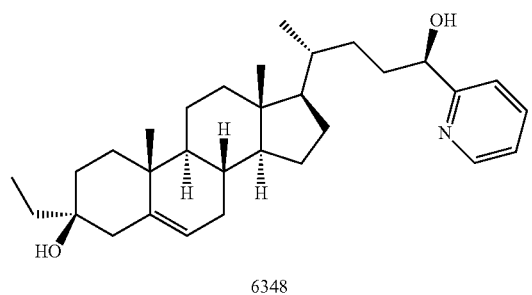

6348

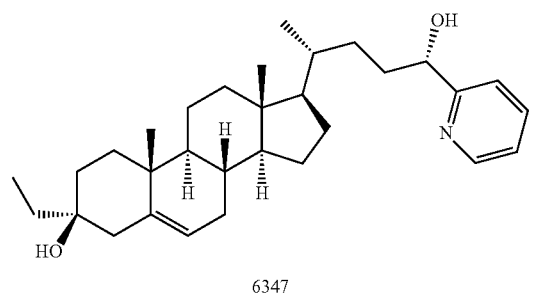

6347

(Stereochemistry Randomly Assigned).

The compound DA-23-7_1 (510 mg, 1.08 mmol) was purified by SFC (Column: Chiralpak AS-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.) to afford 6348 (60 mg, 30%) as solid and 6347 (60 mg, 30%) as a solid.

6348

$^1$H NMR CDCl$_3$ Bruker_P_400 MHz δ 8.59-8.51 (m, 1H), 7.72-7.64 (m, 1H), 7.25-7.17 (m, 2H), 5.32-5.24 (m, 1H), 4.73-4.62 (m, 1H), 4.05-4.01 (m, 1H), 2.40-2.31 (m, 1H), 2.07-1.67 (m, 6H), 1.66-1.57 (m, 3H), 1.50-1.29 (m, 9H), 1.28-1.19 (m, 2H), 1.18-1.03 (m, 5H), 1.03-1.00 (m, 3H), 1.00-0.94 (m, 1H), 0.94-0.88 (m, 4H), 0.88-0.82 (m, 3H), 0.68 (s, 3H).

LCMS Rt=0.839 min in 2 min chromatography, 30-90AB, purity 99%, MS ESI calcd. For $C_{21}H_{48}NO_2[M+H]^+$ 466, found 466.

6347

$^1$H NMR (400 MHz, CDCl$_3$) δ 8.57-8.51 (m, 1H), 7.71-7.65 (m, 1H), 7.25-7.17 (m, 2H), 5.35-5.23 (m, 1H), 4.75-4.67 (m, 1H), 4.12-4.06 (m, 1H), 2.41-2.31 (m, 1H), 2.08-1.91 (m, 3H), 1.88-1.67 (m, 4H), 1.67-1.58 (m, 1H), 1.50-1.32 (m, 6H), 1.31-1.14 (m, 4H), 1.13-1.03 (m, 4H), 1.03-1.01 (m, 2H), 1.01-0.93 (m, 2H), 0.93-0.89 (m, 4H), 0.89-0.81 (m, 4H) 0.68 (s, 3H).

LCMS Rt=0.825 min in 2 min chromatography, 30-90AB, purity 99%, MS ESI calcd. For $C_{21}H_{48}NO_2[M+H]^+$ 466, found 466.

Example 64: Synthesis of 6457, 6458, and 6459

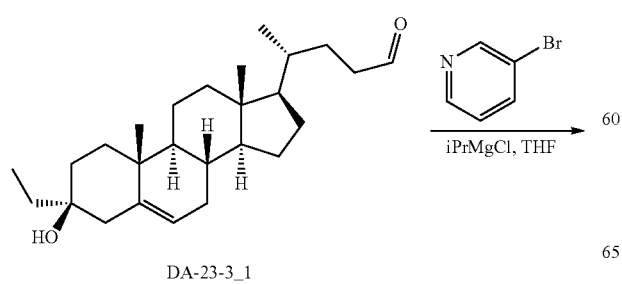

DA-23-3_1

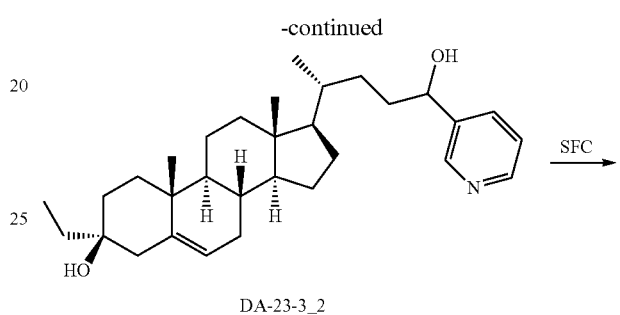

DA-23-3_2

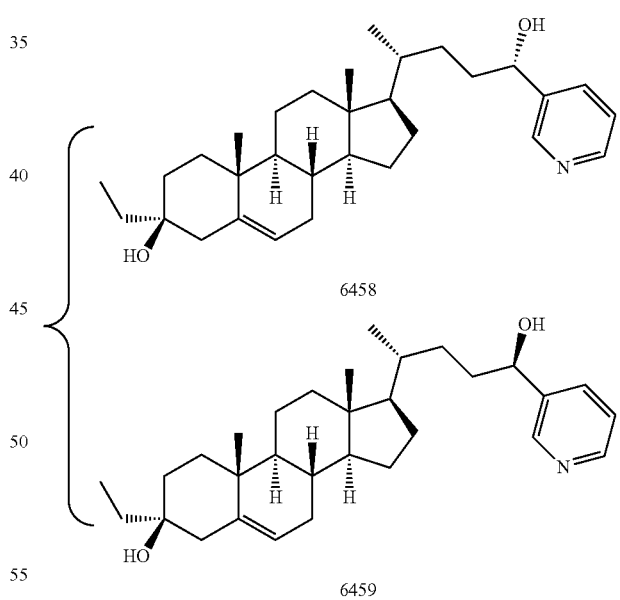

6458

6459

Stereochemistry assigned based on NMR data.

The experimental of intermediate DA-23-3_1 could be found in Example 63.

Synthesis of DA-23-3_2 (6457)

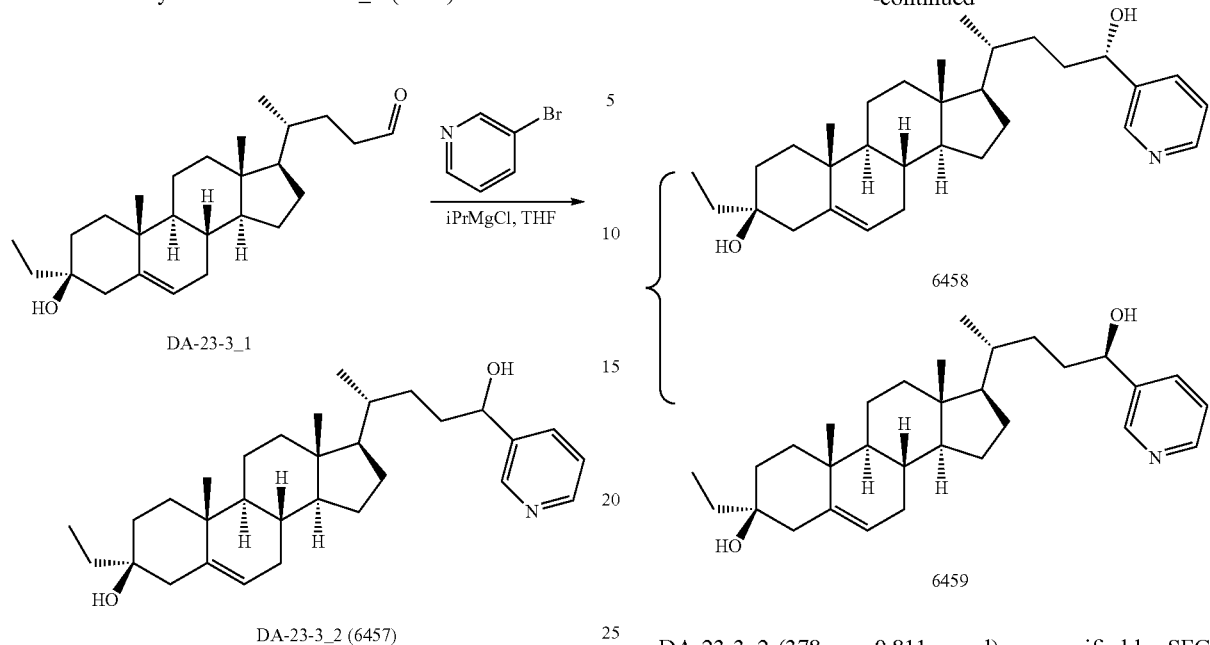

Isopropylmagnesium chloride (20.6 mL, 41.2 mmol, 2 M in THF) was added to a suspension of 3-bromopyridine (6.50 g, 41.2 mmol) in THF (10 mL) at 0° C. The mixture was stirred at 25° C. for 1 h. After cooling to 0° C., a solution of DA-23-3_1 (800 mg, 2.06 mmol) in THF (10 mL) was added. The mixture was stirred at 25° C. for 2 h. To the mixture was added NH$_4$Cl (50 mL, 10% aq.). Combined with another batch from 100 mg of DA-23-3_1, the mixture was extracted with EtOAc (2×50 mL). The organic layer was separated. The combined organic phase was dried over Na$_2$SO$_4$, filtered, concentrated. The residue was purified by flash column (0~100% of EtOAc in PE) to afford impure DA-23-3_2 (560 mg, 58%) as a solid. The impure DA-23-3_2 (560 mg, 1.20 mmol) was triturated from MeCN (20 mL) at 25° C. to give DA-23-3_2 (406 mg, 73%) as a solid.

$^1$H NMR (400 MHz, CDCl$_3$) δ 8.60-8.50 (m, 2H), 7.72-7.68 (m, 1H), 7.28-7.17 (m, 1H), 5.32-5.25 (m, 1H), 4.22-4.10 (m, 1H), 2.40-2.30 (m, 1H), 2.10-1.92 (m, 4H), 1.92-1.68 (m, 4H), 1.68-1.53 (m, 6H), 1.53-1.35 (m, 4H), 1.35-1.01 (m, 10H), 1.01-0.80 (m, 9H), 0.66 (s, 3H).

LCMS Rt=0.921 min in 2 min chromatography, 30-90AB_E, purity 100%, MS ESI calcd. For C$_{31}$H$_{48}$NO$_2$ [M+H]$^+$ 466, found 466.

Synthesis of 6458 and 6459

DA-23-3_2 (378 mg, 0.811 mmol) was purified by SFC (column: AD(250 mm*30 mm, 10 um), gradient: 40-40% B (A=0.1% NH$_3$H$_2$O IPA), flow rate: 60 mL/min) to give DA-23-9 (110 mg, 29%) as a solid and DA-23-10 (120 mg, 31.8%) as a solid.

6458
$^1$H NMR (400 MHz, CDCl$_3$) δ 8.55-8.45 (m, 2H), 7.70-7.60 (m, 1H), 7.25-7.18 (m, 1H), 5.25-5.18 (m, 1H), 4.15-4.05 (m, 1H), 2.30-2.20 (m, 1H), 2.10-1.85 (m, 4H), 1.90-1.62 (m, 5H), 1.52-1.28 (m, 10H), 1.28-0.95 (m, 9H), 0.95-0.80 (m, 6H), 0.80-0.75 (m, 3H), 0.59 (s, 3H).

LCMS Rt=0.926 min in 2 min chromatography, 30-90AB_E, purity 100%, MS ESI calcd. For C$_{31}$H$_{48}$NO$_2$ [M+H]$^+$ 466, found 466.

SFC_E1 Rt=1.603 min in 10 min chromatography, AD_3_IPA_DEA_40_25ML, 100% de.

6459
$^1$H NMR (400 MHz, CDCl$_3$) δ 8.55-8.45 (m, 2H), 7.70-7.60 (m, 1H), 7.25-7.18 (m, 1H), 5.25-5.18 (m, 1H), 4.15-4.05 (m, 1H), 2.30-2.20 (m, 1H), 2.01-1.65 (m, 7H), 1.61-1.53 (m, 3H), 1.53-1.29 (m, 8H), 1.25-1.12 (m, 4H), 1.12-0.88 (m, 12H), 0.88-0.75 (m, 3H), 0.59 (s, 3H).

LCMS Rt=0.928 min in 2 min chromatography, 30-90AB_E, purity 100%, MS ESI calcd. For C$_{31}$H$_{48}$NO$_2$ [M+H]$^+$ 466, found 466.

SFC_E1 Rt=2.037 min in 10 min chromatography, AD_3_IPA_DEA_40_25ML, 98% de.

Example 65: Synthesis of 6544, 6571, and 6572

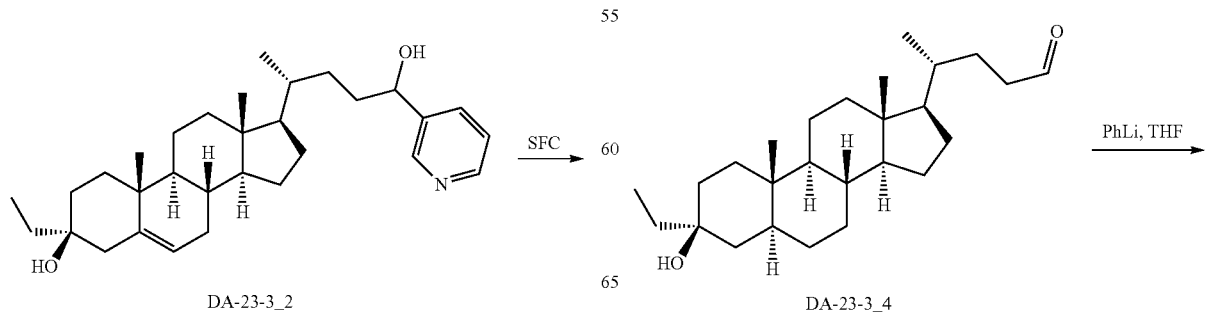

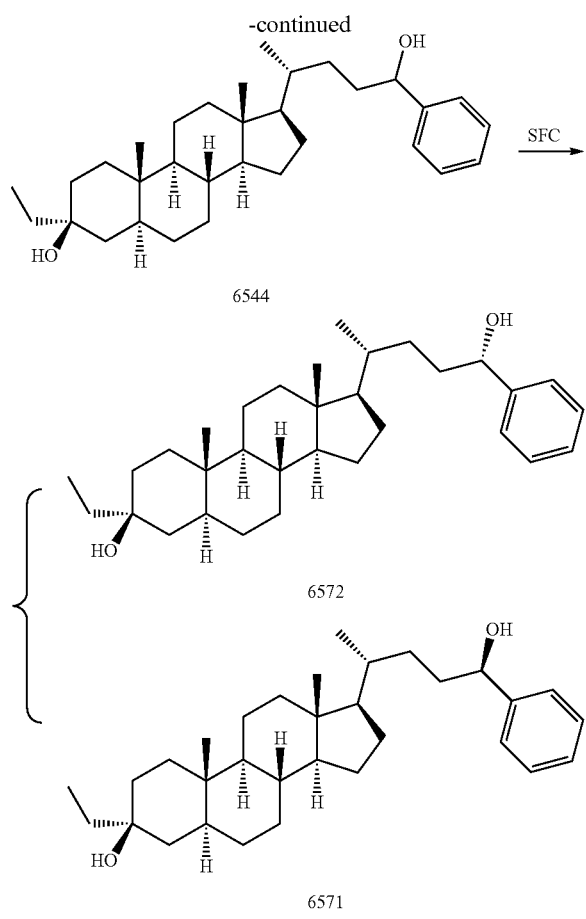

The experimental of intermediate DA-23-3_4 can be found in Example 67.

Synthesis of DA-23-3_5

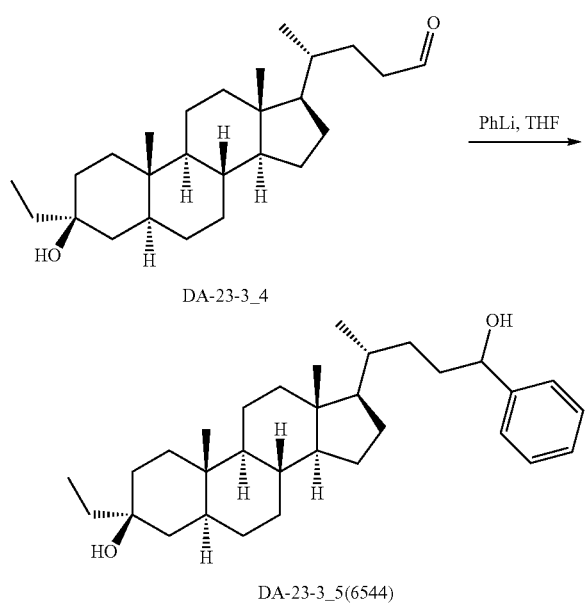

PhLi (1.71 mL, 1.5 M in ether, 2.57 mmol) was added to a solution of DA-23-3_4 (200 mg, 0.514 mmol) in THF (5 mL). The mixture was stirred at 25° C. for 4 h. After cooling, the mixture was treated with NH$_4$Cl (10 mL, sat.). The mixture was extracted with EtOAc (20 mL). The organic layer was separated, dried over Na$_2$SO$_4$, filtered and concentrated in vacuum to give an oil. The mixture was purified by silica gel chromatography (PE/EtOAc=0 to 4/1) to afford DA-23-3_5 (110 mg, 46.0%) as a solid. DA-23-3_5 (20 mg) was used to delivery.

$^1$H NMR (400 MHz, CDCl$_3$) δ 7.35-7.25 (m, 5H), 4.61 (brs, 1H), 1.95-1.88 (m, 1H), 1.80-1.50 (m, 8H), 1.50-1.15 (m, 13H), 1.15-0.83 (m, 15H), 0.82 (s, 3H), 0.68-0.55 (m, 4H).

LCMS Rt=1.286 min in 2.0 min chromatography, 30-90 AB, purity 100%, MS ESI calcd. for C$_{32}$H$_{47}$[M+H−2H$_2$O]$^+$ 431, found 431.

Synthesis of 6571 and 6572

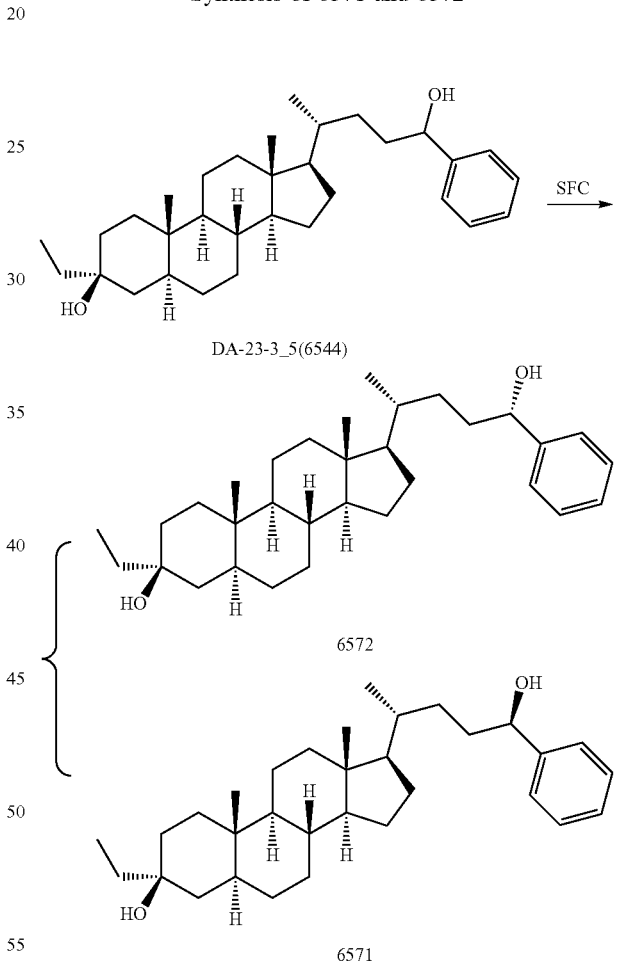

DA-23-3_5 (90 mg, 192 umol) was purified by SFC (Column: AD (150×4.6 mm, 3 um), Gradient: 5%-40% B (A: CO$_2$ B: ethanol) Flow rate: 2.5 mL/min) to afford DA-23-13 (6 mg, 7%) as a solid and DA-23-14 (8 mg, 9%) as a solid.

6571

$^1$H NMR (400 MHz, CDCl$_3$) δ 7.35-7.25 (m, 5H), 4.62 (brs, 1H), 2.00-1.75 (m, 8H), 1.50-1.30 (m, 8H), 1.30-1.05 (m, 10H), 1.05-0.83 (m, 10H), 0.82 (s, 3H), 0.68-0.55 (m, 4H).

LCMS Rt=1.262 min in 2.0 min chromatography, 30-90 AB, purity 100%, MS ESI calcd. for $C_{32}H_{47}[M+H-2H_2O]^+$ 431, found 431.

6572

$^1$H NMR (400 MHz, CDCl$_3$) δ 7.35-7.25 (m, 5H), 4.62 (brs, 1H), 1.95-1.88 (m, 1H), 1.80-1.50 (m, 9H), 1.50-1.15 (m, 13H), 1.15-0.83 (m, 14H), 0.81 (s, 3H), 0.68-0.55 (m, 4H).

LCMS Rt=1.258 min in 2.0 min chromatography, 30-90 AB, purity 100%, MS ESI calcd. for $C_{32}H_{47}$ $[M+H-2H_2O]^+$ 431, found 431.

Synthesis of 6571 to confirm stereochemistry at C24

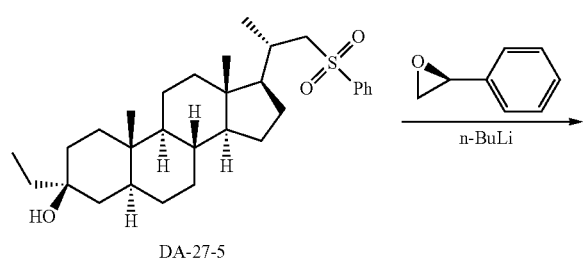

DA-27-5

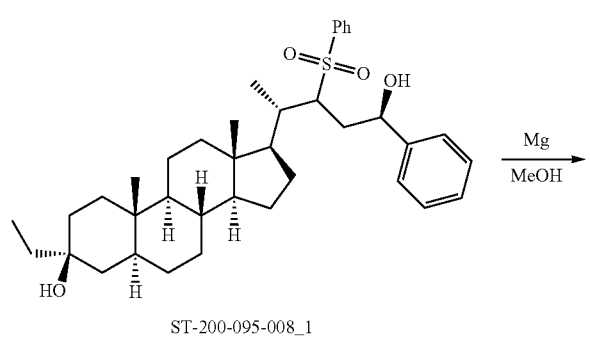

ST-200-095-008_1

ST-200-095-008(6571)

To a solution of DA-27-5 (400 mg, 0.8217 mmol) in anhydrous THF (3 mL) was added n-BuLi (0.984 mL, 2.46 mmol, 2.5M in n-hexane) drop-wise at −70° C. under N$_2$. After stirring at −70° C. for 30 min. a solution of (2S)-2-phenyloxirane (147 mg, 1.23 mmol) in anhydrous THF (0.5 mL) was added drop-wise at −70° C. The reaction mixture was stirred at −70° C. for another 1 h and then stirred at 25° C. (room temperature) for 12 h. The reaction was quenched by saturated NH$_4$Cl.aq (50 mL). The aqueous phase was extracted with EtOAc (3×50 mL). The combine organic phase was washed with saturated brine (2×50 mL), dried over anhydrous Na$_2$SO$_4$, filtered and concentrated in vacuum to give ST-200-095-008_1 (0.5 g, crude) as an oil. The crude residue was directly used the next step.

To a solution of ST-200-095-008_1 (0.5 g, crude) in MeOH (50 mL) was added Mg powder (0.986 g, 41.1 mmol) and NiCl$_2$ (20 mg) at 25° C. under N$_2$. After stirring at 60° C. for 1 h, the reaction mixture was quenched with HCl (100 mL, 1 M) until the reaction became clear. The aqueous phase was extracted with EtOAc (2×100 mL). The combined organic phase was washed with saturated NaHCO$_3$.aq (2×50 mL) and washed whit brine (2×100 mL), dried over anhydrous Na$_2$SO$_4$, filtered and concentrated. The residue was purified by silica gel chromatography (PE/EtOAc=8/1 to 5/1) to afford ST-200-095-008 (250 mg, impure) as a solid, which was re-crystallized from MeCN (20 mL) at 82° C. reflux for 30 mins. The mixture stirred was cool to 25° C. (room temperature). The suspension was filtration in vacuum to get ST-200-095-008 (200 mg, impure) as a solid. The ST-200-095-008 (200 mg, 0.428 mmol) was by SFC (Instrument: SFC-16, Column:OD(250 mm*30 mm, 5 um), Condition:0.1% NH$_3$H$_2$O ETOH, Begin B:45%, End B:45%, FlowRate(ml/min):60, Injections:70) to give ST-200-095-008 (148 mg, 38%) as a solid.

$^1$H NMR (400 MHz, CDCl$_3$) δ 7.38-7.31 (m, 4H), 7.30-7.24 (m, 2H), 4.58-4.54 (m, 1H), 1.96-1.73 (m, 4H), 1.67-1.59 (m, 4H), 1.54-1.14 (m, 15H), 1.13-0.86 (m, 13H), 0.84-0.80 (m, 3H), 0.68-0.59 (m, 4H).

LCMS Rt=1.306 min in 2 min chromatography, 30-90AB_2 MIN_E, purity 100%, MS ESI calcd. for $C_{32}H_{47}$ $[M+H-2H_2O]^+$ 431, found 431.

SFC Rt=5.523 min in 10 min chromatography, OD_3_EtOH_DEA_5_40_25ML ("Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C."), 100% de.

Example 66: Synthesis of 6680 and 6681

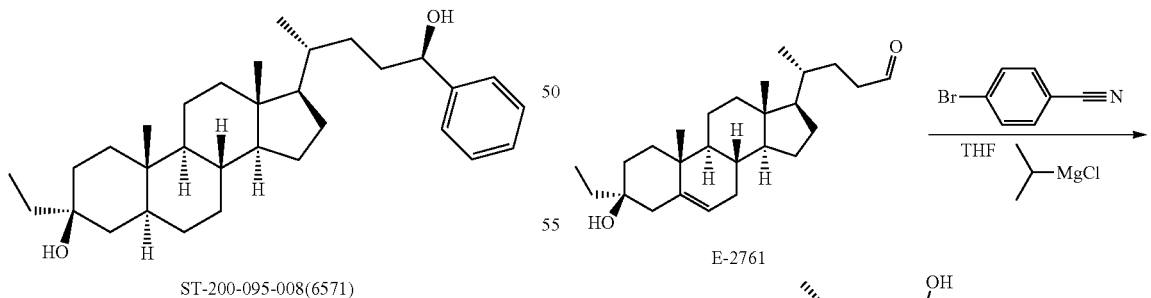

E-2761

DA-62-4_1

294

Synthesis of 6680 and 6681

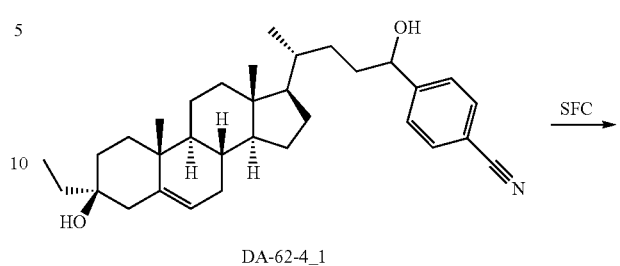

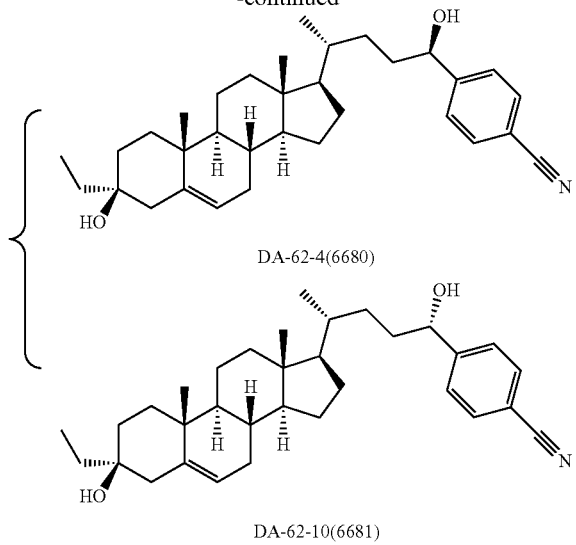

DA-62-4(6680)

DA-62-10(6681)

The stereochemistry at C24 is randomly assigned.

The experimental of intermediate E-2761 can be found in Example 63 or Example 60.

Synthesis of DA-62-4_1

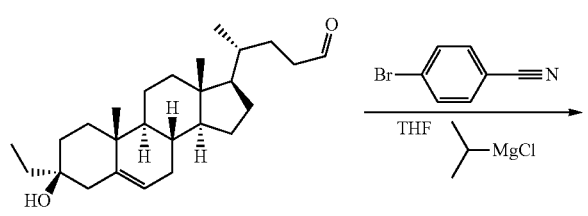

E-2761

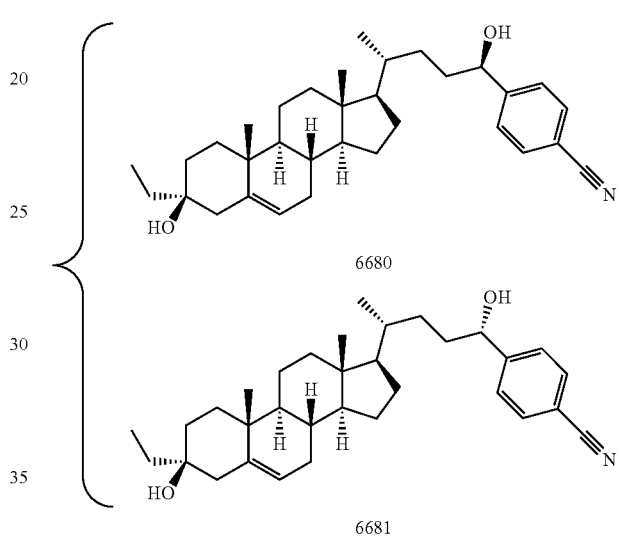

6680

6681

Isopropylmagnesium chloride (2 M, 2.59 mL) was added dropwise to a solution of 1-bromo-4-cyanobenzene (940 mg, 5.19 mmol) in THF (10 mL) at 0° C. under $N_2$. After stirring at 0° C. for 2 h, a solution of E-2761 (200 mg, 0.517 mmol) in THF (10 mL) was added at 0° C. under $N_2$. The mixture was stirred at 0° C. for 2 h and treated with saturated aqueous $NH_4Cl$ (30 mL). The aqueous phase was extracted with EtOAc (3×20 mL). The combined organic phase was washed with saturated brine (2×200 mL), dried over anhydrous $Na_2SO_4$, filtered and concentrated to give an oil, which was purified by flash column (0~20% of EtOAc in PE) to give DA-62-4_1 (140 mg, 55%) as a solid.

DA-62-4_1 (140 mg, 0.285 mmol) was purified by SFC (Column: AD (150×4.6 mm, 3 um), Gradient: 5%-40% B (A: $CO_2$ B: ethanol) Flow rate: 2.5 mL/min) to afford DA-62-4 (32.0 mg, 23%) as a solid and DA-62-10 (33.0 mg, 24%) as a solid. The chiral center at C24 was assigned randomly.

6680:

$^1$H NMR (400 MHz, $CDCl_3$) 7.68-7.60 (m, 2H), 7.50-7.40 (m, 2H), 5.30-5.25 (m, 1H), 4.72-4.62 (m, 1H), 2.40-2.30 (m, 1H), 2.08-1.85 (m, 4H), 1.80-1.55 (m, 6H), 1.50-1.32 (m, 8H), 1.25-1.00 (m, 10H), 1.00-0.75 (m, 9H), 0.66 (s, 3H).

LCMS Rt=1.170 min in 2.0 min chromatography, 30-90 AB, purity 98%, MS ESI calcd. for $C_{33}H_{46}NO$ [M+H−$H_2O$]$^+$ 472, found 472.

6681

$^1$H NMR (400 MHz, $CDCl_3$) 7.68-7.60 (m, 2H), 7.50-7.40 (m, 2H), 5.30-5.25 (m, 1H), 4.72-4.62 (m, 1H), 2.40-2.30 (m, 1H), 2.08-1.85 (m, 4H), 1.80-1.55 (m, 6H), 1.50-1.32 (m, 8H), 1.25-1.00 (m, 10H), 1.00-0.75 (m, 9H), 0.66 (s, 3H).

LCMS Rt=1.174 min in 2.0 min chromatography, 30-90 AB, purity 100%, MS ESI calcd. for $C_{33}H_{46}NO$ [M+H−$H_2O$]$^+$ 472, found 472.

Example 67: Synthesis of 6754 and 6755
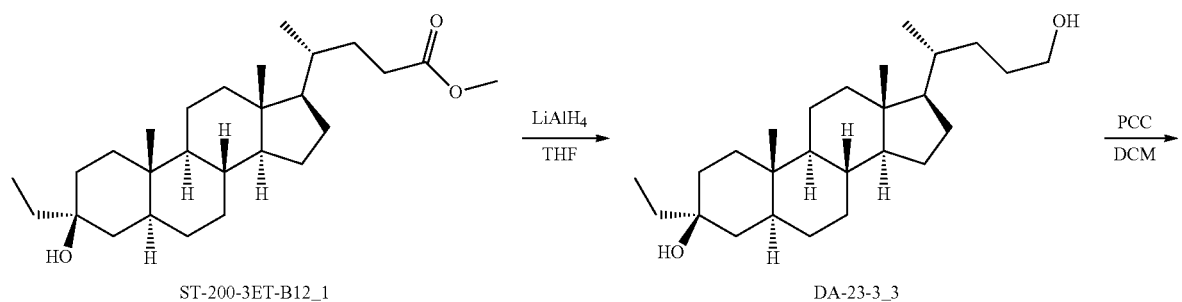
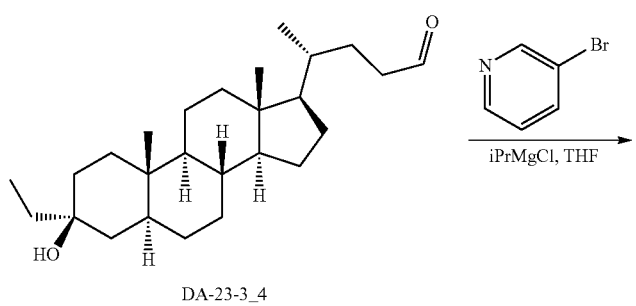
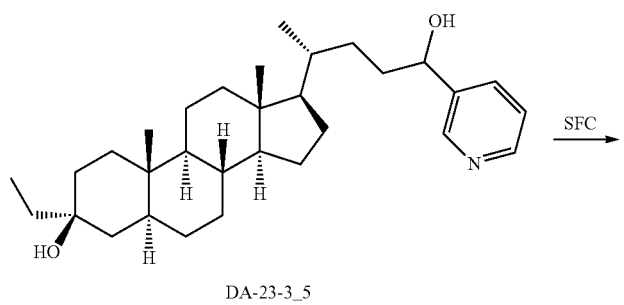
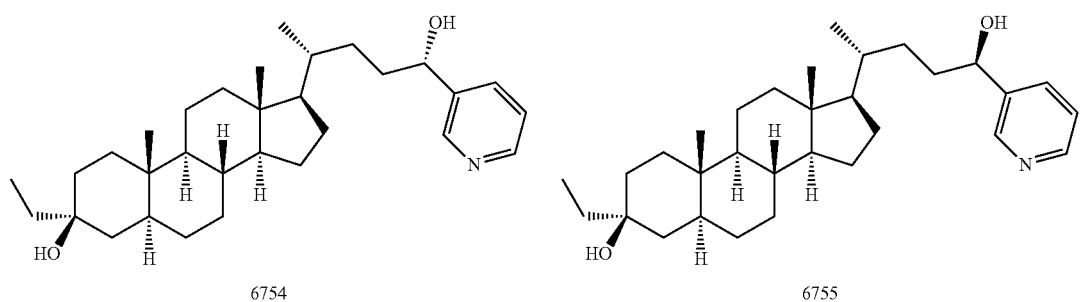

The stereochemistry for 6754 and 6755 has been assigned based on NMR data.

The synthesis of ST-200-3ET-B12_1 can be found in Example 125.

Synthesis of DA-23-3_3

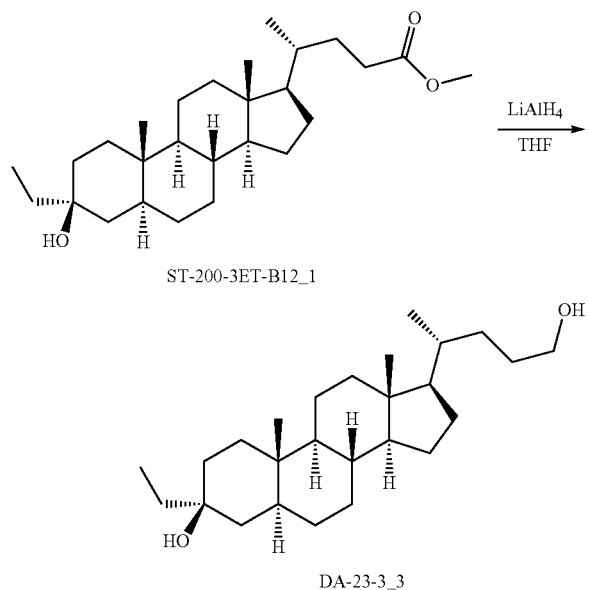

LiAlH$_4$ (198 mg, 2.54 mmol) was added in three portions to a solution of ST-200-3ET-B12_1 (1.1 g, 2.62 mmol) in THF (10 mL) at 0° C. under N$_2$. After stirring at 20° C. for 1 hour, the mixture was quenched with water (10 mL) at 0° C., followed by adding HCl (10 mL, 1 mol/L). The aqueous phase was extracted with EtOAc (2×10 mL). The combined organic phase was washed with saturated brine (2×10 mL), dried over anhydrous Na$_2$SO$_4$, filtered and concentrated. The residue was purified by flash column (0~50% of EtOAc in PE) to give DA-23-3_3 (1 g, 98%) as a solid.

$^1$H NMR CDCl$_3$ 400 MHz S 3.65-3.55 (m, 2H), 1.98-1.92 (m, 1H), 1.88-1.75 (m, 1H), 1.70-1.40 (m, 13H), 1.40-1.19 (m, 7H), 1.19-0.98 (m, 7H), 0.98-0.80 (m, 11H), 0.66-0.61 (m, 4H).

Synthesis of DA-23-3_4

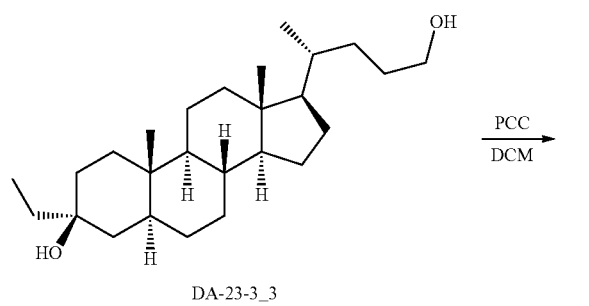

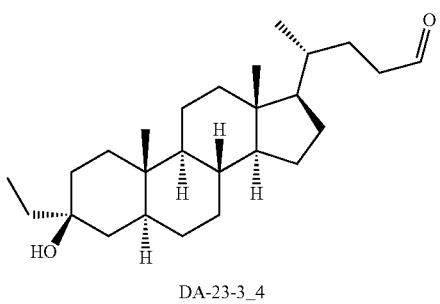

To a solution of DA-23-3_3 (1 g, 2.55 mmol) in anhydrous DCM (30 mL) was added silica gel (1 g) and PCC (1.09 g, 5.10 mmol). After stirring at 20° C. for 1 hours, the reaction mixture was filtered and the filtrate was concentrated. The residue was purified by column chromatography on silica gel (PE/EA=50/1 to 10/1) to give DA-23-3_4 (600 mg, 60%) as a solid.

$^1$H NMR CDCl$_3$ 400 MHz δ 9.98-9.97 (m, 1H), 2.50-2.20 (m, 2H), 2.05-1.50 (m, 3H), 1.50-1.19 (m, 15H), 1.19-0.99 (m, 7H), 0.99-0.82 (m, 12H), 0.70-0.55 (m, 4H).

Synthesis of DA-23-3_5

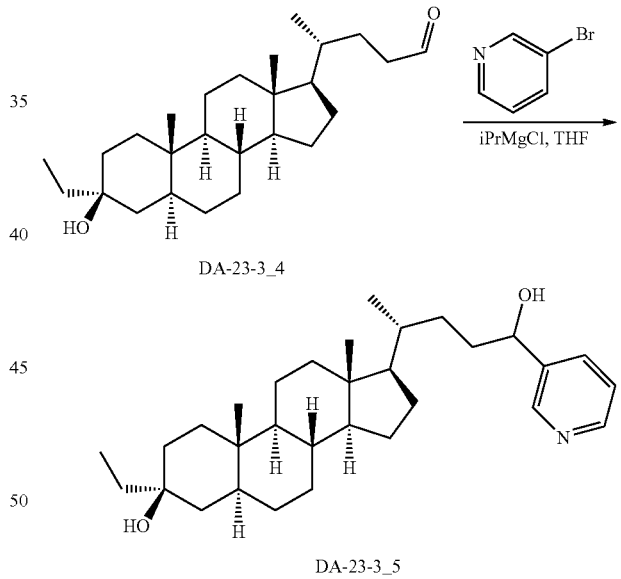

Isopropylmagnesium chloride (7.70 mL, 15.4 mmol, 2 M in THF) was added to a suspension of 3-bromopyridine (2.43 g, 15.4 mmol) in THF (10 mL) at 0° C. The mixture was stirred at 25° C. for 1 hour. To the fresh prepared pyridin-3-ylmagnesium chloride (2.12 g, 15.4 mmol) was added DA-23-3_4 (300 mg, 0.771 mmol) in THF (10 mL) at 0° C. The mixture was stirred at 25° C. for 2 hours and quenched with NH$_4$Cl (20 mL, 10% aq.). The mixture was extracted with EtOAc (2×20 mL). The organic layer was separated. The combined organic phase was dried over Na$_2$SO$_4$, filtered, concentrated to afford DA-23-3_5 (280 mg, crude) as a solid.

Synthesis of 6754 and 6755

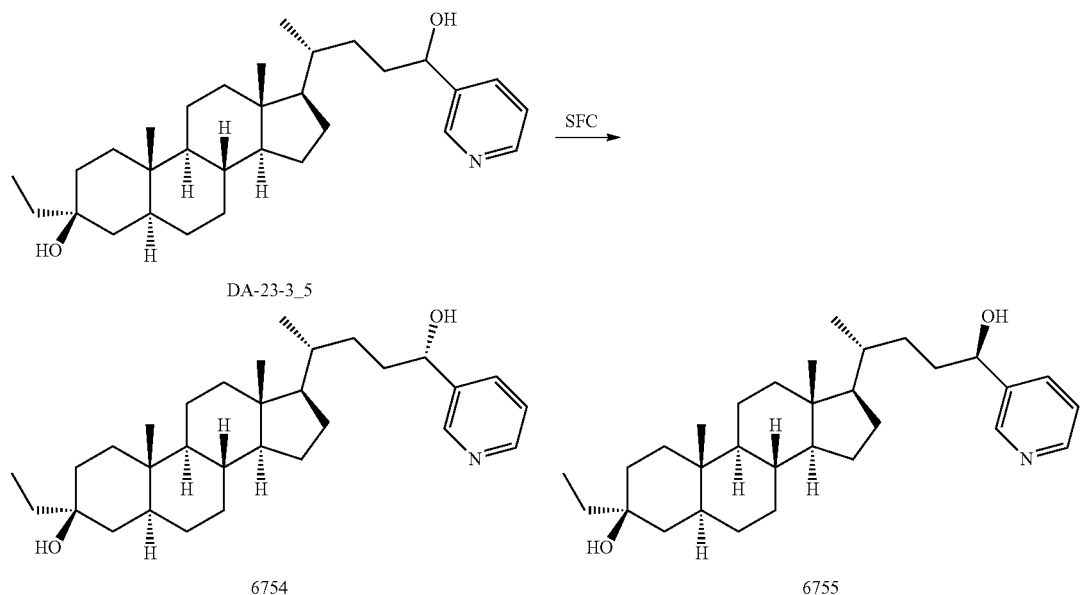

DA-23-3_5

6754

6755

190 mg of DA-23-3_5 was separated with SFC (Column: AD(250 mm*30 mm, 10 um); Condition: 0.1% NH$_3$H$_2$O IPA, 40% B; FlowRate(ml/min): 60) to give 6754 (34 mg, impure) and 6755 (35 mg, impure) as a solid.

34 mg of impure 6754 was re-cystallized from MeCN (5 mL) at 70° C. to give 6754 (14 mg) as a solid.

35 mg of impure 6755 was re-cystallized from MeCN (5 mL) at 70° C. to give 6755 (19 mg) as a solid.

6457:
$^1$H NMR (400 MHz, CDCl$_3$) δ 8.65-8.50 (m, 2H), 7.75-7.60 (m, 1H), 7.35-7.27 (m, 1H), 4.75-4.60 (m, 1H), 2.00-1.60 (m, 8H), 1.55-1.15 (m, 14H), 1.10-0.75 (m, 18H), 0.70-0.50 (m, 4H).

LCMS Rt=0.846 min in 2 min chromatography, 30-90AB_E, purity 99.8%, MS ESI calcd. For C$_{31}$H$_{50}$NO$_2$ [M+H]$^+$ 468, found 468.

6755
$^1$H NMR (400 MHz, CDCl$_3$) δ 8.65-8.50 (m, 2H), 7.75-7.60 (m, 1H), 7.35-7.27 (m, 1H), 4.75-4.60 (m, 1H), 2.00-1.60 (m, 8H), 1.55-1.15 (m, 15H), 1.10-0.75 (m, 17H), 0.70-0.50 (m, 4H).

LCMS Rt=0.836 min in 2 min chromatography, 30-90AB_E, purity 98.3%, MS ESI calcd. For C$_{31}$H$_{50}$NO$_2$ [M+H]$^+$ 468, found 468.

Example 68: Synthesis of 6895 and 6896

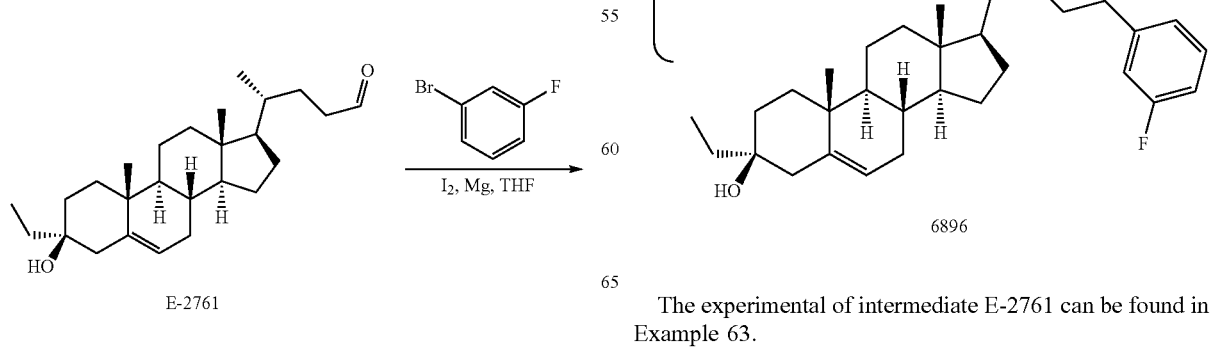

E-2761

DA-62-2_1

6895

6896

The experimental of intermediate E-2761 can be found in Example 63.

Synthesis of DA-62-2_1

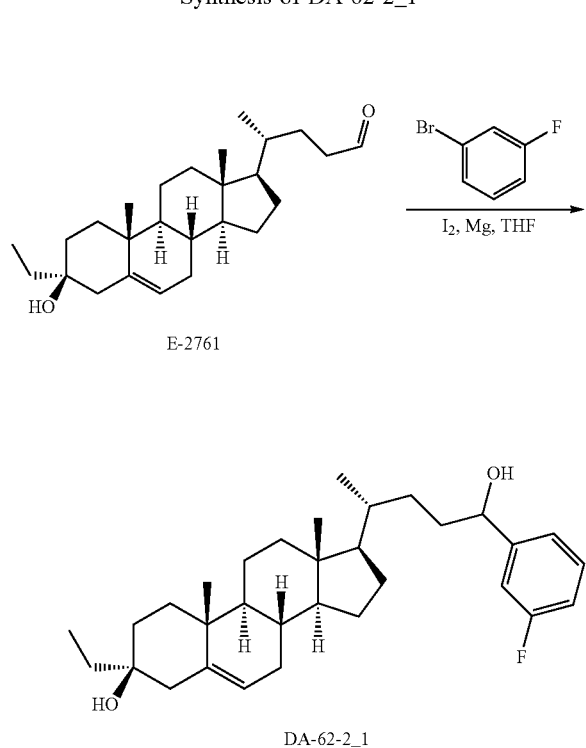

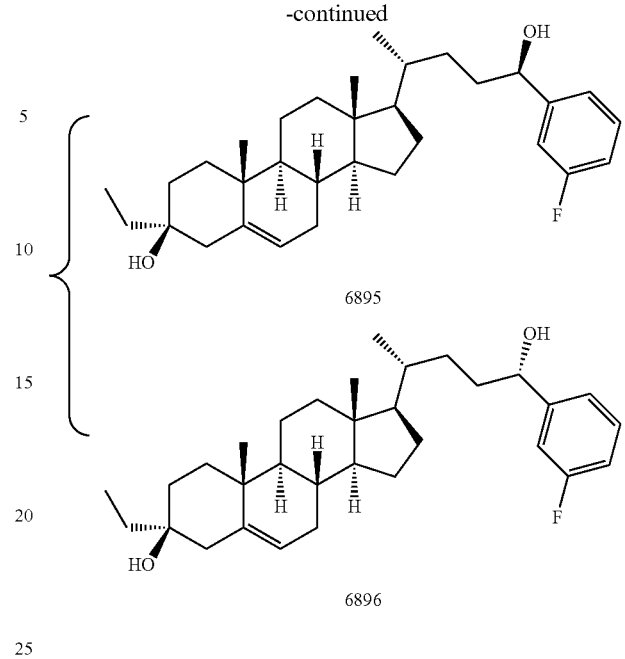

1-bromo-3-fluorobenzene (900 mg, 5.14 mmol) was added to a suspension of magnesium (124 mg, 5.14 mmol) and a small amount of iodine (130 mg, 0.514 mmol) in tetrahydrofuran (3 mL). After stirring for 2 h at 50° C., a solution E-2761 (200 mg, 0.517 mmol) in THF (10 mL) was added at 15° C. under $N_2$. The mixture was stirred at 15° C. for 2 h and quenched with saturated aqueous $NH_4Cl$ (30 mL). The aqueous phase was extracted with EtOAc (3×20 mL). The combined organic phase was washed with saturated brine (2×20 mL), dried over anhydrous $Na_2SO_4$, filtered and concentrated to give an oil. The mixture was purified by flash column (0~20% of EtOAc in PE) to give DA-62-2_1 (120 mg, 48%) as a solid.

$^1$H NMR (400 MHz, $CDCl_3$) δ 7.35-7.25 (m, 1H), 7.10-7.02 (m, 2H), 7.00-6.90 (m, 1H), 5.30-5.25 (m, 1H), 4.68-4.55 (m, 1H), 2.40-2.30 (m, 1H), 2.05-1.90 (m, 3H), 1.90-1.50 (m, 7H), 1.50-1.30 (m, 8H), 1.30-1.15 (m, 3H), 1.15-0.86 (m, 13H), 0.86-0.80 (m, 3H), 0.66 (s, 3H).

Synthesis of 6895 and 6896

DA-62-2_1 (120 mg, 0.248 mmol) was purified by SFC (Column: AD (150×4.6 mm, 3 um), Gradient: 5%-40% B (A: $CO_2$ B: ethanol) Flow rate: 2.5 mL/min) to afford 6895 (32.0 mg, 27%) as a solid and 6896 (40.0 mg, 34%) as a solid.

6895:
$^1$H NMR (400 MHz, $CDCl_3$) δ 7.35-7.25 (m, 1H), 7.10-7.02 (m, 2H), 7.00-6.90 (m, 1H), 5.30-5.25 (m, 1H), 4.68-4.55 (m, 1H), 2.40-2.30 (m, 1H), 2.05-1.90 (m, 3H), 1.90-1.50 (m, 7H), 1.50-1.30 (m, 8H), 1.30-1.13 (m, 4H), 1.13-0.86 (m, 12H), 0.86-0.78 (m, 3H), 0.66 (s, 3H).

LCMS Rt=1.263 min in 2.0 min chromatography, 30-90 AB, purity 100%, MS ESI calcd. for $C_{32}H_{44}F$ [M+H−$2H_2O$]$^-$ 447, found 447.

6896:
$^1$H NMR (400 MHz, $CDCl_3$) δ 7.35-7.25 (m, 1H), 7.10-7.02 (m, 2H), 7.00-6.90 (m, 1H), 5.30-5.25 (m, 1H), 4.65-4.53 (m, 1H), 2.40-2.30 (m, 1H), 2.05-1.90 (m, 3H), 1.90-1.50 (m, 7H), 1.50-1.30 (m, 8H), 1.30-0.86 (m, 16H), 0.86-0.80 (m, 3H), 0.66 (s, 3H).

LCMS Rt=1.261 min in 2.0 min chromatography, 30-90 AB, purity 100%, MS ESI calcd. for $C_{32}H_{44}F$ [M+H−$2H_2O$]$^+$ 447, found 447.

Synthesis of 6896 to Confirm Stereochemistry

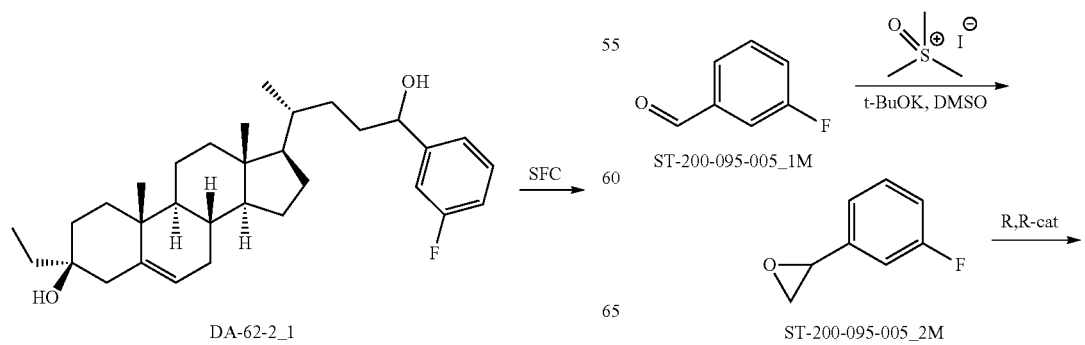

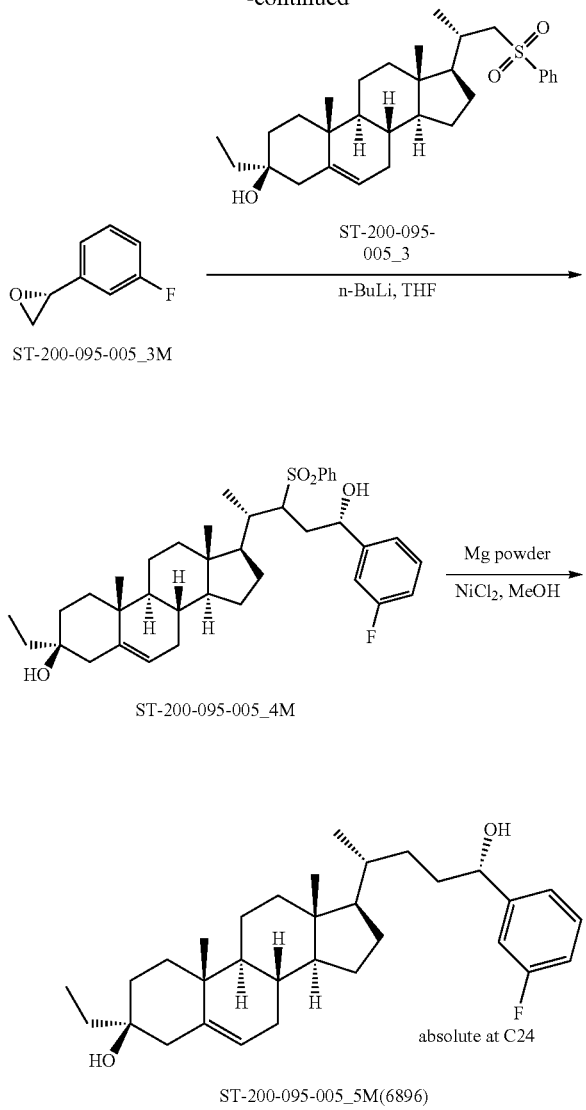

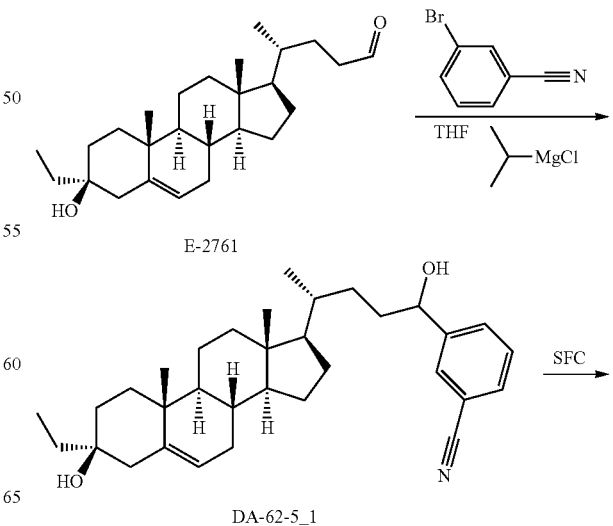

To a mixture of trimethylsulfoxonium iodide (106 g, 482 mmol) in DMSO (200 mL) and THF (150 mL) was added t-BuOK (53.9 g, 482 mmol). The mixture was stirred at 40° C. for 1 hour. The solution was then cooled to 0° C. and ST-200-095-005_1 M (30 g, 241 mmol) in THF (50 mL) was added at 0° C. The reaction mixture was stirred 30 minutes and poured into H$_2$O (300 mL). The resulting mixture was extracted with EtOAc (3×200 mL). The combined organic layers were washed with H$_2$O (2×100 mL), brine (100 mL), dried over anhydrous Na$_2$SO$_4$, filtered and concentrated. The residue was purified by flash column (0~1% of EtOAc in PE) to give product ST-200-095-005_2 M (32 g, 96%) as anoil.

$^1$H NMR (400 MHz, CDCl$_3$) δ 7.35-7.25 (m, 1H), 7.10-7.01 (m, 1H), 7.01-6.80 (m, 2H), 3.80-3.78 (m, 1H), 3.20-3.10 (m, 1H), 2.75-2.70 (m, 1H).

To a solution of R,R-cat (86.9 mg, 0.144 mmol) in toluene (5 mL) was added AcOH (88.8 mg, 1.48 mmol). The mixture was stirred at 25° C. open to air for 30 min and concentrated in vacuum to leave a crude solid. The resulting catalyst residue was dissolved in ST-200-095-005_2 M (5 g, 36.1 mmol) at 25° C. The reaction flask was cooled to 0° C., and H$_2$O (356 mg, 19.8 mmol) was added dropwise over 5 min. The reaction was allowed to warm to 25° C. and stirred 16 hrs. The reaction mixture was purified directly by silica gel chromatography (PE %=100%) to afford ST-200-095-005_3 M (2 g, 40%) as an oil. The ee % was 100%.

$^1$H NMR (400 MHz, CDCl$_3$) δ 7.35-7.25 (m, 1H), 7.10-7.01 (m, 1H), 7.01-6.80 (m, 2H), 3.80-3.78 (m, 1H), 3.20-3.10 (m, 1H), 2.75-2.70 (m, 1H).

To a THF (1 mL) under N$_2$ at −70° C. was added n-BuLi (2.5 M, 3.09 mmol, 1.23 mL). After that, a solution of ST-200-095-005_3 (300 mg, 0.618 mmol) in THF (2 mL) was added dropwise to give a suspension. After stirring at −70° C. for 30 min, a solution of ST-200-095-005_3 M (341 mg, 2.47 mmol) in THF (2 mL) was added. Then reaction was stirred at stirred at 25° C. for 16 hours. The mixture was poured into ice-water (20 mL) and extracted with EtOAc (2×30 mL). The combined organic layers were washed with brine (30 mL), dried over Na$_2$SO$_4$, filtered and concentrated in vacuum to afford ST-200-095-005_4 M (500 mg, crude) as a solid, which was used directly for the next step.

To a solution of ST-200-095-005_4 M (500 mg, 0.802 mmol) in MeOH (100 mL) was added NiCl$_2$ (5 mg) and Mg powder (768 mg, 32.0 mmol) at 65° C. in four portions. The reaction mixture was cooled to 25° C. and quenched by saturated aqueous NH$_4$Cl (100 mL). The mixture was stirred for 1 hour. The resulting mixture was extracted with EtOAc (3×100 mL). The combined organic layers were washed with brine (50 mL), dried over anhydrous Na$_2$SO$_4$, filtered and concentrated. The residue was purified by flash column (0~10% of EtOAc in PE) and re-crystallized from DCM/n-hexane (0.5 mL/10 mL) at 25° C. to give ST-200-095-005_5 M (20 mg, 29%) as a solid.

$^1$H NMR (400 MHz, CDCl$_3$) δ 7.35-7.27 (m, 1H), 7.15-7.01 (m, 1H), 7.01-6.80 (m, 2H), 5.27-5.25 (m, 1H), 4.65-4.60 (m, 1H), 2.40-2.30 (m, 1H), 2.02-1.85 (m, 3H), 1.75-1.65 (m, 7H), 1.65-1.25 (m, 7H), 1.25-1.01 (m, 10H), 0.66 (s, 3H).

LCMS Rt=1.287 min in 2 min chromatography, 30-90AB_2 MIN_E, purity 100%, MS ESI calcd. for C$_{32}$H$_{44}$FO [M+H−2H$_2$O]$^+$ 447, found 447.

Example 69: Synthesis of 6997 and 6998

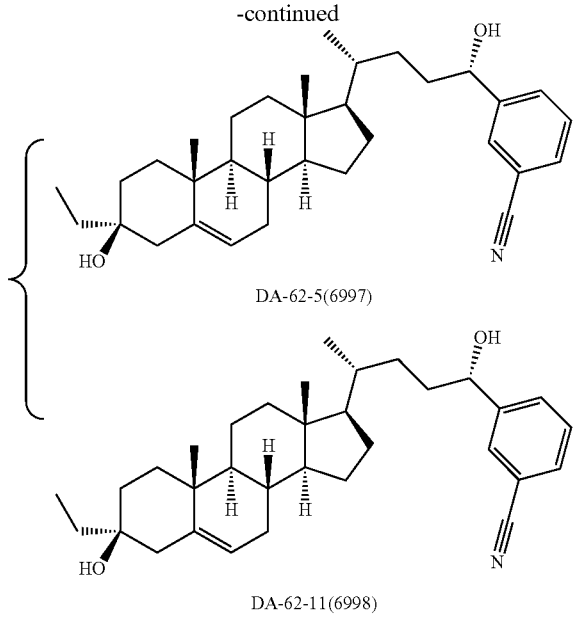

Stereochemistry at C24 was assigned based on NMR data. The experimental of intermediate E-2761 can be found in Example 63.

Synthesis of DA-62-5_1

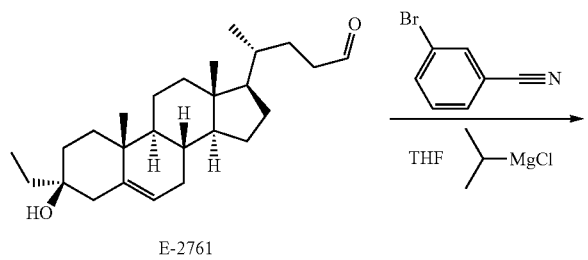

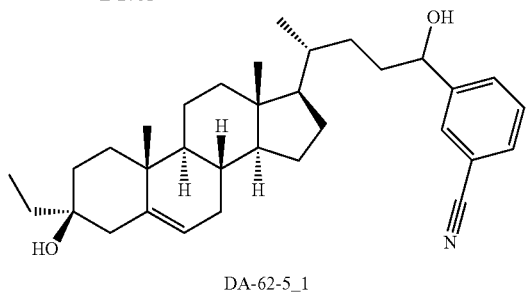

Isopropylmagnesium chloride (2 M, 2.58 mL) was added dropwise to a solution of 1-bromo-3-cyanobenzene (936 mg, 5.17 mmol) in THF (10 mL) at 0° C. under $N_2$. After stirring at 0° C. for 2 h, a solution of E-2761 (200 mg, 0.517 mmol) in THF (10 mL) was added at 0° C. under $N_2$. The mixture was stirred at 0° C. for 2 h and quenched with saturated aqueous $NH_4Cl$ (30 mL) was added. The aqueous phase was extracted with EtOAc (3×20 mL). The combined organic phase was washed with saturated brine (2×20 mL), dried over anhydrous $Na_2SO_4$, filtered and concentrated to give an oil. The mixture was purified by flash column (0~20% of EtOAc in PE) to give DA-62-5_1 (140 mg, 55%) as a solid.

$^1$H NMR (400 MHz, $CDCl_3$) δ 7.70-7.65 (m, 1H), 7.60-7.50 (m, 2H), 7.50-7.40 (m, 1H), 5.30-5.28 (m, 1H), 4.72-4.52 (m, 1H), 2.40-2.30 (m, 1H), 2.05-1.50 (m, 5H), 1.50-1.30 (m, 9H), 1.30-1.15 (m, 4H), 1.15-0.88 (m, 15H), 0.88-0.78 (m, 4H), 0.66 (s, 3H).

Synthesis of 6997 and 6998

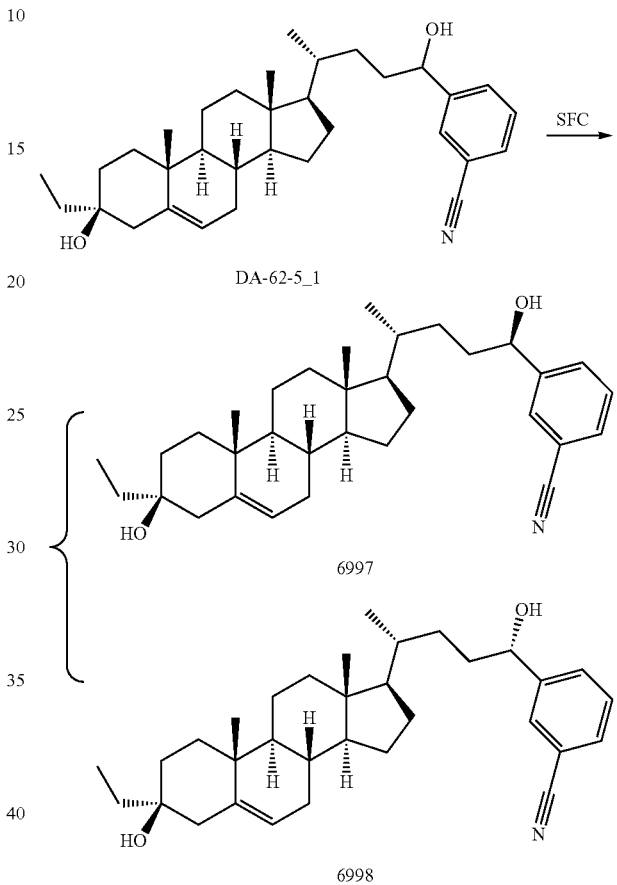

DA-62-5_1 (140 mg, 0.285 mmol) was purified by SFC (Column: AD (150×4.6 mm, 3 um), Gradient: 5%-40% B (A: $CO_2$ B: ethanol) Flow rate: 2.5 mL/min) to afford DA-62-5 (30.0 mg, 22%) as a solid and DA-62-11 (38.0 mg, 27%) as a solid.

6997:
$^1$HNMR (400 MHz, $CDCl_3$) δ 7.35-7.25 (m, 1H), 7.10-7.02 (m, 2H), 7.00-6.90 (m, 1H), 5.30-5.25 (m, 1H), 4.68-4.55 (m, 1H), 2.40-2.30 (m, 1H), 2.05-1.90 (m, 3H), 1.90-1.50 (m, 7H), 1.50-1.30 (m, 8H), 1.30-0.86 (m, 16H), 0.86-0.76 (m, 3H), 0.66 (s, 3H).
LCMS Rt=1.202 min in 2.0 min chromatography, 30-90 AB, purity 99%, MS ESI calcd. for $C_{33}H_{46}NO$ [M+H–$H_2O]^+$ 472, found 472.

6998:
$^1$H NMR (400 MHz, $CDCl_3$) δ 7.35-7.25 (m, 1H), 7.10-7.02 (m, 2H), 7.00-6.90 (m, 1H), 5.30-5.25 (m, 1H), 4.65-4.53 (m, 1H), 2.40-2.30 (m, 1H), 2.05-1.90 (m, 4H), 1.90-1.50 (m, 7H), 1.50-1.30 (m, 7H), 1.30-0.86 (m, 16H), 0.86-0.80 (m, 3H), 0.66 (s, 3H).
LCMS Rt=1.194 min in 2.0 min chromatography, 30-90 AB, purity 100%, MS ESI calcd. for $C_{33}H_{46}NO$ [M+H–$H_2O]^+$ 472, found 472.

Example 70: Synthesis of 7030 and 7032

Synthesis of DA-023

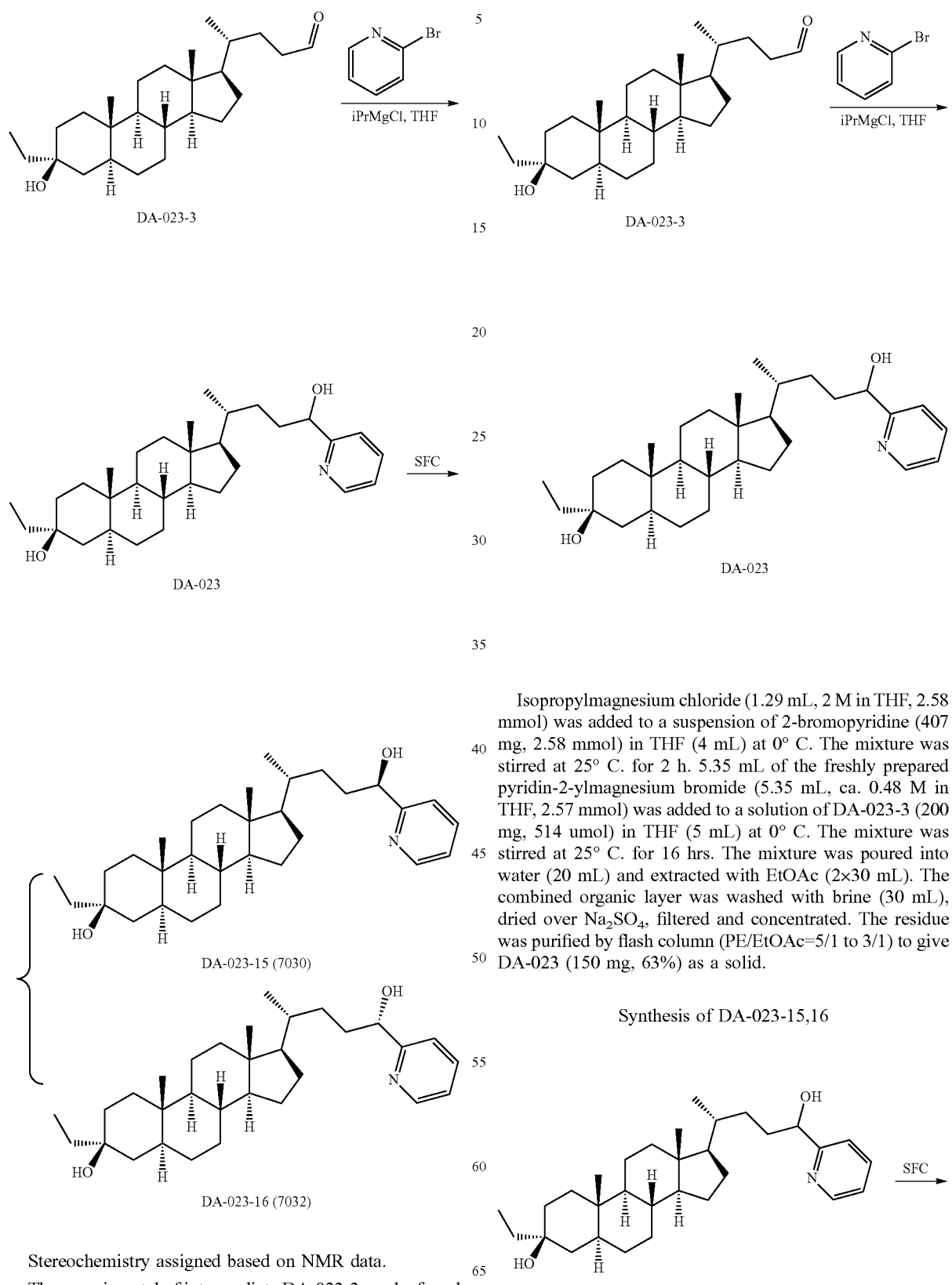

Stereochemistry assigned based on NMR data.

The experimental of intermediate DA-023-3 can be found in Example 126.

Isopropylmagnesium chloride (1.29 mL, 2 M in THF, 2.58 mmol) was added to a suspension of 2-bromopyridine (407 mg, 2.58 mmol) in THF (4 mL) at 0° C. The mixture was stirred at 25° C. for 2 h. 5.35 mL of the freshly prepared pyridin-2-ylmagnesium bromide (5.35 mL, ca. 0.48 M in THF, 2.57 mmol) was added to a solution of DA-023-3 (200 mg, 514 umol) in THF (5 mL) at 0° C. The mixture was stirred at 25° C. for 16 hrs. The mixture was poured into water (20 mL) and extracted with EtOAc (2×30 mL). The combined organic layer was washed with brine (30 mL), dried over $Na_2SO_4$, filtered and concentrated. The residue was purified by flash column (PE/EtOAc=5/1 to 3/1) to give DA-023 (150 mg, 63%) as a solid.

Synthesis of DA-023-15,16

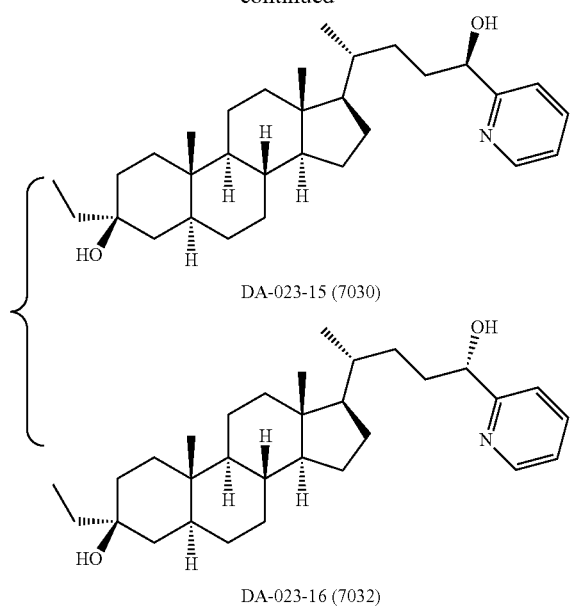

DA-023 (150 mg) was purified by SFC (Column: AS (250 mm*30 mm, 5 um), Condition: 0.1% NH₃H₂O IPA, Gradient: from 25% to 25%, Flow Rate (ml/min): 50 mL/min, 25° C.) to afford DA-023-15 (31 mg, 21%) and DA-023-16 (55 mg, 37%) as a solid.

7030:

$^1$H NMR (400 MHz, DMSO-d$_6$) δ 8.53 (d, J=4 Hz, 1H), 7.70-7.65 (m, 1H), 7.25-7.24 (m, 1H), 7.20-7.17 (m, 1H), 4.71-4.68 (m, 1H), 1.95-1.90 (m, 1H), 1.84-1.51 (m, 12H), 1.47-1.13 (m, 11H), 1.12-0.81 (m, 16H), 0.63-0.58 (m, 4H).

LCMS Rt=0.923 min in 2.0 min chromatography, 30-90 AB, purity 100%, MS ESI calcd. For C$_{31}$H$_{50}$NO$_2$ [M+H]$^+$ 468, found 468.

7032:

$^1$H NMR (400 MHz, DMSO-d$_6$) δ 8.53 (d, J=4 Hz, 1H), 7.70-7.65 (m, 1H), 7.25-7.24 (m, 1H), 7.20-7.17 (m, 1H), 4.71-4.68 (m, 1H), 1.95-1.83 (m, 2H), 1.81-1.31 (m, 16H), 1.28-1.03 (m, 9H), 1.00-0.81 (m, 13H), 0.63-0.58 (m, 4H).

LCMS Rt=0.914 min in 2.0 min chromatography, 30-90 AB, purity 99.5%, MS ESI calcd. For C$_{31}$H$_{50}$NO$_2$ [M+H]$^+$ 468, found 468.

Example 71: Synthesis of 7147 and 7146

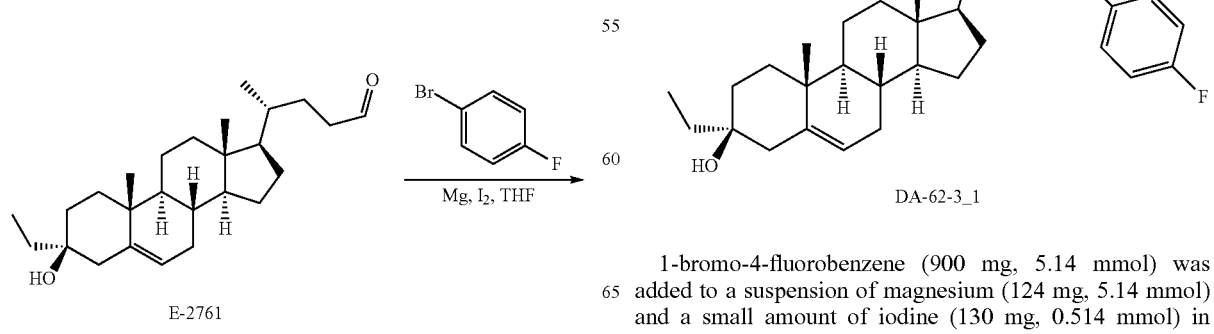

The experimental of intermediate E-02761 can be found in Example 63.

Synthesis of DA-62-3_1

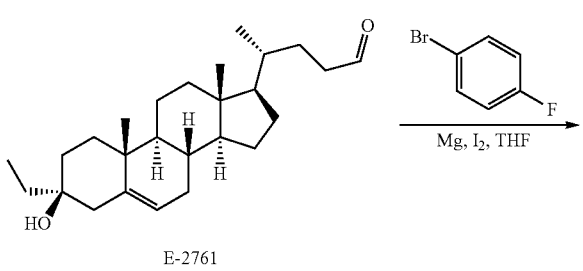

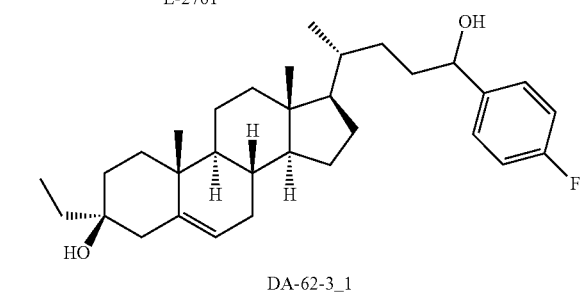

1-bromo-4-fluorobenzene (900 mg, 5.14 mmol) was added to a suspension of magnesium (124 mg, 5.14 mmol) and a small amount of iodine (130 mg, 0.514 mmol) in tetrahydrofuran (10 mL). The mixture was stirred for 2 h at 50° C. A solution of E-2761 (200 mg, 0.517 mmol) in THF (10 mL) was added to the Grignard mixture at 15° C. under $N_2$. The mixture was stirred at 15° C. for 2 h and quenched with saturated aqueous $NH_4Cl$ (30 mL). The aqueous phase was extracted with EtOAc (3×20 mL). The combined organic phase was washed with saturated brine (2×20 mL), dried over anhydrous $Na_2SO_4$, filtered and concentrated to give an oil, which was purified by flash column (0~20% of EtOAc in PE) to give DA-62-3_1 (120 mg, 48%) as a solid.

$^1$H NMR (400 MHz, CDCl$_3$) δ 7.35-7.25 (m, 2H), 7.08-6.95 (m, 2H), 5.28 (brs, 1H), 4.63-4.53 (m, 1H), 2.38-2.30 (m, 1H), 2.00-1.50 (m, 10H), 1.50-1.28 (m, 8H), 1.28-1.00 (m, 10H), 1.00-0.80 (m, 9H), 0.66 (s, 3H).

LCMS Rt=1.453 min in 2.0 min chromatography, 30-90 AB, purity 84%, MS ESI calcd. for $C_{32}H_{44}F$ [M+H−2H$_2$O]$^+$ 447, found 447.

Synthesis of 7146 and 7147

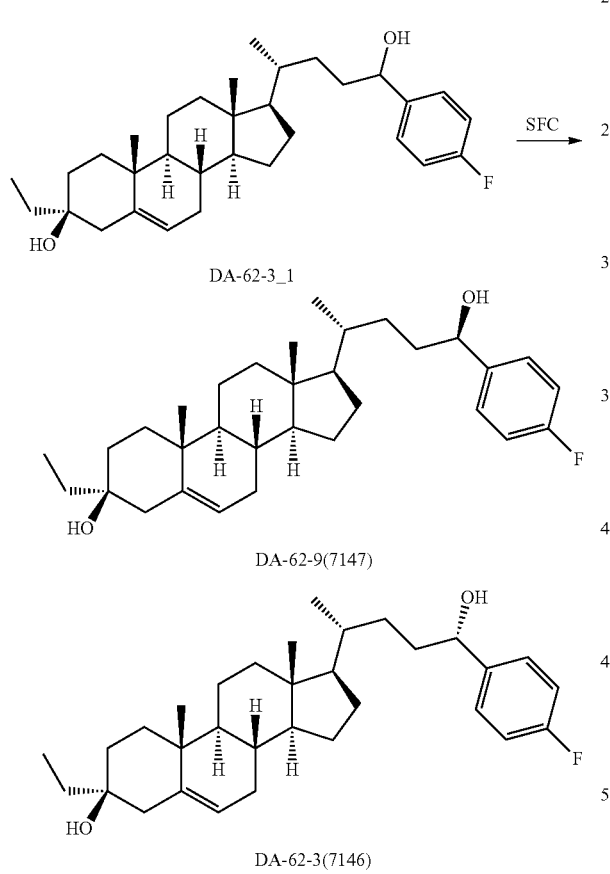

DA-62-3_1 (120 mg, 248 umol) was purified by SFC (Column: AD (150×4.6 mm, 3 um), Gradient: 5%-40% B (A: CO$_2$ B: ethanol) Flow rate: 2.5 mL/min) to afford 7146 (30 mg, 25%) as a solid and 7147 (27 mg, 23%) as a solid.

7146

$^1$H NMR (400 MHz, CDCl$_3$) δ 7.35-7.25 (m, 2H), 7.08-6.95 (m, 2H), 5.28 (brs, 1H), 4.63-4.53 (m, 1H), 2.38-2.30 (m, 1H), 2.05-1.85 (m, 3H), 1.75-1.50 (m, 7H), 1.50-1.28 (m, 7H), 1.28-0.86 (m, 15H), 0.85-0.80 (m, 3H), 0.66 (s, 3H).

LCMS Rt=1.434 min in 2.0 min chromatography, 30-90 AB, purity 100%, MS ESI calcd. for $C_{32}H_{44}F$ [M+H−2H$_2$O]$^+$ 447, found 447.

7147

$^1$H NMR (400 MHz, CDCl$_3$) δ 7.35-7.25 (m, 1H), 7.10-7.02 (m, 2H), 7.00-6.90 (m, 1H), 5.30-5.25 (m, 1H), 4.65-4.53 (m, 1H), 2.40-2.30 (m, 1H), 2.05-1.90 (m, 3H), 1.90-1.50 (m, 7H), 1.50-1.28 (m, 8H), 1.28-0.86 (m, 16H), 0.86-0.80 (m, 3H), 0.66 (s, 3H).

LCMS Rt=1.437 min in 2.0 min chromatography, 30-90 AB, purity 100%, MS ESI calcd. for $C_{32}H_{44}F$ [M+H−2H$_2$O]$^+$ 447, found 447.

Synthesis of 7146 to Determine Stereochemistry

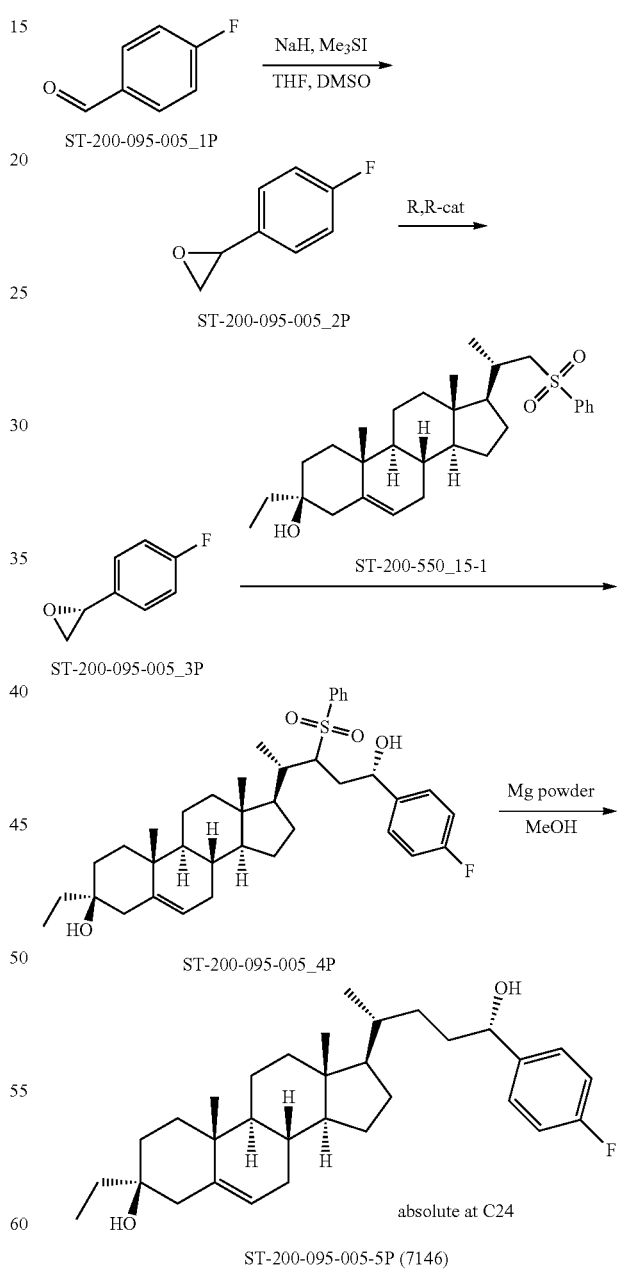

To a solution of Me$_3$SI (32.8 g, 161 mmol) in DMSO (100 mL) and THF (50 mL) was added NaH (6.43 g, 60%, 161 mmol) at 25° C. The reaction mixture was stirred for 20 mins at 25° C., then was cooled to 0° C. and added 4-fluorobenzaldehyde (10 g, 80.5 mmol) in THF (50 mL). The reaction mixture was stirred for 1 h, treated with water (200 mL) and extracted with EtOAc (2×200 mL). The organic phase was washed with water (2×200 mL), brine (200 mL), dried over $Na_2SO_4$, filtered and concentrated to give crude product, which was purified by combi flash (EtOAc/PE=0-5%) to give ST-200-095-005_2P (5.5 g, impure) as colorless oil, which was purified by combi flash (EtOAc/PE=1%) to give ST-200-095-005_2P (4.0 g, 73%) as an oil.

LCMS Rt=1.192 min in 7 min chromatography, 30-90CD_7 MIN_E, purity 99%, MS ESI calcd.

SFC Peak 1: Rt=2.209 min and Peak 2 Rt=2.407 min in 10 min chromatography, O1_EtOH_DEA_5_40_25ML ("Column:(S,S)Whelk-O1 250*4.6 mm, 5 um, Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.").

$^1$H NMR (400 MHz, $CDCl_3$) δ 7.20-7.16 (m, 2H), 6.99-6.94 (m, 2H), 3.79-3.76 (m, 1H), 3.08-3.05 (m, 1H), 2.71-2.68 (m, 1H).

To a solution of R,R-cat (69.4 mg, 0.115 mmol) in toluene (5 mL) was added AcOH (70.8 mg, 1.18 mmol). The mixture was stirred at 25° C. open to air for 30 min and concentrated in vacuo to leave a crude solid. The resulting catalyst residue was dissolved in ST-200-095-005_2P (4 g, 28.9 mmol) at 25° C. The reaction flask was cooled to 0° C., followed by adding $H_2O$ (284 mg, 15.8 mmol) dropwise over 5 min. The reaction was allowed to warm to 25° C. and stirred for 16 hrs. The reaction mixture was purified directly by silica gel chromatography (PE %=100%) to afford ST-200-095-005_3P (460 mg, 11%) as an oil. The ee % was 97%.

LCMS Rt=1.605 min in 2 min chromatography, 10-80CD_3 MIN_E, purity 94%, DAD1A, Sig=220.

SFC Peak 1: Rt=2.202 min and Peak 2 Rt=2.398 min in 10 min chromatography, O1_EtOH_DEA5_40_25ML ("Column:(S,S)Whelk-O1 250*4.6 mm, 5 um, Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.").

$^1$H NMR (400 MHz, $CDCl_3$) δ 7.20-7.16 (m, 2H), 6.99-6.94 (m, 2H), 3.79-3.76 (m, 1H), 3.08-3.05 (m, 1H), 2.71-2.68 (m, 1H).

To a THF (5 mL) under $N_2$ at −70° C. was added n-BuLi (2.5 M, 4.12 mmol, 1.64 mL). After that, a suspension of ST-200-550_15-1 (800 mg, 1.65 mmol) in THF (5 mL) was added drop-wise to give a suspension. After stirring at −70° C. for 30 min, a solution of ST-200-095-005_3P (455 mg, 3.30 mmol) was added. Then reaction was stirred at stirred at 25° C. for 16 hours. The mixture was poured into ice-water (20 mL) and extracted with EtOAc (2×30 mL). The combined organic layers were washed with brine (30 mL), dried over $Na_2SO_4$, filtered and concentrated in vacuum to afford ST-200-095-005_4P (1 g, crude) as an oil, which was used directly for the next step.

To a solution of ST-200-095-005_4P (1 g, crude) in MeOH (50 mL) was added $NiCl_2$ (5 mg) and Mg powder (1.533 g, 64.0 mmol) at 65° C. in four portions. The reaction mixture was cooled to 20° C. and quenched by HCl (1M, 100 mL). The mixture was extracted with EtOAc (3×100 mL). The combined organic layers were washed with brine (50 mL), dried over anhydrous $Na_2SO_4$, filtered and concentrated to give the crude, which was purified by flash column (0~5% of EtOAc in PE) to give ST-200-095-005_5P (41 mg, 5%) as a solid.

$^1$H NMR (400 MHz, $CDCl_3$) δ 7.35-7.27 (m, 2H), 7.05-6.98 (m, 2H), 5.35-5.31 (m, 1H), 4.62-4.58 (m, 1H), 2.41-2.31 (m, 1H), 2.10-1.90 (m, 4H), 1.75-1.58 (m, 8H), 1.52-1.05 (m, 14H), 1.02 (s, 3H), 1.00-0.76 (m, 8H), 0.66 (s, 3H).

LCMS Rt=1.272 min in 2 min chromatography, 30-90AB_2 MIN_E, purity 100%, MS ESI calcd. for $C_{32}H_{44}F$ $[M+H-2H_2O]^+$ 447, found 447.

SFC Peak 1: Rt=2.124 min in 10 min chromatography, AD_3_EtOH_DEA40_25ML ("Column:(S,S)Whelk-O1 250*4.6 mm, 5 um, Mobile phase: A: $CO_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.").

Example 72: Synthesis of 7281 and 7282

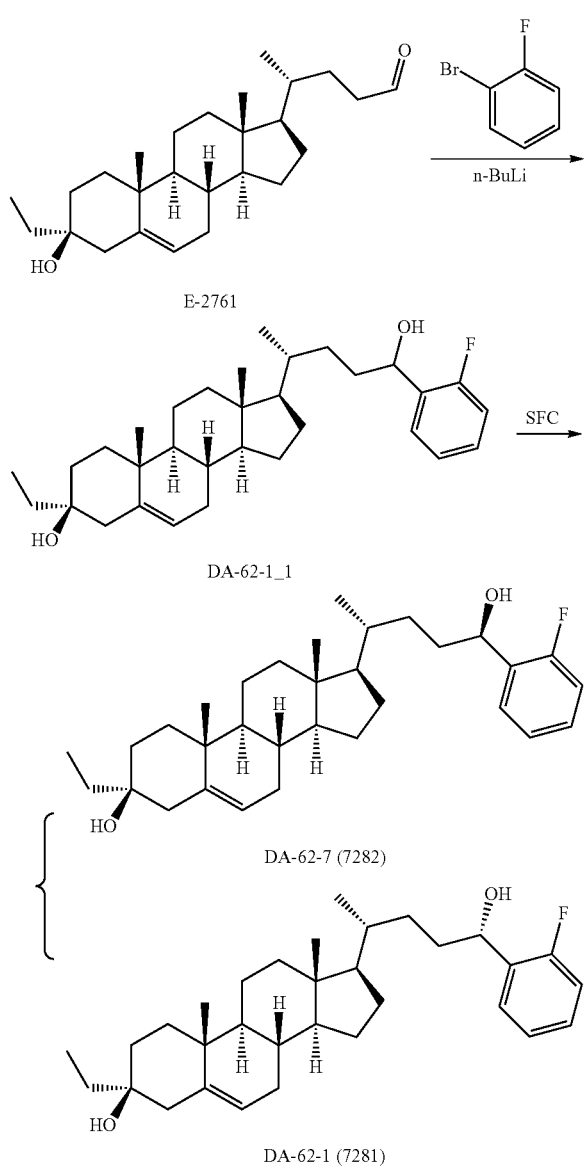

The experimental of intermediate E-2761 can be found in Example 63.

Synthesis of DA-62-1_1

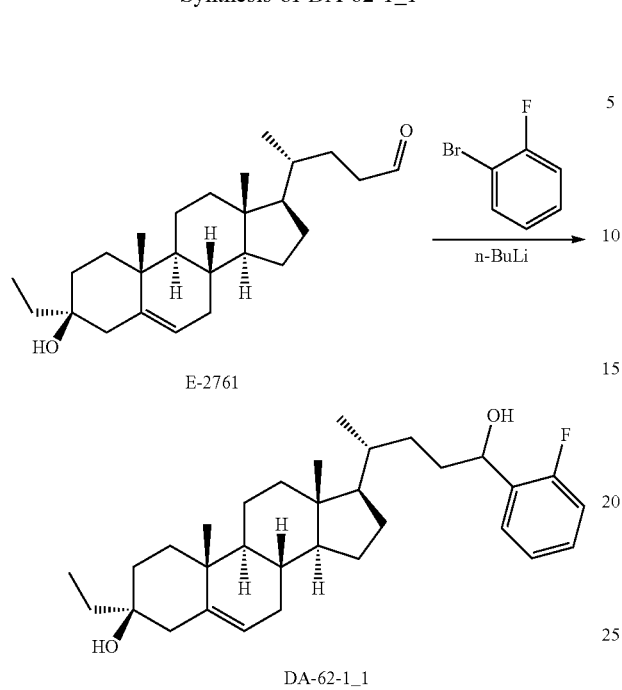

E-2761

DA-62-1_1 n-BuLi (2.5 M, 2.05 mL) was added dropwise to a solution of 1-bromo-2-fluorobenz (900 mg, 5.14 mmol) in THF (10 mL) at −78° C. under $N_2$. After stirring at −78° C. for 30 min, a solution of E-2761 (200 mg, 0.517 mmol) in THF (10 mL) was added at −78° C. under $N_2$. The mixture was stirred at −78° C. for 30 min and quenched with saturated aqueous $NH_4Cl$ (30 mL). The aqueous phase was extracted with EtOAc (3×20 mL). The combined organic phase was washed with saturated brine (2×20 mL), dried over anhydrous $Na_2SO_4$, filtered and concentrated to give an oil, which was purified by flash column (0~20% of EtOAc in PE) to give DA-62-1_1 (110 mg, 44%) as a solid.

$^1$H NMR (400 MHz, $CDCl_3$) δ 7.50-7.42 (m, 1H), 7.25-7.10 (m, 2H), 7.10-6.96 (m, 1H), 5.32-5.25 (m, 1H), 5.02-4.92 (m, 1H), 2.40-2.30 (m, 1H), 2.05-1.50 (m, 9H), 1.50-1.32 (m, 8H), 1.32-1.18 (m, 3H), 1.18-0.75 (m, 17H), 0.66 (s, 3H).

LCMS Rt=1.380 min in 2.0 min chromatography, 30-90 AB, purity 100%, MS ESI calcd. for $C_{32}H_{44}F$ $[M+H-2H_2O]^+$ 447, found 447.

Synthesis of 7281 and 7282

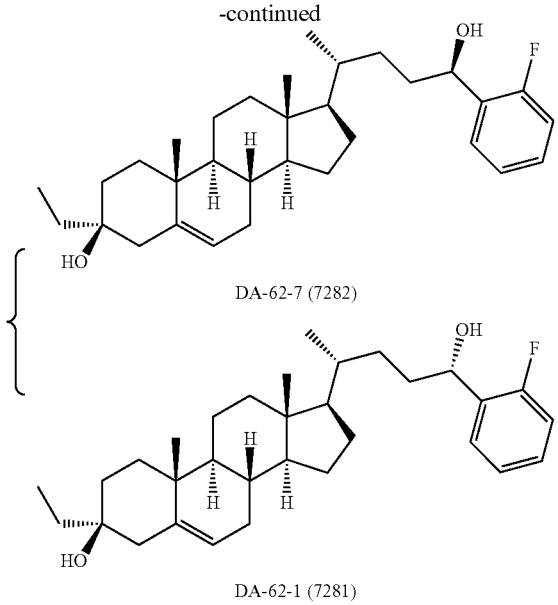

DA-62-7 (7282)

DA-62-1 (7281)

DA-62-1_1 (110 mg, 227 umol) was purified by SFC (Column: AD (150×4.6 mm, 3 um), Gradient: 5%-40% B (A: $CO_2$ B: ethanol) Flow rate: 2.5 mL/min) to afford DA-62-1 (12 mg, 11%) as a solid and DA-62-7 (30 mg, impure) as a solid. The impure DA-62-7 (30 mg, impure) was purified by SFC (Column: AD (150×4.6 mm, 3 um), Gradient: 5%-40% B (A: $CO_2$ B: ethanol) Flow rate: 2.5 mL/min) to afford DA-62-7 (6 mg, 6%) as a solid.

7281

$^1$H NMR (400 MHz, $CDCl_3$) δ 7.48-7.42 (m, 1H), 7.26-7.10 (m, 2H), 7.06-6.96 (m, 1H), 5.32-5.25 (m, 1H), 5.02-4.92 (m, 1H), 2.40-2.30 (m, 1H), 2.05-1.50 (m, 11H), 1.50-1.30 (m, 7H), 1.30-1.18 (m, 2H), 1.18-0.75 (m, 17H), 0.66 (s, 3H).

LCMS Rt=1.362 min in 2.0 min chromatography, 30-90 AB, purity 100%, MS ESI calcd. for $C_{32}H_{44}F$ $[M+H-2H_2O]^+$ 447, found 447.

7282

$^1$H NMR (400 MHz, $CDCl_3$) δ 7.48-7.42 (m, 1H), 7.26-7.10 (m, 2H), 7.06-6.96 (m, 1H), 5.32-5.25 (m, 1H), 5.02-4.92 (m, 1H), 2.40-2.30 (m, 1H), 2.05-1.50 (m, 10H), 1.50-1.32 (m, 8H), 1.32-0.86 (m, 16H), 0.86-0.78 (m, 3H), 0.66 (s, 3H).

HPLC Rt=5.32 min in 7 min chromatography, 50-100 AB, purity 98%,

MS MS ESI calcd. for $C_{32}H_{44}F$ $[M+H-2H_2O]^+$ 447, found 447.

Synthesis to Determine Stereochemistry

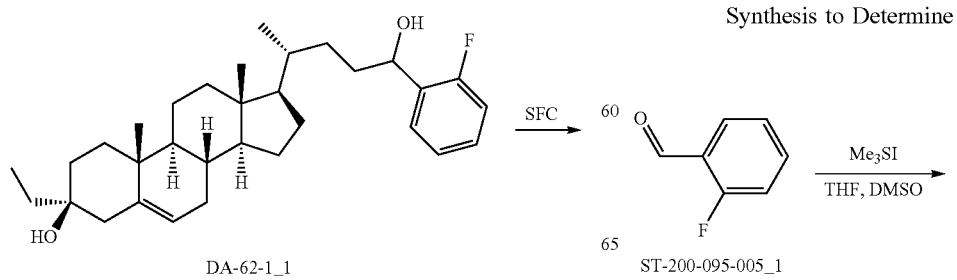

DA-62-1_1

ST-200-095-005_1

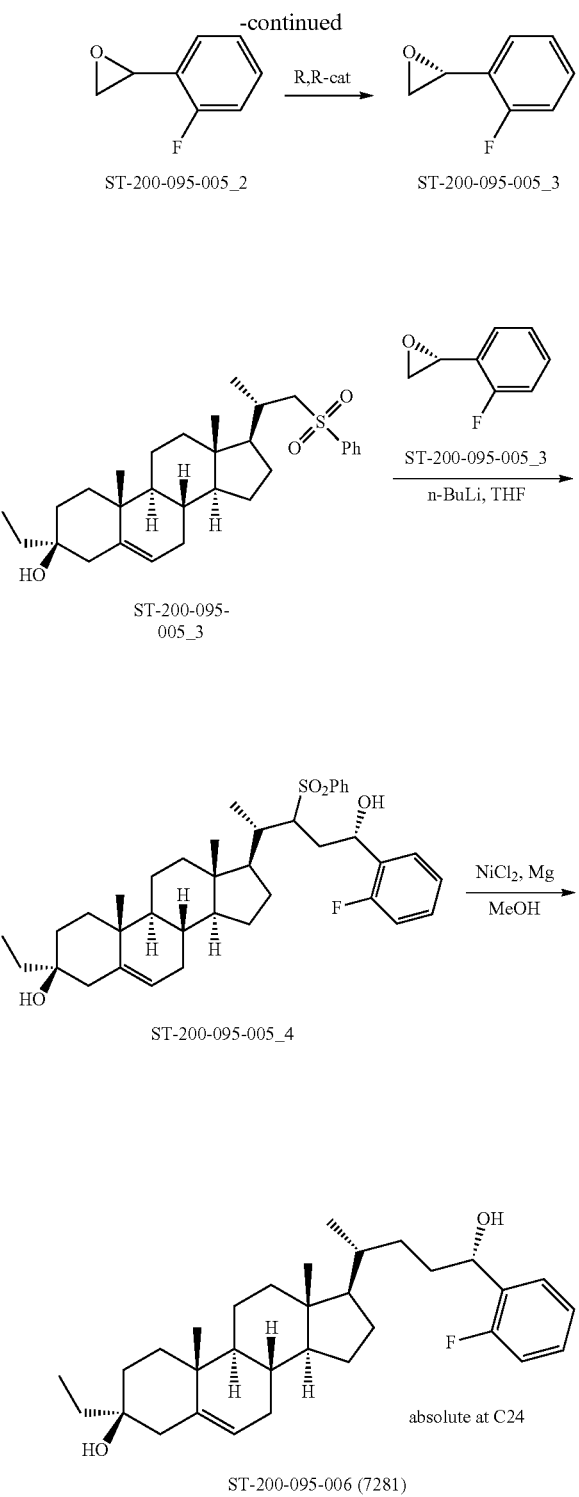

To a solution of Me$_3$SOI (123 g, 562 mmol) in DMSO (150 mL) and THF (75 mL) was added t-BuOK (63 g, 562 mmol) in portions at 25° C. The mixture was stirred at 40° C. for 30 min. Then ST-200-095-005_1 (35 g, 281 mmol) in 75 ml of THF was added dropwise to the mixture at 0° C. After stirring at 25° C. for 1 h, the mixture was poured into ice-water (100 mL) and extracted with EtOAc (2×50 mL). The combined organic phase was washed with brine (100 mL), dried over anhydrous Na$_2$SO$_4$, filtered, concentrated in vacuum. The residue was purified by silica gel column eluted with (PE/EtOAc=20/1) to afford ST-200-095-005_2 (24 g, 62%) as an oil.

$^1$HNMR (400 MHz, CDCl$_3$) δ 7.22-7.16 (m, 1H), 7.13-7.02 (m, 2H), 6.99-6.95 (m, 1H), 4.07 (t, J=4 Hz, 1H), 3.11-3.08 (m, 1H), 2.71-2.70 (m, 1H).

To a solution of R, R-cat (86.9 mg, 0.144 mmol) in toluene (5 mL) was added AcOH (86.4 mg, 1.44 mmol). The mixture was stirred at 25° C. for 30 mins. The solution was concentrated in vacuum to give a crude solid. The resulting catalyst residue was dissolved in ST-200-095-005_2 (5 g, 36.1 mmol) at 25° C., the reaction mixture was cooled to 0° C., and water (356 mg, 19.8 mmol) was added dropwise. The mixture was warmed to 25° C. and stirred for 16 hrs. The product was purified by silica gel column (PE/EtOAc=12/1 to 8/1) to give ST-200-095-005_3 (1 g, 20%) as an oil.

$^1$HNMR (400 MHz, CDCl$_3$) δ 7.22-7.16 (m, 1H), 7.13-7.08 (m, 1H), 7.06-7.02 (m, 1H), 6.99-6.95 (m, 1H), 4.07 (t, J=4 Hz, 1H), 3.11-3.08 (m, 1H), 2.71-2.70 (m, 1H).

SFC Peak 1: Rt=2.015 min in 10 min chromatography, SS Whelk O1_EtOH_DEA_5_40_25ML ("Column:(S,S) Whelk-O1 250*4.6 mm, 5 um, Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C."), 97.1% ee.

To a THF (2 mL) under N$_2$ at −70° C. was added n-BuLi (2.5 M, 1.54 mmol, 0.616 mL). After that, a suspension of ST-200-095-005_3 (300 mg, 0.618 mmol) in THF (2 mL) was added drop-wise to give a suspension. After stirring at −70° C. for 30 min, a solution of (2R)-2-(2-fluorophenyl)oxirane (127 mg, 0.926 mmol) was added. The reaction was stirred at stirred at 25° C. for 16 hours. The mixture was poured into ice-water (20 mL) and extracted with EtOAc (2×30 mL). The combined organic layers were washed with brine (30 mL), dried over Na$_2$SO$_4$, filtered and concentrated in vacuum to afford ST-200-095-005_4 (350 mg, crude) as a solid, which was used directly for the next step.

To a solution of ST-200-095-005_4 (350 mg, 0.561 mmol) and nickel (II) chloride (7 mg, 0.056 mmol) in MeOH (30 mL) was added Mg (294 mg, 11.2 mmol) was added at 25° C. The mixture was stirred at 50° C. for 1 h. After cooling, the mixture was quenched with HCl (100 mL, 2M) until the reaction became clear and extracted with EtOAc (2×50 mL). The combined organic phase was dried over Na$_2$SO$_4$, filtered concentrated and purified by a silica gel column (PE/EtOAc=10/1 to 3/1) to give ST-200-095-006 (150 mg, 56%) as a solid.

$^1$HNMR (400 MHz, CDCl3) 7.44 (t, J=8 Hz, 1H), 7.25-7.21 (m, 1H), 7.15 (t, J=8 Hz, 1H), 7.02 (t, J=8 Hz, 1H), 5.28-5.26 (m, 1H), 5.00-4.90 (m, 1H), 2.39-2.32 (m, 1H), 2.04-1.86 (m, 4H), 1.84-1.60 (m, 7H), 1.55-1.32 (m, 9H), 1.29-0.99 (m, 10H), 0.96-0.90 (m, 4H), 0.84 (t, J=8 Hz, 3H), 0.66 (s, 3H).

LCMS Rt=1.290 min in 2.0 min chromatography, 30-90 AB, purity 100%, MS ESI calcd. For C$_{32}$H$_{44}$F [M−2H$_2$O+H$^+$]=447, found 447.

SFC Rt=5.494 min in 10 min chromatography, AD_3_EtOH_DEA_5_40_25ML ("Column: Chiralpak AD-3150×4.6 mm I.D., 3 um Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C."), 98.86% de.

Example 73: Synthesis of 7300 and 7399

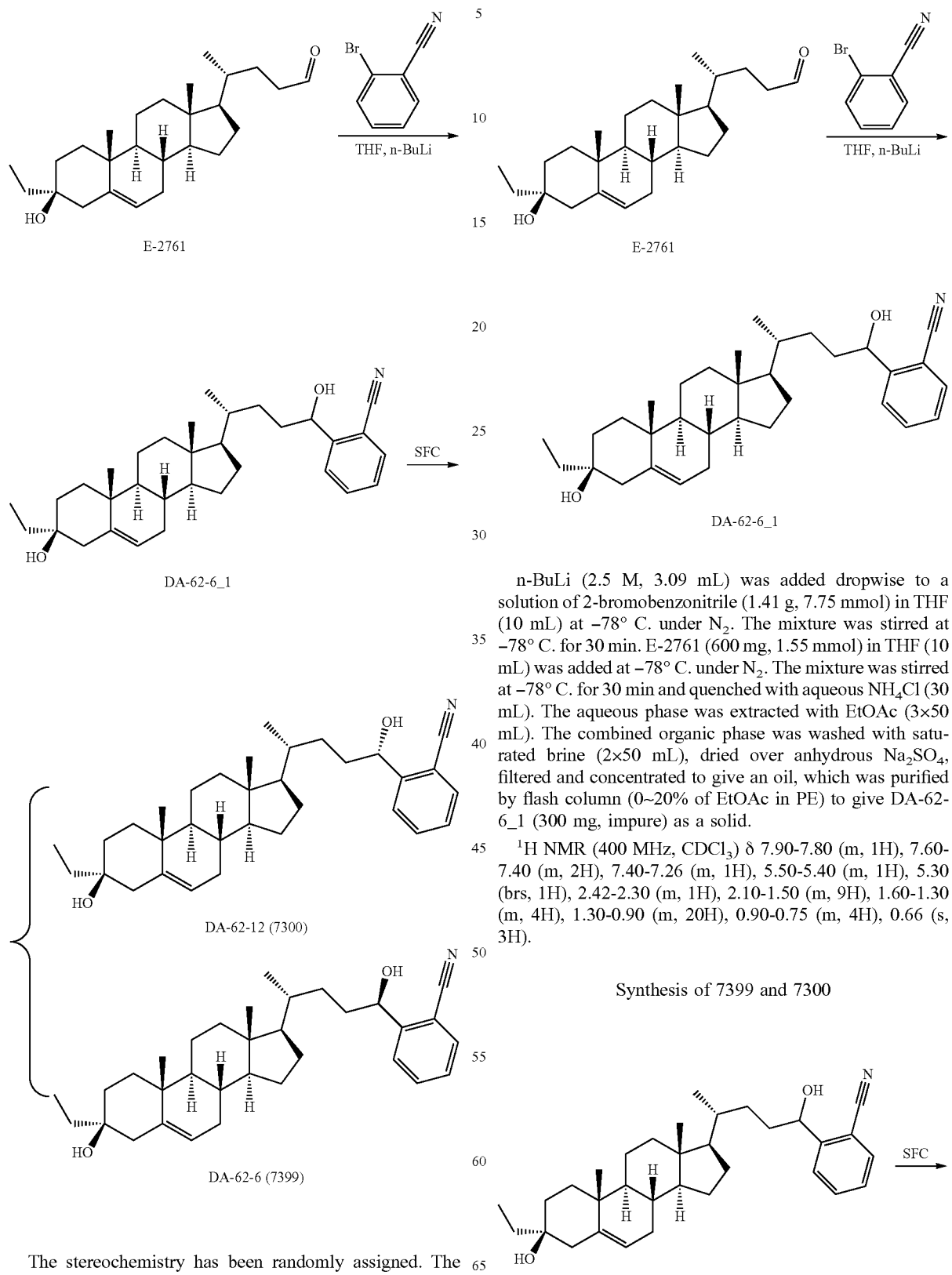

The stereochemistry has been randomly assigned. The experimental of intermediate E-2761 can be found in Example 63.

Synthesis of DA-62-6_1 n-BuLi (2.5 M, 3.09 mL) was added dropwise to a solution of 2-bromobenzonitrile (1.41 g, 7.75 mmol) in THF (10 mL) at −78° C. under $N_2$. The mixture was stirred at −78° C. for 30 min. E-2761 (600 mg, 1.55 mmol) in THF (10 mL) was added at −78° C. under $N_2$. The mixture was stirred at −78° C. for 30 min and quenched with aqueous $NH_4Cl$ (30 mL). The aqueous phase was extracted with EtOAc (3×50 mL). The combined organic phase was washed with saturated brine (2×50 mL), dried over anhydrous $Na_2SO_4$, filtered and concentrated to give an oil, which was purified by flash column (0~20% of EtOAc in PE) to give DA-62-6_1 (300 mg, impure) as a solid.

$^1$H NMR (400 MHz, $CDCl_3$) δ 7.90-7.80 (m, 1H), 7.60-7.40 (m, 2H), 7.40-7.26 (m, 1H), 5.50-5.40 (m, 1H), 5.30 (brs, 1H), 2.42-2.30 (m, 1H), 2.10-1.50 (m, 9H), 1.60-1.30 (m, 4H), 1.30-0.90 (m, 20H), 0.90-0.75 (m, 4H), 0.66 (s, 3H).

Synthesis of 7399 and 7300

-continued

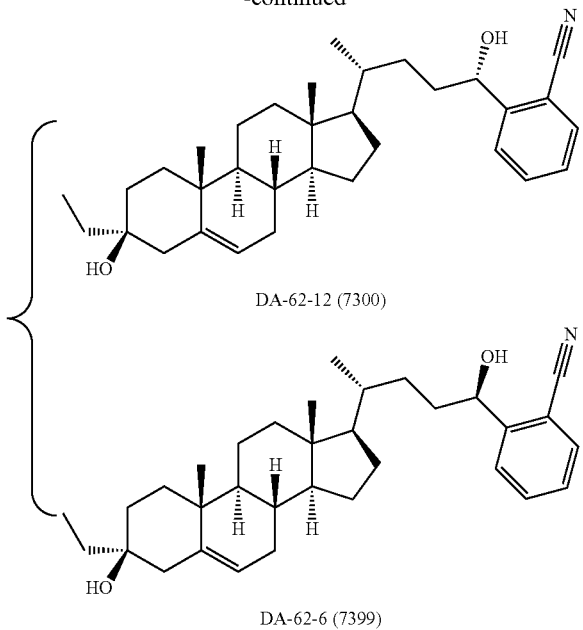

DA-62-12 (7300)

DA-62-6 (7399)

DA-62-6_1 (300 mg, 0.612 mmol) was purified by SFC (Column: AD (150×4.6 mm, 3 um), Gradient: 5%-40% B (A: CO₂ B: ethanol) Flow rate: 2.5 mL/min) to afford DA-62-6 (30.0 mg, impure) as a solid and DA-62-12 (80 mg, impure) as solid. Impure DA-62-6 (30 mg, 0.0612 mmol) was purified by SFC (Column: AS(250 mm*30 mm, 5 um), Gradient: 25%-25% B (A: CO₂ B: 0.1% NH₃H₂O ETOH) Flow rate: 60 mL/min) to afford DA-62-6 (4 mg, 13%) as solid. Impure DA-62-12 (80 mg, 0.163) was purified by SFC (Column: AS(250 mm*30 mm, 5 um), Gradient: 25%-25% B (A: CO₂ B: 0.1% NH₃H₂O ETOH) Flow rate: 60 mL/min) to afford an impure solid, which was triturated from H₂O (10 mL) at 90° C. to give DA-62-12 (3 mg, 4%) as a solid.

7399:

$^1$H NMR (400 MHz, CDCl₃) δ 7.88-7.80 (m, 1H), 7.58-7.42 (m, 2H), 7.35-7.30 (m, 1H), 5.45-5.36 (m, 1H), 5.30-5.27 (m, 1H), 2.40-2.30 (m, 1H), 2.10-1.90 (m, 4H), 1.85-1.50 (m, 8H), 1.50-1.30 (m, 5H), 1.30-1.88 (m, 17H), 0.86-0.76 (m, 3H), 0.66 (s, 3H).

LCMS Rt=0.908 min in 2.0 min chromatography, 30-90 AB, purity 95%, MS ESI calcd. for $C_{33}H_{48}NO_2$ $[M+H]^+$ 490, found 490.

7300:

$^1$H NMR (400 MHz, CDCl₃) δ 7.88-7.75 (m, 1H), 7.58-7.40 (m, 2H), 7.30-7.26 (m, 1H), 5.50-5.40 (m, 1H), 5.30-5.25 (m, 1H), 2.40-2.37 (m, 1H), 2.10-1.50 (m, 13H), 1.50-1.10 (m, 14H), 1.10-0.76 (m, 10H), 0.66 (s, 3H).

LCMS Rt=0.923 min in 2.0 min chromatography, 30-90 AB, purity 94%, MS ESI calcd. for $C_{33}H_{48}NO_2$ $[M+H]^+$ 490, found 490.

Example 74: Synthesis of 7467 and 7468

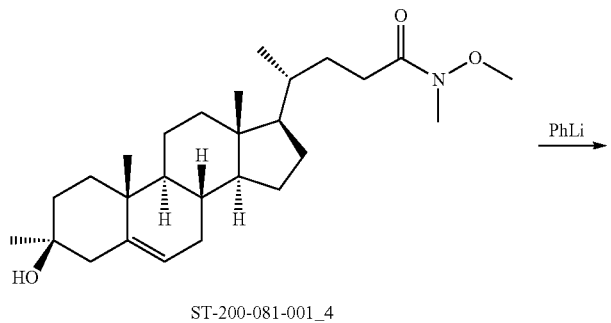

ST-200-081-001_4

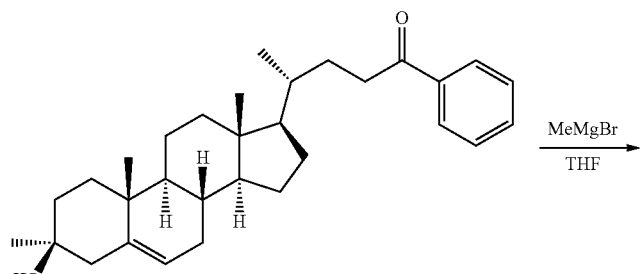

ST-200-081-001_5

323

-continued

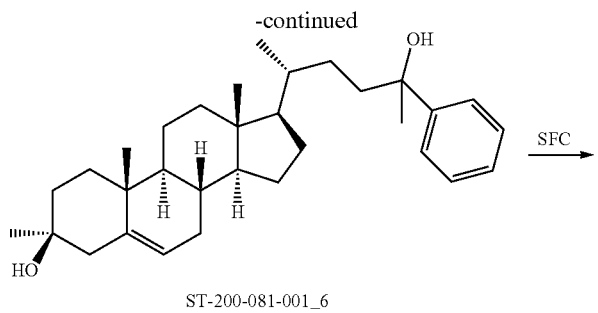
ST-200-081-001_6

SFC →

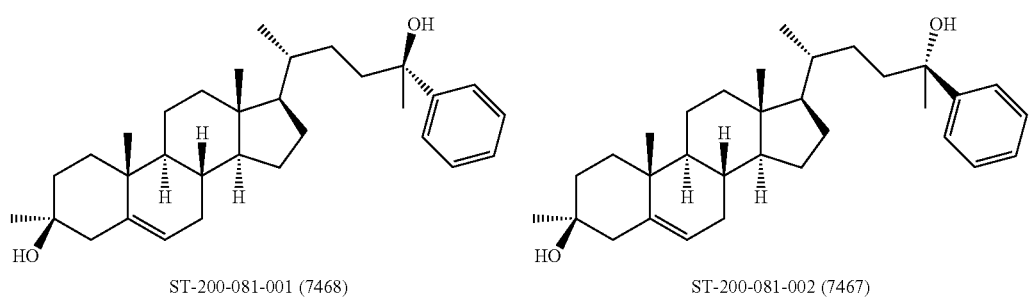

ST-200-081-001 (7468)  ST-200-081-002 (7467)

The stereochemistry was randomly assigned. The experimental of intermediate ST-200-081-001_4 could be found in Example 127.

Synthesis of ST-200-081-001_5

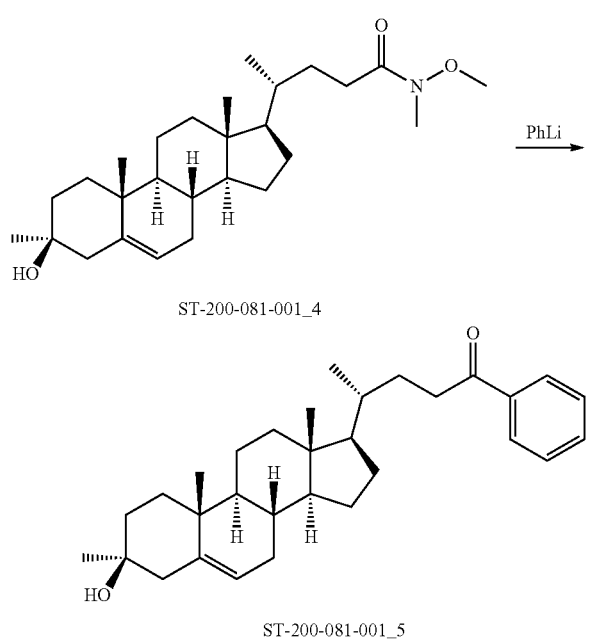
ST-200-081-001_4

PhLi →

ST-200-081-001_5

To a solution of ST-200-081-001_4 (1.3 g, 3.01 mmol) in THF (10 mL) was added PhLi (7.5 mL, 2 M in ether, 15 mmol) at 0° C. under $N_2$ and the mixture was stirred at 25° C. for 30 minutes. After quenching with saturated $NH_4Cl$ (40 mL), the mixture was extracted with EtOAc (3×20 mL). The combined organic layer was washed with brine dried over $Na_2SO_4$, filtered, concentrated in vacuum to give ST-200-081-001_5 (1.6 g, crude) as a solid, which was used directly without further purification.

$^1$H NMR (400 MHz, $CDCl_3$) δ 8.01-7.93 (m, 2H), 7.63-7.29 (m, 7H), 5.34-5.27 (m, 1H), 3.08-2.83 (m, 2H), 2.47-2.38 (m, 1H), 2.01-1.67 (m, 7H), 1.52-1.14 (m, 11H), 1.11 (s, 3H), 1.03-0.97 (m, 7H), 0.69 (s, 3H).

Synthesis of ST-200-081-001_6

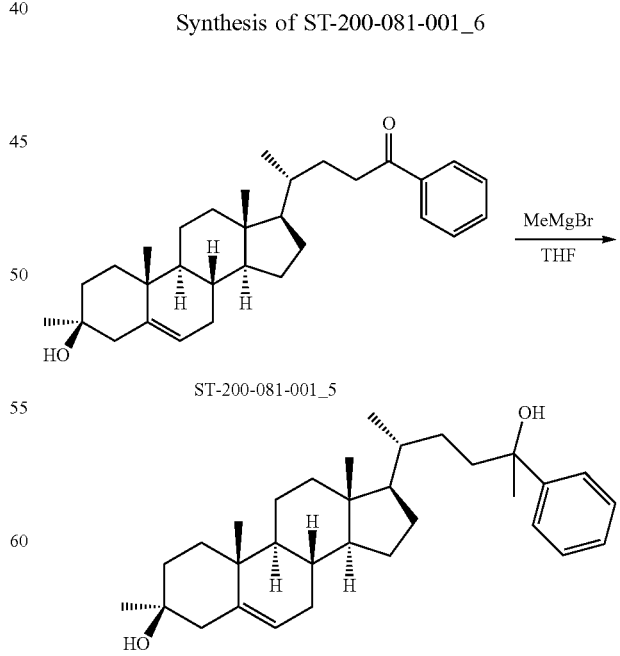

ST-200-081-001_5

MeMgBr / THF →

ST-200-081-001_6

324

To a solution of ST-200-081-001_5 (1.6 g, 3.56 mmol) in THF (10 mL) was added MeLi (11.1 mL, 2 M in ether, 17.8 mmol) at 0° C. under $N_2$ and the mixture was stirred at 25° C. for 30 minutes. The reaction mixture was quenched by saturated $NH_4Cl$ (10 mL) and extracted with ethyl acetate (3×20 mL). The organic layer was washed with brine (60 mL), dried over $Na_2SO_4$ and filtered, concentrated in vacuum and purified by flash column (0~30% of EtOAc in PE) to give ST-200-081-001_6 (1 g, 57%) as a solid.

LCMS Rt=1.374 min in 2 min chromatography, 30-90AB_2 MIN_E, purity 100%, MS ESI calcd. for $C_{32}H_{45}$ $[M+H-2H_2O]^+$ 429, found 429.

Synthesis of 7467 and 7468

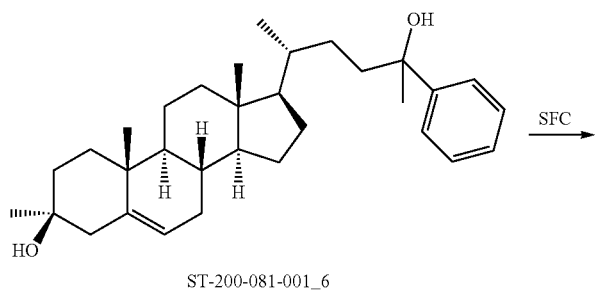

ST-200-081-001_6

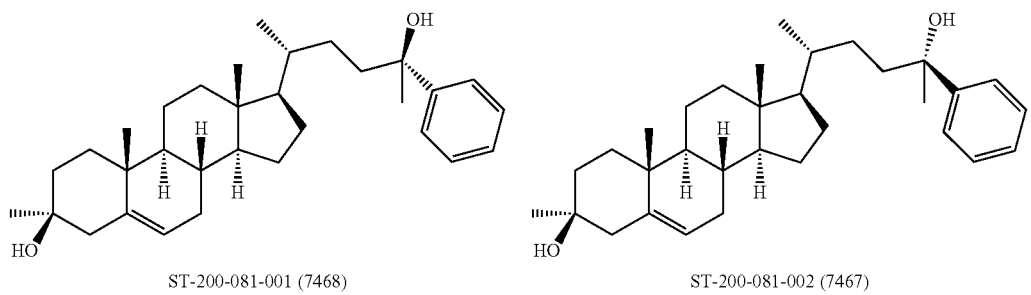

ST-200-081-001 (7468)    ST-200-081-002 (7467)

ST-200-081-001_6 (1 g, 2.15 mmol) was purified by SFC (column: AD(250 mm*30 mm, 5 um)), gradient: 40-40% B (A=0.1% $NH_3/H_2O$, B=EtOH), flow rate: 60 mL/min) to give impure ST-200-081-001 (Peak 1, 390 mg, 39%) and impure ST-200-081-002 (Peak 2, 220 mg, 22%) as a solid. To a solution of impure ST-200-081-001 (390 mg) in THF (15 mL) was added $Pd(OH)_2/C$ (wet, 300 mg) and the mixture was degassed and back-filled with $H_2$ for 3 times. After that, the reaction was stirred at 15° C. under 15 psi of $H_2$ for 4 h. The reaction mixture was filtered through a pad of celite washed with THF (100 mL). The filtrate was concentrated and purified by SFC (column: AD (250 mm*30 mm, 5 um)), gradient: 40-40% B (A=0.1% $NH_3/H_2O$, B=EtOH), flow rate: 60 mL/min) to give ST-200-081-001 (270 mg, 71%) as a solid. Impure ST-200-081-002 was triturated in boiling MeCN (200 mL) concentrated in vacuum to give ST-200-081-002 (208 mg, 94%) as a solid.

ST-200-081-001 (7468):

$^1$H NMR (400 MHz, $CDCl_3$) δ 7.46-7.39 (m, 2H), 7.37-7.29 (m, 2H), 7.26-7.21 (m, 1H), 5.33-5.26 (m, 1H), 2.46-2.37 (m, 1H), 2.01-1.64 (m, 9H), 1.56-1.53 (m, 5H), 1.52-1.12 (m, 10H), 1.10 (s, 3H), 1.09-1.01 (m, 3H), 0.99 (s, 3H), 0.97-0.86 (m, 5H), 0.62 (s, 3H).

LCMS Rt=1.359 min in 2 min chromatography, 30-90AB_2 MIN_E, purity 100%, MS ESI calcd. for $C_{32}H_{45}$ $[M+H-2H_2O]^+$ 429, found 429.

SFC Rt=5.916 min in 10 min chromatography, AD_3_EtOH_DEA_5_40_25ML, 100% de.

ST-200-081-002 (6467):

$^1$H NMR (400 MHz, $CDCl_3$) δ 7.45-7.39 (m, 2H), 7.36-7.31 (m, 2H), 7.25-7.19 (m, 1H), 5.33-5.26 (m, 1H), 2.47-2.37 (m, 1H), 2.01-1.57 (m, 10H), 1.55-1.31 (m, 12H), 1.21-1.12 (m, 2H), 1.10 (s, 3H), 1.08-1.02 (m, 2H), 0.99 (s, 3H), 0.98-0.85 (m, 6H), 0.63 (s, 3H).

LCMS Rt=1.367 min in 2 min chromatography, 30-90AB_2 MIN_E, purity 100%, MS ESI calcd. for $C_{32}H_{45}$ $[M+H-2H_2O]^+$ 429, found 429.

SFC Rt=6.397 min in 10 min chromatography, AD_3_EtOH_DEA_5_40_25ML, 97.26% de.

Example 74B. Biological Data

The Experiments were conducted as described in Example 2 and the results are reported in Table 2-66.

TABLE 2-66

| Compound | Avg EC50 2A (nM) | Avg Emax 2A (%) | Avg EC50 2B (nM) | Avg Emax 2B (%) |
|---|---|---|---|---|
| 154 | >10000 | 18.2 | >10000 | 56.8 |
| 356 | 414.6 | 59.6 | 923.4 | 156.3 |
| 456 | 6710.0 | 53.4 | 6746.8 | 74.8 |
| 559 | 1571.3 | 204.3 | 1564.3 | 373.2 |
| 255 | 646.4 | 159.4 | 153.0 | 131.8 |
| 761 | 475.9 | 301.6 | 249.1 | 197.3 |

TABLE 2-66-continued
| | Compound | Avg EC50 2A (nM) | Avg Emax 2A (%) | Avg EC50 2B (nM) | Avg Emax 2B (%) |
|---|---|---|---|---|---|
| 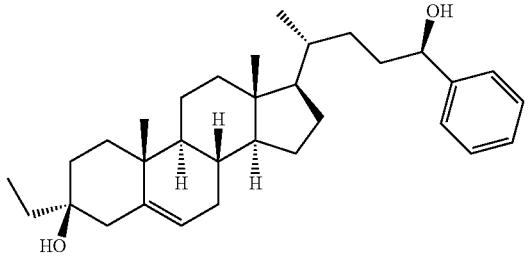 | 861 | 199.6 | 183.1 | 246.9 | 389.8 |
| 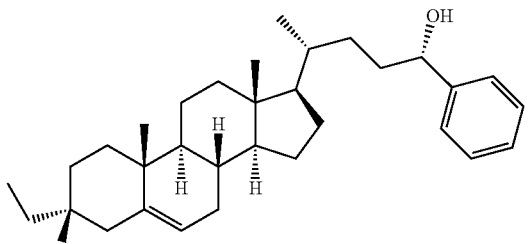 | 961 | 616.7 | 138.5 | 179.8 | 97.4 |
| 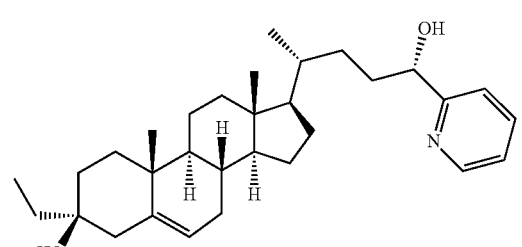 | 6347 | 268.3 | 64.7 | 310.7 | 131.9 |
| 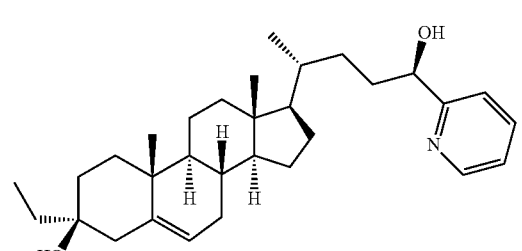 | 6348 | 259.61 | 79.65 | 663.21 | 132.91 |
| 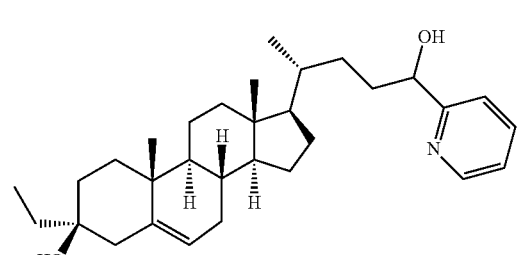 | 6457 | 731.9 | 198.3 | 523.6 | 168.1 |
| 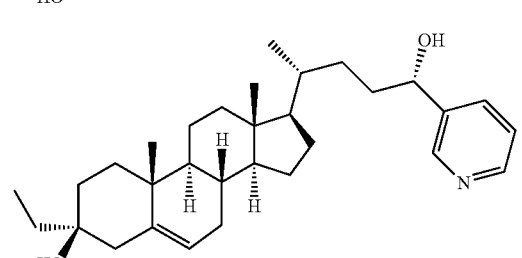 | 6458 | >10000 | 30.9 | 928.9 | 79.4 |

TABLE 2-66-continued
| | Compound | Avg EC50 2A (nM) | Avg Emax 2A (%) | Avg EC50 2B (nM) | Avg Emax 2B (%) |
|---|---|---|---|---|---|
| 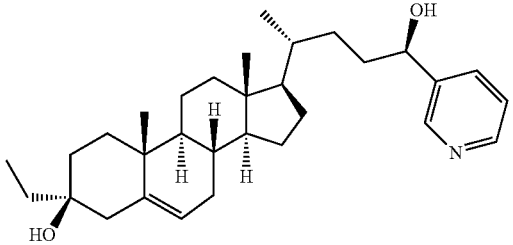 | 6459 | 1327.1 | 156.2 | 909.0 | 184.2 |
| 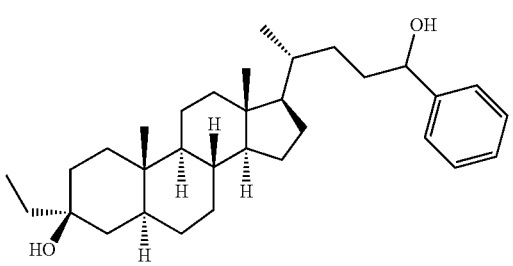 | 6544 | 558.8 | 253.2 | 497.7 | 414.6 |
| 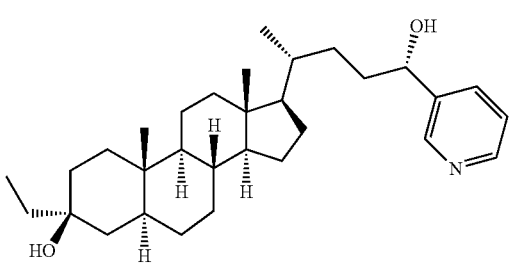 | 6754 | >10000 | 22.3 | >10000 | 38.8 |
| 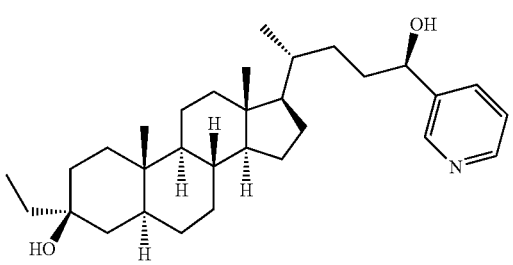 | 6755 | >10000 | 22.8 | >10000 | 44.2 |
| 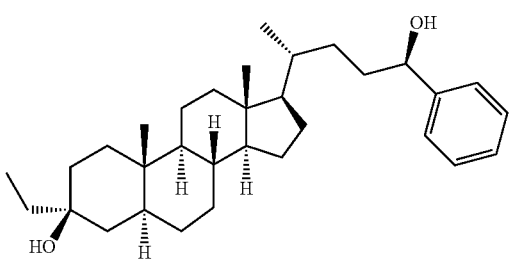 | 6571 | 189.8 | 157.5 | 266.6 | 241.0 |
| 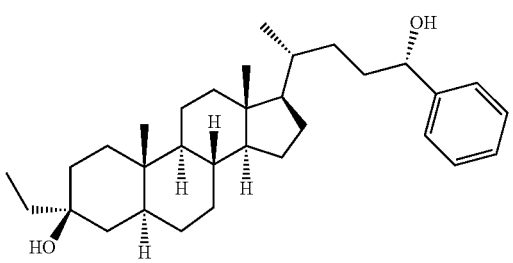 | 6572 | 378.5 | 128.9 | 1341.5 | 250.6 |

TABLE 2-66-continued

| Compound | Avg EC50 2A (nM) | Avg Emax 2A (%) | Avg EC50 2B (nM) | Avg Emax 2B (%) |
|---|---|---|---|---|
| 6680 | 1370.7 | 175.4 | 464.4 | 123.4 |
| 6681 | 365.3 | 171.6 | 359.9 | 165.3 |
| 6895 | 174.1 | 240.9 | 328.8 | 354.3 |
| 6896 | 518.9 | 215.9 | 1676.0 | 402.2 |
| 6997 | 373.4 | 327.2 | 414.3 | 314.7 |
| 6998 | 357.6 | 337.9 | 304.3 | 303.4 |

TABLE 2-66-continued
| Compound | Avg EC50 2A (nM) | Avg Emax 2A (%) | Avg EC50 2B (nM) | Avg Emax 2B (%) |
|---|---|---|---|---|
| 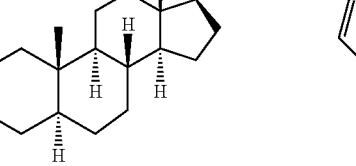 7030 | >10000 | 28.3 | >10000 | 74.7 |
| 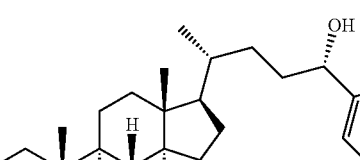 7032 | >10000 | 28.3 | 874.3 | 63.8 |
|  7146 | 119.8 | 103.7 | 215.9 | 167.4 |
| 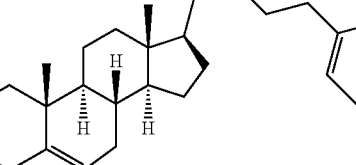 7147 | 147.0 | 200.5 | 91.7 | 241.5 |
| 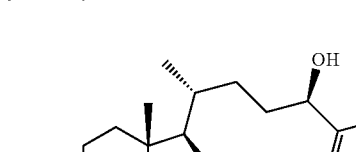 7281 | 248.37 | 98.1 | 302.7 | 125.7 |
| 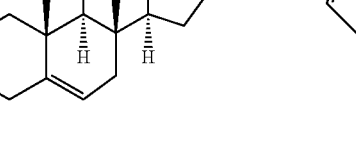 7282 | 95.9 | 208.3 | 173.7 | 289.7 |

TABLE 2-66-continued

| Compound | Avg EC50 2A (nM) | Avg Emax 2A (%) | Avg EC50 2B (nM) | Avg Emax 2B (%) |
|---|---|---|---|---|
| 7399 | 696.1 | 150.1 | 1581.2 | 179.5 |
| 7300 | >10000 | 37.5 | >10000 | 46.9 |
| 7467 | >10000 | 20.5 | >10000 | 8.8 |
| 7468 | 61.4 | 273.4 | 54.2 | 317.4 |
| 660 | 700.6 | 195.2 | 516.8 | 281.1 |

TABLE 2-66-continued
| Compound | Avg EC50 2A (nM) | Avg Emax 2A (%) | Avg EC50 2B (nM) | Avg Emax 2B (%) |
|---|---|---|---|---|
| 6010 | 1104.9 | 238.7 | 1573.5 | 184.0 |
| 6051 | 500.2 | 292.7 | 1262.1 | 292.4 |
| 6052 | 425.9 | 101.8 | 232.3 | 92.2 |
Example 75: Syntheses of Compounds 175, 1A75, and 1B75
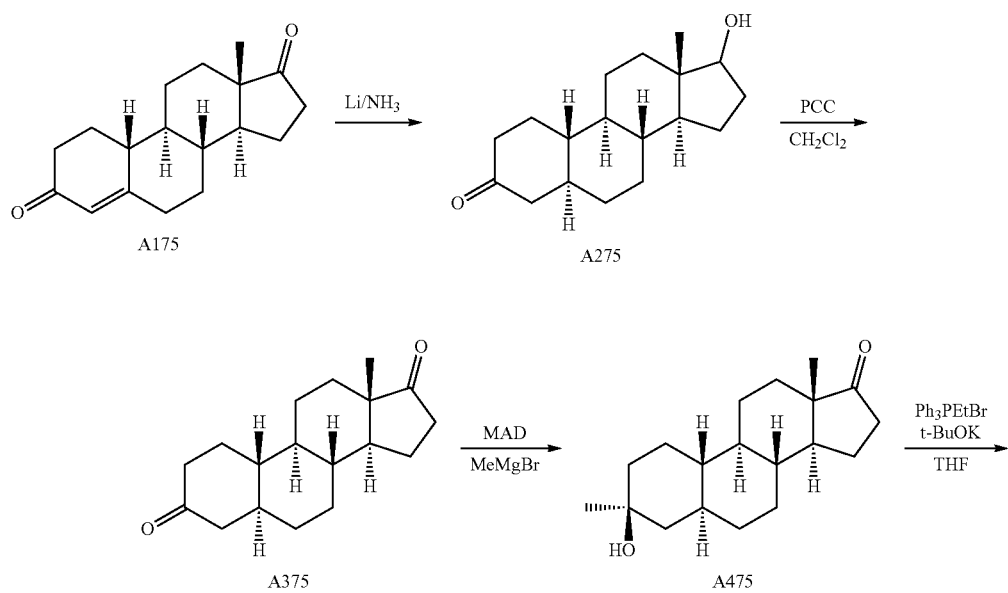

341
-continued
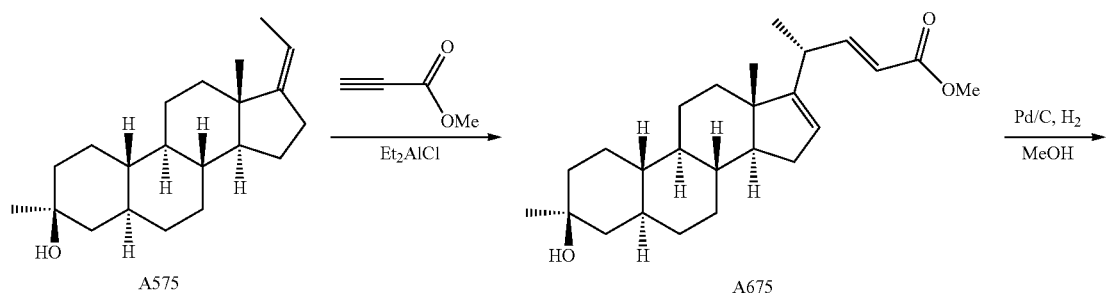
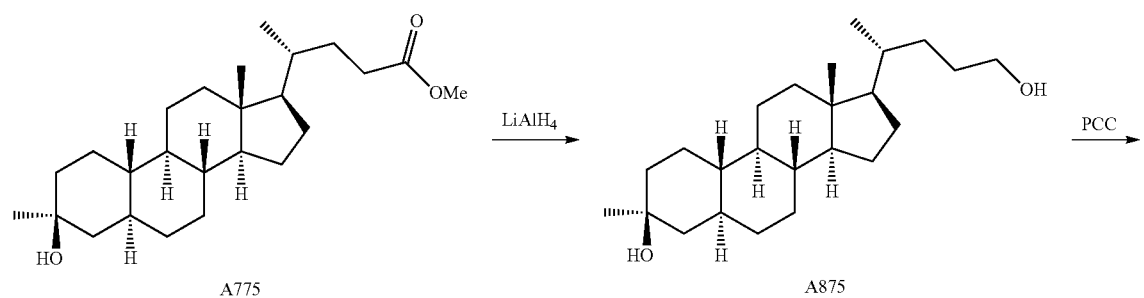
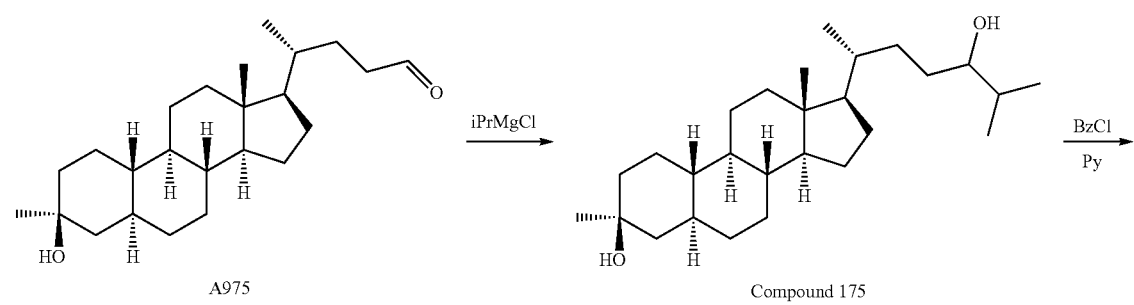
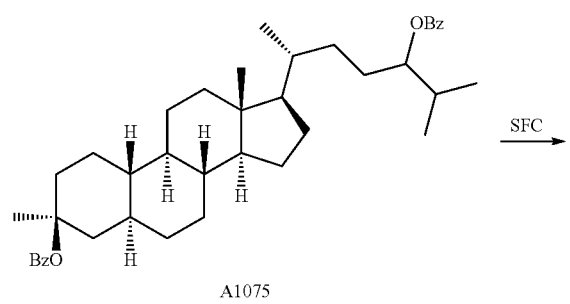

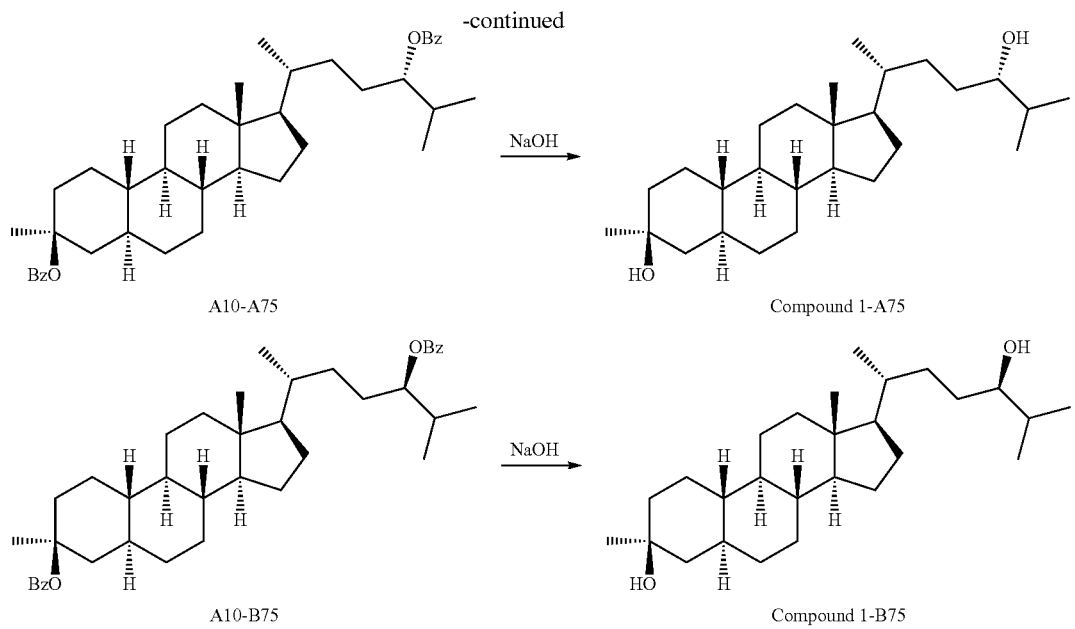

A10-A75 → Compound 1-A75

A10-B75 → Compound 1-B75

Step 1. To freshly prepared liquid ammonia (1.0 L) was added lithium (12.7 g, 1.82 mol) in portions at −70° C. The mixture became deep blue. After stirring at −70° C. for 1 h, a solution of A175 (50 g, 183 mmol) and t-butanol (26.9 g, 364 mmol) in dry THF (600 mL) was added to this mixture with strong stirring, and the temperature was maintained below −60° C. The resultant mixture was stirred at −70° C. for 2 hrs. Ammonium chloride (150 g) was added to reaction mixture. The mixture was warmed to 25° C. and stirred for 16 hrs. The reaction mixture was neutralized with aq. HCl (2.5 M, 1000 mL) and filtered. The filtrate was extracted with EtOAc (1 L×2), washed with brine (1 L), dried over anhydrous $Na_2SO_4$, filtered and concentrated to afford A2 (45 g, crude) as a solid.

$^1$H NMR (400 MHz, $CDCl_3$) δ 3.65-3.57 (m, 1H), 2.06-1.66 (m, 5H), 1.43-0.75 (m, 16H), 0.74 (s, 3H), 0.73-0.59 (m, 3H).

Step 2. To a solution of A275 (43 g, 155 mmol) in $CH_2Cl_2$ (600 mL) was added silica gel (75 g, w/w=1/1.5) and pyridinium chlorochromate (52.3 g, 243 mmol) at 25° C. The mixture was stirred at 25° C. for 2 hrs. The mixture was filtered and the filtrate was concentrated in vacuum. The residue was purified by column chromatography on silica gel (PE/EtOAc=20/1 to 5/1) to afford A375 (22.0 g, 50%) as a solid.

$^1$H NMR (400 MHz, $CDCl_3$) δ 2.52-2.38 (m, 2H), 2.38-2.28 (m, 3H), 2.15-2.05 (m, 2H), 2.05-1.65 (m, 5H), 1.55-1.40 (m, 2H), 1.40-1.15 (m, 6H), 1.15-0.92 (m, 1H), 0.90 (s, 3H), 0.89-0.80 (m, 1H), 0.80-0.65 (m, 1H).

Step 3. To a solution of BHT (48 g, 218 mmol) in toluene (120 mL) was added $AlMe_3$ (2 M in toluene, 120 mL, 218 mmol) at 0° C. and stirred at 10° C. for 1 h. To the MAD solution (109 mmol in 120 mL toluene) was added a solution of A375 (10 g, 36.4 mmol) in DCM (30 mL) at −78° C. After stirring at −78° C. for 1 h, MeMgBr (36.3 mL, 109 mmol) was added at −78° C. The mixture was stirred at −78° C. for 20 mins. The reaction mixture was treated with saturated citric acid (50 mL). The organic phase was separated and the aqueous phase extracted with EtOAc (80 mL). The organic phase was washed with brine (100 mL), dried over $Na_2SO_4$, concentrated in vacuum to give a crude product, which was purified by flash column (0~30% of EtOAc in PE) to give A476 (6 g, 57%) as a solid.

$^1$H NMR (400 MHz, $CDCl_3$) δ 2.50-2.45 (m, 1H), 2.13-1.96 (m, 1H), 1.95-1.70 (m, 6H), 1.70-1.60 (m, 2H), 1.58-1.45 (m, 1H), 1.45-0.95 (m, 13H), 0.95-0.83 (m, 4H), 0.80-0.65 (m, 2H).

Step 4. To a suspension of $PPh_3EtBr$ (22.9 g, 61.8 mmol) in THF (30 mL) was added t-BuOK (6.93 g, 61.8 mmol) at 20° C. After stirring at 40° C. for 30 min, a solution of A475 (6 g, 20.6 mmol) in THF (20 mL) was added at 40° C. and the reaction mixture was stirred at 40° C. for 1 h. The reaction mixture was poured into 50 g of crushed ice and stirred for 15 minutes. The organic layer was separated and the water phase was extracted with EtOAc (30 mL). The combined organic phase was concentrated in vacuo to give a thick oil. The residue was dissolved in 90 mL of MeOH at 60° C., following by treating with 90 mL of water. A precipitate formed. After stirring at 60° C. for 1 h, the precipitate was collected by filtration and washed with a solution of MeOH/water (15 mL/15 mL) and dried under vacuum to give the product A575 as a solid.

$^1$H NMR (400 MHz, $CDCl_3$) δ 5.18-5.06 (m, 1H), 2.42-2.29 (m, 1H), 2.29-2.10 (m, 2H), 1.95-1.84 (m, 1H), 1.84-1.46 (m, 10H), 1.46-1.25 (m, 2H), 1.25-1.05 (m, 10H), 1.05-0.80 (m, 5H), 0.75-0.60 (m, 2H).

Step 5. To a solution of A575 (4.8 g, 3.30 mmol) and methyl propiolate (4.21 mL, 47.4 mmol) in anhydrous dichloromethane (100 mL) under $N_2$ at 0° C. was added dropwise diethylaluminum chloride (1.0 M in toluene, 63.2 mL, 63.2 mmol). The mixture was stirred at 20° C. for 16 hours. The reaction mixture was quenched with aqueous citric acid (100 mL) at 0° C. carefully, and the inner temperature was maintained below 10° C. The resultant mixture was filtered through a pad of celite and extracted with DCM (2×200 mL). The combined organic layers were dried over anhydrous sodium sulfate, filtered and concentrated to give crude A675 as a solid. Combined with another batch, the crude product was purified by flash column (0~30% of EtOAc in PE) to give 6 g of impure product as a solid. The solid was recrystallized from DCM/PE (20 mL/80 mL) to give 3.1 g of pure product as a solid. The mother liquid was concentrated to give 2.8 g of the product as a solid. A total of 5.9 g of the product was obtained (79% yield).

$^1$H NMR (400 MHz, CDCl$_3$) δ 6.96 (dd, J=8.0, 15.6 Hz, 1H), 5.83 (dd, J=0.8, 15.6 Hz, 1H), 5.45-5.38 (m, 1H), 3.75 (s, 3H), 3.10-2.96 (m, 1H), 2.10-2.03 (m, 1H), 1.95-1.55 (m, 9H), 1.45-0.85 (m, 18H), 0.80-0.60 (m, 3H).

Step 6. To a solution of A675 (3 g, 7.76 mmol) in EtOAc (100 mL) was added Pd/C (100 mg, 10%, wet) and the mixture was degassed and back-filled with H$_2$ for 3 times. The reaction was stirred at 15° C. under 15 psi of H$_2$ for 16 hrs. The reaction mixture was filtered through a pad of celite washed with EtOAc (20 mL). The filtrate was concentrated to give 3 g of A775 as an oil, which was used directly for the next step.

$^1$H NMR (400 MHz, CDCl$_3$) δ 3.66 (s, 3H), 2.43-2.30 (m, 1H), 2.30-2.15 (m, 1H), 1.95-1.50 (m, 10H), 1.50-0.96 (m, 17H), 0.96-0.80 (m, 5H), 0.75-0.50 (m, 5H).

Step 7. To a solution of A775 (3 g, 7.68 mmol) in THF (100 mL) was added LiAlH$_4$ (580 mg, 15.3 mmol) at 0° C. under N$_2$. After stirring at this temperature for 1 h, the reaction mixture was treated with water (2 mL) and then the pH was adjusted to 1-2 with saturated citric acid. The water phase was extracted with EtOAc (2×50 mL). The combined organic layers were washed with brine (2×100 mL), dried over Na$_2$SO$_4$, filtered and concentrated to give 2.5 g of crude A875, which was used directly for the next step.

$^1$H NMR (400 MHz, CDCl$_3$) δ 3.70-3.50 (m, 2H), 2.00-1.78 (m, 3H), 1.78-1.52 (m, 8H), 1.52-1.30 (m, 4H), 1.30-0.98 (m, 15H), 0.98-0.80 (m, 5H), 0.75-0.55 (m, 5H).

Step 8. To a solution of A875 (2.5 g, 6.89 mmol) in DCM (200 mL) was added PCC (2.94 g, 13.7 mmol) and silica gel (5 g). After stirring at 20° C. for 2 h, the reaction was filtered through a pad of celite washed with DCM (2×20 mL). The filtrate was concentrated to give 3 g of crude mixture, which was purified by flash column (0~30% of EtOAc in PE) to give 1.5 g of the product as a solid.

$^1$H NMR (400 MHz, CDCl$_3$) δ 9.76 (t, J=1.2 Hz, 1H), 2.53-2.28 (m, 2H), 2.00-1.50 (m, 12H), 1.50-0.98 (m, 13H), 0.98-0.80 (m, 6H), 0.75-0.55 (m, 6H).

Step 9. To a solution of A975 (1.5 g, 4.16 mmol) in THF (100 mL) was added iPrMgCl (6.20 mL, 12.4 mmol) at 0° C. The reaction was stirred at this temperature for 1 h and quenched by adding water (50 mL) and saturated citric acid solution (100 mL). The mixture was then extracted with EtOAc (2×100 mL). The organic layers were combined and washed with brine (100 mL), dried over Na$_2$SO$_4$, filtered and concentrate. The crude residue was purified by flash column (0~20% of EtOAc in DCM) to 1.4 g of the product as a solid. Compound 175 (1.3 g) was triturated with MeCN (50 mL) at 80° C. to give 175 (350 mg) as a solid.

$^1$H NMR (400 MHz, CDCl$_3$) δ 3.38-3.25 (m, 1H), 1.98-1.92 (m, 1H), 1.92-1.76 (m, 2H), 1.76-1.50 (m, 9H), 1.50-1.40 (m, 4H), 1.40-0.97 (m, 14H), 0.97-0.80 (m, 12H), 0.73-0.53 (m, 5H).

LCMS Rt=1.309 min in 2.0 min chromatography, 30-90 AB, MS ESI calcd. for C$_{27}$H$_{45}$ [M+H−2H$_2$O]$^+$ 369, found 369.

Step 10. To a solution of 175 (700 mg, 1.72 mmol) in pyridine (5 mL) was added BzCl (723 mg, 5.15 mmol) at 0° C. and the reaction was stirred at 20° C. for 18 h to give a solution. The reaction mixture was diluted with water (20 mL), extracted with EtOAc (2×20 mL). The organic layer was washed with brine (5×100 mL), dried over Na$_2$SO$_4$, filtered and concentrated. The crude residue was purified by flash column (0~10% of EtOAc in PE) to give 920 mg of an oil. The crude product was separated by SFC (AD(250 mm*30 mm, 5 um)), 0.1% NH$_3$H$_2$O-EtOH) to give 280 mg of peak 1 as A10-A75 as a solid and 285 mg of peak 2 as A10-B75 as a solid.

A10-A75: $^1$H NMR (400 MHz, CDCl$_3$) δ 8.07 (d, J=8.4 Hz, 2H), 8.01 (d, J=8.4 Hz, 2H), 7.58-7.48 (m, 2H), 7.48-7.36 (m, 4H), 5.00-4.90 (m, 1H), 2.40-2.30 (m, 1H), 2.30-2.20 (m, 1H), 2.00-1.85 (m, 3H), 1.80-1.30 (m, 13H), 1.30-0.88 (m, 22H), 0.88-0.70 (m, 1H), 0.70-0.50 (m, 4H).

A10-B75: $^1$H NMR (400 MHz, CDCl$_3$) δ 8.07 (d, J=8.4 Hz, 2H), 8.01 (d, J=8.4 Hz, 2H), 7.58-7.48 (m, 2H), 7.48-7.36 (m, 4H), 5.00-4.92 (m, 1H), 2.47-2.28 (m, 1H), 2.28-2.20 (m, 1H), 2.00-1.85 (m, 3H), 1.80-1.45 (m, 13H), 1.30-0.85 (m, 22H), 0.85-0.70 (m, 1H), 0.70-0.50 (m, 4H).

Step 11. To a solution of A10-A (280 mg, 0.46 mmol) in THF (5 mL) and MeOH (5 mL) was added NaOH (200 mg, 5.00 mmol) and H$_2$O (2 mL) at 25° C. Then the solution was stirred at 50° C. for 16 h. The reaction solution was extracted with EtOAc (2×10 mL). The combined organic layers were dried over Na$_2$SO$_4$, filtered and concentrated in vacuum to give crude product which was purified by a silica gel column (PE/EtOAc=3:1) to give a solid, which was then triturated in hot MeCN (5 mL) to give the desired product Compound 1-A75 (102 mg, 55%) as a solid.

$^1$H NMR (400 MHz, CDCl$_3$) δ 3.38-3.25 (m, 1H), 1.98-1.92 (m, 1H), 1.92-1.76 (m, 2H), 1.76-1.50 (m, 9H), 1.50-1.40 (m, 2H), 1.40-0.97 (m, 17H), 0.97-0.80 (m, 11H), 0.73-0.55 (m, 5H).

LCMS Rt=1.323 min in 2.0 min chromatography, 30-90 AB, MS ESI calcd. for C$_{27}$H$_{45}$ [M+H−2H$_2$O]$^+$ 369, found 369.

Step 12. To a solution of A10-B75 (285 mg, 0.47 mmol) in THF (5 mL) and MeOH (5 mL) was added NaOH (200 mg, 5.00 mmol) and H$_2$O (2 mL) at 25° C. Then the solution was stirred at 50° C. for 16 h. The reaction solution was extracted with EtOAc (2×10 mL). The combined organic layers were dried over Na$_2$SO$_4$, filtered and concentrated in vacuum to give crude product which was purified by a silica gel column (PE/EtOAc=3:1) to give a solid, which was then triturated in hot MeCN (2×1 mL) to give desired product Compound 1-B75 (18 mg, 10%) as a solid.

$^1$H NMR (400 MHz, CDCl$_3$) δ 3.38-3.25 (m, 1H), 1.98-1.92 (m, 1H), 1.92-1.77 (m, 2H), 1.77-1.50 (m, 4H), 1.50-1.30 (m, 6H), 1.30-0.97 (m, 17H), 0.97-0.80 (m, 12H), 0.73-0.55 (m, 5H).

LCMS Rt=1.320 min in 2.0 min chromatography, 30-90 AB, MS ESI calcd. for C$_{27}$H$_{45}$ [M+H−2H$_2$O]$^+$ 369, found 369.

Synthesis of 1A75 to Confirm Stereochemistry

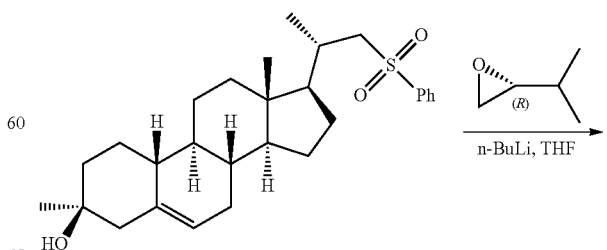

E-2678_1

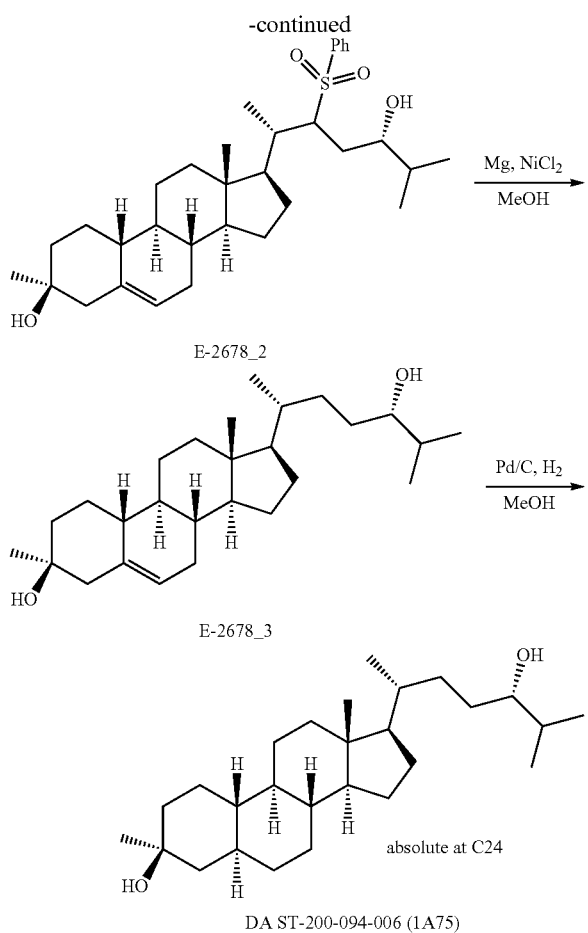

E-2678_2

E-2678_3

DA ST-200-094-006 (1A75)

absolute at C24

To THF (0.5 mL) under N₂ at −70° C. was added n-BuLi (2.5 M, 2.18 mmol, 0.872 mL). After that, a suspension of E-2678_1. (400 mg, 0.875 mmol) in THF (3 mL) was added drop-wise to give a suspension. After stirring at −70° C. for 30 min, a solution of (2R)-2-(propan-2-yl)oxirane (112 mg, 1.31 mmol) in THF (0.5 mL) was added. Then reaction was stirred at stirred at 25° C. for 16 hours. The mixture was poured into ice-water (20 mL) and extracted with EtOAc (2×30 mL). The combined organic layers were washed with brine (50 mL), dried over Na₂SO₄, filtered and concentrated in vacuum to afford E-2678_2 (380 mg, crude) as a solid, which was used directly in the next step.

To a solution of E-2678_2 (380 mg, 0.7 mmol) and nickel (II) chloride (4.53 mg, 0.035 mmol) in MeOH (30 mL) was added Mg powder (336 mg, 14 mmol) was added at 25° C. The mixture was stirred at 50° C. for 1 h. After cooling, the mixture was quenched with HCl (100 mL, 2M) until the reaction became clear and extracted with EtOAc (2×50 mL). The combined organic phase was dried over Na₂SO₄, filtered concentrated and purified by a silica gel column (PE/EtOAc=10/1 to 3/1) to give E-2678_3 (140 mg, 50%) as a solid.

The E-2678_3 (140 mg, 0.347 mmol) was separated by SFC (column: AD (250 mm*30 mm, 5 um)), gradient: 40-40% B (A=0.1% NH₃H₂O ETOH), flow rate: 50 mL/min) to give E-2678_3 (95 mg, 34%) as a solid.

¹HNMR (400 MHz, CDCl₃) δ$_H$ 5.42-5.38 (m, 1H), 3.35-3.26 (m, 1H), 2.20-2.14 (m, 1H), 2.10-1.89 (m, 4H), 1.87-1.59 (m, 6H), 1.54-1.16 (m, 12H), 1.13-0.97 (m, 7H), 0.95-0.75 (m, 11H), 0.68 (s, 3H).

SFC Rt=5.305 min in 10 min chromatography, AD_3_EtOH_DEA_5_40_25ML, 98.5% de.

To a solution of E-2678_3 (95 mg, 0.235 mmol) in MeOH (10 mL) was added Pd/C (0.1 g, <1% water). Then the solution was hydrogenated under 50 psi of hydrogen at 50° C. for 16 hrs. The mixture was filtered through a pad of celite and the filtrate was concentrated in vacuum. The residue was purified by combi-flash (0-15% of EtOAc in PE) to afford DA ST-200-094-006 (23 mg, 24%) as a solid.

¹HNMR (400 MHz, CDCl₃) δ$_H$ 3.35-3.28 (m, 1H), 1.99-1.62 (m, 7H), 1.55-1.33 (m, 7H), 1.31-1.20 (m, 7H), 1.17-0.97 (m, 10H), 0.93-0.75 (m, 11H), 0.73-0.65 (m, 5H).

LCMS Rt=1.269 min in 2.0 min chromatography, 30-90 AB, purity 100%, MS ESI calcd. For C₂₇H₄₅ [M-2H₂O+H]=369, found 369.

Example 76. Syntheses of Compounds 276, 376, and 476

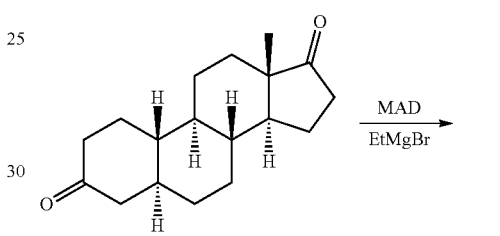

A376

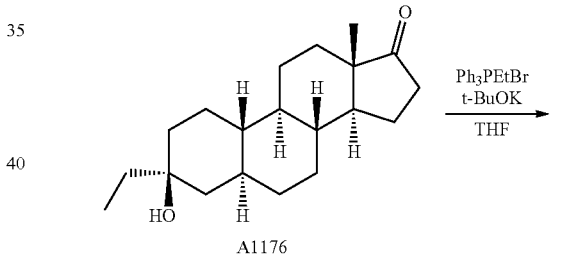

A1176

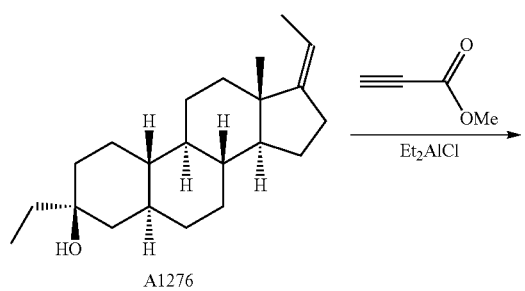

A1276

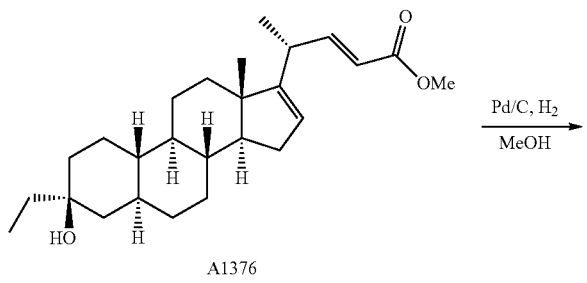

A1376

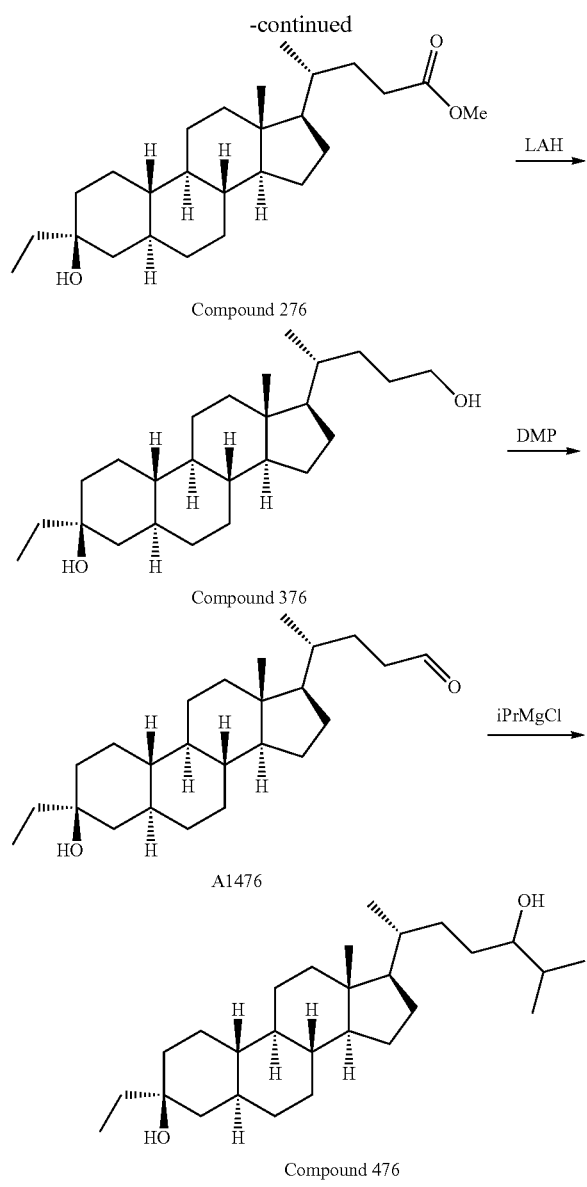

Step 1. To a solution of BHT (41.9 g, 190.58 mmol) in toluene (100 mL) under N₂ at 0° C. was added AlMe₃ (47.6 mL, 2 M in toluene, 95.2 mmol) drop-wise. The mixture was stirred at 25° C. for 1 h. To the mixture was added a solution of A376 (9.21 g, 33.6 mmol) in DCM (30 mL) at −78° C. After stirring at −78° C. for 1 h, EtMgBr (33.3 mL, 100 mmol) was added at −78° C. The mixture was stirred at −78° C. for 1.5 h. The reaction mixture was treated with saturated citric acid (50 mL). The organic phase was separated, extracted with EtOAc (80 mL). The organic phase was washed with brine (2×100 mL), dried over Na₂SO₄, concentrated in vacuum to give A1176 (5.2 g, 51%) as a solid.

$^1$H NMR (400 MHz, CDCl₃) δ 2.47-2.40 (m, 1H), 2.11-2.00 (m, 1H), 1.96-1.77 (m, 6H), 1.69-1.63 (m, 2H), 1.58-1.50 (m, 3H), 1.38-1.20 (m, 6H), 1.56-0.97 (m, 5H), 0.90-0.87 (m, 6H), 0.80-0.64 (m, 2H).

Step 2. To a suspension of PPh₃EtBr (18.2 g, 49.1 mmol) in THF (20 mL) was added t-BuOK (5.50 g, 49.1 mmol) at 20° C. After stirring at 40° C. for 30 mins, a solution of A1176 (5 g, 16.4 mmol) in THF (20 mL) was added at 40° C. and the reaction mixture was stirred at 40° C. for 1 h. The reaction mixture was poured into 50 g of crushed ice and stirred for 15 minutes. The organic layer was separated and the water phase was extracted with EtOAc (30 mL). The combined organic phase was concentrated in vacuum to give thick oil. The residue was dissolved in 90 mL of MeOH at 60° C., following by treating with 90 mL of water and a large amount of a precipitate appeared. After stirring at 60° C. for 1 h, the precipitate was collected by filtration and washed with a solution of MeOH/water (15 mL/15 mL), dried in vacuum to give A1276 (5.0 g, 96%) as a solid.

$^1$H NMR (400 MHz, CDCl₃) δ 5.14-5.09 (m, 1H), 2.39-2.33 (m, 1H), 2.25-2.14 (m, 2H), 1.87-1.75 (m, 3H), 1.66-1.63 (m, 5H), 1.58-1.54 (m, 5H), 1.34-1.25 (m, 2H), 1.19-1.03 (m, 7H), 0.90-0.84 (m, 8H), 0.73-0.64 (m, 2H).

Step 3. To a solution of A1276 (4.5 g, 14.2 mmol) and methyl propiolate (3.78 mL, 42.6 mmol) in anhydrous dichloromethane (100 mL) under N₂ at 0° C. was added dropwise Et₂AlCl (1.0 M in toluene, 56.8 mL, 56.8 mmol). The mixture was stirred at 20° C. for 16 hrs. The reaction mixture was quenched with aqueous saturated citric acid (100 mL) at 0° C. carefully, and the inner temperature was maintained below 10° C. The resultant mixture was filtered through a pad of celite and washed with DCM (2×200 mL). The combined organic layers were dried over anhydrous sodium sulfate, filtered and concentrated to give impure A1376 as a solid. The crude product was combined with another batch of impure product from 0.5 g of A1276, purified by flash column (0~30% of EtOAc in PE) to give A1376 (6 g, 95%) as a solid.

$^1$H NMR (400 MHz, CDCl₃) δ 6.93 (dd, J=8.0, 15.6 Hz, 1H), 5.80 (dd, J=1.2, 15.2 Hz, 1H), 5.39-5.39 (m, 1H), 3.73 (s, 3H), 3.02-2.97 (m, 1H), 2.07-2.01 (m, 1H), 1.85-1.52 (m, 8H), 1.35-0.96 (m, 10H), 0.90-0.84 (m, 8H), 0.76-0.66 (m, 6H).

Step 4. To a solution of A1376 (6 g, 14.9 mmol) in EtOAc (100 mL) was added Pd/C (1 g, 10%, wet) and the mixture was degassed with H₂ for 3 times. After that, the reaction was stirred at 15° C. under 15 psi of H₂ for 16 hrs. The reaction mixture was filtered through a pad of celite and washed with EtOAc (30 mL). The filtrate was concentrated to give Compound 276 (5.8 g, 96%) as a solid.

$^1$H NMR (400 MHz, CDCl₃) δ 3.66 (s, 3H), 2.39-2.31 (m, 1H), 2.25-2.17 (m, 1H), 1.95-1.92 (m, 1H), 1.85-1.78 (m, 4H), 1.68-1.61 (m, 3H), 1.57-1.52 (m, 5H), 1.42-1.40 (m, 2H), 1.35-1.26 (m, 3H), 1.15-1.02 (m, 8H), 0.92-0.82 (m, 8H), 0.81-0.79 (m, 1H), 0.72-0.59 (m, 4H). LCMS R$_t$=1.334 min in 2 min chromatography, 30-90AB, MS ESI calcd. For C₂₆H₄₃O₂ [M+H−H₂O]⁺ 387, found 387.

Step 5. To a solution of Compound 276 (also 175 in Example 75) (200 mg, 0.494 mmol) in THF (40 mL) was added LAH (56.1 mg, 1.48 mmol) at 0° C. under N₂. After stirring at this temperature for 1 h, the reaction mixture was treated with water (2 mL), adjusted to pH=1-2 with saturated citric acid. The water phase was extracted with EtOAc (2×50 mL). The combined organic layers were washed with brine (2×30 mL), dried over Na₂SO₄, filtered and concentrated to give Compound 376 (120 mg, 65%) as a solid.

$^1$H NMR (400 MHz, CDCl₃) δ 3.63-3.60 (m, 2H), 1.96-1.93 (m, 1H), 1.85-1.78 (m, 3H), 1.68-1.52 (m, 10H), 1.48-1.38 (m, 3H), 1.34-1.25 (m, 4H), 1.13-1.07 (m, 9H), 0.93-0.83 (m, 8H), 0.73-0.59 (m, 4H).

LCMS R$_t$=3.826 min in 2 min chromatography, 30-90AB, MS ESI calcd. For C₂₅H₄₃O [M+H−H₂O]⁺ 359, found 359.

Step 6. To a suspension of DMP (2.24 g, 5.30 mmol) in DCM (18 mL) was added a solution of Compound 376 (1 g, 2.65 mmol) in DCM (10 mL) at 20° C. The reaction was stirred for 1 h at 20° C. The mixture was quenched with saturated NaHCO₃ aqueous (20 mL) at 20° C. The mixture was filtered and the organic layers were separated and the aqueous was extracted with DCM (2×20 mL). The combined phase was washed with saturated Na₂S₂O₃ aqueous (50 mL), brine (40 mL), dried over Na₂SO₄, filtered and concentrated under vacuum to give the crude product, which was purified by flash column (0~30% of EtOAc in PE) to give A1476 (920 mg, 93%) as a solid.

¹H NMR (400 MHz, CDCl₃) δ 9.76 (s, 1H), 2.47-2.41 (m, 1H), 2.40-2.32 (m, 1H), 1.97-1.92 (m, 1H), 1.86-1.78 (m, 3H), 1.68-1.52 (m, 6H), 1.44-1.41 (m, 1H), 1.35-1.22 (m, 6H), 1.12-1.03 (m, 8H), 0.92-0.79 (m, 10H), 0.78-0.57 (m, 4H).

Step 7. To a solution of A1476 (910 mg, 2.42 mmol) in THF (60 mL) was added iPrMgCl (12.1 mL, 24.2 mmol) at 0° C. The reaction was stirred at this temperature for 1 h. The reaction was quenched by adding water (30 mL) and saturated citric acid solution (30 mL). The mixture was extracted with EtOAc (2×30 mL). The combined organic layer was washed with brine (30 mL), dried over Na₂SO₄, filtered and concentrate to give an oil, which was purified by silica gel column (PE:EtOAc=50:1 to 4:1) to give Compound 476 (900 mg, 89%) as a solid.

¹H NMR (400 MHz, CDCl₃) δ 3.32-3.30 (m, 1H), 1.96-1.93 (m, 1H), 1.85-1.78 (m, 3H), 1.68-1.52 (m, 12H), 1.43-1.02 (m, 16H), 0.93-0.83 (m, 13H), 0.70-0.61 (m, 4H). LCMS Rt=1.371 min in 2 min chromatography, 30-90AB, MS ESI calcd. For $C_{28}H_{47}$ $[M+H-2H_2O]^+$ 383, found 383.

Example 77. Syntheses of Compounds 4A77 and 4877

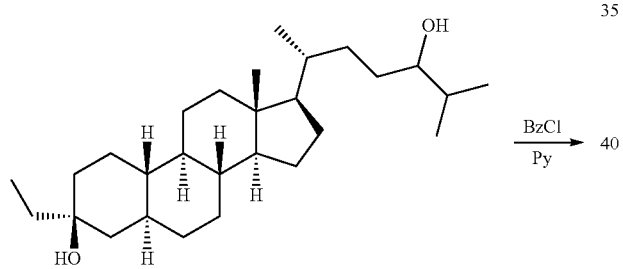

Compound 476

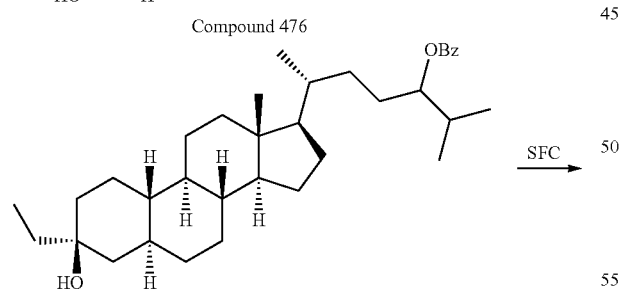

A15

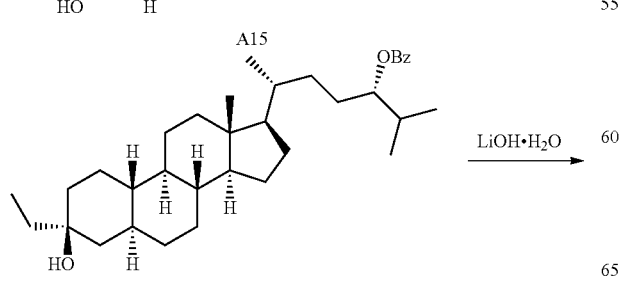

A16-A

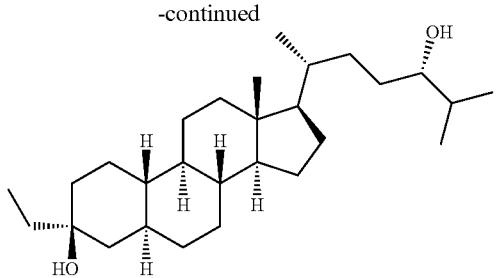

Compound 4A77

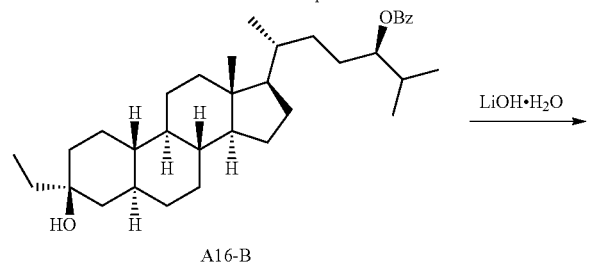

A16-B

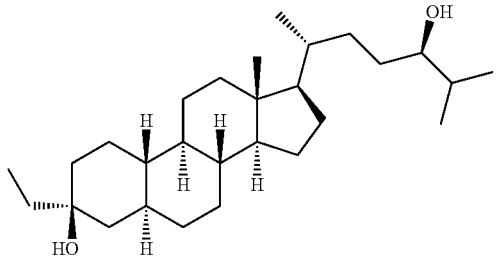

Compound 4B77

Step 1. To a solution of Compound 476 (800 mg, 1.91 mmol) in pyridine (20 mL) was added BzCl (402 mg, 2.86 mmol) at 0° C. and the reaction was stirred at 20° C. for 18 h. The reaction mixture was diluted with water (50 mL), extracted with EtOAc (2×40 mL). The organic layer was washed with brine (5×50 mL), dried over Na₂SO₄, filtered and concentrated. The crude was purified by silica gel column (PE/EtOAc=50/1 to 4/1) to give A15 (600 mg, 60%) as an oil.

¹H NMR (400 MHz, CDCl₃) δ 8.05 (d, J=8.0 Hz, 2H), 7.55 (t, J=7.2 Hz, 1H), 7.45 (d, J=8.0 Hz, 2H), 5.00-4.92 (m, 1H), 2.05-1.20 (m, 13H), 1.20-0.75 (m, 30H), 0.75-0.50 (m, 5H).

A15 was purified by SFC (column: AD (250 mm*30 mm, 5um)), gradient: 40-40% B (A=NH3/H2O, B=MeOH), flow rate: 60 mL/min) to give A16-A (116 mg, 19.4%) and impure A16-B (230 mg).

A16-A: ¹H NMR (400 MHz, CDCl₃) δ 8.05 (d, J=8.0 Hz, 2H), 7.55 (t, J=7.2 Hz, 1H), 7.45 (d, J=8.0 Hz, 2H), 5.00-4.92 (m, 1H), 2.05-1.83 (m, 2H), 1.83-1.20 (m, 11H) 1.20-0.75 (m, 30H), 0.75-0.50 (m, 5H).

A16-B: ¹H NMR (400 MHz, CDCl₃) δ 8.04 (d, J=8 Hz, 2H), 7.55 (t, J=7.2 Hz, 1H), 7.45 (d, J=8.0 Hz, 2H), 5.00-4.92 (m, 1H), 2.05-1.42 (m, 15H), 1.40-1.15 (m, 4H) 1.14-0.75 (m, 24H), 0.73-0.50 (m, 5H).

Step 2. To a solution of A16-A (116 mg, 221 μmol) in THF (2 mL) and MeOH (2 mL) was added LiOH (52.6 mg, 2.20 mmol) and H₂O (1 mL) at 25° C. Then the solution was stirred at 50° C. for 24 h. The reaction solution was extracted with EtOAc (2×10 mL). The combined organic layers were dried over Na₂SO₄, filtered and concentrated in vacuum to give crude product (91 mg), which was purified by flash column (0–5% of acetone in DCM, 25° C.) to give Compound 4A77 (45 mg, 50%) as a solid.

$^1$H NMR (400 MHz, CDCl$_3$) δ 3.33-3.31 (m, 1H), 1.96-1.85 (m, 1H), 1.84-1.77 (m, 3H), 1.68-1.62 (m, 5H), 1.56-1.52 (m, 5H), 1.44-1.33 (m, 4H), 1.31-1.17 (m, 5H), 1.14-0.99 (m, 8H), 0.92-0.79 (m, 13H), 0.73-0.56 (m, 5H). LCMS Rt=1.347 min in 2.0 min chromatography, 30-90 AB, MS ESI calcd. for C$_{28}$H$_{47}$ [M+H−2H$_2$O]$^+$ 383, found 383.

Step 3. To a solution of A16-B (130 mg, 248 μmol) in THF (2 mL) and MeOH (2 mL) and H$_2$O (1 mL) was added lithium hydroxide hydrate (104 mg, 2.48 mmol) at 25° C. Then the solution was stirred at 50° C. for 16 h. The reaction was dilute with water (10 mL) and extracted with EtOAc (2×30 mL). The combined organic layers was washed with brine (50 mL), dried over Na$_2$SO$_4$, filtered and concentrated in vacuum. The residue was purified by silica gel chromatograph (PE/EtOAc=10/1) to afford Compound 4B77 (59 mg, 57%) as a solid.

$^1$H NMR (400 MHz, CDCl$_3$) δ 3.33-3.31 (m, 1H), 1.97-1.88 (m, 1H), 1.84-1.77 (m, 3H), 1.68-1.59 (m, 6H), 1.55-1.52 (m, 5H), 1.46-1.37 (m, 1H), 1.33-1.15 (m, 6H), 1.14-0.99 (m, 9H), 0.94-0.79 (m, 12H), 0.85-0.78 (m, 1H), 0.73-0.56 (m, 5H). LCMS Rt=1.357 min in 2.0 min chromatography, 30-90 AB, MS ESI calcd. for C$_{28}$H$_{46}$ [M+H−2H$_2$O]$^+$ 383, found 383.

Synthesis to Confirm Stereochemistry

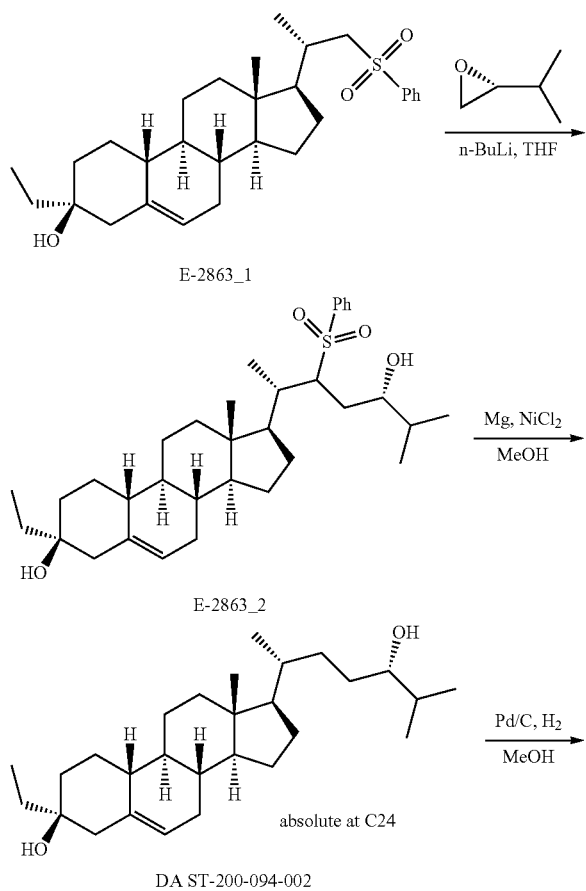

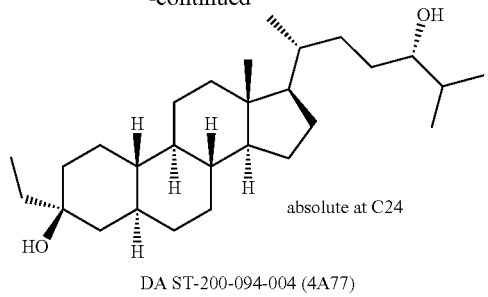

DA ST-200-094-004 (4A77)

To THF (0.5 mL) was added n-BuLi (2.5 M, 2.12 mmol, 0.848 mL) under N$_2$ at −70° C. After that, a suspension of E-2863_1 (400 mg, 0.849 mmol) in THF (3 mL) was added dropwise to give a suspension. After stirring at −70° C. for 30 min, a solution of (2R)-2-(propan-2-yl)oxirane (86.9 mg, 1.01 mmol) in THF (0.5 mL) was added. The reaction was stirred at stirred at 25° C. for 16 hours. The mixture was poured into ice-water (20 mL) and extracted with EA (2×30 mL). The combined organic layers were washed with brine (50 mL), dried over Na$_2$SO$_4$, filtered and concentrated in vacuum to afford E-2863_2 (430 mg, crude) as a solid, which was used directly for the next step.

To a solution of E-2863_2 (430 mg, 0.772 mmol) and nickel (II) chloride (5 mg, 0.0386 mmol) in MeOH (30 mL) was added Mg powder (369 mg, 15.4 mmol) at 25° C. The mixture was stirred at 50° C. for 1 h. After cooling, the mixture was quenched with HCl (100 mL, 2M) until the reaction became clear and extracted with EtOAc (2×50 mL). The combined organic phase was dried over Na$_2$SO$_4$, filtered, concentrated and purified by a silica gel column (PE/EtOAc=10/1 to 3/1) to give DA ST-200-094-002 (160 mg, 50%) as a solid, which was separated by SFC (column: AD (250 mm*30 mm, 5 um)), gradient: 40-40% B (A=0.1% NH$_3$H$_2$O ETOH), flow rate: 50 mL/min) to give DA ST-200-094-002 (85 mg, 53%, 50 mg for delivery) as a solid.

$^1$HNMR (400 MHz, CDCl$_3$) δ 5.42-5.38 (m, 1H), 3.35-3.26 (m, 1H), 2.25-2.21 (m, 1H), 2.07-1.77 (m, 7H), 1.70-1.59 (m, 3H), 1.54-1.36 (m, 7H), 1.32-0.99 (m, 11H), 0.96-0.75 (m, 14H), 0.68 (s, 3H).

LCMS Rt=1.291 min in 2.0 min chromatography, 30-90 AB, purity 100%, MS ESI calcd. For C$_{28}$H$_{47}$O [M−H$_2$O+H]=399, found 399.

SFC Rt=5.654 min in 10 min chromatography, AD_3_EtOH_DEA_5_40_25ML, 96.8% de To a solution of DA ST-200-094-002 (35 mg, 0.0839 mmol) in MeOH (6 mL) was added Pd/C (0.1 g, <1% water). Then the suspension was hydrogenated under 50 psi of hydrogen at 50° C. for 16 hrs. The mixture was filtered through a pad of celite and the filtrate was concentrated in vacuum. The residue was purified by flash column (PE/EtOAc=10/1 to 5/1) to give DA ST-200-094-004 (7 mg, 20%) as a solid.

$^1$HNMR (400 MHz, CDCl$_3$) δ 3.35-3.28 (m, 1H), 2.00-1.91 (m, 1H), 1.87-1.74 (m, 3H), 1.71-1.56 (m, 6H), 1.54-1.35 (m, 8H), 1.32-1.17 (m, 5H), 1.14-0.94 (m, 9H), 0.93-0.76 (m, 13H), 0.73-0.62 (m, 4H).

LCMS Rt=1.350 min in 2.0 min chromatography, 30-90 AB, purity 100%, MS ESI calcd. For C$_{28}$H$_{47}$ [M−2H$_2$O+H]=383, found 383.

Example 78. Synthesis of Compound 561

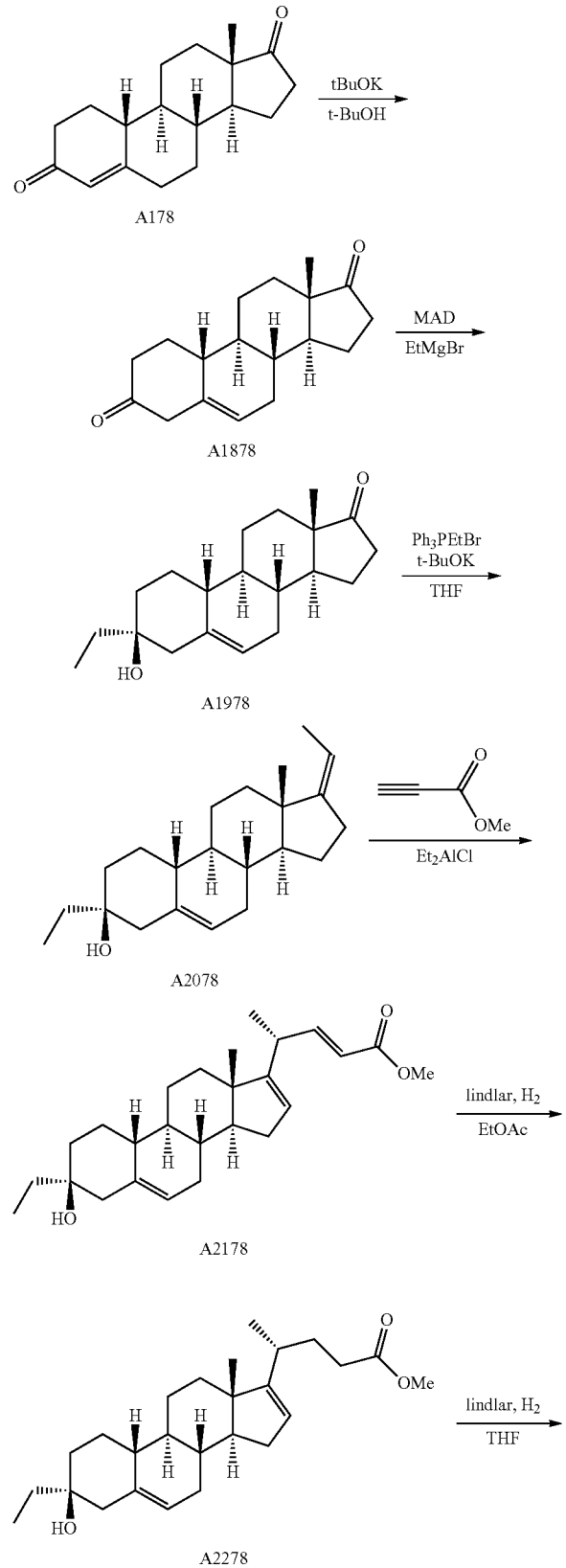

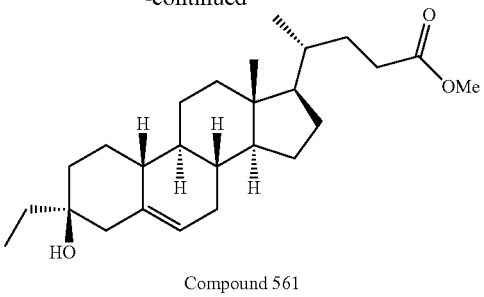

Compound 561

Step 1. t-BuOH (300 mL) was charged into a three-neck round bottom flask under nitrogen at 35° C. and stirred under nitrogen gas bubbling for 10 mins. t-BuOK (45.2 g, 403 mmol) was added to the mixture and stirred under nitrogen gas bubbling for 15 mins. A178 (10 g, 36.7 mmol) was added to the above mixture and stirred under nitrogen gas bubbling at 35° C. for 1.5 hrs. The reaction mixture was poured to 10% aqueous acetic acid (500 mL) and stirred for 15 mins. Water (200 mL) was added to the aqueous and stirred for 30 mins. The pH of the mixture was adjusted to 7~8 with sodium bicarbonate (60 g). The mixture was stirred for 30 mins. The mixture was extracted with PE (3×400 mL). The organic layer was separated, washed with brine (500 mL), dried over anhydrous sodium sulfate, filtered and concentrated below 40° C. to give A1878 (11 g, crude) as an oil.

$^1$H NMR CDCl$_3$ (400 MHz, CDCl$_3$) δ 5.55-5.47 (m, 1H), 3.16-2.94 (m, 2H), 2.52-2.33 (m, 4H), 2.19-1.93 (m, 6H), 1.75-1.61 (m, 2H), 1.56-1.48 (m, 1H), 1.40-1.33 (m, 3H), 1.29-1.22 (m, 1H), 1.01-0.92 (m, 4H).

Step 2. To solution of BHT (52.3 g, 238 mmol) in anhydrous toluene (150 mL) under N$_2$ at 0° C. was added trimethylaluminum (2 M in toluene, 55.0 mL, 110 mmol) drop-wise. The mixture was stirred at 15° C. for 1 hour and cooled to −70° C. Then A1878 (10 g, 36.7 mmol) in toluene (50 mL) was added below −60° C. The resulting mixture was stirred at −70° C. for 1 hour. Ethylmagnesium bromide (36.6 mL, 3.0 M in diethyl ether, 110 mmol) was added drop-wise below −60° C. The reaction mixture was stirred at −70° C. for another 1 hour. The reaction mixture was quenched with saturated citric acid (400 mL) at −70° C. The mixture was warmed to 15° C. slowly and extracted with ethyl acetate (3×400 mL). The combined organic layer was washed with brine (500 mL), dried over Na$_2$SO$_4$, filtered and concentrated. The residue was purified by Combi-flash (0%~30% of EtOAc in PE) to afford A1978 (7.6 g, 69%) as a solid.

$^1$H NMR (400 MHz, CDCl$_3$) δ 5.39-5.32 (m, 1H), 2.43-2.33 (m, 1H), 2.22-2.15 (m, 1H), 2.05-1.86 (m, 6H), 1.80-1.70 (m, 2H), 1.65-1.52 (m, 2H), 1.47-1.29 (m, 5H), 1.26-1.13 (m, 4H), 0.85-0.76 (m, 8H).

Step 3. To a suspension of PPh$_3$EtBr (38.9 g, 105 mmol) in THF (200 mL) under N$_2$ was added t-BuOK (11.7 g, 105 mmol) at 40° C. After stirring at 20° C. for 10 min, A19 (8 g, 26.4 mmol) was added. The reaction mixture was stirred at 40° C. for 1 h. The reaction was quenched with aqueous NH$_4$Cl (250 mL) at 0° C. and extracted with EtOAc (3×200 mL). The combined organic phase was washed with brine (500 mL), dried over Na$_2$SO$_4$, filtered and concentrated. The residue was purified by Combi-flash (0%-30% of EtOAc in PE) to afford A2078 (7.2 g, 87%) as a solid.

$^1$H NMR (400 MHz, CDCl$_3$) δ 5.36-5.29 (m, 1H), 5.12-5.01 (m, 1H), 2.36-2.25 (m, 1H), 2.23-2.05 (m, 3H), 2.00-

1.73 (m, 5H), 1.62-1.48 (m, 7H), 1.43-1.32 (m, 3H), 1.28-1.06 (m, 5H), 0.86-0.73 (m, 8H).

Step 4. To a solution of A2078 (7 g, 22.2 mmol) and methyl propiolate (4.66 g, 55.5 mmol) in DCM (200 mL) were added diethylaluminum chloride (88.8 mL, 88.8 mmol, 1 M in hexane) at 0° C. under $N_2$ drop-wise. The reaction mixture was stirred at 25° C. for 16 h. The reaction mixture was quenched with saturated aqueous $NaHCO_3$ (100 mL) solution, acidified with saturated aqueous citric acid solution to pH=5, extracted with DCM (2×200 mL). The combined organic layer was washed with brine (100 mL), dried over $Na_2SO_4$, filtered and concentrated in vacuum to give a crude product. The crude product was purified by silica gel column (PE/EtOAc=4/1) to give A2178 (6.20 g, 70%) as a solid.

$^1$H NMR (400 MHz, $CDCl_3$) δ 7.00-6.90 (m, 1H), 5.85-5.75 (m, 1H), 5.40-5.30 (m, 2H), 3.73 (s, 3H), 3.05-2.95 (m, 1H), 2.30-2.20 (m, 1H), 2.10-1.75 (m, 9H), 1.75-1.50 (m, 3H), 1.50-1.20 (m, 9H), 0.95-0.80 (m, 5H), 0.78 (s, 3H).

Step 5. To a solution of A2178 (800 mg, 2.00 mmol) in EtOAc (50 mL) was added lindlar catalyst (500 mg) and the reaction mixture was stirred at 20° C. for 4 h under $H_2$. The reaction mixture was filtered with filter paper and concentrated in vacuum to give a crude product. The crude product was purified by silica gel column (PE/EtOAc=10/1) to give A2278 (650 mg, crude).

$^1$H NMR (400 MHz, $CDCl_3$) δ 5.45-5.35 (m, 2H), 3.66 (s, 3H), 2.50-2.40 (m, 1H), 2.35-2.25 (m, 2H), 2.15-2.05 (m, 1H), 2.05-1.95 (m, 3H), 1.95-1.75 (m, 3H), 1.75-1.55 (m, 3H), 1.55-1.40 (m, 7H), 1.40-1.25 (m, 3H), 1.10-1.00 (m, 4H), 1.00-0.85 (m, 4H), 0.85-0.80 (m, 1H), 0.75 (s, 3H).

Step 6. To a solution of A22 (300 mg, 0.748 mmol) in THF (10 mL) was added lindlar catalyst (500 mg) and the reaction mixture was stirred at 20° C. for 4 h under $H_2$. The reaction mixture was filtered with filter paper and concentrated in vacuum to give a crude product. The crude product was purified by silica gel column (PE/EtOAc=10/1) to give an impure product. The impure product was purified by prep-HPLC (0.1% TFA as additive). Most of MeCN was removed by concentration and the remaining solvent was removed by lyophilization to give 561 (27 mg, 9%) as a solid.

$^1$H NMR (400 MHz, $CDCl_3$) δ 5.40-5.35 (m, 1H), 3.66 (s, 3H), 2.40-2.30 (m, 1H), 2.30-2.20 (m, 2H), 2.10-1.80 (m, 8H), 1.55-1.40 (m, 6H), 1.40-1.20 (m, 5H), 1.20-1.00 (m, 5H), 1.00-0.90 (m, 3H), 0.90-0.75 (m, 4H), 0.75-0.70 (m, 1H), 0.68 (s, 3H). LCMS Rt=1.299 min in 2.0 mm chromatography, 30-90 AB, MS ESI calcd. for $C_{26}H_{41}O_2[M+H-H_2O]^+$ 385, found 385.

Example 79. Synthesis of Compound 679

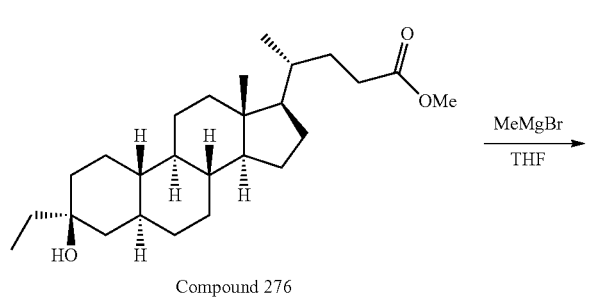

Compound 276

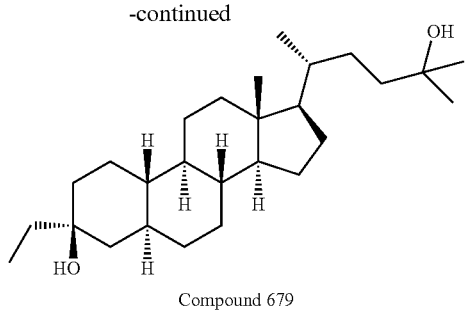

Compound 679

To a solution of 276 (150 mg, 0.37 mmol) in THF (5 mL) was added MeMgBr (616 μL, 3 M in ether) drop-wise at 0° C. under $N_2$. After that, the reaction mixture was stirred at 20° C. for 1 h. The reaction mixture was quenched with saturated aqueous $NH_4Cl$ (15 mL) solution, extracted with EtOAc (2×20 mL). The combined organic layer was washed with brine (20 mL), dried over $Na_2SO_4$, filtered and concentrated in vacuum to give a crude product. The crude product was re-crystallized from MeCN (10 mL) to give 679 (32 mg, 21%) as a solid.

$^1$H NMR (400 MHz, $CDCl_3$) δ 2.05-1.95 (m, 1H), 1.90-1.80 (m, 3H), 1.65-1.60 (m, 3H), 1.60-1.55 (m, 2H), 1.45-1.25 (m, 8H), 1.25-1.15 (m, 8H), 1.15-1.00 (m, 10H), 0.95-0.80 (m, 8H), 0.75-0.55 (m, 5H). LCMS Rt=1.282 min in 2.0 min chromatography, 30-90 AB, MS ESI calcd. for $C_{27}H_{45}$ $[M+H-2H_2O]^+$ 369, found 369.

Example 80. Synthesis of Compound 780

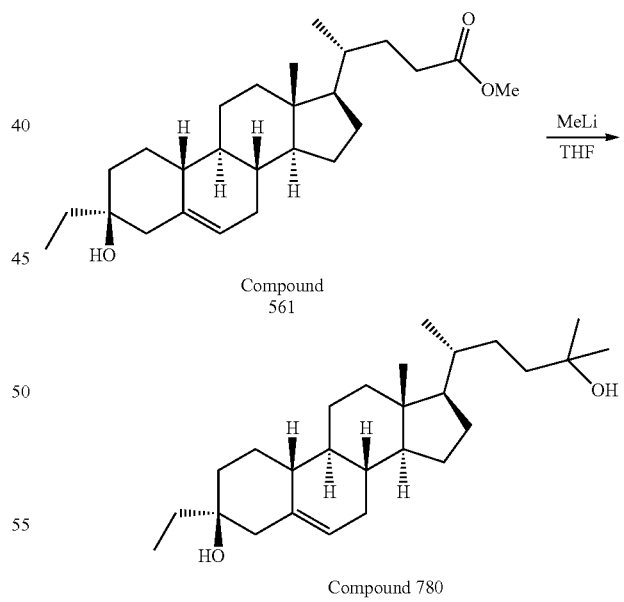

Compound 561

Compound 780

To a solution of 561 (300 mg, impure, 0.745 mmol) in THF (10 mL) was added MeLi (2.32 mL, 3.72 mmol, 1.6M in THF). The mixture was stirred at 25° C. for 30 minutes. The mixture was quenched with sat.$NH_4Cl$ (30 mL) and extracted with EtOAc (3×15 mL). The combined organic phase was dried over $Na_2SO_4$, filtered, concentrated and purified by flash column (0-15% of EtOAc in PE) to give 780 (37 mg, 12%) as a solid.

¹H NMR (400 MHz, CDCl₃) δ 5.40-5.35 (m, 1H), 2.26-2.20 (m, 1H), 2.10-1.75 (m, 7H), 1.68-1.58 (m, 2H), 1.56-1.37 (m, 7H), 1.36-1.24 (m, 4H), 1.23-1.17 (m, 8H), 1.16-0.99 (m, 5H), 0.96-0.90 (m, 3H), 0.89-0.76 (m, 5H), 0.68 (s, 3H).

LCMS Rt=1.222 min in 2.0 min chromatography, 30-90 AB, MS ESI calcd. for C₂₇H₄₃ [M+H−2H₂O]⁺ 367, found 367.

Example 81: Synthesis of 8127

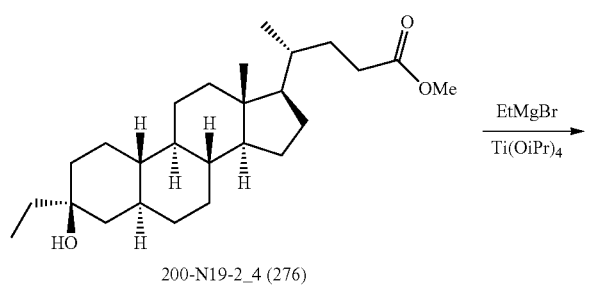

The experimental of intermediate 200-N19-2_4 or 276 can be found in Example 76.

Synthesis of 8127

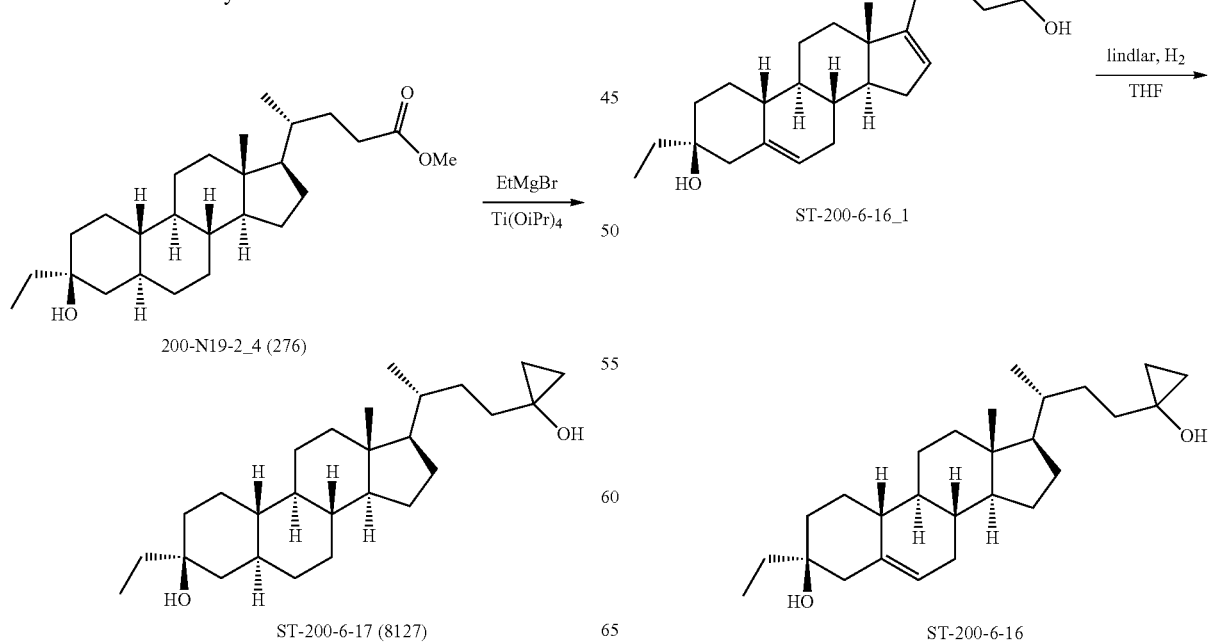

Ti(i-PrO)₄ (140 mg, 0.5 mmol) and EtMgBr (0.6 mL, 3 M in Et2O, 1.72 mmol) were added to a solution of 200-N19-2_4 (200 mg, 0.5 mmol) in THF (2 mL) at 25° C. After that, the reaction mixture was stirred at 25° C. for 15 min under N₂. The reaction mixture was quenched with saturated aqueous NH₄Cl (10 mL) solution and extracted with EtOAc (3×20 mL). The combined organic layer was washed with brine (50 mL), dried over Na₂SO₄, filtered and concentrated in vacuum to give a crude product. The crude product was purified by silica gel column (EtOAc/PE=5/1) to afford an impure product, which was triturated from n-hexane (5 mL) at 25° C. to give 8127 (58 mg, 46%).

¹H NMR (400 MHz, CDCl₃) δ 1.99-1.91 (m, 1H), 1.88-1.59 (m, 10H), 1.48-1.21 (m, 6H), 1.18-0.97 (m, 10H), 0.94-0.81 (m, 9H), 0.79-0.56 (m, 8H), 0.47-0.38 (m, 2H).

LCMS R_t=1.356 min in 2 min chromatography, 30-90AB_2 MIN_E, purity 100%, MS ESI calcd. For C₂₇H₄₃[M+H−2H₂O]⁺ 367, found 367.

Example 82: Synthesis of 8245

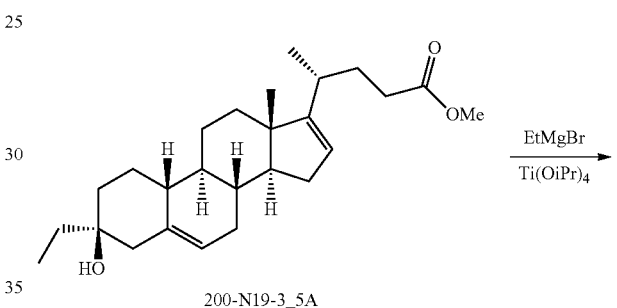

Synthesis of ST-200-6-16_1

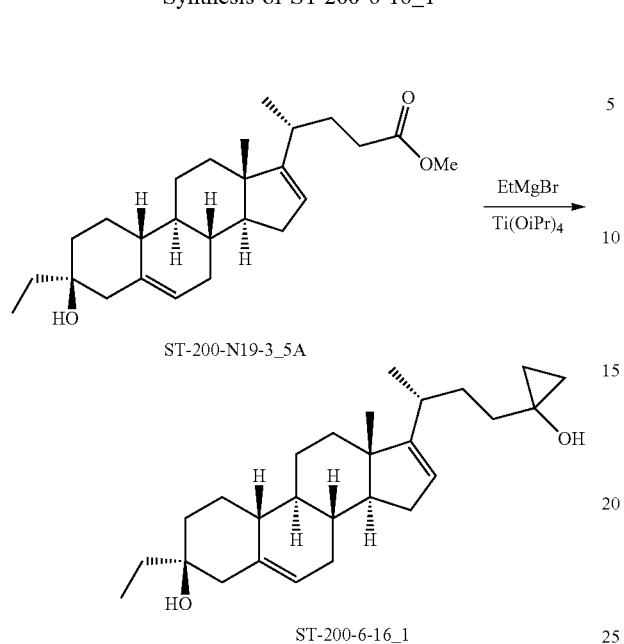

The synthesis for ST-200-N19-3_5A can be found in Example 78. Ti(i-PrO)$_4$ (212 mg, 0.75 mmol) was added to a solution of 200-N19-3_5A (300 mg, 0.75 mmol) in THF (2.5 mL), followed by adding EtMgBr (0.9 mL, 3 M in Et$_2$O, 2.6 mmol) at 25° C. Next, the reaction mixture was stirred at 25° C. for 15 min under N$_2$. The reaction mixture was quenched with saturated aqueous NH$_4$Cl (10 mL) solution and extracted with EtOAc (20 mL×3). The combined organic layer was washed with brine (50 mL), dried over Na$_2$SO$_4$, filtered and concentrated in vacuum to give a crude product. The crude product was purified by silica gel column (EtOAc/PE=5/1) to afford a crude product as a solid, which was purified by re-crystallized from MeCN (5 mL) at 85° C. to give impure product as a solid. The impure sample was further purification by SFC (column: OD(250 mm*30 mm, 10 um)), gradient: 25-25% B (0.1% NH$_3$H$_2$O ETOH), flow rate: 60 mL/min) to give ST-200-6-16_1 (110 mg, 44%).

$^1$H NMR (400 MHz, CDCl$_3$) δ 5.44-5.38 (m, 1H), 5.33-5.28 (m, 1H), 2.29-2.21 (m, 1H), 2.15-1.94 (m, 5H), 1.93-1.79 (m, 3H), 1.78-1.57 (m, 6H), 1.52-1.21 (m, 10H), 1.06-0.98 (m, 3H), 0.92-0.82 (m, 5H), 0.77 (s, 3H), 0.75-0.69 (m, 2H), 0.47-0.39 (m, 2H).

LCMS Rt=1.219 min in 2.0 min chromatography, 30-90AB_2 MIN_E, purity 100%, MS ESI calcd. for C$_{27}$H$_{41}$O [M+H−H$_2$O]$^+$ 381, found 381.

Synthesis of 8245

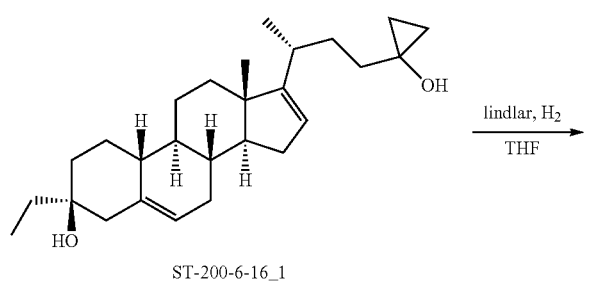

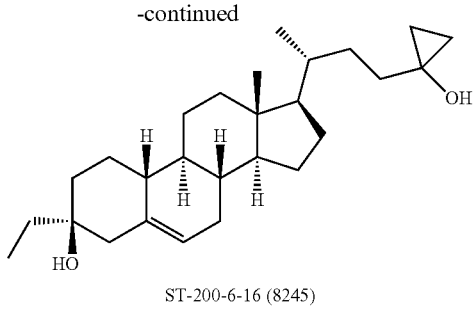

Lindlar catalyst (100 mg) was added to a solution of ST-200-6-16_1 (78 mg, 0.2 mmol) in THF (5 mL) and the mixture was degassed and backed-filled with H$_2$ 3 times. After that, the reaction mixture was stirred at 25° C. for 4 h under H$_2$. The reaction mixture was filtered through a pad of celite washed with THF (100 mL) and concentrated in vacuum to give a crude product, which was re-crystallized from MeCN (5 mL) at 85° C. to give ST-200-6-16 (32 mg, 41%).

$^1$H NMR (400 MHz, CDCl$_3$) δ 5.43-5.34 (m, 1H), 2.27-2.19 (m, 1H), 2.07-1.72 (m, 8H), 1.67-1.59 (m, 3H), 1.55-1.37 (m, 7H), 1.34-0.96 (m, 10H), 0.94-0.91 (m, 3H), 0.89-0.82 (m, 4H), 0.76-0.70 (m, 2H), 0.68 (s, 3H), 0.48-0.37 (m, 2H).

LCMS Rt=1.186 min in 2.0 min chromatography, 30-90AB_2 MIN_E, purity 100%, MS ESI calcd. for C$_{27}$H$_{43}$O [M+H−H$_2$O]$^+$ 383, found 383.

Example 83: Synthesis of 8361, 8378, and 8379

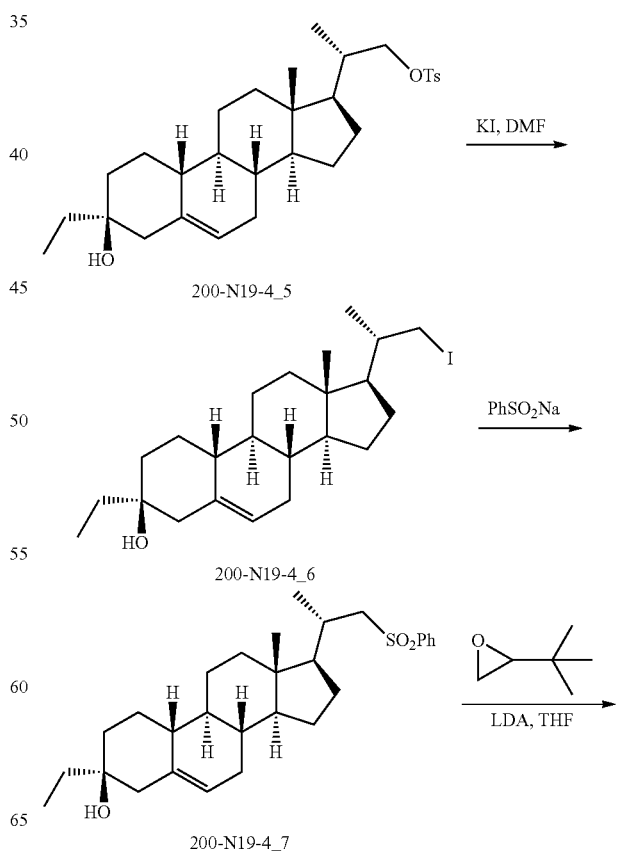

363

-continued

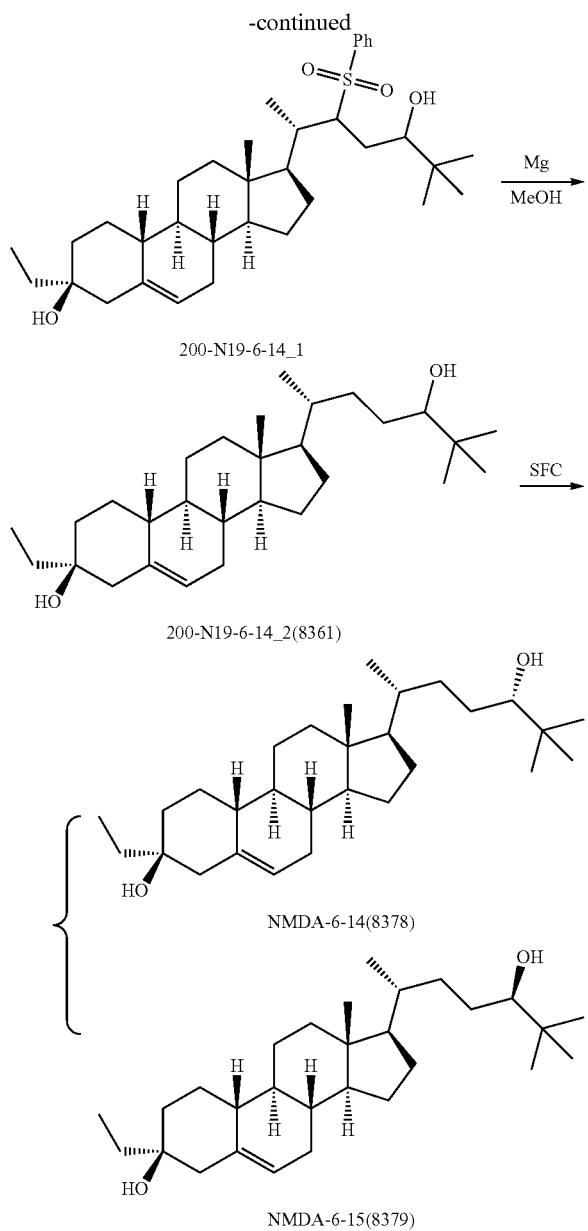

200-N19-6-14_1

200-N19-6-14_2(8361)

NMDA-6-14(8378)

NMDA-6-15(8379)

The synthesis of 200-N19-4_5 can be found in Example 94.

Synthesis of 200-N19-4_6

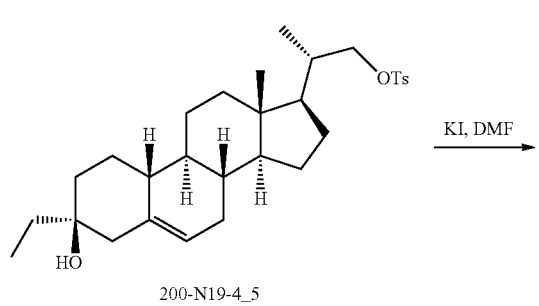

200-N19-4_5

364

-continued

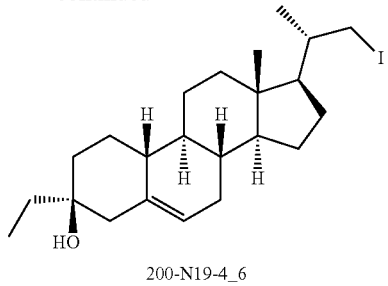

200-N19-4_6

KI (28.0 g, 169 mmol) was added to a solution of 200-N19-4_5 (17 g, 33.9 mmol) in DMF (200 mL) at 25° C. The mixture was stirred at 50° C. for 2 hours. Half of the reaction mixture was poured into water (500 mL). The suspension was extracted with PE (700 mL). The combined organic phase was washed with saturated brine (2×500 mL), dried over anhydrous $Na_2SO_4$, filtered and concentrated to give 200-N19-4_6 (8.5 g, crude) as an oil. The other half of the reaction mixture was used directly for the next step.

$^1$H NMR (400 MHz, $CDCl_3$) δ 5.40-5.35 (m, 1H), 3.35-3.30 (m, 1H), 3.20-3.10 (m, 1H), 2.25-2.15 (m, 1H), 2.05-1.76 (m, 8H), 1.69-1.34 (m, 9H), 1.30-1.13 (m, 7H). 0.92-0.75 (m, 6H). 0.71 (s, 3H).

Synthesis of 200-N19-4_7

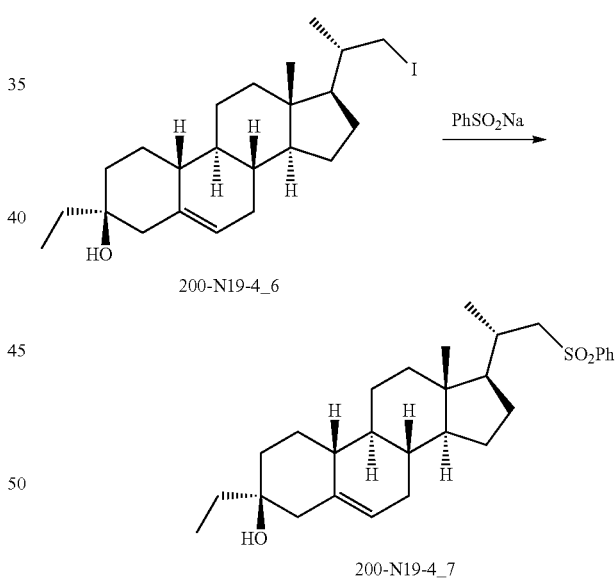

200-N19-4_6

200-N19-4_7

$PhSO_2Na$ (9.15 g, 55.8 mmol) was added to the reaction mixture from the previous step at 25° C. The mixture was stirred at 50° C. for 3 hours. The reaction mixture was poured into water (500 ml) and some solid was produced. The mixture was filtered. The filter cake was washed with water (2×500 ml). The resulting filter cake was dissolved in DCM (500 mL), washed with water (2×500 mL). The combined organic phase was washed with saturated brine (2×500 mL), dried over anhydrous $Na_2SO_4$, filtered and concentrated in vacuum to give 200-N19-4_7 (8.5 g, crude) as a solid, which was re-crystallized from MeCN (50 mL) at reflux (82° C.). After cooling to 25° C., the mixture was filtered and concentrated in vacuum to get 200-N19-4_7 (5 g, 59%) as a solid. Mother liquor filtered and concentrated to give another 2 g of solid.

$^1$H NMR (400 MHz, CDCl$_3$) δ 7.92-7.88 (m, 2H), 7.65-7.53 (m, 3H), 5.38-5.33 (m, 1H), 3.18-3.10 (m, 1H), 2.90-2.80 (m, 1H), 2.25-2.16 (m, 1H), 1.88-1.60 (m, 9H), 1.59-1.35 (m, 5H), 1.29-1.05 (m, 11H), 0.88-0.77 (m, 5H), 0.65 (s, 3H).

Synthesis of 200-N19-6-14_1

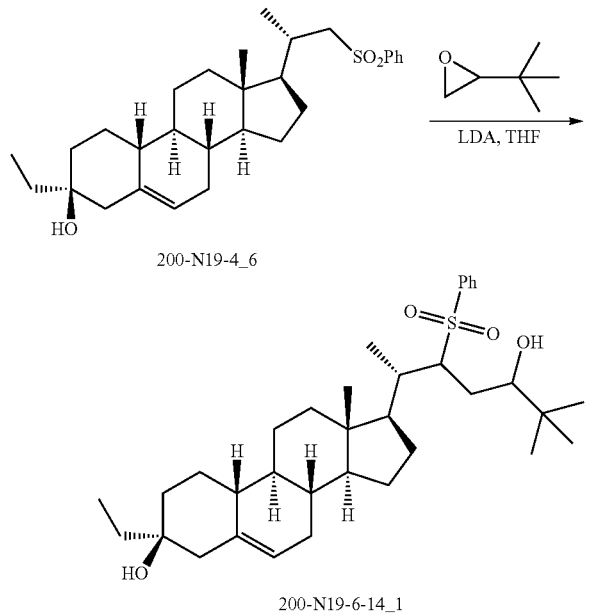

Synthesis of 200-N19-6-14_2 (8361)

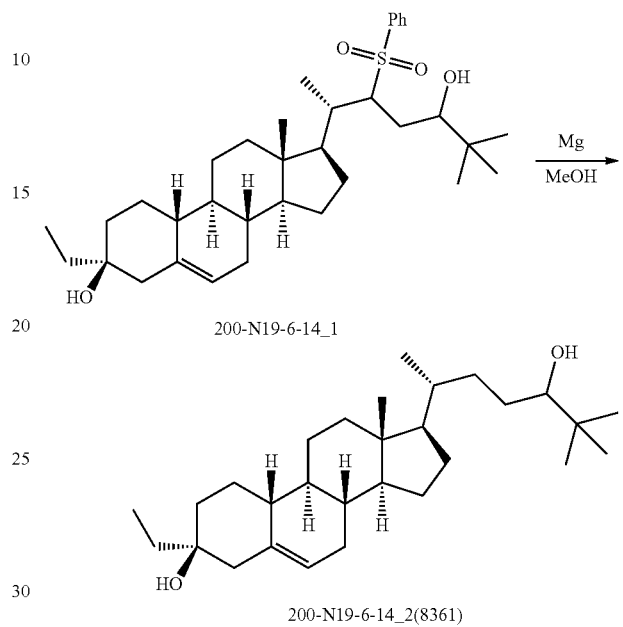

n-BuLi (2 mL, 2.5 M, 5.08 mmol) was added to a solution of diisopropylamine (0.73 mL, 5.08 mmol) in THF (1 mL) under N$_2$ at −70° C. The resulting mixture was warmed to 25° C. and stirred at 25° C. for 30 min. After re-cooling to −70° C., a solution of 200-N19-4_6 (0.6 g, 1.27 mmol) in THF (3 mL) was added at −70° C. The reaction mixture was stirred at −70° C. for 1 hour. 2-(tert-butyl)oxirane (152 mg, 1.52 mmol) was added at −70° C. The reaction mixture was warmed to 25° C. and stirred at 25° C. for 18 hours. The reaction mixture was quenched with saturated NH$_4$Cl aqueous (10 mL) at 0° C., extracted with EtOAc (2×10 mL). The combined organic phase was washed with brine (2×10 mL), dried over Na$_2$SO$_4$, filtered and concentrated under vacuum to give a crude product, which was purified by flash column (0~30% of PE in EtOAc, 50 mins) to give 200-N19-6-14_1 (550 mg) as a solid, which was used directly for the next step.

Mg (1.16 g, powder) was added to a solution of 200-N19-6-14_1 (550 mg, crude) in MeOH (40 mL) at 65° C. The mixture was stirred at 65° C. for 3 hours and quenched by adding HCl (50 mL, 2 M in water). The mixture was extracted with EtOAc (2×50 mL). The organic layers were washed with water (2×100 mL), sat. NaHCO$_3$ (2×100 mL), brine (2×80 mL), dried over Na$_2$SO$_4$, filtered and concentrated to give a crude product, which was purified by flash column (0=20% of PE in EtOAc, 60 mins) to give 200-N19-6-14_2 (190 mg) as a solid. 200-N19-6-14_2 (45 mg) was re-crystallized from MeCN at 70° C. to give 200-N19-6-14_2 (35 mg) as a a solid.

$^1$H NMR (400 MHz, CDCl$_3$) δ 5.45-5.30 (m, 1H), 3.40-3.00 (m, 1H), 2.30-2.15 (m, 1H), 2.10-1.60 (m, 9H), 1.55-1.40 (m, 6H), 1.25-1.00 (m, 11H), 0.95-0.75 (m, 18H), 0.68 (s, 3H).

LCMS Rt=1.338 min in 2 min chromatography, 30-90AB_E, purity 98%, MS ESI calcd. For C$_{29}$H$_{49}$O [M+H−H$_2$O]$^+$ 413.

Synthesis of 8378 and 8379

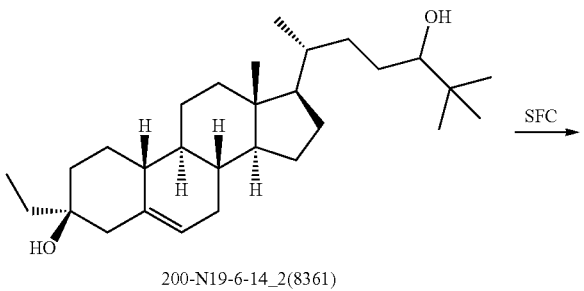

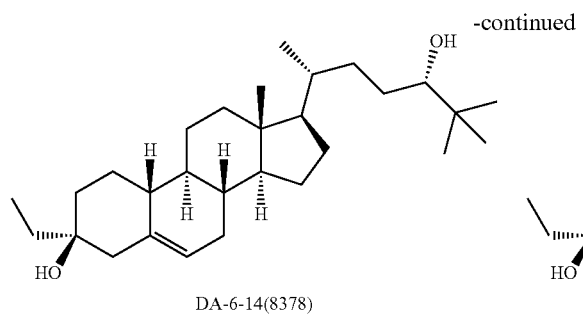

DA-6-14(8378)

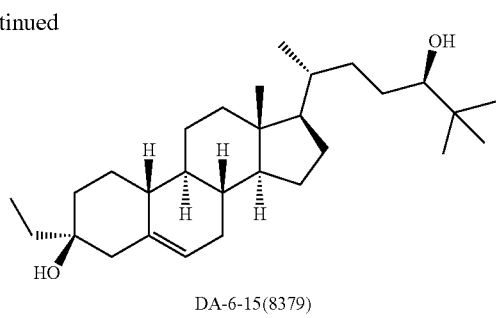

DA-6-15(8379)

200-N19-6-14_2 (145 mg) was separated by SFC (Column: AD (250 mm*30 mm, 10 um); Condition: 0.1% NH₃H₂O ETOH, 40% B; FlowRate(ml/min): 60) to give impure DA-6-14 (70 mg) and impure DA-6-15 (60 mg) both as a solid. The impure DA-6-15 (60 mg) was triturated with MeCN (5 mL) at 25° C. to give DA-6-15 (27 mg, pure) as a solid. The impure DA-6-14 (70 mg) was triturated with MeCN (5 mL) at 25° C. to give DA-6-14 (27 mg, pure) as a solid.

8378:
$^1$H NMR (400 MHz, CDCl₃) δ 5.45-5.30 (m, 1H), 3.40-3.00 (m, 1H), 2.30-2.15 (m, 1H), 2.10-1.60 (m, 10H), 1.55-1.40 (m, 5H), 1.25-1.00 (m, 11H), 0.95-0.75 (m, 18H), 0.68 (s, 3H).

LCMS Rt=1.334 min in 2 min chromatography, 30-90AB_E, purity 100%, MS ESI calcd. For $C_{29}H_{47}$ [M+H–2H₂O]⁺ 395.

$^1$H NMR (400 MHz, CDCl₃) δ 5.45-5.30 (m, 1H), 3.40-3.25 (m, 1H), 2.25-2.15 (m, 1H), 2.05-1.75 (m, 7H), 1.70-1.60 (m, 2H), 1.50-1.30 (m, 8H), 1.20-1.05 (m, 11H), 1.00-0.75 (m, 16H), 0.68 (s, 3H).

LCMS Rt=1.327 min in 2 min chromatography, 30-90AB_E, purity 99%, MS ESI calcd. For $C_{28}H_{47}$ [M+H–2H₂O]⁺ 395.

Synthesis of 8378 to Determine Stereochemistry

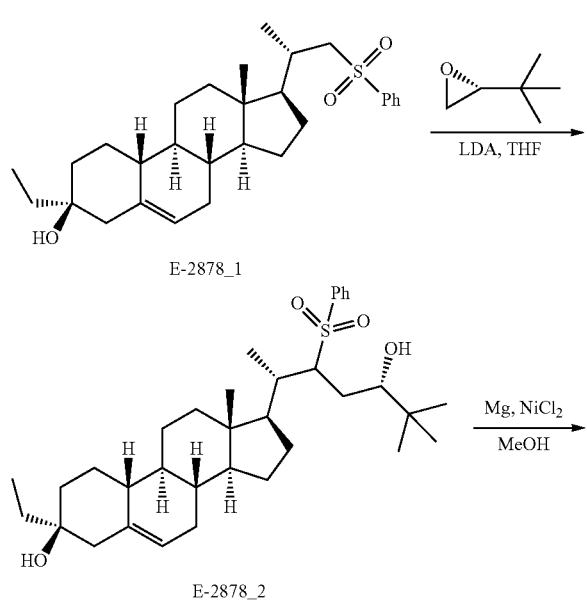

DA ST-200-094-007 (8378)

To a solution of diisopropylamine (0.262 mL, 1.82 mmol) in THF (0.5 mL) under N₂ at –78° C. was added n-BuLi (0.676 mL, 2.5 M, 1.69 mmol). The resulting mixture was warmed to 0° C. and stirred at 0° C. for 10 mins. After re-cooling to –78° C., a solution of E-2878_1 (200 mg, 0.425 mmol) in THF (1.5 mL) was added at –78° C. The reaction mixture was stirred at –78° C. for 1 hr. (R)-2-(tert-butyl)oxirane (51.0 mg, 0.510 mmol) was added at –78° C. The reaction mixture was warmed to 25° C. and stirred at 25° C. for 16 hrs. The reaction mixture was quenched with saturated NH₄Cl aqueous (10 mL) at 0° C., extracted with EtOAc (2×10 mL). The combined organic phase was washed with brine (2×10 mL), dried over Na₂SO₄, filtered and concentrated under vacuum to give E-2878_2 (250 mg, crude) as a solid, which was used directly for the next step.

To a solution of E-2878_2 (250 mg, crude) in MeOH (30 mL) was added Mg powder (840 mg, 35.0 mmol) and NiCl₂ (20 mg) at 60° C. The mixture was stirred at 60° C. for 5 hrs. The reaction was quenched by HCl (50 mL, 2 M in water). The mixture was extracted with EtOAc (2×50 mL). The organic layers were washed with water (2×100 mL), sat. NaHCO₃ (2×100 mL), brine (2×80 mL), dried over Na₂SO₄, filtered and concentrated to give crude product which was purified by flash column (0~20% of EtOAc in PE) to give ST-200-094-007 (100 mg, 53%, impure, 96% de) as a solid. The impure product was re-purified by SFC separation (column: AD (250 mm*30 mm, 5 um), condition: 0.1% NH₃H₂O EtOH, Begin B: 40%, End B: 40%) to give ST-200-094-007 (70 mg, 100% de, impure) as a solid. The ST-200-094-007 (70 mg) was purified by recrystallization (n-BuOH/H₂O=4/1) to give ST-200-094-007 (9 mg, pure,) as a solid and ST-200-094-007 (60 mg, impure) as a solid.

$^1$H NMR (400 MHz, CDCl₃) δ 5.45-5.30 (m, 1H), 3.40-3.00 (m, 1H), 2.30-2.15 (m, 1H), 2.10-1.60 (m, 10H), 1.55-1.40 (m, 5H), 1.25-1.00 (m, 11H), 0.95-0.92 (m, 4H), 0.90 (s, 9H), 0.88-0.82 (m, 5H), 0.68 (s, 3H).

LCMS Rt=1.334 min in 2 min chromatography, 30-90AB_2 MIN_E, purity 100%, MS ESI calcd. for $C_{29}H_{47}$ [M+H–2H₂O]⁺ 395, found 395.

SFC Rt=5.182 min in 10 min chromatography, AD_3_EtOH_DEA_5_40_25ML, 100% de.

Example 84: Synthesis of 8462 and 8463

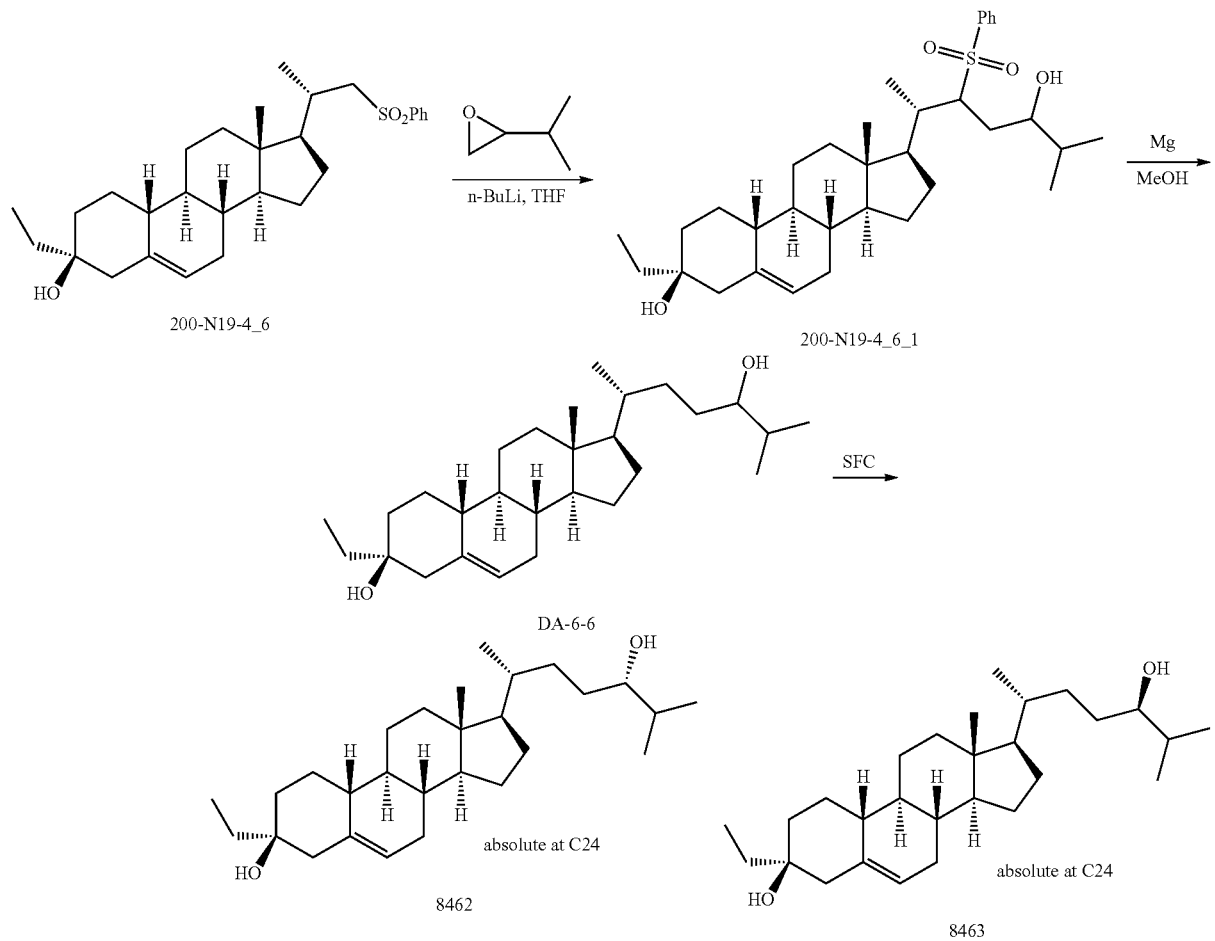

The synthesis of 200-N19-4_6 can be found in Example 83.

During the synthesis of 8462 from chiral epoxide, 8462 was proved to be S-configuration at C24 and 8463 was proved to be R-configuration at C24. See below.

Synthesis of 200-N19-4_6_1

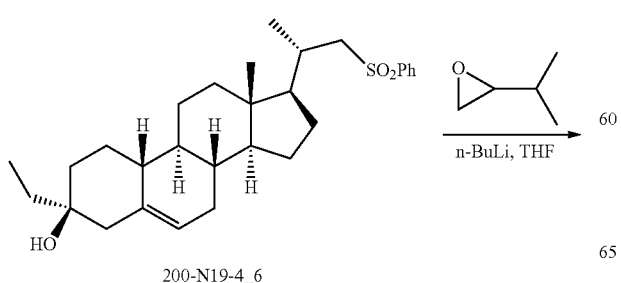

-continued

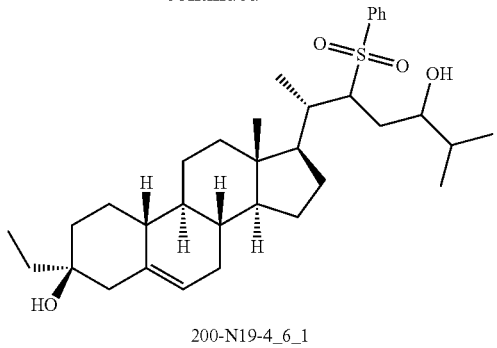

To THF (5 mL) under N₂ at −70° C. was added n-BuLi (4.23 mL, 2.5 M in n-hexane, 10.6 mmol). To the mixture was added dropwise a solution of ST-200-N19-4_6 (2 g, 4.24 mmol) in THF (15 mL) at −70° C. The reaction mixture was stirred at −70° C. for 1 hour. 2-isopropyloxirane (437 mg, 5.08 mmol) was added at −70° C. The reaction mixture was warmed to 25° C. slowly and stirred at 25° C. for 16 hours. The reaction mixture was quenched with saturated NH₄Cl aqueous (50 mL). The mixture was extracted with EtOAc (2×30 mL). The combined organic phase was washed with brine (2×30 mL), dried over Na₂SO₄, filtered and concentrated under vacuum to give st-200-N19-4_6_1 (2 g, crude) as an oil, which was used for the next step directly.

Synthesis of DA-6-6

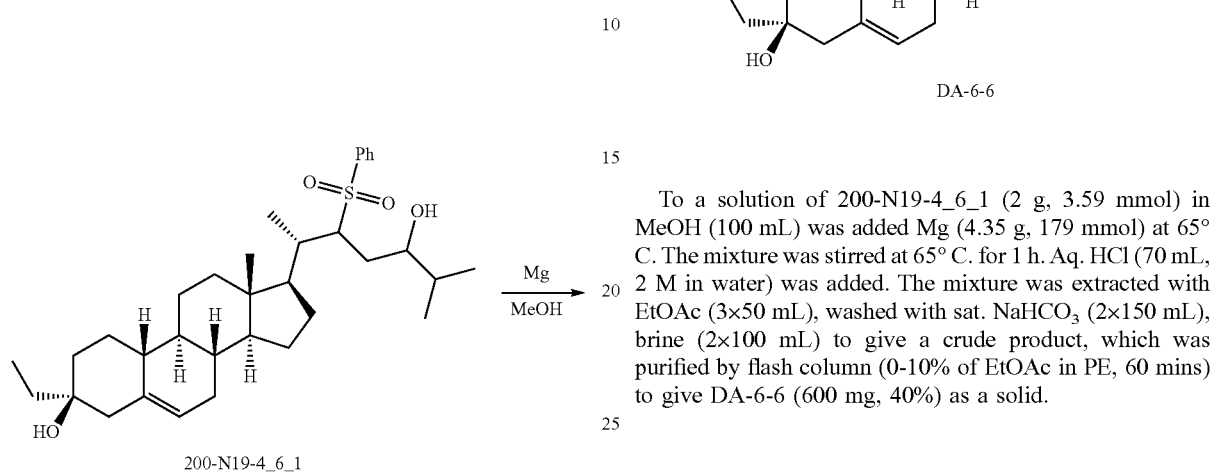

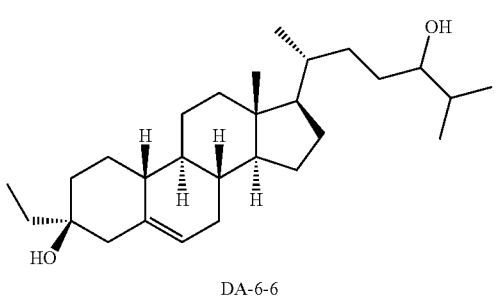

To a solution of 200-N19-4_6_1 (2 g, 3.59 mmol) in MeOH (100 mL) was added Mg (4.35 g, 179 mmol) at 65° C. The mixture was stirred at 65° C. for 1 h. Aq. HCl (70 mL, 2 M in water) was added. The mixture was extracted with EtOAc (3×50 mL), washed with sat. NaHCO₃ (2×150 mL), brine (2×100 mL) to give a crude product, which was purified by flash column (0-10% of EtOAc in PE, 60 mins) to give DA-6-6 (600 mg, 40%) as a solid.

Synthesis of 8462 and 8463

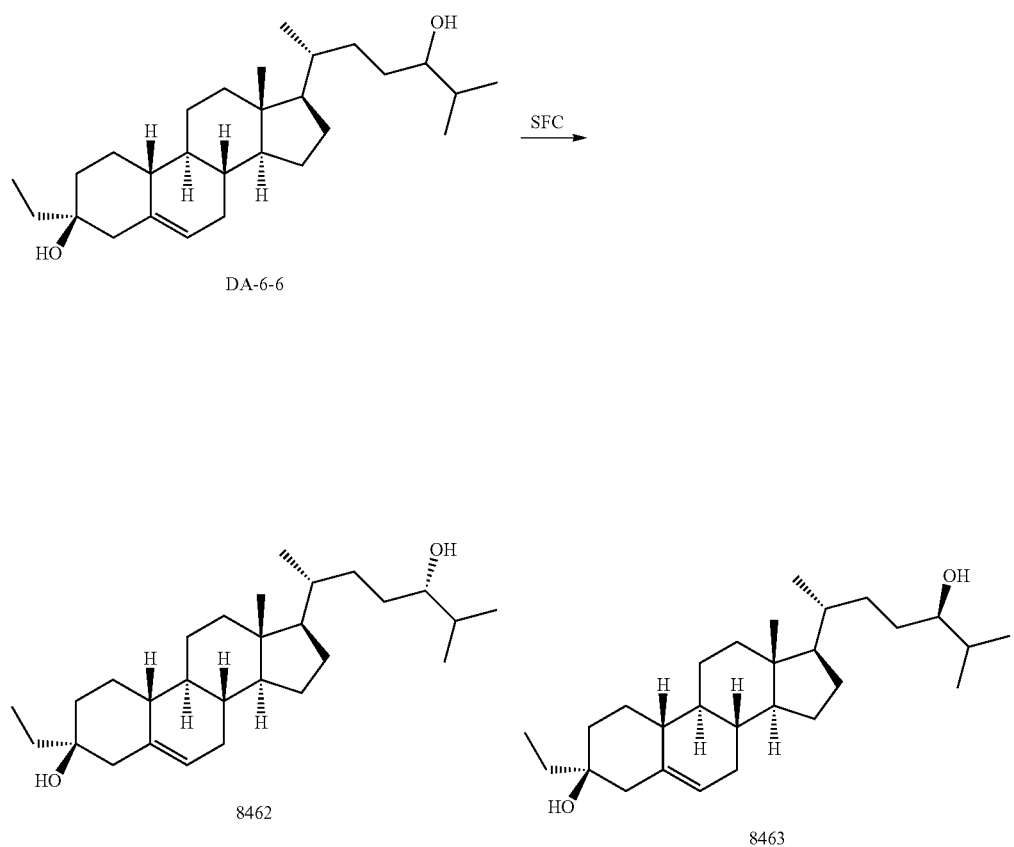

DA-6-6 (600 mg) was separated by SFC (Column: AD(250 mm*30 mm, 10 um); Condition: 0.1% NH$_3$H$_2$O ETOH, 40% B; FlowRate(ml/min): 60) to give 8462 (152 mg, 25%) and 8463 (137 mg, 23%) as a solid.

8462

$^1$H NMR (400 MHz, CDCl$_3$) δ 5.42-5.35 (m, 1H), 3.37-3.25 (m, 1H), 2.27-2.19 (m, 1H), 2.08-1.87 (m, 4H), 1.86-1.75 (m, 3H), 1.71-1.58 (m, 3H), 1.52-1.35 (m, 6H), 1.34-1.17 (m, 7H), 1.16-0.97 (m, 5H), 0.97-0.90 (m, 8H), 0.89-0.82 (m, 5H), 0.81-0.75 (m, 1H), 0.68 (s, 3H).

LCMS Rt=1.285 min in 2.0 min chromatography, 30-90AB_E, purity 100%, MS ESI calcd. for C$_{28}$H$_{47}$O [M+H–H$_2$O]$^+$ 399, found 399.

8463

$^1$H NMR (400 MHz, CDCl$_3$) δ 5.41-5.35 (m, 1H), 3.37-3.25 (m, 1H), 2.27-2.19 (m, 1H), 2.07-1.93 (m, 3H), 1.90-1.78 (m, 3H), 1.63-1.50 (m, 5H), 1.48-1.34 (m, 7H), 1.33-1.15 (m, 7H), 1.14-0.98 (m, 3H), 0.98-0.89 (m, 9H), 0.88-0.82 (m, 4H), 0.81-0.75 (m, 1H), 0.68 (s, 3H).

LCMS Rt=1.278 min in 2.0 min chromatography, 30-90AB_E, purity 100%, MS ESI calcd. for C$_{28}$H$_{47}$O [M+H–H$_2$O]$^+$ 399, found 399.

Synthesis to Confirm Stereochemistry

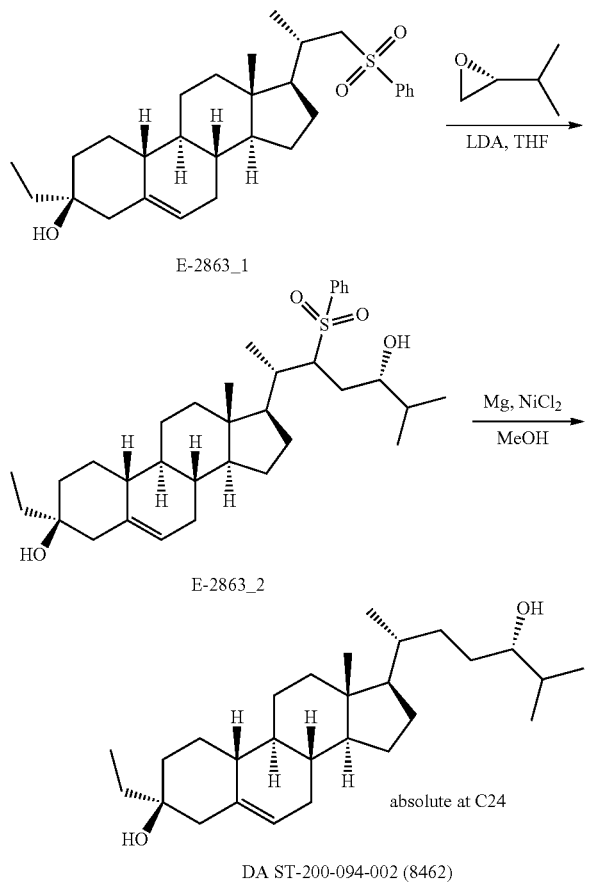

To THF (0.5 mL) was added n-BuLi (2.5 M, 2.12 mmol, 0.848 mL) under N$_2$ at −70° C. After that, a suspension of E-2863_1 (400 mg, 0.849 mmol) in THF (3 mL) was added dropwise to give a suspension. After stirring at −70° C. for 30 min, a solution of (2R)-2-(propan-2-yl)oxirane (86.9 mg, 1.01 mmol) in THF (0.5 mL) was added. The reaction was stirred at stirred at 25° C. for 16 hours. The mixture was poured into ice-water (20 mL) and extracted with EA (2×30 mL). The combined organic layers were washed with brine (50 mL), dried over Na$_2$SO$_4$, filtered and concentrated in vacuum to afford E-2863_2 (430 mg, crude) as a solid, which was used directly for the next step.

To a solution of E-2863_2 (430 mg, 0.772 mmol) and nickel (II) chloride (5 mg, 0.0386 mmol) in MeOH (30 mL) was added Mg powder (369 mg, 15.4 mmol) at 25° C. The mixture was stirred at 50° C. for 1 h. After cooling, the mixture was quenched with HCl (100 mL, 2M) until the reaction became clear and extracted with EtOAc (2×50 mL). The combined organic phase was dried over Na$_2$SO$_4$, filtered, concentrated and purified by a silica gel column (PE/EtOAc=10/1 to 3/1) to give DA ST-200-094-002 (160 mg, 50%) as a solid, which was separated by SFC (column: AD (250 mm*30 mm, Sum)), gradient: 40-40% B (A=0.1% NH$_3$H$_2$O ETOH), flow rate: 50 mL/min) to give DA ST-200-094-002 (85 mg, 53%, 50 mg for delivery) as a solid.

$^1$HNMR (400 MHz, CDCl$_3$) δ 5.42-5.38 (m, 1H), 3.35-3.26 (m, 1H), 2.25-2.21 (m, 1H), 2.07-1.77 (m, 7H), 1.70-1.59 (m, 3H), 1.54-1.36 (m, 7H), 1.32-0.99 (m, 11H), 0.96-0.75 (m, 14H), 0.68 (s, 3H).

LCMS Rt=1.291 min in 2.0 min chromatography, 30-90 AB, purity 100%, MS ESI calcd. For C$_{28}$H$_{47}$O [M–H$_2$O+H]=399, found 399.

Example 85: Synthesis of 8564, 8584, and 8585

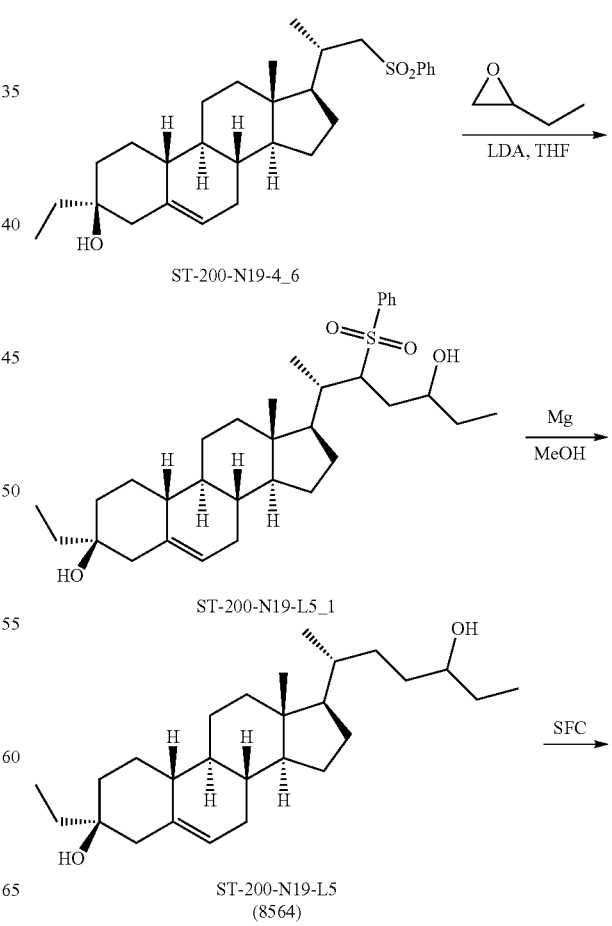

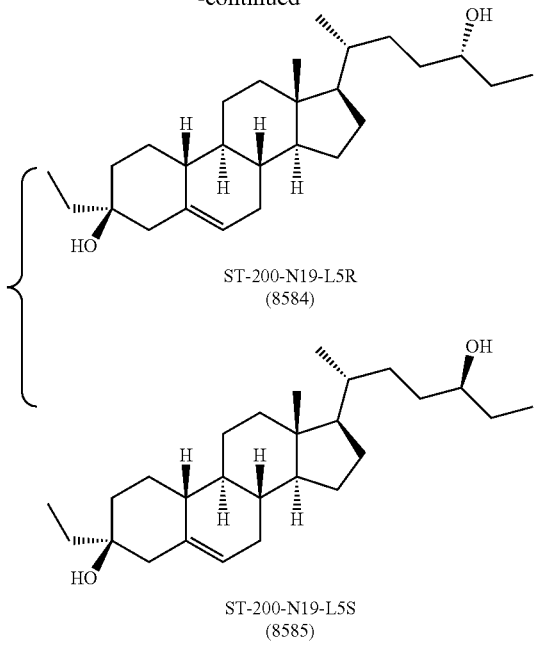

ST-200-N19-L5R
(8584)

ST-200-N19-L5S
(8585)

The experimental of intermediate ST-200-N19-4_6 can be found in Example 83.

Synthesis of ST-200-N19-L5_1

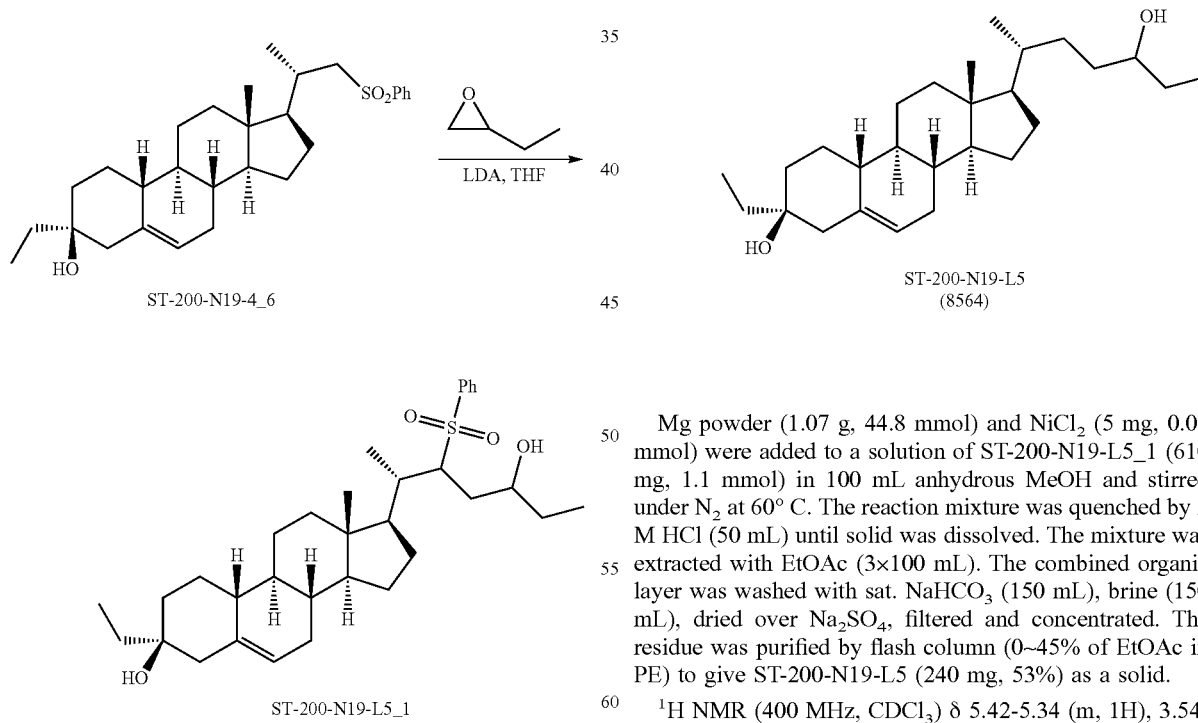

ST-200-N19-4_6

ST-200-N19-L5_1

A suspension of ST-200-N19-4_6 (500 mg, 1.06 mmol) in THF (4 mL) was added dropwise to a solution of n-BuLi (1.05 mL, 2.5 M in hexane, 2.65 mmol) in THF (1 mL) at −70° C. under $N_2$. After stirring for 30 minutes at −70° C., a solution of diisopropylamine (267 mg, 2.65 mmol) was added dropwise at −70° C., followed by adding a solution of 2-ethyloxirane (114 mg, 1.59 mmol) dropwise at −70° C. The mixture was stirred at −70° C. for another 30 min and then warmed to 25° C. gradually. The reaction mixture was stirred at 25° C. for 24 hours, quenched by saturated $NH_4Cl$ aqueous (5 mL), extracted with EtOAc (3×10 mL). The combined organic phase was washed with brine (30 mL), dried over $Na_2SO_4$, filtered and concentrated under vacuum to give ST-200-N19-L5_1 (610 mg, crude) as a solid, which was used directly.

Synthesis of ST-200-N19-L5

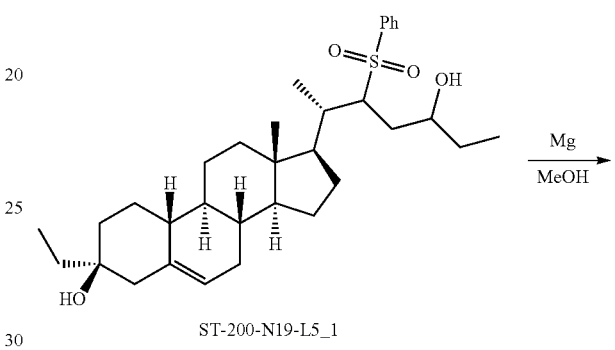

ST-200-N19-L5_1

ST-200-N19-L5
(8564)

Mg powder (1.07 g, 44.8 mmol) and $NiCl_2$ (5 mg, 0.05 mmol) were added to a solution of ST-200-N19-L5_1 (610 mg, 1.1 mmol) in 100 mL anhydrous MeOH and stirred under $N_2$ at 60° C. The reaction mixture was quenched by 2 M HCl (50 mL) until solid was dissolved. The mixture was extracted with EtOAc (3×100 mL). The combined organic layer was washed with sat. $NaHCO_3$ (150 mL), brine (150 mL), dried over $Na_2SO_4$, filtered and concentrated. The residue was purified by flash column (0~45% of EtOAc in PE) to give ST-200-N19-L5 (240 mg, 53%) as a solid.

$^1$H NMR (400 MHz, $CDCl_3$) δ 5.42-5.34 (m, 1H), 3.54-3.42 (m, 1H), 2.28-2.18 (m, 1H), 2.08-1.61 (m, 8H), 1.55-1.36 (m, 10H), 1.34-0.98 (m, 11H), 0.97-0.73 (m, 11H), 0.71-0.63 (m, 3H).

LCMS Rt=1.349 min in 2.0 min chromatography, 30-90AB_2 MIN_E, purity 100%, MS ESI calcd. for $C_{27}H_{45}O$ $[M+H-H_2O]^+$ 385, found 385.

377
Synthesis of ST-200-N19-L5R & ST-200-N19-L5S

378
Synthesis to Determine Stereochemistry (8584 and 9142)

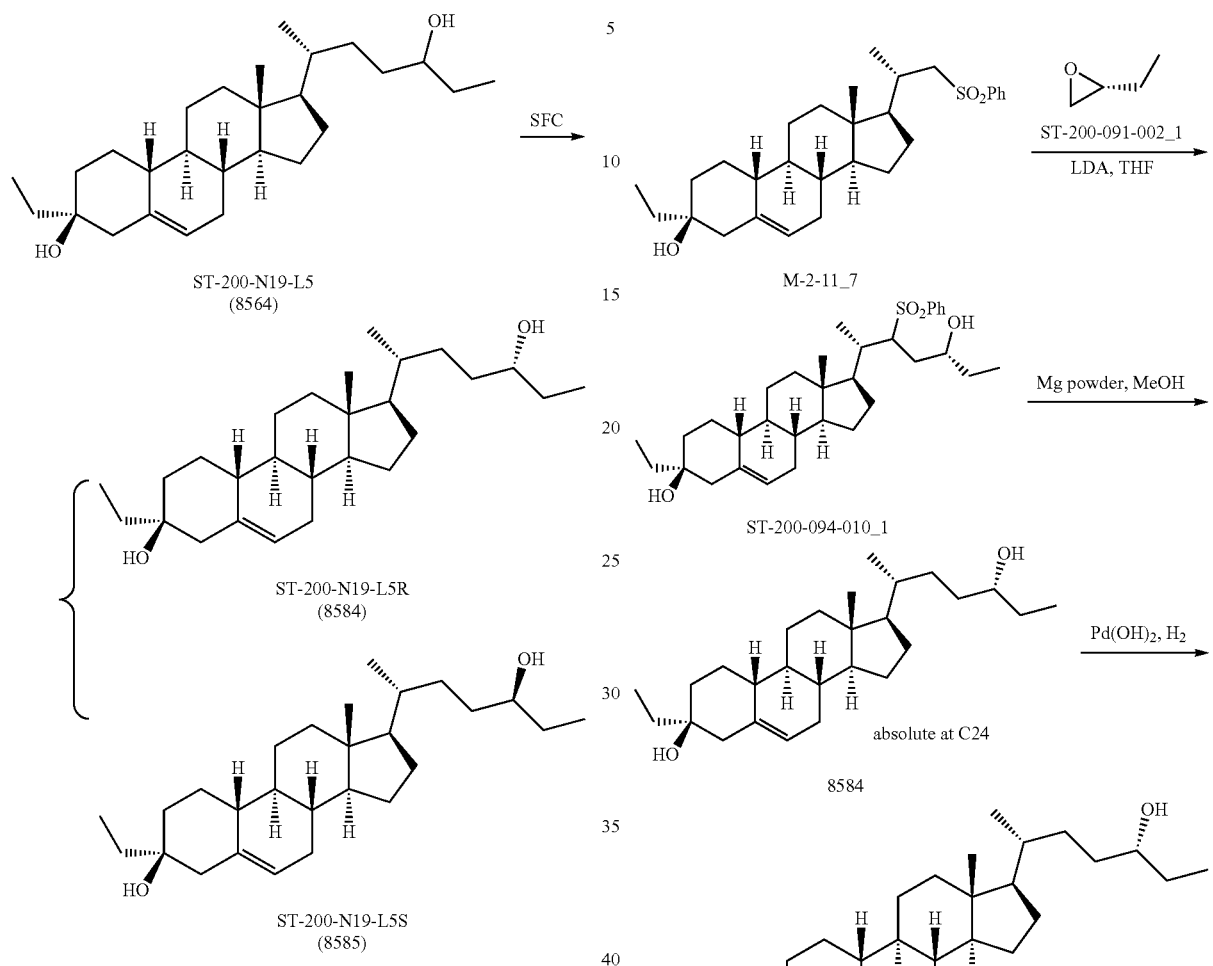

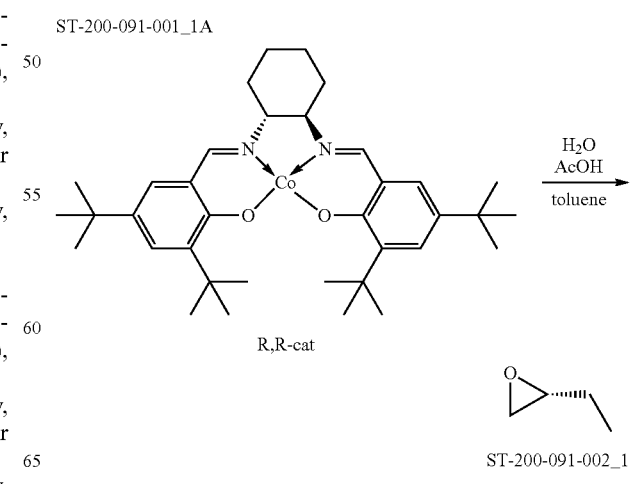

ST-200-N19-L5 (208 mg, 0.52 mmol) was purified by SFC (column: AD (250 mm*30 mm, 10 um)), gradient: 40-40% B (A=0.1% NH$_3$/H$_2$O, B=EtOH), flow rate: 60 mL/min) to give ST-200-N19-L5R (80 mg, 38%) and ST-200-N19-L5S (70 mg, 33%) as a solid.

8584
$^1$H NMR (400 MHz, CDCl$_3$) δ 5.42-5.36 (m, 1H), 3.52-3.41 (m, 1H), 2.27-2.19 (m, 1H), 2.07-1.77 (m, 7H), 1.67-1.56 (m, 2H), 1.54-1.38 (m, 8H), 1.33-0.98 (m, 12H), 0.97-0.90 (m, 6H), 0.88-0.79 (m, 5H), 0.68 (s, 3H).
LCMS Rt=1.353 min in 2 min chromatography, 30-90AB_2 MIN_E, purity 100%, MS ESI calcd. for C$_{27}$H$_{45}$O [M+H−H$_2$O]$^+$ 385, found 385.
SFC Rt=5.762 min in 10 min chromatography, AD_3_EtOH_DEA_5_40_25ML, purity: 100%.

8585
$^1$H NMR (400 MHz, CDCl$_3$) δ 5.42-5.36 (m, 1H), 3.53-3.43 (m, 1H), 2.27-2.19 (m, 1H), 2.08-1.77 (m, 7H), 1.68-1.56 (m, 2H), 1.54-1.32 (m, 10H), 1.29-0.97 (m, 10H), 0.97-0.89 (m, 6H), 0.88-0.74 (m, 5H), 0.68 (s, 3H).
LCMS Rt=1.353 min in 2 min chromatography, 30-90AB_2 MIN_E, purity 100%, MS ESI calcd. for C$_{27}$H$_{45}$O [M+H−H$_2$O]$^+$ 385, found 385.
SFC Rt=6.041 min in 10 min chromatography, AD_3_EtOH_DEA_5_4025ML, purity: 95%.

To a solution of M-2-11_7 (400 mg, 0.849 mmol) in anhydrous THF (3 mL) was added n-BuLi (1.01 mL, 2.54 mmol, 2.5 M in n-hexane) drop-wise at −70° C. under $N_2$. After stirring at −70° C. for 30 mins, a solution of (R)-2-ethyloxirane (91.5 mg, 1.27 mmol) in anhydrous THF (0.5 mL) was added drop-wise at −70° C. The reaction mixture was stirred at −70° C. for another 1 h and then stirred at 25° C. (room temperature) for 12 h. After heating at 60° C. for 2 h, the reaction was quenched by saturated aqueous $NH_4Cl$ (50 mL). The aqueous phase was extracted with EtOAc (3×50 mL). The combine organic phase was washed with saturated brine (2×50 mL). dried over anhydrous $Na_2SO_4$. filtered and concentrated in vacuum to give ST-200-94-10_1 (0.4 g, crude) as an oil, which was used directly of the next step.

To a solution of ST-200-094-010_1 (0.4 g, crude) in MeOH (50 mL) was added Mg powder (883 mg, 36.8 mmol) and $NiCl_2$ (20 mg) at 25° C. under $N_2$. After stirring at 60° C. for 1 h, the reaction mixture was quenched with HCl (100 mL, 1 M) until the reaction became clear. The aqueous phase was extracted with EtOAc (3×80 mL). The combined organic phase was washed with saturated $NaHCO_3$.aq (2×50 mL), washed saturated brine (2×50 mL), dried over anhydrous $Na_2SO_4$, filtered and concentrated. The residue was purified by silica gel chromatography (PE/EtOAc=10/1 to 8/1) to afford 8584 (180 mg, 61%) as a solid.

The ST-200-094-010 (180 mg, 0.447 mmol) was purified by SFC (Column:AD(250 mm*30 mm, 5 um), Condition: 0.1% $NH_3H_2O$ IPA, Begin B:40%, End B:40%) to afford 8584 (120 mg, 67%) as a solid.

$^1$H NMR (400 MHz, $CDCl_3$) $\delta_H$ 5.40-5.37 (m, 1H), 3.48-3.46 (m, 1H), 2.25-2.21 (m, 1H), 2.05-1.74 (m, 7H), 1.65-1.40 (m, 13H), 1.38-1.07 (m, 11H), 1.06-0.96 (m, 6H), 0.85 (s, 3H), 0.68 (s, 3H).

LCMS=1.277 min in 2 min chromatography, 30-90AB_2MIN_E, purity 100%, MS ESI calcd. for $C_{27}H_{45}O$ $[M+H-H_2O]^+$ 385, found 385.

SFC Rt=5.736 min in 10 min chromatography, AD_3_EtOH_DEA_5_4025ML, 99.5% de.

A solution of 8584 (88 mg, 0.2185 mmol) and $Pd(OH)_2$ (80 mg) in MeOH (10 mL) was hydrogenated under 50 psi of hydrogen at 50° C. for 12 hours. The reaction mixture was filtered through a pad of celite and the filter cake was washed with THF (3×100 mL). The filter liquor was concentrated in vacuum. The residue was purified by flash column (10~25% of EtOAc in PE) to give 9142 (27 mg, 31%) as a solid.

$^1$H NMR (400 MHz, $CDCl_3$) $\delta_H$ 3.50-3.41 (m, 1H), 1.99-1.91 (m, 1H), 1.87-1.74 (m, 3H), 1.70-1.60 (m, 3H), 1.53-1.19 (m, 12H), 1.18-0.97 (m, 11H), 0.96-0.78 (m, 12H), 0.75-0.54 (m, 5H).

LCMS Rt=1.292 min in 2 min chromatography, 30-90AB_2 MIN_E, purity 100%, MS ESI calcd. for $C_{27}H_{45}$ $[M+H-2H_2O]^+$ 369, found 369.

Example 86: Synthesis of 8689, 8602, and 8603

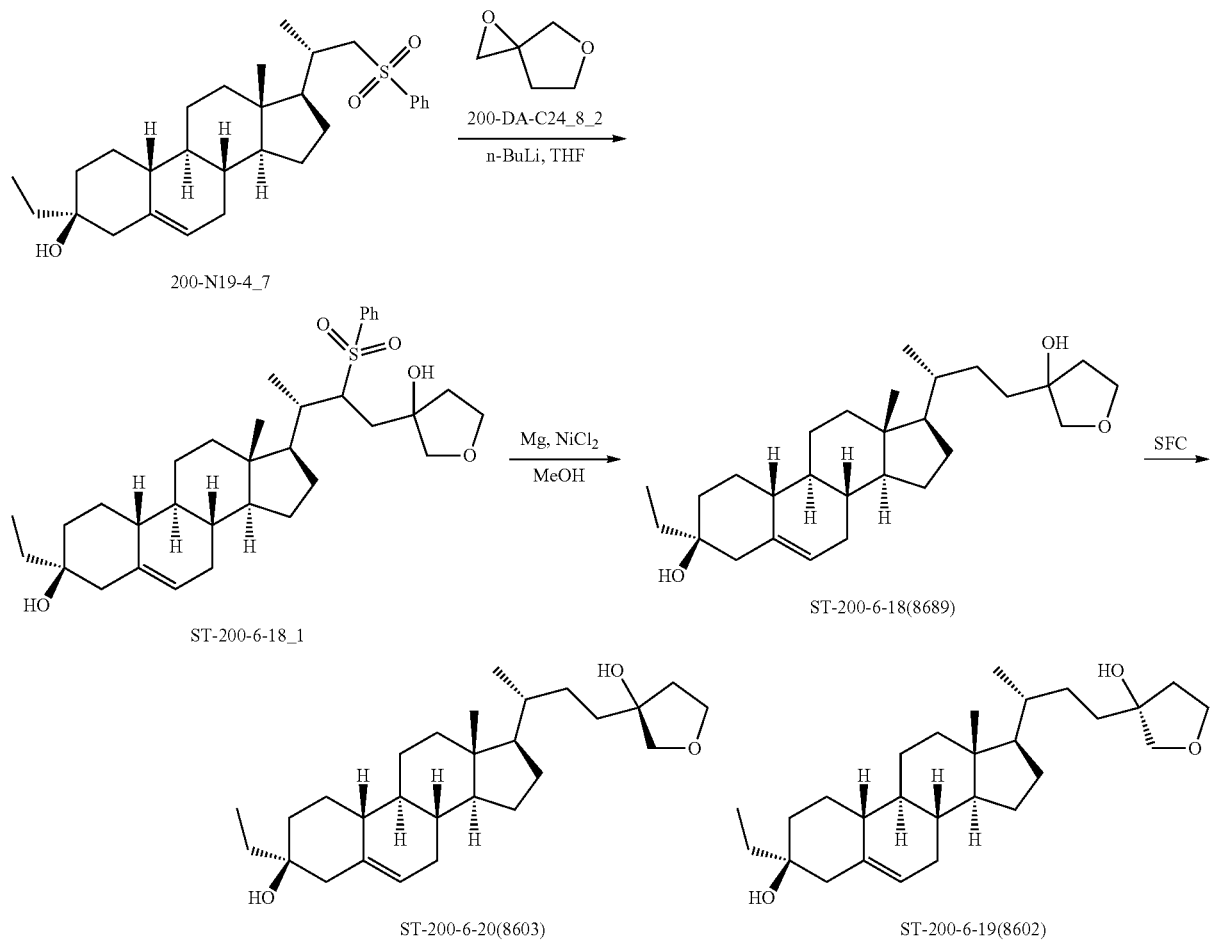

The experimental of intermediate 200-DA-C24_8_2 can be found in Example 15 and the synthesis of 200-N19-4_7 can be found in Example 83.

Synthesis of ST-200-6-18_1

Synthesis of ST-200-6-18

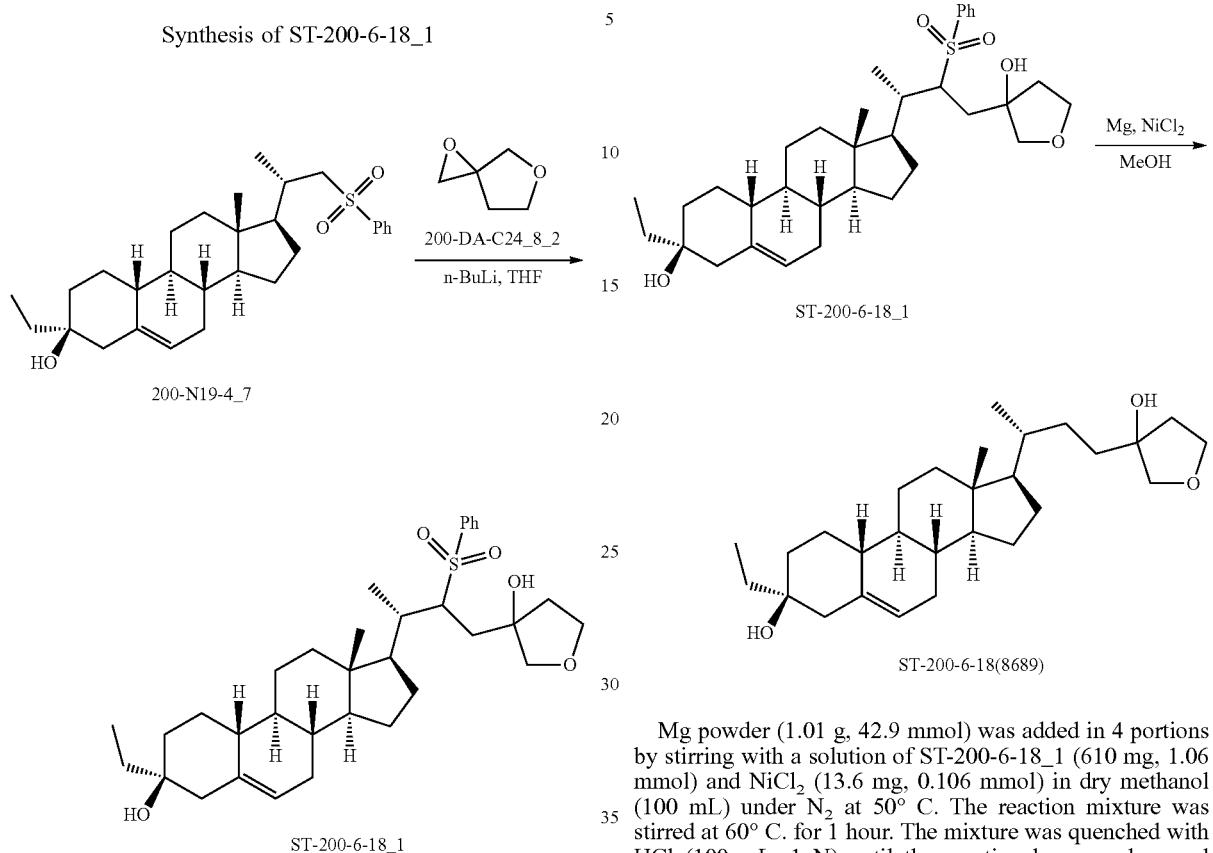

A suspension of 200-N19-4_7 (600 mg, 1.29 mmol) in THF (8 mL) was added dropwise to a solution of n-BuLi (1.54 mL, 2.5 M in hexane, 3.87 mmol) in THF (2 mL) at −65° C. under $N_2$. The mixture was stirred for 30 minutes at −65° C. Next, diisopropylamine (390 mg, 3.87 mmol) was added at −65° C., followed by adding 200-DA-C24_8_2 (387 mg, 3.87 mmol) dropwise at −65° C. The mixture was stirred for another 30 minutes and then warmed to 25° C. gradually and stirred at 25° C. for 16 hours. The reaction was quenched with saturated $NH_4Cl$ aq. (50 mL), extracted with EtOAc (3×50 mL). The combined organic layers were dried over $Na_2SO_4$, concentrated and to give ST-200-6-18_1 (610 mg, crude) as an oil, which was used directly for the next step.

Mg powder (1.01 g, 42.9 mmol) was added in 4 portions by stirring with a solution of ST-200-6-18_1 (610 mg, 1.06 mmol) and $NiCl_2$ (13.6 mg, 0.106 mmol) in dry methanol (100 mL) under $N_2$ at 50° C. The reaction mixture was stirred at 60° C. for 1 hour. The mixture was quenched with HCl (100 mL, 1 N) until the reaction became clear and extracted with EtOAc (3×50 mL). The combined organic phase was dried over $Na_2SO_4$, filtered, concentrated. The residue was purified by flash column (0-30% of EtOAc in PE) to give 140 mg of product as a solid and 100 mg of impure product as a solid. The 140 mg product (0.325 mmol) was re-crystallized triturated from MeCN (10 mL) at 82° C. to give ST-200-6-18 (80 mg) as a solid.

$^1$H NMR (400 MHz, CDCl$_3$) δ 5.40-5.35 (m, 1H), 4.05-3.95 (m, 1H), 3.95-3.83 (m, 1H), 3.72-3.62 (m, 1H), 3.55-3.45 (m, 1H), 2.50-2.40 (m, 1H), 2.05-1.55 (m, 13H), 1.50-1.32 (m, 7H), 1.32-1.03 (m, 9H), 1.03-0.75 (m, 8H), 0.68 (s, 3H).

LCMS Rt=1.086 min in 2.0 min chromatography, 30-90 AB, purity 100%, MS ESI calcd. for $C_{28}H_{45}O_2$ [M+H−H$_2$O]$^+$ 413, found 413.

Synthesis of ST-200-6-19 & ST-200-6-20

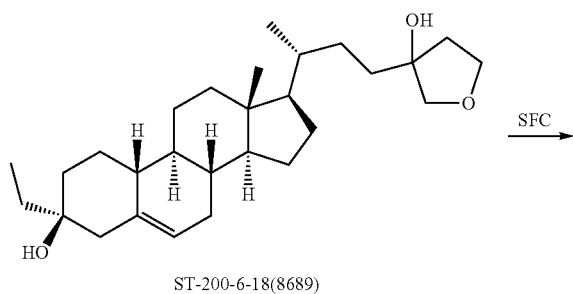

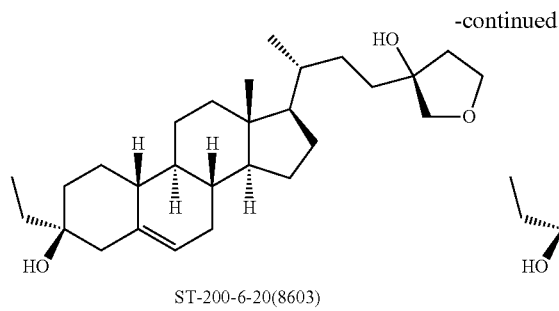

ST-200-6-20(8603)

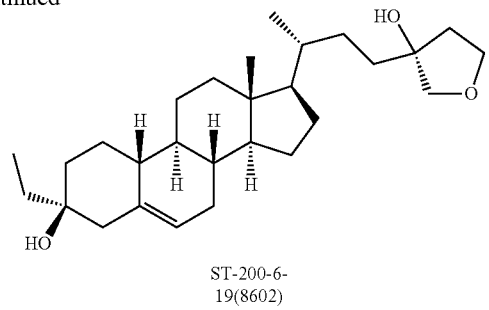

ST-200-6-19(8602)

Stereochemistry was confirmed by Xray data for 8603.

100 mg of ST-200-6-18 (0.232 mmol) was purified by SFC (Column: AD (150×4.6 mm, 3 um), Gradient: 5%-40% B (A: $CO_2$ B: ethanol) Flow rate: 2.5 mL/min) to afford ST-200-6-19 (16.0 mg, 16%) as a solid and ST-200-6-20 (17.0 mg, 17%) as a solid.

8602

$^1$H NMR (400 MHz, $CDCl_3$) δ 5.40-5.35 (m, 1H), 4.05-3.95 (m, 1H), 3.95-3.83 (m, 1H), 3.72-3.62 (m, 1H), 3.55-3.48 (m, 1H), 2.30-2.15 (m, 1H), 2.05-1.55 (m, 12H), 1.50-1.32 (m, 7H), 1.32-1.03 (m, 10H), 1.03-0.70 (m, 8H), 0.68 (s, 3H).

LCMS Rt=1.088 min in 2.0 min chromatography, 30-90 AB, purity 100%, MS ESI calcd. for $C_{28}H_{45}O_2$ $[M+H-H_2O]^+$ 413, found 413.

8603

$^1$H NMR (400 MHz, $CDCl_3$) δ 5.40-5.35 (m, 1H), 4.05-3.95 (m, 1H), 3.95-3.83 (m, 1H), 3.72-3.62 (m, 1H), 3.55-3.48 (m, 1H), 2.50-2.40 (m, 1H), 2.05-1.55 (m, 13H), 1.50-1.32 (m, 6H), 1.32-1.03 (m, 10H), 1.00-0.75 (m, 8H), 0.68 (s, 3H).

LCMS Rt=1.084 min in 2.0 min chromatography, 30-90 AB, purity 100%, MS ESI calcd. for $C_{28}H_{45}O_2$ $[M+H-H_2O]^+$ 413, found 413.

Example 87: Synthesis of 8708

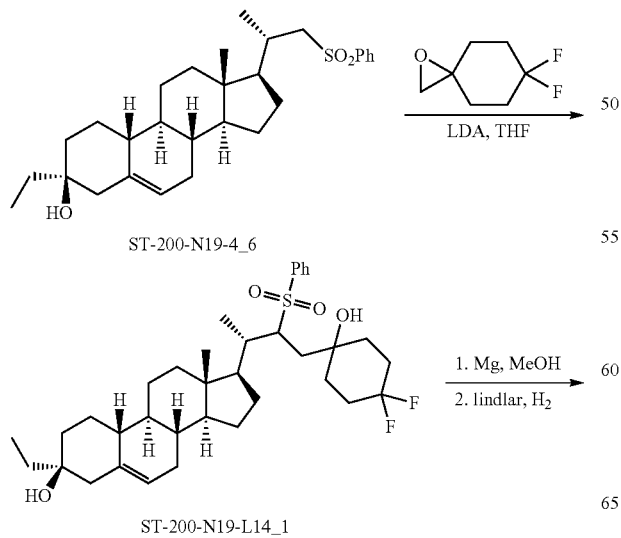

The experimental of intermediate ST-200-N19-4_6 can be found in Example 83.

The synthesis of the epoxide:

To a suspension of $Me_3SI$ (3.93 g, 19.3 mmol) in THF (20 mL) was added a solution of t-BuOK (3.33 g, 29.8 mmol) in THF (10 mL) under $N_2$ at 15° C. The suspension was stirred at 15° C. for 30 mins. A solution of 200-DA-E31_1 (2 g, 14.9 mmol) in THF (5 mL) was added dropwise at 15° C. The mixture was stirred at 15° C. for 16 hrs. The mixture was quenched with Sat.$NH_4Cl$ (50 mL) and extracted with EtOAc (3×20 mL). The combined organic phase was dried over $Na_2SO_4$, filtered, and concentrated to give 200-DA-E31_2 (1.8 g, 82%) as a solid.

$^1$H NMR (400 MHz, $CDCl_3$) δ 2.72 (s, 2H), 2.20-1.85 (m, 8H).

Synthesis of ST-200-N19-L14_1

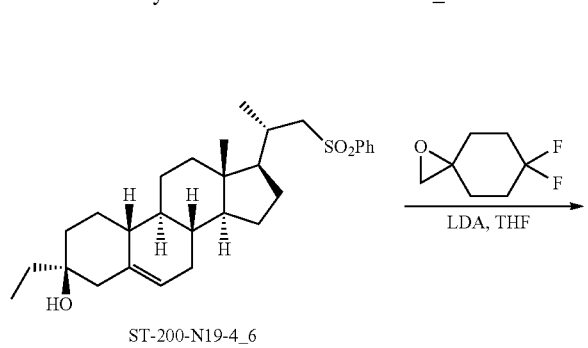

ST-200-N19-4_6

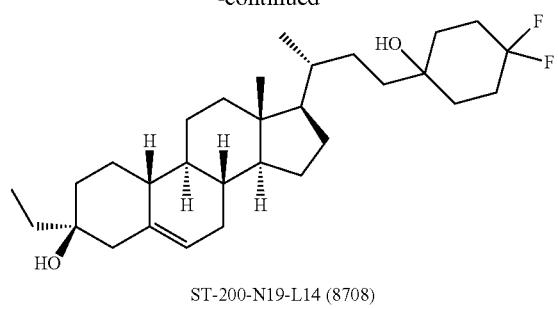

ST-200-N19-L14 (8708)

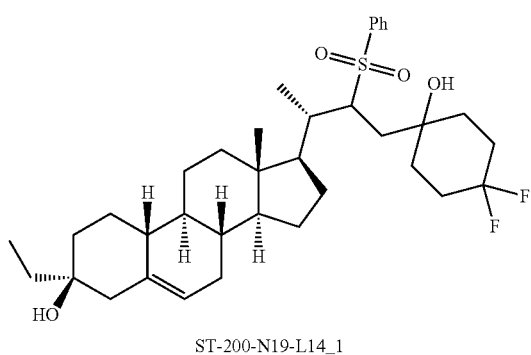

ST-200-N19-L14_1

A suspension of ST-200-N19-4_6 (200 mg, 0.42 mmol) in THF (4 mL) was added dropwise to a solution of n-BuLi (0.4 mL, 2.5 M in hexane, 1.06 mmol) in THF (1 mL) at −70° C. under $N_2$. The mixture was stirred for 30 min at −70° C. A solution of diisopropylamine (107 mg, 1.06 mmol) was added dropwise at −70° C., then a solution of 6,6-difluoro-1-oxaspiro[2.5]octane (94.4 mg, 0.64 mmol) was added dropwise at −70° C. The mixture was stirred for another 30 min and then warmed to 25° C. gradually. The reaction mixture was stirred at 25° C. for 24 hours. The reaction mixture was quenched by saturated $NH_4Cl$ aqueous (5 mL), extracted with EtOAc (3×10 mL). The combined organic phase was washed with brine (30 mL), dried over $Na_2SO_4$, filtered and concentrated under vacuum to give ST-200-N19-L14_1 (290 mg, crude) as a solid, which was used directly for the next step.

Synthesis of ST-200-N19-L14

Mg powder (448 mg, 18.7 mmol) and $NiCl_2$ (5 mg, 0.05 mmol) were added to a solution of ST-200-N19-L14_1 (290 mg, 0.47 mmol) in 50 mL of anhydrous MeOH by stirring under $N_2$ at 60° C. The reaction mixture was quenched by 2 M HCl (50 mL) until solid was dissolved. The mixture was extracted with EtOAc (3×100 mL). The combined organic layer was washed with Sat. $NaHCO_3$ (150 mL), brine (150 mL), dried over $Na_2SO_4$, filtered and concentrated. The residue was purified by flash column (0~15% of EtOAc in PE) to give a solid ($^1$HNMR showed the product contained 10% 22,23-olefin). To a solution of ST-200-N19-L14 in EtOAc (5 mL) was added Lindlar catalyst (100 mg) under $N_2$. The suspension was degassed under vacuum and purged with $H_2$ for three times. Then the solution was hydrogenated under 15 psi of hydrogen at 25° C. for 4 h. The mixture was filtered through a pad of celite and washed with EtOAc (3×10 mL). The filtrate was concentrated and concentrated to give impure ST-200-N19-L14 as a solid ($^1$HNMR showed the product contained 8% 22,23-olefin). Lindlar catalyst (100 mg) was added to a solution of ST-200-N19-L14 in THF/MeOH (3/3 mL) under $N_2$. The suspension was degassed under vacuum and purged with $H_2$ for three times. Then the solution was hydrogenated under 15 psi of hydrogen at 25° C. for 4 h. The mixture was filtered through a pad of celite and washed with THF (3×10 mL). The filtrate was concentrated and triturated from PE (5 mL) and n-hexane (5 mL) at 25° C. to give ST-200-N19-L14 (19 mg, 31%) as a solid.

$^1$H NMR (400 MHz, $CDCl_3$) δ 5.42-5.35 (m, 1H), 2.27-2.19 (m, 1H), 2.17-1.76 (m, 11H), 1.69-1.57 (m, 6H), 1.52-1.21 (m, 11H), 1.19-0.98 (m, 6H), 0.97-0.91 (m, 4H), 0.88-0.74 (m, 5H), 0.68 (s, 3H).

LCMS Rt=1.252 min in 2.0 min chromatography, 30-90AB_2 MIN_E, purity 100%, MS ESI calcd. for $C_{30}H_{47}F_2O$ $[M+H-H_2O]^+$ 461, found 461.

Example 88: Synthesis of 8809

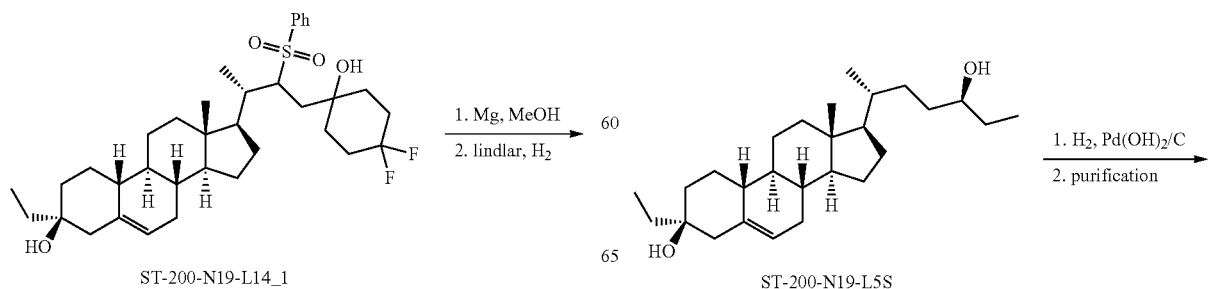

387

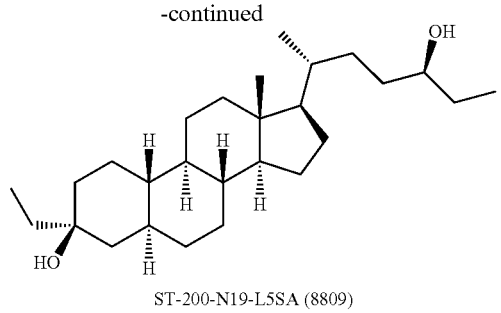

ST-200-N19-L5SA (8809)

The experimental of intermediate ST-200-N19-L5S can be found in Example 85.

Synthesis of ST-200-N19-L5SA

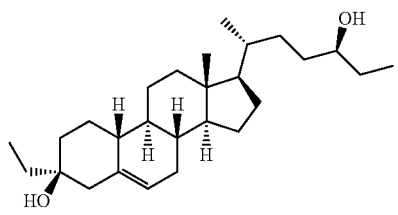

ST-200-N19-L5S

1. H₂, Pd(OH)₂/C
2. purification

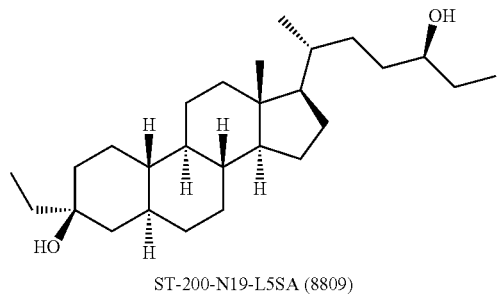

ST-200-N19-L5SA (8809)

Pd(OH)₂/C (100 mg) was added to ST-200-N19-L5S (45 mg, 0.11 mmol) in THF/MeOH (5 mL/5 mL). The mixture was degassed and back-filled with H₂ 3 times. Next, the reaction was stirred at 50° C. under 50 psi of H₂ for 72 h. The reaction mixture was filtered through a pad of celite washed with THF (100 mL). The filtrate was concentrated to give ST-200-N19-L5SA as a solid, which was further triturated in n-hexane (3 mL) to give ST-200-N19-L5SA (5 mg, 11%) as a solid.

$^1$H NMR (400 MHz, CDCl₃) δ 3.53-3.43 (m, 1H), 2.07-1.61 (m, 13H), 1.59-1.21 (m, 13H), 1.20-0.99 (m, 8H), 0.98-0.75 (m, 9H), 0.74-0.53 (m, 4H).

LCMS Rt=1.267 min in 2 min chromatography, 30-90AB_2 MIN_E, purity 100%, MS ESI calcd. for C₂₇H₄₅ [M+H−2H₂O]⁺ 369, found 369.

388

Example 89: Synthesis of 8946 and 8963

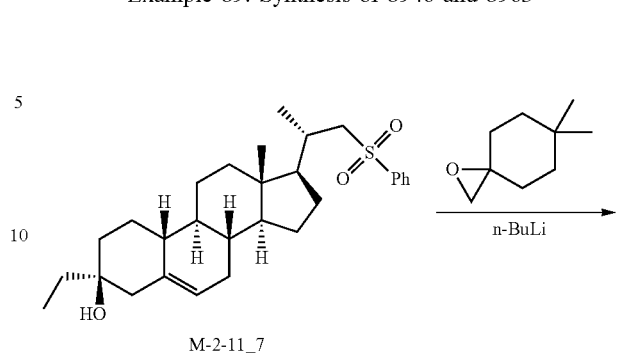

M-2-11_7

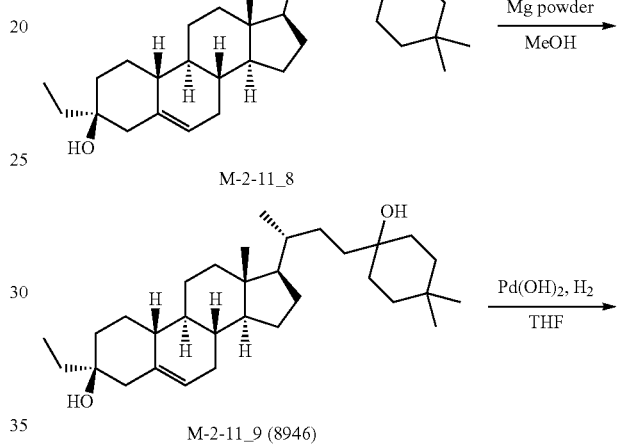

M-2-11_8

M-2-11_9 (8946)

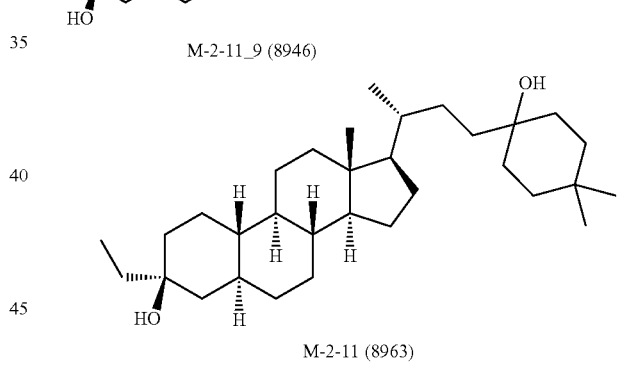

M-2-11 (8963)

The synthesis of M-2-11_7 can be found in Example 83. The synthesis of the epoxide can be found in Example 28.

Synthesis of M-2-11_8

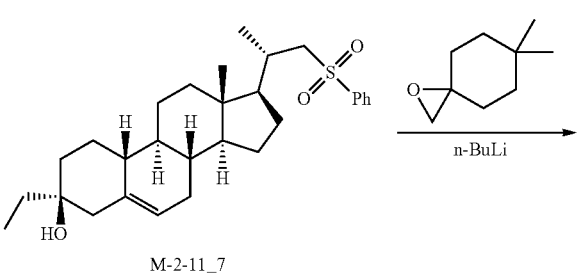

M-2-11_7

-continued

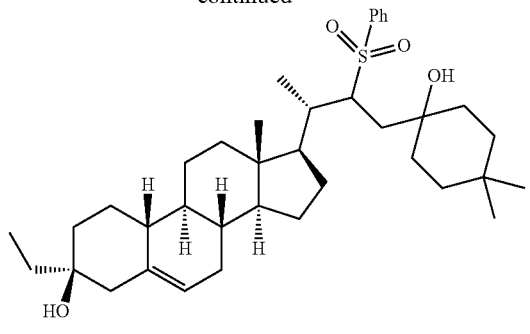

M-2-11_8 n-BuLi (1.01 mL, 2.54 mmol, 2.5 M in hexane) was added to a solution of M-2-11_7 (400 mg, 0.849 mmol) in THF (5 mL) at −70° C. under N$_2$. After stirring at −70° C. for 1 hrs, 6, 6-dimethyl-1-oxaspiro [2.5]octane (236 mg, 1.69 mmol) was added at −70° C. The reaction was allowed to 25° C. and stirred at 25° C. for 12 hours, quenched with NH$_4$Cl (10 mL, sat. aq) and water (30 mL) and extracted with EtOAc (3×10 mL). The organic layers were concentrated in vacuum to give M-2-11_8 (400 mg, crude) as an oil, which was used directly for the next step.

Synthesis of M-2-11_9

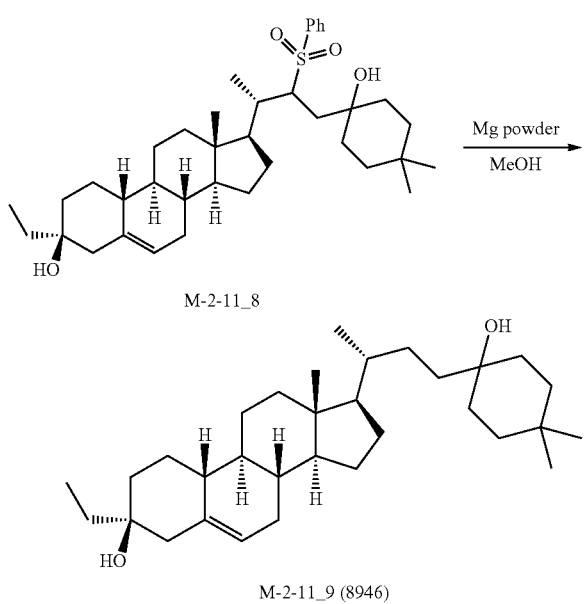

Mg powder (792 mg, 32.6 mmol) was added to a solution of M-2-11_8 (400 mg, crude) in MeOH (80 mL) at 50° C. The mixture was stirred at 50° C. for 1 h. After cooling to 0° C., the mixture was quenched with HCl (50 mL, 2 M) until the reaction became clear and extracted with EtOAc (2×50 mL). The combined organic phase was dried over Na$_2$SO$_4$, filtered and concentrated in vacuum. The residue was purified by flash column (0-40% of EtOAc in PE) to give 150 mg of impure a solid, which was triturated from MeCN (3 mL) at 25° C. to give M-2-11_9 (120 mg, 40%) as a solid.

$^1$H NMR (400 MHz, CDCl$_3$) δ 5.39-5.38 (s, 1H), 2.26-2.21 (m, 1H), 2.05-1.77 (m, 7H), 1.68-1.38 (m, 16H), 1.33-1.00 (m, 14H), 0.96-0.90 (m, 6H), 0.89-0.81 (m, 7H), 0.68 (s, 3H).

LCMS Rt=1.651 min in 2.0 min chromatography, 30-90 AB, purity 100%, MS ESI calcd. for C$_{32}$H$_{51}$ [M+H−2H$_2$O]$^+$ 435, found 435.

Synthesis of M-2-11

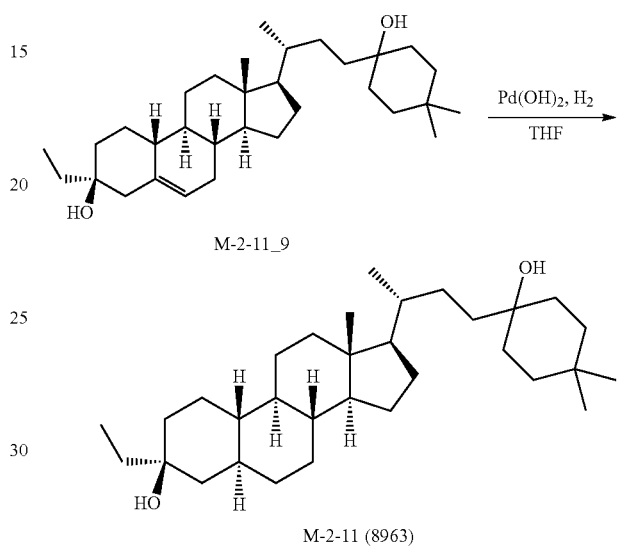

Dry Pd (OH)$_2$ (118 mg, 0.845 mmol) was added to a solution of M-2-11_9 (80 mg, 0.169 mmol) in THF (5 mL) under N$_2$. The suspension was degassed under vacuum and purged with H$_2$ 3 times. The mixture was stirred under H$_2$ (50 psi) at 50° C. for 12 hours to give a black suspension. The reaction mixture was filtered through a pad of celite and washed with THF (3×30 mL). The filtrate was concentrated in vacuum to get M-2-11 (20 mg, 25%) as a solid.

$^1$H NMR (400 MHz, CDCl$_3$) δ 1.97-1.91 (s, 1H), 1.88-1.76 (m, 4H), 1.69-1.60 (m, 3H), 1.59-1.46 (m, 15H), 1.31-1.06 (m, 14H), 0.94-0.86 (m, 15H), 0.69-0.63 (m, 4H).

LCMS Rt=1.718 min in 2.0 min chromatography, 30-90 AB, purity 100%, MS ESI calcd. for C$_{32}$H$_{52}$ [M+H−2H$_2$O]$^+$ 437, found 437.

Example 90: Synthesis of 9062

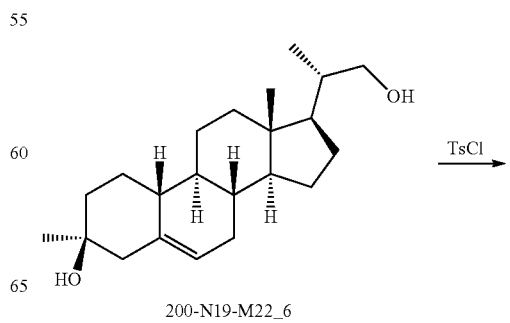

200-N19-M22_6

-continued

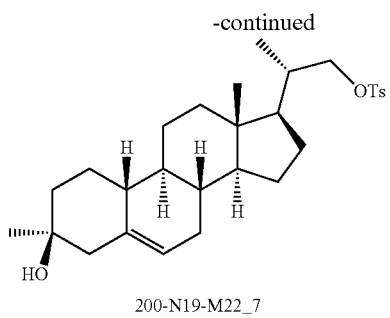

200-N19-M22_7

KI, DMF →

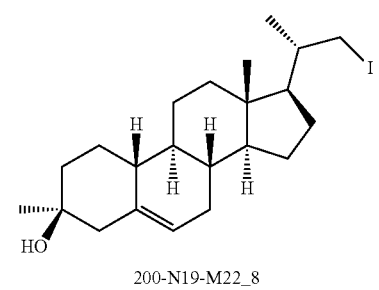

200-N19-M22_8

PhSO₂Na →

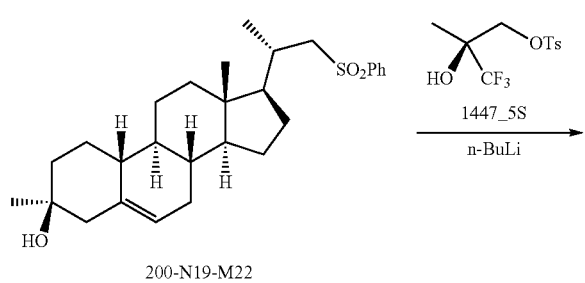

200-N19-M22

1447_5S / n-BuLi →

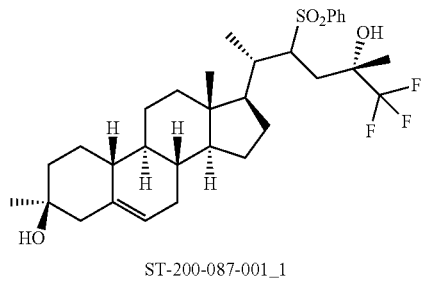

ST-200-087-001_1

1. Mg, MeOH
2. Lindlar, H₂
→

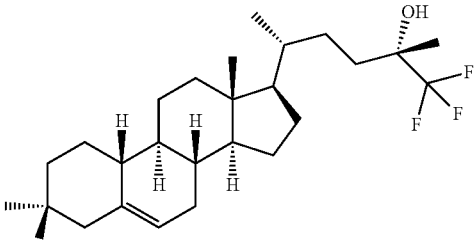

ST-200-087-001(9062)

Synthesis for the experimental of intermediate 200-N19-M22_6 (or M-4-14-2):

Synthesis of 200-N19-3_1

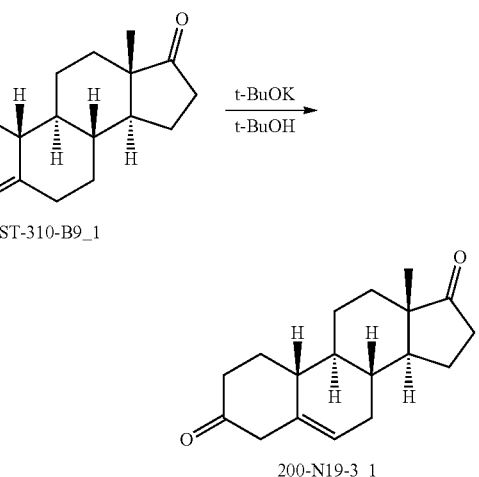

ST-310-B9_1 t-BuOK / t-BuOH →

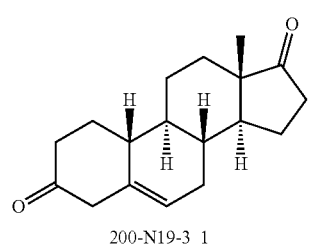

200-N19-3_1 t-BuOH (1.7 L) was charged into a three-neck round bottom flask under N₂ at 35° C. and stirred for 10 mins. t-BuOK (292 g, 2.61 mol) was added to the mixture and stirred until the reaction became clear. After that, ST-310-B9_1 (65 g, 238 mmol) was added to the above mixture and stirred for 1.5 h at 35° C. under N₂. The reaction mixture was poured into 10% aqueous acetic acid (2 L) and stirred for 30 mins, during which the temperature was maintained below 10° C. Then the mixture was treated with water (1.5 L) and the pH was adjusted to 7~8 with NaHCO₃ and stirred for 30 mins. The aqueous phase was extracted with MTBE (3 L). The organic layer was separated, washed with brine (3×1 L), dried over anhydrous Na₂SO₄, filtered and concentrated below 35° C. to give ST-200-N19-3_1 (65 g, crude) as an oil. The crude residue was used directly for the next step.

Synthesis of 200-N19-M22_1

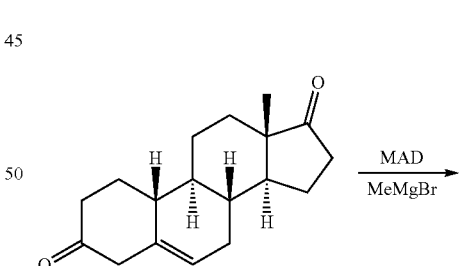

200-N19-3_1

MAD / MeMgBr →

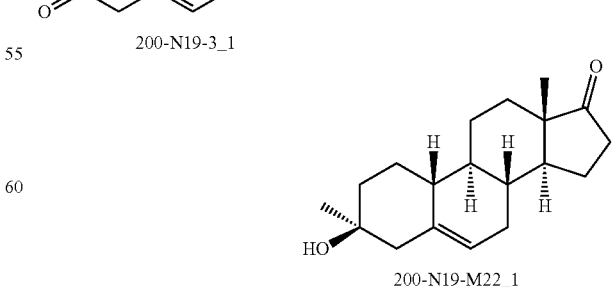

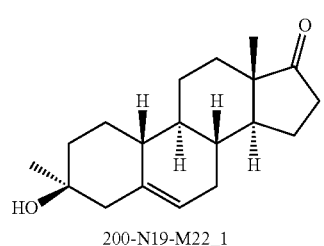

200-N19-M22_1

To a solution of 2,6-di-tert-butyl-4-methylphenol (340 g, 1.54 mol) in toluene (700 mL) was added drop-wise AlMe₃

(385 mL, 770 mmol, 2 M in toluene) at 0° C. The mixture was stirred at 25° C. for 1 h and used directly as MAD solution. A solution of 200-N19-3_1 (60 g, 220 mmol) in anhydrous toluene (200 mL) and anhydrous DCM (200 mL) was added to MAD solution at −70° C. over a period of 30 mins under N₂. The reaction mixture stirring at −70° C. for 1 h. Then MeMgBr (220 mL, 660 mmol, 3M in ethyl ether) was added drop wise at −70° C. and stirred for 1 h. The reaction was poured into saturated aqueous citric acid (2 L) at 0° C. and stirring for 30 min, extracted with EtOAc (2×1 L). The combined organic phase was washed with saturated brine (2×1 L), dried over anhydrous Na₂SO₄, filtered and concentrated. The residue was purified by silica gel chromatography (PE/EtOAc=10/1 to 5/1) to afford 200-N19-M22_1 (33 g, 52%) as a solid.

¹H NMR (400 MHz, CDCl₃) δ 5.46-5.42 (m, 1H), 2.25-2.40 (m, 1H), 2.21-1.60 (m, 13H), 1.35-1.21 (m, 4H), 1.13 (s, 3H), 0.98-0.83 (m, 6H).

Synthesis of M-4-14_1

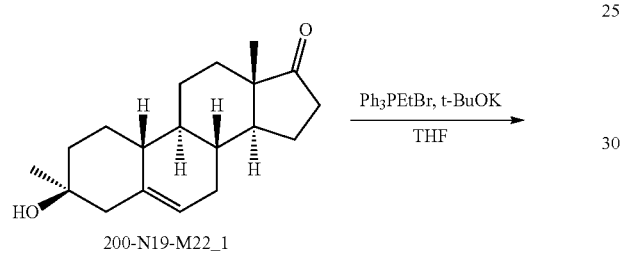

200-N19-M22_1

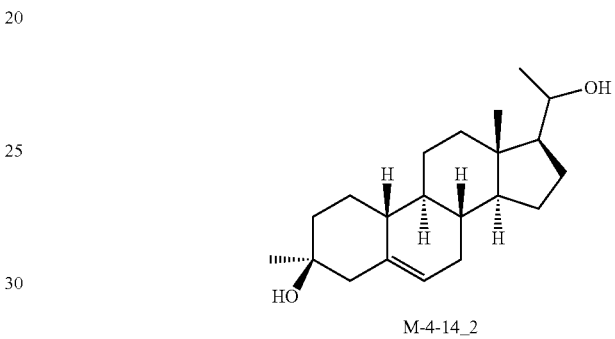

M-4-14_1

To a suspension of Ph₃PEtBr (102 g, 277 mmol) in Anhydrous THF (500 mL) was added t-BuOK (31.0 g, 277 mmol) in one portion at 25° C. under N₂. The reaction mixture turned to dark red. After stirring at 25° C. for 30 min, 200-N19-M22_1 (20 g, 69.3 mmol) was added and stirred for 2 h at 25° C. The reaction was quenched with aq.NH₄Cl (800 mL) at 0° C., extracted with EtOAc (2×500 mL). The combined organic phase was washed with brine (2×500 mL), dried over Na₂SO₄, filtered and concentrated. The residue was purified by silica gel chromatography (PE/EtOAc=10/1 to 5/1) to afford M-4-14_1 (15 g, 72%) as a solid.

¹H NMR (400 MHz, CDCl₃) δ 5.43-5.40 (m, 1H), 5.16-5.10 (m, 1H), 2.41-2.33 (m, 1H), 2.28-1.86 (m, 8H), 1.78-1.71 (m, 1H), 1.69-1.50 (m, 11H), 1.41-1.10 (m, 6H), 0.94-0.81 (s, 3H).

Synthesis of M-4-14_2

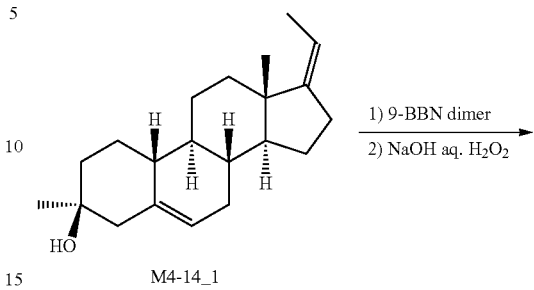

M-4-14_2

To a solution of M-4-14_1 (30 g, 99.8 mmol) in anhydrous THF (500 mL) was added 9-BNN dimer (66.9 g, 299 mmol) and stirred for 30 mins at 0° C. under N₂. The reaction mixture was warmed to 50° C. and stirred for 1 h. after cooled to 0° C. and EtOH (100 mL) was added. NaOH.aq (99.8 mL, 5M, 499 mmol) was added very slowly. H₂O₂ (53.0 g, 499 mmol, 30% in water) was added slowly and the inner temperature was maintained below 30° C. The mixture was warmed to 50° C. and stirred for 1 h. The reaction mixture was cooled and ice-water (1 L) was added and stirred 30 min. filtered and concentrated in vacuum to give M-4-11_2 (30 g, crude) as a solid. The crude material was used directly for the next step.

The synthesis of the tosylate can be found in Example 30.

Synthesis of 200-N19-M22_7

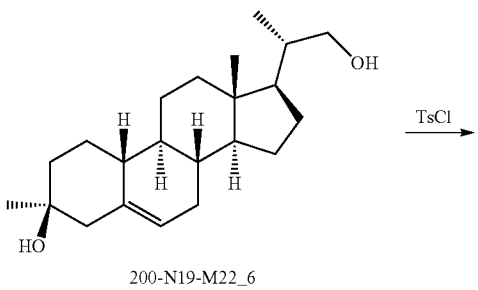

200-N19-M22_6

-continued

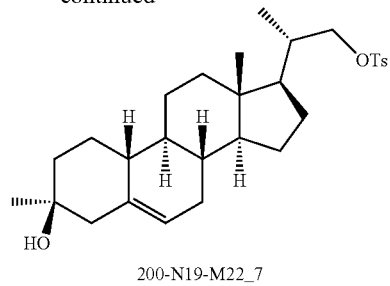

200-N19-M22_7

TEA (21 mL) and TsCl (16.0 g, 84.0 mmol) were added to a solution of 200-N19-M22_6 (7 g, 21.0 mmol) in DCM (150 mL) at 25° C. The mixture was stirred at 40° C. for 12 h. To the reaction was added water (200 mL). The aqueous phase was extracted with DCM (2×200 mL). The combined organic phase was washed with saturated brine (2×200 mL), dried over $Na_2SO_4$, filtered and concentrated was purified by silica gel chromatography (PE/EtOAc=10/1 to 8/1) to afford 200-N19-M22_7 (10 g, 98%) as an oil.

$^1$H NMR (400 MHz, $CDCl_3$) δ 7.79-7.76 (m, 2H), 7.34-7.26 (m, 2H), 5.38-5.29 (m, 1H), 3.95-3.93 (m, 1H), 3.74-3.73 (m, 1H), 2.44 (s, 3H), 2.19-2.14 (m, 1H), 2.09-1.97 (m, 3H), 1.92-1.44 (m, 14H), 1.29-1.08 (m, 6H), 1.05-0.88 (m, 5H), 0.63 (s, 3H).

Synthesis of 200-N19-M22_8

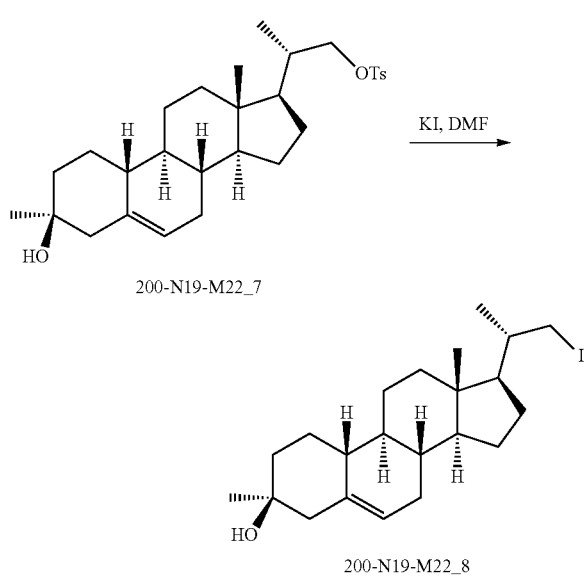

KI (16.9 g, 102 mmol) was added to a solution of 200-N19-M22_7 (10 g, 20.5 mmol) in DMF (100 mL) at 25° C. under $N_2$. The mixture was stirred at 50° C. for 12 h under $N_2$. The residue was poured into ice-water (300 mL) and stirred for 20 min. The aqueous phase was extracted with EtOAc (2×200 mL). The combined organic phase was washed with saturated brine (2×200 mL), dried over anhydrous $Na_2SO_4$, filtered and concentrated to give 200-N19-M22_8 (8 g, 88%) as a solid.

$^1$H NMR (400 MHz, $CDCl_3$) δ 5.41-5.39 (m, 1H), 3.40-3.28 (m, 1H), 3.23-3.13 (m, 1H), 2.19-2.13 (m, 1H), 2.10-1.71 (m, 9H), 1.63-1.34 (m, 7H), 1.16-0.98 (m, 10H), 0.96-0.77 (m, 2H), 0.72 (s, 3H).

Synthesis of 200-N19-M22

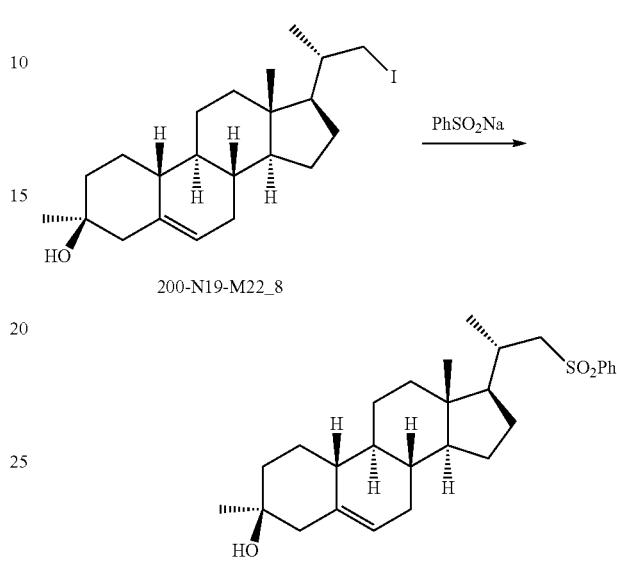

$PhSO_2Na$ (9.27 g, 56.5 mmol) was added to a solution of 200-N19-M22_8 (5 g, 11.3 mmol) in DMF (50 mL) and stirred at 50° C. for 6 h. The reaction mixture was cooled to 25° C. and added water (200 mL). The aqueous phase was extracted with EtOAc (2×100 mL). The combined organic phase was washed with saturated brine (2×100 mL), dried over anhydrous $Na_2SO_4$, filtered and concentrated. The residue was purified by a silica gel column (PE/EtOAc=8/1~5/1) to give 200-N19-M22 (4.0 g) as a solid. The 200-N19-M22 (4.0 g, 8.75 mmol) was re-crystallized from MeCN (50 mL) at 82° C. reflux for 1 hrs. The mixture stirred was cooled to 25° C. (room temperature). The suspension was filtration in vacuum to get 200-N19-M22 (3.5 g, 68%) as a solid.

$^1$H NMR (400 MHz, $CDCl_3$) δ 7.94-7.88 (m, 2H), 7.66-7.54 (m, 3H), 5.39-5.37 (m, 1H), 3.17-3.13 (m, 1H), 2.88-2.81 (m, 1H), 2.18-2.12 (m, 1H), 2.11-1.47 (m, 15H), 1.28-1.08 (m, 8H), 1.07-0.74 (m, 5H), 0.65 (s, 3H).

Synthesis of ST-200-087-001_1

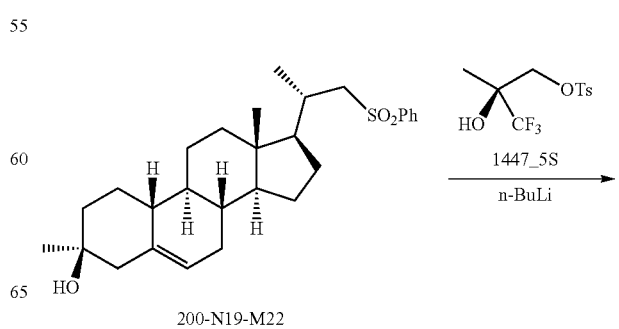

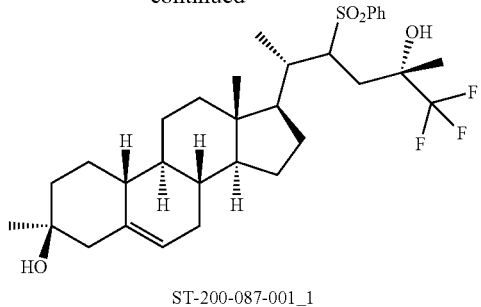

ST-200-087-001_1 n-BuLi (1.22 mL, 3.06 mmol, 2.5M in n-hexane) was added dropwise to a solution of 200-N19-M22 (400 mg, 0.876 mmol) in anhydrous THF (3.5 mL) at −70° C. under $N_2$. After stirring at −70° C. for 30 mins, a solution of (S)-3,3,3-trifluoro-2-hydroxy-2-methylpropyl 4-methylbenzenesulfonate (390 mg, 1.31 mmol) in anhydrous THF (0.5 mL) was added drop-wise at −70° C. and stirred for another 1 h. The reaction mixture was stirred at 25° C. (room temperature) for 12 h. The reaction was quenched by saturated $NH_4Cl$.aq (20 mL). The aqueous phase was extracted with EtOAc (3×50 mL). The combine organic phase was washed whit saturated brine (2×50 mL), drive over anhydrous $Na_2SO_4$, filtered and concentrated in vacuum to give ST-200-087-001_1 (0.4 g, crude) as a solid, which was used directly.

Synthesis of ST-200-087-001

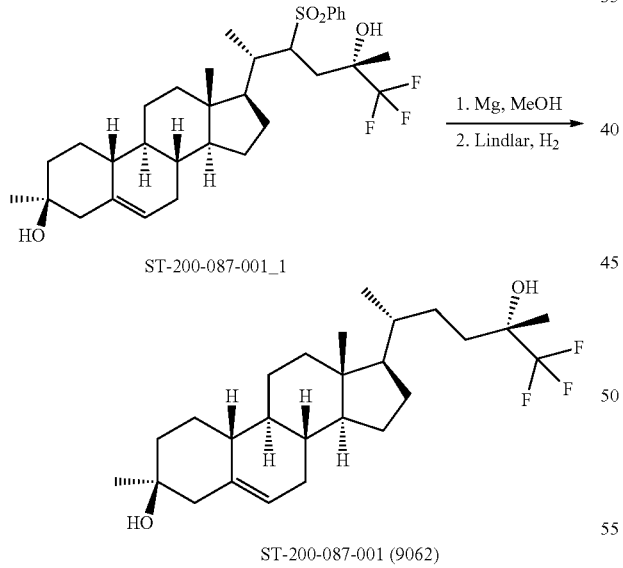

Mg powder (986 mg, 41.1 mmol) and $NiCl_2$ (20 mg) were added to a solution of ST-200-087-001_1 (0.4 g, crude) in MeOH (50 mL) at 25° C. under $N_2$. After stirring at 50° C. for 1 h under $N_2$, the reaction mixture was quenched with HCl (100 mL, 1 M) until the reaction became clear. The aqueous phase was extracted with EtOAc (3×80 mL). The combined organic phase was washed with saturated brine (2×50 mL), dried over anhydrous $Na_2SO_4$, filtered and concentrated. The residue was purified by silica gel chromatography (PE/EtOAc=8/1 to 5/1) to afford ST-200-087-001 (63 mg, 20.7%) as a solid and ST-200-087-001 (80 mg, impure) as a solid.

Lindlar catalyst (300 mg) was added to a solution of ST-200-087-001 (143 mg, 0.323 mmol) in anhydrous THF (2 mL) under $N_2$. The suspension was degassed under vacuum and purged with $H_2$ for three times. The mixture was stirred under $H_2$ (15 psi) at 25° C. for 4 hours to give a black suspension, The reaction mixture was filtered through a pad of Celite and washed with EtOAc (2×30 mL). The filtrate was concentrated in vacuum to give ST-200-087-001 (80 mg, 56%) as a solid.

$^1$H NMR (400 MHz, $CDCl_3$) δ 5.41-5.39 (m, 1H), 2.19-2.14 (m, 1H), 2.10-1.61 (m, 11H), 1.54-1.16 (m, 13H), 1.14-0.73 (m, 12H), 0.69 (s, 3H).

LCMS Rt=1.217 min in 2 min chromatography, 30-90AB_2 MIN_E, purity 100%, MS ESI calcd. for $C_{26}H_{40}F_3O$ $[M+H-H_2O]^+$ 425, found 425.

Example 91: Synthesis of 9142

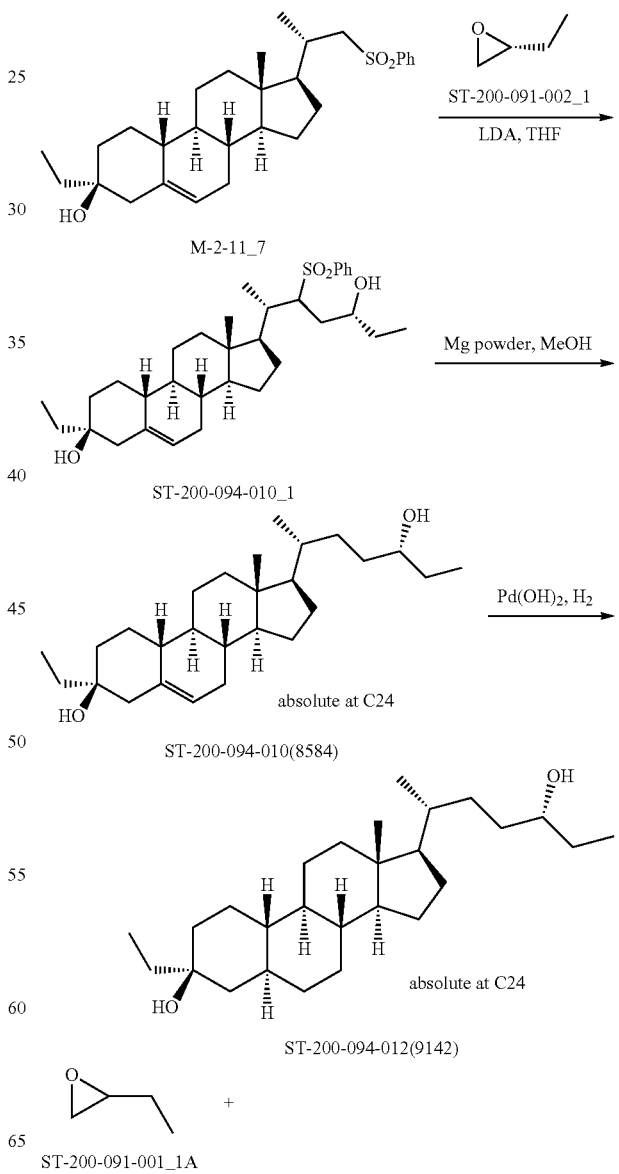

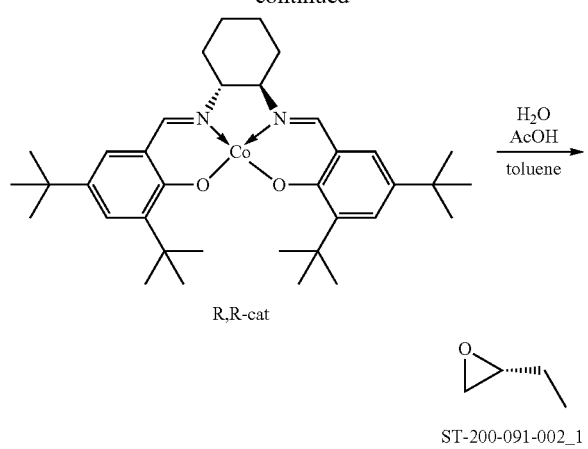

The experimental of intermediate M-2-11_7 can be found in Example 83.

See Example 85 for stereochemistry synthesis.

Synthesis of ST-200-091-002_1

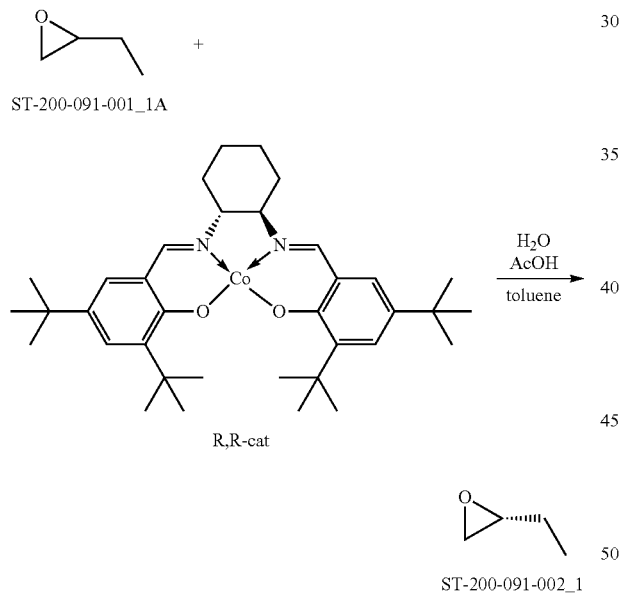

To a solution of R, R-cat (166 mg, 0.276 mmol) in toluene (5 mL) was added AcOH (173 mg, 2.89 mmol). The mixture was stirred at 25° C. open to air for 30 min and concentrated in vacuo to leave a crude solid. The resulting catalyst residue was dissolved in 2-ethyloxirane (10 g, 138 mmol) at 25° C. The reaction flask was cooled to 0° C. and treated with $H_2O$ (1.36 g, 75.9 mmol) dropwise over 5 min. The reaction was allowed to warm to 25° C. and stir 24 hrs and the reaction mixture was distilled to give (R)-2-ethyloxirane (4.4 g, 61.0 mmol).

$^1$H NMR (400 MHz, CDCl$_3$) δ 2.91-2.88 (m, 1H), 2.76-2.71 (m, 1H), 2.49-2.47 (m, 1H), 1.62-1.54 (m, 2H), 1.03-0.97 (m, 3H).

The ee value of the epoxide was determined as following

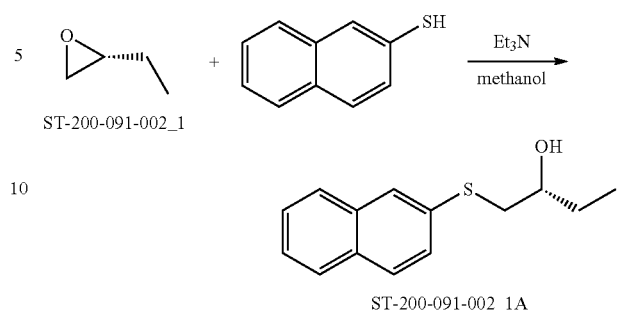

To a solution of (2R)-2-ethyloxirane (100 mg, 1.38 mmol) and naphthalene-2-thiol (221 mg, 1.38 mmol) in methanol (10 mL) was added triethylamine (139 mg, 1.38 mmol). The mixture was stirred at 30° C. for 16 hrs. The reaction mixture was used directly to determine ee % without any treatment. The ee % was determined to be 93.6%.

SFC Rt=5.287 min in 10 min chromatography, AD-3_IPA (DEA)_5_40_2.5ML, 93.6% ee.

Synthesis of ST-200-094-010_1

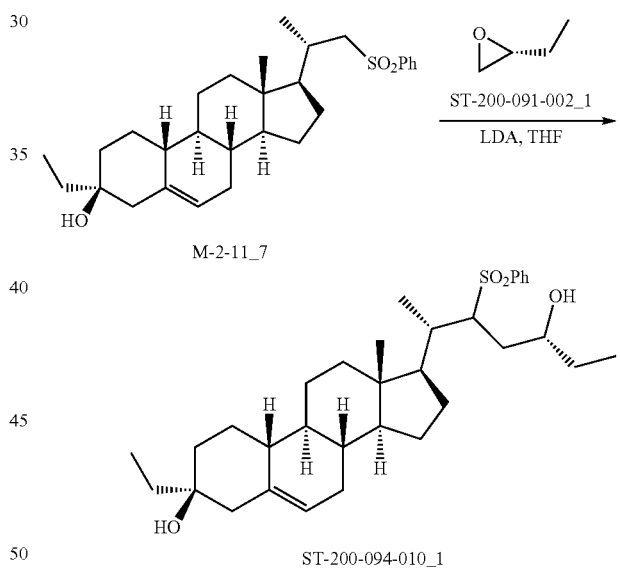

To a solution of M-2-11_7 (400 mg, 0.849 mmol) in anhydrous THF (3 mL) was added n-BuLi (1.01 mL, 2.54 mmol, 2.5 M in n-hexane) drop-wise at −70° C. under $N_2$. After stirring at −70° C. for 30 mins, a solution of (R)-2-ethyloxirane (91.5 mg, 1.27 mmol) in anhydrous THF (0.5 mL) was added drop-wise at −70° C. The reaction mixture was stirred at −70° C. for another 1 h and then stirred at 25° C. (room temperature) for 12 h. After heating at 60° C. for 2 h, the reaction was quenched by saturated aqueous NH$_4$Cl (50 mL). The aqueous phase was extracted with EtOAc (3×50 mL). The combine organic phase was washed with saturated brine (2×50 mL). dried over anhydrous Na$_2$SO$_4$. filtered and concentrated in vacuum to give ST-200-94-10_1 (0.4 g, crude) as an oil, which was used directly of the next step.

Synthesis of ST-200-094-010

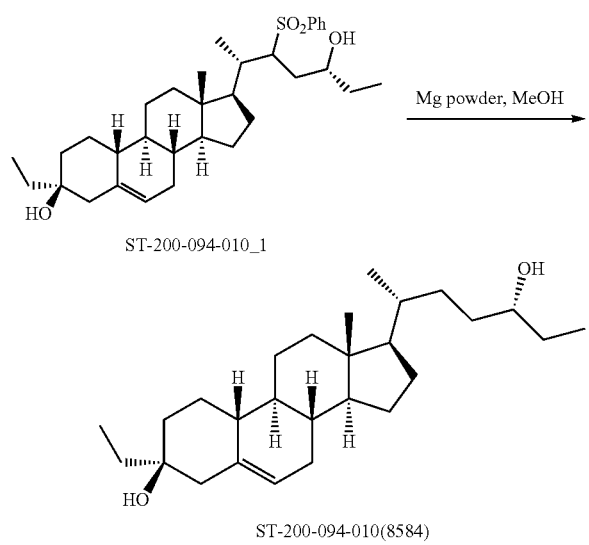

To a solution of ST-200-094-010_1 (0.4 g, crude) in MeOH (50 mL) was added Mg powder (883 mg, 36.8 mmol) and NiCl$_2$ (20 mg) at 25° C. under N$_2$. After stirring at 60° C. for 1 h, the reaction mixture was quenched with HCl (100 mL, 1 M) until the reaction became clear. The aqueous phase was extracted with EtOAc (3×80 mL). The combined organic phase was washed with saturated NaHCO$_3$.aq (2×50 mL), washed saturated brine (2×50 mL), dried over anhydrous Na$_2$SO$_4$, filtered and concentrated. The residue was purified by silica gel chromatography (PE/EtOAc=10/1 to 8/1) to afford ST-200-094-010 (180 mg, 61%) as a solid. The ST-200-094-010 (180 mg, 0.447 mmol) was purified by SFC (Column:AD(250 mm*30 mm, 5 um), Condition:0.1% NH$_3$H$_2$O IPA, Begin B:40%, End B:40%) to afford ST-200-094-010 (120 mg, 67%) as a solid.

$^1$H NMR (400 MHz, CDCl$_3$) δ$_H$ 5.40-5.37 (m, 1H), 3.48-3.46 (m, 1H), 2.25-2.21 (m, 1H), 2.05-1.74 (m, 7H), 1.65-1.40 (m, 13H), 1.38-1.07 (m, 11H), 1.06-0.96 (m, 6H), 0.85 (s, 3H), 0.68 (s, 3H).

LCMS=1.277 min in 2 min chromatography, 30-90AB_2 MIN_E, purity 100%, MS ESI calcd. for C$_{27}$H$_{45}$O [M+H−H$_2$O]$^+$ 385, found 385.

SFC Rt=5.736 min in 10 min chromatography, AD_3_EtOH_DEA_5_40_25ML, 99.5% de.

Synthesis of ST-200-094-012

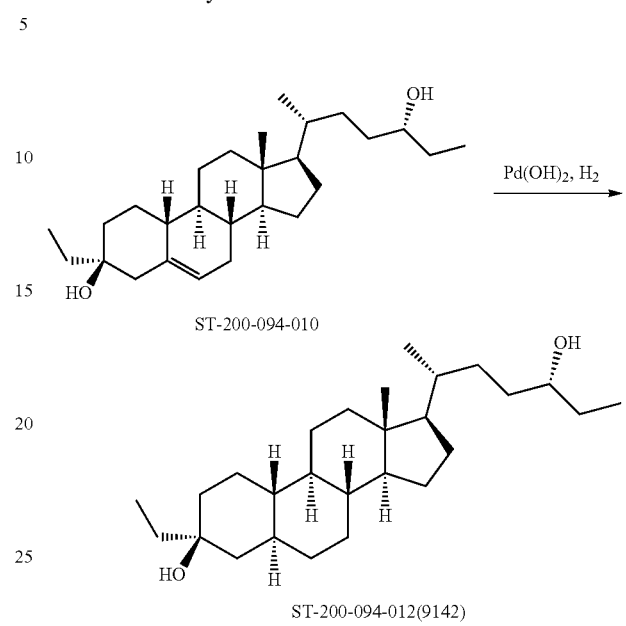

A solution of ST-200-094-010 (88 mg, 0.2185 mmol) and Pd(OH)$_2$ (80 mg) in MeOH (10 mL) was hydrogenated under 50 psi of hydrogen at 50° C. for 12 hours. The reaction mixture was filtered through a pad of celite and the filter cake was washed with THF (3×100 mL). The filter liquor was concentrated in vacuum. The residue was purified by flash column (10~25% of EtOAc in PE) to give ST-200-094-012 (27 mg, 31%) as a solid.

$^1$H NMR (400 MHz, CDCl$_3$) δ$_H$ 3.50-3.41 (m, 1H), 1.99-1.91 (m, 1H), 1.87-1.74 (m, 3H), 1.70-1.60 (m, 3H), 1.53-1.19 (m, 12H), 1.18-0.97 (m, 11H), 0.96-0.78 (m, 12H), 0.75-0.54 (m, 5H).

LCMS Rt=1.292 min in 2 min chromatography, 30-90AB_2 MIN_E, purity 100%, MS ESI calcd. for C$_{27}$H$_{45}$[M+H−2H$_2$O]$^+$ 369, found 369.

Example 93. Biological Data

The experiments were conducted as described in Example 2 and the results are provided in Table 2-61.

TABLE 2-61

| Compound | Avg EC50 2A (nM) | Avg Emax 2A (%) | Avg EC50 2B (nM) | Avg Emax 2B (%) |
|---|---|---|---|---|
| 376 | >10000 | 49.9 | >10000 | 59.8 |

TABLE 2-61-continued

| Compound | Avg EC50 2A (nM) | Avg Emax 2A (%) | Avg EC50 2B (nM) | Avg Emax 2B (%) |
|---|---|---|---|---|
| 1A75 | 671.1 | 457.2 | 439.6 | 308.0 |
| 1B75 | 164.9 | 278.8 | 183.4 | 233.1 |
| 476 | 406.0 | 811.2 | 189.5 | 399.2 |
| 175 | 574.1 | 366.7 | 287.5 | 279.0 |
| 679 | 5113.4 | 104.9 | 280.0 | 171.5 |
| 4A77 | 427.2 | 382.5 | 285.2 | 253.7 |

TABLE 2-61-continued

| Compound | Avg EC50 2A (nM) | Avg Emax 2A (%) | Avg EC50 2B (nM) | Avg Emax 2B (%) |
|---|---|---|---|---|
| 4B77 | 466.8 | 466.6 | 298.2 | 320.5 |
| 780 | 340.9 | 132.1 | 263.2 | 169.7 |
| 8127 | 543.0 | 135.7 | 571.2 | 210.7 |
| 8245 | 524.5 | 73.0 | 267.6 | 119.5 |
| 8361 | 87.0 | 252.0 | 136.3 | 308.8 |
| 8462 | 170.0 | 273.2 | 96.2 | 281.0 |

TABLE 2-61-continued
| Compound | Avg EC50 2A (nM) | Avg Emax 2A (%) | Avg EC50 2B (nM) | Avg Emax 2B (%) |
|---|---|---|---|---|
| 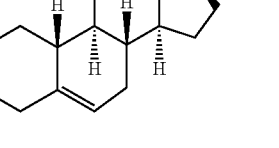 8463 | 102.5 | 291.3 | 85.1 | 324.2 |
| 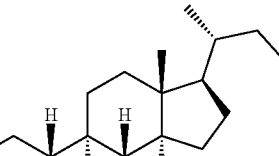 8564 | 468.8 | 252.5 | 489.5 | 310.5 |
| 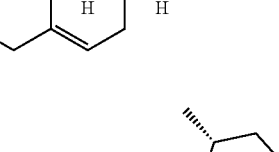 8378 | 123.9 | 195.0 | 208.3 | 258.6 |
| 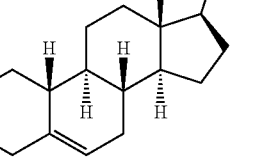 8379 | 73.4 | 251.8 | 78.1 | 358.6 |
| 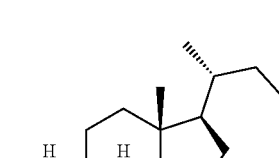 8584 | 332.2 | 284.3 | 244.5 | 363.1 |
| 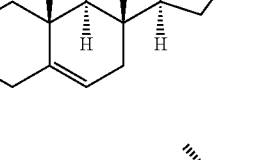 8585 | 286.2 | 194.4 | 236.7 | 232.9 |

TABLE 2-61-continued
| | Compound | Avg EC50 2A (nM) | Avg Emax 2A (%) | Avg EC50 2B (nM) | Avg Emax 2B (%) |
|---|---|---|---|---|---|
| 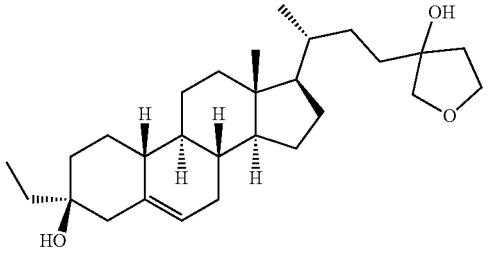 | 8689 | 168.6 | 319.6 | 174.8 | 438.6 |
| 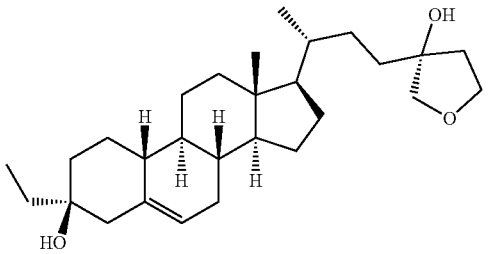 | 8602 | 1047.1 | 271.7 | 433.7 | 262.3 |
| 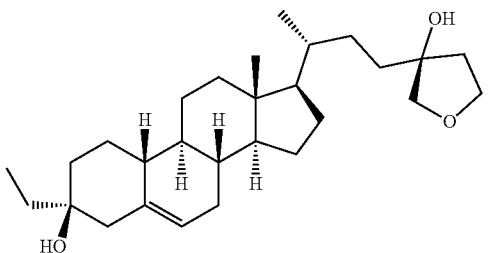 | 8603 | 134.9 | 293.5 | 75.1 | 270.6 |
| 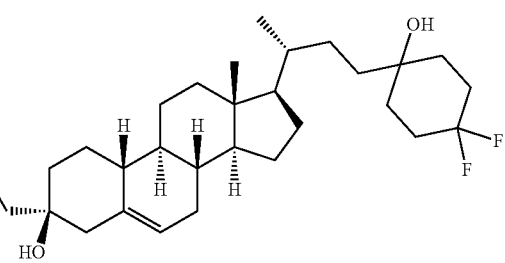 | 8708 | 697.2 | 117.4 | 552.7 | 243.2 |
| 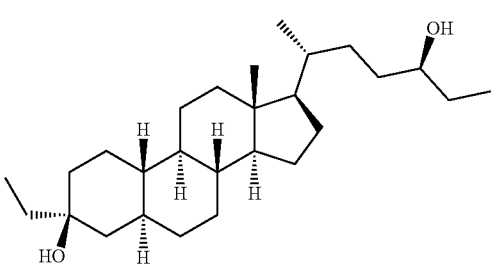 | 8809 | 532.9 | 73.6 | 160.4 | 78.2 |
| 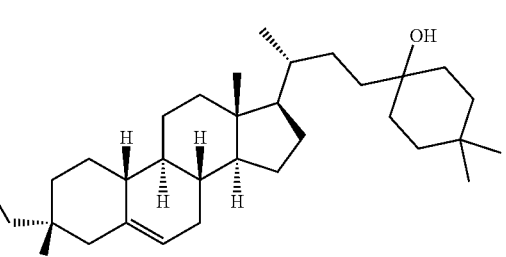 | 8946 | 1596.2 | 262.8 | 1352.5 | 231.4 |

TABLE 2-61-continued
| Compound | Avg EC50 2A (nM) | Avg Emax 2A (%) | Avg EC50 2B (nM) | Avg Emax 2B (%) |
|---|---|---|---|---|
| 8963 | >10000 | 8.4 | >10000 | 55.9 |
| 9062 | 34.5 | 66.5 | 179.0 | 52.2 |
| 9142 | >10000 | 41.6 | 70.4 | 44.8 |
Example 94. Synthesis of Compound 194
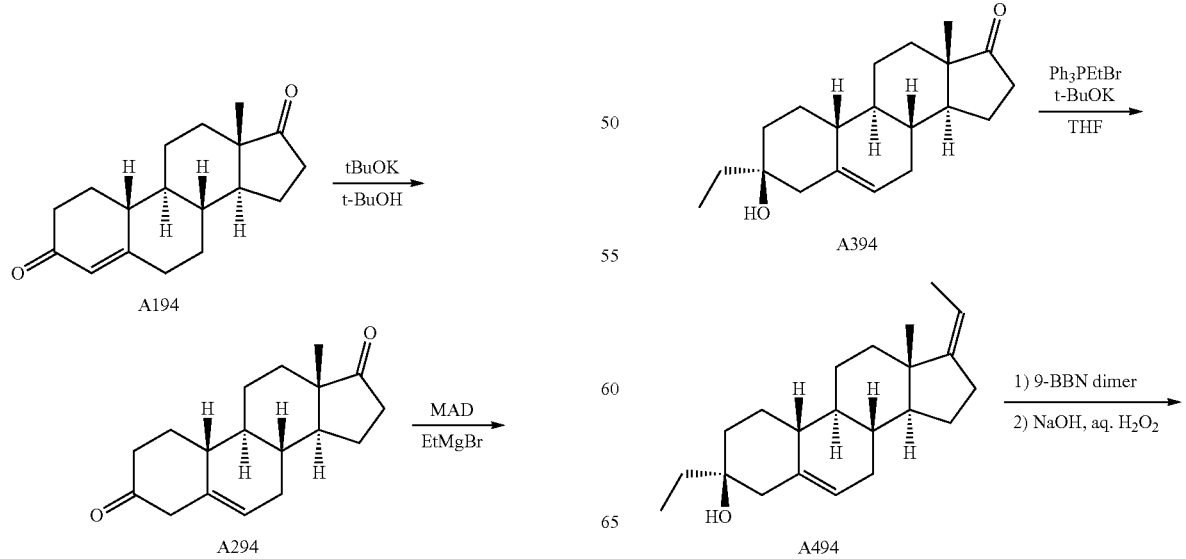

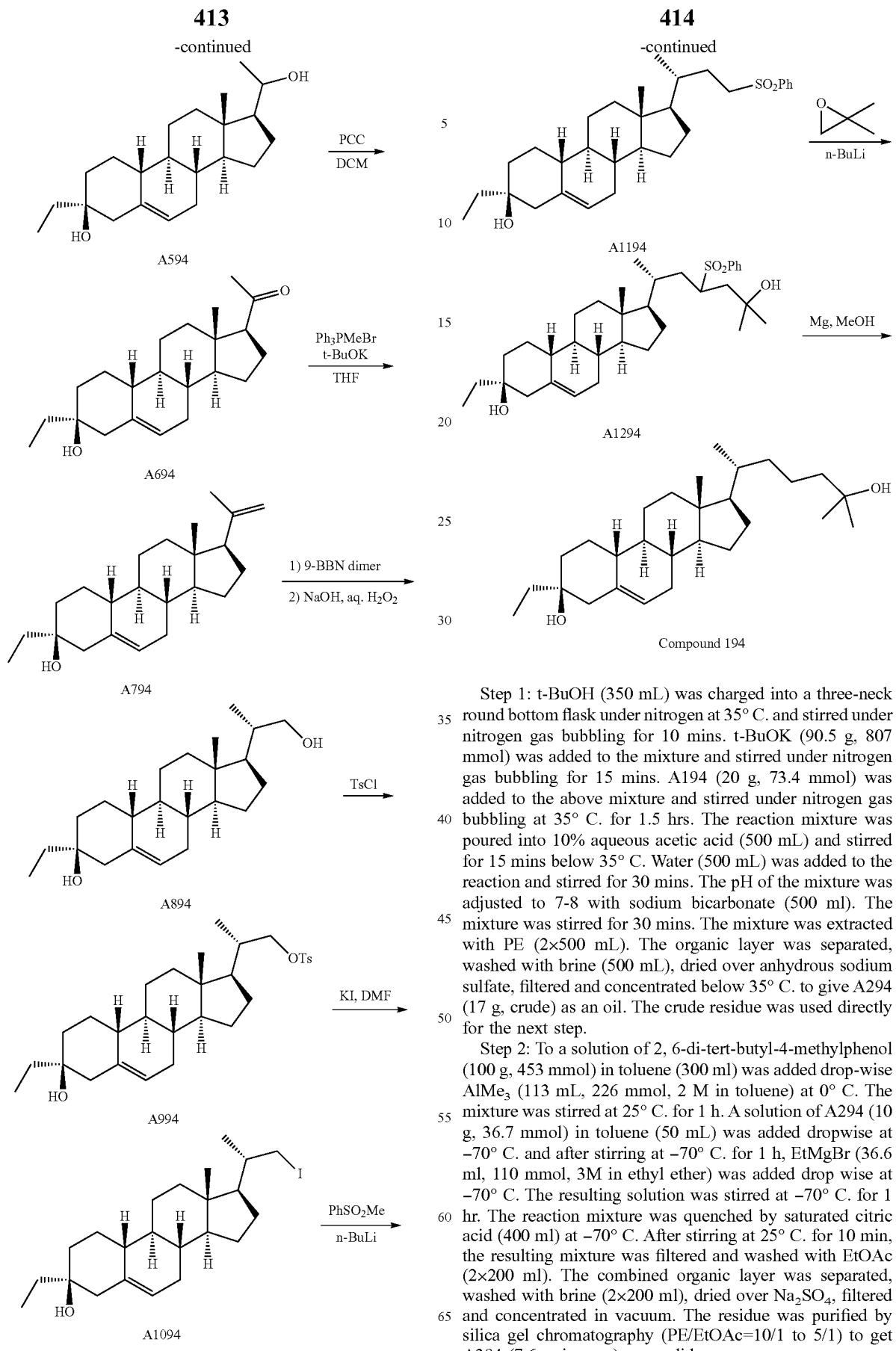

Step 1: t-BuOH (350 mL) was charged into a three-neck round bottom flask under nitrogen at 35° C. and stirred under nitrogen gas bubbling for 10 mins. t-BuOK (90.5 g, 807 mmol) was added to the mixture and stirred under nitrogen gas bubbling for 15 mins. A194 (20 g, 73.4 mmol) was added to the above mixture and stirred under nitrogen gas bubbling at 35° C. for 1.5 hrs. The reaction mixture was poured into 10% aqueous acetic acid (500 mL) and stirred for 15 mins below 35° C. Water (500 mL) was added to the reaction and stirred for 30 mins. The pH of the mixture was adjusted to 7-8 with sodium bicarbonate (500 ml). The mixture was stirred for 30 mins. The mixture was extracted with PE (2×500 mL). The organic layer was separated, washed with brine (500 mL), dried over anhydrous sodium sulfate, filtered and concentrated below 35° C. to give A294 (17 g, crude) as an oil. The crude residue was used directly for the next step.

Step 2: To a solution of 2, 6-di-tert-butyl-4-methylphenol (100 g, 453 mmol) in toluene (300 ml) was added drop-wise AlMe$_3$ (113 mL, 226 mmol, 2 M in toluene) at 0° C. The mixture was stirred at 25° C. for 1 h. A solution of A294 (10 g, 36.7 mmol) in toluene (50 mL) was added dropwise at −70° C. and after stirring at −70° C. for 1 h, EtMgBr (36.6 ml, 110 mmol, 3M in ethyl ether) was added drop wise at −70° C. The resulting solution was stirred at −70° C. for 1 hr. The reaction mixture was quenched by saturated citric acid (400 ml) at −70° C. After stirring at 25° C. for 10 min, the resulting mixture was filtered and washed with EtOAc (2×200 ml). The combined organic layer was separated, washed with brine (2×200 ml), dried over Na$_2$SO$_4$, filtered and concentrated in vacuum. The residue was purified by silica gel chromatography (PE/EtOAc=10/1 to 5/1) to get A394 (7.6 g, impure) as a solid.

¹H NMR (400 MHz, CDCl₃) δ 5.45-5.40 (m, 1H), 2.51-2.38 (m, 1H), 2.49-2.21 (m, 1H), 2.14-1.88 (m, 5H), 1.86-1.77 (m, 2H), 1.73-1.38 (m, 8H), 1.34-1.22 (m, 4H), 0.95-0.81 (m, 8H).

Step 3: To a suspension of PPh₃EtBr (37.1 g, 100 mmol) in THF (200 mL) under N₂ was added t-BuOK (11.2 g, 100 mmol) at 40° C. After stirring at 20° C. for 10 min, A394 (7.6 g, 25.1 mmol) was added. The reaction mixture was stirred at 40° C. for 1 h. The reaction was quenched with saturated aqueous NH₄Cl (200 mL) at 0° C. and extracted with EtOAc (3×200 mL). The combined organic phase was washed with brine (200 mL), dried over Na₂SO₄, filtered and concentrated. The residue was purified by flash chromatography (0%-30% of EtOAc in PE) to afford A494 (5 g, 63%) as a solid.

¹H NMR (400 MHz, CDCl₃) δ 5.45-5.35 (m, 1H), 5.20-5.00 (m, 1H), 2.41-2.30 (m, 1H), 2.29-2.12 (m, 3H), 2.09-1.76 (m, 6H), 1.69-1.38 (m, 15H), 1.35-0.94 (m, 7H).

Step 4: To a solution of A494 (2 g, 6.35 mmol) in THF (20 mL) was added 9-BBN dimer (3.09 g, 12.7 mmol) at 0° C. under N₂. The solution was stirred at 60° C. for 1 h. After cooling to 0° C., a solution of EtOH (20 ml) and NaOH (12.7 ml, 5M, 63.5 mmol) was added very slowly. After addition, H₂O₂ (2.15 mg, 6.35 mmol, 30% in water) was added slowly and the inner temperature was maintained below 10° C. The mixture was stirred at 60° C. under N₂ for 1 hour. The mixture was re-cooled to 30° C., water (100 mL) was added to the solution and extracted with EtOAc (100 mL). The organic layer was washed with brine (2×100 mL) and then the combined organic layer was dried over anhydrous Na₂SO₄, and purified by silica gel chromatography (PE/EtOAc=2/1) to afford impure A594 (1.6 g) as a solid.

¹H NMR (400 MHz, CDCl₃) δ 5.45-5.35 (m, 1H), 3.75-3.62 (m, 1H), 2.28-2.19 (m, 1H), 2.10-1.75 (m, 7H), 1.71-0.97 (m, 19H), 0.92-0.75 (m, 4H), 0.68 (s, 3H).

Step 5: To a solution of A594 (1.6 g, 4.81 mmol) in DCM (20 mL) was added silica gel (2 g) and PCC (2.07 g, 9.62 mmol). The mixture was stirred at 25° C. for 3 hrs. To the mixture was added PE (50 mL) and the mixture was filtered though a pad of silica gel and the solid was washed with PE/DCM (30 mL/30 mL). The mixture was filtered and filtrate was concentrated in vacuum. The residue was purified by silica gel chromatography (PE/EtOAc=10/1 to 5/1) to afford impure A094 (1.2 g) as a solid, which was re-crystallized from MeCN (10 mL) at reflux (82° C.) to give A694 (1.0 g, 84%) as a solid.

¹H NMR (400 MHz, CDCl₃) δ 5.40-5.35 (m, 1H), 2.61-2.45 (m, 1H), 2.30-2.10 (m, 5H), 2.00-1.75 (m, 6H), 1.70-1.10 (m, 14H), 0.90-0.75 (m, 4H); 0.633 (s, 3H).

LCMS Rt=1.058 min in 2.0 min chromatography, 30-90 AB, MS ESI calcd. for $C_{22}H_{33}O$ [M+H−H₂O]⁺ 313, found 313.

Step 6: To a suspension of Ph₃PMeBr (11.1 g, 31.4 mmol) in THF (50 mL) under N₂ was added t-BuOK (3.51 g, 31.4 mmol) at 40° C. After stirring at 25° C. for 10 min, A6 (2.6 g, 7.86 mmol) was added. The reaction mixture was stirred at 40° C. for 1 h. The reaction was quenched with aq.NH₄Cl (100 mL) at 0° C., extracted with EtOAc (2×100 mL). The combined organic phase was washed with brine (2×100 mL), dried over Na₂SO₄, filtered and concentrated. The residue was purified by flash chromatography (0%~30%, EtOAc in PE) to afford A794 (2.4 g, 93%) as a solid.

¹H NMR (400 MHz, CDCl₃) δ 5.45-5.35 (m, 1H), 4.86-4.83 (m, 1H), 8.70-4.65 (m, 1H), 2.27-2.20 (m, 1H), 2.10-1.90 (m, 4H), 1.89-1.50 (m, 11H), 1.49-1.30 (m, 3H), 1.28-1.00 (m, 6H), 0.80-0.60 (m, 5H), 0.59 (s, 3H).

Step 7: To a solution of A794 (2.4 g, 7.30 mmol) in THF (40 mL) was added 9-BBN dimer (4.44 g, 18.2 mmol) at 0° C. under N₂. The solution was stirred at 60° C. for 1 h. After cooling to 0° C., a solution of EtOH (30 ml) and NaOH (14.5 mL, 5M, 73.0 mmol) was added very slowly. After addition, H₂O₂ (7.29 mL, 73.0 mmol, 30% in water) was added slowly and the inner temperature was maintained below 10° C. The mixture was stirred at 60° C. under N₂ for 1 hour. The mixture was re-cooled to 30° C. and water (100 mL) was added to the solution with EtOH (50 mL). A precipitate appeared, which was collected by filtration and concentrated in vacuum to give A894 (1.8 g, 71%) as a solid.

¹H NMR (400 MHz, CDCl₃) δ 5.45-5.35 (m, 1H), 3.69-3.60 (m, 1H), 3.40-3.30 (m, 1H), 2.25-2.00 (m, 1H), 2.08-1.75 (m, 7H), 1.68-1.60 (m, 2H), 1.55-1.38 (m, 5H). 1.36-1.09 (m, 8H), 1.08-0.93 (m, 4H), 0.89-0.76 (m, 5H), 0.70 (s, 3H).

Step 8: To a solution of A894 (1 g, 2.88 mmol) in chloroform (5.5 mL) and pyridine (3.5 mL) was added TsCl (1.42 g, 7.48 mmol) at 25° C. The mixture was stirred at 25° C. for 2 hrs. The reaction mixture was concentrated under vacuum to remove most of the chloroform. To the obtained pyridine mixture was added water (50 mL). A solid was produced, which was collected by filtration and washed with water (5×50 mL). The solid was dissolved in DCM (50 mL), dried over Na₂SO₄, filtered and concentrated under vacuum to give A994 (1.2 g, crude) as an oil, which was used directly for the next step.

Step 9: To a solution of A994 (800 mg, 1.55 mmol) in DMF (6 mL) was added KI (1.23 g, 7.44 mmol) at 25° C. The mixture was stirred at 50° C. for 1 hour. The reaction mixture was poured into water (50 mL) with PE (30 mL). The organic phase was washed with brine (2×30 mL), dried over Na₂SO₄, filtered and concentrated to give A1094 (700 mg, 96%) as an oil.

¹H NMR (400 MHz, CDCl₃) δ 5.45-5.35 (m, 1H), 3.36-3.30 (m, 1H), 3.20-3.10 (m, 1H), 2.30-2.20 (m, 1H), 2.07-1.70 (m, 7H), 1.68-1.60 (m, 2H), 1.32-1.14 (m, 8H), 1.13-0.94 (m, 6H), 0.93-0.74 (m, 7H), 0.72 (s, 3H).

Step 10: To a solution of PhSO₂Me (449 mg, 2.88 mmol) in THF (10 mL) was added n-BuLi (1.04 mL, 2.62 mmol, 2.5 M in hexane) at −70° C. under N₂. The mixture was warmed to 0° C. A suspension of A1094 (600 mg, 1.31 mmol) in THF (10 mL) was added drop-wise at 0° C. After addition, the reaction was allowed to 25° C. The reaction mixture was stirred at 25° C. for 1 hour. The reaction was quenched with saturated aqueous NH₄Cl (30 mL). To the suspension was added water (100 mL) and extracted with EtOAc (3×50 mL). The combined organic phase was concentrated to give a residue which was purified by silica gel chromatography (PE/EtOAc=6/1) to give compound A1194 (1.5 g, impure, containing PhSO₂Me) as an oil. The oil was further purified by silica gel chromatography (DCM/Acetone=50/1) to give A1194 (400 mg, 63%) as an oil.

¹H NMR (400 MHz, CDCl₃) δ 7.90 (d, J=7.6 Hz, 2H), 7.69-7.62 (m, 1H), 7.60-7.51 (m, 2H), 5.40-5.35 (m, 1H), 3.17-3.07 (m, 1H), 3.04-2.93 (m, 1H), 2.22 (dd, J=2.4, 12.8 Hz, 1H), 2.10-1.64 (m, 9H), 1.57-1.35 (m, 7H), 1.31-1.11 (m, 5H), 1.10-0.92 (m, 3H), 0.90-0.82 (m, 7H), 0.81-0.71 (m, 1H), 0.64 (s, 3H).

Step 11: To a solution of n-BuLi (0.468 mL, 2.5 M in hexane, 1.17 mmol) in THF (0.5 mL) at −65° C. under N₂ was added a suspension of A1194 (200 mg, 0.39 mmol) in THF (2.5 mL) dropwise. The mixture was stirred for 30 minutes at −65° C. Then 2,2-dimethyloxirane (42.1 mg, 0.585 mmol) was added dropwise at −65° C. The mixture was stirred for another 30 minutes and then gradually warmed to 25° C. The reaction mixture was stirred at 25° C. for 16 hours. The reaction mixture was quenched with saturated aqueous NH₄Cl (30 mL) and extracted with ethyl acetate (3×20 mL). The combined organic phase was washed with brine (30 mL), dried over Na₂SO₄, filtered and concentrated under vacuum to give A1294 (210 mg) as an oil, which was used directly for the next step.

Step 12: To a solution of A1294 (210 mg, 0.3771 mmol) and nickel(II) chloride (5.02 mg, 0.03875 mmol) in dry methanol (100 mL) was added magnesium powder (372 mg, 15.5 mol) in 3 portions under N₂ with stirring at 50° C. to initiate continuous hydrogen generation. The reaction mixture was stirred at 60° C. for 1 hour. The reaction mixture was quenched with 2 M HCl (30 mL) which was added dropwise at 10° C. until the solid was dissolved. After extracting with EtOAc (2×50 mL), the combined organic layer was washed with saturated aqueous NaHCO₃ (30 mL), brine (30 mL) then dried over Na₂SO₄, filtered and concentrated under vacuum to give a solid, which was purified by silica gel chromatography (PE/EtOAc=10/1) to give 100 mg of impure product, which was triturated from MeCN (5 mL) to give Compound 194 (16.5 mg, 11%) as a solid along with 80 mg of impure product.

$^1$H NMR (400 MHz, CDCl₃) δ 5.40-5.36 (m, 1H), 2.23 (dd, J=2.8, 13.2 Hz, 1H), 2.08-1.89 (m, 4H), 1.85-1.76 (m, 3H), 1.67-1.58 (m, 2H), 1.53-1.32 (m, 9H), 1.32-1.23 (m, 4H), 1.21 (s, 6H), 1.20-1.15 (m, 3H), 1.15-0.97 (m, 4H), 0.93 (d, J=6.8 Hz, 3H), 0.86 (t, J=7.2 Hz, 4H), 0.83-0.74 (m, 1H), 0.68 (s, 3H).

LCMS Rt=1.355 min in 2.0 min chromatography, 30-90AB, purity 94.6% (ELSD), MS ESI calcd. for C₂₈H₄₇O [M+H−H₂O]⁺ 399, found 399.

Example 95: Synthesis of 9567

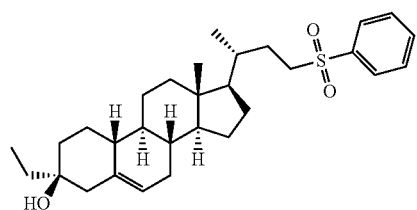
200-N19-4_7

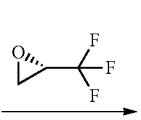
LDA, THF

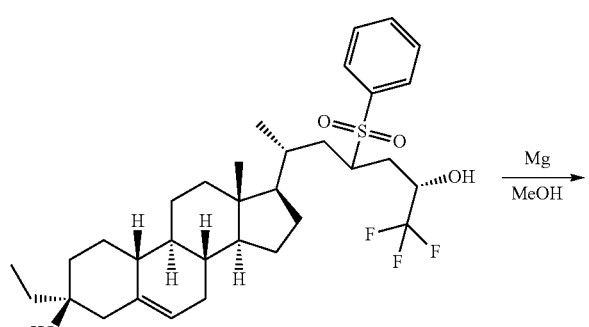
ST-200-52-9_1

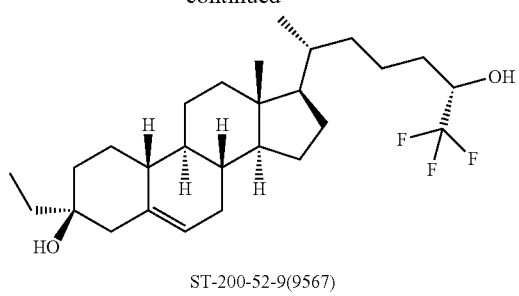
ST-200-52-9(9567)

The synthesis of 200-N19-4_7 can be found in Example 94.

Synthesis of ST-200-52-9_1

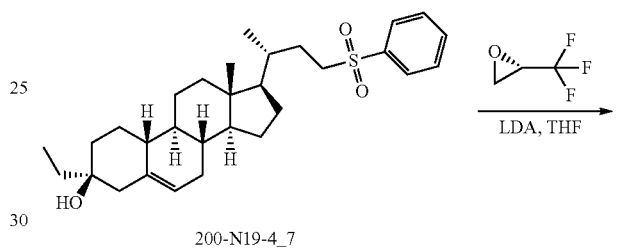
200-N19-4_7

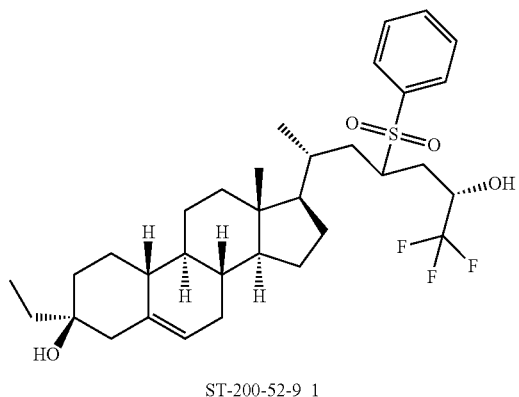
ST-200-52-9_1 n-BuLi (0.99 mL, 2.5 M, 2.47 mmol) was added to a solution of diisopropylamine (0.38 mL, 2.66 mmol) in THF (1 mL) under N₂ at −70° C. The resulting mixture was warmed to 25° C. and stirred at 25° C. for 30 min. After re-cooling to −70° C., a solution of 200-N19-4_7 (0.3 g, 0.62 mmol) in THF (3 mL) was added at −70° C. After stirring at −70° C. for 1 hour, (S)-2-(trifluoromethyl)oxirane (69.3 mg, 0.62 mmol) was added at −70° C. The reaction mixture was warmed to 25° C. and stirred at 25° C. for 18 hours. The reaction mixture was quenched with saturated NH₄Cl aqueous (6 mL) at 0° C. The mixture was extracted with EtOAc (2×8 mL). The combined organic phase was washed with brine (2×10 mL), dried over Na₂SO₄, filtered and concentrated under vacuum to give a crude product, which was used directly for the next step.

419

Synthesis of ST-200-52-9

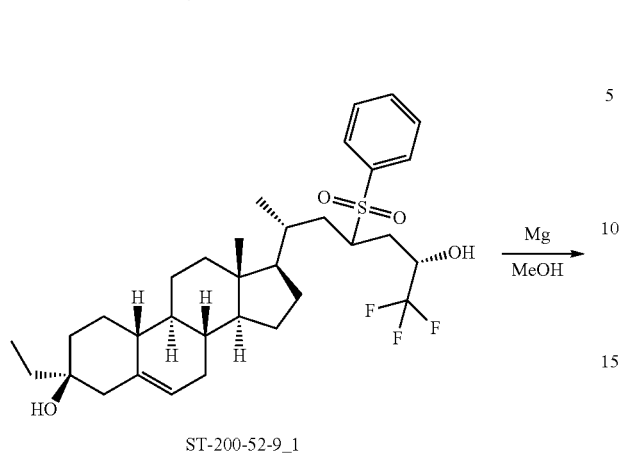

ST-200-52-9_1

ST-200-52-9(9567)

Mg powder (513 mg, 21.4 mmol) was added in 4 portions under $N_2$ with stirring at 50° C. to a solution of ST-200-52-9_1 (320 mg, 0.536 mmol) and $NiCl_2$ (6.91 mg, 0.054 mmol) in dry methanol (50 mL). After stirring at 60° C. for 1 hour, the mixture was quenched with HCl (50 mL, 1N) until the reaction became clear and extracted with EtOAc (3×30 mL). The combined organic phase was dried over $Na_2SO_4$, filtered, concentrated. The residue was purified by flash column (0-15% of EtOAc in PE) to give ST-200-52-9 (11 mg, 5%) as a solid.

$^1$H NMR (400 MHz, $CDCl_3$) δ 5.42-5.35 (m, 1H), 3.95-3.83 (m, 1H), 2.25-2.17 (m, 1H), 2.05-1.83 (m, 5H), 1.83-1.75 (m, 3H), 1.75-1.50 (m, 3H), 1.50-1.30 (m, 6H), 1.30-0.98 (m, 11H), 0.94 (s, 3H), 0.90-0.72 (m, 6H), 0.68 (s, 3H).

LCMS Rt=1.253 min in 2.0 min chromatography, 30-90AB_2 MIN_E, 100% purity, MS ESI calcd. for $C_{27}H_{42}F_3O_2$ $[M+H-H_2O]^+$ 439, found 439.

Example 96: Synthesis of 9670

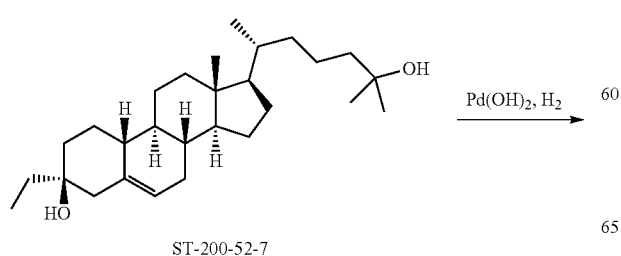

ST-200-52-7

420

-continued

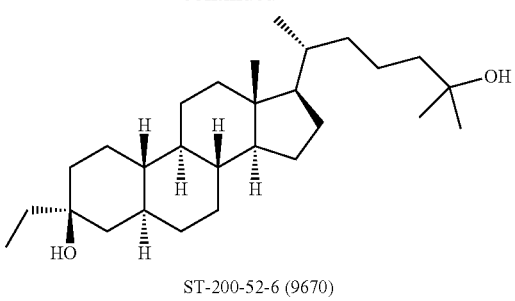

ST-200-52-6 (9670)

The synthesis of ST-200-52-7 can be found in Example 94.

Synthesis of ST-200-52-6

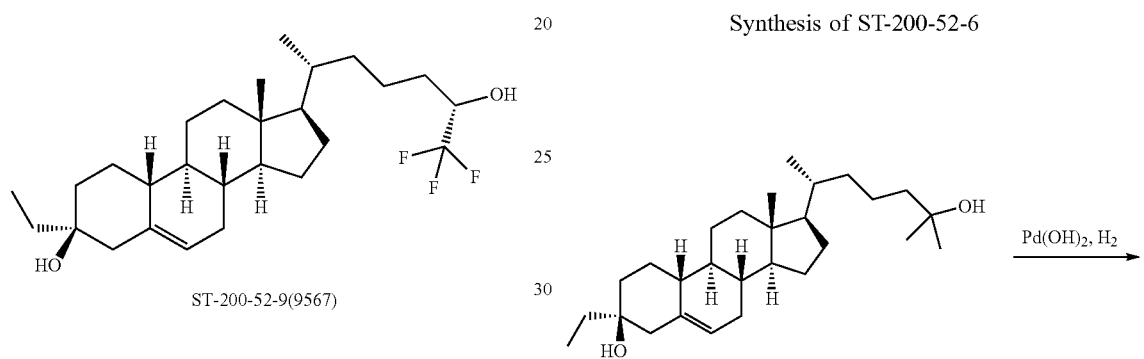

ST-200-52-7

ST-200-52-6 (9670)

Pd(OH)$_2$/C (thy, 200 mg) was added to a solution of ST-200-52-7 (200 mg, 0.479 mmol) in MeOH (30 mL). The mixture was hydrogenated under 50 psi at 50° C. for 48 hrs. The mixture was filtered, concentrated and purified by combi-flash (0-10% of EtOAc in PE) to give ST-200-52-6 (33 mg, 16%) as a a solid.

$^1$H NMR (400 MHz, $CDCl_3$) δ 1.99-1.90 (m, 1H), 1.88-1.75 (m, 3H), 1.69-1.56 (m, 4H), 1.55-1.52 (m, 4H), 1.48-1.32 (m, 5H), 1.31-1.23 (m, 2H), 1.22-1.15 (m, 9H), 1.13-0.99 (m, 9H), 0.95-0.78 (m, 8H), 0.74-0.53 (m, 5H).

LCMS Rt=1.299 min in 2.0 min chromatography, 30-90 AB, purity 100%, MS ESI calcd. for $C_{28}H_{47}[M+H-2H_2O]^+$ 383, found 383.

Example 97: Synthesis of 9792

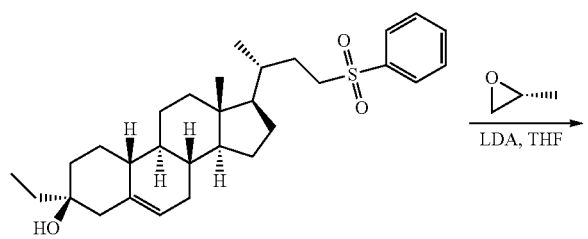

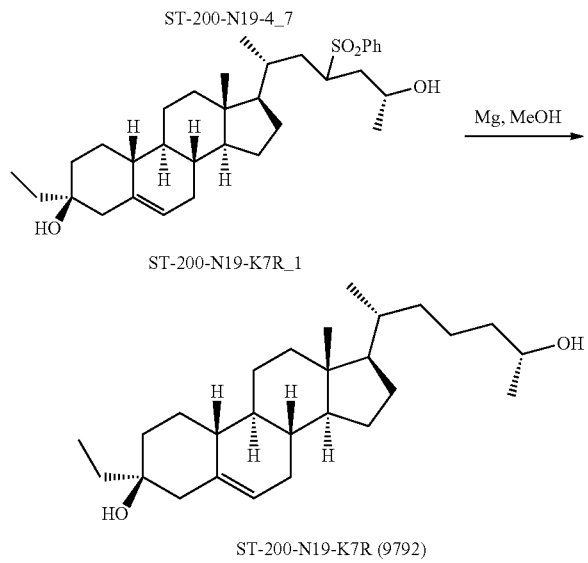

The synthesis of ST-200-N19-4_7 can be found in Example 94.

Synthesis of ST-200-N19-K7R_1

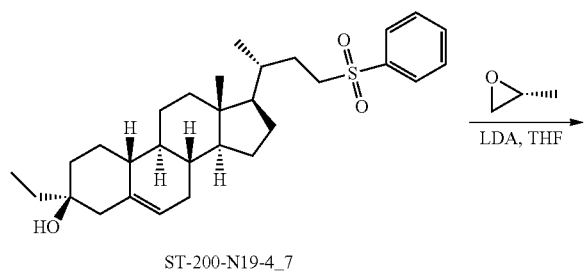

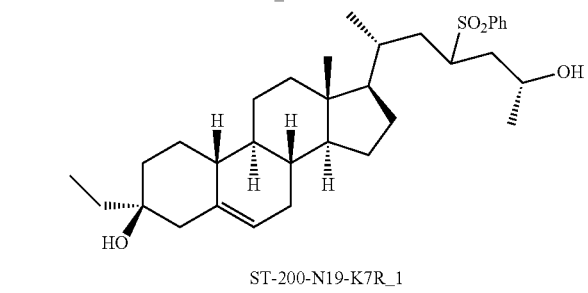

n-BuLi (0.408 mL, 2.5 M, 1.02 mmol, 2.5 eq) was added to THF (0.5 mL) under $N_2$ at −70° C. Next, a suspension of ST-200-N19-4_7 (200 mg, 0.412 mmol, 1.0 eq.) in THF (1.5 mL) was added dropwise to give a suspension. After stirring at −70° C. for 30 min, (R)-2-methyloxiraane (35.8 mg, 0.618 mmol, 1.5 eq.) was added dropwise. Then reaction was stirred at 25° C. for 12 hrs. The reaction was quenched with sat.$NH_4Cl$ (30 mL), extracted with EtOAc (3×15 mL). The combined organic layers were dried over $Na_2SO_4$, filtered and concentrated to give crude product (250 mg) as a solid, which was used directly for the next step.

Synthesis of ST-200-N19-K7R

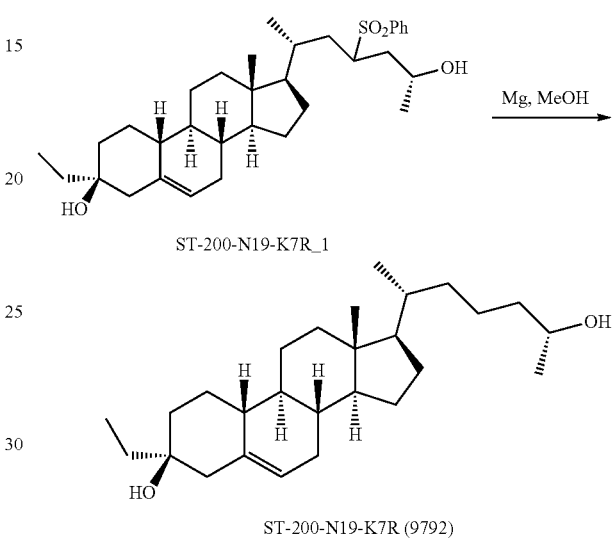

Mg powder (441 mg, 18.4 mmol) was added in one portion to a solution of ST-200-N19-K7R_1 (250 mg, 0.46 mmol) in MeOH (30 mL) at 65° C. The mixture was stirred at 65° C. for 1 h. The mixture was quenched with HCl (50 mL, 2 M) until the reaction became clear and extracted with DCM (3×15 mL). The combined organic phase was dried over $Na_2SO_4$, filtered, concentrated and purified by flash column (0-10% of EtOAc in PE) to give ST-200-N19-K7R (27 mg, 14%) as a solid.

$^1$H NMR (400 MHz, $CDCl_3$) δ 5.40-5.36 (m, 1H), 3.87-3.71 (m, 1H), 2.27-2.18 (m, 1H), 2.08-1.88 (m, 4H), 1.87-1.73 (m, 3H), 1.67-1.58 (m, 1H), 1.53-1.34 (m, 9H), 1.31-1.22 (m, 5H), 1.21-1.11 (m, 7H), 1.10-0.98 (m, 3H), 0.95-0.89 (m, 3H), 0.88-0.83 (m, 4H), 0.82-0.74 (m, 1H), 0.67 (s, 3H).

LCMS Rt=1.246 min in 2.0 min chromatography, 30-90 AB_E, purity 100%, MS ESI calcd. for $C_{27}H_{45}O$ [M+H−$H_2O$]$^+$ 385, found 385.

Example 98: Synthesis of 9810 and 9813

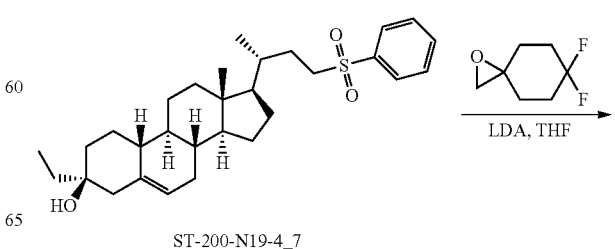

-continued

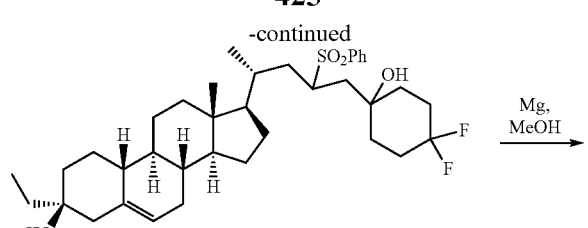

ST-200-N19-K14_1

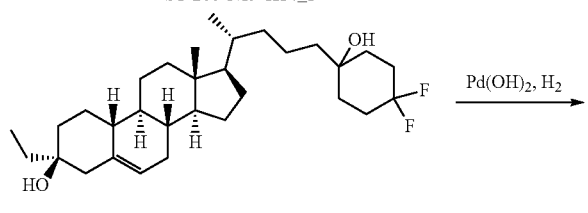

ST-200-N19-K14 (9810)

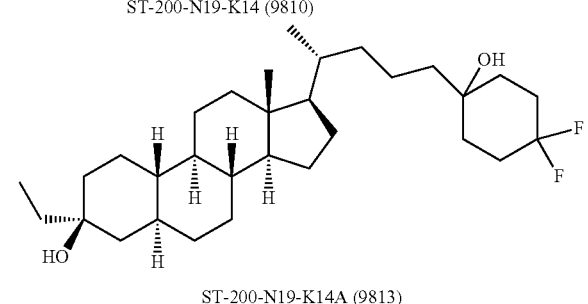

ST-200-N19-K14A (9813)

The synthesis of ST-200-N19-4_7 can be found in Example 94. The synthesis of 6,6-difluoro-1-oxaspiro[2.5]octane can be found in Example 87.

Synthesis of ST-200-N19-K14_1

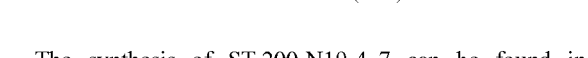

ST-200-N19-4_7

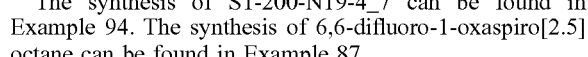

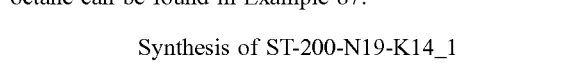

ST-200-N19-K14_1 n-BuLi (0.656 mL, 2.5 M in hexane, 1.64 mmol) was added to a solution of diisopropylamine (179 mg, 0.442 mmol) in THF (1 mL) under $N_2$ at −70° C. The mixture was warmed to 25° C. After re-cooling to −70° C., a suspension of ST-200-N19-4_7 (200 mg, 0.412 mmol) in THF (5 mL) was added dropwise under $N_2$. After stirring at −70° C. for 30 min, 6,6-difluoro-1-oxaspiro[2.5]octane (91.5 mg, 0.618 mmol) was added at −70° C. The reaction mixture was warmed to 25° C. slowly and stirred at 25° C. for 16 hours. The reaction mixture was quenched with saturated $NH_4Cl$ aqueous (15 mL). The mixture was extracted with EtOAc (2×15 mL). The combined organic phase was washed with brine (2×20 mL), dried over $Na_2SO_4$, filtered and concentrated under vacuum to give ST-200-N19-K14_1 (200 mg, crude) as an oil, which was used directly for the next step.

Synthesis of ST-200-N19-K14

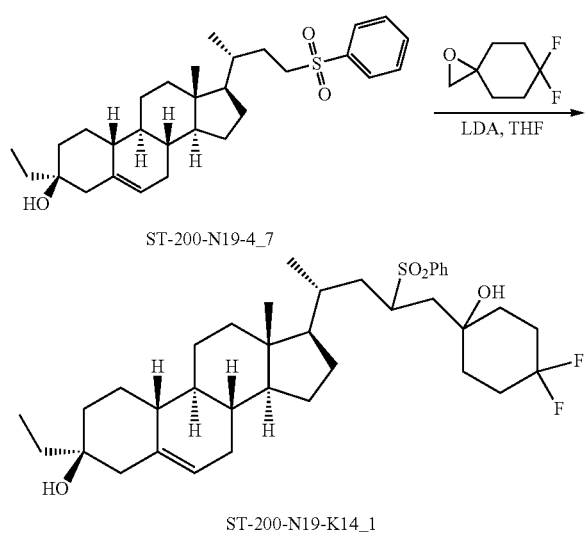

ST-200-N19-K14_1

ST-200-N19-K14 (9810)

A solution of ST-200-N19-K14_1 (200 mg, 0.316 ummol) in MeOH (30 mL) was heated at 65° C. Mg powder (302 mg, 12.6 mmol) and $NiCl_2$ (12.1 mg, 0.0948 umol) were added in one portion at 65° C. The mixture was reflux at 65° C. for 1 h and quenched with HCl (50 mL, 2N) until the reaction became clear. The mixture was extracted with DCM (3×20 mL). The combined organic layer was dried over $Na_2SO_4$, filtered, concentrated and purified by silica gel chromatography (0-15% of EtOAc in PE) to give ST-200-N19-K14 (100 mg, 64%) as a solid.

$^1$H NMR (400 MHz, $CDCl_3$) δ 5.41-5.36 (m, 1H), 2.27-2.20 (m, 1H), 2.19-2.03 (m, 3H), 2.02-1.88 (m, 5H), 1.86-1.73 (m, 3H), 1.71-1.59 (m, 5H), 1.54-1.33 (m, 10H), 1.32-1.15 (m, 6H), 1.14-1.00 (m, 4H), 0.99-0.97 (m, 1H), 0.96-0.89 (m, 3H), 0.88-0.74 (m, 5H), 0.68 (s, 3H).

LCMS Rt=1.322 min in 2.0 min chromatography, 30-90 AB_E, purity 100%, MS ESI calcd. for $C_{31}H_{47}F_2$ [M+H−2H$_2$O]$^+$ 457, found 457.

Synthesis of ST-200-N19-K14A

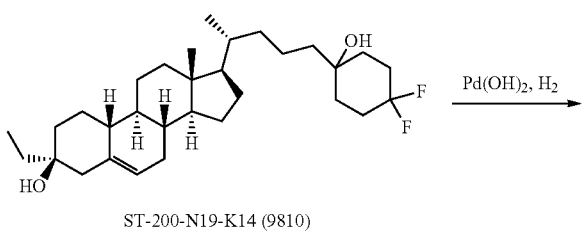

ST-200-N19-K14 (9810)

425

-continued

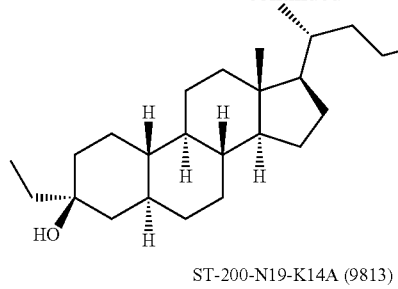

ST-200-N19-K14A (9813)

Pd(OH)$_2$ (70 mg, dry) was added to a solution of ST-200-N19-K14 (70 mg, 0.142 mmol) in MeOH (20 mL). The mixture was hydrogenated at 50° C. (50 Psi) for 48 hrs. The mixture was filtered, concentrated and purified by combi-flash (0-10% of EtOAc in PE) to give ST-200-N19-K14A (20 mg, 28%) as a solid.

$^1$H NMR (400 MHz, CDCl$_3$) δ 2.24-1.99 (m, 2H), 1.97-1.73 (m, 6H), 1.71-1.57 (m, 8H), 1.55-1.32 (m, 8H), 1.30-1.16 (m, 4H), 1.13-0.97 (m, 11H), 0.94-0.78 (m, 8H), 0.74-0.55 (m, 5H).

LCMS Rt=1.344 min in 2.0 min chromatography, 30-90 AB_E, purity 100%, MS ESI calcd. for C$_{31}$H$_{49}$F$_2$[M+H−2H$_2$O]$^+$ 459, found 459.

Example 99: Synthesis of 9911

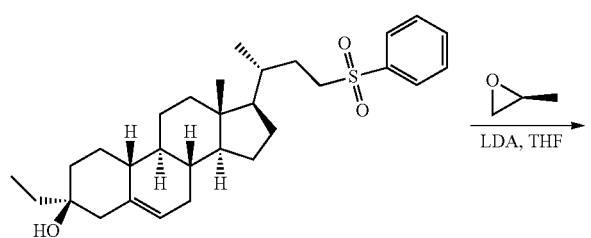

ST-200-N19-4_7

The experimental of intermediate ST-200-N19-4_7 can be found in Example 94.

426

Synthesis of ST-200-N19-K75_1

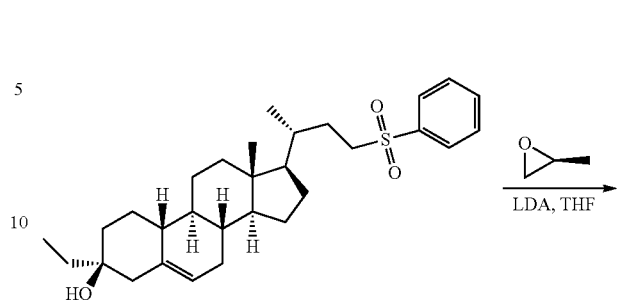

n-BuLi (0.408 mL, 2.5 M, 1.02 mmol) was added to THF (0.5 mL) under N$_2$ at −70° C. After that, a suspension of ST-200-N19-4_7 (200 mg, 0.412 mmol, 1.0 eq.) in THF (1.5 mL) was added dropwise to give a suspension. After stirring at −70° C. for 30 min, (S)-2-methyloxirane (35.8 mg, 0.618 mmol) was added dropwise. Then reaction was stirred at 25° C. for 12 hrs. The reaction was quenched with sat.NH$_4$Cl (30 mL), extracted with EtOAc (3×15 mL). The combined organic layers were dried over Na$_2$SO$_4$, filtered and concentrated to give crude product (250 mg) as a a solid, which was used directly for the next step.

Synthesis of ST-200-N19-K7S

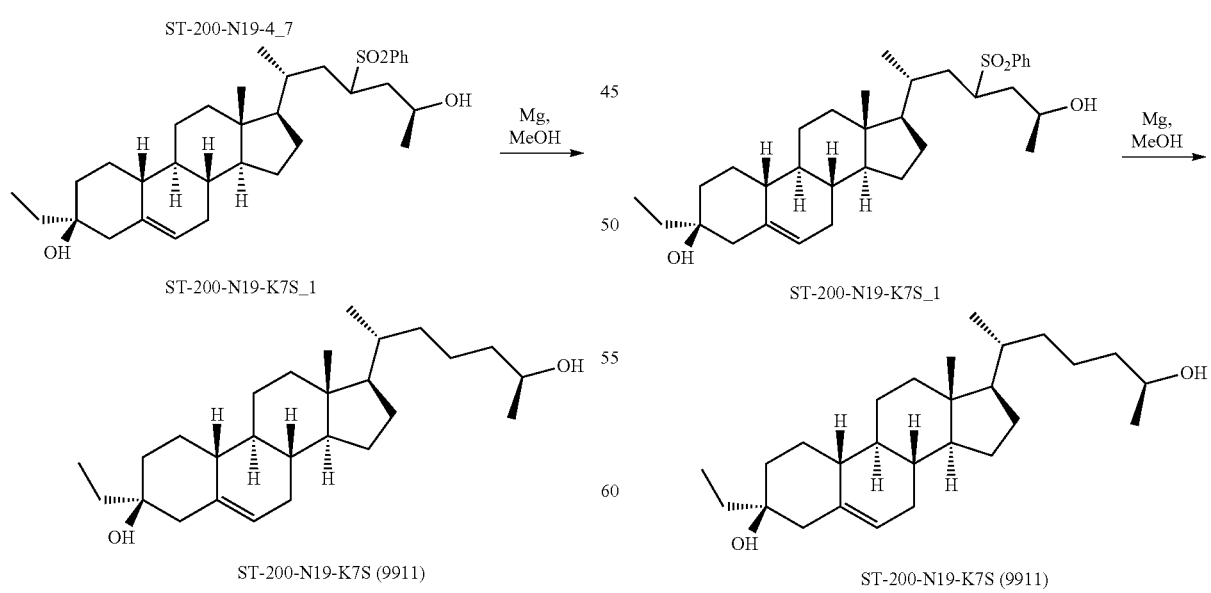

Mg powder (357 mg, 14.7 mmol) was added to a solution of ST-200-N19-K7S_1 (200 mg, 0.368 mmol) and nickel (II)

chloride (9.53 mg, 0.074 mmol) in dry methanol (50 mL) under N₂ and the resulting mixture was stirred at 50° C. to initiate continuous hydrogen generation. The reaction mixture was stirred at 60° C. for 1 hour. The reaction mixture was quenched by 2M HCl (100 mL) which was added dropwise at 10° C. until solid was dissolved. After extracting with EtOAc (2×150 mL), the combined organic layer was washed with sat. NaHCO₃ aq. (300 mL), brine (300 mL), dried over Na₂SO₄, filtered and concentrated under vacuum to give a solid, which was purified by silica gel chromatography (PE/THF=4/1) to give a crude residue, which was purified by re-chrystallization from MeCN (10 mL) to afford ST-200-N19-K7S (52 mg, 35%) as a solid.

¹H NMR (400 MHz, CDCl₃) δ 5.40-5.35 (m, 1H), 3.80-3.70 (m, 1H), 2.25-2.20 (m, 1H), 2.05-1.75 (m, 7H), 1.69-1.15 (m, 20H), 1.14-0.70 (m, 13H), 0.67 (s, 3H).

LCMS Rt=1.241 min in 2.0 min chromatography, 30-90 AB, purity 100%, MS ESI calcd. for C₂₇H₄₅O [M+H−H₂O]⁻ 385, found 385.

Example 100: Synthesis for 10012, 10042, and 10043

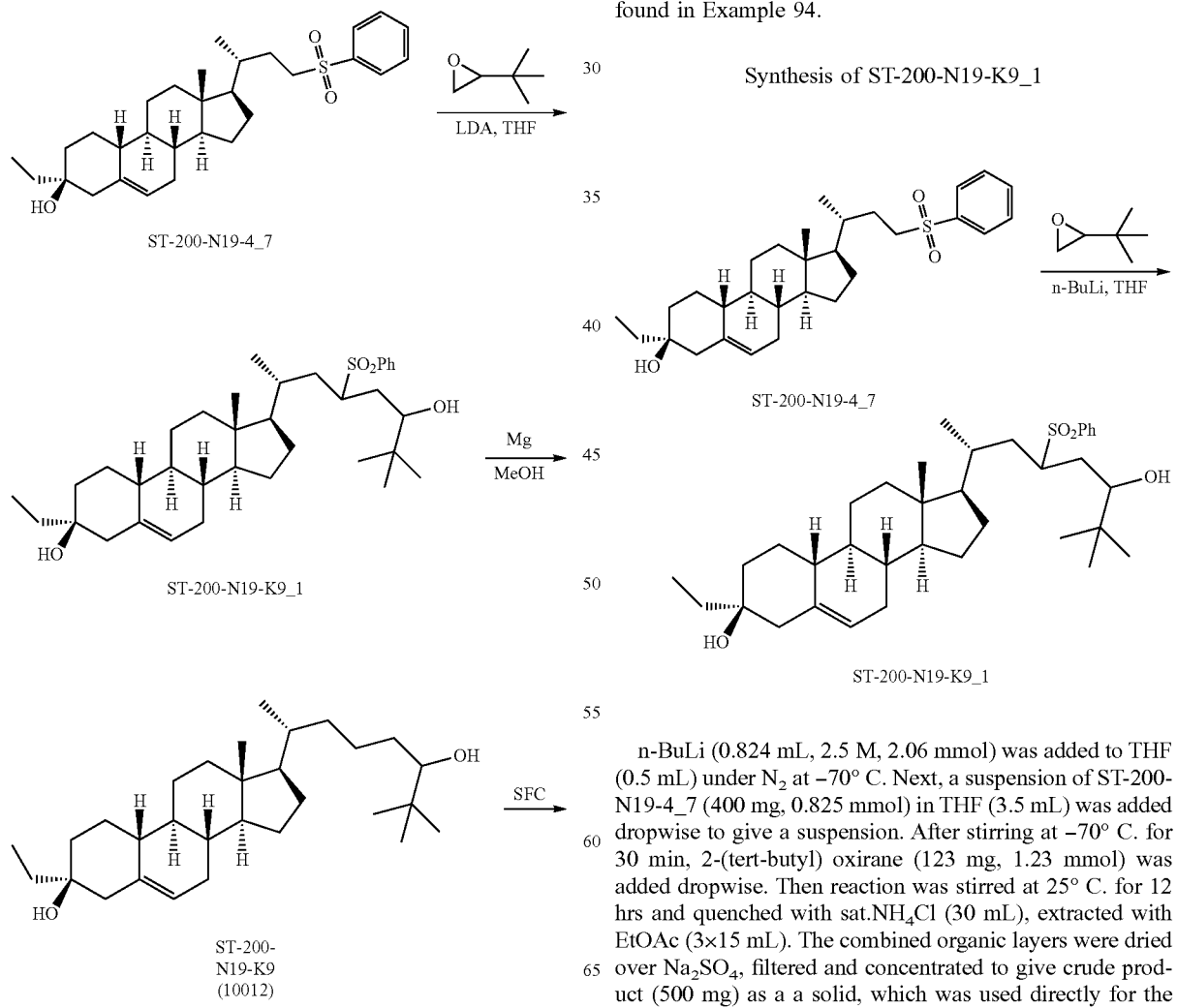

The experimental of intermediate ST-200-N19-4_7 can be found in Example 94.

Synthesis of ST-200-N19-K9_1 n-BuLi (0.824 mL, 2.5 M, 2.06 mmol) was added to THF (0.5 mL) under N₂ at −70° C. Next, a suspension of ST-200-N19-4_7 (400 mg, 0.825 mmol) in THF (3.5 mL) was added dropwise to give a suspension. After stirring at −70° C. for 30 min, 2-(tert-butyl) oxirane (123 mg, 1.23 mmol) was added dropwise. Then reaction was stirred at 25° C. for 12 hrs and quenched with sat.NH₄Cl (30 mL), extracted with EtOAc (3×15 mL). The combined organic layers were dried over Na₂SO₄, filtered and concentrated to give crude product (500 mg) as a a solid, which was used directly for the next step.

Synthesis of ST-200-N19-K9 (10012)

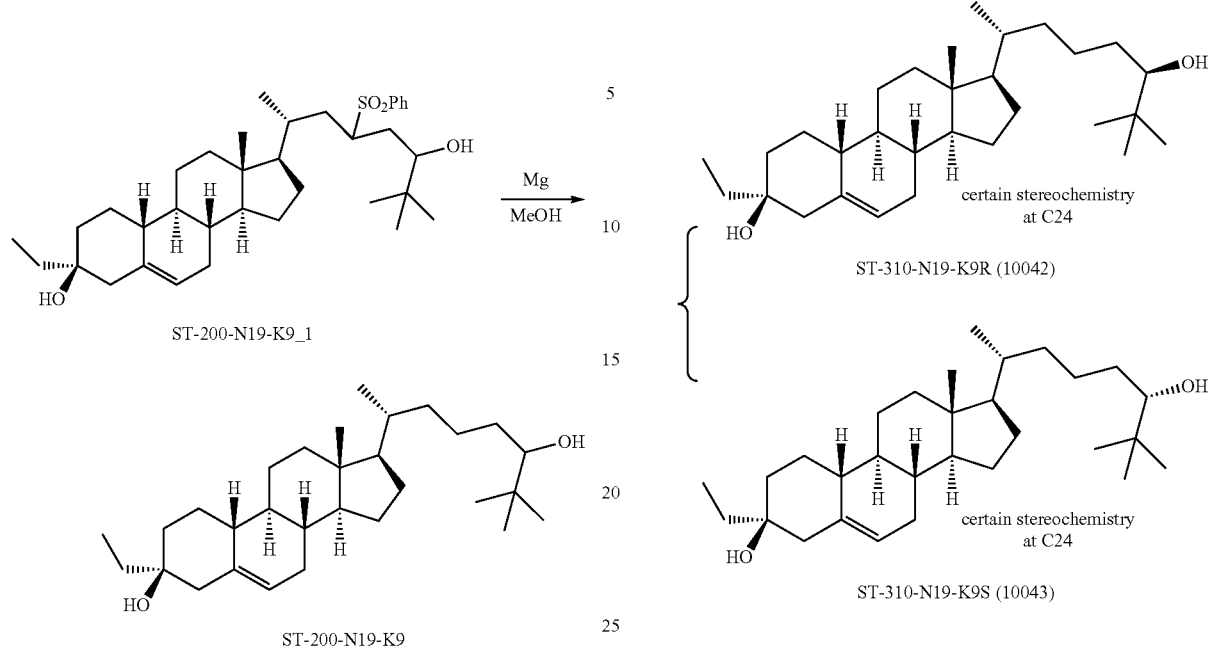

Mg powder (663 mg, 27.3 mmol) was added to a solution of ST-200-N19-K9_1 (400 mg, 0.683 mmol) and nickel (II) chloride (17.6 mg, 0.136 mmol) in dry methanol (50 mL) under N₂ and the resulting mixture was stirred at 50° C. to initiate continuous hydrogen generation. The reaction mixture was stirred at 60° C. for 1 hour. The reaction mixture was quenched by 2M HCl (100 mL) which was added dropwise at 10° C. until solid was dissolved. After extracting with EtOAc (2×150 mL), the combined organic layer was washed with sat. NaHCO₃ aq. (300 mL), brine (300 mL), dried over Na₂SO₄, filtered and concentrated under vacuum to give a solid, which was purified by silica gel chromatography (PE/THF=4/1) to give a crude product, which was re-crystallized from MeCN (10 mL) to afford ST-200-N19-K9 (160 mg, 53%) as a solid.

$^1$H NMR (400 MHz, CDCl$_3$) δ 5.40-5.35 (m, 1H), 3.25-3.15 (m, 1H), 2.25-2.20 (m, 1H), 2.10-1.60 (m, 9H), 1.50-1.00 (m, 19H), 0.90-0.75 (m, 18H), 0.67 (s, 3H).

LCMS Rt=1.412 min in 2.0 min chromatography, 30-90 AB, purity 100%, MS ESI calcd. for C$_{30}$H$_{51}$O [M+H−H$_2$O]$^+$ 427, found 427.

ST-200-N19-K9 (120 mg, 0.269 mmol) was purified by SFC (AD(250 mm*30 mm, 10 um), gradient: 40-40% B (A=0.1% NH$_3$/H$_2$OIPA, B=MeOH), flow rate: 60 mL/min) to give ST-200-N19-K9R (Peak 1, 44 mg, 37%) and ST-200-N19-K9S (Peak 2, 45 mg, 38%) as a solid. The stereochemistry at C25 of 10042 and 10043 was confirmed by asymmetric synthesis of 10042 and 10043 from chiral epoxides.

ST-200-N19-K9R (10042):

$^1$H NMR (400 MHz, CDCl$_3$) δ 5.40-5.35 (m, 1H), 3.25-3.15 (m, 1H), 2.25-2.20 (m, 1H), 2.10-1.55 (m, 9H), 1.50-1.30 (m, 8H), 1.29-1.00 (m, 11H), 0.95-0.75 (m, 18H), 0.67 (s, 3H).

LCMS Rt=1.402 min in 2.0 min chromatography, 30-90 AB, purity 100%, MS ESI calcd. for C$_{30}$H$_{51}$O [M+H−H$_2$O]$^+$ 427, found 427.

SFC Rt=6.347 min in 10 min chromatography, AD_3_IPA_DEA5_40_25ML, 100% de.

ST-200-N19-K9S (10043):

$^1$H NMR (400 MHz, CDCl$_3$) δ 5.40-5.35 (m, 1H), 3.25-3.15 (m, 1H), 2.25-2.20 (m, 1H), 2.10-1.75 (m, 7H), 1.74-1.35 (m, 7H), 1.34-1.00 (m, 13H), 0.99-0.75 (m, 19H), 0.67 (s, 3H).

LCMS Rt=1.402 min in 2.0 min chromatography, 30-90 AB, purity 99.2%, MS ESI calcd. for C$_{30}$H$_{51}$O [M+H−H$_2$O]$^-$ 427, found 427.

SFC Rt=6.940 min in 10 min chromatography, AD_3_IPA_DEA_5_40_25ML, 99.5% de.

Synthesis of 10042 and 10043

Synthesis for Confirming Stereochemistry

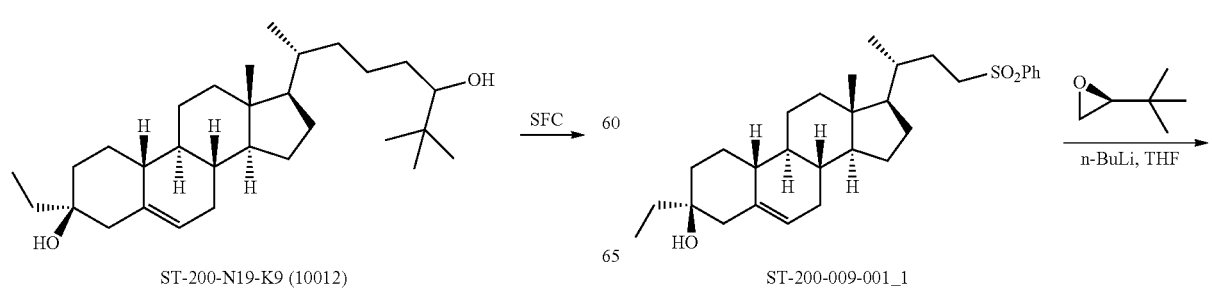

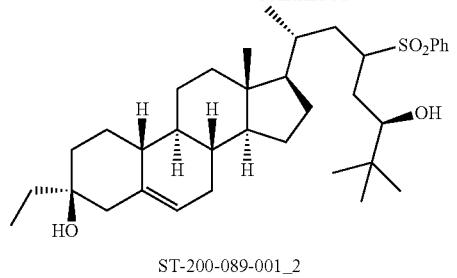

ST-200-089-001_2

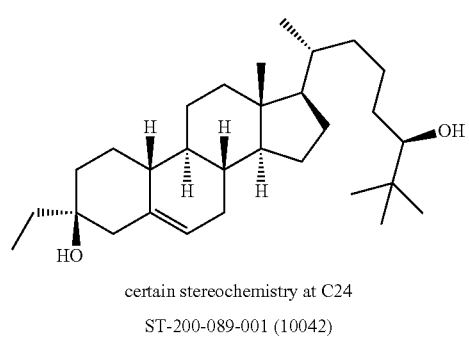

certain stereochemistry at C24
ST-200-089-001 (10042)

ST-200-009-001_1 (300 mg, 0.618 mmol) in THF (2 mL, dry) was added to a solution of n-BuLi (0.616 mL, 2.5 M in hexane) in THF (0.5 mL, dry) at −70° C. After stirring at −70° C. for 0.5 h, a solution of (S)-2-(tert-butyl)oxirane (92.7 mg, 0.926 mmol) in THF (0.5 mL, dry) was added dropwise. After stirring at 25° C. for another 16 hrs, the mixture was quenched with sat. NH₄Cl (5 mL). The mixture was extracted with EtOAc (2×10 mL). The combined organic layer was washed with brine (5 mL), dried over Na₂SO₄, filtered and concentrated to give ST-200-089-001_2 (360 mg, crude) as a solid, which was used directly for next step.

NiCl₂ (8.85 mg, 0.683 mmol) was added to a mixture of ST-200-089-001_2 (360 mg, crude) in MeOH (20 mL) at 25° C. Then the mixture was stirred at 60° C. and Mg powder (828 mg, 34.1 mmol) was added in three bathes for 2 hrs. The reaction was quenched with HCl (1M, 10 mL), the mixture was extracted with EtOAc (2×15 mL). The combined organic layer was washed with brine (10 mL), dried over Na₂SO₄, filtered and concentrated. The residue was purified by flash-combi (0~30% of EtOAc in PE) to give ST-200-089-001 (115 mg, impure) as a solid, which was further purified by SFC (AD(250 mm*30 mm, 10 um), gradient: 40-40% B (A=0.1% NH₃/H₂OIPA, B=MeOH), flow rate: 50 mL/min) to give ST-200-089-001 (77 mg, 28% yield for 2 steps) as a solid.

$^1$H NMR (400 MHz, CDCl₃) δ 5.41-5.35 (m, 1H), 3.25-3.15 (m, 1H), 2.25-2.20 (m, 1H), 2.10-1.90 (m, 4H), 1.90-1.75 (m, 3H), 1.69-1.50 (m, 3H), 1.50-1.33 (m, 8H), 1.33-1.13 (m, 7H), 1.13-0.98 (m, 4H), 0.98-0.90 (m, 3H), 0.90-0.78 (m, 14H), 0.67 (s, 3H).

LCMS Rt=1.467 min in 2 min chromatography, 30-90AB_2 MIN_E, purity 100%, MS ESI calcd. for C₃₀H₅₁O [M+H−H₂O]⁺ 427, found 427.

SFC Rt=6.135 min in 10 min chromatography, AD_3_EtOH_DEA_5_40_25ML, 100% de.

Example 101: Synthesis for 10114 and 10115

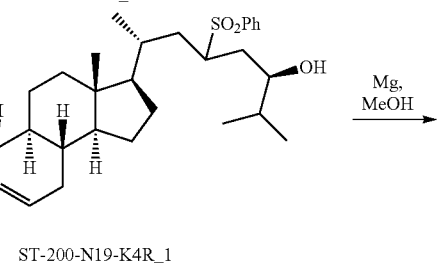

ST-200-N19-4_7

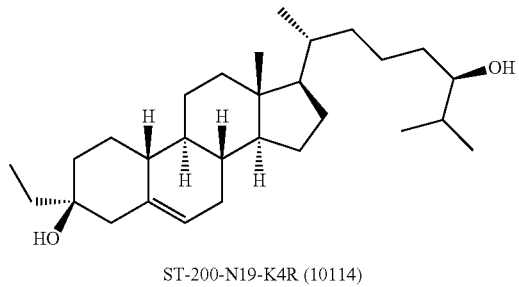

ST-200-N19-K4R_1

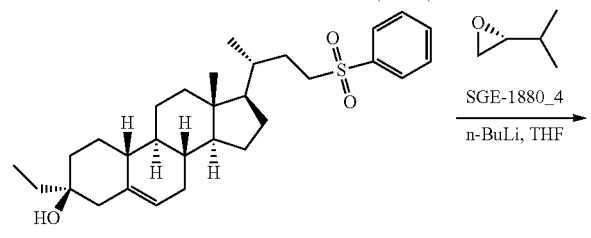

ST-200-N19-K4R (10114)

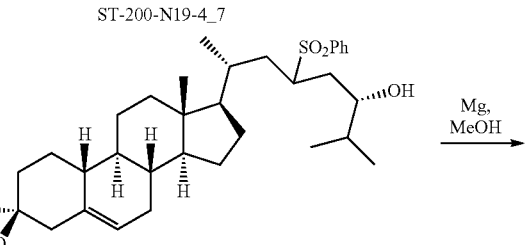

ST-200-N19-4_7

ST-200-N19-K4S_1

ST-200-N19-K4S (10115)

The synthesis of ST-200-N19-4_7 can be found in Example 94.

Synthesis of ST-200-N19-K4R_1

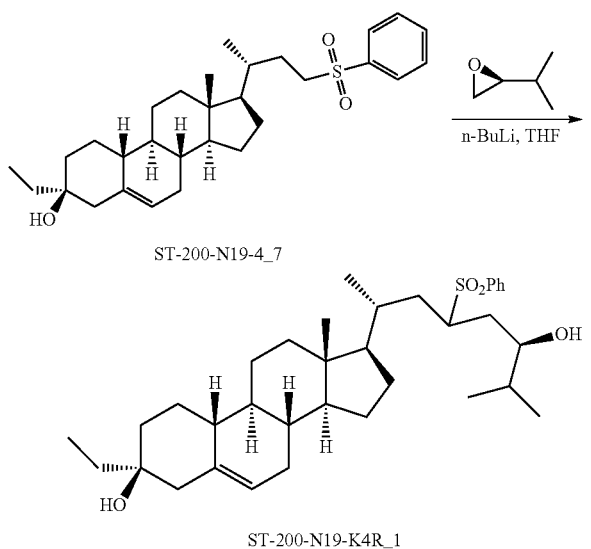

n-BuLi (0.408 mL, 2.5 M, 1.02 mmol, 2.5 eq) was added to THF (0.5 mL) under $N_2$ at −70° C. Next, a suspension of ST-200-N19-4_7 (200 mg, 0.412 mmol, 1.0 eq.) in THF (1.5 mL) was added dropwise to give a suspension. After stirring at −70° C. for 30 min, (S)-2-isopropyloxirane (53.2 mg, 0.618 mmol, 1.5 eq.) was added dropwise. Then reaction was stirred at 25° C. for 12 hrs. The reaction was quenched with sat.$NH_4Cl$ (30 mL), extracted with EtOAc (3×15 mL). The combined organic layers were dried over $Na_2SO_4$, filtered and concentrated to give crude product (250 mg) as a solid, which was used directly for the next step.

Synthesis of ST-200-N19-K4R

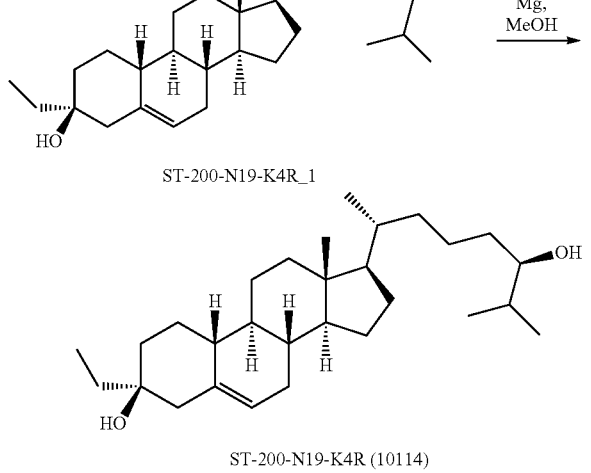

$NiCl_2$ (11.3 mg, 0.0874 mmol) and Mg powder (417 mg, 17.4 mmol) were added in one portion to a solution of ST-200-N19-K4R_1 (250 mg, 0.437 mmol) in MeOH (30 mL) at 65° C. The mixture was stirred at 65° C. for 1 h. The mixture was quenched with HCl (50 mL, 2 N) until the reaction became clear and extracted with DCM (3×20 mL). The combined organic phase was dried over $Na_2SO_4$, filtered, concentrated and purified by flash column (0-10% of EtOAc in PE) to give ST-200-N19-K4R (38 mg, 20%) as a solid.

$^1$H NMR (400 MHz, $CDCl_3$) δ 5.41-5.36 (m, 1H), 3.41-3.31 (m, 1H), 2.27-2.20 (m, 1H), 2.07-1.89 (m, 4H), 1.88-1.75 (m, 3H), 1.70-1.59 (m, 3H), 1.54-1.33 (m, 10H), 1.30-1.16 (m, 6H), 1.15-0.97 (m, 4H), 0.95-0.88 (m, 9H), 0.88-0.82 (m, 4H), 0.82-0.74 (m, 1H), 0.68 (s, 3H).

LCMS Rt=1.362 min in 2.0 min chromatography, 30-90 AB_E, purity 100%, MS ESI calcd. for $C_{29}H_{49}O$ $[M+H-H_2O]^+$ 413, found 413.

Synthesis of ST-200-N19-K4S_1

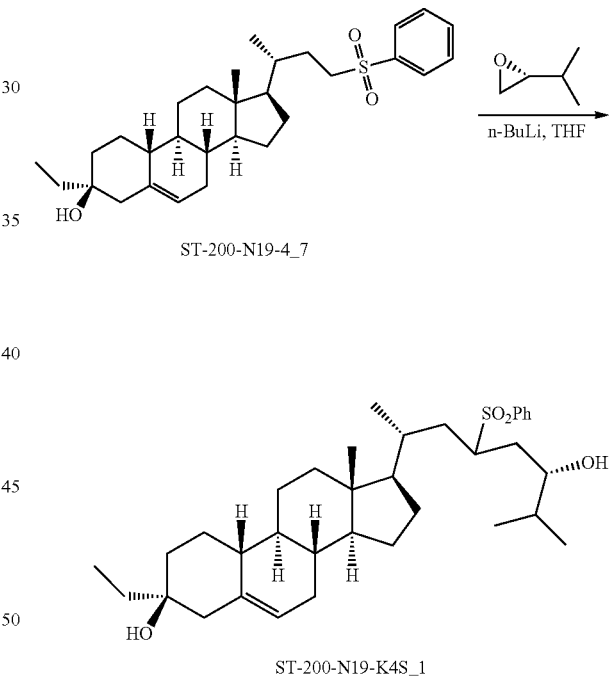

n-BuLi (0.408 mL, 2.5 M, 1.02 mmol, 2.5 eq) was added to THF (0.5 mL) under $N_2$ at −70° C. Next, a suspension of ST-200-N19-4_7 (200 mg, 0.412 mmol, 1.0 eq.) in THF (1.5 mL) was added dropwise to give a suspension. After stirring at −70° C. for 30 min, (R)-2-isopropyloxirane (53.2 mg, 0.618 mmol, 1.5 eq.) was added dropwise. Then reaction was stirred at 25° C. for 12 hrs. The reaction was quenched with sat.$NH_4Cl$ (30 mL), extracted with EtOAc (3×15 mL). The combined organic layers were dried over $Na_2SO_4$, filtered and concentrated to give crude product (250 mg) as a solid, which was used directly for the next step.

Synthesis of ST-200-N19-K4S

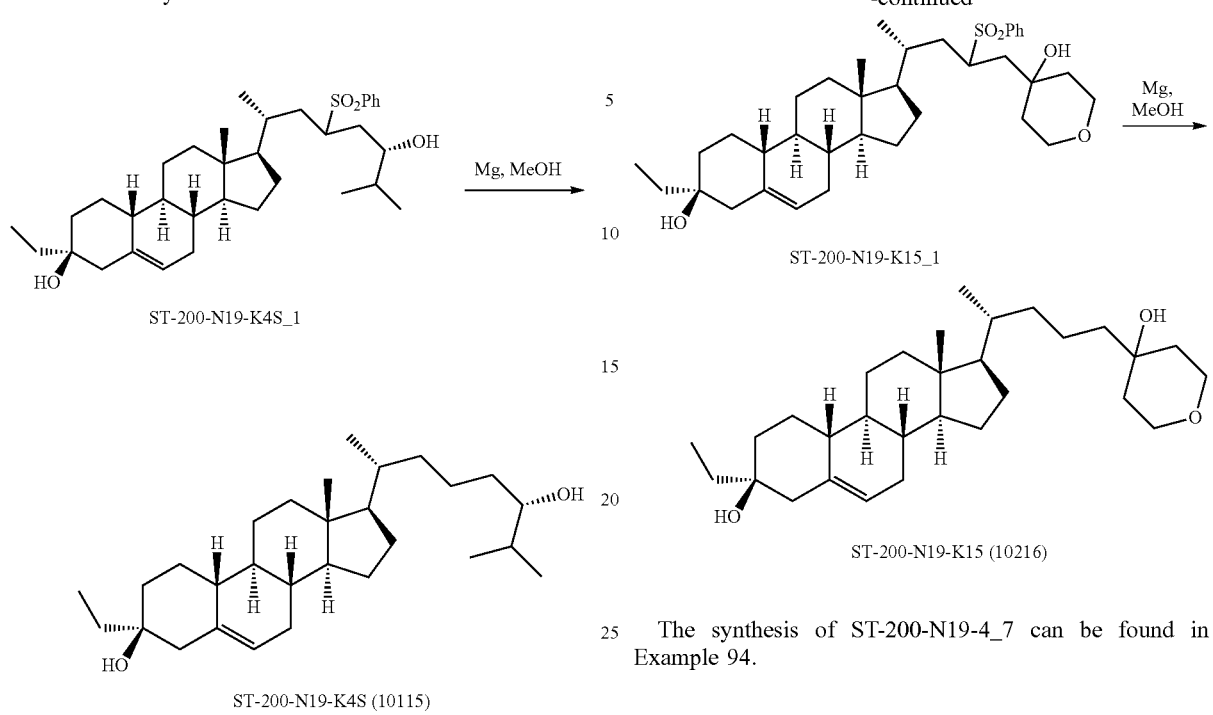

NiCl₂ (11.3 mg, 0.0874 mmol) and Mg powder (417 mg, 17.4 mmol) were added in one portion to a solution of ST-200-N19-K4S_1 (250 mg, 0.437 mmol) in MeOH (30 mL) at 65° C. The mixture was stirred at 65° C. for 1 h. The mixture was quenched with HCl (50 mL, 2 N) until the reaction became clear and extracted with DCM (3×20 mL). The combined organic phase was dried over Na₂SO₄, filtered, concentrated and purified by flash column (0-10% of EtOAc in PE) to give ST-200-N19-K4S (36 mg, 19%) as a solid.

¹H NMR (400 MHz, CDCl₃) δ 5.41-5.36 (m, 1H), 3.41-3.31 (m, 1H), 2.27-2.20 (m, 1H), 2.07-1.89 (m, 4H), 1.88-1.75 (m, 3H), 1.71-1.57 (m, 3H), 1.55-1.35 (m, 9H), 1.34-1.23 (m, 4H), 1.22-0.99 (m, 7H), 0.95-0.89 (m, 9H), 0.88-0.82 (m, 4H), 0.82-0.74 (m, 1H), 0.68 (s, 3H).

LCMS Rt=1.356 min in 2.0 min chromatography, 30-90 AB_E, purity 100%, MS ESI calcd. for C₂₉H₄₉O [M+H−H₂O]⁺ 413, found 413.

Example 102: Synthesis for 10216

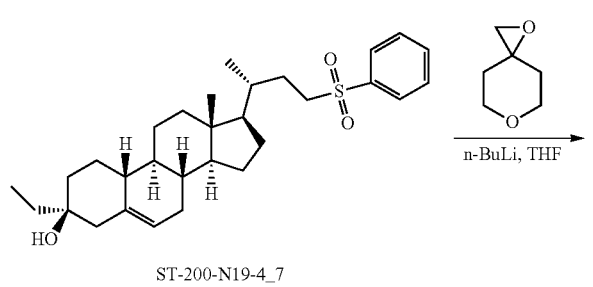

The synthesis of ST-200-N19-4_7 can be found in Example 94.

Synthesis of ST-200-N19-K15_1 n-BuLi (0.408 mL, 2.5 M, 1.02 mmol, 2.5 eq) was added to THF (0.5 mL) under N₂ at −70° C. Next, a suspension of ST-200-N19-4_7 (200 mg, 0.412 mmol, 1.0 eq.) in THF (1.5 mL) was added dropwise to give a suspension. After stirring at −70° C. for 30 min, 1,6-dioxaspiro[2.5]octane (70.5 mg, 0.618 mmol, 1.5 eq.) was added dropwise. Then reaction was stirred at 25° C. for 12 hrs. The reaction was quenched with sat.NH₄Cl (30 mL), extracted with EtOAc (3×15 mL). The combined organic layers were dried over Na₂SO₄, filtered and concentrated to give crude product (250 mg) as a solid, which was used directly for the next step.

Synthesis of ST-200-N19-K15

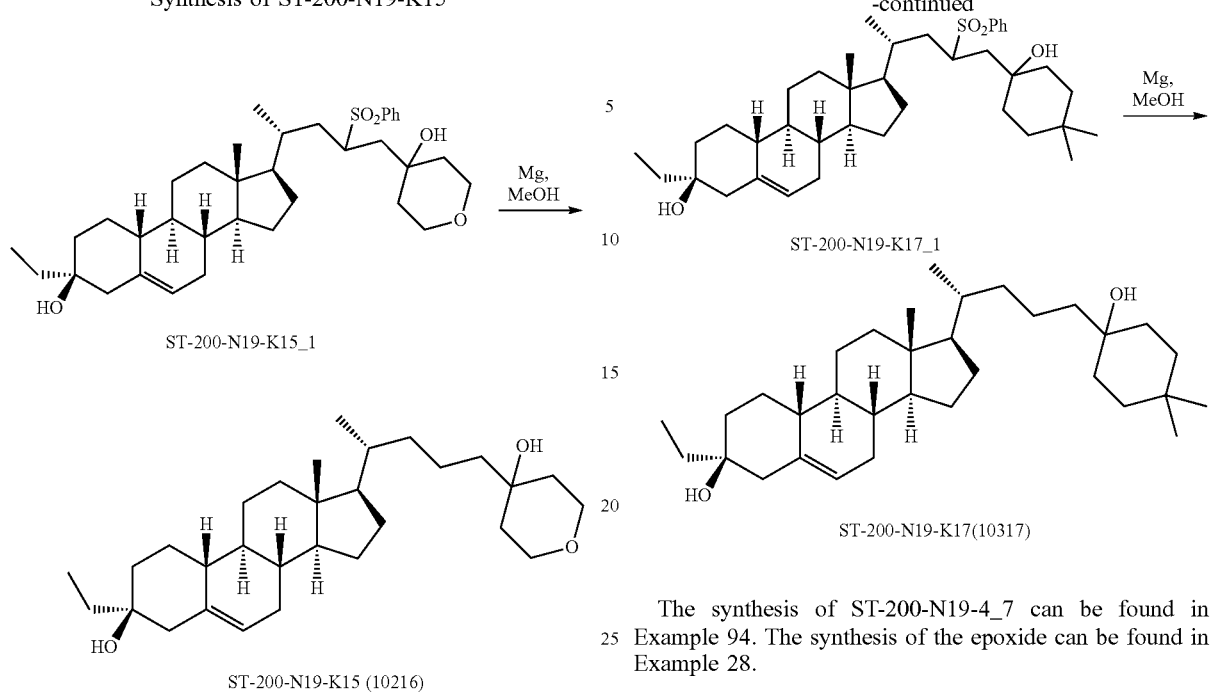

NiCl₂ (10.8 mg, 0.0834 mmol) and Mg powder (398 mg, 16.6 mmol) were added in one portion to a solution of ST-200-N19-K15_1 (250 mg, 0.417 mmol) in MeOH (30 mL) at 65° C. The mixture was stirred at 65° C. for 1 h. The mixture was quenched with HCl (50 mL, 2 N) until the reaction became clear and extracted with DCM (3×20 mL). The combined organic phase was dried over Na₂SO₄, filtered, concentrated and purified by flash column (0-10% of EtOAc in PE) to give ST-200-N19-K15 (43 mg, 22%) as a solid.

$^1$H NMR (400 MHz, CDCl₃) δ 5.44-5.33 (m, 1H), 3.81-3.69 (m, 4H), 2.27-2.19 (m, 1H), 2.07-1.88 (m, 4H), 1.87-1.76 (m, 3H), 1.71-1.58 (m, 3H), 1.53-1.32 (m, 11H), 1.31-1.13 (m, 7H), 1.12-1.07 (m, 2H), 1.06-0.95 (m, 3H), 0.94-0.89 (m, 3H), 0.88-0.82 (m, 4H), 0.82-0.75 (m, 1H), 0.68 (s, 3H).

LCMS Rt=1.200 min in 2.0 min chromatography, 30-90 AB_E, purity 100%, MS ESI calcd. for $C_{30}H_{47}O$ [M+H−2H₂O]⁺ 423, found 423.

Example 103: Synthesis for 10317

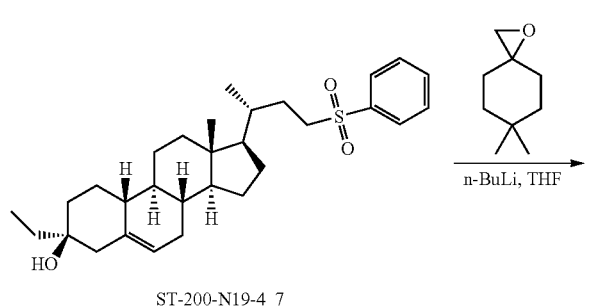

The synthesis of ST-200-N19-4_7 can be found in Example 94. The synthesis of the epoxide can be found in Example 28.

Synthesis of ST-200-N19-K17_1

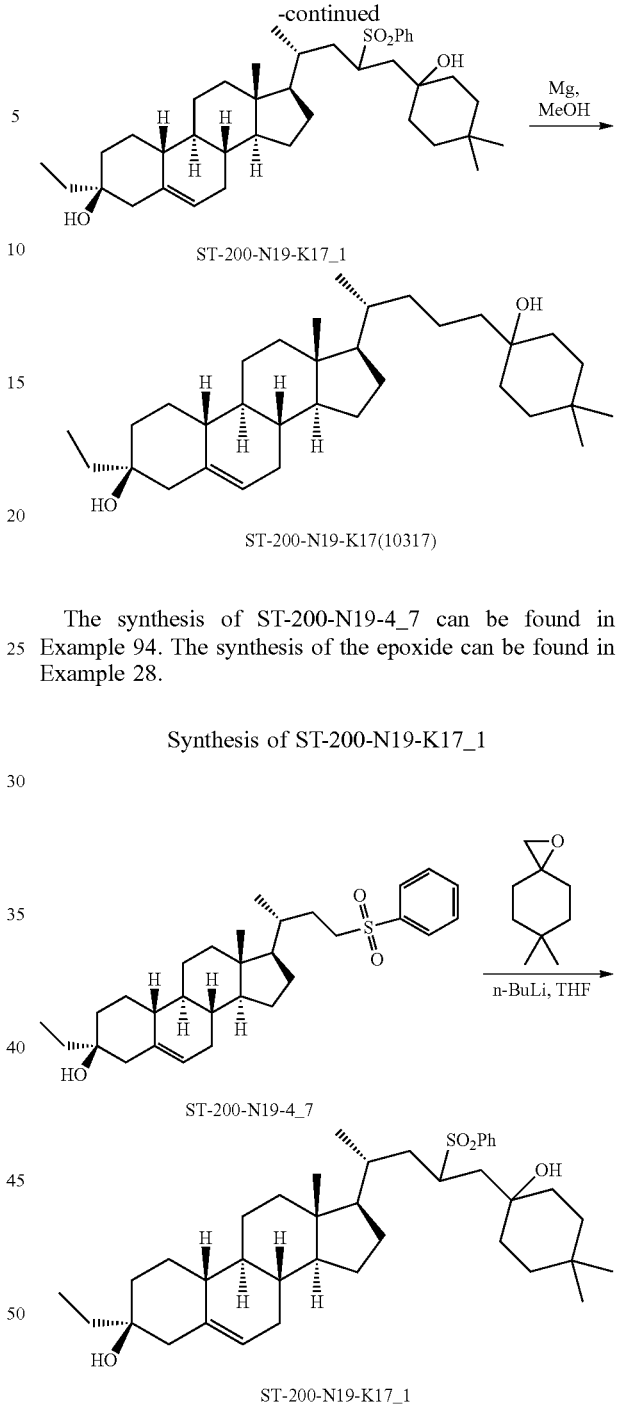

n-BuLi (0.408 mL, 2.5 M, 1.02 mmol, 2.5 eq) was added to THF (0.5 mL) under N₂ at −70° C. Next, a suspension of ST-200-N19-4_7 (200 mg, 0.412 mmol, 1.0 eq.) in THF (1.5 mL) was added dropwise to give a suspension. After stirring at −70° C. for 30 min, 6,6-dimethyl-1-oxaspiro[2.5]octane (86.6 mg, 0.618 mmol, 1.5 eq.) was added dropwise. Then reaction was stirred at 25° C. for 12 hrs. The reaction was quenched with sat.NH₄Cl (30 mL), extracted with EtOAc (3×15 mL). The combined organic layers were dried over Na₂SO₄, filtered and concentrated to give crude product (250 mg) as a solid, which was used directly for the next step.

Synthesis of ST-200-N19-K17

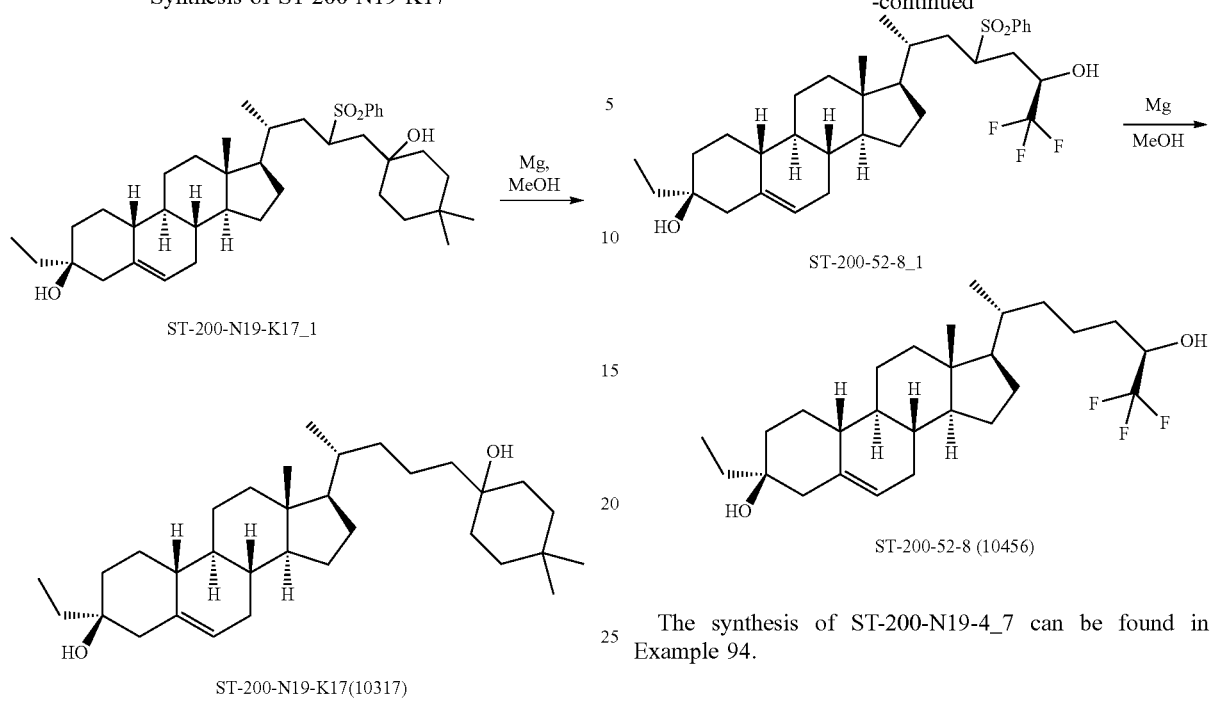

NiCl$_2$ (10.3 mg, 0.08 mmol) and Mg powder (384 mg, 16.0 mmol) were added in one portion to a solution of ST-200-N19-K17_1 (250 mg, 0.4 mmol) in MeOH (30 mL) at 65° C. The mixture was stirred at 65° C. for 1 h. The mixture was quenched with HCl (50 mL, 2 N) until the reaction became clear and extracted with DCM (3×20 mL). The combined organic phase was dried over Na$_2$SO$_4$, filtered, concentrated and purified by flash column (0-10% of EtOAc in PE) to give impure ST-200-N19-K17 (58 mg, 30%) as a solid, which was triturated with hexane (3 mL). The mixture was filtered to give pure ST-200-N19-K17 (33 mgas a solid.

$^1$H NMR (400 MHz, CDCl$_3$) δ 5.44-5.33 (m, 1H), 2.27-2.2 (m, 1H), 2.07-1.88 (m, 4H), 1.87-1.75 (m, 3H), 1.68-1.57 (m, 2H), 1.52-1.45 (m, 7H), 1.44-1.32 (m, 7H), 1.28-1.15 (m, 8H), 1.14-0.95 (m, 6H), 0.94-0.89 (m, 6H), 0.89-0.82 (m, 7H), 0.82-0.74 (m, 1H), 0.68 (s, 3H).

LCMS Rt=1.516 min in 2.0 min chromatography, 30-90 AB_E, purity 100%, MS ESI calcd. for C$_{33}$H$_{53}$ [M+H–2H$_2$O]$^+$ 449, found 449.

Example 104: Synthesis for 10456

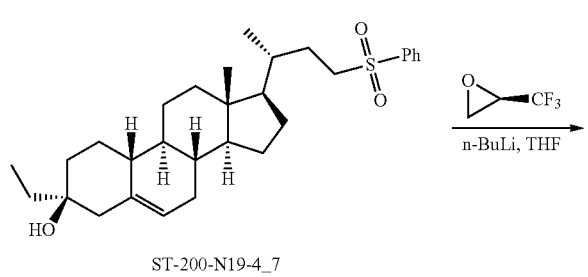

The synthesis of ST-200-N19-4_7 can be found in Example 94.

Synthesis of ST-200-52-8_1 n-BuLi (0.246 mL, 2.5 M, 0.617 mmol) was added to THF (0.3 mL) under N$_2$ at –70° C. A solution of ST-200-N19-4_7 (0.12 g, 0.247 mmol) in THF (1 mL) was added at –70° C. After stirring at –70° C. for 1 hour, (R)-2-(trifluoromethyl) oxirane (41.4 mg, 0.37 mmol) was added at –70° C. The reaction mixture was warmed to 15° C. and stirred at 15° C. for 18 hrs. The reaction mixture was quenched with saturated NH$_4$Cl aqueous (6 mL) at 0° C. The mixture was extracted with EtOAc (2×8 mL). The combined organic phase was washed with brine (2×10 mL), dried over Na$_2$SO$_4$, filtered and concentrated under vacuum to give a crude product ST-200-52-8_1 (150 mg, crude) as a solid, which was used directly for the next step.

Synthesis of ST-200-52-8

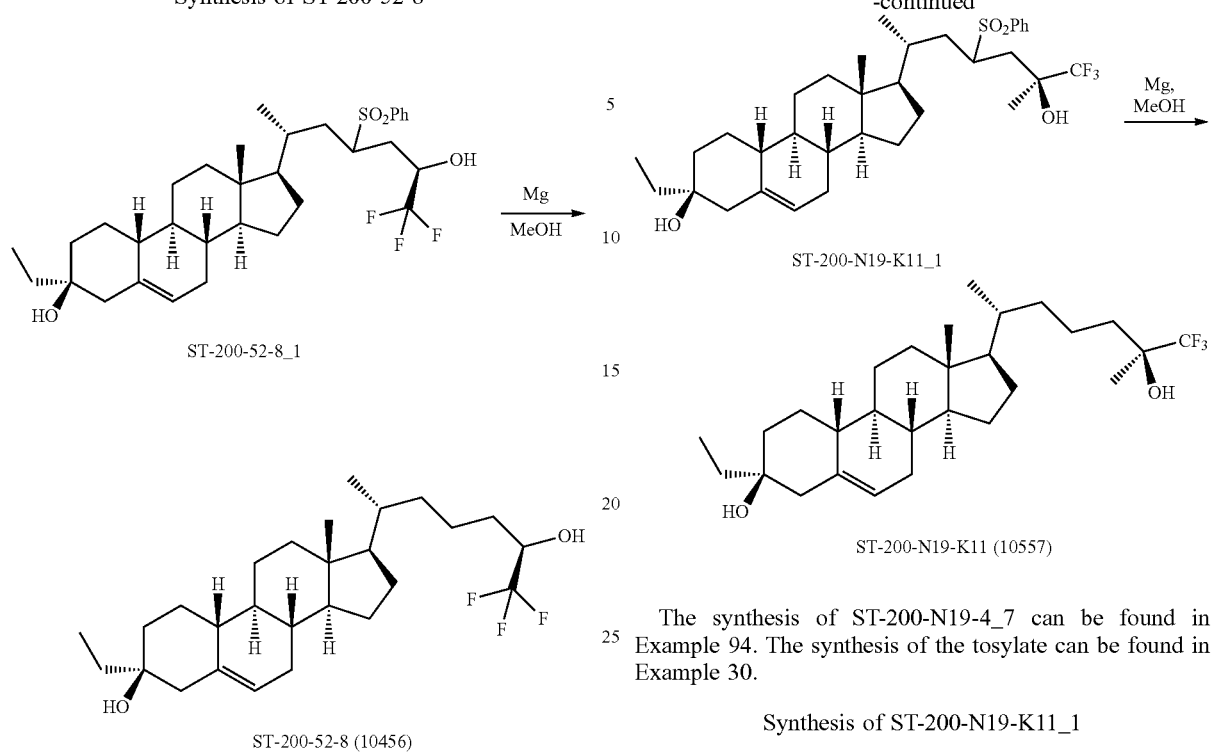

ST-200-52-8_1

ST-200-52-8 (10456)

NiCl$_2$ (6.5 mg, 0.0502 mmol) and Mg powder (240 mg, 10.0 mmol) were added in one to a solution of ST-200-52-8_1 (150 mg, 0.251 mmol) in MeOH (30 mL) at 65° C. The mixture was stirred at 65° C. for 1 h. The mixture was quenched with HCl (50 mL, 2 N) until the reaction became clear and extracted with DCM (3×20 mL). The combined organic phase was dried over Na$_2$SO$_4$, filtered, concentrated and purified by flash column (0-10% of EtOAc in PE) to give ST-200-52-8 (20 mg, 17%) as a solid.

$^1$H NMR (400 MHz, CDCl$_3$) δ 5.43-5.34 (m, 1H), 3.98-3.85 (m, 1H), 2.27-2.19 (m, 1H), 2.06-1.88 (m, 5H), 1.87-1.76 (m, 3H), 1.68-1.57 (m, 4H), 1.53-1.34 (m, 8H), 1.29-1.15 (m, 5H), 1.13-0.98 (m, 4H), 0.95-0.89 (m, 3H), 0.89-0.82 (m, 4H), 0.81-0.74 (m, 1H), 0.68 (s, 3H).

LCMS Rt=1.255 min in 2.0 min chromatography, 30-90AB_E, purity 100%, MS ESI calcd. for C$_{27}$H$_{42}$F$_3$O [M+H−H$_2$O]$^+$ 439, found 439.

Example 105: Synthesis for 10557

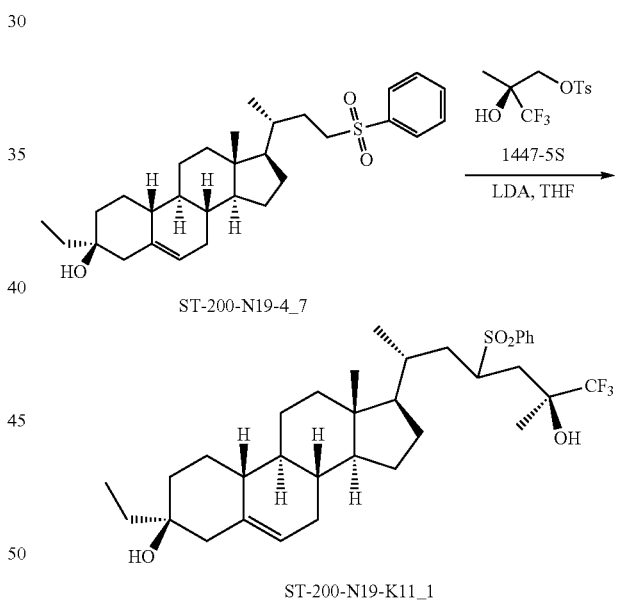

ST-200-N19-4_7

ST-200-N19-K11_1

ST-200-N19-K11 (10557)

The synthesis of ST-200-N19-4_7 can be found in Example 94. The synthesis of the tosylate can be found in Example 30.

Synthesis of ST-200-N19-K11_1 n-BuLi (0.656 mL, 2.5 M in hexane, 1.64 mmol) was added to a solution of diisopropylamine (179 mg, 1.77 mmol) in THF (1 mL) under N$_2$ at −70° C. The mixture was warmed to 25° C. After re-cooling to −70° C., a suspension of ST-200-N19-4_7 (200 mg, 0.412 mmol) in THF (5 mL) was added dropwise under N$_2$ at −70° C. After stirring at −70° C. for 30 min, (S)-3,3,3-trifluoro-2-hydroxy-2-methylpropyl 4-methylbenzenesulfonate (184 mg, 0.618 mmol) was added. The reaction mixture was warmed to 25° C. slowly and stirred at 25° C. for 16 hrs. The reaction mixture was quenched with saturated NH$_4$Cl aqueous (15 mL). The mixture was extracted with EtOAc (2×15 mL). The combined organic phase was washed with brine (2×20 mL), dried over Na$_2$SO$_4$, filtered and concentrated under vacuum to give ST-200-N19-K11_11 (200 mg, crude) as an oil, which was used for the next step directly.

Synthesis of ST-200-N19-K11

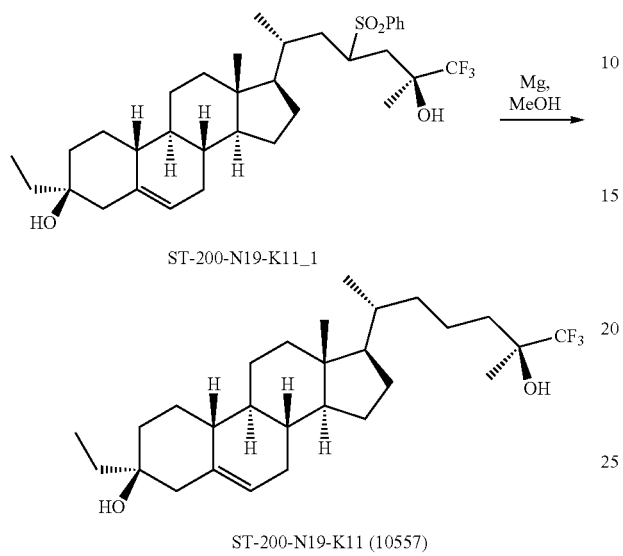

A solution of ST-200-N19-K11_1 (200 mg, 0.327 mmol) in MeOH (30 mL) was heated at 65° C. Mg powder (312 mg, 13.0 mmol) and NiCl$_2$ (12.5 mg, 0.0981 mmol) were added in one portion at 65° C. The mixture was refluxed at 65° C. for 1 h. The mixture was quenched with HCl (50 mL, 2N) until the reaction became clear and extracted with DCM (3×20 mL). The combined organic layer was dried over Na$_2$SO$_4$, filtered, concentrated and purified by silica gel chromatography (0-15% of EtOAc in PE) to give impure ST-200-N19-K11 (26 mg, 17%) as a solid, which was triturated with hexane (3 mL) to give ST-200-N19-K11 (13 mg, 50%) as a solid.

$^1$H NMR (400 MHz, CDCl$_3$) δ 5.41-5.36 (m, 1H), 2.27-2.19 (m, 1H), 2.08-1.95 (m, 3H), 1.93-1.75 (m, 5H), 1.69-1.57 (m, 4H), 1.55-1.37 (m, 7H), 1.34 (s, 3H), 1.30-1.15 (m, 6H), 1.14-0.97 (m, 4H), 0.96-0.89 (m, 3H), 0.88-0.74 (m, 5H), 0.68 (s, 3H).

LCMS Rt=1.261 min in 2.0 min chromatography, 30-90AB_E, purity 100%, MS ESI calcd. for C$_{28}$H$_{44}$F$_3$O [M+H−H$_2$O]$^+$ 453, found 453.

Example 106: Synthesis for 10673

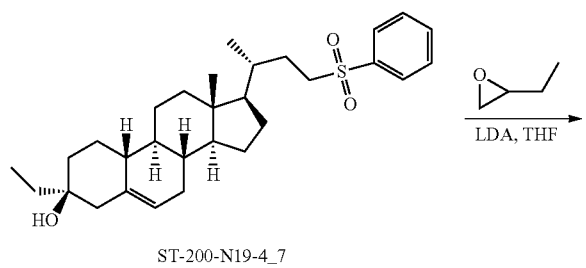

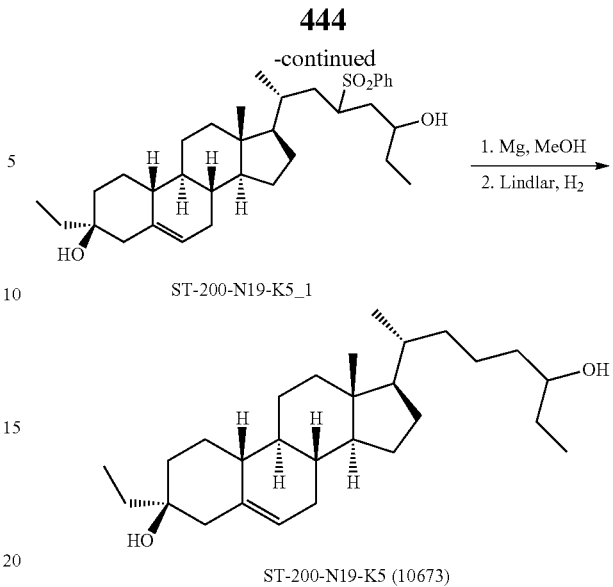

The synthesis of 200-N19-4_7 can be found in Example 94.

Synthesis of ST-200-N19-K5_1

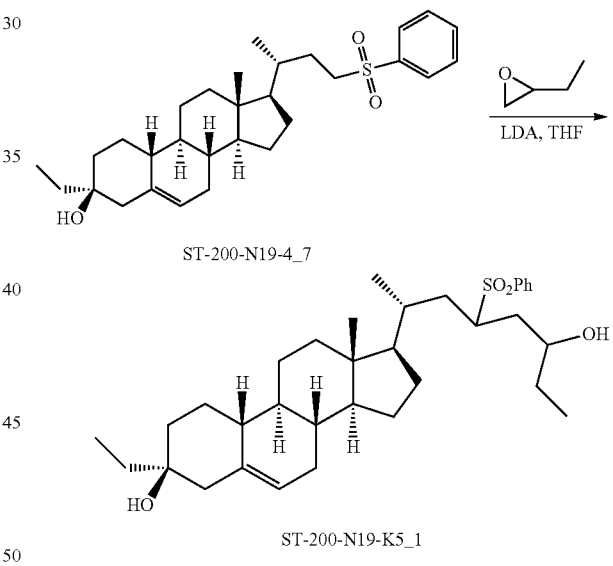

A suspension of ST-200-N19-4_7 (400 mg, 0.8251 mmol) in THF (4 mL) was added dropwise at −70° C. under N$_2$ to a solution of n-BuLi (5.0 mL, 2.5 M in hexane, 6.5 mmol) in THF (2 mL) inside sealed tube (10 mL). The mixture was stirred for 30 minutes at −70° C. A solution of diisopropylamine (274 mg, 2.7 mmol) was added dropwise at −70° C., then a solution of 2-ethyloxirane (178 mg, 2.47 mmol) was added dropwise at −70° C. The mixture was stirred for another 30 min and then warmed to 25° C. gradually. The reaction mixture was stirred at 25° C. for 15 hour. The reaction mixture was quenched by saturated NH$_4$Cl aqueous (30 mL), extracted with EtOAc (3×50 mL). The combined organic phase was washed with brine (50 mL), dried over Na$_2$SO$_4$, filtered and concentrated under vacuum to give ST-200-N19-K5_1 (450 mg, crude), which was used directly for the next step.

Synthesis of ST-200-N19-K5

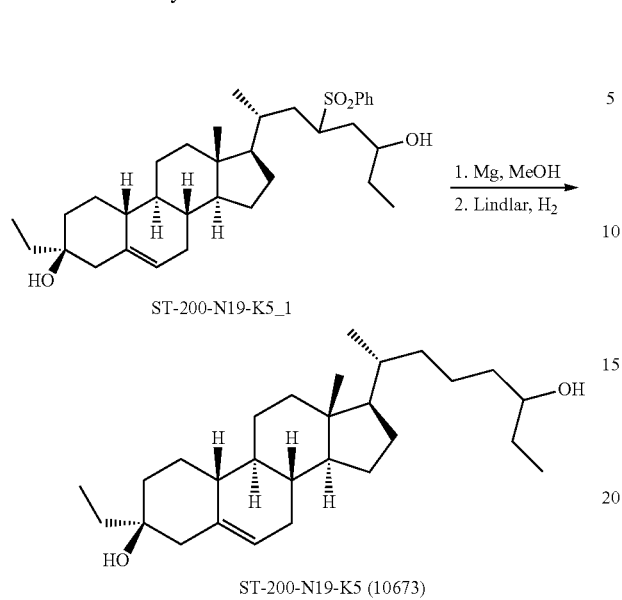

A solution of ST-310-N19-K5_1 (0.45 g, 0.808 mmol) in MeOH (30 mL) was heated at 60° C. Mg powder (775 mg, 32.3 mmol) was added in four portions at 60° C. The mixture was stirred at 60° C. for 1 h. The mixture was quenched with HCl (30 mL, 2 M) until the reaction became clear and extracted with DCM (2×30 mL). The combined organic phase was dried over $Na_2SO_4$, filtered, concentrated and purified by flash column (0-30% of EtOAc in PE) to give 330 mg of impure product, which was purified by flash column (0-20% of EtOAc in PE) to give pure 150 mg of a solid. The solid (150 mg, 0.873 mmol) in THF (5 mL) was added lindlar catalyst (100 mg). The mixture was stirred at 25° C. under $H_2$ (15 Psi) for 16 hrs. The mixture was filtered and concentrated to give ST-200-N19-K5 (100 mg, crude) as a solid. The residue was triturated from n-hexane (2 mL) at 20° C. to give ST-200-N19-K5 (50 mg) as solid 1H NMR (400 MHz, $CDCl_3$) δ 5.39-5.37 (m, 1H), 3.51 (s, 1H), 2.25-2.21 (m, 1H), 2.05-1.70 (m, 7H), 1.65-1.50 (m, 4H), 1.50-1.25 (m, 10H), 1.25-1.15 (m, 6H), 1.14-1.10 (m, 4H), 0.94-0.91 (m, 6H), 0.88-0.83 (m, 5H), 0.67 (s, 3H).

LCMS Rt=1.269 min in 2 min chromatography, 30-90AB_2 MIN_E, purity 99%, MS ESI calcd. For $C_{28}H_{47}O^+$ [M+H–$H_2O$]+ 399, found 399.

Example 107: Synthesis for 10790

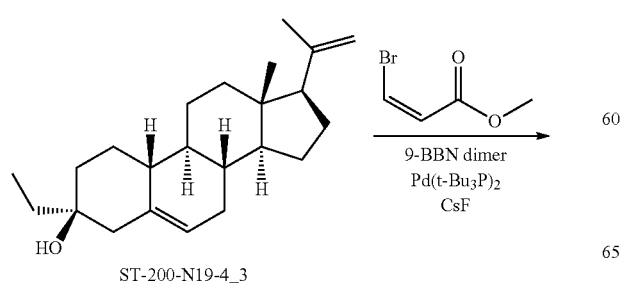

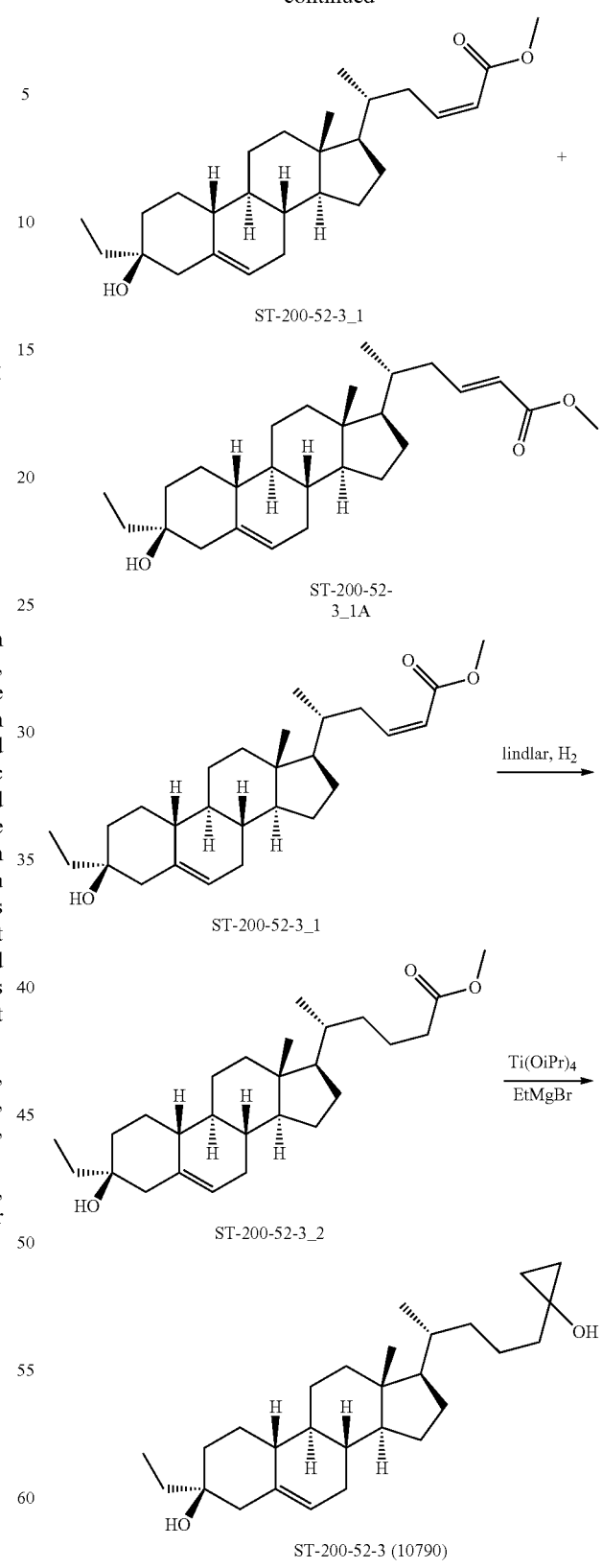

The experimental of intermediate ST-200-N19-4_3 can be found in Example 94.

Synthesis of ST-200-52-3_1, ST-200-52-3

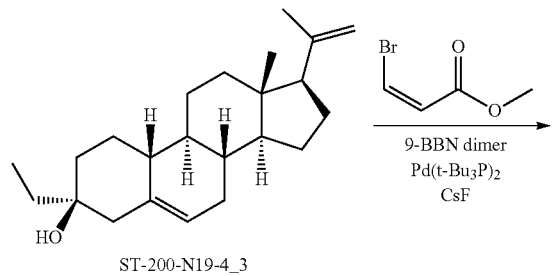

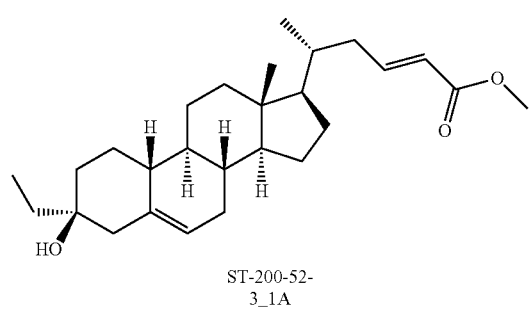

9-BBN dimer (2.22 g, 9.12 mmol) was added to a solution of 200-N19-4_3 (2 g, 6.08 mmol) in anhydrous THF (20 mL) under nitrogen atmosphere at 30° C. The mixture was stirred at 65° C. for 3 hours. The reaction mixture was cooled to 30° C., and (Z)-methyl 3-bromoacrylate (1.20 g, 7.29 mmol), CsF (1.83 g, 12.1 mmol) and Pd(t-Bu$_3$P)$_2$ (310 mg, 0.608 mmol) were added to the mixture. The resulting mixture was stirred at 65° C. for 16 hours. The reaction was cooled, quenched with water (300 mL), extracted with EtOAc (3×300 mL). The combined organic layer was dried over anhydrous sodium sulfate, filtered and concentrated under vacuum to give a residue, which was purified by combi-flash (5%-15% of EtOAc in PE) to give ST-200-52-3_1 (400 mg, 16%) as a solid, ST-200-52-3_1A (340 mg, 13%) as solid, and the mixture of ST-200-52-3_1 and ST-200-52-3_1A (340 mg) as a solid.

$^1$H NMR (400 MHz, CDCl$_3$) δ 6.29-6.23 (m, 1H), 5.82 (d, J=12.0 Hz, 1H), 5.39-5.34 (m, 1H), 3.70 (s, 3H), 2.65-2.55 (m, 2H), 2.23 (dd, J=3.2, 13.2 Hz, 1H), 2.08-1.78 (m, 8H), 1.72-1.58 (m, 5H), 1.53-1.38 (m, 6H), 1.37-0.99 (m, 5H), 0.95 (d, J=6.4 Hz, 3H), 0.86 (t, J=7.2 Hz, 3H), 0.70 (s, 3H).

Synthesis of ST-200-52-32

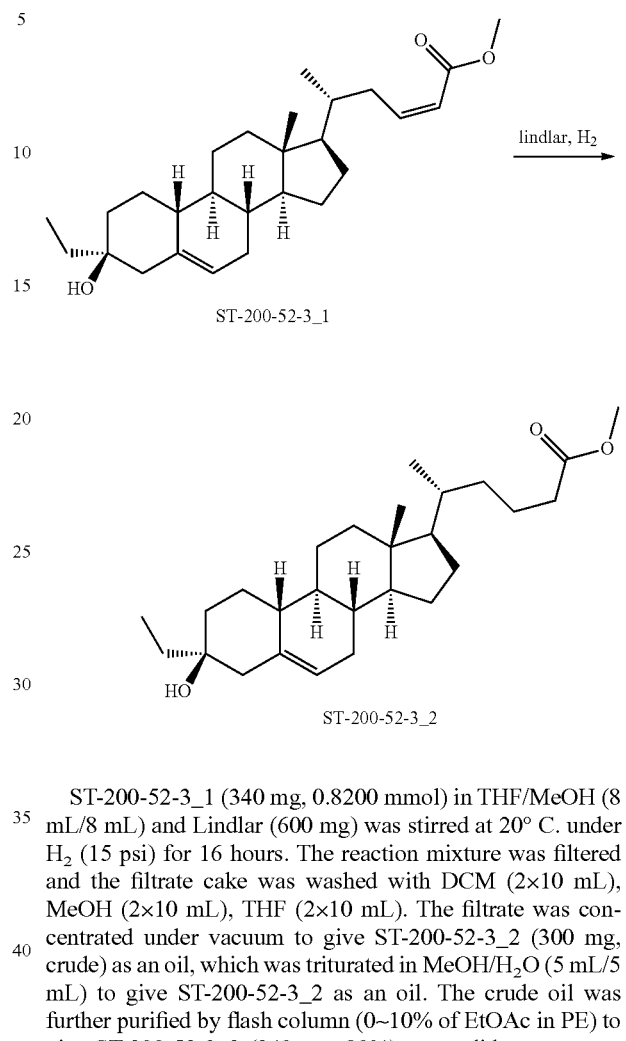

ST-200-52-3_1 (340 mg, 0.8200 mmol) in THF/MeOH (8 mL/8 mL) and Lindlar (600 mg) was stirred at 20° C. under H$_2$ (15 psi) for 16 hours. The reaction mixture was filtered and the filtrate cake was washed with DCM (2×10 mL), MeOH (2×10 mL), THF (2×10 mL). The filtrate was concentrated under vacuum to give ST-200-52-3_2 (300 mg, crude) as an oil, which was triturated in MeOH/H$_2$O (5 mL/5 mL) to give ST-200-52-3_2 as an oil. The crude oil was further purified by flash column (0~10% of EtOAc in PE) to give ST-200-52-3_2 (240 mg, 80%) as a solid.

$^1$H NMR (400 MHz, CDCl$_3$) δ 5.44-5.35 (m, 1H), 3.66 (s, 3H), 2.38-2.17 (m, 3H), 2.02-1.76 (m, 7H), 1.61-1.37 (m, 10H), 1.28-0.99 (m, 9H), 0.96-0.76 (m, 8H), 0.74-0.65 (m, 3H).

Synthesis of 10790

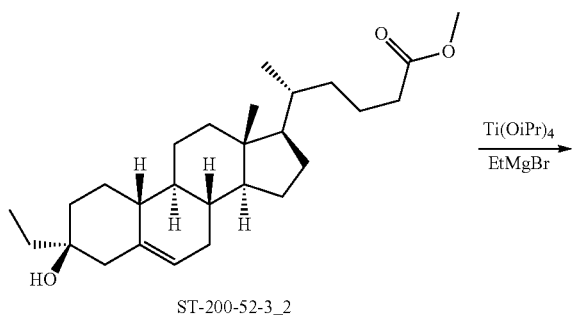

-continued

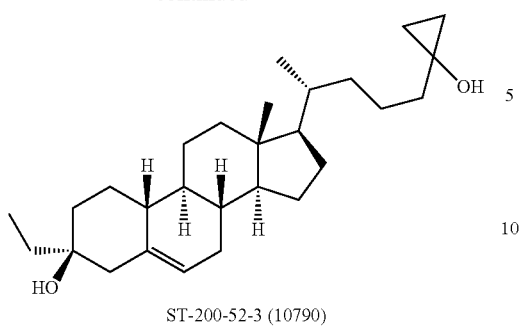

ST-200-52-3 (10790)

Ti(i-PrO)$_4$ (163 mg, 0.58 mmol) and EtMgBr (0.7 mL, 3 M in Et$_2$O, 2 mmol) were added to a solution of ST-200-52-3_2 (240 mg, 0.58 mmol) in THF (2 mL) at 25° C. The reaction mixture was stirred at 25° C. for 15 min under N$_2$. The reaction mixture was quenched with saturated aqueous NH$_4$Cl (10 mL) solution and extracted with EtOAc (3×20 mL). The combined organic layer was washed with brine (50 mL), dried over Na$_2$SO$_4$, filtered and concentrated in vacuum to give a crude product, which was purified by flash column (0~15% of EtOAc in PE) to afford a crude a solid. The solid was further triturated from MeCN (5 mL) and purified by silica gel chromatography (PE/EtOAc=10/1) to afford ST-200-52-3 (15 mg, 6%) as a solid.

$^1$H NMR (400 MHz, CDCl$_3$) δ 5.44-5.35 (m, 1H), 2.27-2.19 (m, 1H), 2.07-1.61 (m, 10H), 1.51-1.34 (m, 8H), 1.31-0.98 (m, 11H), 0.97-0.92 (m, 3H), 0.89-0.82 (m, 5H), 0.76-0.71 (m, 2H), 0.68 (s, 3H), 0.48-0.39 (m, 2H).

LCMS Rt=1.226 min in 2 min chromatography, 30-90AB_2 MIN_E, purity 100%, MS ESI calcd. for C$_{28}$H$_{45}$O [M+H–H$_2$O]$^+$ 397, found 397.

Example 108: Synthesis of 10841

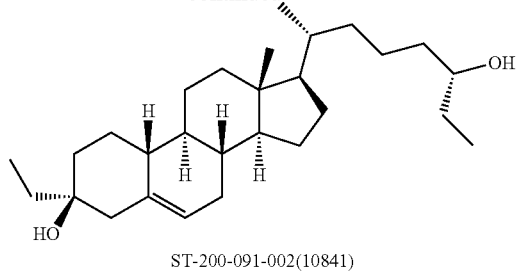

ST-200-091-002(10841)

The experimental of intermediate ST-200-N19-4_7 can be found in Example 94.

Synthesis of ST-200-091-002_2

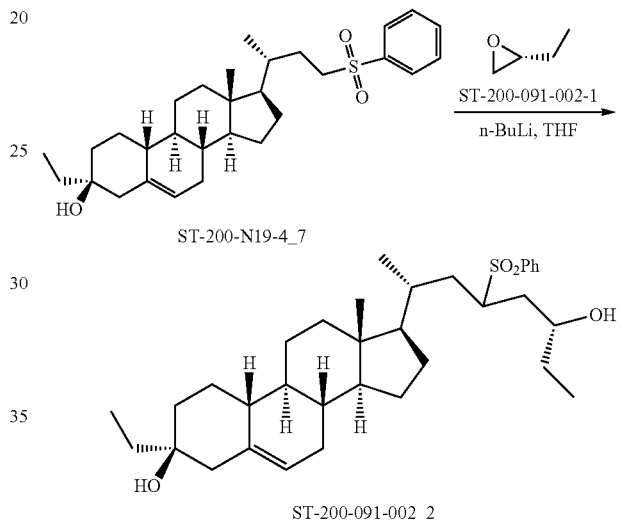

To a solution of ST-200-N19-4_7 (500 mg, 1.03 mmol) in anhydrous THF (3 mL) was added n-BuLi (1.23 mL, 3.09 mmol, 2.5M in n-hexane) drop-wise at −70° C. under N$_2$. The reaction mixture was stirred at −70° C. for 30 mins. To the mixture was added a solution of (R)-2-ethyloxirane (111 mg, 1.54 mmol) in anhydrous THF (0.5 mL) drop-wise at −70° C. and stirred for another 1 h. The reaction mixture was then stirred at 25° C. for 12 h. The reaction was quenched with saturated aqueous NH$_4$Cl (50 mL). The aqueous phase was extracted with EtOAc (3×50 mL). The combine organic phase was washed whit saturated brine (2×50 mL), dried over anhydrous Na$_2$SO$_4$, filtered and concentrated in vacuum to give ST-200-091-002_2 (0.5 g, crude) as an oil.

Synthesis of ST-200-091-002

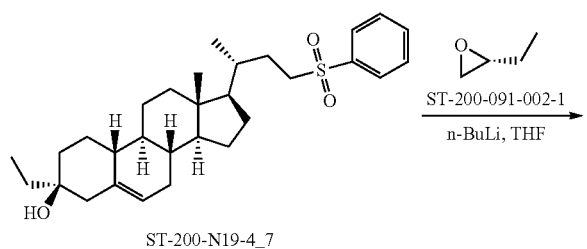

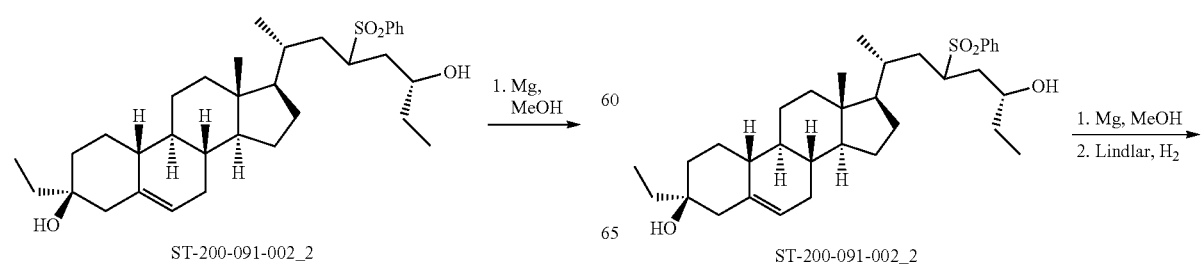

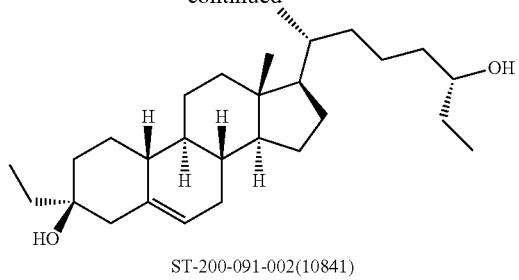

ST-200-091-002(10841)

To a solution of ST-200-091-002_2 (0.5 g, crude) in MeOH (50 mL) was added Mg powder (1.07 g, 44.8 mmol) and NiCl$_2$ (20 mg) at 25° C. under N$_2$. After stirring at 50° C. for 1 h, the reaction mixture was quenched with HCl (100 mL, 1 M) until the reaction became clear. The aqueous phase was extracted with EtOAc (3×80 mL). The combined organic phase was washed with saturated brine (2×50 mL), dried over anhydrous Na$_2$SO$_4$, filtered and concentrated. The residue was purified by silica gel chromatography (PE/EtOAc=10/1 to 8/1) to afford ST-200-091-002 (120 mg, 32%) as a solid, which was purified by SFC (Column:AD (250 mm*30 mm, 5 um), Condition:0.1% NH$_3$H$_2$O ETOH, Begin B:40%, End B:40%) to afford ST-200-091-002 (50 mg, 42.0%) as a solid.

$^1$H NMR (400 MHz, CDCl$_3$) δ 5.38-5.36 (m, 1H), 3.55-3.49 (m, 1H), 2.29-2.20 (m, 1H), 2.05-1.75 (m, 7H), 1.65-1.31 (m, 13H), 1.30-1.15 (m, 7H), 1.14-0.76 (m, 15H), 0.68 (s, 3H).

LCMS Rt=1.326 min in 2 min chromatography, 30-90AB_2 MIN_E, purity 100%, MS ESI calcd. for C$_{28}$H$_{47}$O [M+H−H$_2$O]$^+$ 399, found 399.

Example 109: Synthesis of 10949

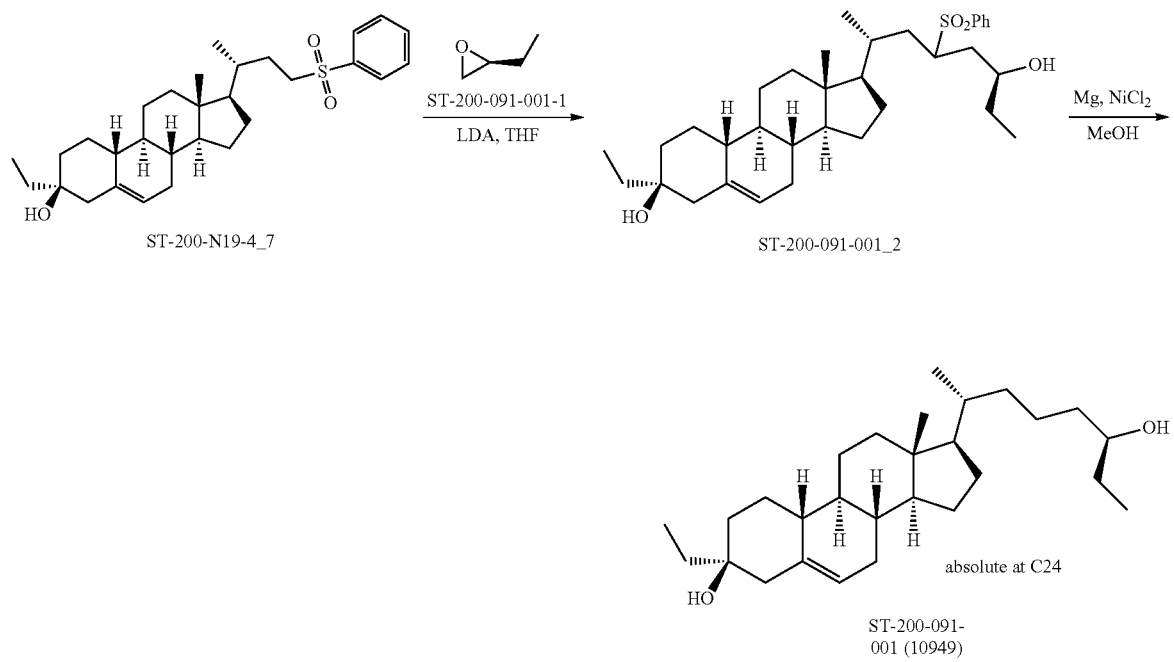

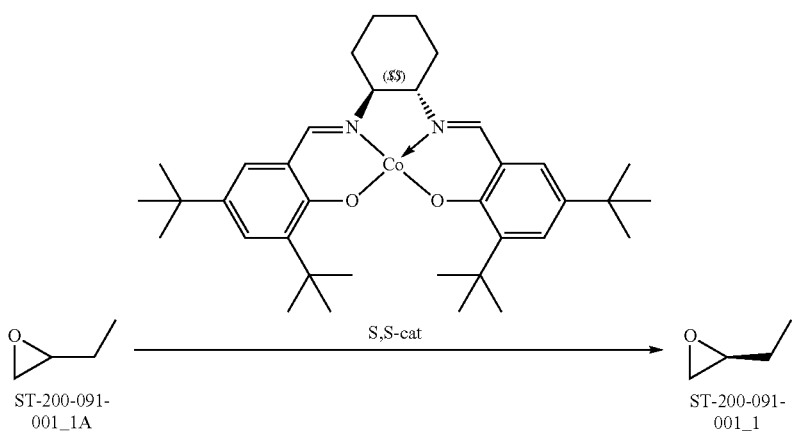

The experimental of intermediate ST-200-N19-4_7 can be found in Example 94.

Synthesis of ST-200-091-001_2

Synthesis of ST-200-091-001

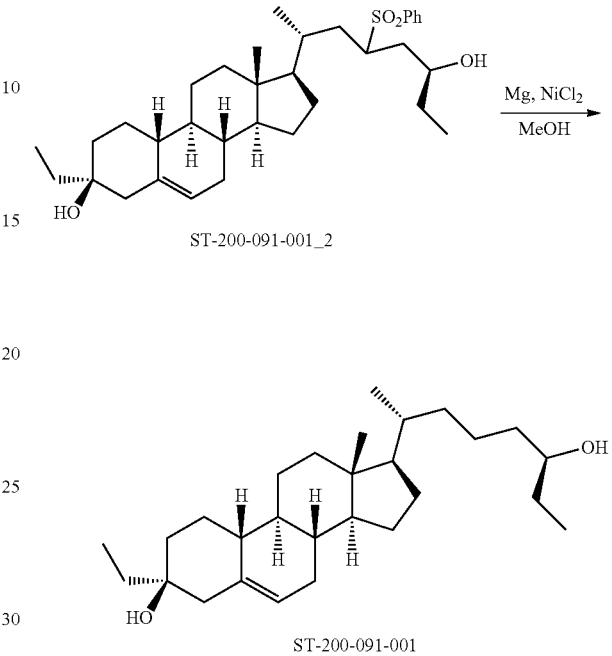

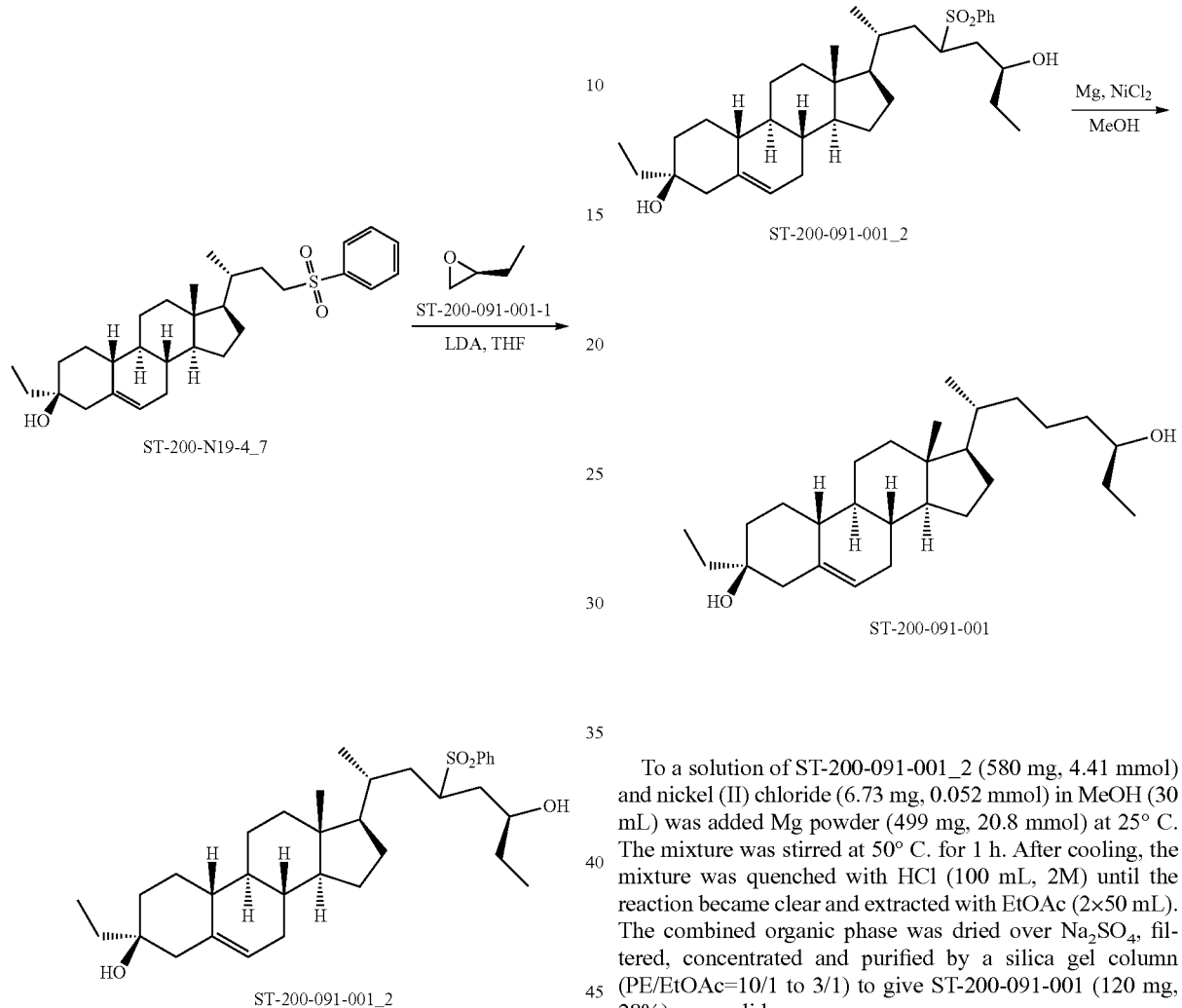

To a THF (0.5 mL) under N₂ at −70° C. was added n-BuLi (2.5 M, 2.57 mmol, 1.02 mL). After that, a suspension of ST-200-N19-4_7 (500 mg, 1.03 mmol) in THF (3 mL) was added drop-wise to give a suspension. After stirring at −70° C. for 30 min, a solution of (S)-2-ethyloxirane (88.6 mg, 1.23 mmol) in THF (0.5 mL) was added. Then reaction was stirred at stirred at 25° C. for 16 hours. The mixture was poured into ice-water (20 mL) and extracted with EtOAc (2×30 mL). The combined organic layers were washed with brine (50 mL), dried over Na₂SO₄, filtered and concentrated in vacuum to afford ST-200-091-001_2 (580 mg, crude) as a solid, which was used directly for the next step.

To a solution of ST-200-091-001_2 (580 mg, 4.41 mmol) and nickel (II) chloride (6.73 mg, 0.052 mmol) in MeOH (30 mL) was added Mg powder (499 mg, 20.8 mmol) at 25° C. The mixture was stirred at 50° C. for 1 h. After cooling, the mixture was quenched with HCl (100 mL, 2M) until the reaction became clear and extracted with EtOAc (2×50 mL). The combined organic phase was dried over Na₂SO₄, filtered, concentrated and purified by a silica gel column (PE/EtOAc=10/1 to 3/1) to give ST-200-091-001 (120 mg, 28%) as a solid.

The ST-200-091-001 (120 mg, 0.287 mmol) was separated by SFC (column: AD (250 mm*30 mm, 5 um)), gradient: 50-50% B (A=0.1% NH₃H₂O ETOH), flow rate: 60 mL/min) to give ST-200-091-001 (58 mg, 14%) as a solid.

¹HNMR (400 MHz, CDCl₃) δ 5.42-5.38 (m, 1H), 3.57-3.47 (m, 1H), 2.25-2.21 (m, 1H), 2.07-1.88 (m, 4H), 1.86-1.78 (m, 3H), 1.68-1.59 (m, 2H), 1.52-1.31 (m, 12H), 1.29-0.98 (m, 10H), 0.96-0.75 (m, 11H), 0.68 (s, 3H).

LCMS Rt=1.318 min in 2.0 min chromatography, 30-90 AB, purity 100%, MS ESI calcd. For C₂₈H₄₇O [M−H₂O+H]⁺ 399, found 399.

SFC Rt=6.962 min in 10 min chromatography, AD_3_EtOH_DEA_5_40_25ML, 99.4% de

Example 110. Biological Data

Experiments conducted as described in Example 2 and results are reported in Table 2-62.

TABLE 2-62

| Compound | Avg EC50 2A (nM) | Avg Emax 2A (%) | Avg EC50 2B (nM) | Avg Emax 2B (%) |
| --- | --- | --- | --- | --- |
| 194 | 200.3 | 161.8 | 143.5 | 192.5 |
| 9567 | 327.5 | 104.0 | 378.1 | 124.3 |
| 9670 | 366.1 | 153.8 | 219.9 | 213.2 |
| 9792 | 334.2 | 64.5 | 284.9 | 58.2 |
| 9810 | 124.0 | 87.1 | 151.2 | 91.6 |
| 9911 | 252.6 | 233.7 | 287.6 | 326 |

TABLE 2-62-continued
| Compound | Avg EC50 2A (nM) | Avg Emax 2A (%) | Avg EC50 2B (nM) | Avg Emax 2B (%) |
|---|---|---|---|---|
| 10012 | 790.0 | 154.1 | 909.6 | 167.6 |
| 9813 | 469.2 | 68.7 | 267.7 | 99.9 |
| 10114 | 320.8 | 146.3 | 505.6 | 179.1 |
| 10115 | 555.9 | 191.6 | 458.2 | 225.6 |
| 10216 | 1196.8 | 79.3 | 445.6 | 120.7 |
| 10317 | >10000 | 56.7 | >10000 | 59.9 |
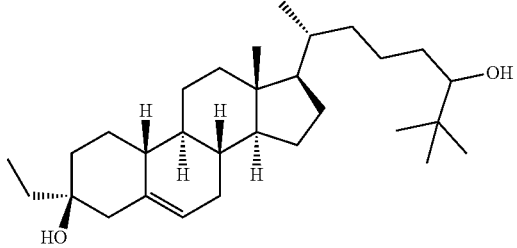
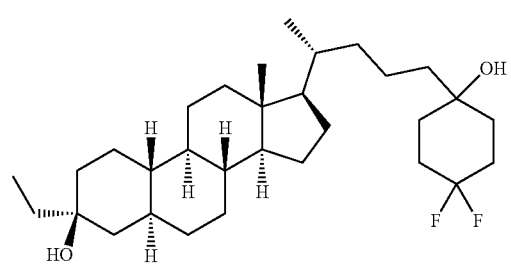
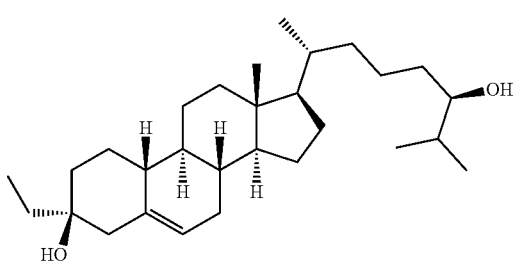
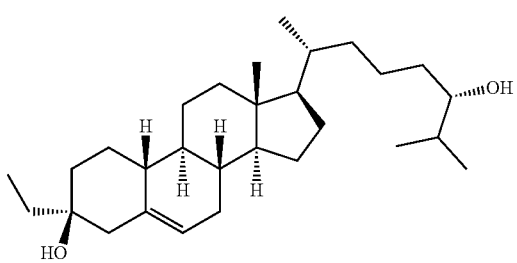
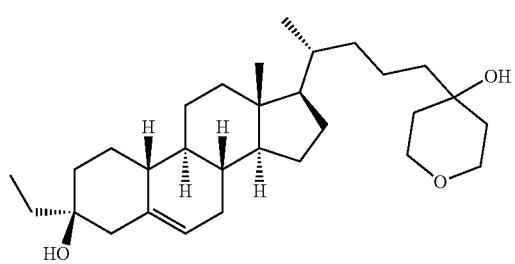
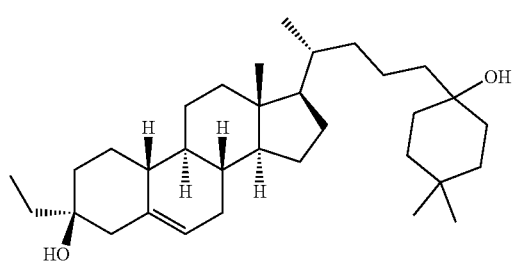

TABLE 2-62-continued
| | Compound | Avg EC50 2A (nM) | Avg Emax 2A (%) | Avg EC50 2B (nM) | Avg Emax 2B (%) |
|---|---|---|---|---|---|
| 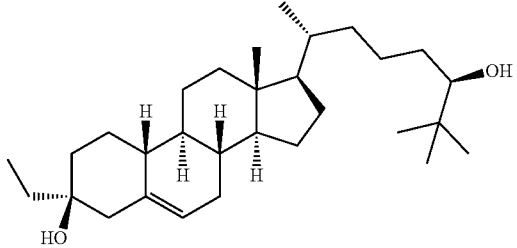 | 10042 | >10000 | 65.9 | 1877.4 | 112.8 |
| 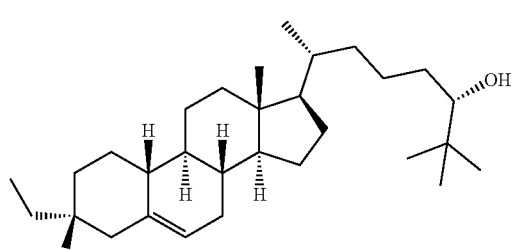 | 10043 | 897.3 | 145.7 | 1067.0 | 210.6 |
| 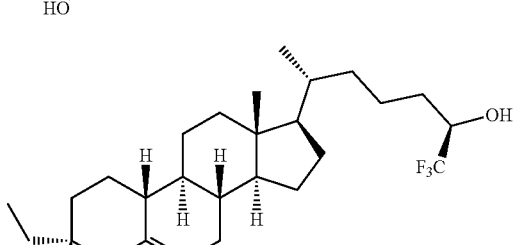 | 10456 | 239.6 | 230.6 | 208.6 | 265.7 |
| 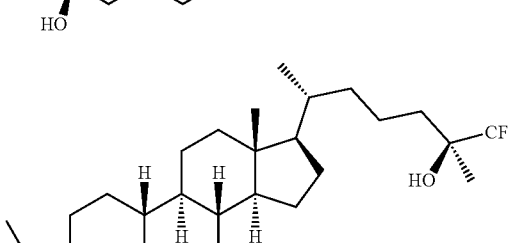 | 10557 | 286.8 | 189.7 | 191.7 | 202.5 |
| 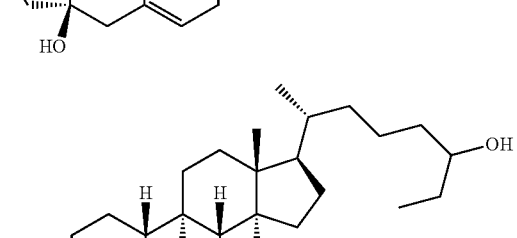 | 10673 | 253.6 | 215.5 | 180.1 | 213.5 |
| 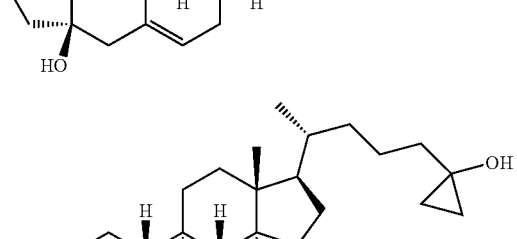 | 10790 | 203.8 | 159.8 | 270.5 | 245.8 |

TABLE 2-62-continued

| Compound | Avg EC50 2A (nM) | Avg Emax 2A (%) | Avg EC50 2B (nM) | Avg Emax 2B (%) |
|---|---|---|---|---|
| 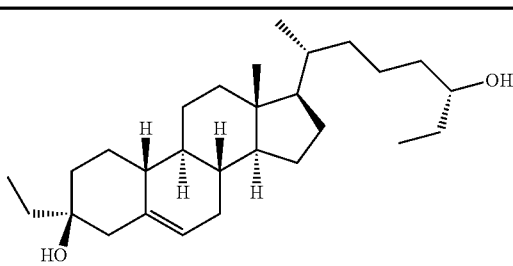 10841 | >10000 | 15.6 | >10000 | 30.1 |
| 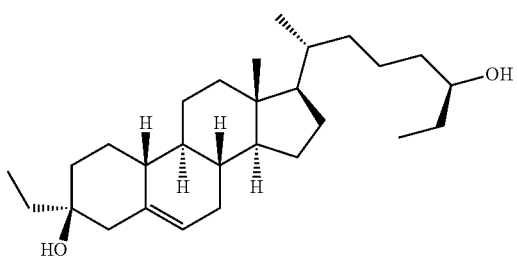 10949 | 66.4 | 97.4 | 138.1 | 147.4 |

Example 111. Synthesis of Compound A-1

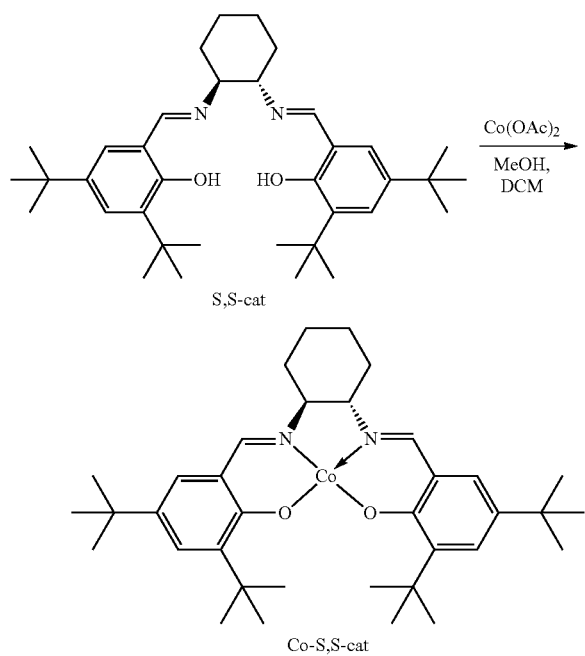

Step 1. To a solution of S,S-cat (2 g, 3.65 mmol) in anhydrous DCM (30 mL) was added a solution of cobalt(II) acetate (775 mg, 4.38 mmol) in MeOH (30 mL) under nitrogen at 20° C. The mixture was stirred for 30 mins at 20° C. and at 0° C. for 1 h. The precipitated solid was filtered, washed with cold MeOH (2×30 mL) and dried in vacuum to give Co—S,S-cat (1.6 g, 73%) as a solid.

Step 2. To a solution of Co—S,S-cat (1.07 g, 1.78 mmol) in toluene (30 mL) was added AcOH (1.12 g, 18.7 mmol). The mixture was stirred at 20° C. for 30 mins. The solution was concentrated in vacuum to give a crude solid. The resulting catalyst residue was dissolved in neat A-0 (100 g, 892 mmol) at 20° C., the reaction mixture was cooled to 0° C., and water (8.82 g, 490 mmol) was added dropwise. The mixture was warmed to 20° C. and stirred for 48 hrs. A-1 (44 g) was isolated by distillation from the reaction mixture.

$^1$H NMR (400 MHz, DMSO-d6) δ 3.96 (s, 1H), 3.11-2.98 (m, 2H).

The e.e. of A-1 was determined by opening the epoxide with benzylamine. A-1 (200 mg, 1.78 mmol) was added to dry benzylamine (190 mg, 1.78 mmol), and the mixture was stirred at 20° C. for 2 hrs. A solid precipitated, which was triturated from petroleum ether to afford the product (260 mg, 67%) as a solid. The e.e. of this product was determined to be 100% by chiral HPLC. (Column: CD-PH 250*4.6 mm I.D., Sum; Mobile phase: from 10% to 80% of B in A (A:Water with 0.069% TFA B:Acetonitrile); Flow rate: 0.8 mL/min; Column Temperature: 30° C.).

Example 112. Synthesis of Compound 112

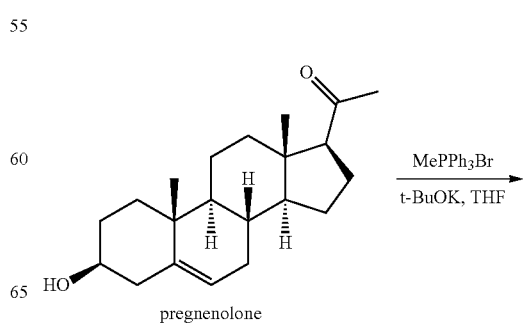

pregnenolone

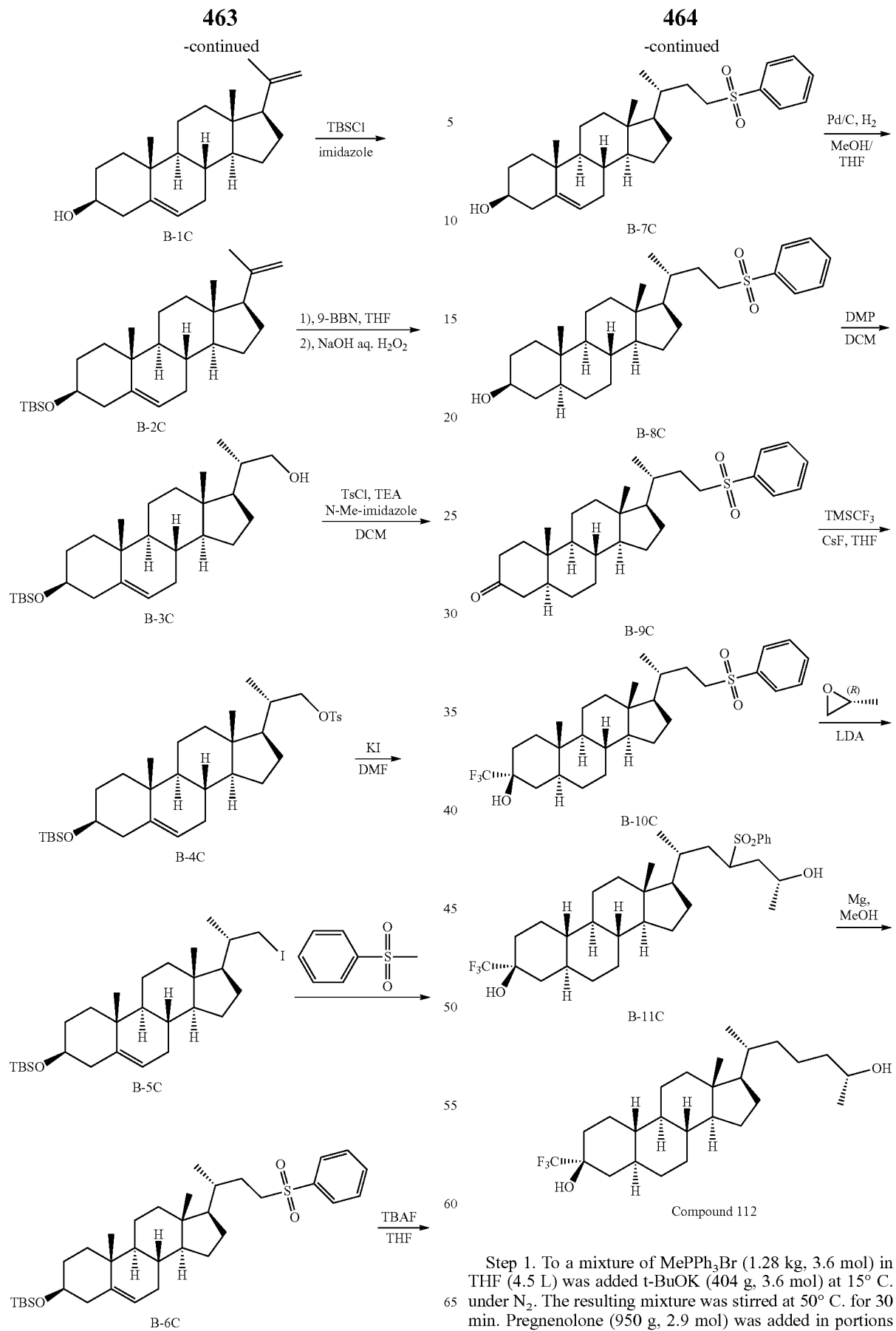
Step 1. To a mixture of MePPh$_3$Br (1.28 kg, 3.6 mol) in THF (4.5 L) was added t-BuOK (404 g, 3.6 mol) at 15° C. under N$_2$. The resulting mixture was stirred at 50° C. for 30 min. Pregnenolone (950 g, 2.9 mol) was added in portions below 65° C. The reaction mixture was stirred at 50° C. for 1 hour. The combined mixture was quenched with saturated NH₄Cl aqueous (1 L) at 15° C. THF layer was separated. The aqueous was extracted with EtOAc (2×2 L). The combined organic phase was concentrated under vacuum to give a solid. The solid was further purified by trituration with MeOH/H₂O (1:1, 15 L) at reflux to give B-1C (940 g, 99%) as a solid.

$^1$H NMR (400 MHz, CDCl₃) δ 5.40-5.32 (m, 1H), 4.85 (s, 1H), 4.71 (s, 1H), 3.58-3.46 (m, 1H), 2.36-2.16 (m, 2H), 2.08-1.94 (m, 2H), 1.92-1.62 (m, 9H), 1.61-1.39 (m, 6H), 1.29-1.03 (m, 4H), 1.01 (s, 3H), 0.99-0.91 (m, 1H), 0.59 (s, 3H).

Step 2. To a solution of B-1C (4 kg, 12.7 mol) in DCM (30 L) was added imidazole (1.72 kg, 25.4 mol) and TBSCl (2.86 kg, 19.0 mol) at 25° C. The reaction mixture was stirred at 25° C. for 16 hrs. The reaction mixture was treated with water (10 L). The organic phase was concentrated to give crude product which was triturated in MeOH (15 L) at reflux to give B-2C (5.02 kg, 92%) as a solid.

$^1$H NMR (400 MHz, CDCl₃) δ 5.38-5.28 (m, 1H), 4.85 (s, 1H), 4.71 (s, 1H), 3.57-3.41 (m, 1H), 2.33-2.11 (m, 2H), 2.10-1.94 (m, 2H), 1.90-1.61 (m, 8H), 1.60-1.38 (m, 6H), 1.28-1.03 (m, 4H), 1.00 (s, 3H), 0.98-0.91 (m, 1H), 0.89 (s, 9H), 0.58 (s, 3H), 0.06 (s, 6H).

Step 3. To a solution of B-2C (1.69 kg, 3.94 mol) in THF (8 L) was added 9-BBN dimer (671 g, 2.75 mol) and the reaction was stirred at 25° C. under N₂ for 1 h and a solid was formed. To the reaction mixture was added ethanol (2.26 L, 39.4 mol) and NaOH (3.94 L, 5 M, 19.7 mol) and the mixture became clear. Then H₂O₂ (3.94 L, 10 M, 39.4 mol) was added dropwise at 25° C. and the inner temperature was raised to reflux. The mixture was cooled and stirred for 16 hrs and a solid was formed. This was followed by adding Na₂SO₃ (2.5 L, 20% aq.) and water (5 L) at 25° C. The mixture was stirred for 1 h. After the stirrer was turned off, a clear lower layer and another upper suspension layer were formed. The clear lower layer was discarded. The upper suspension layer was treated with water (20 L). The mixture was stirred for 15 mins. The mixture was filtered. The solid was washed with water until pH<9 to give the wet product. The wet product B-3C was dissolved in DCM (100 L). The organic layer was separated, dried over Na₂SO₄, filtered and concentrated to 20 L. The residue was used in the next step directly.

$^1$H NMR (400 MHz, CDCl₃) δ 5.40-5.23 (m, 1H), 3.70-3.60 (m, 1H), 3.55-3.42 (m, 1H), 3.41-3.31 (m, 1H), 2.31-2.20 (m, 1H), 2.20-2.11 (m, 1H), 2.06-1.91 (m, 2H), 1.89-1.67 (m, 3H), 1.65-1.39 (m, 7H), 1.38-1.08 (m, 6H), 1.05 (d, J=6.4 Hz, 3H), 1.00 (s, 3H), 0.99-0.91 (m, 2H), 0.88 (s, 9H), 0.70 (s, 3H), 0.05 (s, 6H).

Step 4. To a solution of B-3C (theoretical mass: 5.2 kg, 11.6 mol) in DCM (15 L) was added N-methyl-imidazole (1.37 L, 17.4 mol) and TEA (3.2 L, 23.2 mol) at 25° C. Then TsCl (2.53 kg, 13.3 mol) was added into the solution in portions to keep the inner temperature between 25 to 30° C. The reaction mixture was stirred at 25° C. for 1 h. To the mixture was added water (10 L), citric acid (20%, 1 L). HCl (1 M) was added till pH=3. The organic layer was separated, washed with water (2×10 L), NaHCO₃ (sat. aq. 5 L) and brine (5 L), dried over Na₂SO₄, filtered and concentrated to give B-4C (6.63 kg, 95% for 2 steps) as a solid.

$^1$H NMR (400 MHz, CDCl₃) δ 7.78 (d, J=8.4 Hz, 2H), 7.34 (d, J=8.0 Hz, 2H), 5.37-5.25 (m, 1H), 3.96 (dd, J=2.8, 9.2 Hz, 1H), 3.79 (dd, J=6.4, 9.2 Hz, 1H), 3.53-3.41 (m, 1H), 2.45 (s, 3H), 2.32-2.20 (m, 1H), 2.20-2.11 (m, 1H), 2.01-1.88 (m, 2H), 1.84-1.61 (m, 4H), 1.56-1.31 (m, 6H), 1.23-1.02 (m, 5H), 1.02-0.95 (m, 7H), 0.93-0.90 (m, 1H), 0.88 (s, 9H), 0.63 (s, 3H), 0.05 (s, 6H).

Step 5. To a solution of B-4C (10 g, 16.6 mmol) in DMF (300 mL) was added KI (6.88 g, 41.5 mmol). The suspension was stirred at 50° C. for 2 hrs. The mixture was quenched with water (500 mL) and extracted with PE (3×150 mL). The combined organic phase was dried over Na₂SO₄, filtered and concentrated. The residue was triturated with EtOAc (50 mL) and filtered to give B-5C (7 g, 76%) as a solid.

$^1$H NMR (400 MHz, CDCl₃) δ 5.32-5.28 (m, 1H), 3.52-3.40 (m, 1H), 3.38-3.30 (m, 1H), 3.20-3.11 (m, 1H), 2.32-2.10 (m, 2H), 2.00-1.90 (m, 1H), 1.90-1.35 (m, 13H), 1.30-1.15 (m, 4H), 1.15-0.96 (m, 6H), 0.96-0.80 (m, 10H), 0.71 (s, 3H), 0.06 (s, 6H).

Step 6. To a solution of (methylsulfonyl) benzene (24.5 g, 157 mmol) in THF (200 mL) was added n-BuLi (57.2 mL, 143 mmol) at −70° C. under N₂. The mixture was stirred at −70° C. for 30 minutes. A solution of B-5C (40 g, 71.8 mmol) in THF (200 mL) was added dropwise at 25° C. After addition, the reaction was allowed to stir at 25° C. for 3 h. The reaction was quenched with sat.NH₄Cl (50 mL) and extracted with EtOAc (2×20 mL). The combined organic phase was dried over Na₂SO₄, filtered, concentrated to give B-6C (40 g, 95%).

$^1$H NMR (400 MHz, CDCl₃) δ 7.90-7.86 (m, 2H), 7.68-7.61 (m, 1H), 7.60-7.52 (m, 2H), 5.33-5.29 (m, 1H), 3.50-3.42 (m, 1H), 3.17-3.06 (m, 1H), 3.04-2.96 (m, 1H), 2.31-2.11 (m, 3H), 1.99-1.90 (m, 2H), 1.87-1.67 (m, 5H), 1.51-1.40 (m, 7H); 1.24-0.82 (m, 27H); 0.68-0.58 (m, 3H).

Step 7. To a suspension of B-6C (31.0 g, 54.7 mmol) in THF (100 mL) was added TBAF (21.4 kg, 82.0 mmol). The mixture was stirred at 65° C. for 1 h. The mixture turned clear. To the mixture was added water (300 mL) and stirred at 80° C. for 2 h. The mixture was filtered after cooling. The solid was washed with water (300 ml), dried in air to give B-7C (17 g, crude) as a solid, which was used directly for the next step.

Step 8. To a solution of B-7C (10.5 g, 22.3 mmol) in MeOH (100 mL) and THF (100 mL) was added Pd/C (2 g, <1% water). Then the solution was hydrogenated under 30 psi of hydrogen at 25° C. for 48 h. The reaction was conducted in parallel twice. The mixture was filtered through a pad of celite and the filtrate was concentrated in vacuum. The product was triturated by MeCN (100 mL) to afford B-8C (15 g, 71%) as a solid.

$^1$H NMR (400 MHz, CDCl₃) δ 7.91-7.89 (m, 2H), 7.67-7.64 (m, 1H), 7.59-7.55 (m, 2H), 3.60-3.55 (m, 1H), 3.15-3.06 (m, 1H), 3.02-2.94 (m, 1H), 1.89-1.70 (m, 3H), 1.69-1.64 (m, 3H), 1.53-1.20 (m, 12H), 1.15-0.89 (m, 7H), 0.86 (m, 4H), 0.78 (s, 3H), 0.63-0.56 (m, 4H)

Step 9. To a solution of B-8C (5.0 g, 10.5 mmol) in DCM (50 mL) was added DMP (8.90 g, 21.0 mmol) at 25° C. The mixture was stirred at 25° C. for 30 mins. The reaction was quenched with saturated aqueous NaHCO₃ (50 mL) and the pH was adjusted to 7~8. Then saturated Na₂S₂O₃ (100 mL) was added to the solution and extracted with DCM (100 mL). The combined organic layer was dried over anhydrous Na₂SO₄, filtered and concentrated to give B-9C (4.6 g, crude) as a solid, which was used in the next step without further purification.

$^1$H NMR (400 MHz, CDCl₃) δ 7.96-7.86 (m, 2H), 7.61-7.53 (m, 3H), 3.17-3.04 (m, 1H), 3.03-2.94 (m, 1H), 2.42-2.15 (m, 3H), 2.10-1.80 (m, 4H), 1.73-1.63 (m, 2H), 1.60 (s, 3H), 1.55-1.45 (m, 4H), 1.40-1.24 (m, 5H), 1.24-1.15 (m, 1H); 1.14-1.03 (m, 2H); 0.99 (s, 3H); 0.90-0.84 (m, 4H); 0.74-0.65 (m, 1H); 0.63 (s, 3H).

467

Step 10. To a solution of B-9C (4.6 g, 9.77 mmol) and CsF (2.96 g, 19.5 mmol) in THF (50 mL) was added dropwise TMSCF$_3$ (2.77 g, 19.5 mmol) at 0° C. The mixture was stirred and kept below 10° C. for 30 mins. To the mixture was added TBAF (24.4 mL, 1 M in THF, 24.4 mmol) at 10° C. The mixture was stirred and kept below 10° C. for 30 mins. To the mixture was added water (20 mL) and extracted with EtOAc (2×30 mL). The combined organic layers were washed with brine (50 mL) and dried over Na$_2$SO$_4$. The residue was purified by silica gel chromatography (PE/EtOAc=10/1) to afford B-10C (2.4 g, impure) as a solid. The impure B-10C (2.4 g) was purified by preparative HPLC (column: Phenomena Luna C18 250*50 mm*10 um, gradient: 20-100% B (A=water (0.05% HCl)-ACN, B=acetonitrile), flow rate: 100 mL/min, 25° C.) to obtain B-10C (1.6 g, 30%) as a foam.

$^1$H NMR (400 MHz, CDCl$_3$) δ 7.91-7.89 (m, 2H), 7.67-7.64 (m, 1H), 7.59-7.55 (m, 2H), 3.16-3.08 (m, 1H), 3.02-2.94 (m, 1H), 2.08-2.02 (m, 2H), 1.91-1.78 (m, 3H), 1.70-1.60 (m, 4H), 1.53-1.01 (m, 13H), 1.07-0.92 (m, 4H), 0.87-0.85 (m, 3H), 0.83 (s, 3H), 0.68-0.63 (m, 1H), 0.61 (m, 3H).

Step 11. To a solution of n-BuLi (440 μL, 2.5 M in hexane, 1.10 mmol) in THF (0.5 mL) at −65° C. under N$_2$ was added a suspension of B-10C (200 mg, 0.3698 mmol) in THF (2.5 mL) dropwise. The mixture was stirred for 30 minutes at −65° C. Diisopropylamine (111 mg, 1.10 mmol) was added at −65° C. After that, (R)-2-methyloxirane (32.2 mg, 0.5547 mmol) was added drop wise at −65° C. The mixture was stirred for another 30 minutes and then warmed to 25° C. gradually and stirred at 25° C. for 16 hours. The reaction mixture was quenched by saturated NH$_4$Cl aqueous (30 mL), extracted with ethyl acetate (3×20 mL). The combined organic phase was washed with brine (30 mL), dried over Na$_2$SO$_4$, filtered and concentrated under vacuum to give B-11C (250 mg, crude) as a solid, which was used directly for the next step.

Step 12. To a solution of B-11C (250 mg, 0.417 mmol) in MeOH (10 mL) was added Mg powder (398 mg, 16.6 mmol) and added NiCl$_2$ (100 mg, 0.771 mmol) was added at 60° C. The mixture was stirred at 60° C. for 3 hrs. After cooling, the mixture was quenched with HCl (50 mL, 1M) and ice-water (50 mL) until the reaction became clear and extracted with EtOAc (2×50 mL). The organic layers were washed with brine (2×50 mL), dried over Na$_2$SO$_4$, filtered, concentrated. The residue was purified by a silica gel column (PE/EtOAc=10/1) to give Compound 112 (33 mg) as a solid.

$^1$H NMR (400 MHz, CDCl$_3$) δ 3.80-3.76 (m, 1H), 2.08-1.93 (m, 3H), 1.86-1.77 (m, 2H), 1.70-1.62 (m, 3H), 1.54-1.44 (m, 4H), 1.42-1.32 (m, 6H), 1.31-1.22 (m, 5H), 1.20-1.18 (m, 4H), 1.14-0.96 (m, 6H), 0.94-0.86 (m, 4H), 0.85 (s, 3H), 0.70-0.66 (m, 1H), 0.65 (s, 3H).

LCMS Rt=1.265 min in 2.0 min chromatography, 30-90 AB

MS MS ESI calcd. for C$_{27}$H$_{44}$F$_3$O [M+H−H$_2$O]$^+$ 441, found 441

468

Example 113. Synthesis of Compound 2113

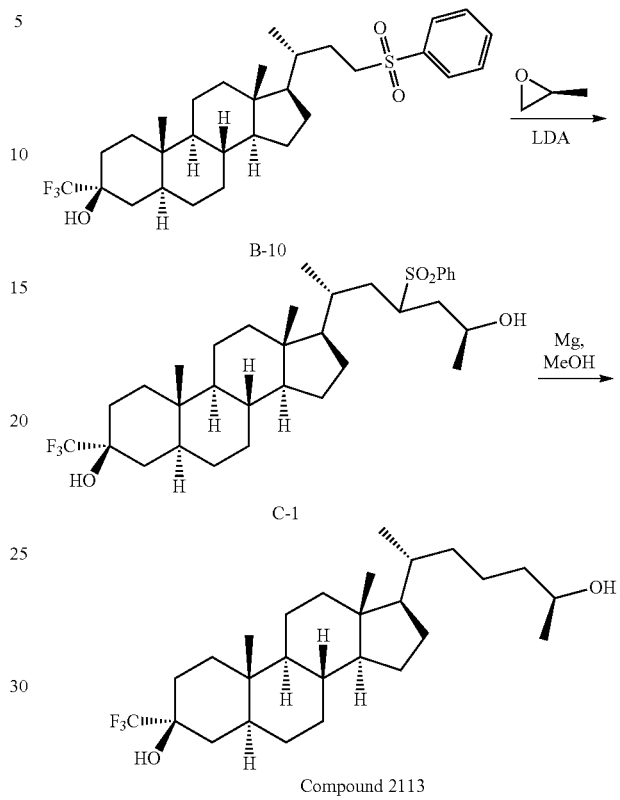

Compound 2113

Step 1. To a solution of n-BuLi (440 μL, 2.5 M in hexane, 1.10 mmol) in THF (0.5 mL) at −65° C. under nitrogen was added a suspension of B-10 (200 mg, 0.3698 mmol) in THF (2.5 mL) was added drop-wise. The mixture was stirred for 30 minutes at −65° C., followed by the addition of diisopropylamine (111 mg, 1.10 mmol). After that, (S)-2-methyloxirane (32.2 mg, 0.5547 mmol) was added drop-wise at −65° C. The mixture was stirred for another 30 minutes and then warmed to 25° C. gradually and stirred at 25° C. for 16 hours. The reaction mixture was quenched by saturated NH$_4$Cl aqueous (30 mL), extracted with ethyl acetate (3×20 mL). The combined organic phase was washed with brine (30 mL), dried over Na$_2$SO$_4$, filtered and concentrated under vacuum to give C-1 (250 mg, crude) as a solid, which was used directly for the next step.

Step 2. To a solution of C-1 (250 mg, crude) in MeOH (5 mL) was added Mg (202 mg, 8.34 mmol) under nitrogen. After that, the reaction mixture was stirred at 60° C. for 1 h under N$_2$. Aq. HCl (1M, 10 mL) was added. The mixture was extracted with EtOAc (2×10 mL). The organic layer washed with saturated aqueous NaHCO$_3$ (10 mL) solution and brine (10 mL), dried over anhydrous Na$_2$SO$_4$, filtered and concentrated in vacuum to give a crude product. The crude product was purified by silica gel column (EtOAc/PE=1/10 to 1/5) to give impure Compound 2113 (100 mg) as a solid, which was re-crystallized from DCM/acetonitrile (5 mL, 2/3) at 25° C. to give Compound 2113 (52 mg, 52%) as a solid.

$^1$H NMR (400 MHz, CDCl$_3$) δ 3.79 (s, 1H), 2.08-1.94 (m, 3H), 1.82-1.79 (m, 2H), 1.66-1.01 (m, 28H), 0.91-0.90 (m, 4H), 0.85 (s, 3H), 0.71-0.65 (m, 4H).

LCMS Rt=1.267 min in 2.0 min chromatography, 30-90 AB, MS ESI calcd. for $C_{27}H_{44}F_3O$ [M+H−H$_2$O]$^+$ 441, found 441.

Example 114. Synthesis of Compound 3114

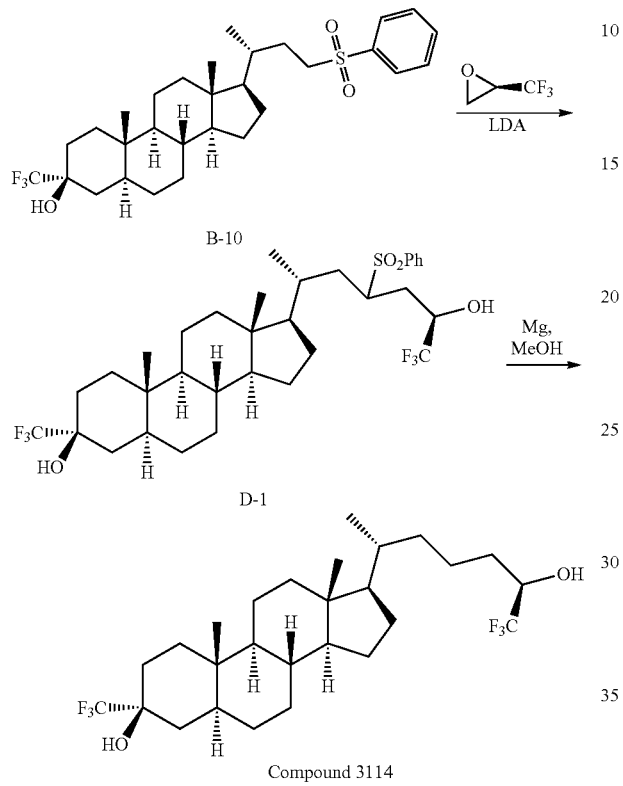

Compound 3114

Step 1. To a solution of diisopropylamine (156 mg, 1.55 mmol) in THF (0.5 mL) was added n-BuLi (0.552 mL, 1.38 mmol, 2.5M in hexane) under N$_2$ at −70° C. Then a solution of B-10 (300 mg, 0.554 mmol) in THF (3 mL) was added slowly. The mixture was stirred at −70° C. for 30 minutes and then (R)-2-(trifluoromethyl)oxirane (A-1) (93.2 mg, 0.831 mmol) was added and the reaction was stirred at 25° C. for 16 hrs. The mixture was quenched with saturated NH$_4$Cl (30 mL) and extracted with EtOAc (3×10 mL). The combined organic phase was dried over Na$_2$SO$_4$, filtered and concentrated to give crude D-1 (350 mg) as a solid, which was used directly in the next step.

Step 2. To a solution of D-1 (350 mg, 0.536 mmol) in MeOH (30 mL) was added Mg powder (520 mg, 21.4 mmol) at 55° C. The mixture was stirred at 60° C. for 30 minutes under N$_2$. The mixture was quenched with HCl (50 mL, 1N) until the reaction became clear and extracted with DCM (2×30 mL). The combined organic phase was dried over Na$_2$SO$_4$, filtered, concentrated and purified by flash column (0-10% of EtOAc in PE) to give Compound 3114 (65 mg, 24%) as a solid.

$^1$H NMR (400 MHz, CDCl$_3$) δ 3.93-3.88 (m, 1H), 2.08-2.01 (m, 1H), 2.00-1.92 (m, 3H), 1.85-1.75 (m, 2H), 1.70-1.58 (m, 5H), 1.50-1.32 (m, 8H), 1.31-1.13 (m, 6H), 1.12-0.96 (m, 5H), 0.95-0.92 (m, 4H), 0.90 (s, 3H), 0.70-0.60 (m, 4H).

LCMS Rt=1.280 min in 2.0 min chromatography, 30-90 AB
MS ESI calcd. for $C_{27}H_{41}F_6O$ [M+H−H$_2$O]$^+$ 495, found 495.

Example 115. Synthesis of Compound 4115

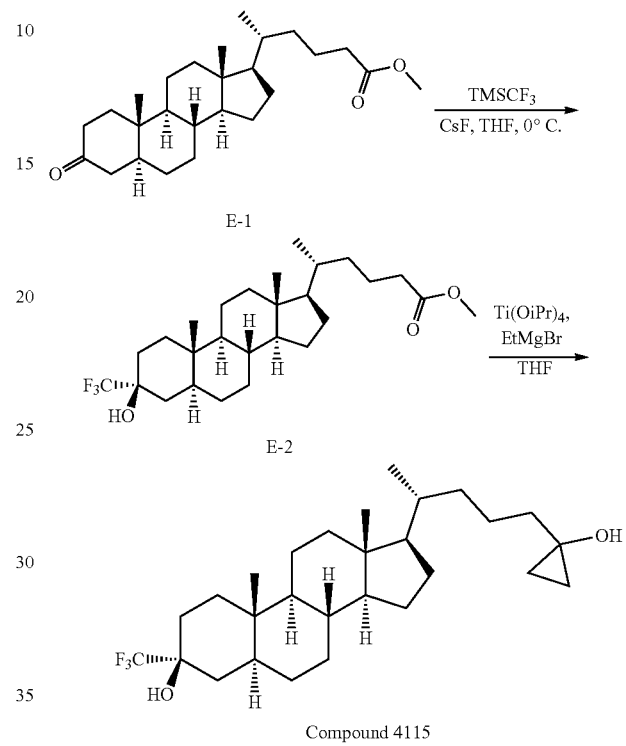

Compound 4115

Step 1. To a solution of E-1 (200 mg, mmol, preparation described in WO9827106 and U.S. Pat. No. 5,856,535) and CsF (141 mg, 0.99 mmol) in THF (5 mL) was added drop wise TMSCF$_3$ (150 mg, 0.99 mmol) at 0° C. The mixture was stirred and kept below 10° C. for 10 mins. Then TBAF (2.5 mL, 1 M in THF, 2.5 mmol) was added at 10° C. and the mixture was stirred and kept below 10° C. for 10 mins. The reaction mixture was quenched by adding water (20 mL) and extracted with EtOAc (2×30 mL). The combined organic layers was washed with brine (50 mL), dried over Na$_2$SO$_4$, filtered and concentrated in vacuum. The residue was purified by silica gel chromatograph (PE/EtOAc=5/1) to afford E-2 (146 mg, 59%) as a solid.

$^1$H NMR (400 MHz, CDCl$_3$) δ 3.66 (s, 3H), 2.31-2.21 (m, 2H), 2.08-1.92 (m, 2H), 1.82-1.77 (m, 2H), 1.71-1.65 (m, 4H), 1.50-1.20 (m, 14H), 1.10-0.99 (m, 5H), 0.92-0.84 (m, 7H), 0.71-0.67 (m, 1H), 0.64 (s, 3H).

Step 2. To a solution of E-2 (146 mg, 0.31 mmol) in THF (1.5 mL) was added Ti(i-PrO)$_4$ (87.5 mg, 0.31 mmol) and followed by adding EtMgBr (0.36 mL, 3 M in Et$_2$O, 1.07 mmol) dropwise at 25° C. After that, the reaction mixture was stirred at 25° C. for 15 min under N$_2$. The reaction mixture was quenched with saturated aqueous NH$_4$Cl (20 mL) solution and extracted with EtOAc (3×20 mL). The combined organic layer was washed with brine (50 mL), dried over Na$_2$SO$_4$, filtered and concentrated in vacuum to give a crude product, which was purified by silica gel column (EtOAc/PE=5/1) to afford Compound 4115 (45 mg, 31%) as a solid.

¹H NMR (400 MHz, CDCl₃) δ 2.10-2.03 (m, 1H), 2.01-1.92 (m, 2H), 1.87-1.77 (m, 2H), 1.75 (s, 1H), 1.72-1.60 (m, 3H), 1.54-1.35 (m, 10H), 1.31-0.98 (m, 12H), 0.92 (d, J=6.5 Hz, 3H), 0.85 (s, 3H), 0.74-0.72 (m, 2H), 0.70-0.67 (m, 1H), 0.65 (s, 3H), 0.45-0.43 (m, 2H). MS ESI calcd. For $C_{28}H_{46}F_3O_2$ [M+H]⁺ 471, found 471.

Example 116. Synthesis of Compound 5116

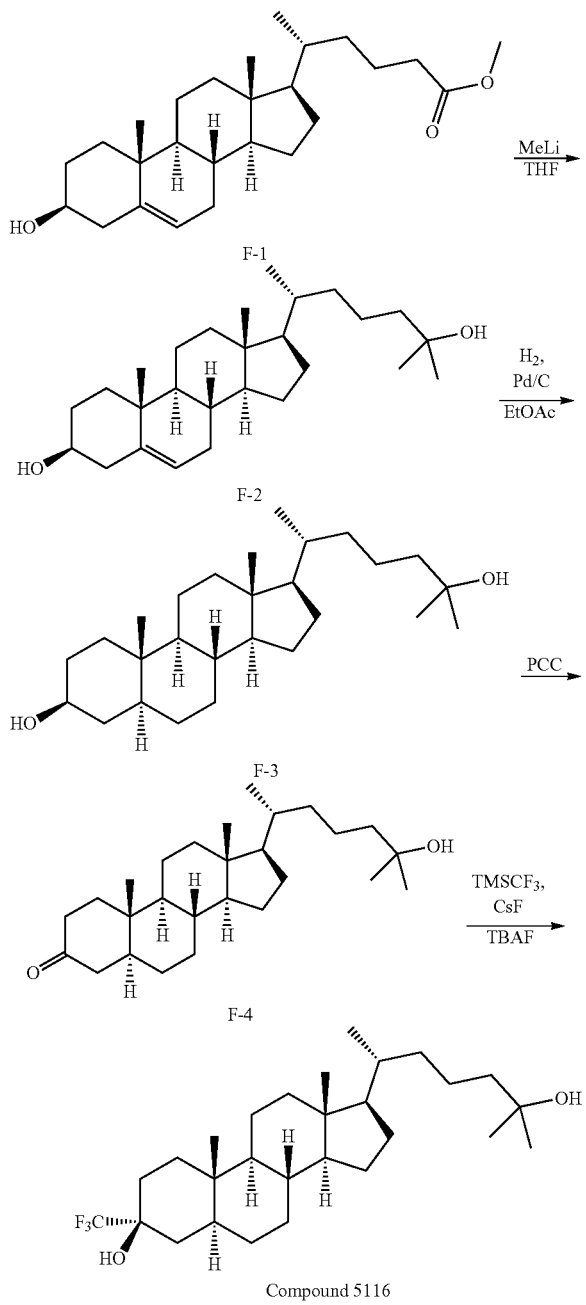

Step 1. To a solution of F-1 (see WO 2017007836 for its synthesis) (7 g, 17.3 mmol) in THF (70 mL) was added MeLi (54.0 mL, 86.4 mmol, 1.6 M in diethyl ether) at 0° C. under N₂. The reaction was warmed to 25° C. and stirred at 25° C. for 1 h. The reaction was quenched with ice water (200 mL), filtered and extracted with EtOAc (2×200 mL). The combined organic layers were dried over Na₂SO₄, filtered and concentrated in vacuum to give F-2 (8 g, crude) as a solid.

¹H NMR (400 MHz, CDCl₃) δ 5.4-5.3 (m, 1H), 3.6-3.45 (m, 1H), 2.35-2.25 (m, 2H), 2.05-1.9 (m, 2H), 1.88-1.75 (m, 3H), 1.54-1.26 (m, 15H) 1.24-1.15 (m, 6H), 1.15-1.1 (m, 6H), 1.01-0.95 (m, 3H), 0.93-0.91 (m, 4H), 0.7-0.6 (m, 3H).

Step 2. To a solution of F-2 (2 g, 4.96 mmol) in MeOH/THF (40 mL/10 mL) was added Pd/C (dry, 10%, 0.8 g). After degassing and back-filling with H₂ for three times, the reaction mixture was stirred for 48 h at 50° C. in H₂ atmosphere (50 psi). The mixture was filtered and concentrated in vacuum to give F-3 (2 g, crude) as a solid.

¹H NMR (400 MHz, CDCl₃) δ 3.65-3.50 (m, 1H), 2.01-1.85 (m, 1H), 1.84-1.75 (m, 2H), 1.73-1.57 (m, 5H), 1.55-1.50 (m, 8H), 1.49-1.3 (m, 6H) 1.29-1.15 (m, 6H), 1.15-0.95 (m, 9H), 0.94-0.8 (m, 3H), 0.79-0.75 (m, 3H), 0.7-0.5 (m, 4H).

Step 3. To the solution of F-3 (2.06 g, 5.10 mmol) in DCM (20 mL) was added PCC (2.21 g, 10.2 mmol) at 25° C., The reaction was stirred at 25° C. for 2 h, The mixture was concentrated in vacuum to give crude F-4 (1.6 g), which was purified by column chromatography on silica gel (0-20% of EtOAc in PE) to give F-4 (1.2 g) as a solid.

¹H NMR (400 MHz, CDCl₃) δ 2.45-2.25 (m, 3H), 2.20-1.9 (m, 3H), 1.82-1.75 (m, 1H), 1.73-1.6 (m, 1H), 1.57-1.25 (m, 14H), 1.24-1.1 (m, 14H) 1.09-0.95 (m, 3H), 0.94-0.79 (m, 3H), 0.77-0.6 (m, 4H).

Step 4. To a solution of F-4 (100 mg, 248 μmol) in THF (5 mL) was added TMSCF₃ (176 mg, 1.24 mmol) and TBAF (0.5 mL, 1 M in THF, 0.5 mmol). The mixture was stirred at 10° C. for 1 h. To the mixture was added TBAF (2.48 mL, 1 M in THF, 2.48 mmol). The mixture was stirred at 30° C. for another 2 h. The mixture was concentrated in vacuum. The residue was dissolved in EtOAc (50 mL), washed with water (2×50 mL), brine (50 mL), dried over Na₂SO₄, filtered, concentrated in vacuum to give crude Compound 5116 (80 mg) as a solid. 50 mg of crude Compound 5116 was triturated with acetonitrile (10 mL) at 50° C. Then the precipitate was collected by filtration and concentrated in vacuum to give Compound 5116 (20 mg).

¹H NMR (400 MHz, CDCl₃) δ 2.13-1.97 (m, 2H), 1.96-1.8 (m, 1H), 1.79-1.7 (m, 2H), 1.69-1.61 (m, 4H), 1.60-1.25 (m, 15H), 1.24-1.15 (m, 6H), 1.14-0.92 (m, 7H), 0.9-0.8 (m, 3H), 0.79-0.76 (m, 3H), 0.75-0.55 (m, 4H). LCMS Rt=1.305 min in 2 min chromatography, 30-90 AB, MS ESI calcd. For $C_{28}H_{46}F_3O$ [M+H−H₂O]⁺ 455, found 455.

Example 117: Synthesis for 11786

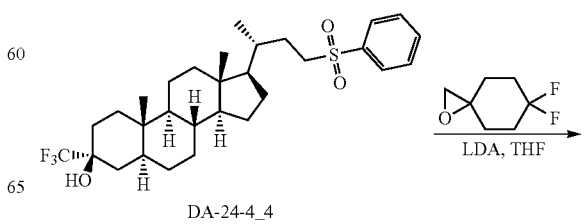

473

-continued

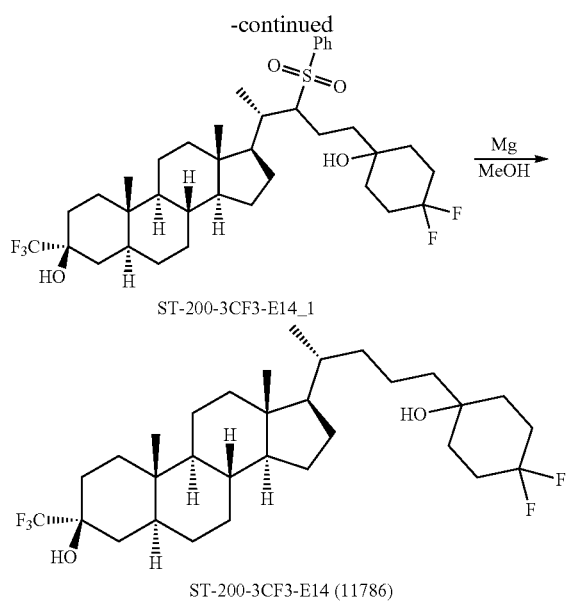

ST-200-3CF3-E14_1

ST-200-3CF3-E14 (11786)

The synthesis of DA-24-4_4 can be found in Example 112. The synthesis of epoxide can be found in Example 87.

Synthesis of ST-200-3CF3-E14_1

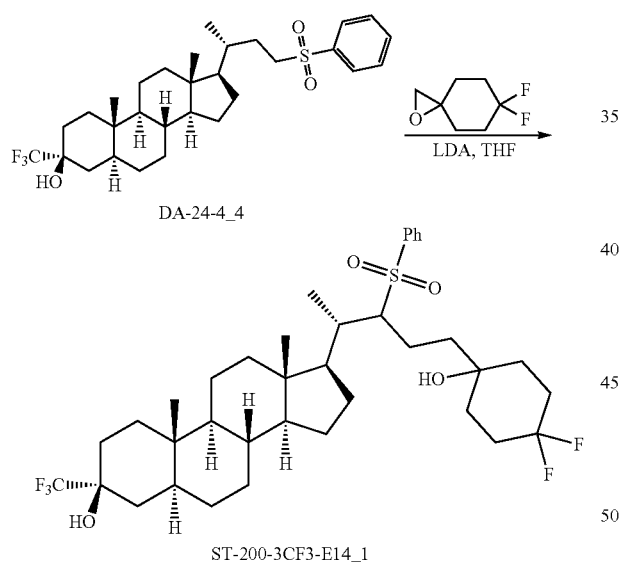

DA-24-4_4

ST-200-3CF3-E14_1

To THF (0.5 mL) was added BuLi (0.368 mL, 2.5 M in hexane, 0.922 mmol). A solution of DA-24-4-4 (200 mg, 0.369 mmol) in THF (3 mL) was added at −70° C. The mixture was stirred at −70° C. for 1 h and iPr₂NH (104 mg, 1.03 mmol) was added. After 10 minutes, a solution of 6,6-difluoro-1-oxaspiro[2.5]octane (163 mg, 0.553 mmol, 50% purity) was added at −70° C. The mixture was stirred at −70° C. for another 1 h. The mixture was warmed to 25° C. and stirred for 16 hrs. To the mixture was added NH₄Cl (50 mL, sat. aq.). The mixture was extracted with EtOAc (2×30 mL). The organic layer was separated, dried over Na₂SO₄, filtered, and concentrated to give ST-200-3CF3-E14_1 (250 mg, crude) as a solid, which was used directly for the next.

474

Synthesis of ST-200-3CF3-E14

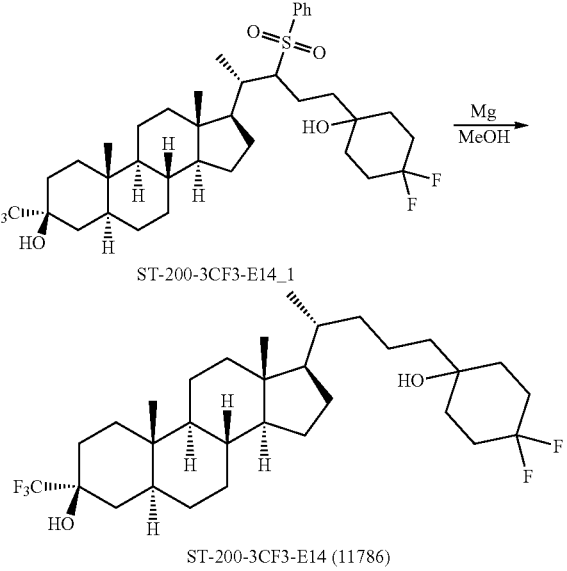

ST-200-3CF3-E14_1

ST-200-3CF3-E14 (11786)

To a solution of ST-200-3CF3-E14_1 (250 mg, 0.362 mmol) in MeOH (20 mL) was added Mg powder (349 mg, 14.4 mmol) at 55° C. The mixture was stirred at 60° C. for 16 hrs. The mixture was quenched with HCl (50 mL, 1 N) until the reaction became clear and extracted with DCM (2×30 mL). The combined organic phase was dried over Na₂SO₄, filtered, concentrated and purified by flash column (0-10% of EtOAc in PE) to give ST-200-3CF3-E14 (22 mg, 11%) as a solid.

$^1$H NMR (400 MHz, CDCl$_3$) δ 2.10-2.01 (m, 3H), 1.99-1.88 (m, 4H), 1.86-1.72 (m, 2H), 1.70-1.58 (m, 7H), 1.56-1.32 (m, 10H), 1.31-1.13 (m, 7H), 1.11-0.97 (m, 6H), 0.95-0.86 (m, 4H), 0.84 (s, 3H), 0.65 (s, 3H).

LCMS Rt=1.329 min in 2.0 min chromatography, 30-90 AB, purity 98.9%, the MS did not show molecular ion by different methods.

Example 118: Synthesis for 11828

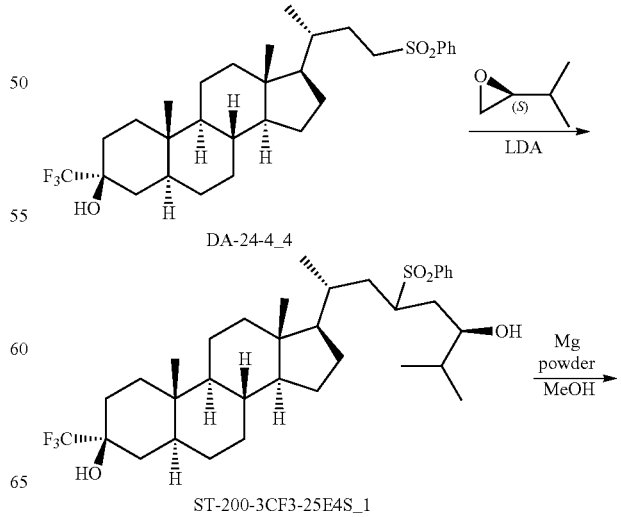

DA-24-4_4

ST-200-3CF3-25E4S_1

-continued

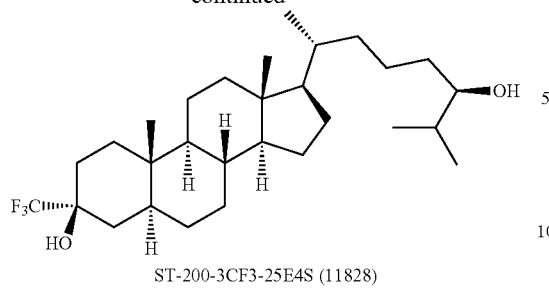

ST-200-3CF3-25E4S (11828)

The synthesis of DA-24-4_4 can be found in Example 112.

Synthesis of ST-200-3CF3-25E4S_1

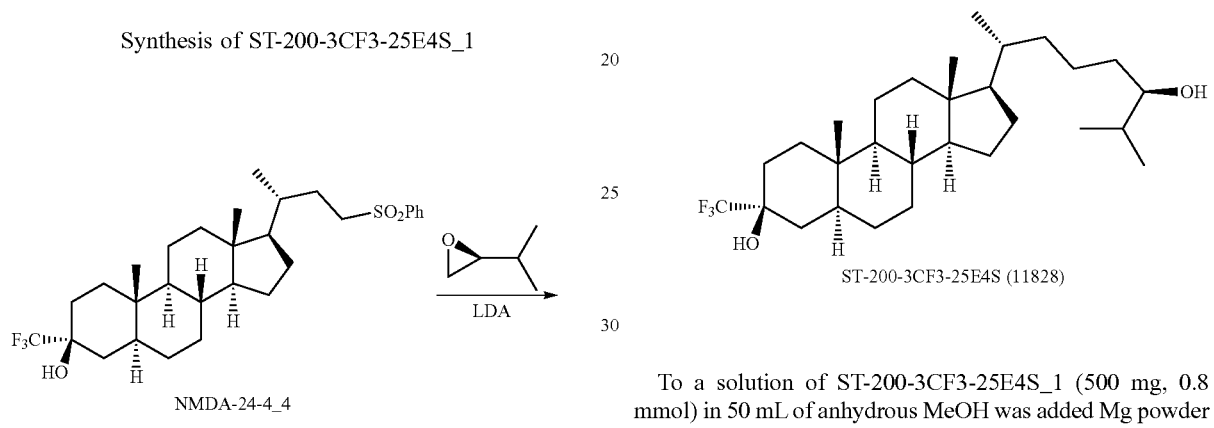

To a solution of n-BuLi (0.46 mL, 2.5 M in hexane, 1.15 mmol) in THF (1 mL) at −70° C. under N₂ a suspension of DA-24-4_4 (250 mg, 0.46 mmol) in THF (4 mL) was added dropwise. The mixture was stirred for 30 minutes at −70° C. A solution of diisopropylamine (116 mg, 1.15 mmol) was added dropwise at −70° C., then a solution of (S)-2-isopropyloxirane (59.6 mg, 0.69 mmol) was added dropwise at −70° C. The mixture was stirred for another 30 min and then warmed to 25° C. gradually. The reaction mixture was stirred at 25° C. for 24 hour. The reaction mixture was quenched by saturated NH₄Cl aqueous (5 mL), extracted with EtOAc (3×10 mL). The combined organic phase was washed with brine (30 mL), dried over Na₂SO₄, filtered and concentrated under vacuum to give ST-200-3CF3-25E4S_1 (500 mg, crude) as a solid, which was used directly for the next step.

Synthesis of ST-200-3CF3-25E4S

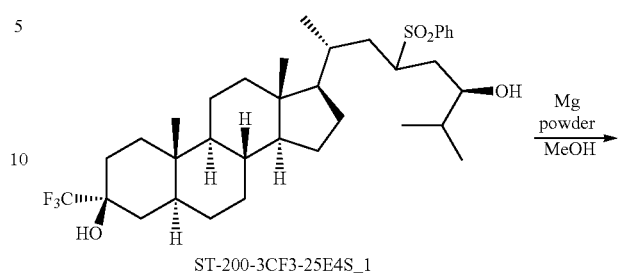

ST-200-3CF3-25E4S_1

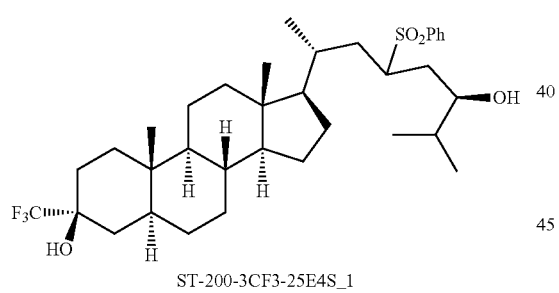

ST-200-3CF3-25E4S (11828)

To a solution of ST-200-3CF3-25E4S_1 (500 mg, 0.8 mmol) in 50 mL of anhydrous MeOH was added Mg powder (763 mg, 31.8 mmol) and NiCl₂ (1 mg, 0.008 mmol) with stirring under N₂ at 60° C. The reaction mixture was quenched by 2 M HCl (50 mL) until solid was dissolved. The mixture was extracted with EtOAc (3×50 mL). The combined organic layer was washed with Sat. NaHCO₃ (100 mL), brine (100 mL), dried over Na₂SO₄, filtered and concentrated. The residue was purified by flash column (0~10% of EtOAc in PE) to give to give a solid, which was triturated from n-hexane (5 mL) at 25° C. to give ST-200-3CF3-25E4S (102 mg, 68%) as solid.

¹H NMR (400 MHz, CDCl₃) δ 3.44-3.29 (m, 1H), 2.11-1.91 (m, 3H), 1.87-1.60 (m, 6H), 1.52-1.32 (m, 10H), 1.31-0.97 (m, 12H), 0.95-0.88 (m, 10H), 0.86-0.81 (m, 3H), 0.73-0.61 (m, 4H).

LCMS Rt=1.503 min in 2 min chromatography, 30-90AB_2 MIN_E, purity 100%, MS ESI calcd. For $C_{29}H_{48}F_3O$ $[M+H-H_2O]^+$ 469, found 469.

Example 119: Synthesis for 11934

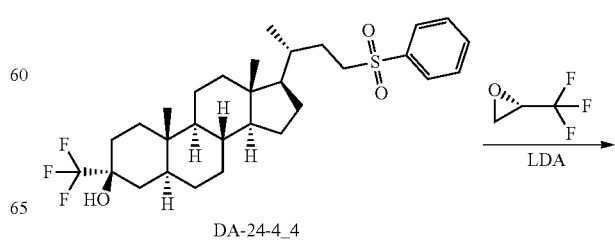

DA-24-4_4

-continued

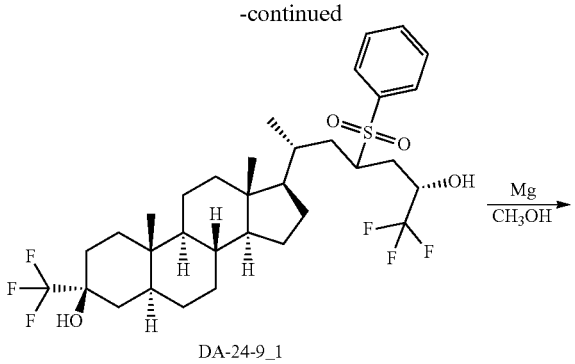

DA-24-9_1

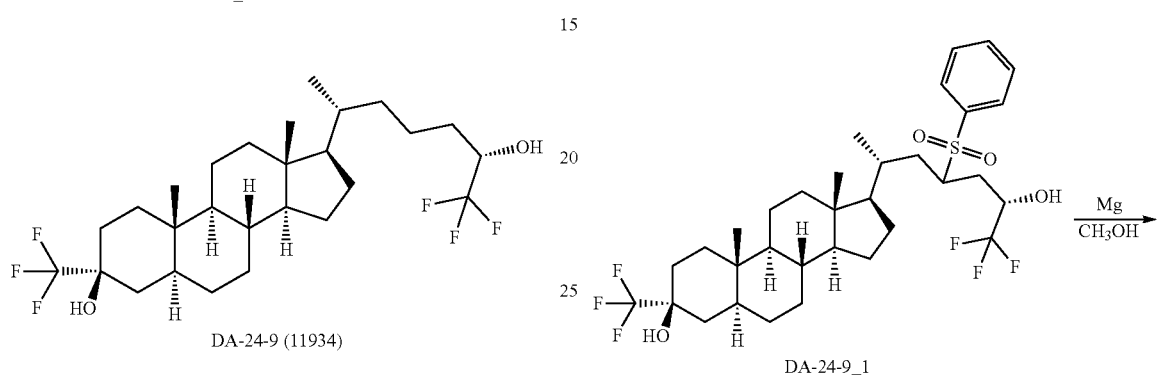

DA-24-9 (11934)

The synthesis of DA-24-4_4 can be found in Example 112.

Synthesis of DA-24-9_1

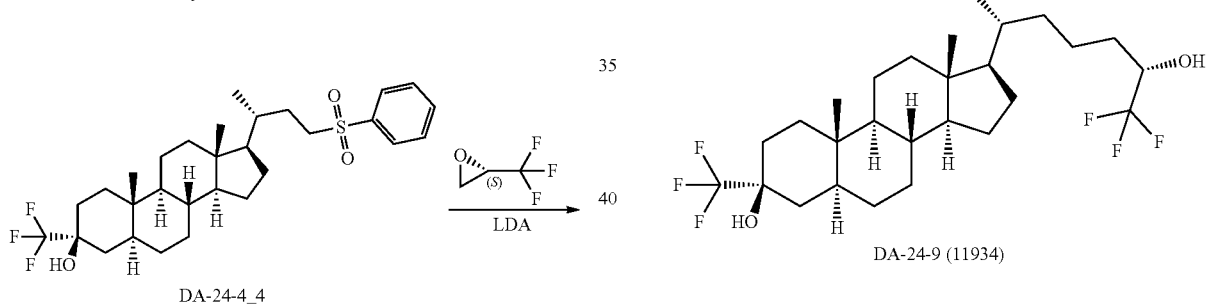

To a solution of n-BuLi (552 μL, 2.5 M in hexane, 1.38 mmol) in THF (1 mL) at −65° C. under N₂ was added a suspension of DA-24-4_4 (250 mg, 0.462 mmol) in THF (4 mL) was added dropwise. The mixture was stirred for 30 minutes at −65° C. Diisopropylamine (139 mg, 1.38 mmol) was added at −65° C. (S)-2-(trifluoromethyl)oxirane (154 mg, 1.38 mmol) was added dropwise at −65° C. The mixture was stirred for another 30 minutes and then warmed to 25° C. gradually. The reaction mixture was stirred at 25° C. for 16 hours and quenched with sat. NH₄Cl aq. (50 mL), extracted with EtOAc (3×50 mL). The combined organic layers were dried over Na₂SO₄, filtered and concentrated to give DA-24-9_1 (250 mg, crude) as a solid, which was used directly for the next step.

Synthesis of DA-24-9

To a solution of DA-24-91 (250 mg, 0.382 mmol) and NiCl₂ (4.92 mg, 0.038 mmol) in dry methanol (50 mL) was added Mg powder (364 mg, 15.2 mmol) in 4 portions under N₂ with stirring at 50° C. The reaction mixture was stirred at 60° C. for 1 hour. The mixture was quenched with HCl (50 mL, 1N) until the reaction became clear and extracted with EtOAc (3×30 mL). The combined organic phase was dried over Na₂SO₄, filtered, concentrated. The residue was purified by flash column (0-15% of EtOAc in PE) to give impure DA-24-9 (65 mg) as a solid, which was triturated from n-hexane (10 mL) at 68° C. for 2 h to give DA-24-9 (23 mg, 12%) as a solid.

$^1$H NMR (400 MHz, CDCl₃) δ 3.95-3.85 (m, 1H), 2.08-1.90 (m, 4H), 1.70-1.58 (m, 7H), 1.50-1.13 (m, 14H), 1.13-0.98 (m, 5H), 0.98-0.85 (m, 4H), 0.85 (s, 3H), 0.70-0.60 (m, 4H).

HPLC Rt=3.15 min in 8.0 min chromatography, 50-100_AB_1.2 ml_E, purity 100%.

HRMS MS ESI calcd. for $C_{27}H_{41}F_6[M+H-H_2O]+$ 495.3056, found 495.3050.

Example 120: Synthesis of 12055

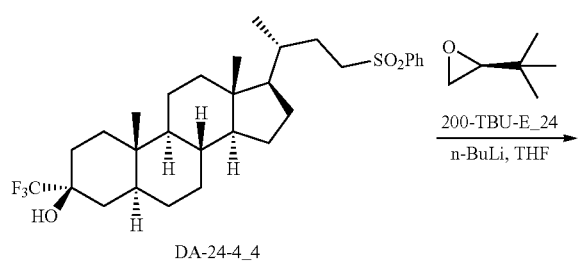
DA-24-4_4

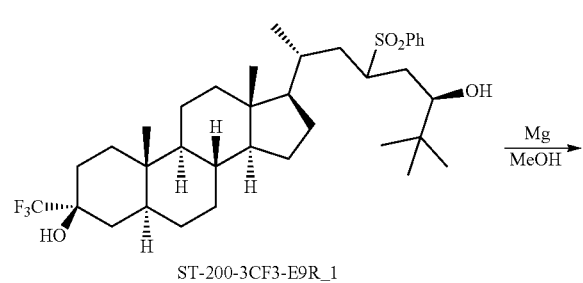
ST-200-3CF3-E9R_1

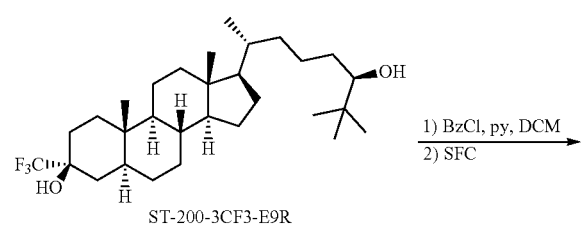
ST-200-3CF3-E9R

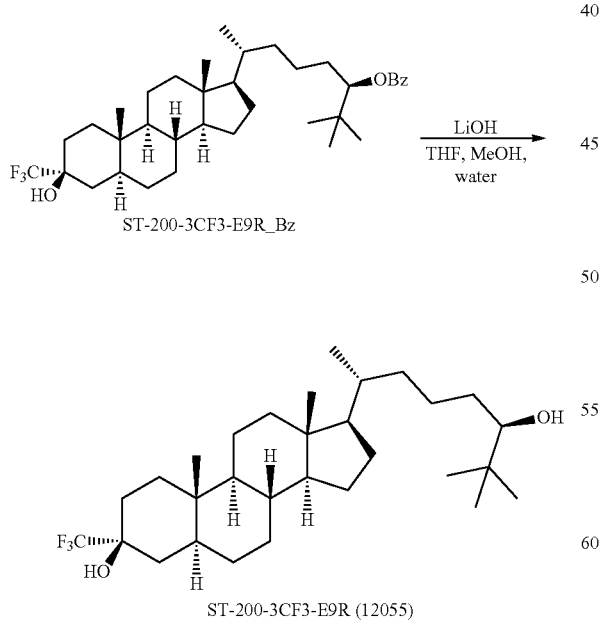
ST-200-3CF3-E9R_Bz

ST-200-3CF3-E9R (12055)

The synthesis of DA-24-4_4 can be found in Example 112.

Synthesis of ST-200-3CF3-E9R_1

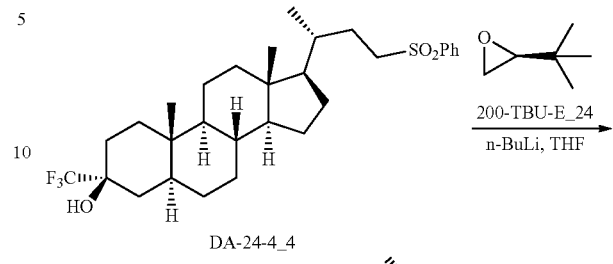
DA-24-4_4

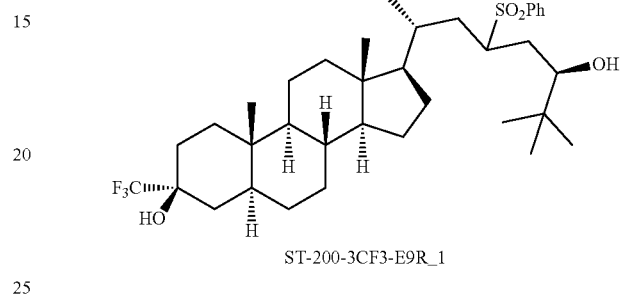
ST-200-3CF3-E9R_1

To THF (0.5 mL) was added BuLi (0.46 mL, 2.5 M in hexane, 1.15 mmol). A solution of DA-24-4_4 (250 mg, 0.462 mmol) in THF (3 mL) was added at −70° C. After stirring at −70° C. for 1 h, diisopropylamine (130 mg, 1.29 mmol) was added. After 10 minutes, (S)-2-(tert-butyl)oxirane (69.4 mg, 0.693 mmol) was added at −70° C. The mixture was stirred at −70° C. for another 1 h. The mixture was warmed to 25° C. and stirred for 16 hrs. To the mixture was added $NH_4Cl$ (50 mL, sat. aq.). The mixture was extracted with EtOAc (2×30 mL). The organic layer was separated, dried over $Na_2SO_4$, filtered, and concentrated to give ST-200-3CF3-E9R_1 (250 mg, crude) as a solid, which was used directly for the next step.

Synthesis of ST-200-3CF3-E9R

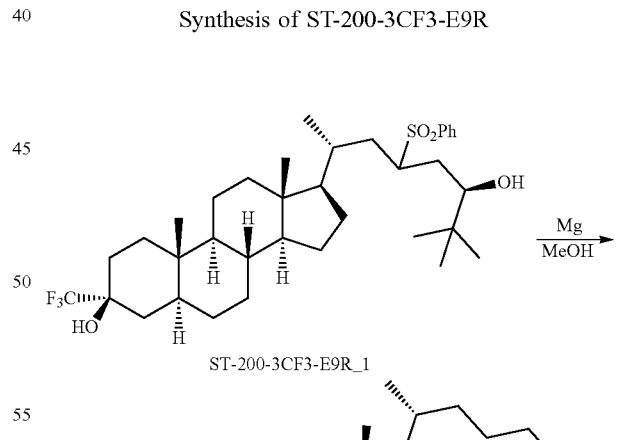
ST-200-3CF3-E9R_1

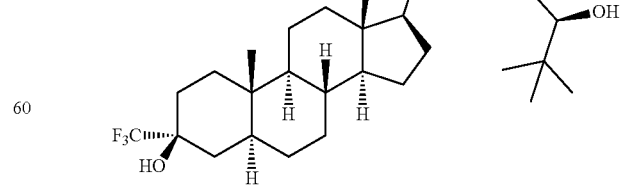
ST-200-3CF3-E9R

To a solution of ST-200-3CF3-E9R 1 (250 mg, 0.390 mmol) in MeOH (20 mL) was added Mg powder (374 mg, 15.6 mmol) at 55° C. The mixture was stirred at 60° C. for 16 hrs. The mixture was quenched with HCl (50 mL, 1 M) until the reaction became clear and extracted with DCM (2×30 mL). The combined organic phase was dried over Na₂SO₄, filtered, concentrated. The residue was purified by flash column (0-10% of EtOAc in PE) to give ST-200-3CF3-E9R (150 mg, 77%) as a solid. This material was converted to the benzoate ester to facilitate purification of the compound as shown in the next step.

¹H NMR (400 MHz, CDCl₃) δ 3.22-3.15 (m, 1H), 2.10-1.93 (m, 3H), 1.88-1.75 (m, 2H), 1.72-1.58 (m, 3H), 1.58-0.97 (m, 23H), 0.97-0.80 (m, 15H), 0.75-0.68 (m, 1H), 0.65 (s, 3H).

Synthesis of ST-200-3CF3-E9R_Bz

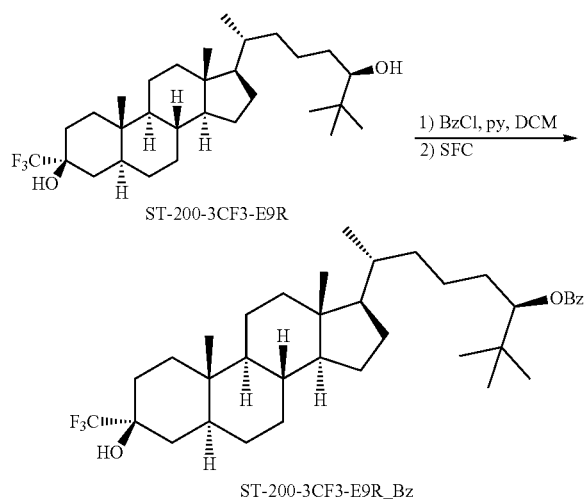

To a solution of ST-200-3CF3_E9R (180 mg, 0.359 mmol) in DCM (2 mL) was added py (567 mg, 7.18 mmol) and BzCl (251 mg, 1.79 mmol). The mixture was stirred at 25° C. for 2 h. The mixture was washed with NaHCO₃ (5 mL, 10% aq), HCl (5 mL, 2 M), purified by prep-TLC (PE:EtOAc=50:1) to give ST-200-3CF3-E9R_Bz (150 mg) as a solid. The crude ST-200-3CF3-E9R_Bz (150 mg) was purified by SFC (Instrument: SFC-14; Column: AD(250 mm*30 mm, 10 um); Condition: 0.1% NH₃H₂O EtOH; Begin B: 30%; End B: 30%; FlowRate(ml/min): 60ML/MIN; Injections: 180) to give pure ST-200-3CF3-E9R_Bz (100 mg) as an oil.

Synthesis of ST-200-3CF3-E9R

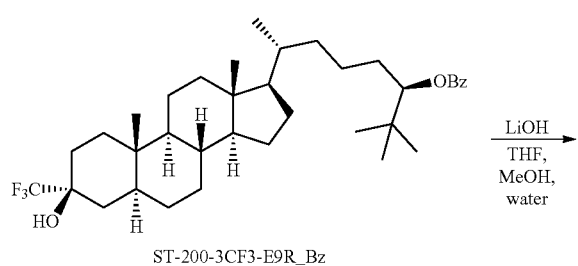

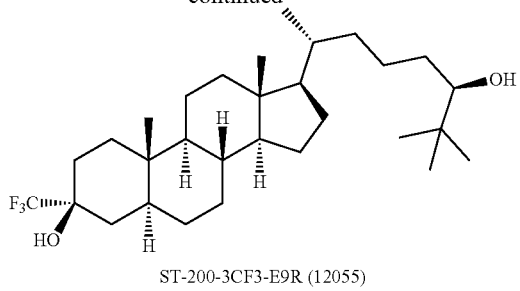

To a solution of ST-200-3CF3-E9R_Bz (100 mg, 0.165 mmol) in THF (1 mL) was added MeOH (0.5 mL), water (0.5 mL) and LiOH.H₂O (69.2 mg, 1.65 mmol), The mixture was stirred at 50° C. for 72 h. To the mixture was added water (2 mL). The mixture was extracted with EtOAc (5 mL). The organic layer was separated, concentrated in vacuum, purified by silica gel column (PE/DCM/EtOAc=40/1/1 to 20/1/1) to give ST-200-3CF3-E9R (60 mg, 73%) as a solid. The impure was re-crystallized from MeCN (0.5 mL) to give ST-200-3CF3-E9R (22 mg) as a solid.

¹H NMR (400 MHz, CDCl₃) δ 3.18 (dd, J=5.2, 10.0 Hz, 1H), 2.10-1.93 (m, 3H), 1.88-1.75 (m, 2H), 1.72-1.58 (m, 4H), 1.55-1.28 (m, 12H), 1.28-0.95 (m, 10H), 0.91 (d, J=6.8 Hz, 3H), 0.89 (s, 9H), 0.85 (s, 3H), 0.75-0.68 (m, 1H), 0.65 (s, 3H).

HPLC Rt=6.63 min in 8.0 min chromatography, 50-100_AB_E, purity 97.3%.

Example 121: Synthesis for 12156

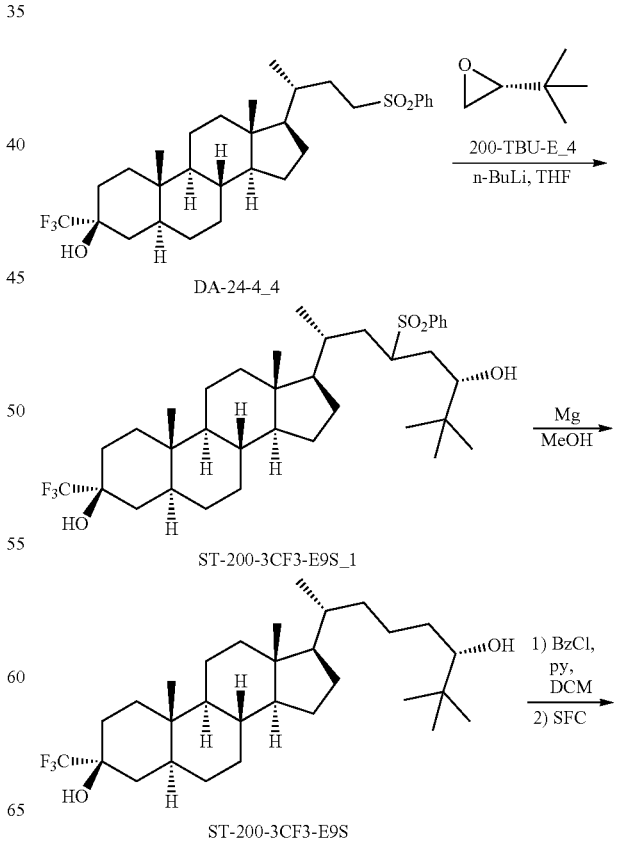

-continued

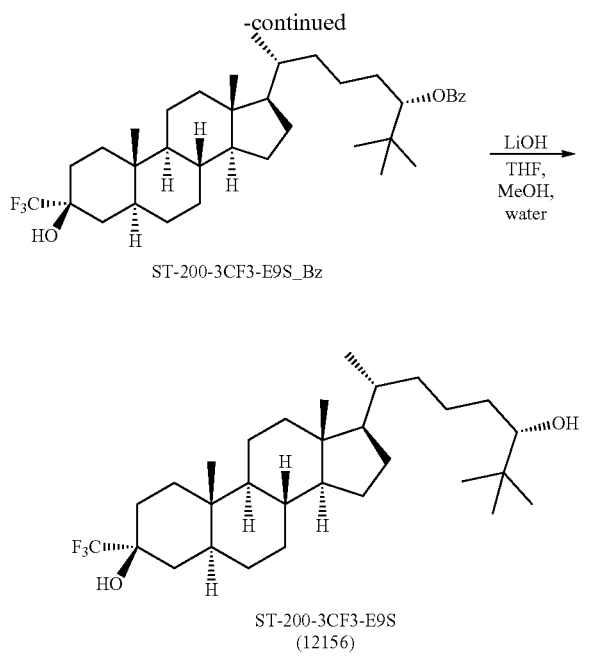

The synthesis of DA-24-4_4 can be found in Example 112.

Synthesis of ST-200-3CF3-E9S_1

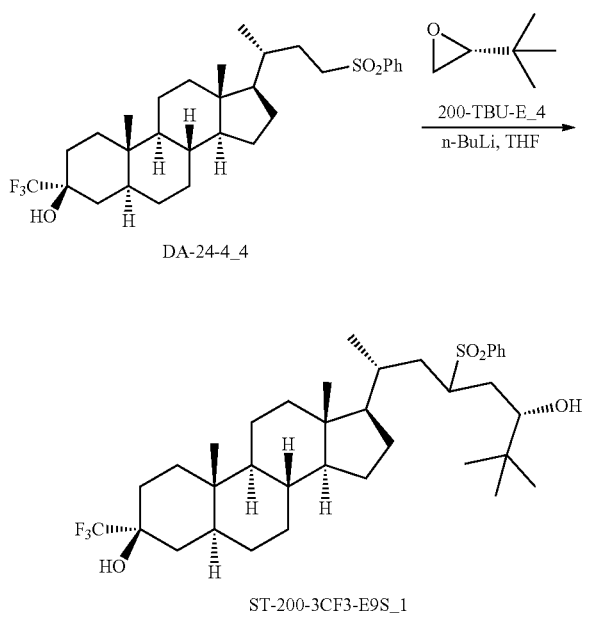

To THF (0.5 mL) was added BuLi (0.46 mL, 2.5 M in hexane, 1.15 mmol). A solution of DA-24-4_4 (250 mg, 0.462 mmol) in THF (3 mL) was added at −70° C. After stirring at −70° C. for 1 h, diisopropylamine (130 mg, 1.29 mmol) was added. After 10 minutes. (R)-2-(tert-butyl)oxirane (69.4 mg, 0.693 mmol) was added at −70° C. The mixture was stirred at −70° C. for another 1 h. The mixture was warmed to 25° C. and stirred for 16 hrs. To the mixture was added NH$_4$Cl (50 mL, sat. aq.). The mixture was extracted with EtOAc (2×30 mL). The organic layer was separated, dried over Na$_2$SO$_4$, filtered, and concentrated to give ST-200-3CF3-E9S_1 (250 mg, crude) as a solid, which was used directly for the next step.

Synthesis of ST-200-3CF3-E9S

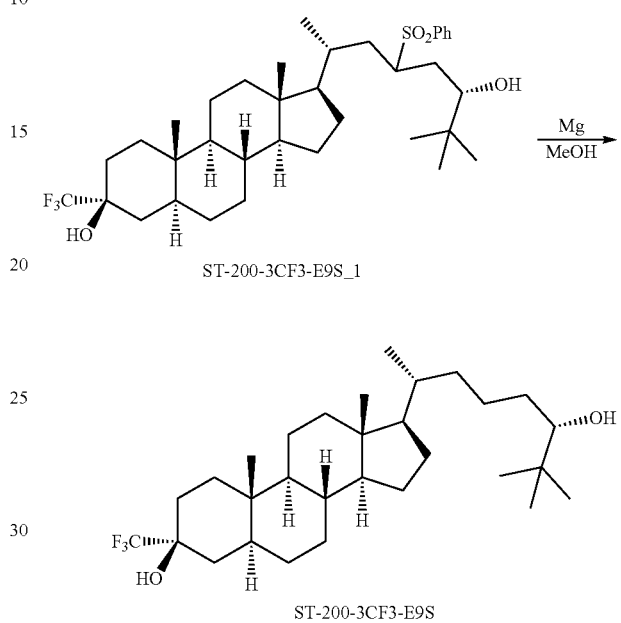

To a solution of ST-200-3CF3-E9S_1 (250 mg, 0.390 mmol) and NiCl$_2$ (5.03 mg, 0.039 mmol) in dry methanol (20 mL) was added Mg powder (374 mg, 15.6 mmol) in 4 portions under N$_2$ with stirring at 50° C. The reaction mixture was stirred at 60° C. for 1 hour. The mixture was quenched with HCl (50 mL, 1 M) until the reaction became clear and extracted with DCM (2×30 mL). The combined organic phase was dried over Na$_2$SO$_4$, filtered, concentrated and purified by flash column (0-10% of EtOAc in PE) to give ST-200-3CF3-E9S (120 mg, 61%) as a solid $^1$H NMR (400 MHz, CDCl$_3$) δ 3.22-3.12 (m, 1H), 2.10-1.90 (m, 3H), 1.90-1.76 (m, 2H), 1.76-1.58 (m, 4H), 1.58-1.32 (m, 7H), 1.32-0.94 (m, 18H), 0.94-0.88 (m, 9H), 0.85 (s, 3H), 0.65 (m, 4H).

Synthesis of ST-200-3CF3-E9S_Bz

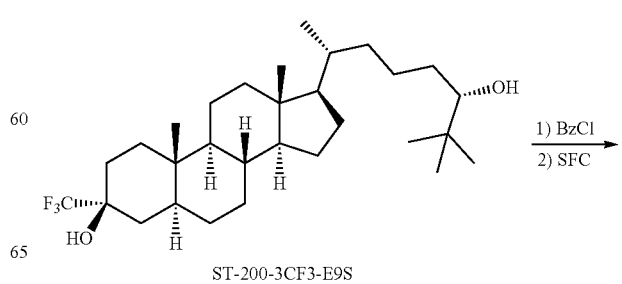

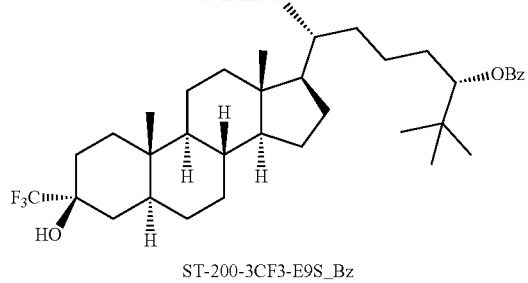

ST-200-3CF3-E9S_Bz

To a solution of ST-200-3CF3_E9S (120 mg, 0.239 mmol) in DCM (2 mL) was added py (377 mg, 4.77 mmol) and BzCl (167 mg, 1.19 mmol). The mixture was stirred at 25° C. for 2 h. The mixture was washed with NaHCO₃ (5 mL, 10% aq), HCl (5 mL, 2 M), purified by prep-TLC (PE:EtOAc=50:1) to give ST-200-3CF3-E9R_Bz (140 mg) as a solid. The crude ST-200-3CF3-E9S_Bz (140 mg) was purified by SFC (Instrument: SFC-14; Column: AD(250 mm*30 mm, 10 um); Condition: 0.1% NH₃H₂O EtOH; Begin B: 30%; End B: 30%; FlowRate(ml/min): 60ML/MIN; Injections: 60) to give pure ST-200-3CF3-E9S_Bz (100 mg) as an oil.

Synthesis of ST-200-3CF3-E9S

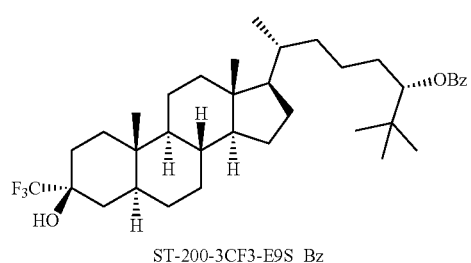

ST-200-3CF3-E9S_Bz $\xrightarrow{\text{LiOH, THF, MeOH, water}}$

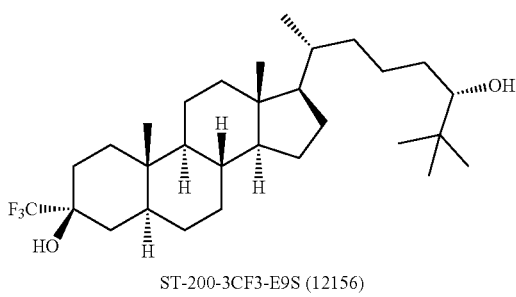

ST-200-3CF3-E9S (12156)

To a solution of ST-200-3CF3-E9S_Bz (100 mg, 0.165 mmol) in THF (1 mL) was added MeOH (0.5 mL), water (0.5 mL) and LiOH.H₂O (69.2 mg, 1.65 mmol), The mixture was stirred at 50° C. for 72 h. To the mixture was added water (2 mL). The mixture was extracted with EtOAc (5 mL). The organic layer was separated, concentrated in vacuum, purified by silica gel column (PE/DCM/EtOAc=40/1/1 to 20/1/1) to give ST-200-3CF3-E9S (60 mg, 73%) as a solid. The impure was re-crystallized from MeCN (1 mL) to give ST-200-3CF3-E9S (35 mg) as a solid.

$^1$H NMR (400 MHz, CDCl₃) δ 3.22-3.12 (m, 1H), 2.10-1.92 (m, 3H), 1.89-1.78 (m, 2H), 1.72-1.57 (m, 5H), 1.55-1.28 (m, 10H), 1.28-0.93 (m, 11H), 0.91 (d, J=6.4 Hz, 3H), 0.89 (s, 9H), 0.85 (s, 3H), 0.74-0.67 (m, 1H), 0.65 (s, 3H).

HPLC Rt=6.61 min in 8.0 min chromatography, 50-100_AB_E, purity 100%.

Example 123: Biological Data

The experiments were conducted as described in Example 2 and the results are shown in Table 2-60.

TABLE 2-60

| Compound | Avg EC50 2A (nM) | Avg Emax 2A (%) | Avg EC50 2B (nM) | Avg Emax 2B (%) |
|---|---|---|---|---|
| 4115 | 91.9 | 186.5 | 113.6 | 195.2 |
| 5116 | 101.7 | 185.1 | 130.4 | 213.8 |

TABLE 2-60-continued

| Compound | Avg EC50 2A (nM) | Avg Emax 2A (%) | Avg EC50 2B (nM) | Avg Emax 2B (%) |
|---|---|---|---|---|
| 3114 | 382.1 | 318.0 | 243.5 | 293.6 |
| 112 | 480.1 | 92.6 | 478.0 | 150.8 |
| 2113 | 380.4 | 402.7 | 412.8 | 285.0 |
| 11786 | 583.9 | 152.0 | 1008.7 | 151.0 |
| 11828 | 146.6 | 142.3 | 76.9 | 114.5 |

TABLE 2-60-continued

| Compound | Avg EC50 2A (nM) | Avg Emax 2A (%) | Avg EC50 2B (nM) | Avg Emax 2B (%) |
|---|---|---|---|---|
| 11934 | 729.2 | 113.4 | 469.7 | 70.0 |
| 12055 | 506.2 | 113.8 | 1134.5 | 184.7 |
| 12156 | 153.9 | 43.2 | 2456.4 | 111.2 |

Example 125: Synthesis

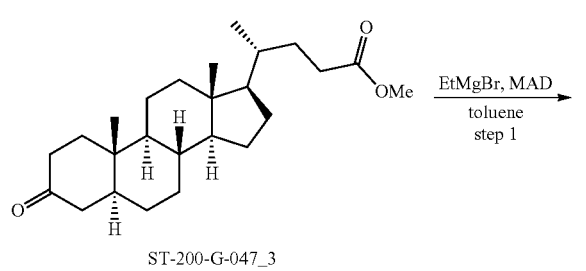

ST-200-G-047_3

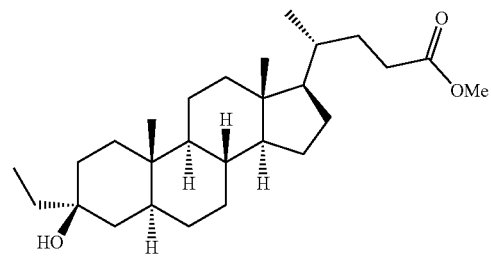

ST-200-G-062_1

To a solution of 2,6-di-tert-butyl-4-methylphenol (17 g, 77.1 mmol) in toluene (50 mL) was added trimethylaluminum (19.2 mL, 2M in toluene) at 10° C. The mixture was stirred at 20° C. for 1 h. This MAD solution was used in the next step directly without analysis.

To a solution of MAD (77.1 mmol) in toluene (50 mL) was added a solution of (R)-methyl 4-((5S,8R,9S,10S,13R,14S,17R)-10,13-dimethyl-3-oxohexadecahydro-1H-cyclopenta[a]phenanthren-17-yl) pentanoate (5 g, 12.8 mmol) in toluene (20 mL) dropwise at −70° C. dropwise under $N_2$. The mixture was stirred at −70° C. for 1 hour. A solution of EtMgBr (12.7 mL, 3M) was added dropwise at −70° C. The mixture was stirred at −70° C. for another 3 hours. When TLC showed most of starting material was consumed and a new spot was produced, the reaction mixture was quenched with citric acid (150 mL, sat. aq.). The reaction was warmed to 25° C. The organic was separated and concentrated in vacuum. The crude was purified by column chromatography on silica gel (EA:PE=200:1 to 10:1) to give (R)-methyl 4-((3S,5S,8R,9S,10S,13R,14S,17R)-3-ethyl-3-hydroxy-10,13-dimethylhexadecahydro-1H-cyclopenta[a]phenanthren-17-yl)pentanoate (3.8 g) as a solid.

$^1$H NMR (400 MHz, CDCl$_3$) δ 3.66 (s, 3H), 2.41-2.30 (m, 1H), 2.26-2.15 (m, 1H), 1.94 (td, J=3.3, 12.5 Hz, 1H), 1.90-1.73 (m, 2H), 1.69-1.58 (m, 3H), 1.56-0.84 (m, 28H), 0.82 (s, 3H), 0.64 (s, 4H).

Example 126

Synthesis of DA-23-3_3

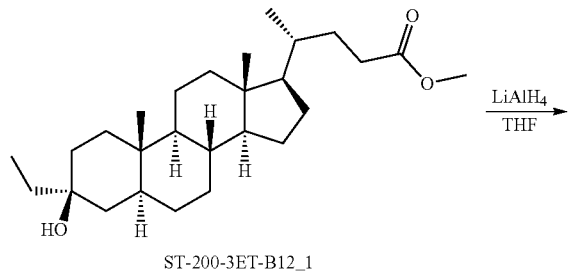

ST-200-3ET-B12_1

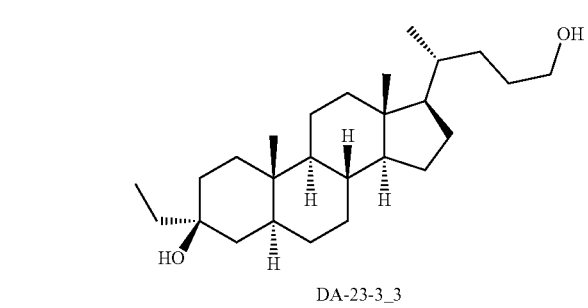

DA-23-3_3

LiAlH$_4$ (198 mg, 2.54 mmol) was added in three portions to a solution of ST-200-3ET-B12_1 (1.1 g, 2.62 mmol) in THF (10 mL) at 0° C. under N$_2$. After stirring at 20° C. for 1 hour, the mixture was quenched with water (10 mL) at 0° C., followed by adding HCl (10 mL, 1 mol/L). The aqueous phase was extracted with EtOAc (2×10 mL). The combined organic phase was washed with saturated brine (2×10 mL), dried over anhydrous Na$_2$SO$_4$, filtered and concentrated. The residue was purified by flash column (0~50% of EtOAc in PE) to give DA-23-3_3 (1 g, 98%) as a solid.

$^1$H NMR CDCl$_3$ 400 MHz δ 3.65-3.55 (m, 2H), 1.98-1.92 (m, 1H), 1.88-1.75 (m, 1H), 1.70-1.40 (m, 13H), 1.40-1.19 (m, 7H), 1.19-0.98 (m, 7H), 0.98-0.80 (m, 11H), 0.66-0.61 (m, 4H).

Synthesis of DA-23-3_4

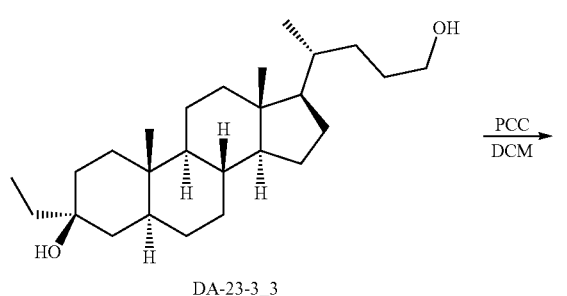

DA-23-3_3

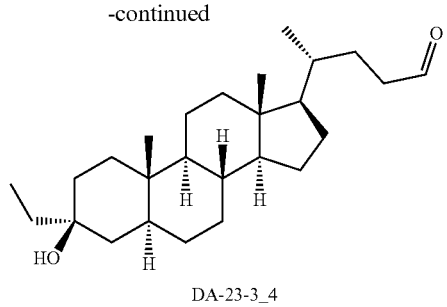

DA-23-3_4

To a solution of DA-23-3_3 (1 g, 2.55 mmol) in anhydrous DCM (30 mL) was added silica gel (1 g) and PCC (1.09 g, 5.10 mmol). After stirring at 20° C. for 1 hours, the reaction mixture was filtered and the filtrate was concentrated. The residue was purified by column chromatography on silica gel (PE/EA=50/1 to 10/1) to give DA-23-3_4 (600 mg, 60%) as a solid.

$^1$H NMR CDCl$_3$ 400 MHz δ 9.98-9.97 (m, 1H), 2.50-2.20 (m, 2H), 2.05-1.50 (m, 3H), 1.50-1.19 (m, 15H), 1.19-0.99 (m, 7H), 0.99-0.82 (m, 12H), 0.70-0.55 (m, 4H).

Example 127

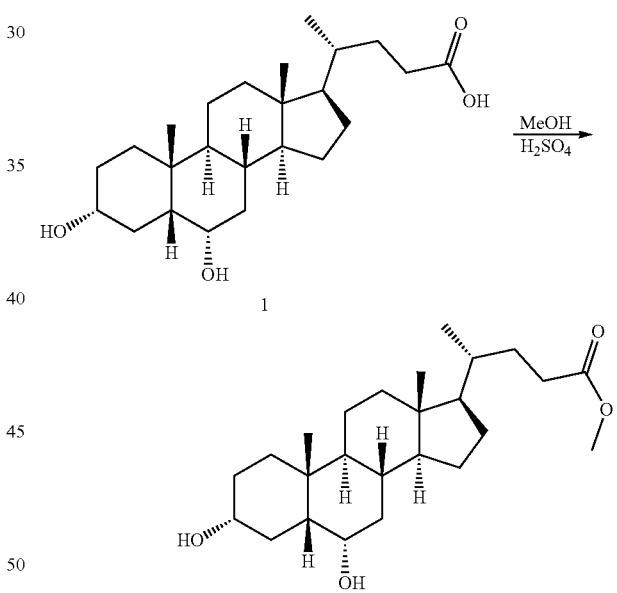

To a solution of compound 1 (100 g, 255 mmol, 1.0 eq) in dry MeOH (500 mL) was added concentrated H$_2$SO$_4$ (14 mL). The mixture was heated to reflux overnight and then cooled to room temperature. The mixture was quenched with aq. saturated NaHCO$_3$ solution (0.5 L) and then evaporated to remove MeOH. The residue mixture was extracted with EtOAc (300 mL×3). The combined organic layers were washed with brine (200 mL), dried over Na$_2$SO$_4$ and evaporated to give the product (100 g crude, 96%) as a powder.

$^1$H NMR: (400 MHz, CDCl$_3$) δ 4.09-4.02 (m, 1H), 3.66 (s, 3H), 3.63-3.58 (m, 1H), 2.39-2.31 (m, 1H), 2.25-2.15 (m, 1H), 1.97-1.91 (m, 1H), 1.91-1.55 (m, 10H), 1.52-1.02 (m, 14H), 0.95-0.88 (m, 6H), 0.62 (s, 3H).

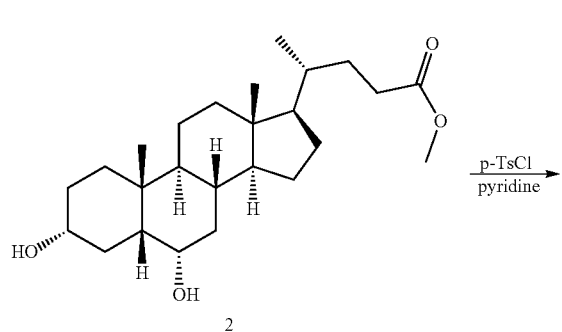

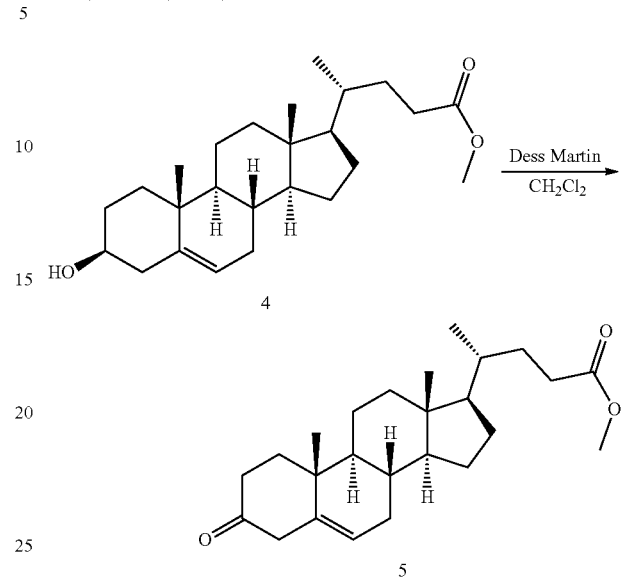

¹H NMR (400 MHz, CDCl₃) δ 5.32-5.38 (m, 1H), 3.66 (s, 3H), 3.47-3.57 (m, 1H), 2.16-2.41 (m, 4H), 1.93-2.04 (m, 2H), 1.74-1.92 (m, 4H), 1.30-1.59 (m, 9H), 0.90-1.19 (m, 12H), 0.68 (s, 3H)

To a solution of compound 2 (250 g, 615 mmol, 1.0 eq) in dry pyridine (0.8 L) was added a solution of TsCl (352 g, 1844 mmol, 3.0 eq) in dry pyridine (200 mL). The mixture was stirred at room temperature for 18 h. Ice chips were added gradually to the mixture, and the precipitated solid was filtered, washed with aq. 10% HCl solution (400 mL×3) and water (400 mL×2), and then evaporated to dryness to give crude product (500 g, crude) as a powder, which was used to next step directly To a solution of compound 4 (33 g, 85 mmol, 1.0 eq) in dry CH₂Cl₂ (700 mL) was added Dess-Martin reagent (72 g, 170 mmol, 2.0 eq) in portions at 0° C. Then the reaction mixture was stirred at room temperature for 1 h. TLC (PE:EA=3:1) showed the starting material was consumed completely. The reaction mixture were quenched with a saturated aqueous solution of NaHCO₃/Na₂S₂O₃=1:3 (250 mL). The organic phase was washed with brine (200 mL×2) and dried over Na₂SO₄, and the solvent was evaporated to afford desired product (35 g, crude), which was used in the next step without further purification.

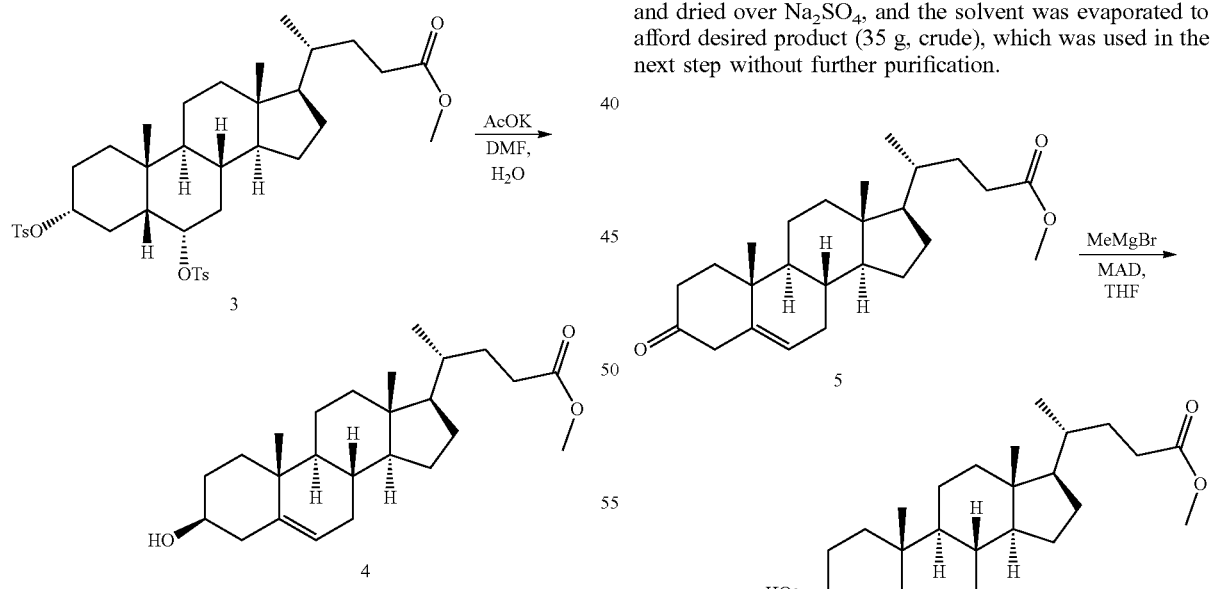

A mixture of compound 3 (250 g crude), CH₃COOK (24 g, 245 mmol, 0.77 eq), water (150 mL) and DMF (900 mL) was heated at reflux for 24 h. The solution was cooled to room temperature, with ice chips added gradually. The precipitated solid was filtered off and washed with water (100 mL×2). The crude solid was purified on silica gel column (PE/EtOAc=8/1) to give compound 4 (40 g, yield 34.3% of two steps) as solid.

To a solution of MAD (0.42 mol, 3.0 eq) in toluene, freshly prepared by addition of a solution of Me₃Al (210 mL, 0.42 mmol, 2 M in hexane) to a stirred solution of 2,6-di-tert-butyl-4-methylphenol (185 g, 0.84 mol) in toluene (200 mL) followed by stirring for 1 h at room temperature, was added dropwise a solution of compound 5 (54 g, 0.14 mol, 1.0 eq) in toluene (200 mL) at −78° C. under nitrogen. Then the reaction mixture was stirred for 30 min, a solution of MeMgBr (140 mL, 0.42 mol, 3.0 eq, 3 M in ether) was added dropwise at −78° C. The reaction mixture was warmed to −40° C. and stirred at this temperature for 3 h. TLC (PE:EA=3:1) showed that the starting material was consumed completely. The mixture was poured into aqueous saturated NH$_4$Cl solution (100 mL) and extracted with EtOAc (300 mL×2). The combined organic phases were dried over Na$_2$SO$_4$, and the solvent was evaporated to afford crude product. The crude product was purified on silica gel chromatography eluted with PE:EA=10:1 to give the pure target (30 g, 53%) as powder.

$^1$H NMR: (400 MHz, CDCl$_3$) δ 5.31-5.29 (m, 1H), 3.66 (s, 3H), 2.39-2.33 (m, 2H), 2.24-2.22 (m, 1H), 1.99-1.95 (m, 3H), 1.85-1.68 (m, 4H), 1.59-1.40 (m, 8H), 1.31-1.26 (m, 2H), 1.17-1.01 (m, 11H), 0.93-0.91 (m, 4H), 0.67 (s, 3H).

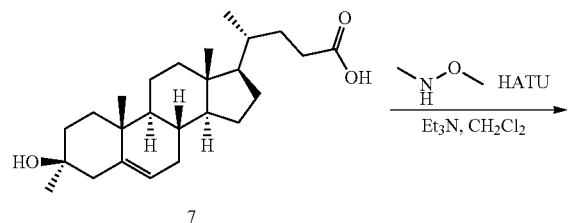

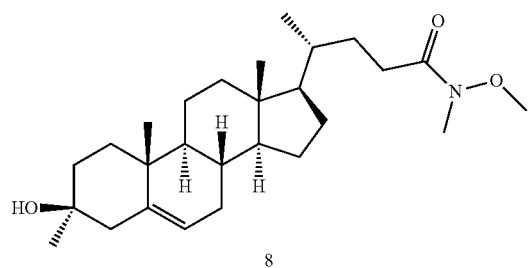

A mixture of compound 7 (32.0 g, 82.35 mmol), N,O-dimethylhydroxylamine (16.07 g, 164.70 mmol), HATU (37.57 g, 98.82 mmol) and Et$_3$N (46.0 mL, 329.40 mmol) in 500 mL anhydrous CH$_2$Cl$_2$ was stirred for 18 h at room temperature. TLC showed the reaction was completed. Then CH$_2$Cl$_2$ was added to the mixture and the resulting solution was washed with water, 1 N HCl aqueous, saturated aqueous NaHCO$_3$ and brine, dried over anhydrous Na$_2$SO$_4$, filtered and concentrated, purified by silica gel (PE:EtOAc=10:1 to 3:1) to afford the target compound 8 (17.0 g, yield:47.8%) as a solid.

$^1$H NMR: (400 MHz, CDCl$_3$) δ 5.31-5.29 (m, 1H), 3.69 (s, 3H), 3.17 (s, 3H), 3.03 (s, 2H), 2.47-2.29 (m, 3H), 2.04-1.68 (m, 7H), 1.60-1.43 (m, 7H), 1.38-1.30 (m, 2H), 1.20-1.08 (m, 6H), 1.03-0.91 (m, 8H), 0.68 (s, 3H).

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I-66):

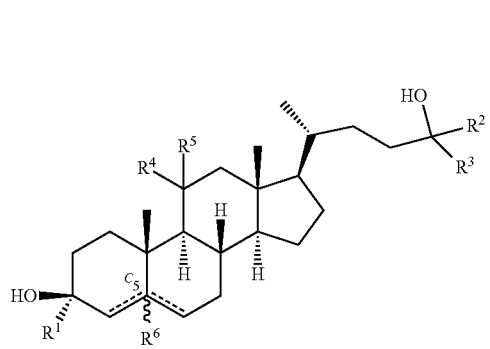

(I-66)

or a pharmaceutically acceptable salt thereof, wherein:
$R^1$ is substituted or unsubstituted $C_1$-$C_6$alkyl;
$R^2$ is substituted or unsubstituted aralkyl, substituted or unsubstituted heteroaralkyl, substituted or unsubstituted aryl, or substituted or unsubstituted heteroaryl;
$R^3$ is hydrogen, substituted or unsubstituted $C_1$-$C_6$alkyl, substituted or unsubstituted carbocyclyl, substituted or unsubstituted heterocyclyl, substituted or unsubstituted aryl, or substituted or unsubstituted heteroaryl;
each of $R^4$ and $R^5$ is independently hydrogen, halo, or —$OR^C$, wherein $R^C$ is hydrogen or unsubstituted or substituted $C_1$-$C_3$alkyl, or
$R^4$ and $R^5$, together with the carbon atom to which they are attached, form an oxo group;
$R^6$ is absent or hydrogen; and
═══ represents a single or double bond, wherein when one of ═══ is a double bond, the other ═══ is a single bond; wherein when both of ═══ are single bonds, $R^6$ is hydrogen; and wherein when one of ═══ is a double bond, $R^6$ is absent.

2. The compound of claim 1, or the pharmaceutically acceptable salt thereof, wherein $R^2$ is substituted or unsubstituted aryl, substituted or unsubstituted heteroaryl, or substituted or unsubstituted aralkyl.

3. A compound, or a pharmaceutically acceptable salt thereof, selected from the group consisting of:

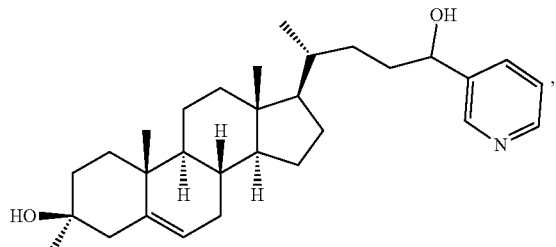

,

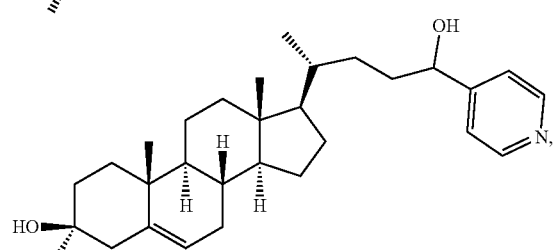

,

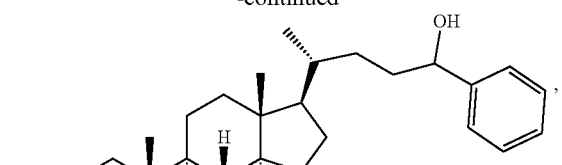

,

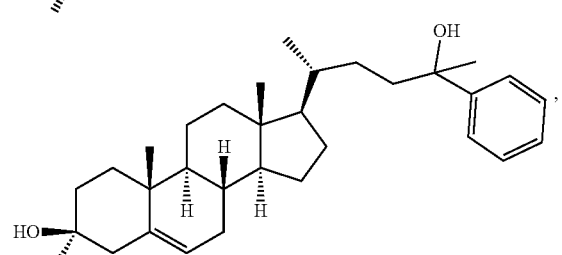

,

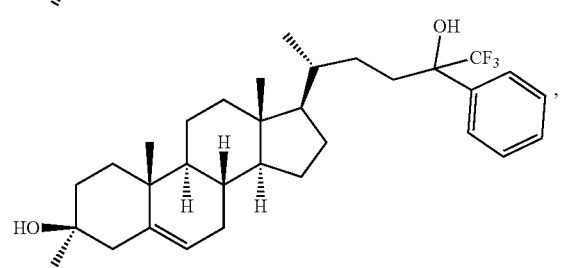

,

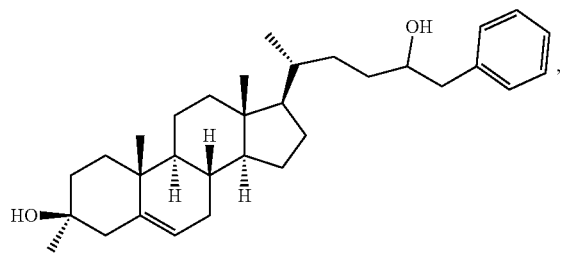

,

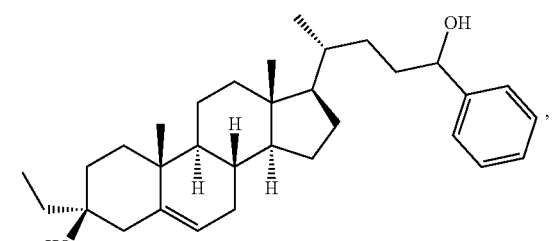

,

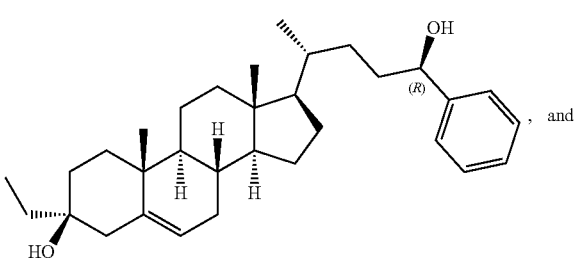

, and

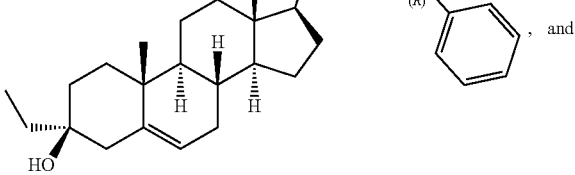

,

499

-continued

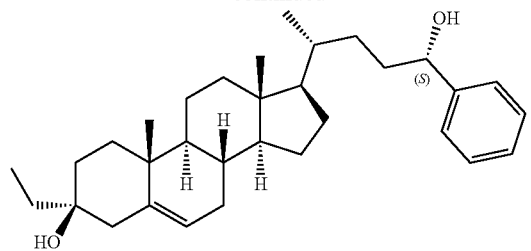

4. A pharmaceutical composition comprising a compound of claim 1, or a pharmaceutically acceptable salt thereof, and a pharmaceutically acceptable carrier.

5. The compound of claim 2, or the pharmaceutically acceptable salt thereof, wherein $R^2$ is substituted or unsubstituted phenyl, substituted or unsubstituted benzyl, or substituted or unsubstituted pyridyl.

6. The compound of claim 5, or the pharmaceutically acceptable salt thereof, wherein $R^2$ is unsubstituted phenyl, unsubstituted benzyl, or unsubstituted pyridyl.

7. The compound of claim 3, wherein the compound is selected from the group consisting of:

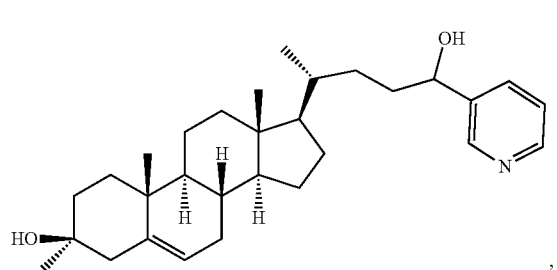

,

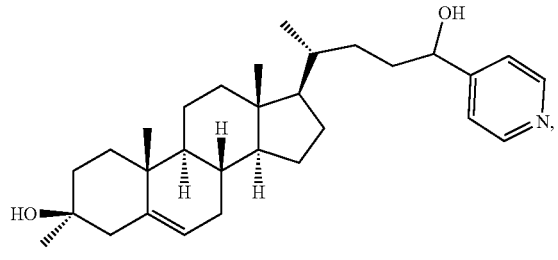

,

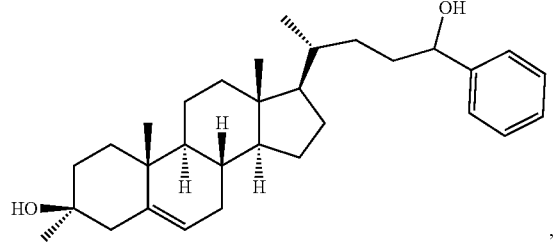

,

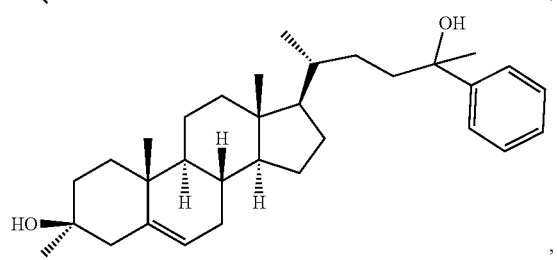

,

500

-continued

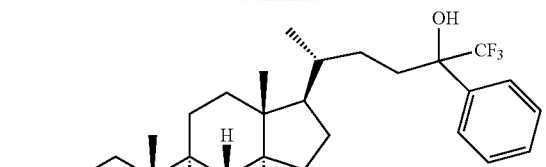

8. The pharmaceutically acceptable salt of claim 3, wherein the compound is selected from the group consisting of:

501
-continued
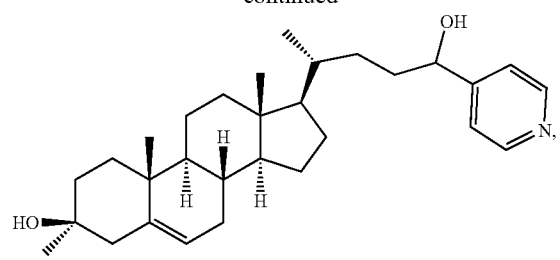
,
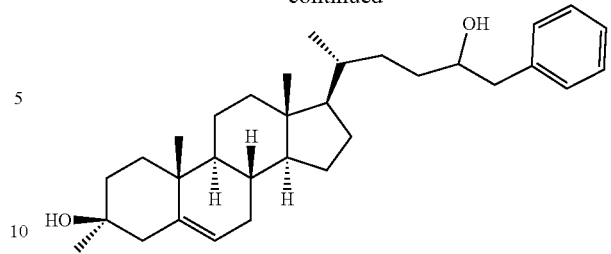
,
502
-continued
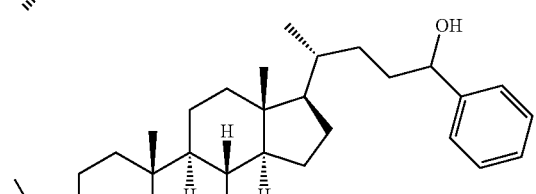
,
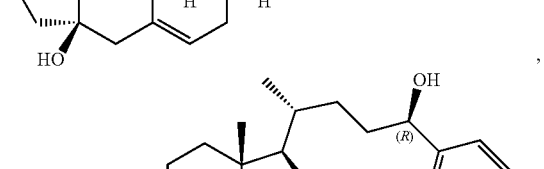
,
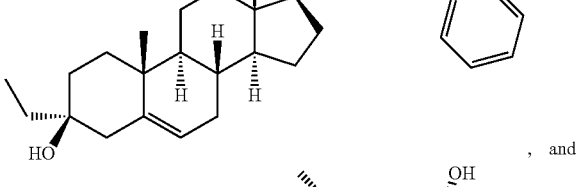
, and
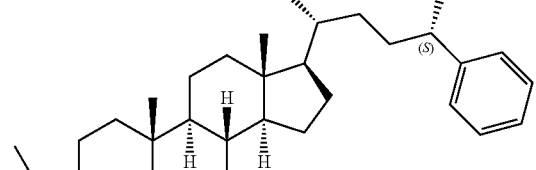
.
* * * * *